(12) United States Patent
Linghu et al.

(10) Patent No.: US 11,782,064 B2
(45) Date of Patent: Oct. 10, 2023

(54) METHODS FOR SIMULTANEOUS MEASUREMENT OF MULTIPLE BIOLOGICAL SIGNALS FROM SPECTRALLY IDENTICAL FLUORESCENT REPORTERS

(71) Applicant: Massachusetts Institute of Technology, Cambridge, MA (US)

(72) Inventors: Changyang Linghu, Cambridge, MA (US); Shannon L. Johnson, Cambridge, MA (US); Edward Stuart Boyden, Chestnut Hill, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 239 days.

(21) Appl. No.: 17/020,803

(22) Filed: Sep. 14, 2020

(65) Prior Publication Data
US 2021/0080472 A1 Mar. 18, 2021

Related U.S. Application Data

(60) Provisional application No. 62/899,416, filed on Sep. 12, 2019.

(51) Int. Cl.
*G01N 33/68* (2006.01)
*G01N 33/50* (2006.01)
(Continued)

(52) U.S. Cl.
CPC ....... *G01N 33/6872* (2013.01); *C07K 14/705* (2013.01); *C12N 15/10* (2013.01); *C12N 15/62* (2013.01); *C12N 15/63* (2013.01); *G01N 33/5005* (2013.01); *G01N 33/582* (2013.01); *C07K 2319/01* (2013.01); *C07K 2319/60* (2013.01); *C07K 2319/735* (2013.01)

(58) Field of Classification Search
CPC .......... C07K 2319/735; C07K 2319/70; C07K 2319/60; C07K 2319/01; G01N 33/582; G01N 33/5005; G01N 33/6872; C12N 15/62

See application file for complete search history.

(56) References Cited

U.S. PATENT DOCUMENTS

2016/0305939 A1* 10/2016 Shemesh ............ G01N 33/5005
2018/0251497 A1*  9/2018 Brangwynne ............ C07K 1/14

OTHER PUBLICATIONS

Hackley, C.R., Mazzoni, E. 0. and Blau, J. (2018) "cAMPr: A single-wavelength fluorescent sensor for cyclic AMP." Science signaling. American Association for the Advancement of Science, 11 (520), p. 1-27.

(Continued)

*Primary Examiner* — Gary B Nickol
*Assistant Examiner* — Amelia Nicole Dickens
(74) *Attorney, Agent, or Firm* — Pierce Atwood LLP

(57) ABSTRACT

The invention, in some aspects, relates to the preparation and use of signaling reporter islands (SiRIs) in single cells. Compositions of the invention that produce SiRIs can be delivered to a cell resulting in the presence of one or more SiRIs in the cell. Methods of the invention include detecting signals generated by elements in the SiRIs in a cell and use of the detected signals to determine and analyze simultaneous physiological processes within the cell, or cells.

18 Claims, 94 Drawing Sheets
(94 of 94 Drawing Sheet(s) Filed in Color)

Specification includes a Sequence Listing.

(51) Int. Cl.
*G01N 33/58* (2006.01)
*C12N 15/62* (2006.01)
*C07K 14/705* (2006.01)
*C12N 15/63* (2006.01)
*C12N 15/10* (2006.01)

(56) References Cited

OTHER PUBLICATIONS

Hancock, J. F. et al. (1991) "A CAAX or a CAAL motif and a second signal are sufficient for plasma membrane targeting of ras proteins." The EMBO journal. European Molecular Biology Organization, 10(13), pp. 4033-4039.

Hanson, M. G. et al. (1998) "Cyclic AMP Elevation is Sufficient to Promote the Survival of Spinal Motor Neurons in Vitro." Journal of Neuroscience, 18(18), pp. 7361-7371.

Hardingham, G. E., Arnold, F. J. L. and Bading, H. (2001) "Nuclear calcium signaling controls CREB-mediated gene expression triggered by synaptic activity." Nature Neuroscience. Nature Publishing Group, 4(3), pp. 261-267.

Hocine, S. et al. (2013) "Single-molecule analysis of gene expression using two-color RNA labeling in live yeast." Nature Methods, 10(2), pp. 119-121.

Holt, C. E. and Schuman, E. M. (2013) "The Central Dogma Decentralized: New Perspectives on RNA Function and Local Translation in Neurons." Neuron. Cell Press, 80(3), pp. 648-6.

Hopp, T. P. et al. (1988) "A Short Polypeptide Marker Sequence Useful for Recombinant Protein Identification and Purification." Bio/Technology. Nature Publishing Group, 6(10), pp. 1204-1210.

Howe, AK. (2011) "Cross-talk between calcium and protein kinase A in the regulation of cell migration." Current Opinion in Cell Biology, pp. 554-561.

Hsia, Y. et al. (2016) "Design of a hyperstable 60-subunit protein icosahedron." Nature. Nature Publishing Group, 535(7610), pp. 136-139.

Huang P.-S. et al. (2014) "High thermodynamic stability of parametrically designed helical bundles." Science (New York, NY). Europe PMC Funders, 346(6208), pp. 481-485.

Huang, P.-S., Boyken, S. E. and Baker, D. (2016) "The coming of age of de novo protein design." Nature. Nature Publishing Group, 537(7620), pp. 320-327.

Huang, Y.-Y. and Kandel, E. R. (1994) Recruitment of Long-lasting and Protein Kinase A-dependent Long-term Potentiation in the CA I Region of Hippocampus Requires Repeated Tetanization. Learning & Memory 1:74-82.

Indelicato, G. et al. (2016) "Principles Governing the Self-Assembly of Coiled-Coil Protein Nanoparticles." Biophysical Journal, 110(3), pp. 646-660.

Kandel E. R., Dudai, Y. and Mayford, M. R. (2014) "The Molecular and Systems Biology of Memory." Cell. Cell Press, pp. 163-186.

King, N. P. et al. (2012) "Computational design of self-assembling protein nanomaterials with atomic level accuracy." Science (New York, NY). Howard Hughes Medical Institute, 336(6085), pp. 1171-1174.

King, N. P. et al. (2014) "Accurate design of co-assembling multi-component protein nanomaterials." Nature. NIH Public Access, 510(7503), pp. 103-108.

Klapoetke, N. C. et al. (2014) "Independent Optical Excitation of Distinct Neural Populations." Nature Methods. NIH Public Access, 11(3), pp. 338-346.

Ku, T. et al. (2016) "Multiplexed and scalable super-resolution imaging of three-dimensional protein localization in size-adjustable tissues." Nature Biotechnology. Nature Publishing Group, 34(9), pp. 973-981.

Lai, Y.-T. et al. (2014) "Structure of a Designed Protein Cage that Self-Assembles into a Highly Porous Cube." Nature Chemistry. NIH Public Access, 6(12), pp. 1065-1071.

Lai, Y.-T. et al. (2016) "Designing and defining dynamic protein cage nanoassemblies in solution." Science Advances. American Association for the Advancement of Science, 2(12), pp. 1-12.

Lai, Y.-T., Cascio, D. and Yeates, T. O. (2012) "Structure of a 16-nm Cage Designed by Using Protein Oligomers." Science (New York, NY), 336(6085), p. 1129.

Lee, H.K. et al. (1998) "NMDA induces long-term synaptic depression and dephosphorylation of the GluR1 subunit of AMPA receptors in hippocampus." Neuron. Cell Press, 21(5), pp. 1151-1162.

Li, S. et al. (2013) "Environmental novelty activates 2-adrenergic signaling to prevent the impairment of hippocampal LTP by A β-oligomers." Neuron. Cell Press, 77(5), pp. 929-941.

Li, W. et al. (2018) "Reduced Cyclic Adenosine Monophosphate Level in Hippocampal CAI Participates in Propofol Induced Amnesia in Rats." Frontiers in Neuroscience, 12., p. 1-8.

Lim, F., Downey, T. P. and Peabody, D. S. (2001) "Translational repression and specific RNA binding by the Coat Protein of the Pseudomonas Phage PP7." The Journal of Biological Chemistry. American Society for Biochemistry and Molecular Biology, 276(25), pp. 22507-225013.

Lin, J. R. et al. (2018) "Highly multiplexed immunofluorescence imaging of human tissues and tumors using t-CyCIF and conventional optical microscopes." eLife. eLife Sciences Publications Ltd, 7, p. 1-4.

Lyford G. L. et al. (1995) "Arc, a Growth Factor and Activity-Regulated Gene, Encodes a Novel Cytoskeleton-Associated Protein that is Enriched in Neuronal Dendrites." Neuron. Cell Press, 14(2), pp. 433-445.

Makino, H. and Malinow, R. (2009) "AMPA Receptor Incorporation into Synapses during LTP: The Role of Lateral Movement and Exocytosis." Neuron, 64(3), pp. 381-390.

Mao, L. et al. (2005) "Role of Protein Phosphatase 2A in mGluR5-regulated MEK/ERK Phosphorylation in Neurons." Journal of Biological Chemistry, 280(13), pp. 12602-12610.

Martin, K. et al., "mRNA Localization: Gene Expression in the Spatial Dimension." Cell 136, 719-730, Feb. 20, 2009.

Martin, R. M. et al. (2013) "Live-Cell Visualization of Pre-mRNA Splicing with Single-30 Molecule Sensitivity." Cell Reports, 4(6), pp. 1144-1155.

Mehta, S. and Zhang, J. (2011) "Reporting from the Field: Genetically Encoded Fluorescent Reporters Uncover Signaling Dynamics in Living Biological Systems." Annual Review of Biochemistry. Annual Reviews, 80(1), pp. 375-401.

Mehta, S. et al. (2018) "Single-fluorophore Biosensors for Sensitive and Multiplexed Detection of Signalling Activities." Nature Cell Biology. Nature Publishing Group, 20(10), pp. 1215-1225.

Menard, C. and Quirion, R. (2012) "Group I metabotropic glutamate receptor function and its regulation of learning and memory in the aging brain." Frontiers in Pharmacology, Oct. 3, p. 1-12.

Micheva, K. D. and Smith, S. J. (2007) "Array Tomography: A New Tool for Imaging the Molecular Architecture and Ultrastructure of Neural Circuits." Neuron. Cell Press, 55(1), pp. 25-36.

Miedlich, S., Gama, L. and Breitwieser, G. E. (2002) "Calcium Sensing Receptor Activation by a Calcimimetic Suggests a Link between Cooperativity and Intracellular Calcium Oscillations." Journal of Biological Chemistry, 277(51), pp. 49691-49699.

Mironov, S. L. et al. (2009) "Imaging cytoplasmic cAMP in mouse brainstem neurons." BMC Neuroscience, p. 1-11.

Mo, G. C.H. et al. (2017) "Genetically encoded biosensors for visualizing live-cell biochemical activity at super resolution." Nature Methods. Nature Publishing Group, 14(4), pp. 427-434.

Moffitt, J. R. et al. (2016) "High-performance multiplexed fluorescence in situ hybridization in culture and tissue with matrix imprinting and clearing." Proceedings of the National Academy of Sciences of the United States of America. National Academy of Sciences, 113(50), pp. 14456-14461.

Moll, J. R. et al. (2001) "Designed heterodimerizing leucine zippers with a ranger of pIs and stabilities up to 10-15 M." Protein Science. Wiley-Blackwell, 10(3), pp. 649-655.

Murphy, J. G. et al. (2014) "AKAP-Anchored PKA Maintains Neuronal L-type Calcium Channel Activity and NFAT Transcriptional Signaling." Cell Reports. Elsevier, 7(5), pp. 1577-1588.

(56) References Cited

OTHER PUBLICATIONS

Murray, E. et al. (2015) "Simple, Scalable Proteomic Imaging for High-Dimensional Profiling of Intact Systems." Cell. Cell Press, 163(6), pp. 1500-1514.
Negi, S. et al. "LocSigDB: a database of protein localization signals." Database, vol. 2015, 1-7.
Negron, C. and Keating, A E. (2014) "A Set of Computationally Designed Orthogonal Antiparallel Homodimers that Expands the Synthetic Coiled-Coil Toolkit." Journal of the American Chemical Society. American Chemical Society, 136(47), pp. 16544-16556.
Ni, Q. et al. (2011) "Signaling Diversity of PKA Achieved Via a Ca2+-cAMP-PKA Oscillatory Circuit," Nature Chemical Biology. Nature Publishing Group, 7(1), pp. 34-40.
Oakley, M. G. and Kim, P. S. (1998) "A Buried Polar Interaction Can Direct the Relative Orientation of Helices in a Coiled Coil." Biochemistry, 37(36), pp. 12603-12610.
Ohadi, D. et al. (Nov. 19, 2019) "Computational Modeling Reveals Frequency Modulation of Calcium-cAMP/PKA Pathway in Dendritic Spines." Biophysical Journal. Biophysical Society, 117(10), pp. 1963-1980.
Ohta, Y. et al. (2018) "Red fluorescent cAMP indicator with increased affinity and expanded dynamic range." Scientific Reports. Nature Publishing Group, 8(1). p. 1-9.
Oliveira, AF. and Yasuda, R. (2013) "An Improved Ras Sensor for Highly Sensitive and Quantitative FRET-FLIM Imaging." PLoS ONE. 8(1), p. e52874. p. 1-5.
Otmakhov, N. et al. (2004) "Forskolin-Induced LTP in the CAI Hippocampal Region Is NMDA Receptor Dependent." Journal of Neurophysiology, 91(5), pp. 1955-1962.
Abrams, T. W., Karl, K. A. and Kandel, E. R. (1991) "Biochemical studies of stimulus convergence during classical conditioning in Aplysia: Dual regulation of adenylate cyclase by Ca2+/calmodulin and transmitter." Journal of Neuroscience. Society for Neuroscience, 11 (9), pp. 2655-2665.
Adamala, K. P., Martin-Alarcon, D. A and Boyden, E. S. (2016) "Programmable RNA-binding protein composed of repeats of a single modular unit." Proceedings of the National Academy of Sciences of the United States of America. National Academy of Sciences, 113(19), pp. E2579-E2588.
Asano, S. M. et al. (2018) "Expansion Microscopy: Protocols for Imaging Proteins and RNA in Cells and Tissues." Current Protocols in Cell Biology. John Wiley and Sons Inc., 80(1).
Averaimo, S. and Nicol, X. (2014) "Intermingled cAMP, cGMP and calcium spatiotemporal dynamics in developing neuronal circuits." Frontiers in Cellular Neuroscience. Frontiers, 8, p. 376.
Bale, J. B. et al. (2016) "Accurate design of megadalton-scale two-component icosahedral protein complexes." Science. American Association for the Advancement of Science, 353(6297), pp. 389-394.
Barco A, Alarcon, J.M. and Kandel, E. R. (2002) "Expression of constitutively active CREB protein facilitates the late phase of long-term potentiation by enhancing synaptic capture." Cell. Cell Press, 108(5), pp. 689-703.
Belousov, V. Vet al. (2006) "Genetically encoded fluorescent indicator for intracellular hydrogen peroxide." Nature Methods, 3(4), pp. 281-286.
Berg, J., Hung, Y. P. and Yellen, G. (2009) "A genetically encoded fluorescent reporter of ATP:ADP ratio." Nature Methods. Nature Publishing Group, 6(2), pp. 161-166.
Bertrand et al., "Localization of ASH1 mRNA Particles in Living Yeast." Molecular Cell, vol. 2, 437-445, Oct. 1998.
Bito, H., Deisseroth, K. and Tsien, R. W. (1996) "CREB Phosphorylation and Dephosphorylation: A Ca2+- and Stimulus Duration-Dependent Switch for Hippocampal Gene Expression." Cell. Cell Press, 87(7), pp. 1203-1214.
Bodenmiller, B. (2016) "Multiplexed Epitope-Based Tissue Imaging for Discovery and Healthcare Applications." Cell Systems. Cell Press, pp. 225-238.
Borodinsky, L. N. and Spitzer, N. C. (2006) "Second messenger pas de deux: the coordinated dance between calcium and cAMP." Science's STKE: signal transduction knowledge environment. American Association for the Advancement of Science, pp. 1-4.
Boyken, S. E. et al. (2016) "De novo design of protein homo-oligomers with modular hydrogen-bond network-mediated specificity." Science. American Association for the Advancement of Science, 352(6286), pp. 680-687.
Boyle, AL. et al. (2012) "Squaring the Circle in Peptide Assembly: From Fibers to Discrete Nanostructures by de Novo Design." Journal of the American Chemical Society, 134(37), pp. 15457-15467.
Buxbaum AR., Haimovich, G. and Singer, R.H. (2015) "In the right place at the right time: visualizing and understanding mRNA localization." Nature Reviews Molecular Cell Biology. Nature Publishing Group, 16(2), pp. 95-109.
Buxbaum AR., Wu, B. and Singer, R.H. (2014) "Single β-Actin mRNA Detection in Neurons Reveals a Mechanism for Regulating its Translatability." Science (New York, NY). American Association for the Advancement of Science, 343(6169), pp. 419-422.
Careaga, M. et al. (2014) "Group I metabotropic glutamate receptor mediated dynamic immune dysfunction in children with fragile X syndrome." Journal of Neuroinflammation, 11(1), p. 1-10.
Chalifoux, J. R. and Carter, AG. (2010) "GABAB Receptors Modulate NMDA Receptor Calcium Signals in Dendritic Spines." Neuron. Cell Press, 66(1), pp. 101-111.
Chavez-Noriega, L. E. and Stevens, C. F. (1992) "Modulation of synaptic efficacy in field CAI of the rat hippocampus by forskolin." Brain research, 574(1-2), pp. 85-92.
Chen, F., Tillberg, P. W. and Boyden, E. S. (2015) "Expansion microscopy." Science. American Association for the Advancement of Science, 347(6221), pp. 543-548.
Chen, T.-W. et al. (2013) "Ultrasensitive fluorescent proteins for imaging neuronal activity." Nature. Nature Publishing Group, 499(7458), pp. 295-30.
Chen, X. et al., "Fusion Protein Linkers: Property, Design and Functionality." Adv Drug Deliv Rev. Oct. 15, 2013;65(10): 1357-1369.
Chen, Z. et al. (2019) "Programmable design of orthogonal protein heterodimers." Nature Publishing Group, pp. 106-111.
Chijiwa, T. et al. (1990) "Inhibition of forskolin-induced neurite outgrowth and protein phosphorylation by a newly synthesized selective inhibitor of cyclic AMP-dependent protein kinase, N-[2-(p-bromocinnamylamino)ethyl]-5-isoquinolinesulfonamide (H-89), of PC12D pheochromocytoma cells." Journal of Biological Chemistry, 265(9), pp. 5267-5272.
Cho-Chung, Y. S. (1990) "Role of Cyclic AMP Receptor Proteins in Growth, Differentiation, and Suppression of Malignancy: New Approaches to Therapy," Cancer Research. American Association for Cancer Research, 50(22), pp. 7093-7100.
Chuong, A S. et al. (2014) "Noninvasive optical inhibition with a red-shifted microbial rhodopsin." Nature Neuroscience. Nature Publishing Group, 17(8), pp. 1123-1129.
Cooper, D. M. F., Mons, N. and Karpen, J. W. (1995) "Adenylyl cyclases and the interaction between calcium and cAMP signalling." Nature. Nature Publishing Group, 374(6521), pp. 421-424.
Davis, L., Banker, G. A and Steward, 0. (1987) "Selective dendritic transport of RNA in hippocampal neurons in culture." Nature. Nature Publishing Group, 330(6147), pp. 477-479.
Delebecque, C. J. et al. (2011) "Organization of Intracellular Reactions with Rationally Designed RNA Assemblies." Science, 333(6041), pp. 470-474.
Depry, C., Allen, M. D. and Zhang, J. (2011) "Visualization of PKA activity in plasma membrane microdomains." Molecular bioSystems, 7(1), pp. 52-58.
Dictenberg, J. B. et al. (2008) "A Direct Role for FMRP in Activity-Dependent Dendritic mRNA Transport Links Filopodial-Spine Morphogenesis to Fragile X Syndrome." Developmental Cell. Cell Press, 14(6), pp. 926-939.
Ding, Y. et al. (2015) "Ratiometric biosensors based on dimerization-dependent fluorescent protein exchange." Nature Methods. Nature Publishing Group, 12(3), pp. 195-198.
Dipilato, L. M. and Zhang, J. (2009) "The role of membrane microdomains in shaping beta2-adrenergic receptor-mediated cAMP dynamics." Molecular bioSystems, 5(8), pp. 832-837.

(56) References Cited

OTHER PUBLICATIONS

Donnes, P. et al., "Predicting Protein Subcellular Localization: Past, Present, and Future." Geno. Prot. Bioinfo. vol. 2 No. 4, Nov. 2004.
Dyachok, O. et al. (2006) "Oscillations of cyclic AMP in hormone-stimulated insulin-secreting-cells." Nature. Nature Publishing Group, 439(7074), pp. 349-352.
Ferguson, G.D. and Storm, D.R. (2004) "Why calcium-stimulated adenylyl cyclases?" Physiology. American Physiological Society, pp. 271-276.
Fletcher, J.M. et al. (2012) "A Basis Set of de Novo Coiled-Coil Peptide Oligomers for Rational Protein Design and Synthetic Biology." ACS Synthetic Biology, 1(6), pp. 240-250.
Fourcaudot, E. et al. (2009) "L-type voltage-dependent Ca2+ channels mediate expression of presynaptic LTP in amygdala." Nature Neuroscience, 12(9), pp. 1093-1095.
Franklin, N. C. (1985) "Conservation of genome form but not sequence in the transcription antitermination determinants of bacteriophages lambda, phi 21 and P22." Journal of molecular biology, 181(1), pp. 75-84.
Frey, U., Huang, Y. Y. and Kandel, E. R. (1993) "Effects of cAMP simulate a late stage of LTP in hippocampal CAI neurons." Science (New York, NY), 260(5114), pp. 1661-1664.
Garcia-Seisdedos, H. et al. (2017) "Proteins evolve on the edge of supramolecular self-assembly." Natureg Publishing Group, 548(7666), p. 1-19.
Giese, K. P. and Mizuno, K. (2013) "The roles of protein kinases in learning and memory." Learning and Memory, pp. 540-552.
Golding, I. and Cox, E. C. (2004) "RNA dynamics in live *Escherichia coli* cells." Proceedings of the National Academy of Sciences, 101(31), pp. 11310-11315.
Gonen, S. et al. (2015) "Design of ordered two-dimensional arrays mediated by noncovalent protein-protein interfaces." Science (New York, NY). American Association for the Advancement of Science, 348(6241), pp. 1365-1368.
Gorbunova, Y. V. and Spitzer, N. C. (2002) "Dynamic interactions of cyclic AMP transients and spontaneous Ca2+ spikes." Nature. Nature Publishing Group, 418(6893), pp. 93-96.
Govindarajan, A et al. (2011) "The Dendritic Branch Is the Preferred Integrative Unit for Protein Synthesis-Dependent LTP." Neuron, 69(1), pp. 132-146.
Gradisar, H. et al. (2013) "Design of a single-chain polypeptide tetrahedron assembled from coiled-coil segments." Nature Chemical Biology. Nature Publishing Group, 9(6), pp. 362-366.
Grigoryan, G. and Segal, M. (2013) "Prenatal stress alters noradrenergic modulation of LTP in hippocampal slices." Journal of Neurophysiology. American Physiological Society, 110(2), pp. 279-285.
Grigoryan, G. et al. (2011) "Computational Design of Virus-Like Protein Assemblies on Carbon Nanotube Surfaces." Science (New York, NY). NIH Public Access, 332(6033), pp. 1071-1076.
Otsuguro, K. et al. (2005) "Characterization of Forskolin-Induced Ca2+ Signals in Rat Olfactory Receptor Neurons," Journal of Pharmacological Sciences, 97(4), pp. 510-518.
Partridge, J. G. et al. (2014) "Contrasting actions of group I metabotropic glutamate receptors in distinct mouse striatal neurones," Journal of Physiology. Blackwell Publishing Ltd, 592(13), pp. 2721-2733.
Piatkevich K. D. et al. (2018) "A robotic multidimensional directed evolution approach applied to fluorescent voltage reporters article," Nature Chemical Biology. Nature Publishing Group, 14(4), pp. 352-360.
Qian, H. et al. (2017) "Phosphorylation of Serl928 mediates the enhanced activity of the L-type Ca2+ channel Cavl.2 by the 2-adrenergic receptor in neurons," p. 1-26, Science Signaling. American Association for the Advancement of Science, 10(463).
Redmond, L., Kashani, AH. and Ghosh, A (2002) "Calcium Regulation of Dendritic Growth via CaM Kinase IV and CREB-Mediated Transcription," Neuron. Cell Press, 34(6), pp. 999-1010.
Roberson, E. D. and David Sweatt, J. (1996) Transient Activation of Cyclic AMP-dependent Protein Kinase during Hippocampal Long-term Potentiation*, The Journal of Biological Chemistry. p. 30436-30441.
Sassone-Corsi, P. (2012) "The Cyclic AMP pathway," Cold Spring Harbor Perspectives in Biology. Cold Spring Harbor Laboratory Press, 4(12), p. 1-4.
Schmidt, U. et al. (2018) "Cell Detection with Star-convex Polygons," in Lecture Notes in Computer Science (including subseries Lecture Notes in Artificial Intelligence and Lecture Notes in Bioinformatics). Springer Verlag, pp. 1-8.
Shah, S. et al. (2017) "seqFISH Accurately Detects Transcripts in Single Cells and Reveals Robust Spatial Organization in the Hippocampus," Neuron. Elsevier, 94(4), p. 752-758.
Shekhawat, S. S. et al. (2009) "An Autoinhibited Coiled-Coil Design Strategy for Split-Protein Protease Sensors," Journal of the American Chemical Society, 131(42), pp. 15284-15290.
Shelly, M. et al. (2010) "Local and Long-Range Reciprocal Regulation of cAMP and cGMP in Axon/Dendrite Formation," Science, 327(5965), pp. 547-552.
Sheng, M., Thompson, M.A. and Greenberg, M. E. (1991) "CREB: a Ca(2+)-regulated transcription factor phosphorylated by calmodulin-dependent kinases," Science (New York, NY). American Association for the Advancement of Science, 252(5011), pp. 1427-1430.
Shimozono, S. et al. (2013) "Visualization of an endogenous retinoic acid gradient across embryonic development," Nature. Nature Publishing Group, 496(7445), pp. 1-5.
Siso-Nadal, F. et al. (2009) "Cross-talk between Signaling Pathways Can Generate Robust Oscillations in Calcium and cAMP," PLoS ONE, 4(10), p. 1-10.
Skeberdis, V. A et al. (2006) "Protein kinase A regulates calcium permeability of NMDA receptors," Nature Neuroscience. Nature Publishing Group, 9(4), pp. 501-510.
Song, Y. et al. (2013) "High-resolution Comparative Modeling with RosettaCM," Structure, 21(10), pp. 1735-1742.
Southern, J. A et al. (1991) "Identification of an epitope on the P and V proteins of simian virus 5 that distinguishes between two isolates with different biological characteristics," Journal of General Virology, 72(7), pp. 1551-1557.
Tadross, M. R., Tsien, R. W. and Yue, D. T. (2013) "Ca2+ channel nanodomains boost local Ca2+ amplitude," Proceedings of the National Academy of Sciences of the United States of America. National Academy of Sciences, 110(39), pp. 15794-15799.
Tarantino, N. et al. (2014) "Tnf and Il-1 exhibit distinct ubiquitin requirements for inducing NEMO-IKK supramolecular structures," Journal of Cell Biology, 204(2), pp. 231-245.
Tenner, B. et al. (2020) "Spatially compartmentalized phase regulation of a Ca2+-cAMP-PKA oscillatory circuit," bioRxiv. Cold Spring Harbor Laboratory, p. 34 34 pages, published Nov. 17, 2020 eLife.
Thomas, M. J. et al. (1996) "Activity-dependent β-adrenergic Modulation of Low Frequency Stimulation Induced LTP in the Hippocampal CAI Region," Neuron. Cell Press, 17(3), pp. 475-482.
Thomson, AR. et al. (2014) "Computational design of water-soluble a-helical barrels," Science, 346(6208), pp. 485-488.
Tillberg, P. W. et al. (2016) "Protein-retention expansion microscopy of cells and tissues labeled using standard fluorescent proteins and antibodies," Nature Biotechnology. Nature Publishing Group, 34(9), pp. 987-992.
Tinevez, J.-Y. et al. (2017) "TrackMate: An open and extensible platform for single-particle tracking," Methods. Academic Press, 115, pp. 80-90.
Tripet,B. et al. (1996) "Engineering a de nova-designed coiled-coil heterodimerization domain for the rapid detection, purification and characterization of recombinantly expressed peptides and proteins," "Protein Engineering, Design and Selection." Oxford University Press, 9(11), pp. 1029-1042.
Trudeau,L. E., Emery, D. G. and Haydon, P. G. (1996) "Direct Modulation of the Secretory Machinery Underlies PKA-dependent Synaptic Facilitation in Hippocampal Neurons," Neuron, 17(4), pp. 789-797.

(56) References Cited

OTHER PUBLICATIONS

Van Der Zee, E. A and Douma, B. R. K. (1997) "Historical review of research on protein kinase C in learning and memory," Progress in Neuro-Psychopharmacology and Biological Psychiatry. Elsevier Inc., 21(3), pp. 379-406.
Vay, L. et al. (2007) "Modulation of Ca(2+) release and Ca(2+) oscillations in HeLa cells and fibroblasts by mitochondrial Ca(2+) uniporter stimulation.," The Journal of Physiology. Wiley-Blackwell, 580(Pt 1), pp. 39-49.
Vinkenborg, J. L. et al. (2009) "Imaging of Intracellular free Zn2t in real time using genetically-encodes FRET sensors" Nature Methods. Nature Publishing Group, 6(10), pp. 737-740.
Violin, J. D. et al. (2003) "A genetically encoded fluorescent reporter reveals oscillatory phosphorylation by protein kinase C.," The Journal of Cell Biology, 161(5), pp. 899-909.
Viswanathan, S. et al. (2015) "High-performance probes for light and electron microscopy," Nature Methods. Nature Publishing Group, 12(6), pp. 568-576.
Waltereit, R. and Weller, M. (2003) "Signaling from cAMP/PKA to MAPK and synaptic plasticity," Molecular Neurobiology. Humana Press, 27(1), pp. 99-106.
Wang, G. et al. (2006) "Identification of genes targeted by the androgen and PKA signaling pathways in prostate cancer cells," Oncogene, 25(55), pp. 7311-7323.
Wang, H. and Zhuo, M. (2012) "Group I metabotropic glutamate receptor-mediated gene transcription and implications for synaptic plasticity and diseases," Frontiers in Pharmacology, Nov. 3, p. 1-8.
Weighert, M. et al. (2019) "Star-convex Polyhedra for 3D Object Detection and Segmentation in Microscopy." p. 3666-3673.
Williams, M. R. et al. (2001) "Role of the endoplasmic reticulum in shaping calcium dynamics in human lens cells," Investigative ophthalmology & visual science, 42(5), pp. 1009-1017.
Wilson, I. A. et al. (1984) "The structure of an antigenic determinant in a protein." Cell, 37(3), pp. 767-778.
Wong, ST et al. (1999) "Calcium-stimulated adenylyl cyclase activity is critical for hippocampus-dependent long-term memory and late phase LTP.," Neuron, 23(4), pp. 787-798.
Wozny, C. et al. (2008) "Differential cAMP Signaling at Hippocampal Output Synapses." p. 14358-14362.
Wroblewska A et al. (2018) "Protein Barcodes Enable High-Dimensional Single-Cell CRISPR Screens," Cell. Elsevier, 175(4), p. 1141-1155.
Wu, B. et al. (2015) "Synonymous modification results in high-fidelity gene expression of repetitive protein and nucleotide sequences.," Genes & development. Cold Spring Harbor Laboratory Press, 29(8), pp. 876-886.
Wu, B. et al. (2016) "Translation dynamics of single mRNAs in live cells and neurons.," Science (New York, NY). American Association for the Advancement of Science, 352(6292), pp. 1430-1435.
Wu, B., Chao, J. A and Singer, R.H. (2012) "Fluorescence Fluctuation Spectroscopy Enables Quantitative Imaging of Single mRNAs in Living Cells," Biophysical Journal, 102(12), pp. 2936-2944.
Zaccai, N. R. et al. (2011) "A de novo peptide hexamer with a mutable channel," Nature Chemical Biology, 7(12), pp. 935-941.
Zanassi, P. et al. (2001) "CAMP-dependent protein kinase induces cAMP-response element-binding protein phosphorylation via an intracellular calcium release/ERK-dependent pathway in striatal neurons.," The Journal of biological chemistry. American Society for Biochemistry and Molecular Biology, 276(15), pp. 11487-11495.
Zhang, Q. et al. (2018) "Visualizing Dynamics of Cell Signaling In Vivo with a Phase Separation-Based Kinase Reporter.," Molecular Cell. NIH Public Access, 69(2), pp. 334-346.

\* cited by examiner

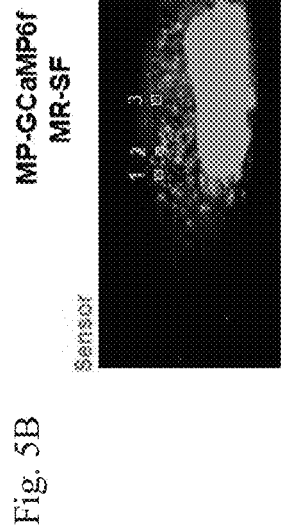
Fig. 5A
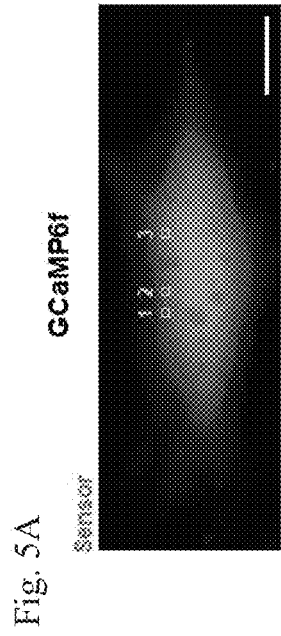
Fig. 5C
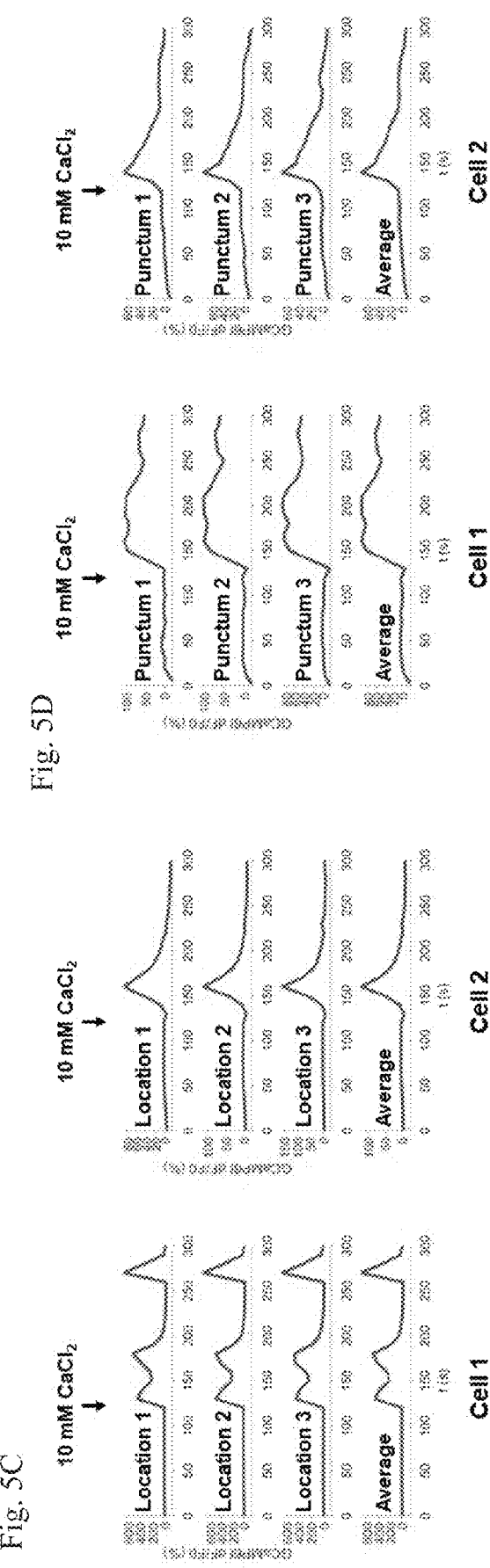
Fig. 5B
Fig. 5D

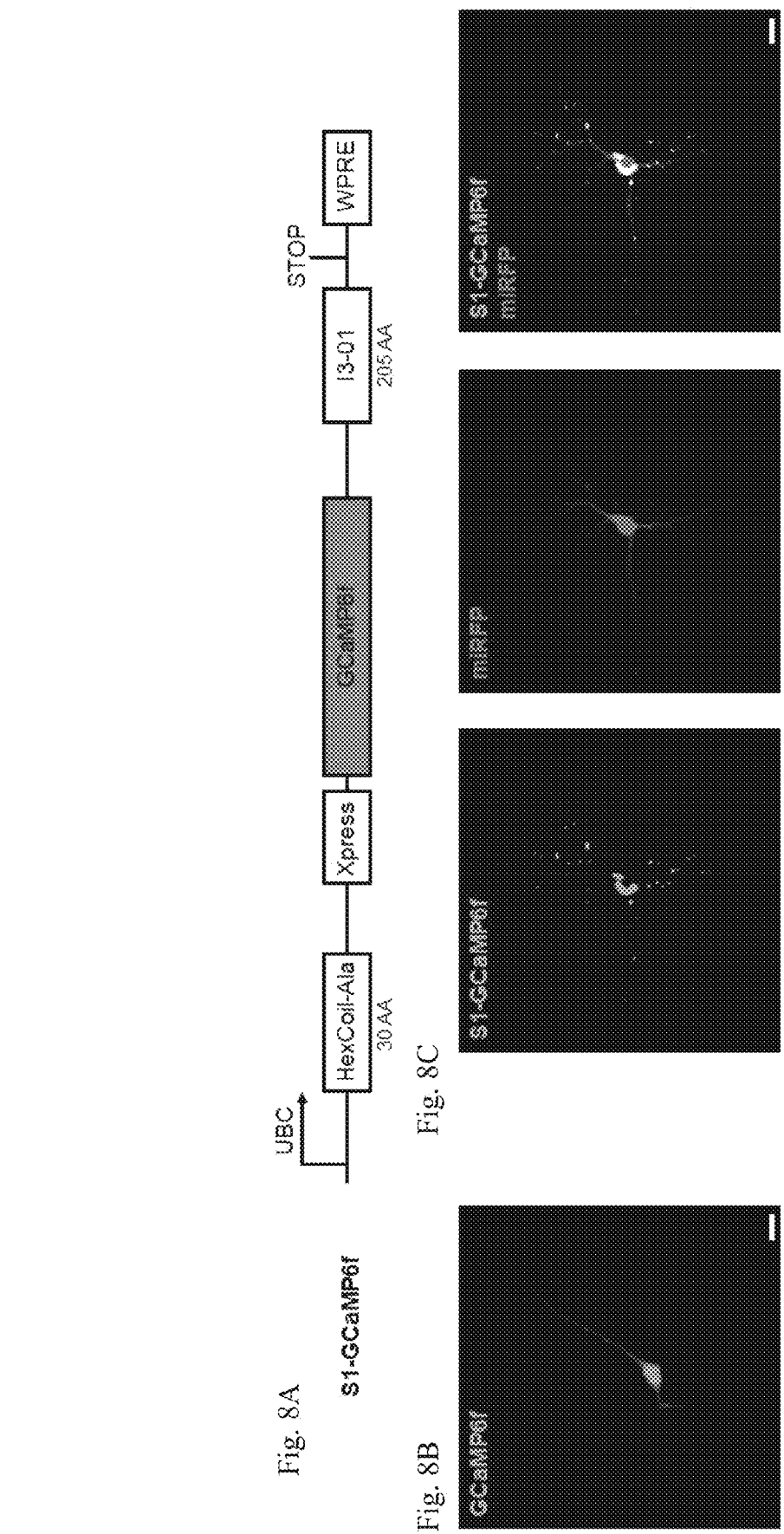

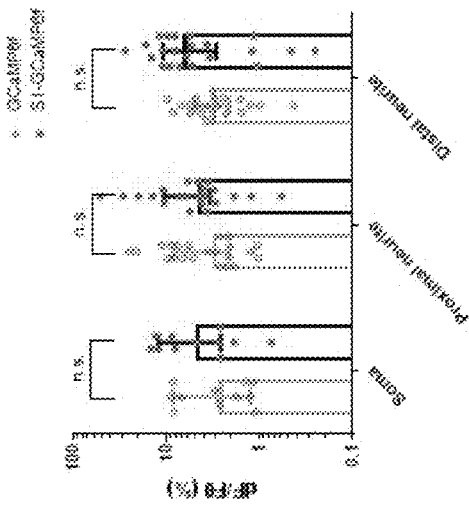
Fig. 8D
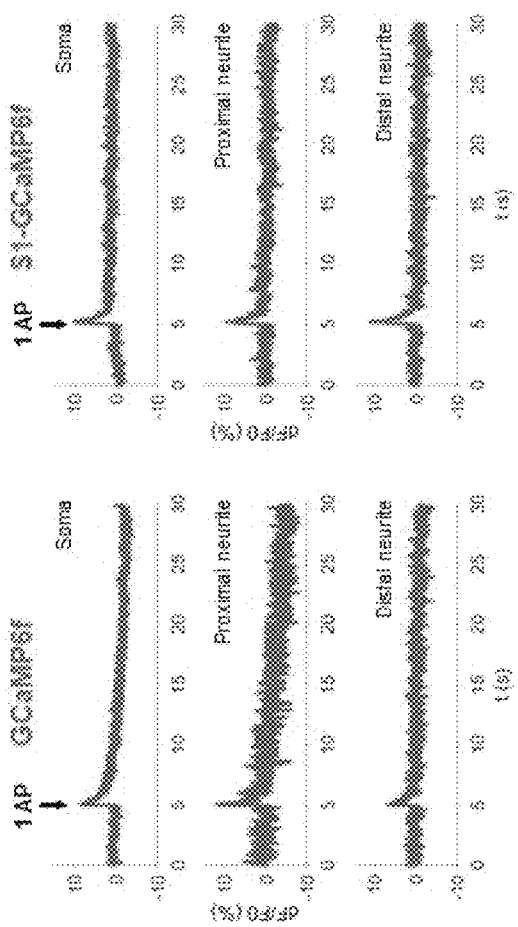
Fig. 8E
Fig. 8F
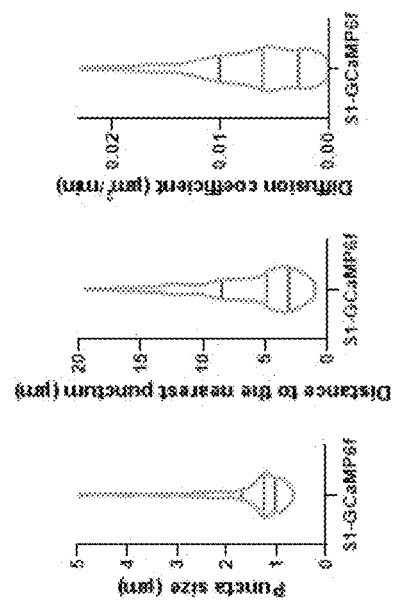
Fig. 8G
Fig. 8H
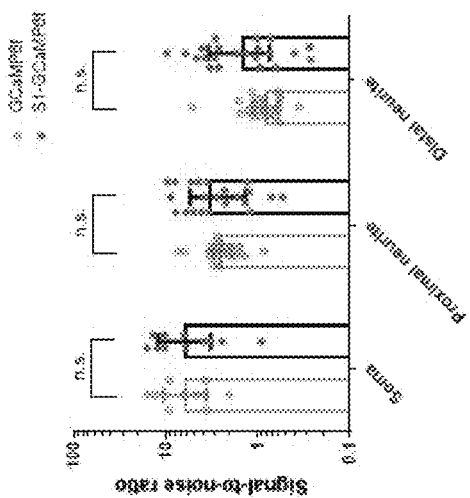

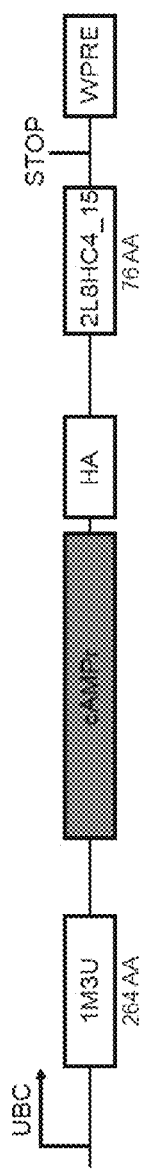
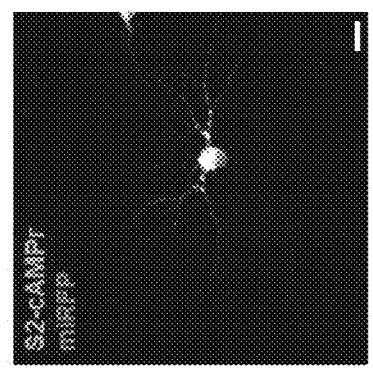
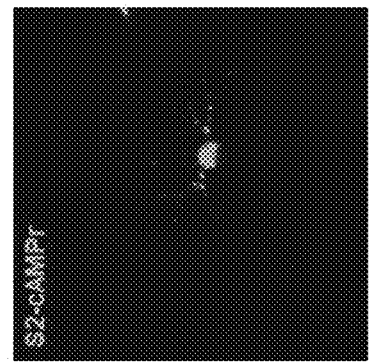
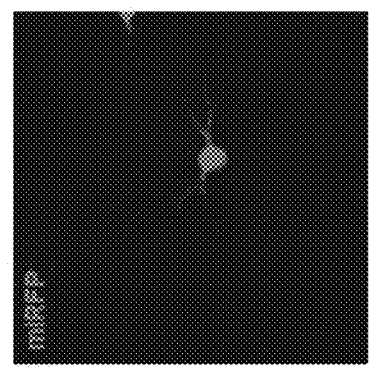
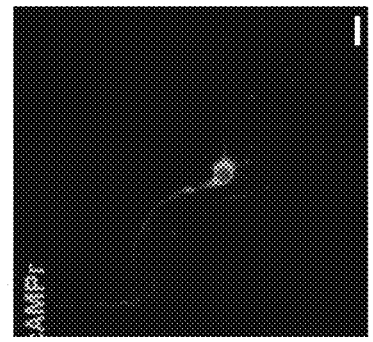
Fig. 8I S2-cAMPr
Fig. 8J
Fig. 8K

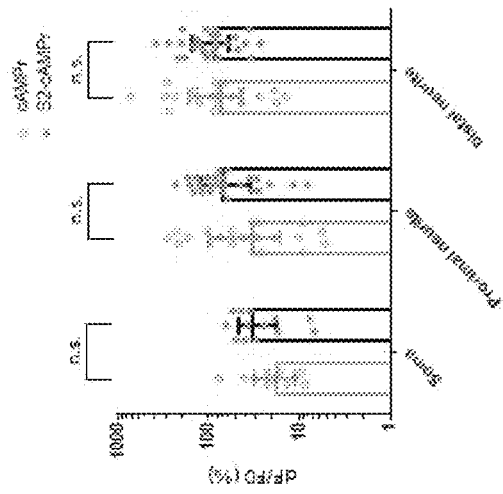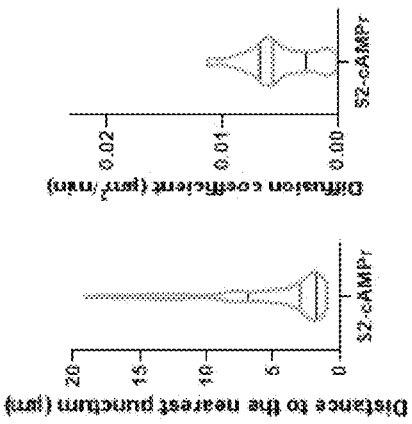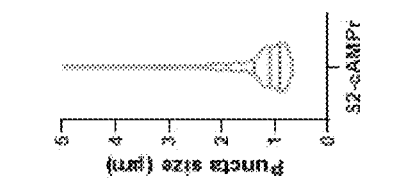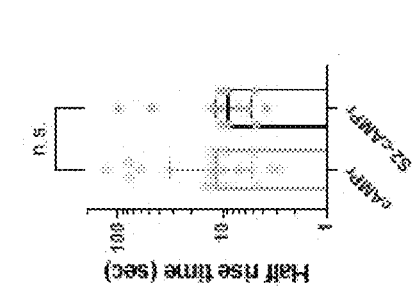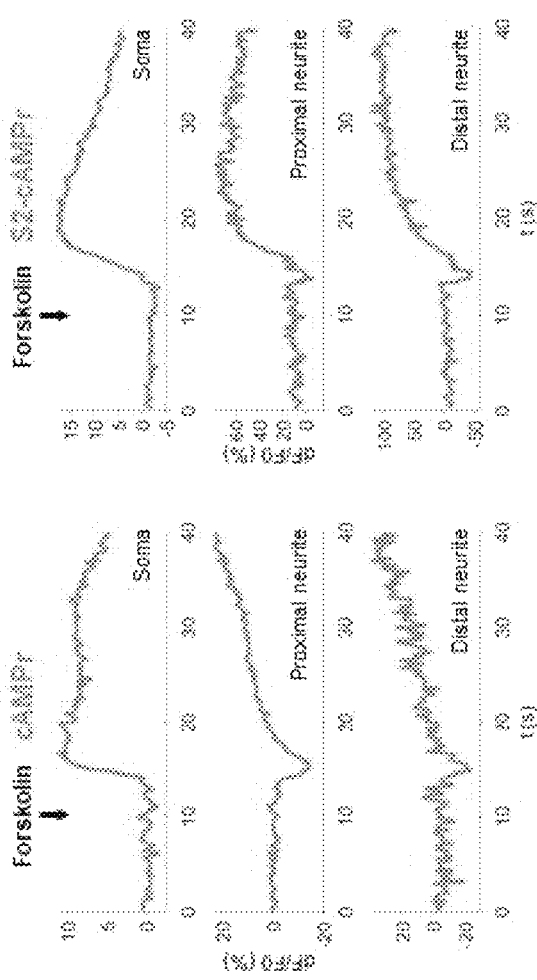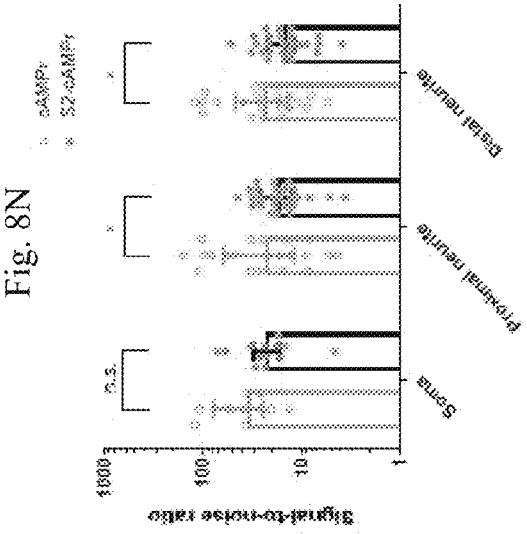

Fig. 8Q S3-ExRaiAKAR

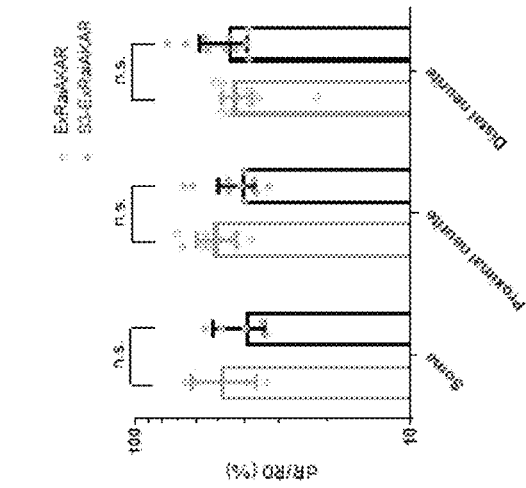
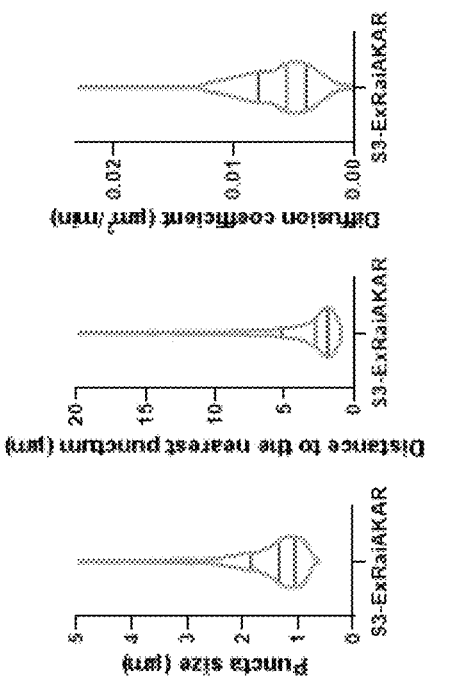
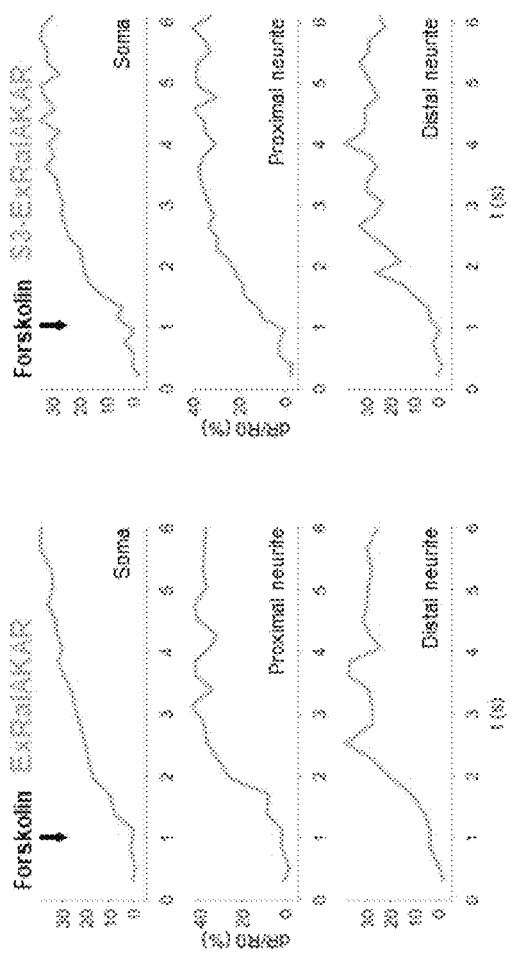
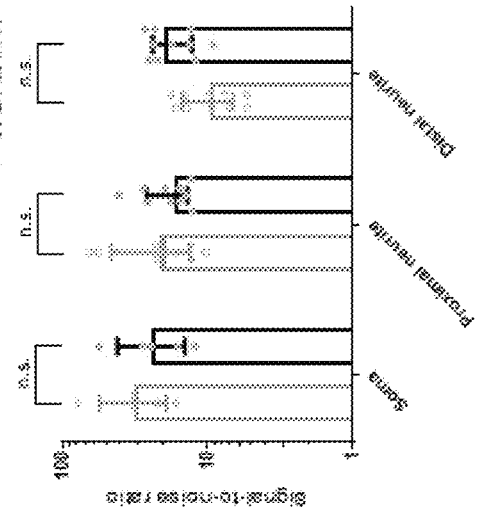

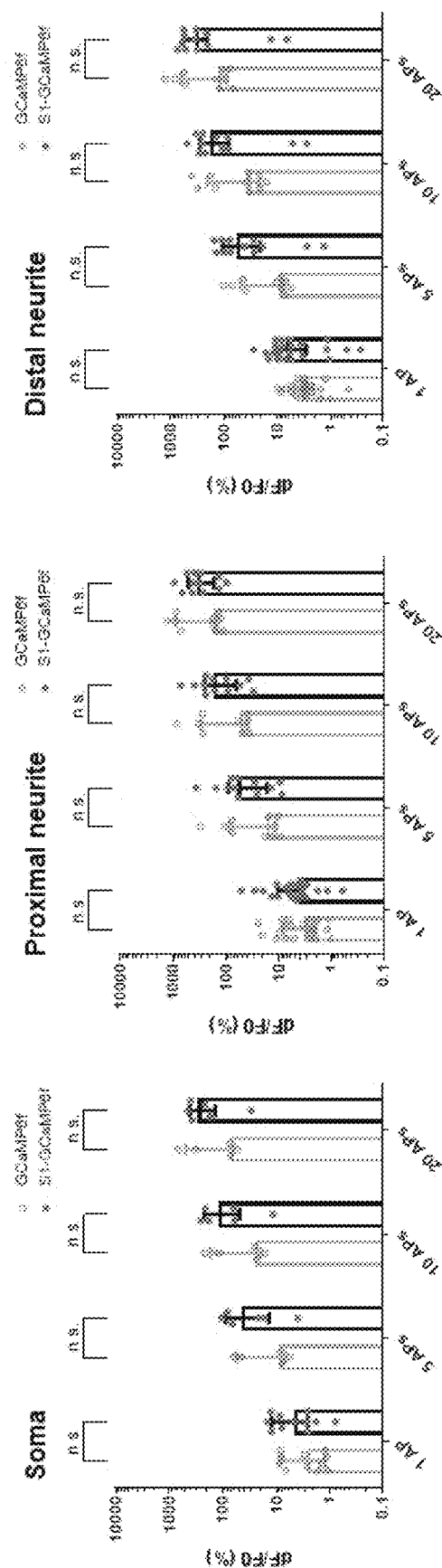
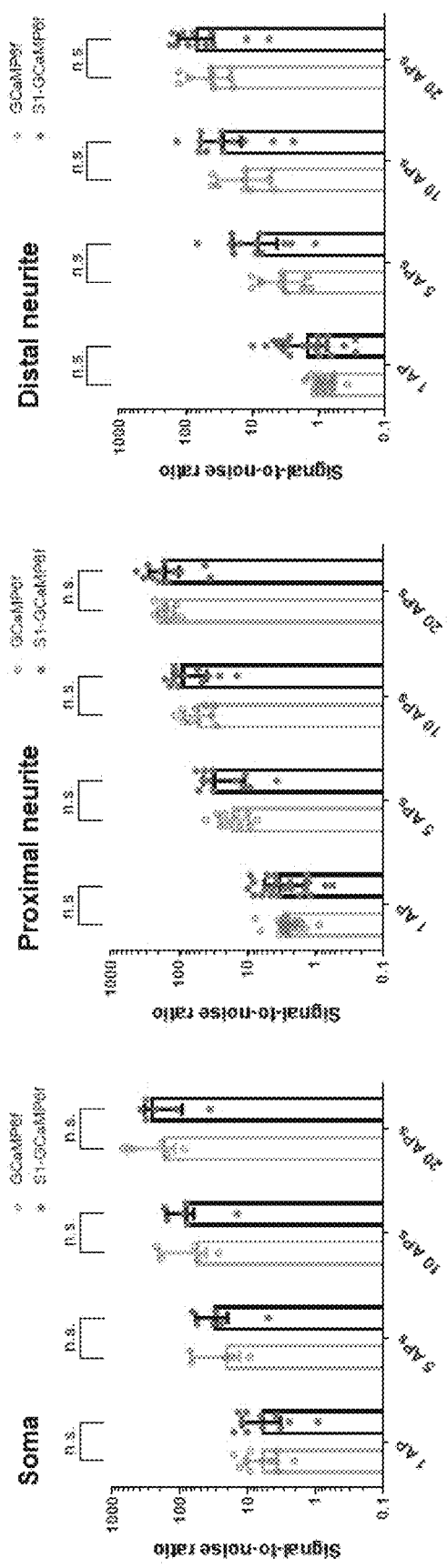
Fig. 9C
Fig. 9D

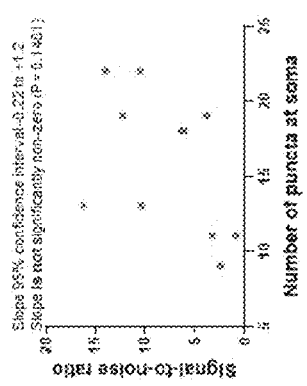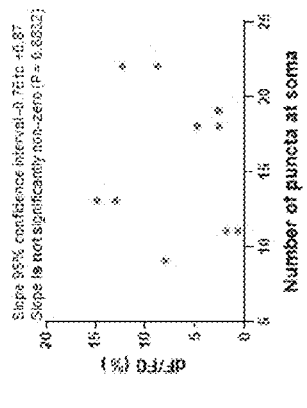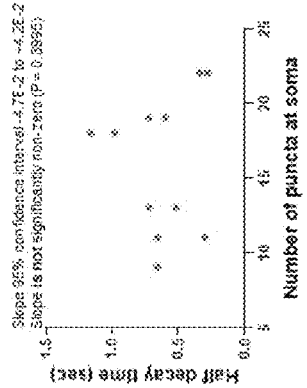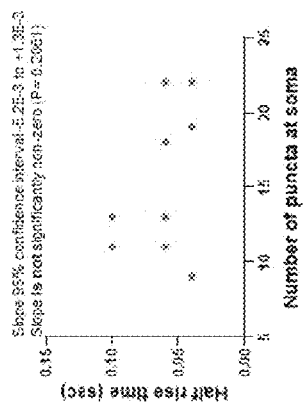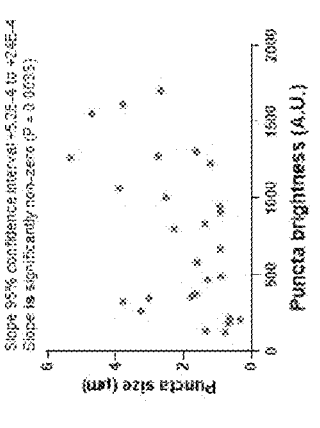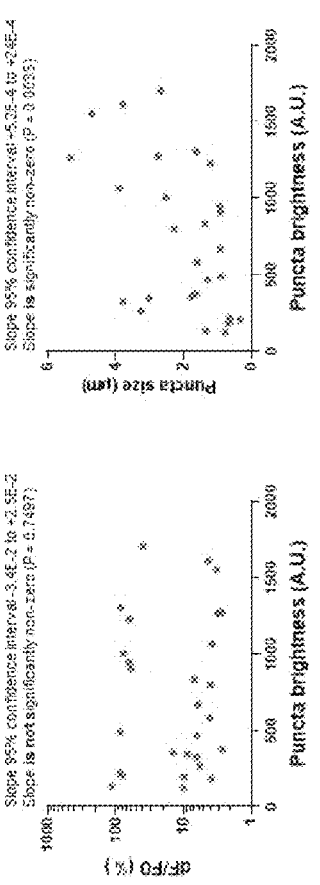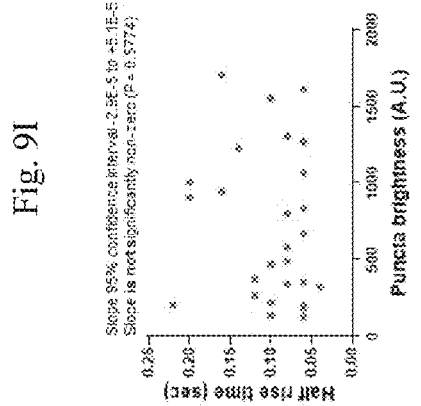

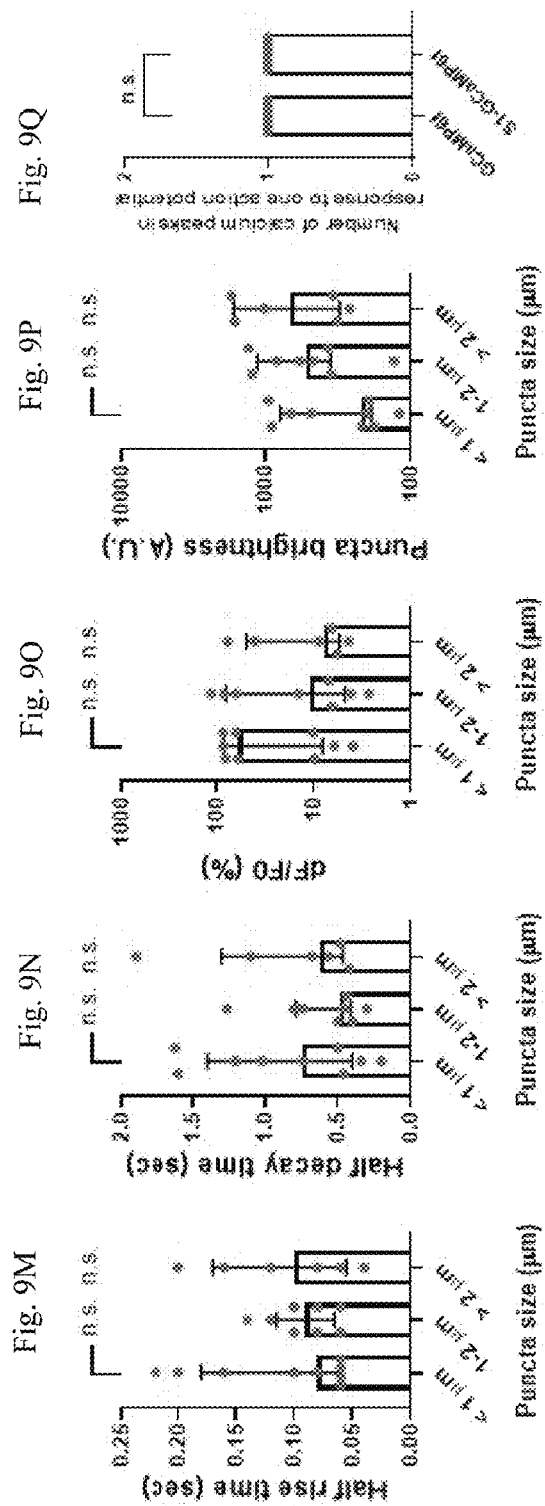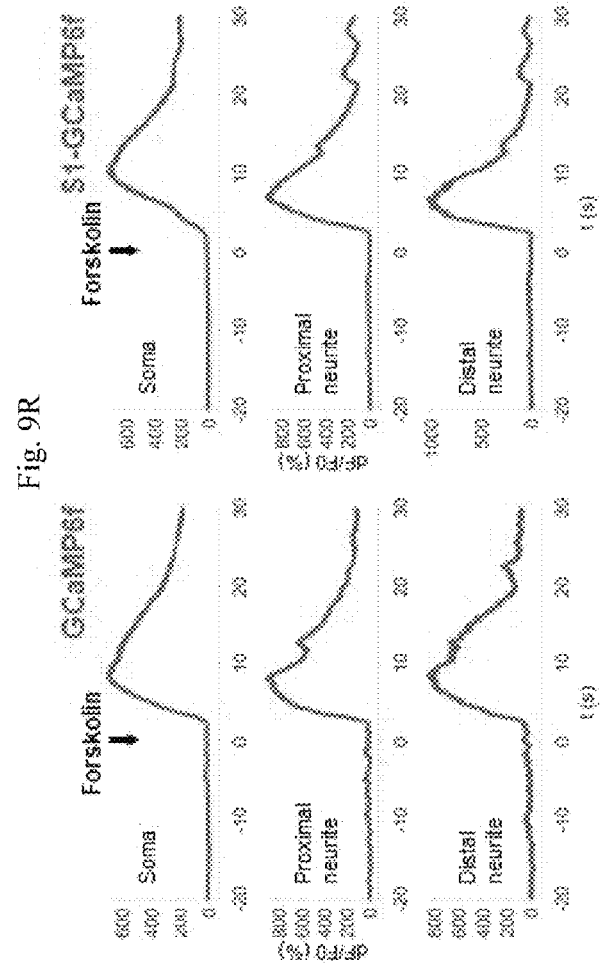

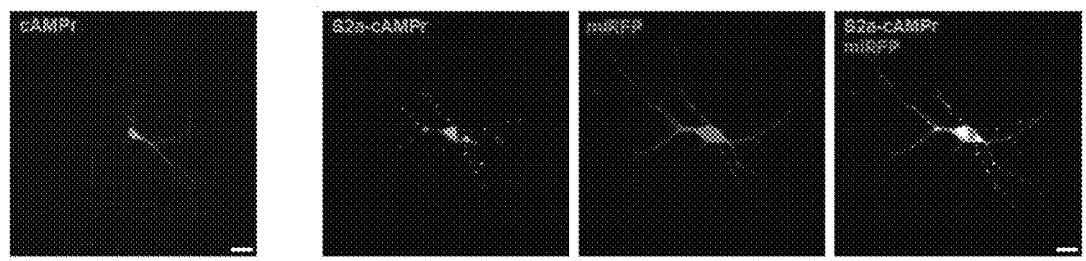
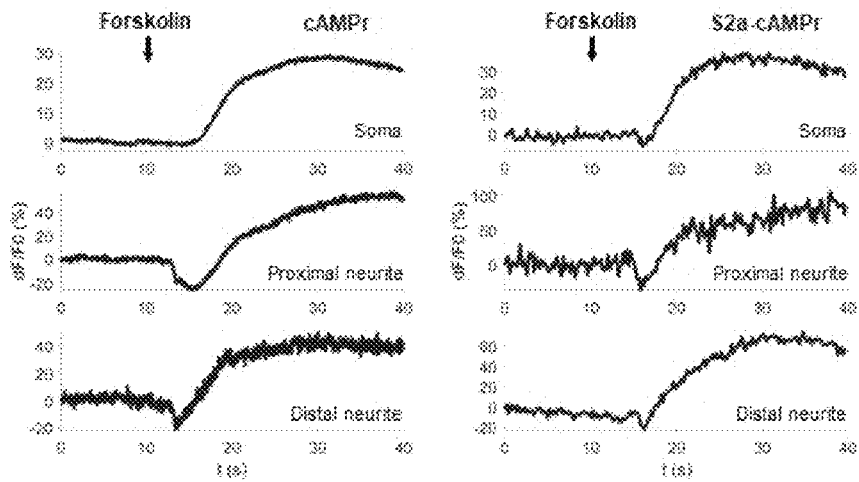
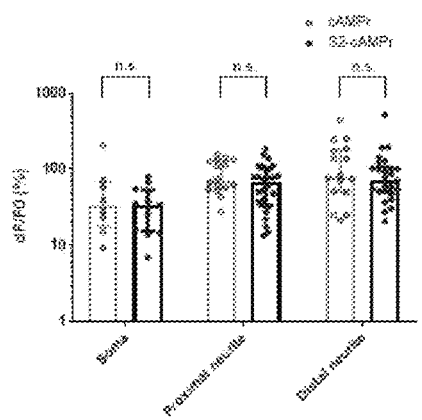
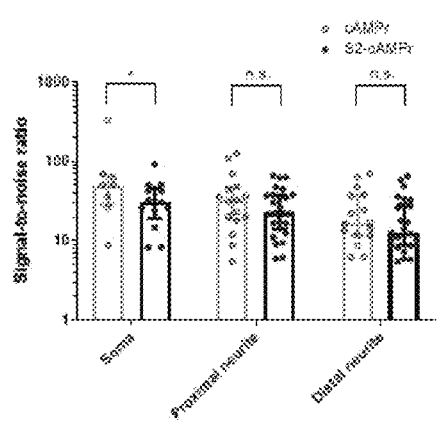
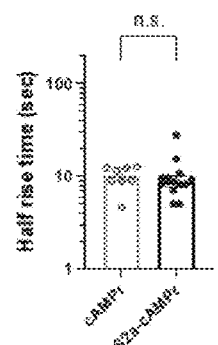

Fig. 13B                    Fig. 13C

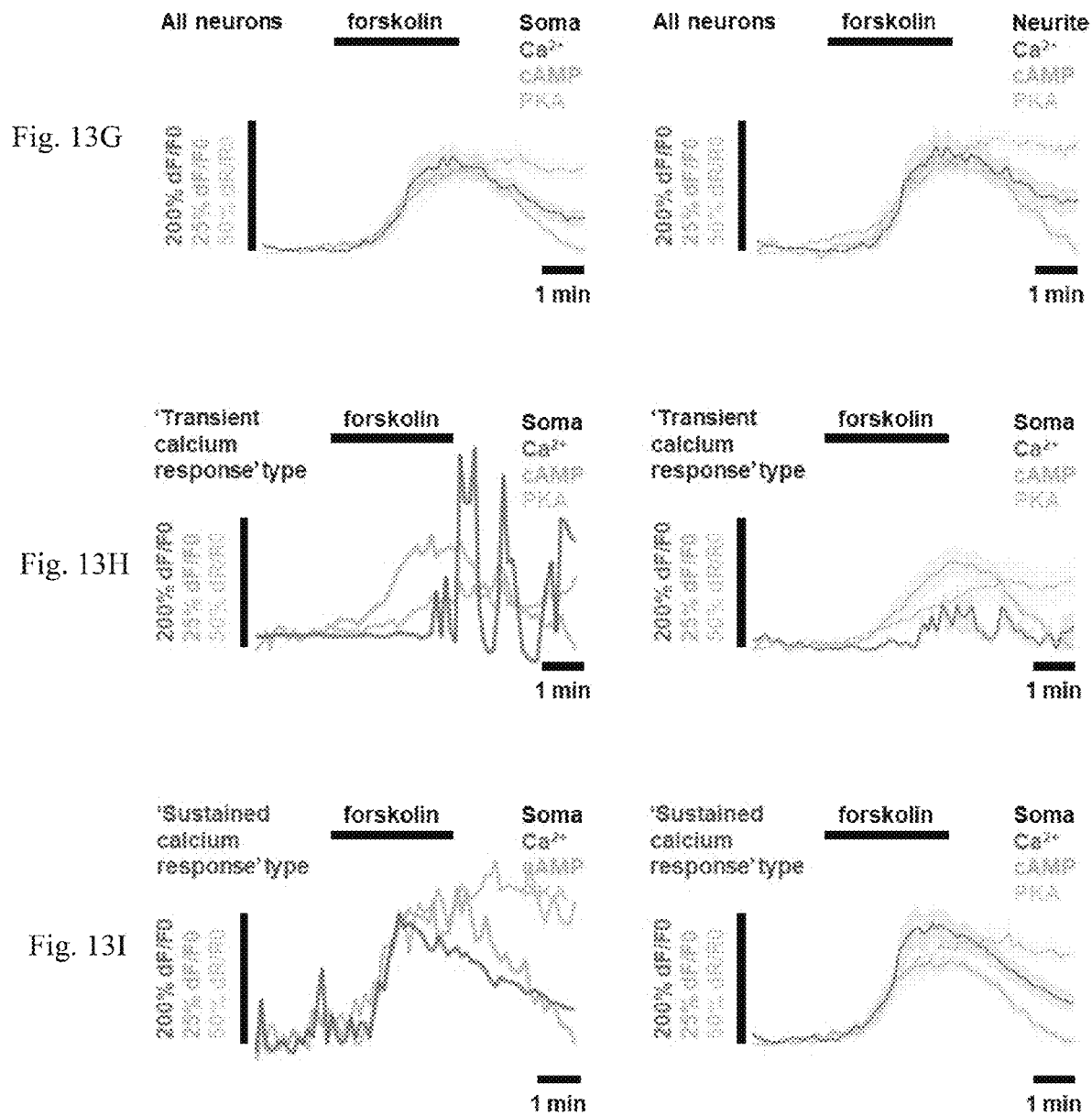

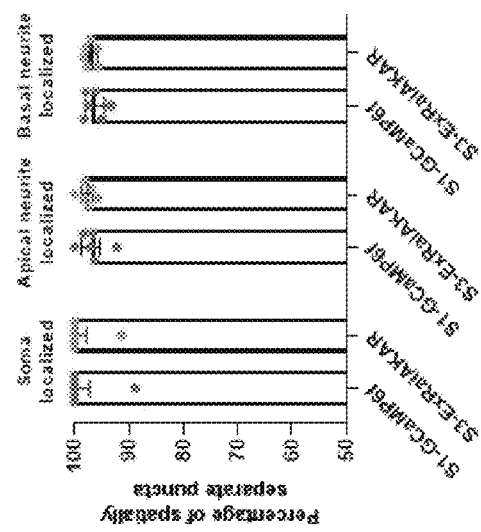
Fig. 14E
Fig. 14D
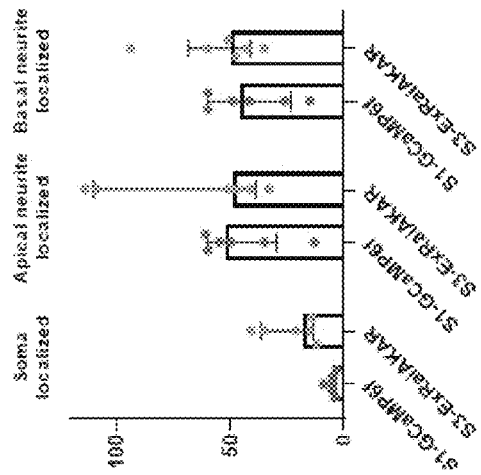
Fig. 14F

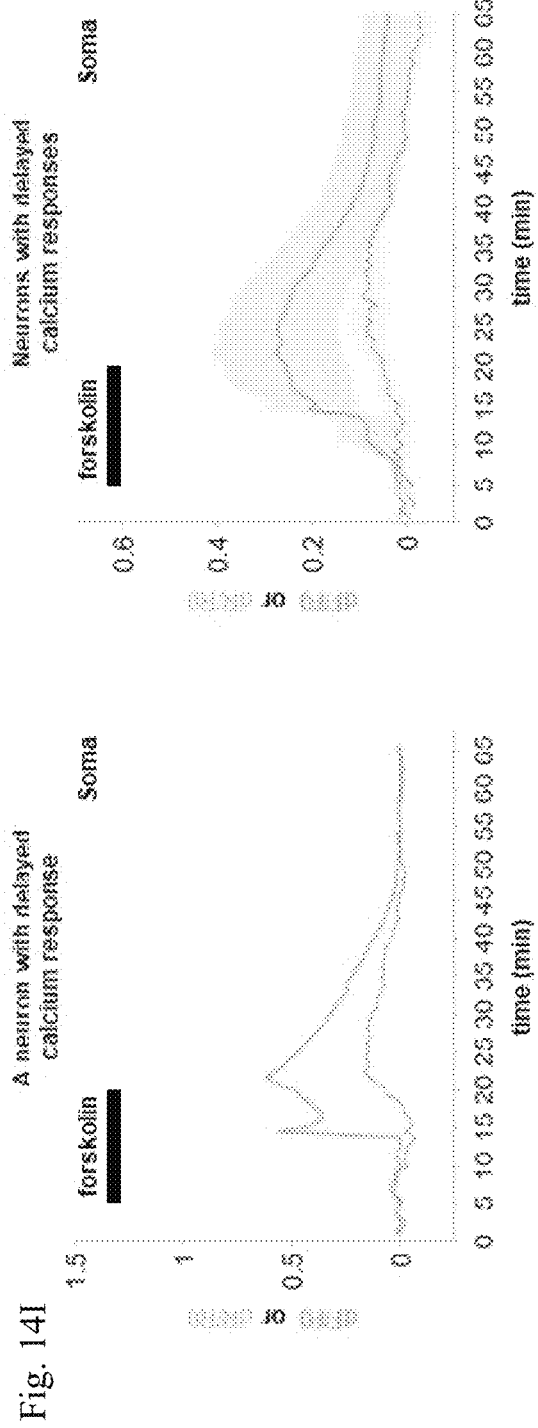
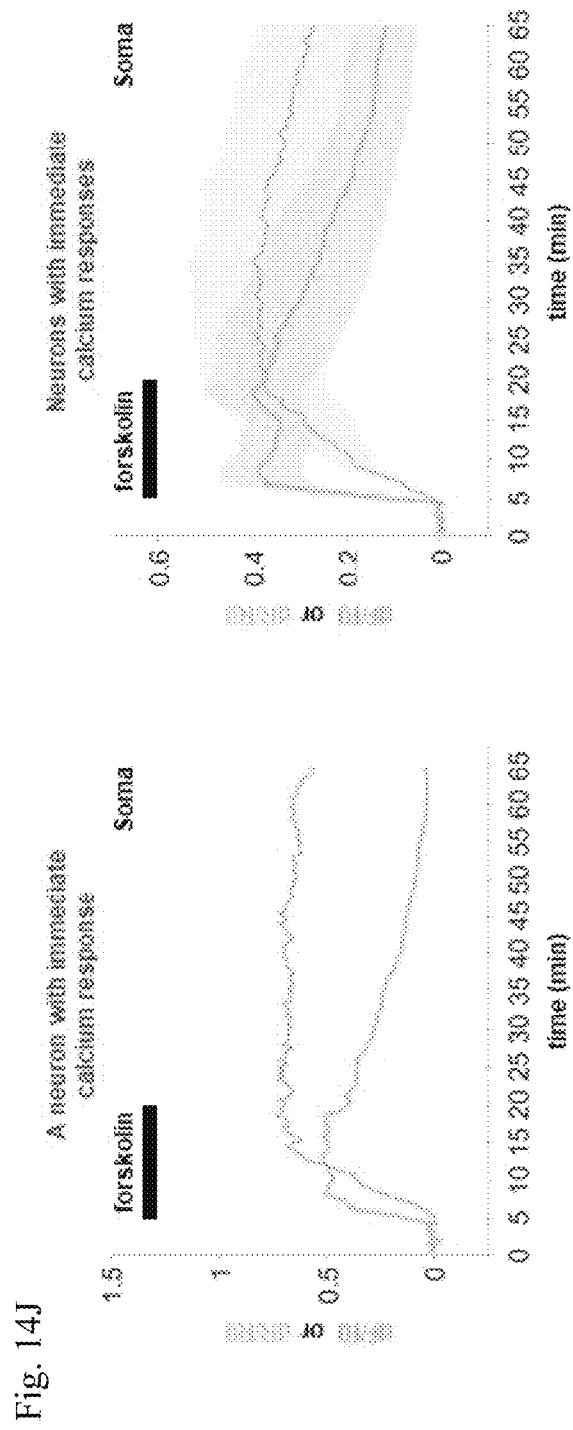
Fig. 14I
Fig. 14J

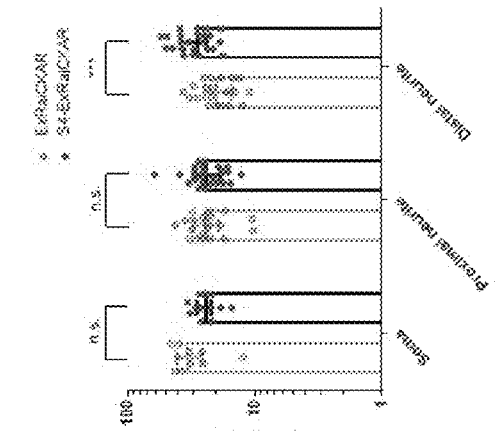
Fig. 15D
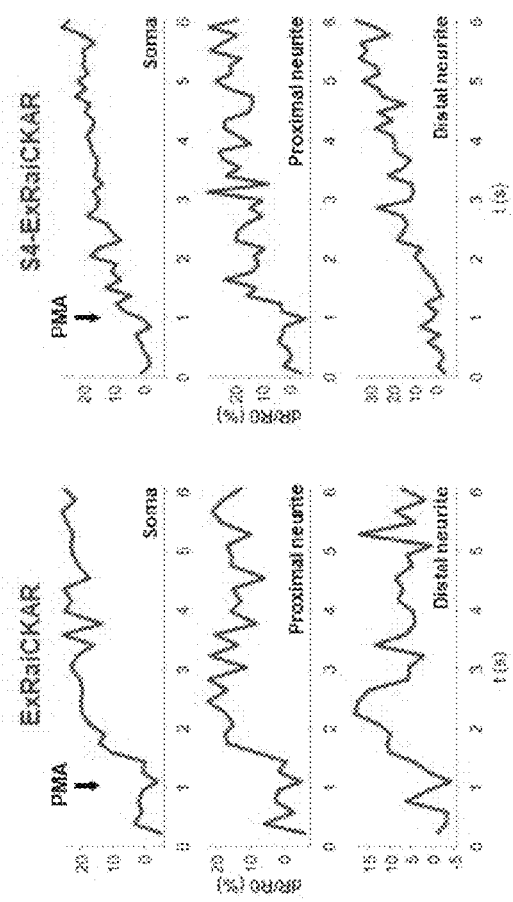
Fig. 15E
Fig. 15F
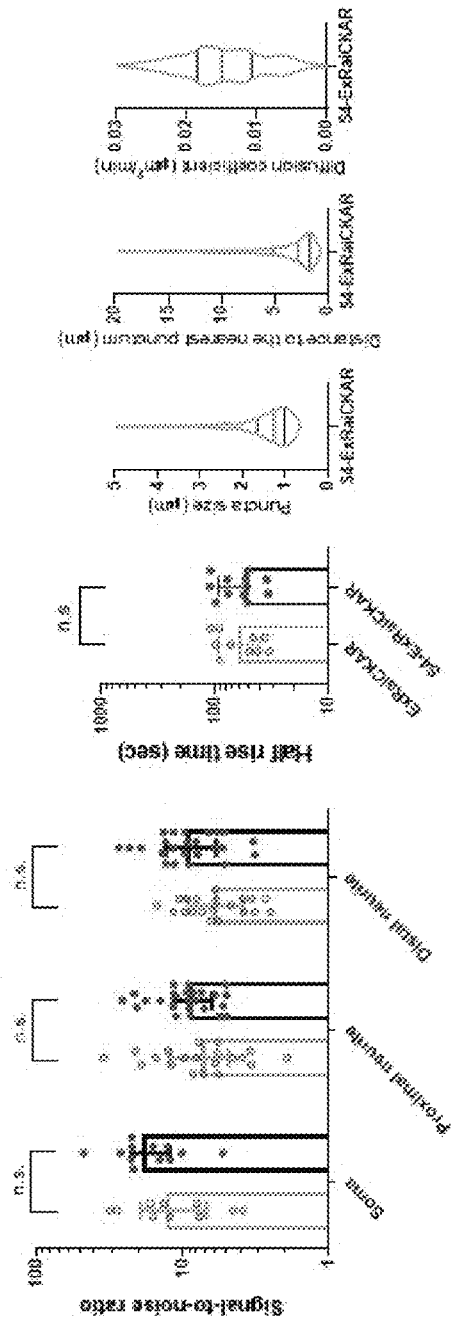
Fig. 15G
Fig. 15H

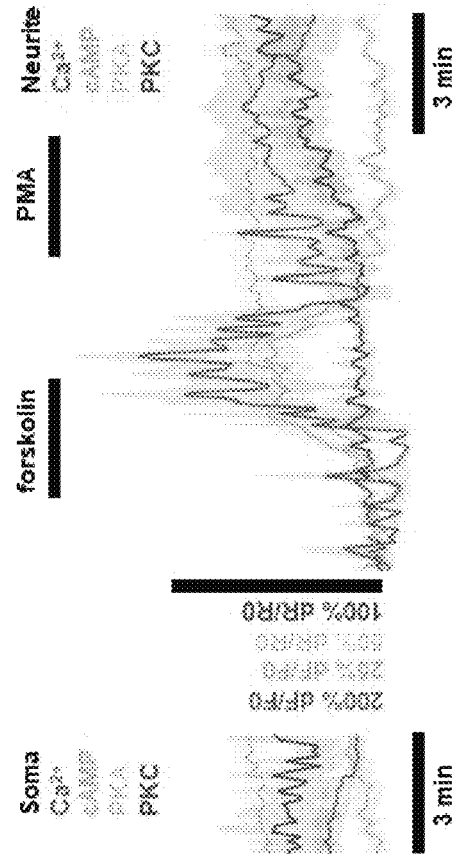
Fig. 15M
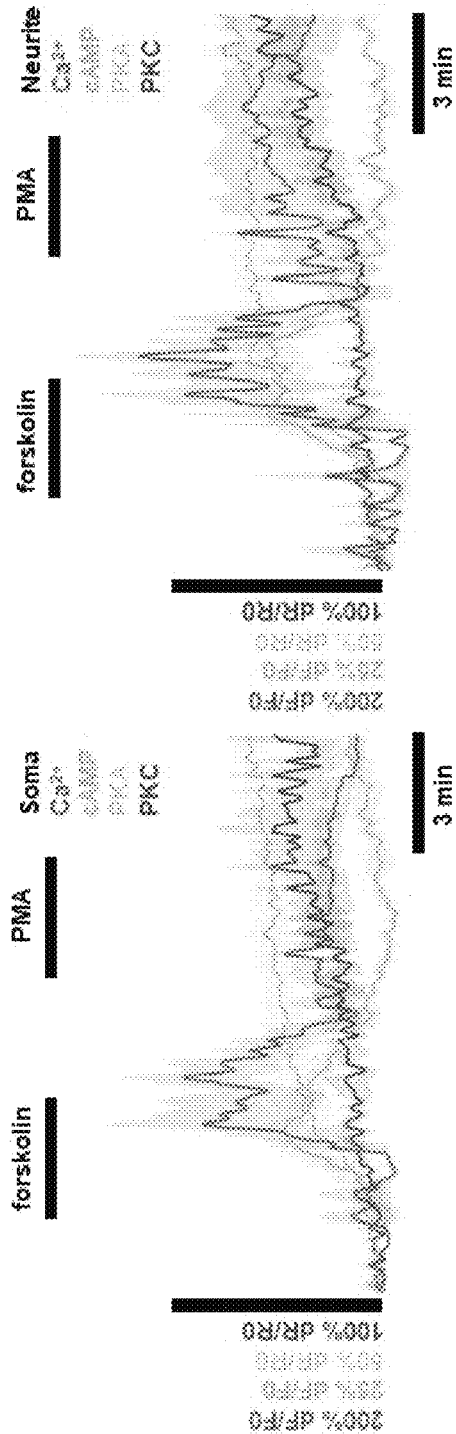
Fig. 15N
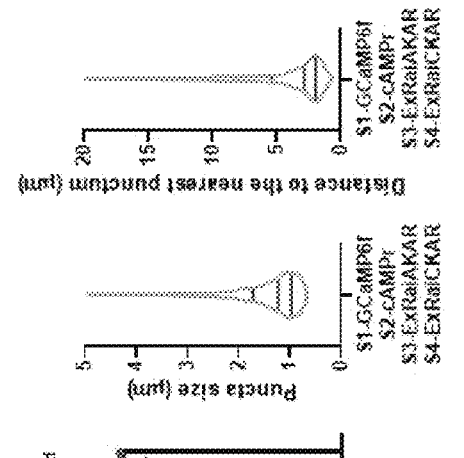
Fig. 15Q
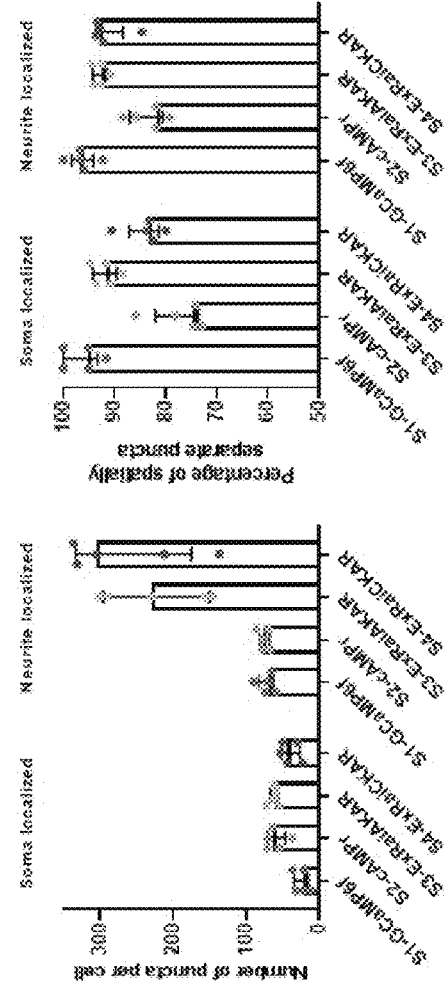
Fig. 15O
Fig. 15P

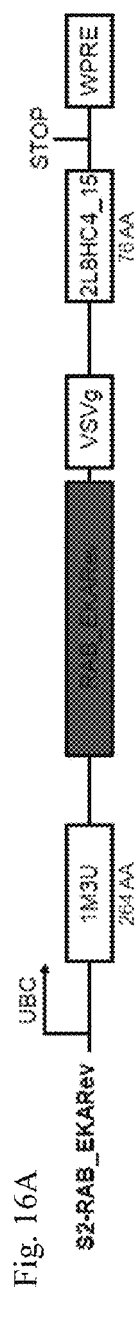
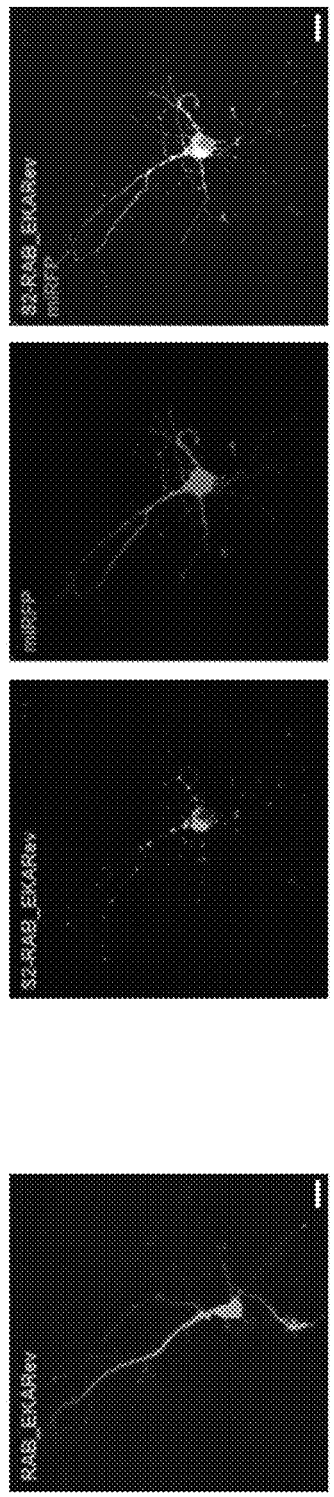
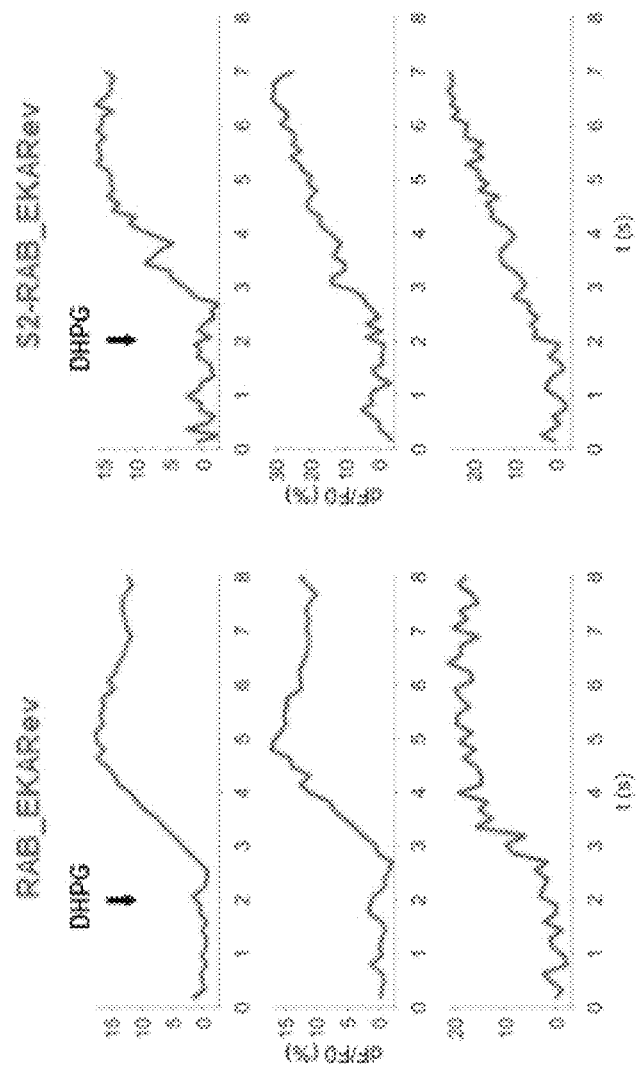
Fig. 16A
Fig. 16B
Fig. 16C
Fig. 16D

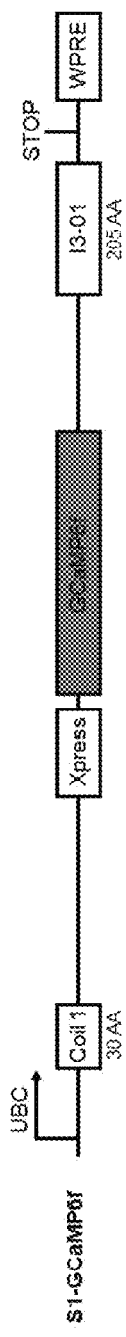
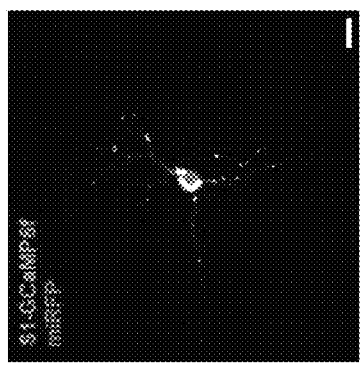
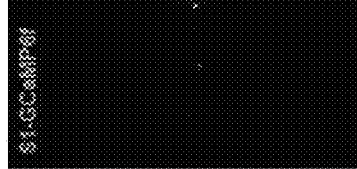
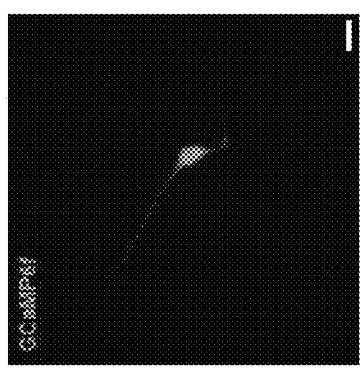
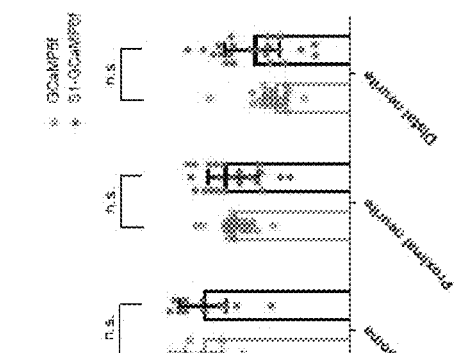
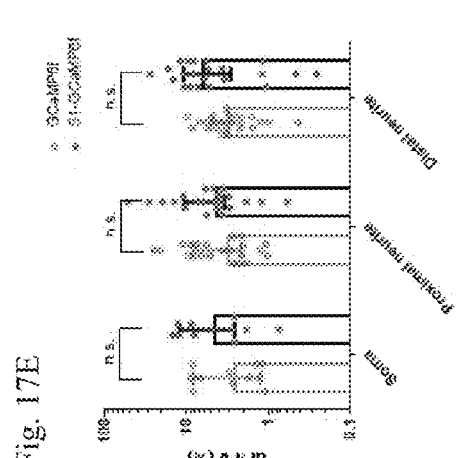
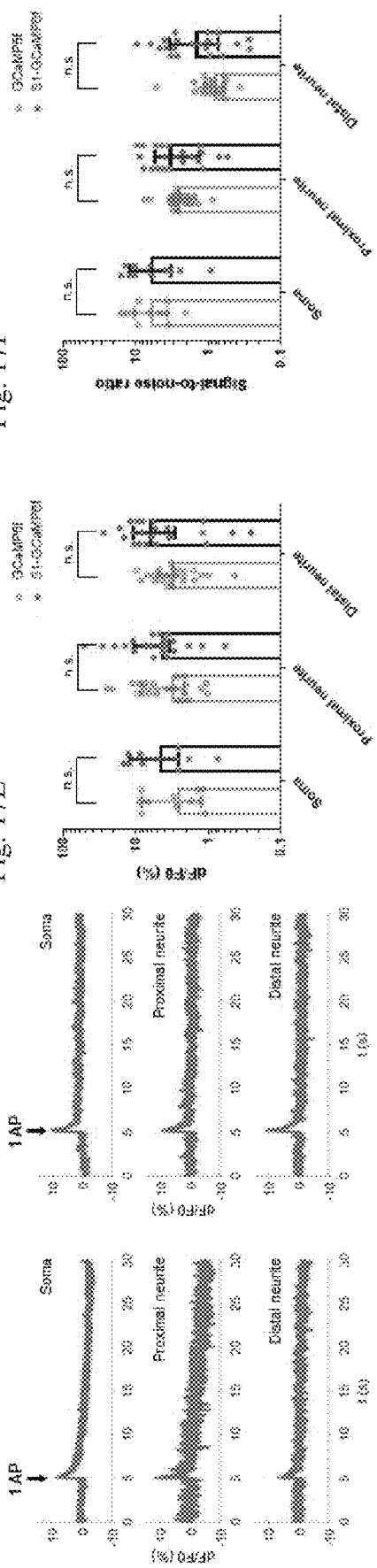

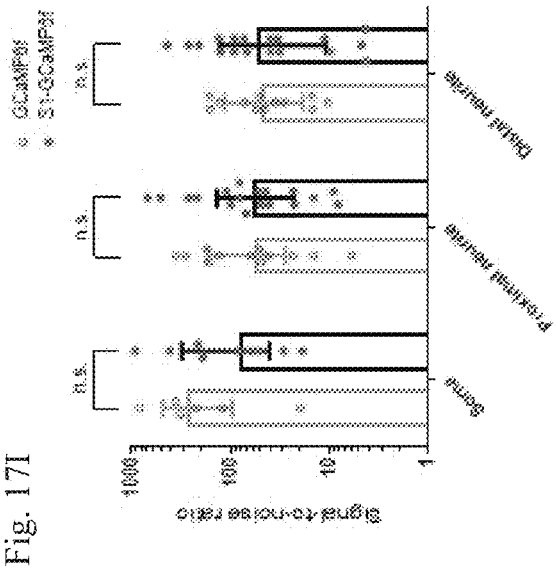
Fig. 17G
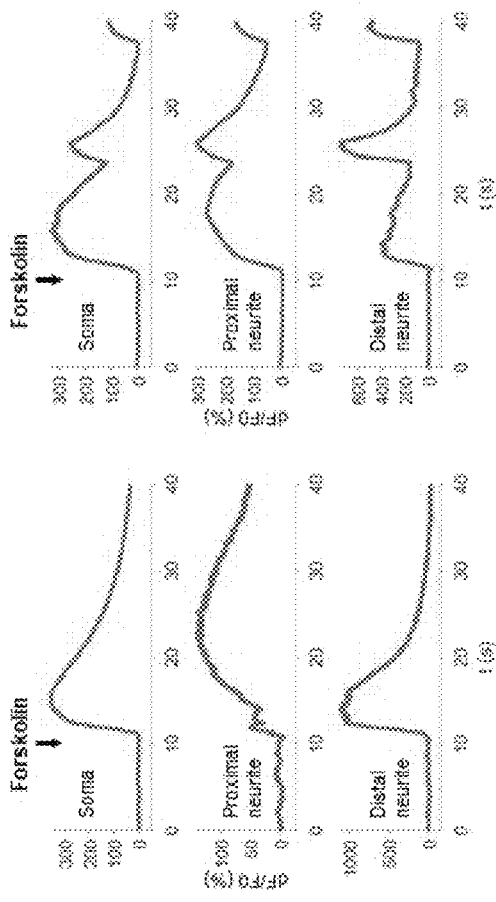
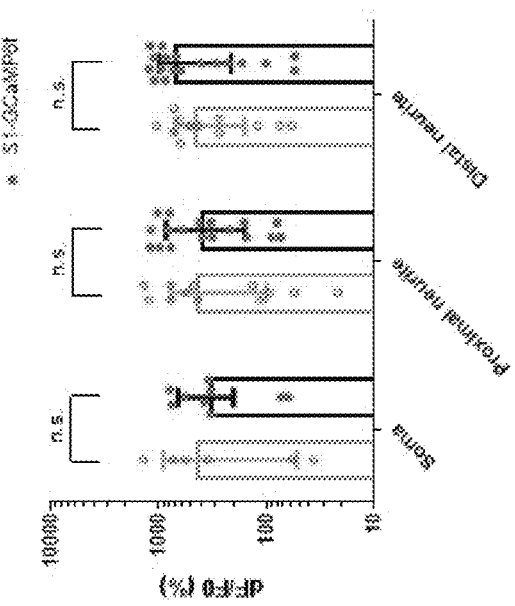
Fig. 17H
Fig. 17I

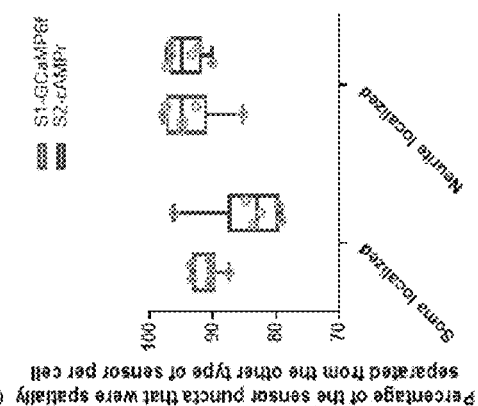
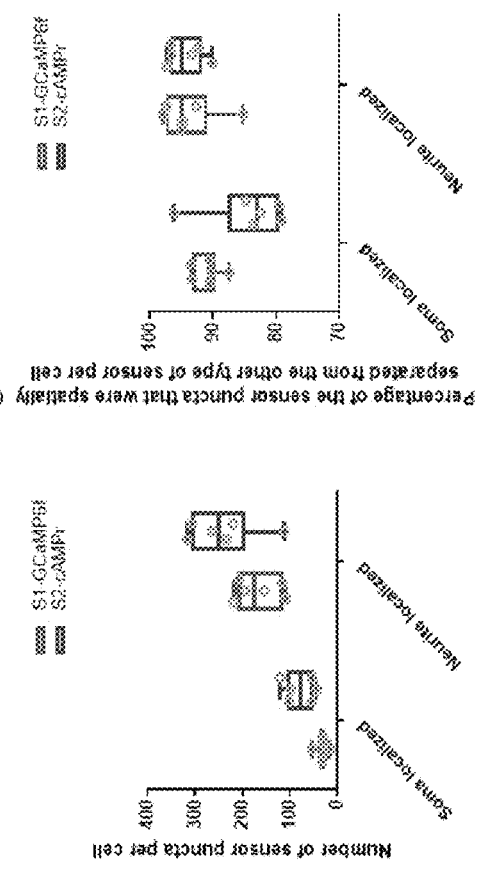
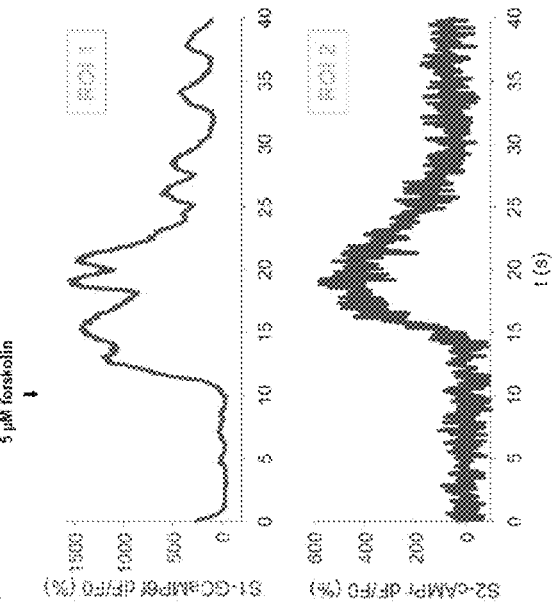
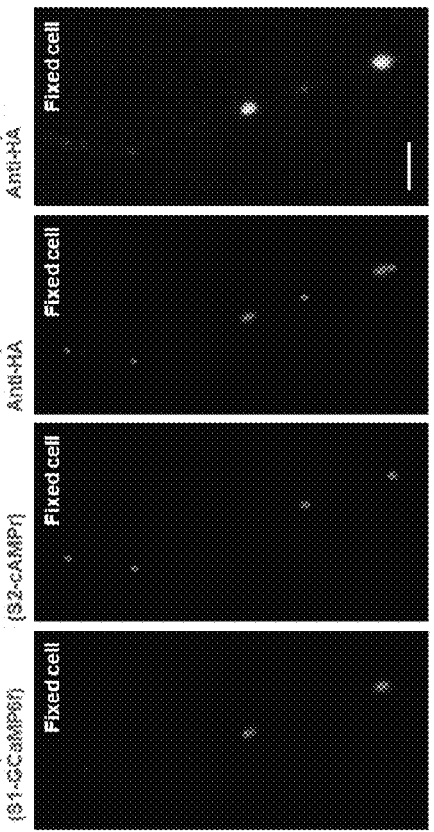
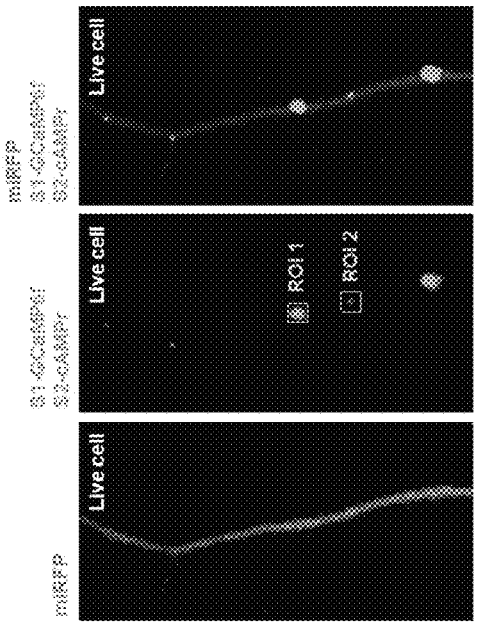

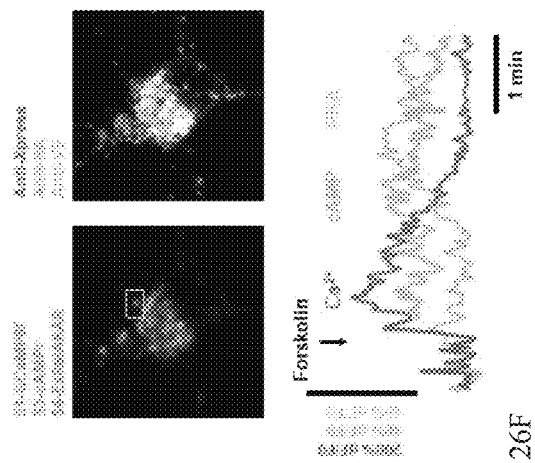
Fig. 26A  Fig. 26B  Fig. 26C
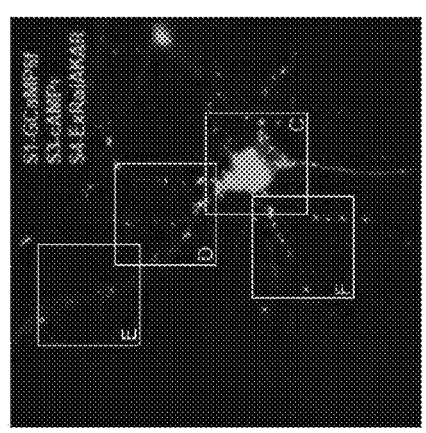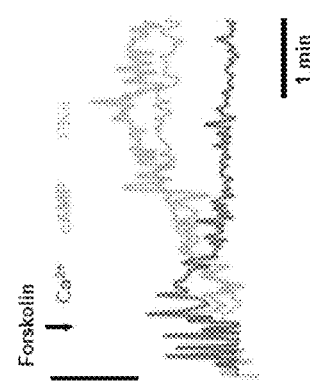
Fig. 26D  Fig. 26E  Fig. 26F
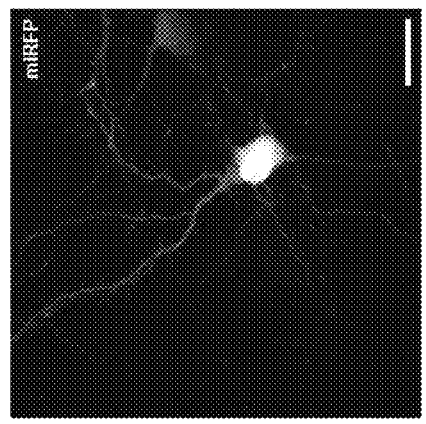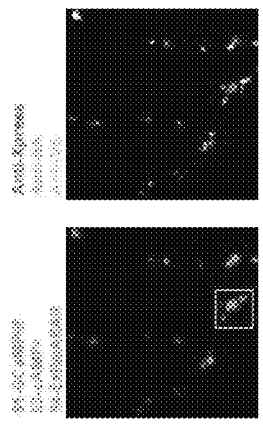

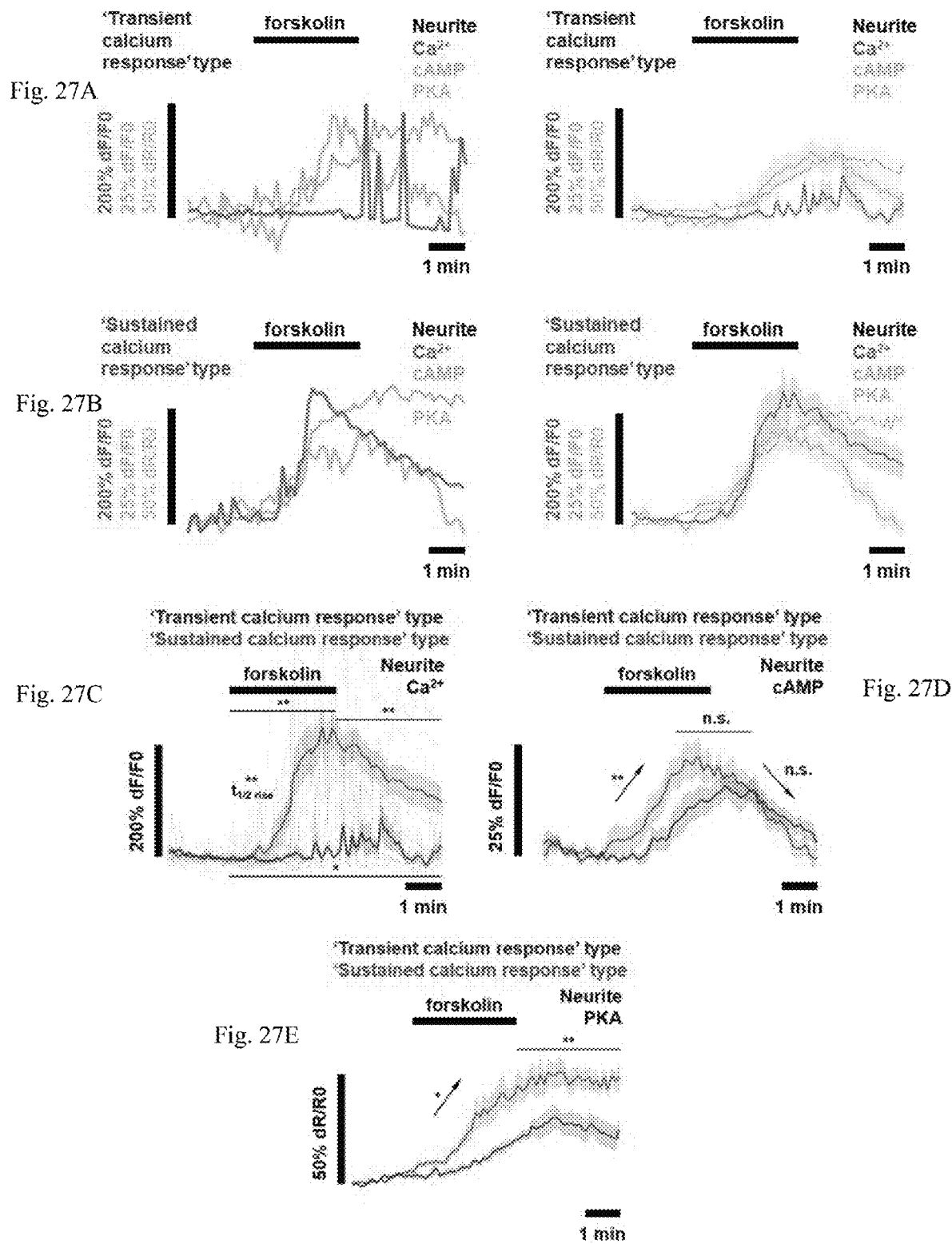

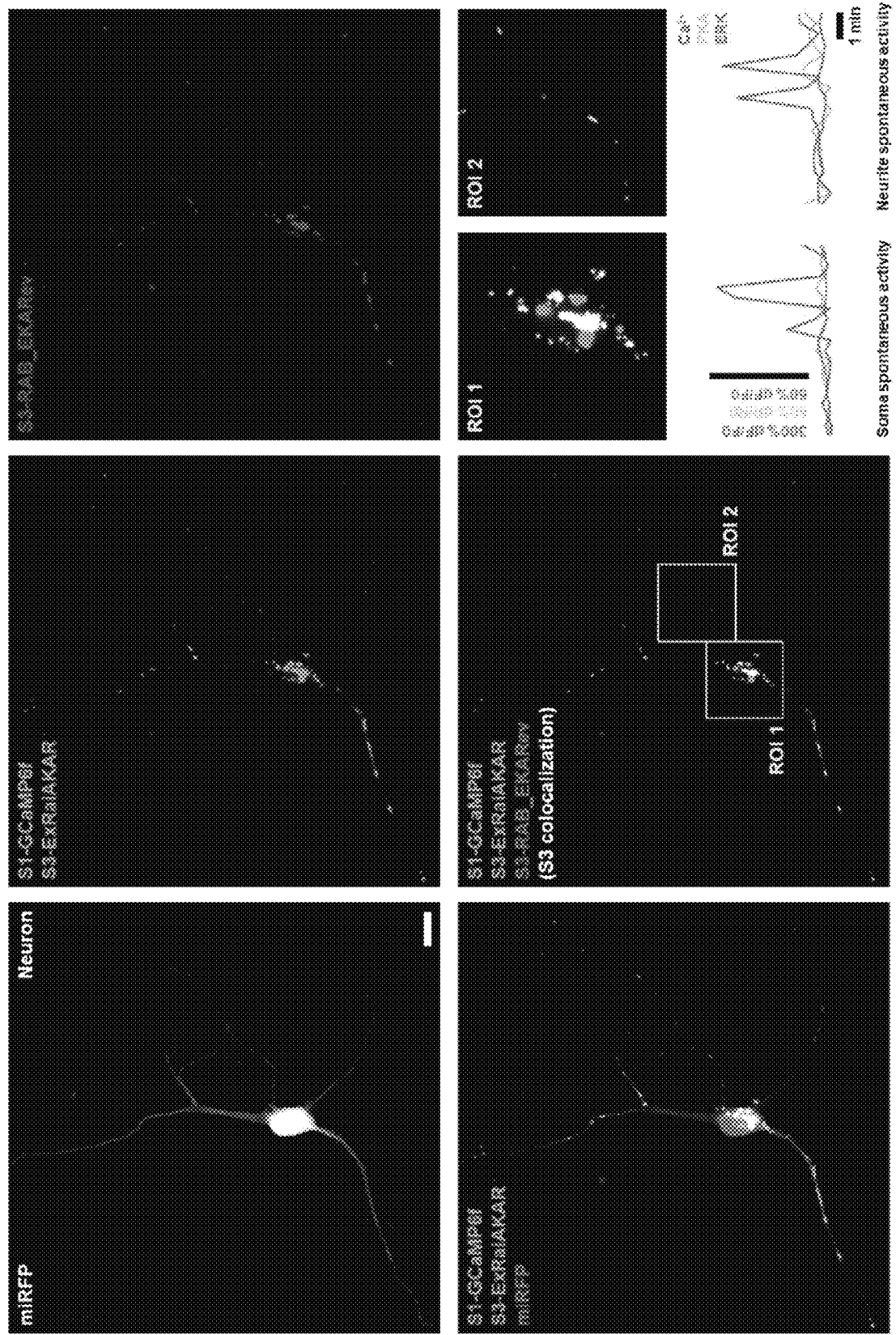

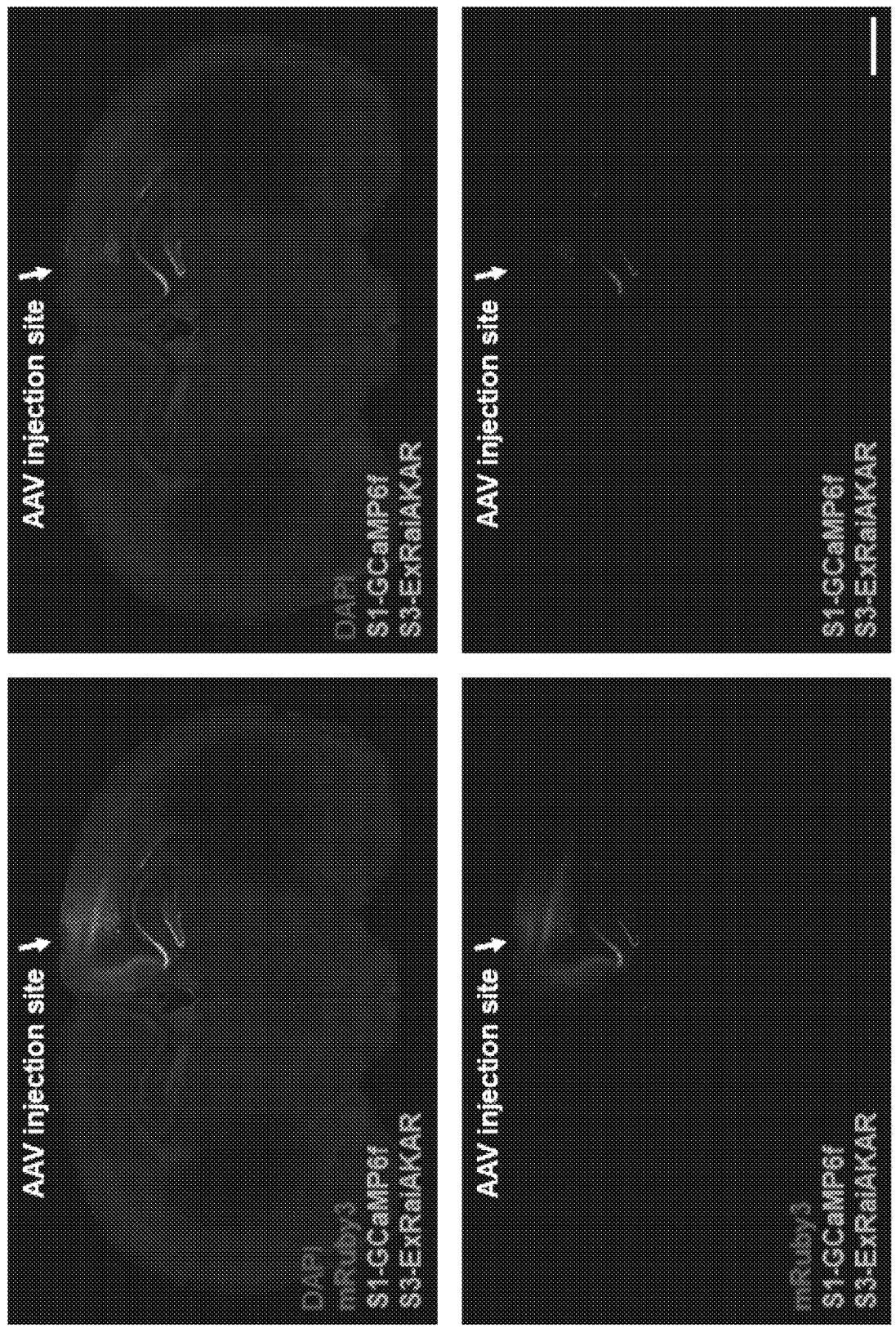

GFAP
DAPI
S1-GCaMP6f
S3-ExRaiAKAR

Cortex | CA1

Non-injected hemisphere

Injected hemisphere

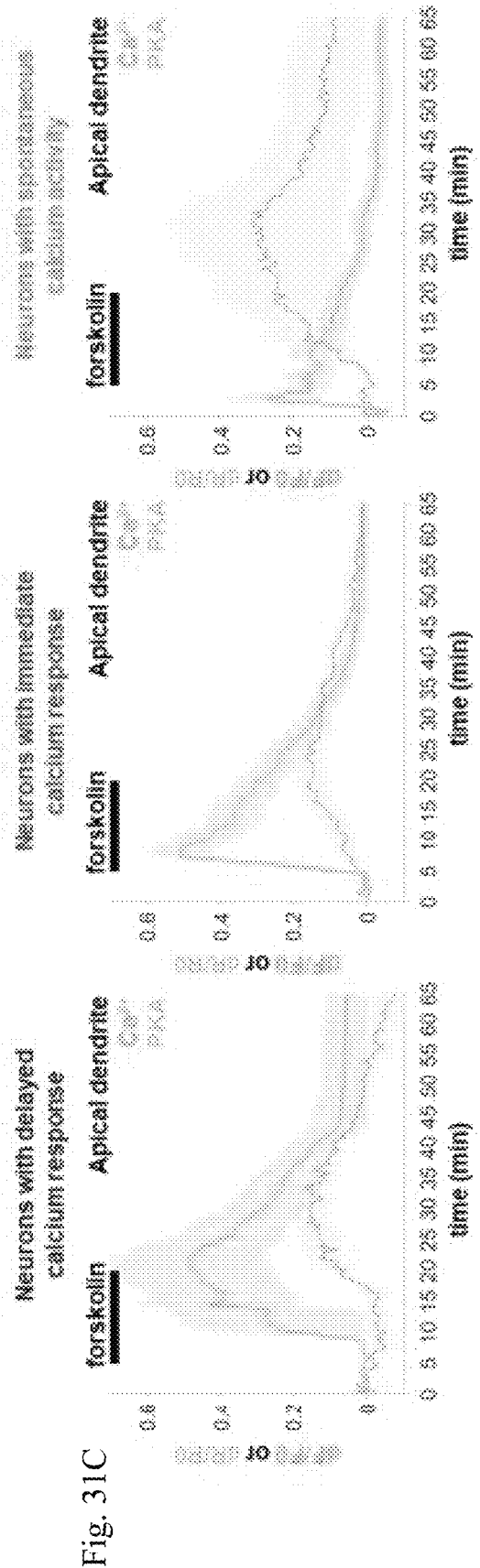
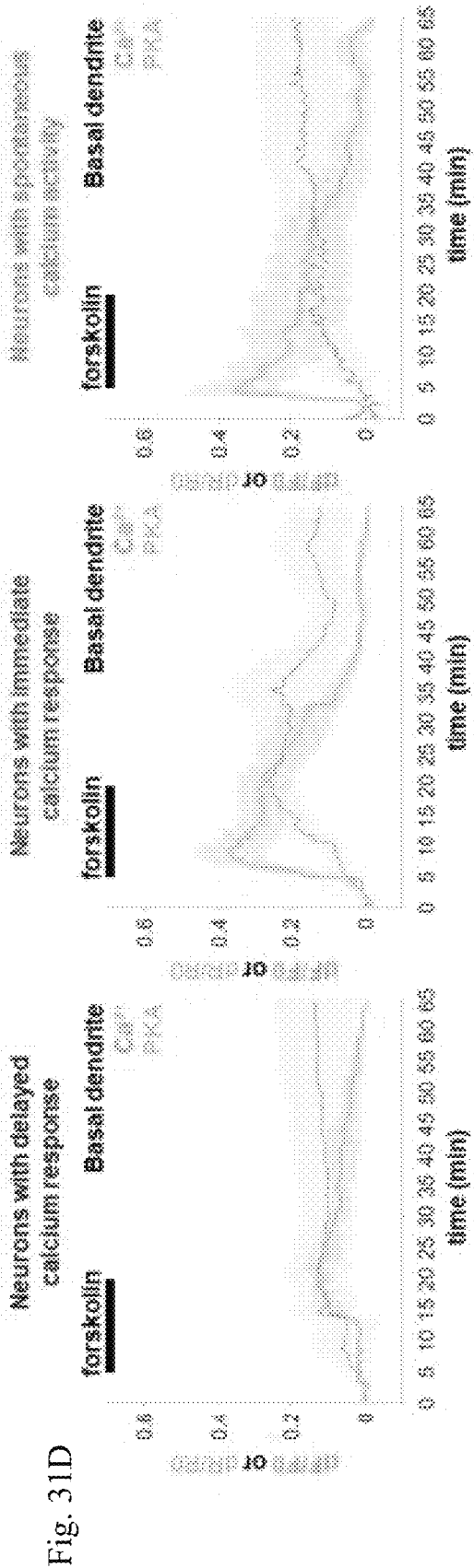
Fig. 31C
Fig. 31D

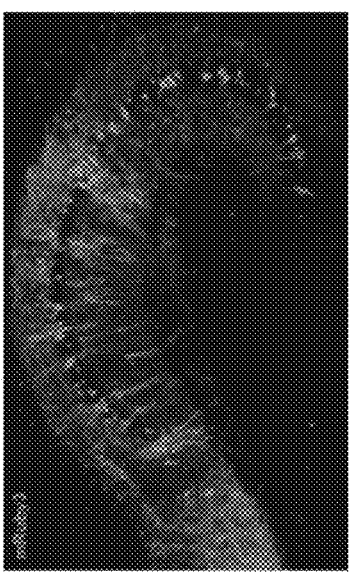
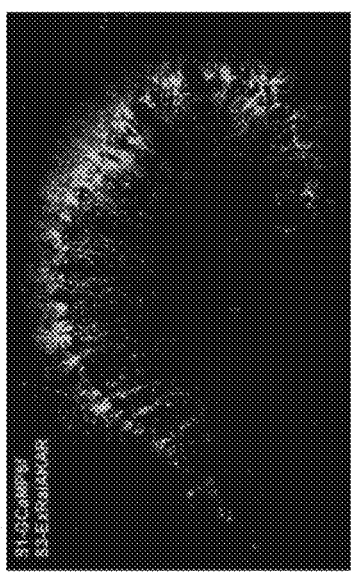
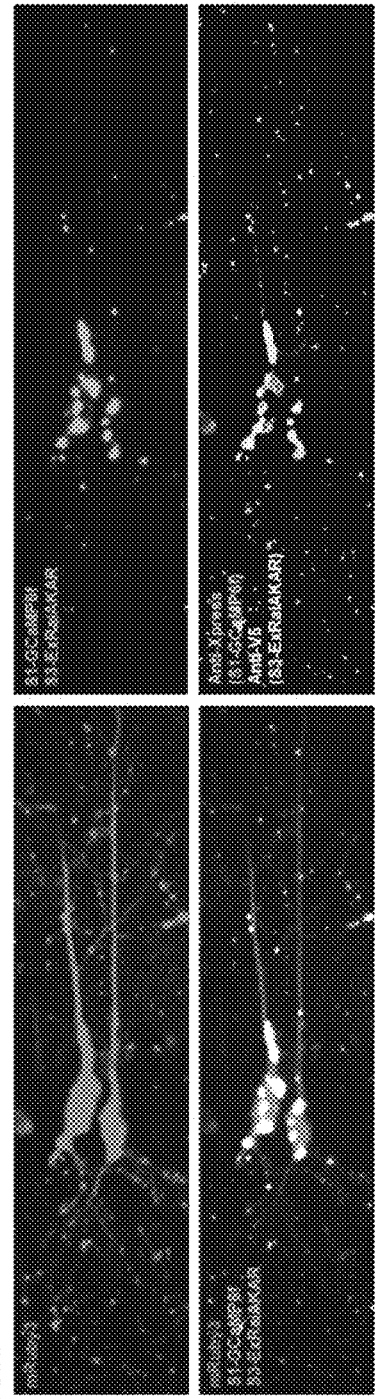
Fig. 32A
Fig. 32C
Fig. 32B

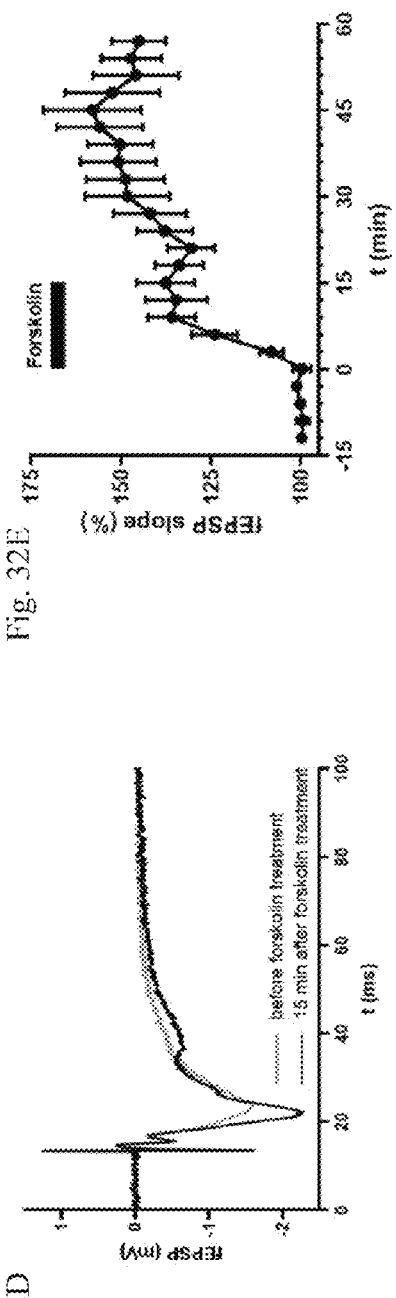
Fig. 32D
Fig. 32E
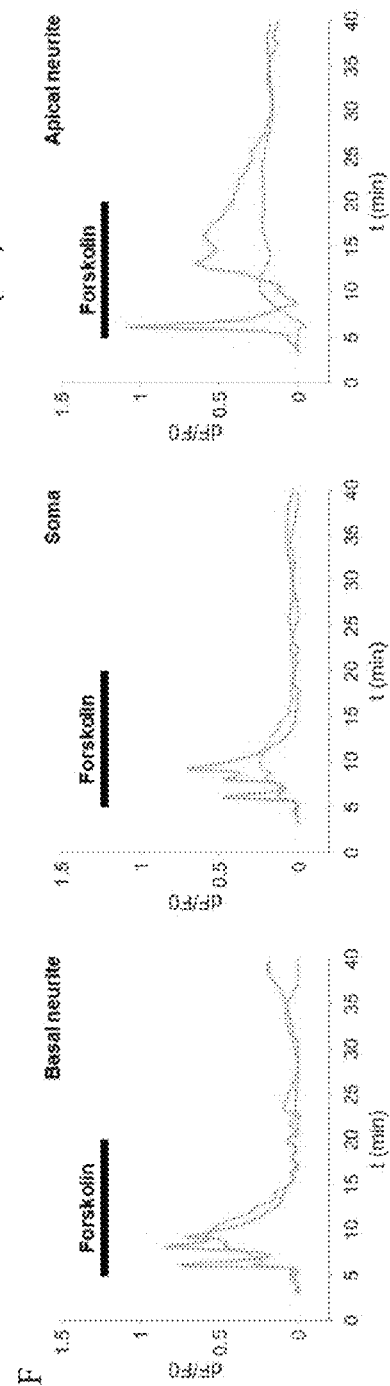
Fig. 32F
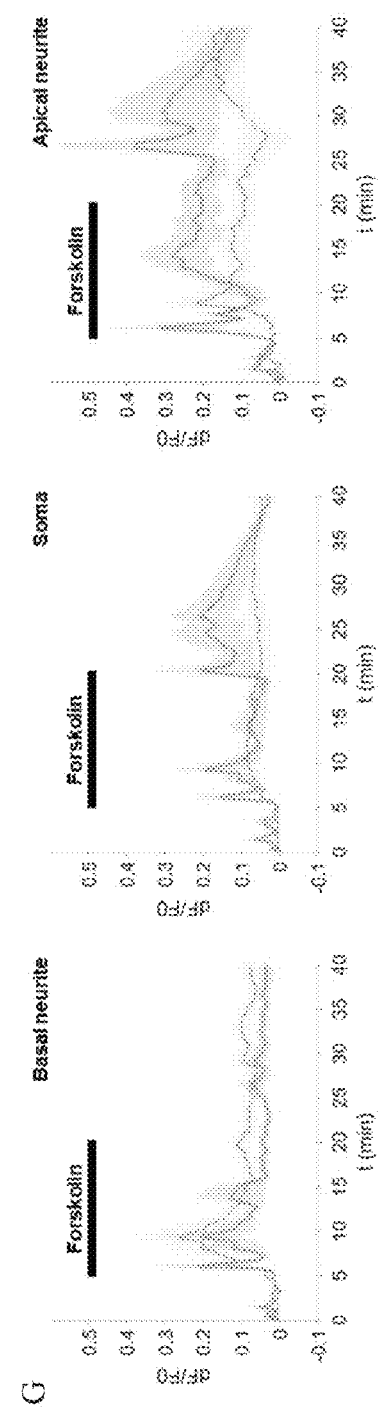
Fig. 32G

METHODS FOR SIMULTANEOUS MEASUREMENT OF MULTIPLE BIOLOGICAL SIGNALS FROM SPECTRALLY IDENTICAL FLUORESCENT REPORTERS

RELATED APPLICATIONS

This application claims benefit under 35 U.S.C. § 119(e) of U.S. Provisional application Ser. No. 62/899,416 filed Sep. 12, 2019, the disclosure of which is incorporated by reference herein in its entirety.

GOVERNMENT INTEREST

This invention was made with government support under W911NF1510548 6933228 awarded by the U. S. Army Research Laboratory and the U. S. Army Research Office; NIH 1R24MH106075 6930901, NIH R44EB021054 6935482, NIH 1R01DA045549 6937110, NIH 1R01MH114031 6937063, NIH 2R01DA029639 6932279, NIH 1R01EB024261 6936689, NIH Director's Pioneer Award 1DP1NS087724 6928706, and NIH 1R01GM104948 6926932 awarded by the National Institutes of Health; and NSF CBET 1344219 6928628 awarded by the National Science Foundation. The Government has certain rights in the invention.

FIELD OF THE INVENTION

The invention, in some aspects relates to compositions and methods for preparing and using signaling reporter islands for spatially multiplexed imaging in cells and subjects.

BACKGROUND OF THE INVENTION

Biological signals can contain dozens to hundreds of different biomolecular building blocks, which interact in complex ways within cells. For example, intracellular $Ca^{2+}$ dynamics, cyclic AMP (cAMP) levels, and protein kinase activities can all interact within single cells—with consequences for the proliferation and differentiation of cancer cells (Cho-Chung, 1990) and for plasticity and learning in the nervous system (Frey, Huang and Kandel, 1993; Trudeau, Emery and Haydon, 1996; Averaimo and Nicol, 2014), amongst many key biological phenomena. Accordingly, there has been a push by many biologists to create genetically encoded fluorescent indicators of each of these biological signals (DiPilato and Zhang, 2009; Depry, Allen and Zhang, 2011; Chen et al., 2013; Hackley, Mazzoni and Blau, 2018), as well as of many other biological signals (Violin et al., 2003; Belousov et al., 2006; Berg, Hung and Yellen, 2009; Vinkenborg et al., 2009; Oliveira and Yasuda, 2013; Shimozono et al., 2013; Ding et al., 2015, and US Patent Publication US2016/0305939). Because such biomolecular building blocks can exist in different quantities and in different functional states in different cells, but prior methods do not permit simultaneously imaging of multiple biological signals at the same time in individual cells, and so are not adequate for assessing multiple signals in a single physiological cascade (Mehta et al., 2018). On a conventional fluorescence microscope, reporters with different fluorescent spectra can be used simultaneously, but not reporters based on the same fluorophore, because the signals of the same fluorophores mix and result in ambiguous data. Thus the number of reporters used is limited to the number of spectrally resolvable channels on the microscope.

SUMMARY OF THE INVENTION

According to one aspect of the invention, a composition for RNA-protein-binding-based (RPB) clustering of independently selected reporter molecules in a cell is provided, the composition including: (a) a fusion protein component that includes: (i) one or more independently selected reporter protein elements, (ii) one or more independently selected RNA binding protein elements, (iii) zero, one, or more independently selected epitope tag elements, (iv) zero, one, or more independently selected localization protein motif elements, (v) zero, one, or more independently selected protein linker elements, wherein when present, each of the protein linker elements is positioned between two of the elements of (i), (ii), (iii), and (iv); and (b) an RNA component that includes: (v) a plurality of independently selected RNA molecules including a plurality of independently selected binding sequence elements recognized by the one or more RNA binding protein elements of (a)(ii). In some embodiments, the plurality of binding sequence elements in (b)(vi) includes ten or more binding sequences. In some embodiments, the RNA binding protein elements include one or more of a non-programmable RNA binding element. In certain embodiments, the non-programmable RNA binding elements include one or more of: an MS2 coat protein, a PP7 coat protein, a Lambda N protein, a Q-beta coat protein, a BglG protein, a U1Ap protein, HTLV-1 Rex protein, a TAT protein, an REV protein, and an eiF4A protein. In some embodiments, the RNA binding protein elements include one or more of a programmable RNA binding element. In some embodiments, the programmable RNA binding elements include one or more of a Pumilio homology domain (PumHD) and a Pumilio-based assembly (Pumby). In certain embodiments, when present, the epitope tag elements comprise one or more of an Xpress™ tag, an HA tag, and a V5 tag, an OLLAS tag, a VSVg tag, an S1 (Strep I) tag, an NWS (Strep II) tag, an E epitope (E tag), a FLAG tag, an E2 tag, an AU1 tag, an AU5 tag, an Myc tag, a Spot-tag, a NE tag, an AviTag™, a C-tag, a Calmodulin-tag, a polyglutamate tag, an Rho1D4-tag, an S-tag, an SBP-tag, a Softag™ 1, a Softag™ 3, a TC tag, and a Ty tag. In some embodiments, the localization protein motif element includes one or more of a subcellular localization protein and a trafficking protein. In some embodiments, the localization protein motif element includes one or more of a nucleus localization motif, a plasma membrane localization motif, and a synapse localization motif. In certain embodiments, when present the protein linker element(s) include one or more glycine-rich linkers. In some embodiments, the glycine-rich linkers include one or more of: a GSG linker, a (GGSGGT)x2 linker (SEQ ID NO: 13), a (GGSGGT)x4 linker (SEQ ID NO: 14), a (GGSGGSGGT)x3 linker (SEQ ID NO: 15), a (GGGS)x2 linker (SEQ ID NO: 67), and a (GGGS)x4 linker (SEQ ID NO: 68). In certain embodiments, when present the protein linker elements include one or more non-glycine-rich linkers. In some embodiments, the non-glycine-rich linkers include one of (EAAAK)x2 and APAPAP. In some embodiments, when two or more protein linker elements are present they include at least one each of a glycine rich linker and a non-glycine rich linker. In certain embodiments, the binding sequence elements include one or more of: an MS2 binding sequence, a PP7 binding sequence, and a lambda N binding sequence (BoxB), a Q-beta binding sequence, a BglG binding sequence, an U1Ap aptamer sequence, an HTLV-1 Rex responsive element (RxRE), a TAR sequence, an RRE sequence, and an eiF4A aptamer sequence. In some embodiments, the binding sequence elements include one or more of a sequence that recognizes and selectively binds the programmable binding protein. In some embodiments, the independently selected reporter protein element is a voltage indicator polypeptide, a calcium indicator polypeptide, a potassium indicator polypeptide, a pH indicator polypeptide, or a magnesium indicator polypeptide. In some embodiments, the independently selected reporter protein element is GCaMP6, GCaMP6f, GCaMP6m, GCaMP6s, jGCaMP7, jGCaMP7f, jGCaMP7m, jGCaMP7s, jGCaMP7b, jGCaMP7c, GCaMP-X, jRGECO1, jRCaMP1, NIRGECO, BCaMP, ICUE, ICUE3, cAMPr, Epac-based cAMP indicator, AKAR, AKAR4, ExRai-AKAR, ExRai-AKAR2, CKAR, ExRai-CKAR, EKARev, or RAB-EKARev. In certain embodiments, the independently selected reporter protein element is a GCaMP6f polypeptide or an ICUE3 polypeptide.

According to another aspect of the invention a cell that includes any embodiment of an aforementioned composition.

According to another aspect of the invention, a cell that includes two or more of any embodiments of an aforementioned composition are provided and one or more of the elements of (i)-(iv) and the RNA binding sequence elements are different in each of the two or more of the compositions.

According to another aspect of the invention a vector that encodes a fusion protein of any embodiment of any aforementioned composition of the invention is provided. In some aspects of the invention a cell that includes any embodiment of any aforementioned vector of the invention is provided.

According to another aspect of the invention, a composition for protein self-assembly (PSA) based clustering of independently selected reporter molecules in a cell is provided, the composition included a fusion protein that includes: (a) one or more independently selected reporter protein elements, (b) one or more independently selected self-assembly protein elements, (c) zero, one, or more independently selected epitope tag elements, (d) zero, one, or more localization protein motif elements, and (e) zero, one, or more independently selected protein linker elements, wherein when present, each of the protein linker elements is positioned between two of the elements of (a), (b), (c), and (d). In certain embodiments, the self-assembly protein elements include one or more of a polyhedron-forming protein, a coiled-coil forming protein, a supramolecular self-assembly protein, and a protein oligomer. In some embodiments, the polyhedron-forming protein is I3-01, O3-33, ATC-HL3, or 3VDX. In some embodiments, the coiled-coil forming protein is HexCoil-Ala, 5H2L_2, EE, or RR. In some embodiments, the supramolecular self-assembly protein is 2AN9 or 1M3U. In certain embodiments, the protein oligomer is 5L6HC3_1 or 2L8HC4_15. In some embodiments, when present, the epitope tag elements includes one or more of an Xpress™ tag, an HA tag, and a V5 tag, an OLLAS tag, a VSVg tag, an S1 (Strep I) tag, an NWS (Strep II) tag, an E epitope (E tag), a FLAG tag, an E2 tag, an AU1 tag, an AU5 tag, an Myc tag, a Spot-tag, a NE tag, an AviTag™, a C-tag, a Calmodulin-tag, a polyglutamate tag, an Rho1D4-tag, an S-tag, an SBP-tag, a Softag™ 1, a Softag™ 3, a TC tag, and a Ty tag. In certain embodiments, the localization protein motif element includes one or more of a subcellular localization protein and a trafficking protein. In some embodiments, the localization protein motif element includes one or more of a nucleus localization motif, a plasma membrane localization motif, and a synapse localization motif. In some embodiments, when present the protein linker elements include one or more glycine-rich linkers. In some embodiments, the glycine-rich linkers include one or more of: a GSG linker, a GSG linker, a (GGSGGT)x2 linker (SEQ ID NO: 13), a (GGSGGT)x4 linker (SEQ ID NO: 14), a (GGSGGSGGT)x3 linker (SEQ ID NO: 15), a (GGGS)x2 linker (SEQ ID NO: 67), and a (GGGS)x4 linker (SEQ ID NO: 68). In certain embodiments, when present the protein linker elements includes one or more non-glycine-rich linkers. In some embodiments, the non-glycine-rich linkers include one of (EAAAK)x2 and APAPAP. In some embodiments, when two or more protein linker elements are present they include at least one each of a glycine rich linker and a non-glycine rich linker. In certain embodiments, the independently selected reporter protein element is a voltage indicator polypeptide, a calcium indicator polypeptide, a potassium indicator polypeptide, a pH indicator polypeptide, or a magnesium indicator polypeptide. In some embodiments, the independently selected reporter protein element is GCaMP6, GCaMP6f, GCaMP6m, GCaMP6s, jGCaMP7, jGCaMP7f, jGCaMP7m, jGCaMP7s, jGCaMP7b, jGCaMP7c, GCaMP-X, jRGECO1, jRCaMP1, NIRGECO, BCaMP, ICUE, ICUE3, cAMPr, Epac-based cAMP indicator, AKAR, AKAR4, ExRai-AKAR, ExRai-AKAR2, CKAR, ExRai-CKAR, EKARev, or RAB-EKARev. In certain embodiments, the independently selected reporter protein element is a GCaMP6f polypeptide or an ICUE3 polypeptide.

According to another aspect of the invention a cell that includes any embodiment of an aforementioned composition.

According to another aspect of the invention, a cell that includes two or more of any embodiments of an aforementioned composition are provided and one or more of the elements of (a)-(e) are different in each of the two or more of the compositions.

According to another aspect of the invention a vector that encodes a fusion protein of any embodiment of any aforementioned composition of the invention is provided. In some aspects of the invention a cell that includes any embodiment of any aforementioned vector of the invention is provided.

According to another aspect of the invention a cell is provided that includes one or more of an embodiment of a composition for RNA-protein-binding-based (RPB) clustering of independently selected reporter molecules in a cell and one or more of an embodiment of a composition for protein self-assembly (PSA) based clustering of independently selected reporter molecules in a cell.

According to another aspect of the invention, a method of determining a physiological process in a cell is provided, the method including (a) expressing in a cell a plurality of each of two or more independently selected reporter protein elements each capable of generating an identifiable signal; (b) forming one or more clusters from the plurality of the two or more independently selected reporter protein elements in the cell, wherein each of the two or more independently selected reporter protein elements are in different clusters; (c) positioning the one or more formed clusters in the cell such that a distance between a cluster formed with one of the independently selected reporter protein elements and a cluster formed with another of the independently selected reporter protein elements is sufficient to (i) resolve the signal generated by the two independently selected reporter protein elements in the positioned clusters and (ii) simultaneously determine the signal generated by each of the independently selected reporter protein elements in the positioned clusters; (d) detecting the identifiable signals generated from the independently selected reporter protein elements in the positioned clusters; and (e) analyzing the detected signals to determine one or more physiological processes of the cell. In some embodiments, the signals generated by the two or more independently selected reporter protein elements include fluorescent signals. In certain embodiments, at least two of the fluorescent reporter protein elements generate spectrally overlapping signals. In some embodiments, the analyzing includes assessing two or more different physiological processes in the cell. In some embodiments, the analyzing includes assessing two or more simultaneous physiological processes in the cell. In some embodiments, the physiological process includes one or more of: pH of the cell, voltage in the cell, and the presence of one or more of: calcium, magnesium, chloride, and potassium in the cell. In certain embodiments, the method also includes externally stimulating the cell that includes the positioned clusters and determining the signals generated by the independently selected reporter protein elements in the positioned clusters. In some embodiments, the externally stimulating includes contacting the cell with one or more of: forskolin, Tetradecanoylphorbol acetate (PMA), (S)-3,5-Dihydroxyphenylglycine (DHPG), N-Methyl-D-aspartic acid (NMDA), a cancer therapeutic agent, an antibody or active fragment thereof, a toxin, an agonist of a receptor, an antagonist of a receptor, an electrical field, a magnetic field, light, gas, a temperature change, a gravity change, a pH change, a whole-cell patch clamp. In some embodiments, the method does not include externally stimulating the cell that includes the positioned clusters and determining the signals generated by the independently selected reporter protein elements in the positioned clusters. In some embodiments, the physiological process includes one or more of: a function of the cell, a response of the cell, ion flux in the cell, a therapeutic response of the cell; and an activation of the cell. In certain embodiments, the method also includes (f) repeating steps (d)-(e) for two or more different clusters formed from the two or more independently selected reporter protein elements each capable of generating an identifiable signal and positioned as in step (c). In some embodiments, the distance between the cluster formed with one of the independently selected reporter protein elements and the cluster formed with the other of the independently selected reporter protein elements is about 1-2 microns, 1-3 microns, 1-4 microns, 1-5 microns, 1-6 microns, 1-7 microns, or 1-8 microns. In some embodiments, the distance between the cluster formed with one of the independently selected reporter protein elements and the cluster formed with the other of the independently selected reporter protein elements is 2-8 microns. In certain embodiments, the signals generated by the independently selected reporter protein elements are detected with one or more of: video microscopy, computerized microscopic imaging, fluorescence microscopy, and confocal microscopy, light microscopy, light microscopy, light sheet microscopy, light field microscopy, and endoscopy. In some embodiments, the analyzing includes one or more of: live cell imaging, immunostaining, RNA FISH, live cell recording, an immunostaining method, an in situ hybridization method, determining fluorescence intensity, subtracting background fluorescence, a cluster/puncta localization means, an expansion microscopy means, a fluorescence microscopy means, a light microscopy means, and a fluorescence-lifetime imaging microscopy means. In certain embodiments, the cell is in, or has been obtained from, a cell culture, tissue culture, or a subject. In some embodiments, the cell is a vertebrate cell. In some embodiments, the cell is a human cell. In certain embodiments, the cell also includes two or more of any embodiment of an aforementioned composition for RNA-protein-binding-based (RPB) clustering of independently selected reporter molecules and one or more of the elements (i)-(v) and the RNA binding sequences are different in each of the two or more of the composition. In some embodiments, the two or more of the composition each form and position the clusters of different independently selected reporter protein elements. In some embodiments, the cell also includes two or more of any embodiment of an aforementioned composition for protein self-assembly (PSA) based clustering of independently selected reporter molecules and one or more of the elements of (a)-(e) are different in each of the two or more of the composition. In certain embodiments, the two or more of the composition each form and position the clusters of different independently selected reporter protein elements. In some embodiments, the cell includes one or more of one or more of any embodiment of an aforementioned composition for RNA-protein-binding-based (RPB) clustering of independently selected reporter molecules in a cell and one or more of any embodiment of an aforementioned composition for protein self-assembly (PSA) based clustering of independently selected reporter molecules in a cell.

According to another aspect of the invention, a method of identifying an effect of a candidate agent on a physiological process in a cell is provided, the method including (a) preparing a cell that includes one or more of any embodiment of an aforementioned composition for RNA-protein-binding-based (RPB) clustering of independently selected reporter molecules in a cell, wherein the prepared cell includes formed and positioned clusters of the independently selected reporter protein element; (b) contacting the prepared cell with a candidate agent; (c) detecting the identifiable signals generated from the independently selected reporter protein elements in the positioned clusters; (d) analyzing the detected signals to determine one or more physiological processes of the contacted cell; and (e) comparing the determined physiological process of the contacted cell with the determined physiological process of a control cell, wherein a difference identifies an effect of the candidate agent on a physiological process in the contacted cell. In some embodiments, the control cell is a cell that includes the composition but is not contacted with the candidate agent. In certain embodiments, the cell includes two or more of the compositions and at least one of the elements (i)-(v) and the RNA binding sequences are different in each of the two or more of the compositions. In some embodiments, the two or more of the composition each form and position the clusters of different independently selected reporter protein elements. In certain embodiments, the candidate agent is one or more of a pharmaceutical agent, an electrical agent, a magnetic agent, a temperature change agent, an environmental agent, and a therapeutic agent.

According to another aspect of the invention, a method of identifying an effect of a candidate agent on a physiological process in a cell is provided, the method including: (a) preparing a cell that includes one or more of any embodiment of an aforementioned composition for protein self-assembly (PSA) based clustering of independently selected reporter molecules, wherein the prepared cell includes formed and positioned clusters of the independently selected reporter protein element; (b) contacting the prepared cell with a candidate agent; (c) detecting the identifiable signals generated from the independently selected reporter protein elements in the positioned clusters; (d) analyzing the detected signals to determine one or more physiological processes of the contacted cell; and (e) comparing the determined physiological process of the contacted cell with the determined physiological process of a control cell, wherein a difference identifies an effect of the candidate agent on a physiological process in the contacted cell. In some embodiments, the control cell is a cell including the composition but not contacted with the candidate agent. In certain embodiments, the cell includes two or more of the compositions and one or more of the elements of (a)-(e) are different in each of the two or more of the compositions. In some embodiments, the two or more of the composition each form and position the clusters of different independently selected reporter protein elements. In some embodiments, the candidate agent is one or more of a pharmaceutical agent, an electrical agent, a magnetic agent, a temperature change agent, an environmental agent, and a therapeutic agent.

According to another aspect of the invention, a method of identifying an effect of a candidate agent on a physiological process in a cell is provided, the method including (a) preparing a cell that includes one or more of any embodiment of an aforementioned composition for RNA-protein-binding-based (RPB) clustering of independently selected reporter molecules and one or more of any embodiment of an aforementioned composition for protein self-assembly (PSA) based clustering of independently selected reporter molecules, and the prepared cell includes formed and positioned clusters of the independently selected reporter protein elements; (b) contacting the prepared cell with a candidate agent; (c) detecting the identifiable signals generated from the independently selected reporter protein elements in the positioned clusters; (d) analyzing the detected signals to determine one or more physiological processes of the contacted cell; and (e) comparing the determined physiological process of the contacted cell with the determined physiological process of a control cell, wherein a difference identifies an effect of the candidate agent on a physiological process in the contacted cell. In certain embodiments, the control cell is a cell includes the two or more compositions but is not contacted with the candidate agent. In some embodiments, the cell includes two or more of any embodiment of an aforementioned composition for RNA-protein-binding-based (RPB) clustering of independently selected reporter molecules and one or more of the elements of (i)-(vi) are different in each of the two or more of the composition. In some embodiments, the two or more of the composition each form and position the clusters of different independently selected reporter protein elements. In certain embodiments the cell includes two or more of any embodiment of an aforementioned composition for protein self-assembly (PSA) based clustering of independently selected reporter molecules, and one or more of the elements of (a)-(e) are different in each of the two or more of the composition. In some embodiments, the two or more of the composition each form and position the clusters of different independently selected reporter protein elements. In certain embodiments, the candidate agent is one or more of a pharmaceutical agent, an electrical agent, a magnetic agent, a temperature change agent, an environmental agent, and a therapeutic agent. In some embodiments, the cell includes two or more of any embodiment of an aforementioned composition for RNA-protein-binding-based (RPB) clustering of independently selected reporter molecules and one or more of the elements of (i)-(vi) are different in each of the two or more of the composition and the cell also includes two or more of any embodiment of an aforementioned composition for protein self-assembly (PSA) based clustering of independently selected reporter molecules, and one or more of the elements of (a)-(e) are different in each of the two or more of the composition. In some embodiments, the two or more of the composition each form and position the clusters of different independently selected reporter protein elements. In certain embodiments, the candidate agent is one or more of a pharmaceutical agent, an electrical agent, a magnetic agent, a temperature change agent, an environmental agent, and a therapeutic agent.

BRIEF DESCRIPTION OF THE DRAWINGS

FIG. 1A shows a schematic illustrating that by clustering fluorescent reporters of different cellular signals at distinct points in space, which are distant enough to be resolved by a microscope but close enough to spatially sample the relevant biology, multiple fluorescent reporters (left panel) even with identical fluorescent spectra (middle panel) can be simultaneously imaged in a single cell, followed by post hoc reconstruction of sensor identity in fixed cells via epitope immunostaining, RNA FISH, or other highly multiplexed fixed cell imaging methods (right panels). Green dots, live cell appearance of puncta formed by clustered fluorescent reporters distributed throughout a cell (represented as a shape enclosed by curved black lines); black boxes, regions-of-interest (ROIs) for time course measurements; green traces, time course measurements of fluorescent signals from ROIs obtained during live cell imaging; red and blue dots, identification of fluorescent reporter identity by highly multiplexed fixed cell imaging methods (e.g., immunostaining); red and blue traces, the fluorescent signal time courses, now annotated with sensor identity. FIG. 1B shows a schematic illustrating how fluorescent reporter clustering, and thus spatial multiplexing, could be achieved by assembling different fluorescent reporters on distinct RNA scaffolds. FIG. 1C shows a schematic illustrating how fluorescent reporter clustering, and thus spatial multiplexing, could be achieved by assembling different fluorescent reporters onto distinct scaffolds via self-assembling proteins motifs. FIG. 1D shows another schematic illustrating how fluorescent reporter clustering, and thus spatial multiplexing, could be achieved by assembling different fluorescent reporters onto distinct scaffolds via self-assembling proteins motifs.

FIG. 2A shows schematic diagrams of the designs of the sensor vectors (MS2 protein with GCaMP6f, or MP-GCaMP6f, PP7 protein with ICUE3, or PP-ICUE3) and the scaffold vectors (MS2 RNA scaffold, MR-SF; PP7 RNA scaffold, PR-SF). UBC, ubiquitin C promoter; CAG, CMV early enhancer/chicken β actin promoter; NLS, SV40 nuclear localization sequence; HA, influenza hemagglutinin epitope; V5, simian virus 5-derived epitope; tdMCP, tandem dimer MS2 coat protein; tdPCP, tandem dimer PP7 coat protein; MBS, MS2 binding site; PBS, PP7 binding site; Actb UTR, 3' untranslated region of mouse β actin mRNA (nucleotides 1-441); STOP, stop codon; WPRE, woodchuck hepatitis virus posttranscriptional regulatory element. FIG. 2B shows representative images of live HeLa cells transfected with MP-GCaMP6f transfected alone (left), with the corresponding scaffold vector MR-SF (middle), or with PR-SF (right). Scale bars, 10 µm throughout this figure. FIG. 2C shows a box plot of the number of cytosolic fluorescent puncta per cell from the transfected HeLa cells described in FIG. 2B (n=9 cells from 3 cultures for MP-GCaMP6f only; n=18 cells from 9 cultures for MP-GCaMP6f+MR-SF; n=11 cells from 5 cultures for MP-GCaMP6f+PR-SF); Kruskal-Wallis analysis of variance followed by post-hoc Dunn's multiple comparison test. For all box plots used herein and in subsequent figures: middle horizontal line, median; top and bottom horizontal lines, 25% and 75% percentiles; top and bottom whiskers, minimum and maximum values unless specifically noted otherwise in figure description; hollow circles, individual values. FIG. 2D shows representative images of live HeLa cells transfected with PP-ICUE3 alone (left), with MR-SF (middle), or with the corresponding scaffold vector PR-SF (right). FIG. 2E shows a box plot of the number of cytosolic fluorescent puncta per cell from the transfected HeLa cells described in FIG. 2D (n=28 cells from 5 cultures for PP-ICUE3 only; n=35 cells from 5 cultures for PP-ICUE3+ MR-SF; n=38 cells from 11 cultures for PP-ICUE3+PR-SF); Kruskal-Wallis analysis of variance followed by post-hoc Dunn's multiple comparison test. FIG. 2F shows representative images of fixed HeLa cells co-transfected with MP-GCaMP6f and MR-SF or PP-GCaMP6f and PR-SF after RNA FISH against the expressed mRNA from MR-SF ("MR FISH") or PR-SF ("PR FISH"). FIG. 2G shows a box plot of the percentage of sensor puncta that also bear RNA FISH puncta per cell (n=19 cells from 4 cultures for MP-GCaMP6f and MR-SF; n=22 cells from 5 cultures for PP-ICUE3 and PR-SF); Wilcoxon rank sum test. For FIG. 2A-G, Table 1 lists motif sequences, Table 2 lists all tested constructs, Tables 3, 4, 5, provide statistical information for FIGS. 2C, 2E, and 2G, respectively, ***, P<0.001; n.s., not significant.

FIG. 3A shows schematic diagrams of the construct designs of the sensor vectors (LambdaN22 protein with GCaMP6f, or LP-GCaMP6f, LambdaN22 protein with AKAR4, or LP-AKAR4) and the scaffold vector (LambdaN22 RNA scaffold, LR-SF). UBC, ubiquitin C promoter; CAG, CMV early enhancer/chicken β actin promoter; LNP, LambdaN22 protein; NLS, SV40 nuclear localization sequence; HA, influenza hemagglutinin epitope; FLAG, synthetic peptide FLAG epitope; BoxB, LambdaN22 binding site; Actb UTR, 3' untranslated region of mouse β actin mRNA (nucleotides 1-441); STOP, stop codon; WPRE, woodchuck hepatitis virus posttranscriptional regulatory element (Table 1, motif sequences; Table 2, all tested constructs). FIG. 3B shows representative images of live HeLa cells transfected with LP-GCaMP6f only, LP-GCaMP6f+LR-SF, LP-AKAR4+ LR-SF, LP-GCaMP6f+MR-SF, LP-GCaMP6f+PR-SF, or PP-GCaMP6f+LR-SF. Scale bar, 20 µm.

FIG. 4A shows representative fluorescent signals recorded during live cell imaging from three HeLa cells expressing GCaMP6f (left) and from three sensor puncta from three different HeLa cells expressing MP-GCaMP6f and MR-SF (right), after 10 mM CaCl$_2$ stimulation. dF/F0, fluorescence change in the GFP channel. FIG. 4B shows a box plot of the peak fluorescence change from the HeLa cells described in FIG. 4A under 10 mM CaCl$_2$ stimulation (n=44 cells from 2 cultures for GCaMP6f, n=39 cells from 5 cultures for MP-GCaMP6f and MR-SF); Wilcoxon rank sum test. FIG. 4C shows a box plot of the signal-to-noise ratio (with noise defined as the standard deviation of the baseline pre-stimulus throughout this paper) from the HeLa cells described in FIG. 4A under 10 mM CaCl$_2$) stimulation (n=44 cells from 2 cultures for GCaMP6f, n=39 cells from 5 cultures for MP-GCaMP6f and MR-SF); Wilcoxon rank sum test. FIG. 4D shows representative fluorescent signals recorded during live cell imaging from 3 HeLa cells expressing ICUE3 (left) and from 3 sensor puncta from 3 different HeLa cells expressing PP-ICUE3 and PR-SF (right), after 20 µM forskolin stimulation. d(C/Y)/(C/Y), change of the fluorescence ratio between CFP channel and YFP channel. FIG. 4E shows a box plot of the peak fluorescence change from the transfected HeLa cells described in FIG. 4D under 20 µM forskolin stimulation (n=27 cells from 3 cultures for ICUE3; n=14 cells from 7 cultures for PP-ICUE3 and PR-SF); Wilcoxon rank sum test. FIG. 4F shows a box plot of the signal-to-noise ratio from the HeLa cells described in FIG. 4D under 20 µM forskolin stimulation (n=27 cells from 3 cultures for ICUE3; n=14 cells from 7 cultures for PP-ICUE3 and PR-SF); Wilcoxon rank sum test). FIG. 4G shows a graph of the mean squared displacement of the sensor puncta locations in live HeLa cells expressing MP-GCaMP6f and MR-SF (red) or PP-ICUE3 and PR-SF (blue) versus time (n=314 puncta from 14 cells from 6 cultures for MP-GCaMP6f and MR-SF; n=678 puncta from 14 cells from 7 cultures for PP-ICUE3 and PR-SF. Red and blue lines, mean; red and blue shaded boundaries, standard deviation. FIG. 4H shows a box plot of the diffusion coefficients of the sensor puncta in FIG. 3G (Wilcoxon rank sum test); top and bottom whiskers represent $10^{th}$ and $90^{th}$ percentiles; individual values not shown. FIG. 4I shows a histogram of the distances between one puncta and its nearest-neighbor punctum in HeLa cells expressing MP-GCaMP6f and MR-SF or PP-ICUE3 and PR-SF (n=142 puncta from 5 cells from 5 cultures for MP-GCaMP6f and MR-SF; n=254 puncta from 5 cells from 5 cultures for PP-ICUE3 and PR-SF). Table 6 provides full statistics for FIGS. 4B, C, E, F, and H; n.s., not significant.

FIG. 5A-H presents photomicrographs and graphs of the results of experiments examining Cytosolic $Ca^{2+}$ and cAMP responses in HeLa cells at different subcellular locations. Related to FIG. 4. FIG. 5A shows a representative image of live HeLa cells expressing GCaMP6f Orange squares, regions-of-interest (ROIs) for fluorescent signal measurement throughout this figure. Scale bars, 20 µm throughout this figure. FIG. 5B shows representative images of live HeLa cells expressing MP-GCaMP6f+MR-SF and stained with NucBlue™ against the cell nucleus. FIG. 5C shows graphs of fluorescent signals recorded during live cell imaging from 2 HeLa cells expressing GCaMP6f under 10 mM CaCl$_2$) stimulation at t=120 s. Throughout this figure: dF/F0, fluorescence change in the GFP channel; Location 1, the fluorescent signal from a random 1 µm2 ROI in the cytosol; Location 2, the fluorescent signal from a 1 µm2 ROI that was 5 µm away from Location 1; Location 3, the fluorescent signal from a 1 µm2 ROI that was 15 µm away from Location 1; average, the fluorescent signal averaged from the three fluorescent signals above. FIG. 5D shows graphs of fluorescent signals recorded during live cell imaging from 2 HeLa cells expressing MP-GCaMP6f+MR-SF under 10 mM CaCl$_2$ stimulation at t=120 s. Throughout this figure: Punctum 1, the fluorescent signal from a random punctum in the cytosol; Punctum 2, the fluorescent signal from a punctum that was 5 µm away from Punctum 1; Punctum 3, the fluorescent signal from a punctum that was 15 µm away from Punctum 1; average, the fluorescent signal averaged from the three fluorescent signals above. FIG. 5E shows a representative image of live HeLa cells expressing ICUE3. FIG. 5F shows representative images of live HeLa cells expressing PP-ICUE3+PR-SF and stained with NucBlue™ against the cell nucleus. FIG. 5G shows graphs of fluorescent signals recorded during live cell imaging from 2 HeLa cells expressing ICUE3 under 20 µM forskolin stimulation at t=120 s. Throughout this figure: d(C/Y)/(C/Y), change of the fluorescence ratio between CFP channel and YFP channel. FIG. 5H shows graphs of fluorescent signals recorded during live cell imaging from 2 HeLa cells expressing PP-ICUE3+PR-SF under 20 µM forskolin stimulation at t=120 S.

FIG. 6A shows representative images (top row) of HeLa cells quadruply transfected with MP-GCaMP6f, MR-SF, PP-ICUE3, and PR-SF (MP-GCaMP6f, PP-ICUE3 shown in green), and then fixed and immunostained against HA epitope (anti-HA, red) and V5 epitope (anti-V5, blue); scale bar, 10 µm. The bottom row shows enlarged images of the regions highlighted by yellow boxes in the top row; scale bar, 1 µm. FIG. 6B shows a box plot of the percentage of the puncta of the indicated sensor that did not contain the other type of sensor, per cell, as identified by dual immunostaining (n=9 cells from 5 cultures, each; Wilcoxon rank sum test). FIG. 6C shows graphs of fluorescent signals recorded from live HeLa cells co-transfected with MP-GCaMP6f, MR-SF, PP-ICUE3, and PR-SF after 10 mM $CaCl_2$) stimulation at t=2 min (n=9 cells from 7 cultures). Red traces, dF/F0(%) of a single punctum in the cell that was identified as clustered GCaMP6f by post hoc immunostaining; blue traces, d(C/Y)/(C/Y) (%) of a punctum in the cell that was identified as clustered ICUE3 by post hoc immunostaining. FIG. 6D shows a scatterplot of the peak fluorescent responses of the cells in FIG. 6C after 10 mM $CaCl_2$) stimulation (n=9 cells from 7 cultures). FIG. 6E shows graphs of fluorescent signals recorded from live HeLa cells co-transfected with MP-GCaMP6f, MR-SF, PP-ICUE3, and PR-SF under 20 µM forskolin stimulation at t=2 min and then 10 mM $CaCl_2$) stimulation at t=5 min (n=4 cells from 2 cultures). Red traces, dF/F0(%) of a punctum in the cell that was identified as assembled GCaMP6f by post hoc immunostaining; blue traces, d(C/Y)/(C/Y) (%) of a punctum in the cell that was identified as assembled ICUE3 by post hoc immunostaining. For FIG. 6A-E, full statistics for FIG. 6B are provided in Table 7; n.s., not significant.

FIG. 7A shows representative images of cultured mouse hippocampal neurons expressing MP-mRuby2, PP-GFP, MR-SF, and PR-SF, with miRFP as a morphological marker. Orange rectangles, ROIs that are enlarged in the panels on the right; white arrows, spatially separated red and green puncta; scale bars, 10 µm. FIG. 7B shows representative images of cultured mouse hippocampal neurons expressing MP-GCaMP6f and MR-SF. Scale bar, 20 µm. FIG. 7C shows representative images of cultured mouse hippocampal neurons expressing PP-GCaMP6f and PR-SF. Scale bar, 20 µm.

FIG. 8A-X provides graphs and traces demonstrating design and characterization of fluorescent reporters clustered by protein scaffolds in neurons. (FIG. 8A) Construct design of S1-GCaMP6f. GCaMP6f, GFP-based fluorescent calcium reporter; HexCoil-Ala, a homo-tetramer; Xpress, epitope; I3-01, self-assembling subunit of I3-01 dodecahedron (60-mer); AA, amino acid (see Table 1 for sequences of the motifs; see Table 2 for all tested constructs). (FIG. 8B) Representative confocal image of live cultured mouse hippocampal neuron expressing GCaMP6f Scale bar, 20 µm throughout this figure. (FIG. 8C) Representative confocal image of live cultured mouse hippocampal neuron expressing S1-GCaMP6f and miRFP as a cell morphology marker. (FIG. 8D) Representative fluorescent signals recorded from the soma, proximal neurites (5-25 µm away from soma throughout this figure), and distal neurites (50-250 µm away from soma throughout this figure) of a cultured mouse hippocampal neuron expressing GCaMP6f (left) or S1-GCaMP6f (right) in response to a single action potential (1 AP) at t=5 s triggered by current injection via whole-cell patch clamp at the soma. dF/F0, fluorescence changes in the GFP channel. Each fluorescent signal for the clustered fluorescent reporter was measured from a single punctum, throughout this paper, unless otherwise specified. (E) Bar plot of the peak fluorescence changes in the GFP channel at the soma, proximal neurites, and distal neurites of cultured mouse hippocampal neurons expressing GCaMP6f or S1-GCaMP6f in response to a single action potential (n=11 values from soma, 22 values from proximal neurites, and 22 values from distal neurites from 11 total trials from 6 neurons from 3 cultures for each of GCaMP6f and S1-GCaMP6f, for each trial, the calcium responses from the soma and two proximal neurites and two distal neurites were analyzed). Bar plots of medians with interquartile ranges are used throughout this paper, with individual values plotted as dots. n.s., not significant; two-way analysis of variance followed by post-hoc Bonferroni corrected multiple comparisons test; see Tables 11-13, 30-32, and 41-43 for full statistics for FIG. 8. (FIG. 8F) Signal-to-noise ratio in the GFP channel at the soma, proximal neurites, and distal neurites for the neurons of FIG. 8E. Noise is defined as standard deviation of pre-stimulus baseline throughout this paper. (FIG. 8G) Half rise time and half decay time of reported calcium transients at the soma, for the neurons of FIG. 8E. (FIG. 8H) Violin plots of puncta size (left), distance to the nearest punctum (middle), and diffusion constant over 1 hour (right), for puncta of S1-GCaMP6f in neurons (n=349 puncta from 5 neurons from 5 cultures for puncta size and distance to the nearest punctum; n=63 puncta from 1 neuron from 1 culture for diffusion constant). Red line, median; black line, interquartile ranges. (FIGS. 8I-K) As in FIG. 8A-C, but for S2-cAMPr. cAMPr, GFP-based fluorescent cAMP reporter; 1M3U, self-assembling subunit of 1M3U filament assembly; HA, influenza hemagglutinin epitope; 2L8HC4_15, a homo-tetramer; AA, amino acid. (FIG. 8L-N) As in FIG. 8D-F, but for neurons expressing cAMPr (or S2-cAMPr) together with miRFP, and stimulated with 5 µM forskolin stimulation at t=10 s (n=11 somata, 22 proximal neurites, and 22 distal neurites from 11 neurons from 5 cultures for cAMPr; n=13 somata, 26 proximal neurites, and 26 distal neurites from 13 neurons from 6 cultures for S2-cAMPr). n.s., not significant; *, P<0.05. (FIG. 8O) Half rise time of reported cAMP signals at the soma, for the neurons of FIG. 8M. (FIG. 8P) As in FIG. 8H, but for S2-cAMPr (n=410 puncta from 5 neurons from 5 cultures for puncta size and distance to the nearest punctum; n=44 puncta from 1 neuron from 1 culture for diffusion constant). (FIGS. 8Q-S) As in FIG. 8A-C, but for S3-ExRaiAKAR. ExRaiAKAR, GFP-based fluorescent PKA reporter; 3VDX, self-assembling subunit of 3VDX tetrahedron (12-mer); V5, simian virus 5-derived epitope; 5L6HC3_1, a homo-trimer; AA, amino acid. (FIG. 8T-V) As in FIG. 8A-C, but for neurons expressing ExRaiAKAR (or S3-ExRaiAKAR) together with miRFP, and stimulated with 5 µM forskolin stimulation at t=1 min (n=5 somata, 10 proximal neurites, and 10 distal neurites from 5 neurons from 4 cultures for ExRaiAKAR; n=5 somata, 10 proximal neurites, and 10 distal neurites from 5 neurons from 5 cultures for S3-ExRaiAKAR). dR/R0, changes of fluorescence ratio between 488 nm excitation and 405 nm excitation when imaged in the GFP emission channel. n.s., not significant. (FIG. 8W) Half rise time of reported PKA signals at the soma, for the neurons of FIG. 8U. (FIG. 8X) As in FIG. 8H, but for S3-ExRaiAKAR (n=1125 puncta from 5 neurons from 4 cultures for puncta size and distance to the nearest punctum; n=63 puncta from 1 neuron from 1 culture for diffusion constant).

(FIG. 9A-B) Representative fluorescent signals recorded from the soma, proximal neurites (5-25 µm away from soma throughout this figure), and distal neurites (50-250 µm away from soma throughout this figure) of a cultured mouse hippocampal neuron expressing GCaMP6f (FIG. 9A) or S1-GCaMP6f (FIG. 9B) in response to a single action potential (1AP), 5 action potentials (5AP), 10 action potentials (10AP), and 20 action potentials (20AP) triggered by current injection via whole-cell patch clamp at the soma. dF/F0, fluorescence change in the GFP channel. Each fluorescent signal for S1-GCaMP6f was measured from a single punctum. (FIG. 9C) Bar plots of the peak fluorescence changes in the GFP channel at the soma, proximal neurites, and distal neurites of cultured mouse hippocampal neurons expressing GCaMP6f or S1-GCaMP6f in response to a single (n=11 values from soma, 22 values from proximal neurites, and 22 values from distal neurites from 11 total trials from 6 neurons from 3 cultures for each of GCaMP6f and S1-GCaMP6f, for each trial, the calcium responses from the soma and two proximal neurites and two distal neurites were analyzed) or multiple (5AP, 10AP, or 20AP; n=5 values from soma, 10 values from proximal neurites, and 10 values from distal neurites from 5 total trials from 5 neurons from 3 cultures for GCaMP6f, n=6 values from soma, 12 values from proximal neurites, and 12 values from distal neurites from 6 total trials from 6 neurons from 3 cultures for S1-GCaMP6f, for each trial, the calcium responses from the soma and two proximal neurites and two distal neurites were analyzed) action potentials. Bar plots of medians with interquartile ranges are used throughout this figure, with individual values plotted as dots. n.s., not significant; two-way analysis of variance followed by post-hoc Bonferroni corrected multiple comparisons test; see Tables 14-27 for full statistics for FIG. 9. (FIG. 9D) Bar plots of the signal-to-noise ratio in the GFP channel at the soma, proximal neurites, and distal neurites for the neurons of FIG. 9C. (FIG. 9E-H) Scatter plots of half rise time (FIG. 9E), half decay time (FIG. 9F), peak fluorescence change (FIG. 9G), and signal-to-noise ratio (FIG. 9H) versus the number of puncta at the soma, per cell, for the recorded somatic calcium transients in response to a single action potential in S1-GCaMP6f expressing neurons (n=6 neurons from 3 cultures). (FIG. 9I-L) Scatter plots of half rise time (FIG. 9I), half decay time (FIG. 9J), peak fluorescence change (K), and punctum size (FIG. 9L) versus punctum brightness for the recorded somatic calcium transients in response to a single action potential in S1-GCaMP6f expressing neurons (n=6 neurons from 3 cultures). (FIG. 9M-P) Bar plots of half rise time (FIG. 9M), half decay time (FIG. 9N), peak fluorescence change (FIG. 9O), and punctum brightness (FIG. 9P) versus somatic punctum size for the recorded somatic calcium transients in response to a single action potential in S1-GCaMP6f expressing neurons (n=6 neurons from 3 cultures). n.s., not significant; Kruskal-Wallis analysis of variance followed by post-hoc test via Dunn's test with '<1 µm' as control group. (FIG. 9Q) Bar plot of the number of somatic calcium peaks in response to a single action potential for GCaMP6f and S1-GCaMP6f expressing neurons of FIG. 9C. n.s., not significant; Wilcoxon rank sum test. FIG. 9 (FIG. 9R) Representative fluorescent signals recorded from the soma, proximal neurites, and distal of a cultured mouse hippocampal neuron expressing GCaMP6f and a neuron expressing S1-GCaMP6f, with 5 µM forskolin stimulation at t=10 s. dF/F0, fluorescence changes in GFP channel. Each fluorescent signal for S1-GCaMP6f was measured from a single punctum. (S) Bar plot of the peak fluorescence changes in the GFP channel at the soma, proximal neurites, and distal neurites of cultured mouse hippocampal neurons expressing GCaMP6f or S1-GCaMP6f under 5 µM forskolin stimulation (n=6 somata, 12 proximal neurites, and 12 distal neurites from 6 neurons from 4 cultures for GCaMP6f, n=9 somata, 18 proximal neurites, and 18 distal neurites from 9 neurons from 9 cultures for S1-GCaMP6f). n.s., not significant; two-way analysis of variance followed by post-hoc Bonferroni corrected multiple comparisons test. (FIG. 9W-Z) Violin plots of the puncta size (FIG. 9W), distance to the nearest punctum (FIG. 9X), and puncta brightness (FIG. 9Y), and bar plot of number of puncta per cell (FIG. 9Z), for S1-GCaMP6f in neurons (n=792, 1314, 1230, 881, and 283 puncta in 9, 11, 11, 10, and 4 neurons from 1, 1, 1, 1, and 1 culture for 100 ng, 250 ng, 500 ng, 750 ng, and 1000 ng, respectively). Red line, median; black line, interquartile ranges; 100 ng, 250 ng, 500 ng, 750 ng, and 1000 ng, the mass of DNA of the SiRI construct used in calcium phosphate transfection per well in 24-well plates, with extra pUC19 dummy DNA added so that the total transfected DNA per well was 1500 ng; Dc was measured in live neurons 4 days after transfection on DIV 9; n.s., not significant; *, P<0.05; , P<0.01; *, P<0.001; Kruskal-Wallis analysis of variance followed by post-hoc test via Dunn's test with '100 ng' as control group. See Tables 14-27 for full statistics for FIG. 9.

FIG. 10A-Q provides photomicrographic images, traces, and graphs illustrating design of S2a-cAMPr and utilization for multiplexed SiRI imaging. Related to FIG. 8. (FIG. 10A) Construct design of S2a-cAMPr. O3-33, self-assembling subunit of O3-33 octahedron (24-mer); HA, influenza hemagglutinin epitope; 5H2L_2, a homo-pentamer; AA, amino acid (see Table 1 for sequences of the motifs; see Table 2 for all tested constructs). (FIG. 10B) A representative confocal image of a live cultured mouse hippocampal neuron expressing cAMPr. Scale bar, 20 µm. (FIG. 10C) Representative confocal images of a live cultured mouse hippocampal neuron expressing S2a-cAMPr and miRFP as a cell morphology marker. Scale bar, 20 µm. (FIG. 10D)

Representative fluorescent signals recorded from the soma, proximal neurites (5-25 µm away from soma), and distal neurites (50-250 µm away from soma) of cultured mouse hippocampal neurons expressing cAMPr or S2a-cAMPr with 5 µM forskolin stimulation at t=10 s. dF/F0, fluorescence changes in GFP channel. Each fluorescent signal for S2a-cAMPr was measured from a single punctum. FIG. 10 (FIG. 10E) Bar plot of the peak fluorescence changes in GFP channel at the soma, proximal neurites (5-25 µm away from soma), and distal neurites (50-250 µm away from soma) of cultured mouse hippocampal neurons expressing cAMPr or S2a-cAMPr after 5 µM forskolin stimulation (n=8 somata, 16 proximal neurites, and 16 distal neurites from 8 neurons from 5 cultures for cAMPr; n=13 somata, 26 proximal neurites, and 26 distal neurites from 13 neurons from 9 cultures for S2a-cAMPr). Bar plots of medians with interquartile ranges are used throughout this figure, with individual values plotted as dots. n.s., not significant; two-way analysis of variance followed by post-hoc Sidak's multiple comparisons test; see Tables 38-40 for full statistics for FIG. 10. (FIG. 10F) Signal-to-noise ratio in the GFP channel at the soma, proximal neurites, and distal neurites for the neurons of FIG. 10E. n.s., not significant; *, P<0.05. (FIG. 10G) Half rise time of reported cAMP signals at the soma, for the neurons of FIG. 10E. n.s., not significant. (FIG. 10Q) Box plot of the percentage of the soma-localized or neurite-localized fluorescent reporter puncta that did not contain the other type of reporter, per cell, as identified by immunostaining in neurons co-expressing S1-GCaMP6f, S2a-cAMPr, and miRFP (n=6 neurons from 6 cultures).

(FIG. 11A) Maximum intensity projection (MIP) confocal images of HeLa cells co-expressing S1-GCaMP6f, S2-cAMPr, S3-ExRaiAKAR, and the cell morphological marker, miRFP. Live, images taken from live cell imaging; Fixed, images taken after fixation and immunostaining against Xpress (magenta), HA (cyan), and V5 (yellow). Scale bar, 20 µm. (FIG. 11B) Recorded fluorescent signals of $Ca^{2+}$ (magenta), cAMP (cyan), and PKA (yellow) activities of individual HeLa cells under forskolin stimulation by pipetting 100 µL of 100 µM forskolin in FLUOROBRITE™ DMEM dropwise onto a HeLa cell culture in 1.9 mL FLUOROBRITE™ DMEM (for a 5 µM final concentration of forskolin applied to the HeLa cell culture) at t=2 min (n=4 cells co-expressing S1-GCaMP6f, S2-cAMPr, S3-ExRaiAKAR, and miRFP from 2 cultures). $Ca^{2+}$ and cAMP signals are plotted as dF/F0 (fluorescence intensity change) and PKA signals are plotted as dR/R0 (change of fluorescence ratio between 488 nm excitation and 405 nm excitation when imaging in the GFP emission channel). (FIG. 11C) Averaged fluorescent signals of $Ca^{2+}$ (magenta), cAMP (cyan), and PKA (yellow) activities of HeLa cells shown in FIG. 11B (n=4 cells co-expressing S1-GCaMP6f, S2-cAMPr, S3-ExRaiAKAR, and miRFP from 2 cultures). Colored lines, mean; colored and shaded boundaries, standard error of mean.

(FIG. 12 A) Maximum intensity projection (MIP) confocal images of the live cultured mouse hippocampal neuron co-expressing S1-GCaMP6f, S2-cAMPr, S3-ExRaiAKAR, and miRFP shown in FIG. 13A. Upper left panel, under miRFP channel; upper right panel, under GFP channel; bottom panel, a composite image from GFP and miRFP channels. Orange squares, boundaries of the regions to be shown in enlarged views in FIG. 12B-F. Scale bars, 20 µm. (FIG. 12B-F) Top left, an enlarged view of the corresponding region marked in FIG. 12A (by the corresponding letter) under green channel. Top right, an MIP confocal image of the same region after fixation and immunostaining against Xpress (magenta), HA (cyan), and V5 (yellow). Bottom, recorded $Ca^{2+}$ (magenta), cAMP (cyan), and PKA (yellow) activities measured from puncta indicated by white arrowheads in the top right view during live cell imaging under 50 µM forskolin stimulation for 3 minutes. Scale bars, 2 µm. Note that FIG. 12E and FIG. 12C in this figure are identical to FIG. 13B and FIG. 13C, respectively. (FIG. 12G-I) Bar plots of Pearson correlation coefficients of the $Ca^{2+}$ (FIG. 12G; n=8 neurons from 8 cultures), cAMP (FIG. 12H; n=5 neurons from 5 cultures), or PKA (FIG. 12I; n=5 neurons from 5 cultures) responses recorded from soma- and neurite-localized puncta within single cultured mouse hippocampal neurons co-expressing S1-GCaMP6f, S2-cAMPr, S3-ExRaiAKAR, and miRFP. Two puncta at the soma (or along a neurite) were defined to be adjacent if they were less than 5 µm apart, and as distant if they were at least 10 µm apart at the soma (or at least 20

Figure 1A:
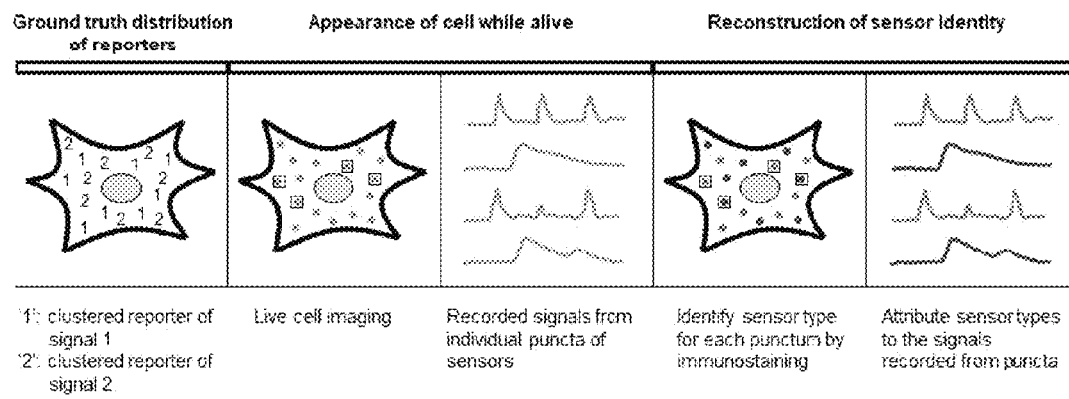
FIG. 1A-D presents a schematic diagram illustrating how spatial multiplexing of signals can increase the number of physiological signals simultaneously imaged in a single cell.

μm apart along a neurite). Neurite-localized puncta in this analysis were 20-60 μm away from the soma. Bar plots of medians with interquartile ranges are used, with individual values plotted as dots. n.s., not significant; *, $P<0.05$; **, $P<0.01$; Kruskal-Wallis analysis of variance followed by post-hoc Dunn's multiple comparisons test with 'two adjacent puncta at soma' as control group; see Tables 46-48 for full statistics for FIG. 12.

FIG. 13A-L presents schematics, photomicrographs, and graphs reporting the results of spatially multiplexed imaging of three GFP-based reporters for calcium, cAMP, and PKA in single cultured neurons under forskolin stimulation. (FIG. 13A) Maximum intensity projection (MIP) confocal images of a representative live cultured mouse hippocampal neuron co-expressing S1-GCaMP6f, S2-cAMPr, S3-ExRaiAKAR, and the cell morphological marker, miRFP. Left panel, miRFP channel; right panel, GFP channel with high image contrast for better visualization of neurite-localized puncta. Yellow squares, enlarged in FIG. 13B-C. Scale bar, 20 μm. See FIG. 12 for more enlarged views of the neuron. (FIG. 13B) Top left, enlarged view of the soma region indicated in FIG. 13A with "B", with reduced image contrast for less saturated pixels in this field of view. Top right, MTP confocal image of the same region after fixation and immunostaining against Xpress (magenta), HA (cyan), and V5 (yellow). Bottom, recorded $Ca^{2+}$ (magenta), cAMP (cyan), and PKA (yellow) activities measured from puncta indicated by white arrowheads in the top right view during live cell imaging after 3 min of 50 μM forskolin stimulation. Scale bar, 2 μm. (FIG. 13C) As in FIG. 13B, but for the neurite region indicated in FIG. 13A with "C". (FIG. 13D) Bar plot of the number of soma-localized and neurite-localized puncta per cell identified by immunostaining of neurons co-expressing S1-GCaMP6f, S2-cAMPr, S3-ExRaiAKAR, and miRFP (n=5 neurons from 5 cultures; counted in 3D volumes). (FIG. 13E) Bar plot of the percentage of the soma-localized or neurite-localized puncta of S1-GCaMP6f, S2-cAMPr, or S3-ExRaiAKAR that did not contain the other types of reporters, per cell, for the neurons of FIG. 13D. (FIG. 13F) Violin plots of the puncta size (left) and distance to the nearest punctum (right) of all puncta in the GFP channel in live neurons co-expressing S1-GCaMP6f, S2-cAMPr, S3-ExRaiAKAR, and miRFP (n=890 puncta from 5 neurons from 5 cultures). Red line, median; black line, interquartile ranges. (FIG. 13G) Averaged fluorescent signals of $Ca^{2+}$ (magenta), cAMP (cyan), and PKA activities (yellow) at the soma (left) and on a proximal neurite (right; puncta 20-60 μm away from soma) under 50 μM forskolin stimulation for 3 minutes (n=24 neurons from 16 cultures). Throughout this paper: colored centerlines, mean; colored, shaded boundaries, standard error of mean. (FIG. 13H) Somatic $Ca^{2+}$, cAMP, and PKA activities from a representative neuron with a transient calcium response at the soma (left), and averaged somatic $Ca^{2+}$, cAMP, and PKA activities from all neurons with transient calcium responses at the soma (right; n=7 neurons from 6 cultures) under 50 μM forskolin stimulation for 3 minutes. (FIG. 13I) As in FIG. 13H, but for neurons with sustained calcium responses at the soma (n=17 neurons from 12 cultures). (FIG. 13J) Averaged somatic $Ca^{2+}$ activity from neurons with transient calcium responses at the soma (blue; n=7 neurons from 6 cultures) and from neurons with sustained calcium responses at the soma (red; n=17 neurons from 12 cultures). Thin and light colored lines, somatic $Ca^{2+}$ activities from individual neurons. n.s., not significant; *, $P<0.05$; **, $P<0.01$; Wilcoxon rank sum tests for peak responses over indicated time windows (horizontal lines) and times to half rise ($t_{1/2}$ rise); see Tables 49-51 for full statistics for FIG. 13. (FIG. 13K) Averaged somatic cAMP activity for the neurons of FIG. 13J. n.s., not significant; *, $P<0.05$; Wilcoxon rank sum tests for rise slopes (arrow near the rise phase), decay slopes (arrow near the decay phase), and peak responses (horizontal line near the peak response). (FIG. 13L) Averaged somatic PKA activity for the neurons of FIG. 13J. *, $P<0.05$; ***, $P<0.001$; Wilcoxon rank sum tests for rise slopes (arrow near the rise phase) and peak responses (horizontal line near the peak response).

FIG. 14A-L presents schematics, photomicrographs, and graphs reporting the results of the spatially multiplexed imaging of $Ca^{2+}$ and PKA activities via two GFP-based reporters in brain slice under forskolin stimulation. (FIG. 14A) Representative confocal images of hippocampus CA1 region in sagittal brain slices from mice co-expressing S1-GCaMP6f, S3-ExRaiAKAR, and the cell morphological marker mRuby3-6×FLAG by hippocampus-targeted in utero electroporation. Scale bar, 200 μm. (FIG. 14B) Maximum intensity projection (MIP) confocal images of a representative live CA1 pyramidal neuron from mice co-expressing S1-GCaMP6f (green), S3-ExRaiAKAR (green), and the cell morphological marker mRuby3-6×FLAG (magenta). Yellow squares, boundaries of regions of interest (ROIs) shown in enlarged views in FIG. 14C. Scale bar, 20 μm. (FIG. 14C) MIP confocal images of the ROIs defined in FIG. 14B before (left; S1-GCaMP6f and S3-ExRaiAKAR in the GFP channel) and after (right; cyan, anti-Xpress; yellow, anti-V5) immunostaining. Scale bars, 2.5 μm. (FIG. 14D) Bar plot of the number of soma-localized, apical dendrite-localized, or basal dendrite-localized puncta of S1-GCaMP6f or S3-ExRaiAKAR per cell identified by immunostaining of brain slices from mice co-expressing S1-GCaMP6f, S3-ExRaiAKAR, and mRuby3-6×FLAG (n=6 CA1 pyramidal neurons from 4 slices from 3 mice; counted in 3D volumes). Bar plots of medians with interquartile ranges are used throughout this figure, with individual values plotted as dots. (FIG. 14E) Bar plot of the percentage of the soma-localized, apical dendrite-localized, or basal dendrite-localized puncta of S1-GCaMP6f or S3-ExRaiAKAR that did not contain the other type of reporter, per cell, for the neurons of FIG. 14D. (FIG. 14F) Violin plots of punctum size (left) and distance to the nearest punctum (right), for all puncta in the GFP channel in live CA1 pyramidal neurons co-expressing S1-GCaMP6f, S3-ExRaiAKAR, and mRuby3-6×FLAG in acute brain slices (n=479 puncta from 5 CA1 pyramidal neurons from 3 slices from 3 mice). Red line, median; black line, interquartile ranges. (FIG. 14G) Representative fluorescent signals for $Ca^{2+}$ (cyan) and PKA (yellow) activities at the soma (left), at a location on the apical dendrite (middle), and at a location on the basal dendrite (right) of CA1 pyramidal neurons before, during, and after a 15-min-long 50 μM forskolin stimulation. Each fluorescent signal was measured from a single punctum. (FIG. 14H) Averaged fluorescent signals at the soma (left), at a location on the apical dendrite (middle; sampled at locations 30-100 μm away from soma throughout this figure), and at a location on the basal dendrite (right; sampled at locations 10-40 μm away from soma throughout this figure) obtained as in FIG. 14G (n=14 neurons from 6 slices from 3 mice). Throughout this figure: colored lines, mean; colored, shaded boundaries, standard error of mean. (FIG. 14I) Somatic $Ca^{2+}$ and PKA activities from a representative neuron where the forskolin treatment induced a delayed somatic calcium response (left) and the averaged soma $Ca^{2+}$ and PKA activities from all neurons with delayed somatic calcium responses (right; n=6 neurons from 5 slices from 3 mice). (FIG. 14J) As in FIG.

14J, but for neurons with immediate somatic calcium responses (right; n=6 neurons from 2 slices from 2 mice). (FIG. 14K) Averaged somatic $Ca^{2+}$ activity from neurons with delayed somatic calcium responses (blue; n=6 neurons from 5 slices from 3 mice) and from neurons with immediate somatic calcium responses (red; n=6 neurons from 2 slices from 2 mice). n.s., not significant; **, P<0.01; Wilcoxon rank sum tests for peak responses over indicated time windows (horizontal lines) and times to half rise ($t_{1/2}$ rise); see Tables 74-75 for full statistics for FIG. 14. (FIG. 14L) Averaged somatic PKA activity from neurons of FIG. 14K. *, P<0.05; **, P<0.01; Wilcoxon rank sum tests for rise slopes (arrow near the rise phase), peak responses (horizontal line), and durations of PKA activation (arrow on the right hand side of the panel).

Figure 15A:
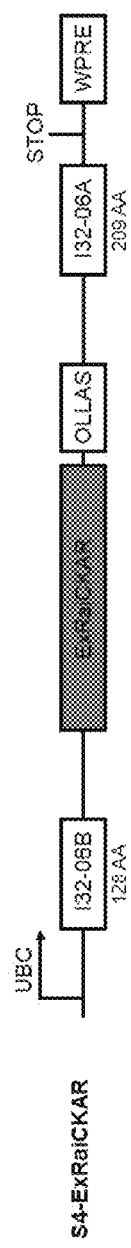
Figure 15B:
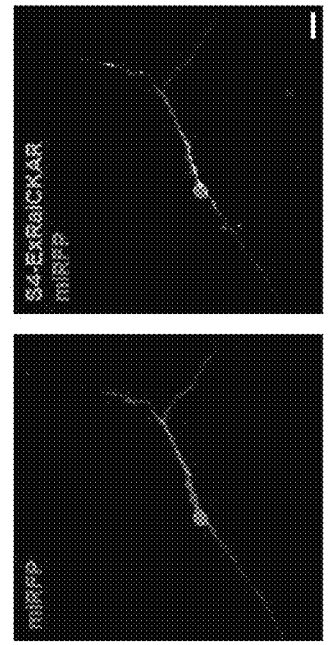
Figure 15B:
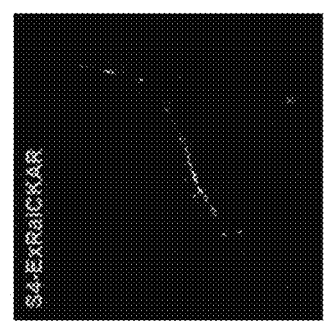
Figure 15C:
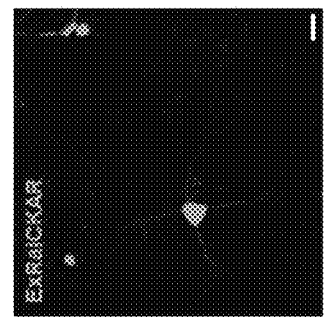
Figure 15I:
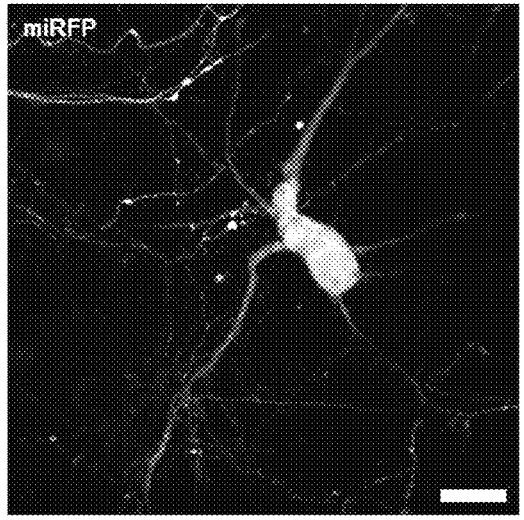
Figure 15J:

FIG. 15A-Q presents schematics, photomicrographs, and graphs reporting the results of the spatially multiplexed imaging of four GFP-based reporters for $Ca^{2+}$, cAMP, PKA, and PKC activities in single cultured neurons. (FIG. 15A) Construct design of S4-ExRaiCKAR. ExRaiCKAR, a GFP-based fluorescent PKC reporter; I32-06B, self-assembling subunit B of I32-06 two-component icosahedron; OLLAS, E. coli OmpF linker and mouse langerin fusion sequence; I32-06A, self-assembling subunit A of I32-06 two-component icosahedron; AA, amino acid (see Table 1 for sequences of the motifs; see Table 2 for all tested constructs). (FIG. 15B) Representative confocal image of live cultured mouse hippocampal neurons expressing ExRaiCKAR. Scale bar, 20 µm. (FIG. 15C) Representative confocal image of live cultured mouse hippocampal neurons expressing S4-ExRaiCKAR and miRFP as a cell morphology marker. Scale bar, 20 µm. (FIG. 15D) Representative fluorescent signals recorded from the soma, proximal neurites (5-25 µm away from soma throughout this figure), and distal neurites (50-250 µm away from soma throughout this figure) of cultured mouse hippocampal neurons expressing ExRaiCKAR or S4-ExRaiCKAR under 100 ng/ml phorbol 12-myristate 13-acetate (PMA) stimulation at t=1 min. dF/F0, fluorescence changes in GFP channel. Each fluorescent signal for S4-ExRaiCKAR was measured from a single punctum. (FIG. 15E) Bar plot of the peak fluorescence changes in the GFP channel at the soma, and at locations along the proximal neurites and distal neurites of cultured mouse hippocampal neurons expressing ExRaiCKAR or S4-ExRaiCKAR under 100 ng/ml PMA stimulation (n=10 somata, 20 proximal neurites, and 20 distal neurites from 10 neurons from 4 cultures for ExRaiCKAR; n=11 somata, 22 proximal neurites, and 22 distal neurites from 11 neurons from 4 cultures for S4-ExRaiCKAR). n.s., not significant; ***, P<0.001; two-way analysis of variance followed by post-hoc Bonferroni corrected multiple comparisons test; see Tables 53-55 for full statistics for FIG. 15. (FIG. 15F) Signal-to-noise ratio in the GFP channel at the soma, proximal neurites, and distal neurites for the neurons of FIG. 15E. (FIG. 15G) Half rise time of reported PKC signals at the soma, for the neurons of FIG. 15E. (FIG. 15H) Violin plots of punctum size (left), distance to the nearest punctum (middle), and diffusion constant over 1 hour (right) for S4-ExRaiCKAR in neurons (n=1007 puncta from 5 neurons from 4 cultures for puncta size and distance to the nearest punctum; n=117 puncta from 2 neurons from 1 culture for diffusion constant). Red line, median; black line, interquartile ranges. (FIG. 15I) A maximum intensity projection (MIP) confocal image in the miRFP channel of a representative live cultured mouse hippocampal neuron co-expressing S1-GCaMP6f, S2-cAMPr, S3-ExRaiAKAR, S4-ExRaiCKAR, and the cell morphological marker miRFP. Scale bar, 20 µm. (FIG. 15J) An MIP confocal image in the GFP channel of the same neuron shown in FIG. 15I. Orange rectangles, boundaries of the regions to be shown in enlarged views in FIG. 15K-L. (FIG. 15K) Top left, the enlarged view of the somatic region in FIG. 15J. Top right, an MIP confocal image of the same region after fixation and two rounds of immunostaining against HA (cyan) and OLLAS (red) in the first round and Xpress (magenta) and V5 (yellow) in the second round. Bottom, recorded fluorescent signals of $Ca^{2+}$ (magenta), cAMP (cyan), PKA (yellow), and PKC (red) activities measured from puncta indicated by white arrowheads in the top right view during live cell imaging under two stimulations, 50 µM forskolin for 3 minutes and 100 ng/mL PMA for 3 minutes. (FIG. 15L) As in FIG. 15K, but for the neuritic region in FIG. 15J. (FIG. 15M) Averaged fluorescent signals of $Ca^{2+}$ (magenta), cAMP (cyan), PKA (yellow), and PKC (red) activities at the soma under two stimulations, 50 µM forskolin for 3 minutes and 100 ng/mL PMA for 3 minutes (n=5 neurons from 5 cultures). Colored lines, mean; colored, shaded boundaries, standard error of mean. (FIG. 15N) As in FIG. 15M, but for neurite signals (from locations 20-60 µm away from the soma). (FIG. 15O) Bar plot of the number of soma-localized or neurite-localized puncta per cell for S1-GCaMP6f, S2-cAMPr, S3-ExRaiAKAR, and S4-ExRaiCKAR identified by two rounds of immunostaining in neurons co-expressing S1-GCaMP6f, S2-cAMPr, S3-ExRaiAKAR, S4-ExRaiCKAR, and miRFP (n=5 neurons from 5 cultures; counted in 3D volumes). (FIG. 15P) Bar plot of the percentage of the soma-localized or neurite-localized puncta of S1-GCaMP6f, S2-cAMPr, S3-ExRaiAKAR, or S4-ExRaiCKAR that did not contain the other types of reporters, per cell, for the neurons of FIG. 15O. (FIG. 15Q) Violin plots of the puncta size (left) and distance to the nearest punctum (right) of all puncta in the GFP channel in live neurons co-expressing S1-GCaMP6f, S2-cAMPr, S3-ExRaiAKAR, S4-ExRaiCKAR, and miRFP (n=1612 puncta from 5 neurons from 5 cultures). Red line, median; black line, interquartile ranges.

FIG. 16A-K presents schematics, photomicrographs, and graphs reporting the results of the combined spatial and spectral multiplexing for simultaneous imaging of five signals within single neurons. (FIG. 16A) Construct design of S2-RAB_EKARev. RAB_EKARev, an RFP-based fluorescent ERK reporter; 1M3U, self-assembling subunit of 1M3U assembly; VSVg, vesicular stomatitis virus G protein fragment epitope; 2L8HC4_15, a homo-tetramer; AA, amino acid (see Table 1 for sequences of the motifs; see Table 2 for all tested constructs). (FIG. 16B) A representative confocal image of live cultured mouse hippocampal neurons expressing RAB_EKARev. Scale bar, 20 µm. (FIG. 16C) Representative confocal image of a live cultured mouse hippocampal neuron expressing S2-RAB_EKARev and miRFP as a cell morphology marker. Scale bar, 20 µm. (FIG. 16D) Representative fluorescent signals recorded from the soma, proximal neurites (5-25 µm away from soma throughout this figure), and distal neurites (50-250 µm away from soma throughout this figure) of cultured mouse hippocampal neurons expressing RAB_EKARev or S2-RAB_EKARev under 100 µM DHPG stimulation at t=2 min. dF/F0, fluorescence changes in RFP channel. Each fluorescent signal for S2-RAB_EKARev was measured from a single punctum. (FIG. 16E) Bar plot of the peak fluorescence changes in the RFP channel at the soma, and at locations along proximal neurites and distal neurites, of cultured mouse hippocampal neurons expressing RAB_EKARev or S2-RAB_EKARev under 100 µM DHPG stimulation (n=5 somata, 10 proximal neurites, and 10 distal neurites from 5 neurons from 5 cultures for RAB_EKARev; n=5 somata, 10 proximal neurites, and 10 distal neurites from 5 neurons from 5 cultures for S2-RAB_EKARev). n.s., not significant; two-way analysis of variance followed by post-hoc Bonferroni corrected multiple comparisons test; see Tables 65-67 for full statistics for FIG. 16. (FIG. 16F) Signal-to-noise ratio in the RFP channel at the soma, proximal neurites, and distal neurites for the neurons of FIG. 16E. (FIG. 16G) Half rise time of reported ERK signals at the soma, for the neurons of FIG. 16E. (FIG. 16H) Maximum intensity projection (MIP) confocal images in the miRFP channel (left), GFP channel (middle), and GFP and RFP channels merged (right), of a representative live cultured mouse hippocampal neuron co-expressing S1-GCaMP6f, S2-cAMPr, S3-ExRaiAKAR, S4-ExRaiCKAR, S2-RAB_EKARev, and the cell morphological marker miRFP. Scale bar, 20 µm. (FIG. 16I) A composite image from the registration between the MIP confocal image of the same neuron in FIG. 16H in the RFP channel before fixation and the MIP confocal image of the same neuron after fixation and immunostaining against Xpress (magenta), V5 (yellow), and OLLAS (red). (FIG. 16J) Recorded fluorescent signals for $Ca^{2+}$ (magenta), cAMP (cyan), PKA (yellow), PKC (red), and ERK (green) activities at the soma (left) and neurites (right; 30 µm away from soma) of the same neuron in FIG. 16H under two stimulations, 100 µM DHPG for 3 minutes and 50 µM forskolin for 3 minutes. Each fluorescent signal was measured from a single punctum. (FIG. 16K) Averaged fluorescent signals of $Ca^{2+}$ (magenta), cAMP (cyan), PKA (yellow), PKC (red), and ERK (green) activities at the soma (left) and along neurites (right; 20-60 µm away from soma) under two stimulations, 100 µM DHPG for 3 minutes and 50 µM forskolin for 3 minutes (n=4 neurons from 3 cultures). Colored lines, mean; colored, shaded boundaries, standard error of mean.

Figure 5E:
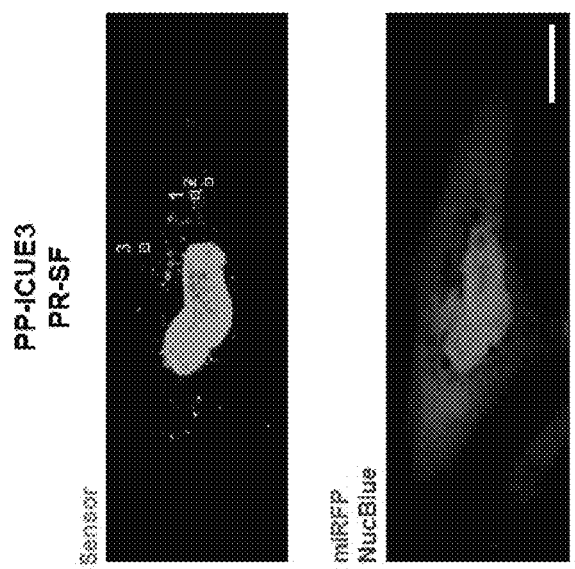
Figure 5F:
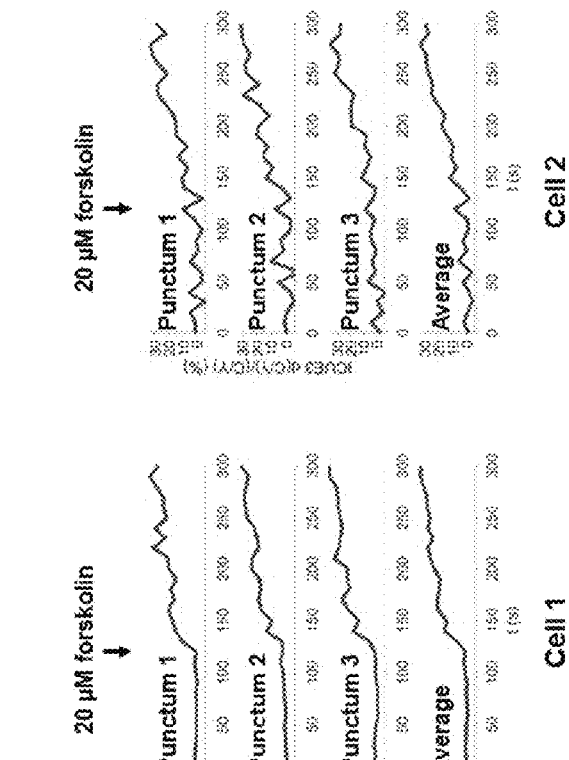
Figure 5G:
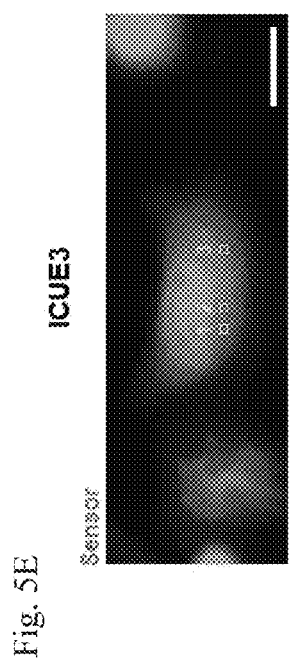
Figure 5H:
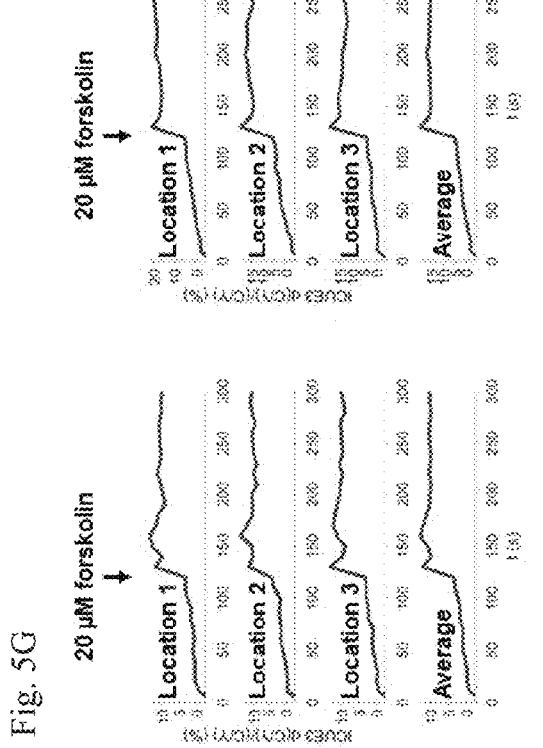
Figure 17J:
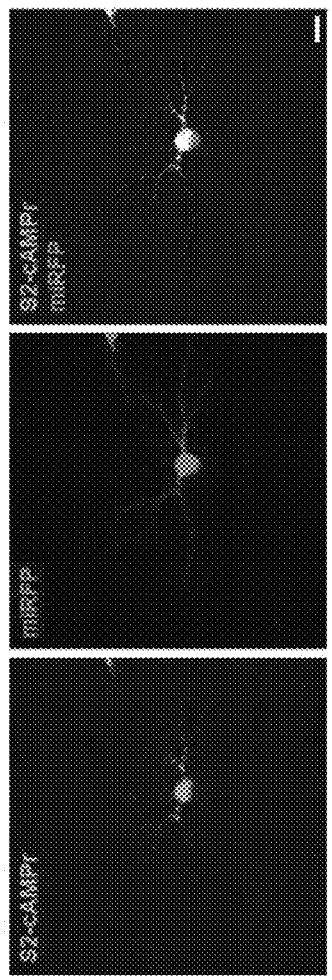
Figure 17K:
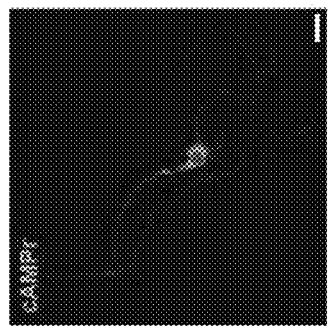
Figure 17L:
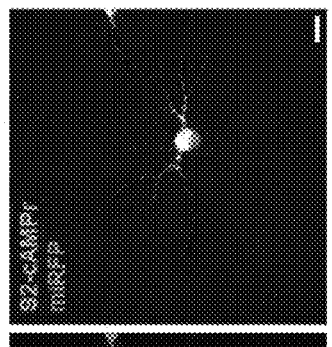
Figure 17M:
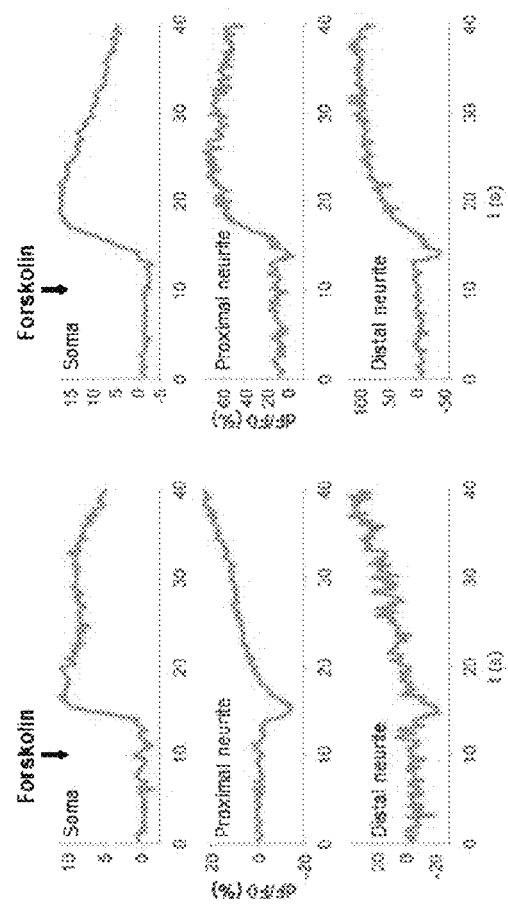
Figure 17N:
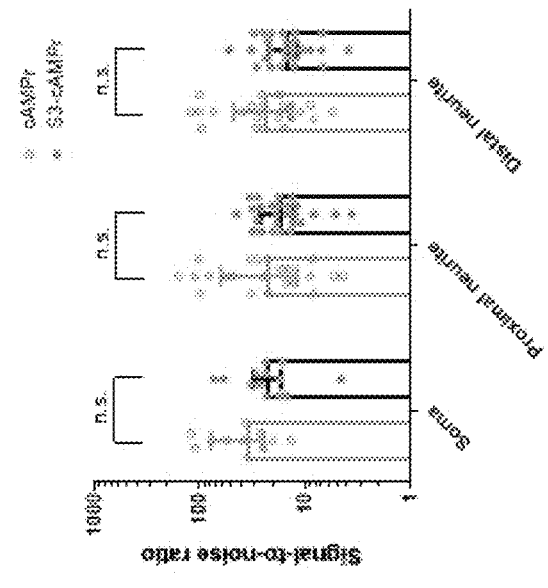
Figure 17O:
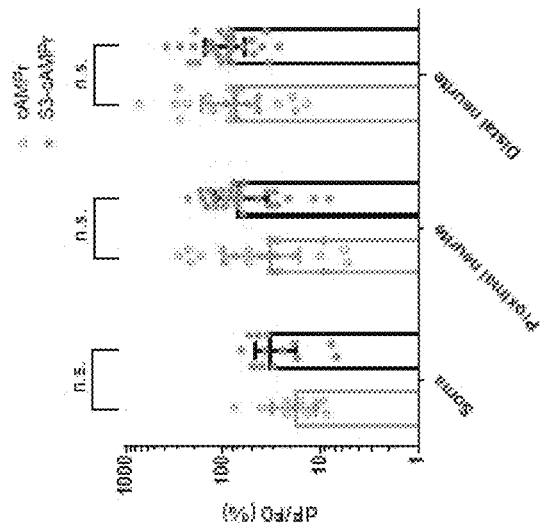
Figure 17P:
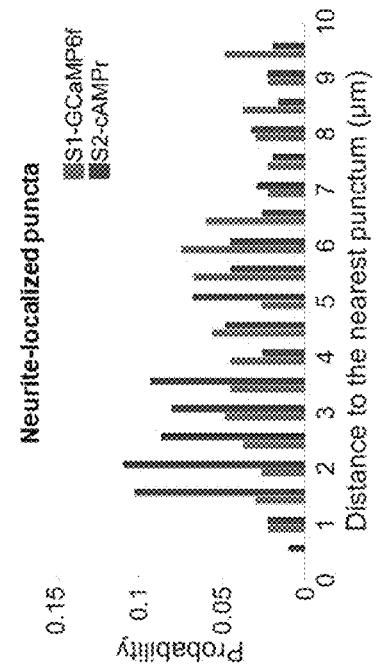
Figure 17Q:
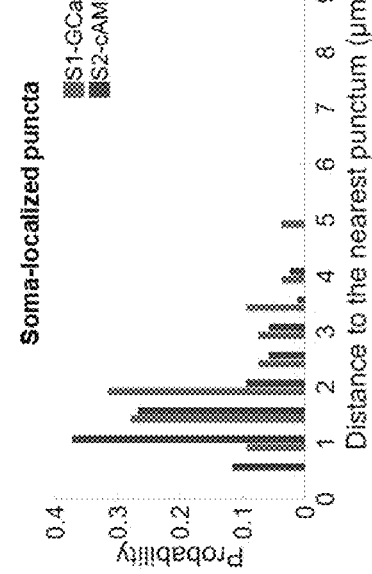
Figure 17R:
Figure 17S:
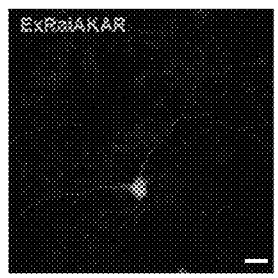
Figure 17T:
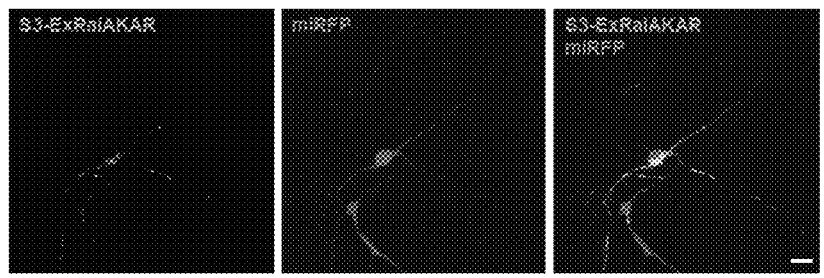
Figure 17U:
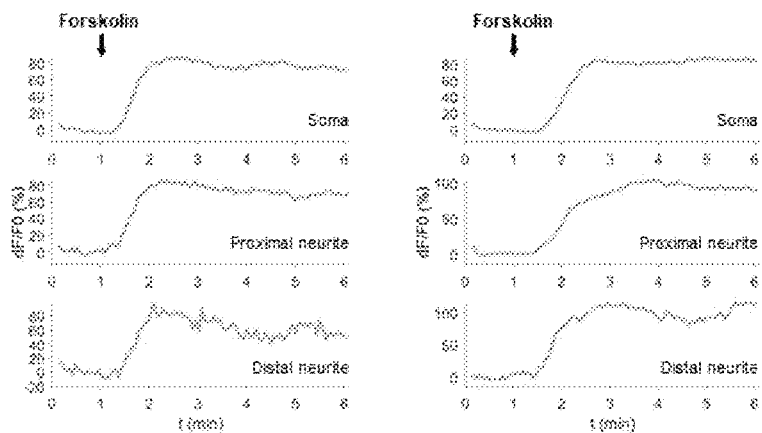
Figure 17V:
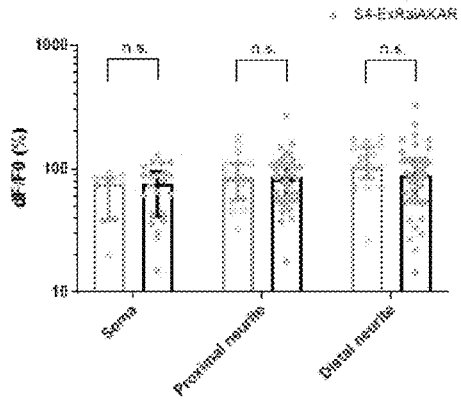
Figure 17W:
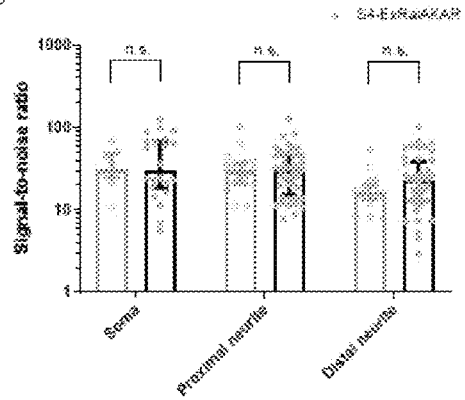

FIG. 17A-W presents schematics, photomicrographs, and graphs reporting the results of the design and functional characterization of fluorescent sensors clustered by protein scaffolds in neurons. FIG. 17A shows a schematic diagram of the construct design of S1-GCaMP6f. Coil 1, homotetramer HexCoil-Ala; Xpress, synthetic peptide Xpress epitope; I3-01, self-assembling subunit of I3-01 dodecahedron (60-mer); O3-33, self-assembling subunit of O3-33 octahedron (24-mer); HA, influenza hemagglutinin epitope; Coil 2, homo-pentamer 5H2L_2; AA, amino acid. All motif sequences used in FIG. 17A-W are listed in Table 1; Table 2 lists all tested constructs. FIG. 17B shows a representative image of live cultured mouse hippocampal neurons expressing GCaMP6f Scale bar, 20 µm throughout this figure. FIG. 17C shows representative images of live cultured mouse hippocampal neurons expressing S1-GCaMP6f and miRFP as a cell morphology marker. FIG. 17D shows representative fluorescent signals recorded from the soma, proximal neurites (5-25 µm away from soma throughout this figure), and distal neurites (50-250 µm away from soma throughout this figure) of a cultured mouse hippocampal neuron expressing GCaMP6f (left) or S1-GCaMP6f (right) in response to single action potential (1 AP) at t=5 s triggered by current injection via whole-cell patch clamp at the soma. dF/F0, fluorescence change in GFP channel. Each fluorescent signal for S1-GCaMP6f was measured from a single punctum. FIG. 5E shows a bar plot of the peak fluorescence change in the GFP channel at the soma, proximal neurites, and distal neurites of cultured mouse hippocampal neurons expressing GCaMP6f or S1-GCaMP6f in response to a single action potential. Bar plots of medians with interquartile ranges are used throughout this study, with individual values plotted as dots. Two-way analysis of variance followed by post-hoc Bonferroni corrected multiple comparisons test. FIG. 17F shows a bar plot of the signal-to-noise ratio in the GFP channel at the soma, proximal neurites, and distal neurites of cultured mouse hippocampal neurons expressing GCaMP6f or S1-GCaMP6f in response to single action potential. n.s., not significant; two-way analysis of variance followed by post-hoc Bonferroni corrected multiple comparisons test. FIG. 17G shows representative fluorescent signals recorded from the soma, proximal neurites, and distal of a cultured mouse hippocampal neuron expressing GCaMP6f and a neuron expressing S1-GCaMP6f, with 5 µM forskolin stimulation at t=10 s. Each fluorescent signal for S1-GCaMP6f was measured from a single punctum. FIG. 17H shows a bar plot of the peak fluorescence change in the GFP channel at the soma, proximal neurites, and distal neurites of cultured mouse hippocampal neurons expressing GCaMP6f or S1-GCaMP6f under 5 µM forskolin stimulation; two-way analysis of variance followed by post-hoc Bonferroni corrected multiple comparisons test. FIG. 17I shows a bar plot of the signal-to-noise ratio in the GFP channel at the soma, proximal neurites, and distal neurites of cultured mouse hippocampal neurons expressing GCaMP6f or S1-GCaMP6f under 5 µM forskolin stimulation. Two-way analysis of variance followed by post-hoc Bonferroni corrected multiple comparisons test. FIG. 17J presents a schematic diagram showing the construct design of S2a-cAMPr: 1M3U, self-assembling subunit of 1M3U assembly; HA, influenza hemagglutinin epitope; 2L8HC4_15, a homo-tetramer; AA, amino acid. FIG. 17K shows a representative image of live cultured mouse hippocampal neurons expressing cAMPr. FIG. 17L shows representative images of live cultured mouse hippocampal neurons expressing S2a-cAMPr and miRFP as a cell morphology marker. FIG. 17M shows representative fluorescent signals recorded from the soma, proximal neurites, and distal neurites of cultured mouse hippocampal neurons expressing cAMPr or S2a-cAMPr under 5 µM forskolin stimulation at t=10 s. dF/F0, fluorescence change in GFP channel. Each fluorescent signal for S2a-cAMPr was measured from a single punctum. FIG. 17N shows a bar plot of the peak fluorescence change in GFP channel at the soma, proximal neurites, and distal neurites of cultured mouse hippocampal neurons expressing cAMPr or S2a-cAMPr under 5 µM forskolin stimulation. n.s., not significant; two-way analysis of variance followed by post-hoc Bonferroni corrected multiple comparisons test. FIG. 17O shows a bar plot of the signal-to-noise ratio in the GFP channel at the soma, proximal neurites, and distal neurites of cultured mouse hippocampal neurons expressing cAMPr or S2a-cAMPr under 5 µM forskolin stimulation. n.s., not significant; two-way analysis of variance followed by post-hoc Bonferroni corrected multiple comparisons test. FIG. 17P shows a histogram of the distance to the nearest punctum for each soma-localized punctum in cultured mouse hippocampal neurons expressing S1-GCaMP6f or S2a-cAMPr. FIG. 17Q shows a histogram of the distance to the nearest punctum for each neurite-localized punctum in cultured mouse hippocampal neurons expressing S1-GCaMP6f or S2a-cAMPr. FIG. 17R presents a schematic diagram of the construct design of S3-ExRaiAKAR: 3VDX, self-assembling subunit of 3VDX tetrahedron (12-mer); V5, simian virus 5-derived epitope; 5L6HC3_1, a homo-trimer; AA, amino acid. FIG. 17S shows a representative image of live cultured mouse hippocampal neurons expressing ExRaiAKAR. FIG. 17T shows representative images of live cultured mouse hippocampal neurons expressing S3-ExRaiAKAR and miRFP as a cell morphology marker. FIG. 17U shows representative fluorescent signals recorded from the soma, proximal neurites, and distal neurites of cultured mouse hippocampal neurons expressing ExRaiAKAR (left panel) or S3-ExRaiAKAR (right panel) under 5 µM forskolin stimulation at t=1 min. dF/F0, fluorescence change in GFP channel. FIG. 17V shows a bar plot of the peak fluorescence change in GFP channel at the soma, proximal neurites, and distal neurites of cultured mouse hippocampal neurons expressing ExRaiAKAR or S3-ExRaiAKAR under 5 µM forskolin stimulation; two-way analysis of variance followed by post-hoc Bonferroni corrected multiple comparisons test. FIG. 17W shows a bar plot of the signal-to-noise ratio in the GFP channel at the soma, proximal neurites, and distal neurites of cultured mouse hippocampal neurons expressing ExRaiAKAR or S3-ExRaiAKAR under 5 µM forskolin stimulation; two-way analysis of variance followed by post-hoc Bonferroni corrected multiple comparisons test. Table 8 provides statistics for FIGS. 17E, F, H, and I; Table 9 provides statistics for FIG. 17H; Table 10 provides statistics for FIG. 17I; Table 35 provides statistics for FIG. 17N, O; Table 36 provides statistics for FIG. 17J; and Table 37 provides statistics for FIG. 17K.

FIG. 18A-G presents graphs of results of electrophysiological properties of cultured mouse hippocampal neurons expressing SiRIs. Related to FIGS. 8 and 15. Bar plots of medians with interquartile ranges are used throughout this figure, with individual values plotted as dots. n.s., not significant; Kruskal-Wallis analysis of variance followed by post-hoc test via Dunn's test with non-expressing neurons, labeled as 'Negative', as control group throughout the figure; see Tables 56-62 for full statistics for FIG. 18. (FIG. 18A) Resting potential. (FIG. 18B) Membrane resistance. (FIG. 18C) Membrane capacitance. (FIG. 18D) Holding current while held at −65 mV. (FIG. 18E) Action potential amplitude. (FIG. 18F) Action potential width. (FIG. 18G) Action potential threshold. For FIG. 18A-D, n=6 neurons from 4 cultures for Negative; n=6 neurons from 2 cultures for GCaMP6f, n=9 neurons from 5 cultures for S1-GCaMP6f, n=6 neurons from 4 cultures for S2-cAMPr; n=5 neurons from 3 cultures for S3-ExRaiAKAR; n=5 neurons from 3 cultures for S4-ExRaiCKAR; n=7 neurons from 3 cultures for S2a-cAMPr. For FIG. 18E-G, n=6 neurons from 2 cultures for Negative; n=6 neurons from 2 cultures for GCaMP6f, n=5 neurons from 3 cultures for S1-GCaMP6f, n=6 neurons from 4 cultures for S2-cAMPr; n=5 neurons from 3 cultures for S3-ExRaiAKAR; n=5 neurons from 3 cultures for S4-ExRaiCKAR; n=5 neurons from 3 cultures for S2a-cAMPr.

FIG. 19A-D shows photomicrographs of immunostaining of cellular organelles in SiRI-expressing neurons. Related to FIGS. 8 and 15. Representative confocal images of cultured mouse hippocampal neurons expressing (FIG. 19A) S1-GCaMP6f (anti-AIF staining, n=5 neurons from 2 cultures; anti-EEA1 staining, n=5 neurons from 2 cultures; anti-Lamp1 staining, n=5 neurons from 2 cultures; anti-PDI staining, n=4 neurons from 2 cultures; anti-RCAS1 staining, n=4 neurons from 2 cultures), (FIG. 19(B) S2-cAMPr (anti-AIF staining, n=4 neurons from 1 culture; anti-EEA1 staining, n=6 neurons from 1 culture; anti-Lamp1 staining, n=2 neurons from 1 culture; anti-PDI staining, n=2 neurons from 1 culture; anti-RCAS1 staining, n=4 neurons from 1 culture), (FIG. 19C) S3-ExRaiAKAR (anti-AIF staining, n=6 neurons from 1 culture; anti-EEA1 staining, n=5 neurons from 1 culture; anti-Lamp1 staining, n=2 neurons from 1 culture; anti-PDI staining, n=5 neurons from 1 culture; anti-RCAS1 staining, n=5 neurons from 1 culture), or (FIG. 19D) S4-ExRaiCKAR (anti-AIF staining, n=4 neurons from 1 culture; anti-EEA1 staining, n=4 neurons from 1 culture; anti-Lamp1 staining, n=6 neurons from 1 culture; anti-PDI staining, n=4 neurons from 1 culture; anti-RCAS1 staining, n=5 neurons from 1 culture). Cells were immunostained against mitochondria (via anti-AIF), endosomes (via anti-EEA1), lysosomes (via anti-Lamp1), Golgi apparatus (via anti-PDI), or endoplasmic reticulum (ER; via anti-RCAS1). SiRI puncta in the GFP channel were colored cyan and immunostaining signals were colored magenta. Scale bar, 10 µm.

Figure 20:
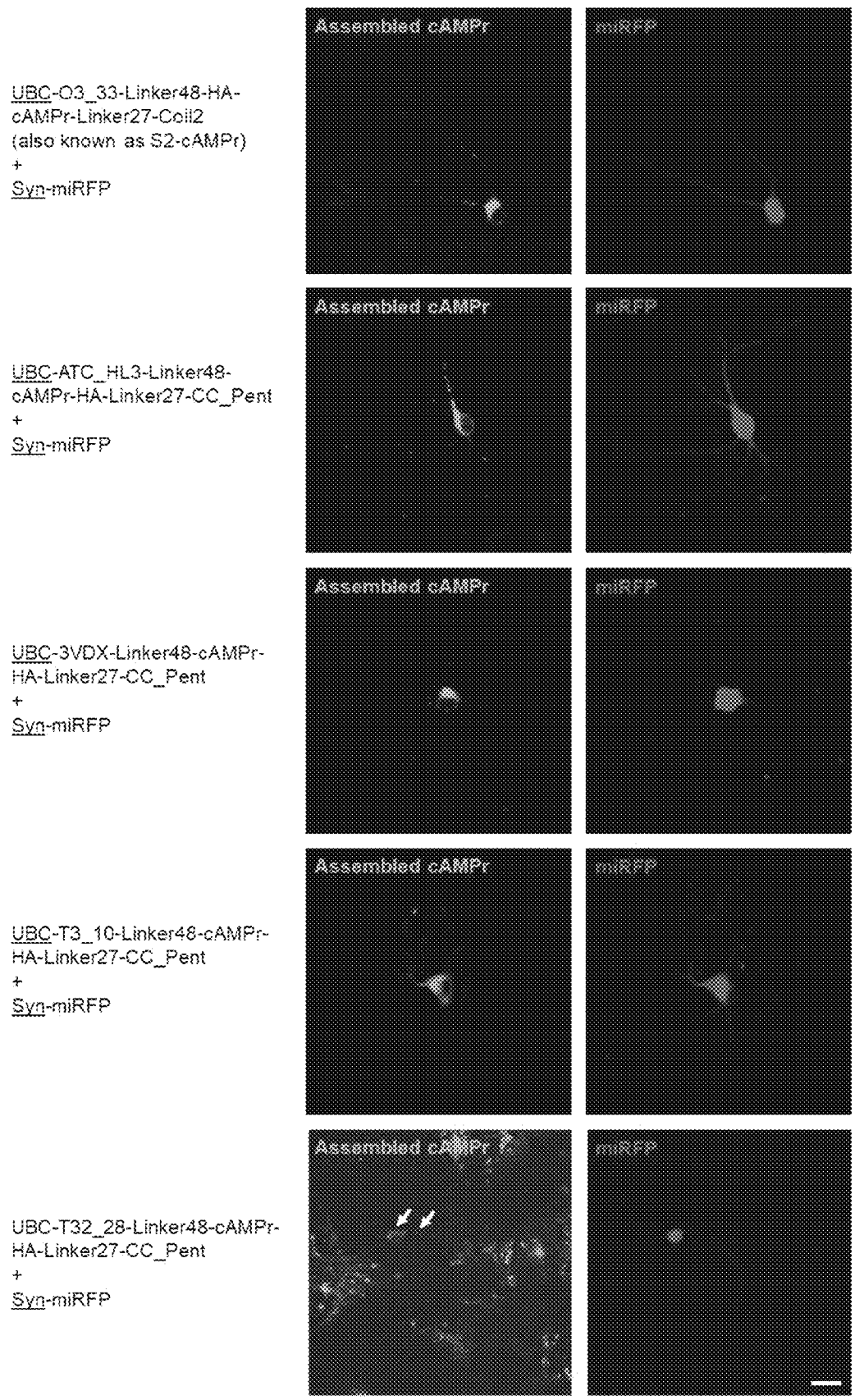

FIG. 20 shows photomicrographs of the expression of four different protein scaffolds that, upon self-assembly, can cluster cAMPr in live neurons. Related to FIG. 17. Representative images of cultured mouse hippocampal neurons expressing four representative variants of protein scaffold-assembled cAMPr together with miRFP as a cell morphology marker (Table 1, motif sequences; Table 2, all tested constructs). For the variant shown in the last row, the expression was very weak and the brightness of cAMPr puncta (white arrows) was at a similar level to the autofluorescence from untransfected cells nearby. Scale bar, 20 µm.

FIG. 21A-H provides graphs showing results demonstrating degree of clustering of SiRI constructs at soma and neurite locations in cultured mouse hippocampal neurons after different of gene dosages. Related to FIGS. 8 and 15. (FIG. 21A-B) Degree of clustering of S1-GCaMP6f at soma (FIG. 21A) and neurite (about 50 µm away from the soma, throughout this figure) locations (FIG. 21B) (n=8, 10, 8, 10, and 5 neurons from 1, 1, 1, 1, and 1 culture for 100 ng, 250 ng, 500 ng, 750 ng, and 1000 ng, respectively). (FIG. 21C-D) Degree of clustering of S2-cAMPr at soma (FIG. 21C) and neurite locations (FIG. 21D) (n=5, 12, 11, 11, and 5 neurons from 1, 1, 1, 1, and 1 culture for 100 ng, 250 ng, 500 ng, 750 ng, and 1000 ng, respectively). (FIG. 21E-F) Degree of clustering of S3-ExRaiAKAR at soma (FIG. 21E) and neurite locations (FIG. 21F) (n=5, 5, 5, 5, and 5 neurons from 1, 1, 1, 1, and 1 culture for 100 ng, 250 ng, 500 ng, 750 ng, and 1000 ng, respectively). (FIG. 21G-H) Degree of clustering of S4-ExRaiCKAR at soma (FIG. 21G) and neurite locations (FIG. 21H) (n=11, 14, 6, 8, and 5 neurons from 2, 2, 1, 1, and 2 culture(s) for 100 ng, 250 ng, 500 ng, 750 ng, and 1000 ng, respectively). Degree of clustering (or 'Dc'), the fluorescence intensity ratio between the puncta and non-puncta cytosol in SiRI-expressing cells; 100 ng, 250 ng, 500 ng, 750 ng, and 1000 ng, the mass of DNA of each SiRI construct used in calcium phosphate transfection per well in 24-well plates, with extra pUC19 dummy DNA added so that the total transfected DNA per well was 1500 ng; Dc was measured in live neurons 4 days after transfection on DIV 9; bar plots of medians with interquartile ranges are used throughout this figure, with individual values plotted as dots; n.s., not significant; Kruskal-Wallis analysis of variance followed by post-hoc test via Dunn's test with '100 ng' as control group throughout the figure; see Tables 28-29, 33-34, 44-45, and 63-64 for full statistics for FIG. 21.

Figure 22A:
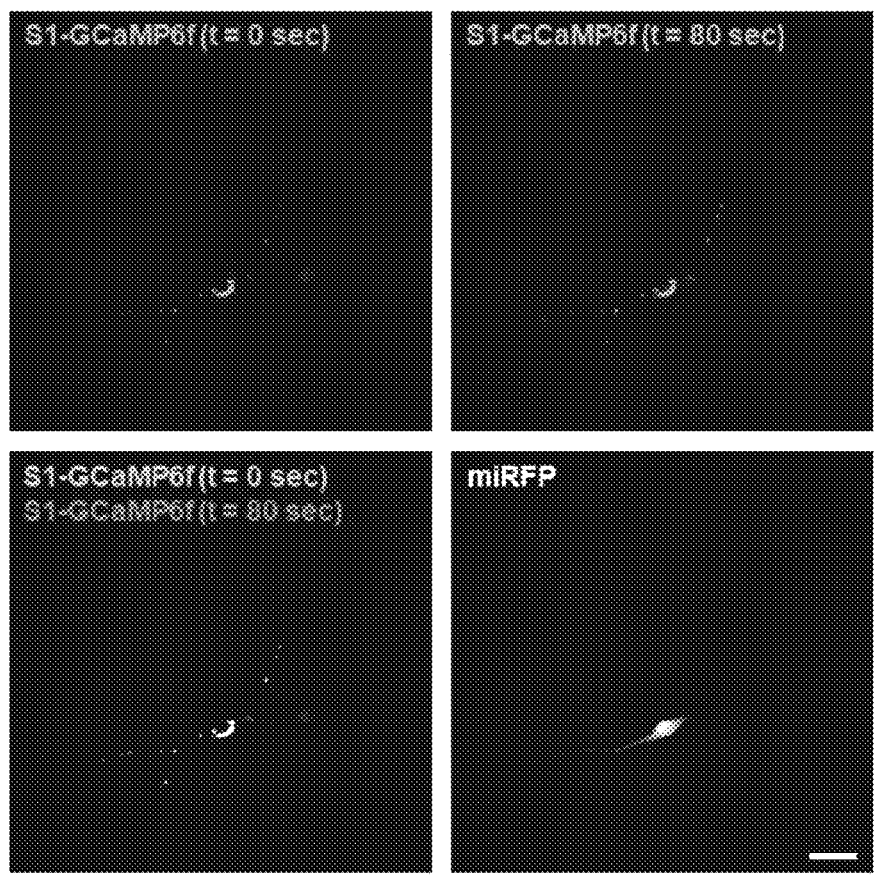
Figure 22B:
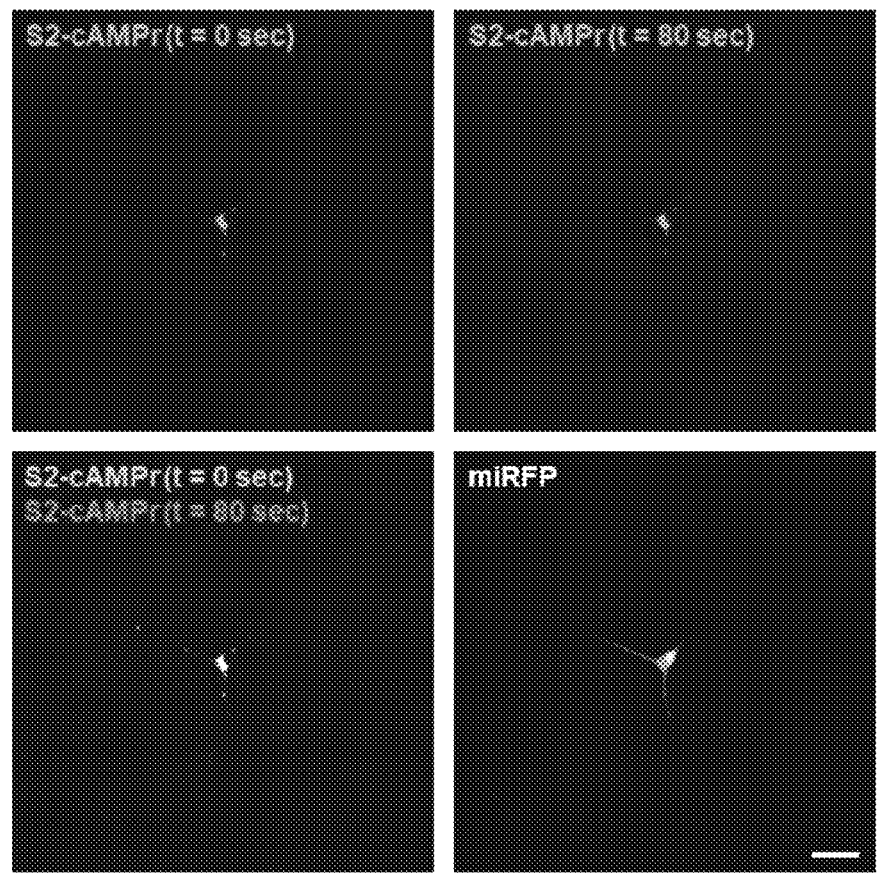

FIG. 22A-B presents photomicrographs showing that puncta of S1-GCaMP6f and S2a-cAMPr are stationary during recording. Related to FIG. 17. FIG. 22A shows representative images of live cultured mouse hippocampal neurons expressing S1-GCaMP6f and miRFP before (t=0 sec) and after (t=80 sec) continuous recording for 80 seconds. Scale bar, 20 µm throughout this figure. FIG. 22B shows representative images of live cultured mouse hippocampal neurons expressing S2a-cAMPr and miRFP before (t=0 sec) and after (t=80 sec) continuous recording for 80 seconds.

Figure 23A:
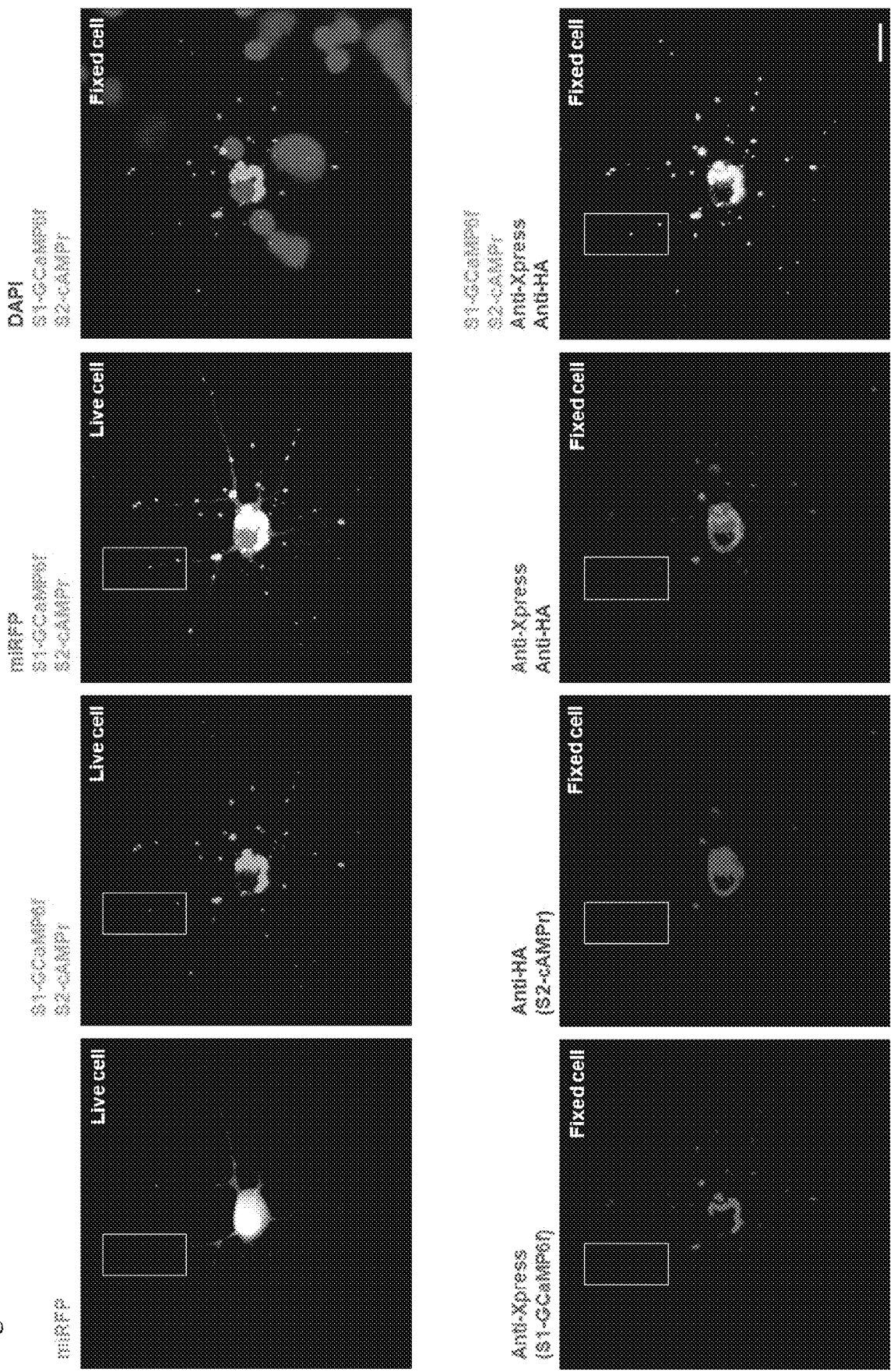

FIG. 23A-E presents photomicrographs, and graphs reporting the results of spatially multiplexed imaging of multiple GFP-based sensors in single neurons. FIG. 23A shows representative images of live cultured mouse hippocampal neurons co-expressing S1-GCaMP6f and S2a-cAMPr, as well as the morphological marker miRFP (first three panels in the top row) and after fixation, immunostaining (with anti-Xpress to mark GCaMP6f and anti-HA to mark cAMPr), and DAPI staining to mark the cell nucleus (the remaining five panels). Yellow rectangles, boundaries of the regions to be shown in enlarged views in FIG. 23B. Scale bar, 20 μm. FIG. 23B shows enlarged views of the regions in the yellow rectangles of FIG. 23A. Orange squares indicate regions-of-interest (ROIs) containing puncta whose fluorescent signal time courses are plotted in FIG. 23C. Scale bar, 5 μm. FIG. 23C shows graphs of recorded fluorescent signals in the two ROIs marked in B during live cell imaging with 5 μM forskolin stimulation at t=10 s. FIG. 23D shows a box plot of the number of soma-localized or neurite-localized S1-GCaMP6f or S2-cAMPr puncta per cell identified by immunostaining in neurons co-expressing S1-GCaMP6f, S2-cAMPr, and miRFP (n=6 neurons from 6 cultures). FIG. 23E shows a box plot of the percentage of the soma-localized or neurite-localized sensor puncta that did not contain the other type of sensor, per cell, as identified by immunostaining in neurons co-expressing S1-GCaMP6f, S2-cAMPr, and miRFP (n=6 neurons from 6 cultures).

Figure 24A:
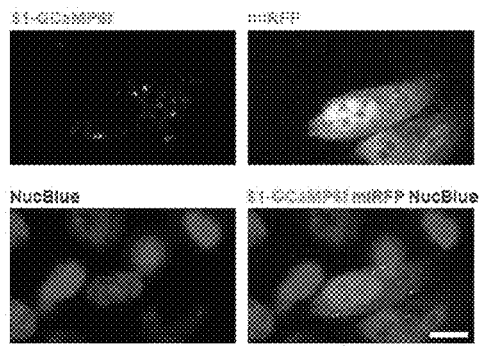
Figure 24B:
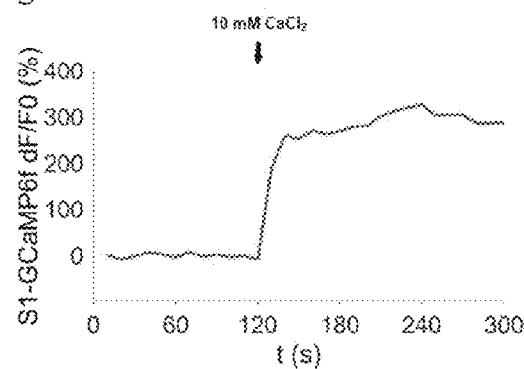
Figure 24C:
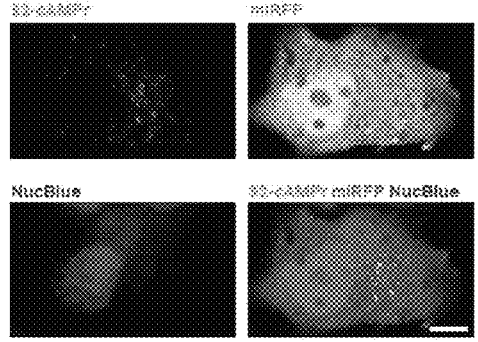
Figure 24D:
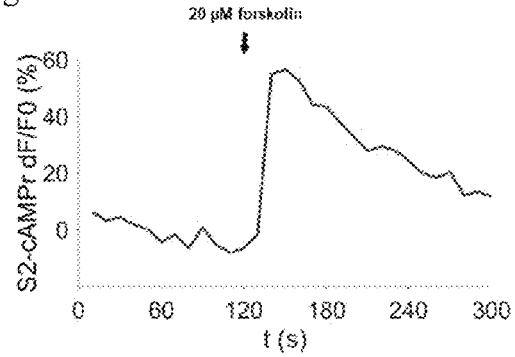
Figure 24E:
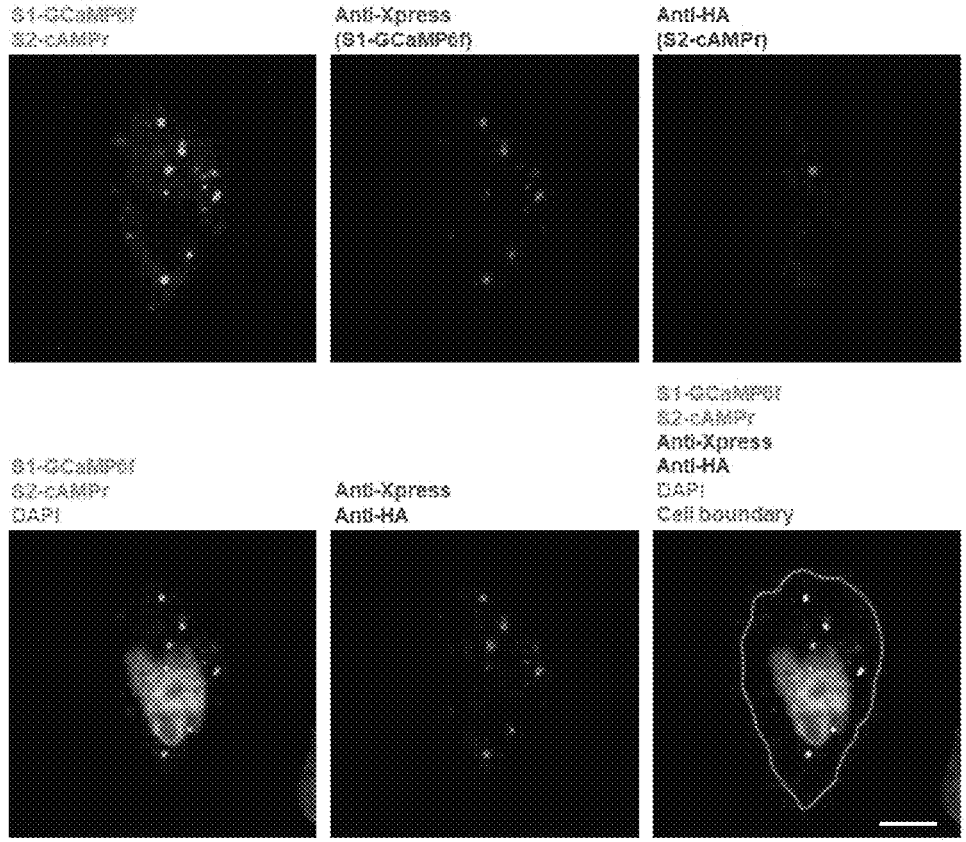

FIG. 24A-E provides results relating to experiments demonstrating that S1-GCaMP6f and S2a-cAMPr formed functional and spatially separate clusters in HeLa cells. Related to FIG. 5 and FIG. 16. FIG. 24A provides a representative image of live HeLa cells expressing S1-GCaMP6f, as well as the morphological marker miRFP, and stained with NucBlue™ against the cell nucleus. Scale bars, 10 μm throughout this figure. FIG. 24B shows representative fluorescent signal recorded during live cell imaging from the HeLa cells in A under 10 mM $CaCl_2$) stimulation at t=120 s. Throughout this figure: dF/F0, fluorescence change in the GFP channel. FIG. 24C provides a representative image of live HeLa cells expressing S2a-cAMPr, as well as the morphological marker miRFP, and stained with NucBlue™ against the cell nucleus. FIG. 24D illustrates representative fluorescent signal recorded during live cell imaging from the HeLa cells in C under 20 μM forskolin stimulation at t=120 s. FIG. 24E provides representative images of HeLa cells co-expressing S1-GCaMP6f and S2a-cAMPr. All images in FIG. 24E were taken after fixation, immunostaining against the Xpress epitope and HA epitope, and DAPI staining against the cell nucleus.

Figure 25:
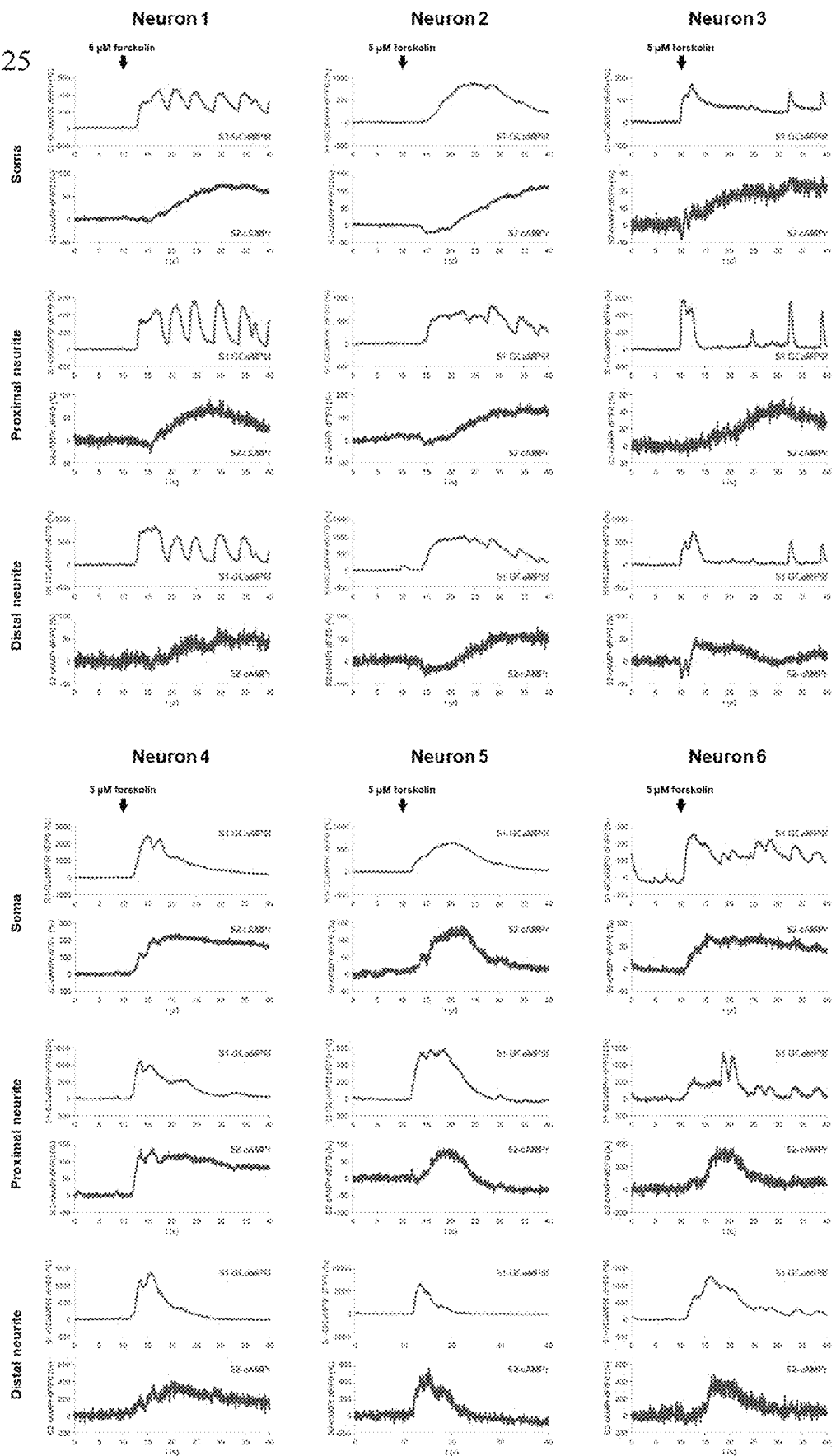

FIG. 25 presents graphs of simultaneous recording of $Ca^{2+}$ and cAMP in neurons with two fluorescent sensors, S1-GCaMP6f and S2a-cAMPr, which have identical spectra. Fluorescent signals were recorded from the soma, proximal neurites (5-25 μm away from soma), and distal neurites (50-250 μm away from soma) of cultured mouse hippocampal neurons co-expressing S1-GCaMP6f and S2a-cAMPr with 5 μM forskolin stimulation at t=10 s (n=6 neurons from 6 cultures). Each fluorescent signal was measured from a single punctum of S1-GCaMP6f or S2a-cAMPr.

Figure 26G:
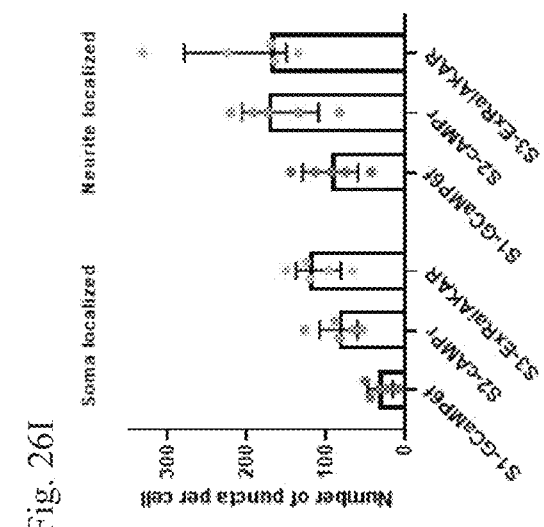
Figure 26H:
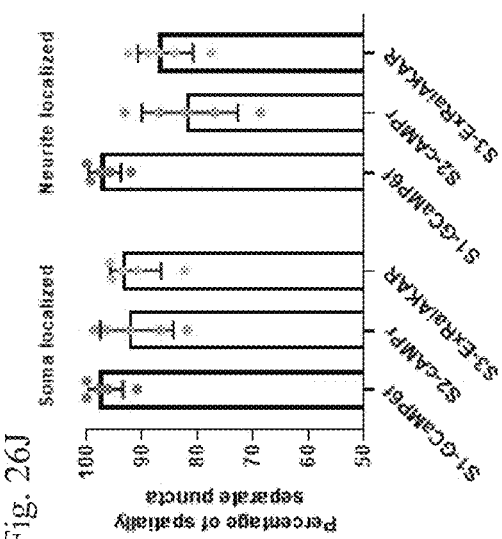
Figure 26I:
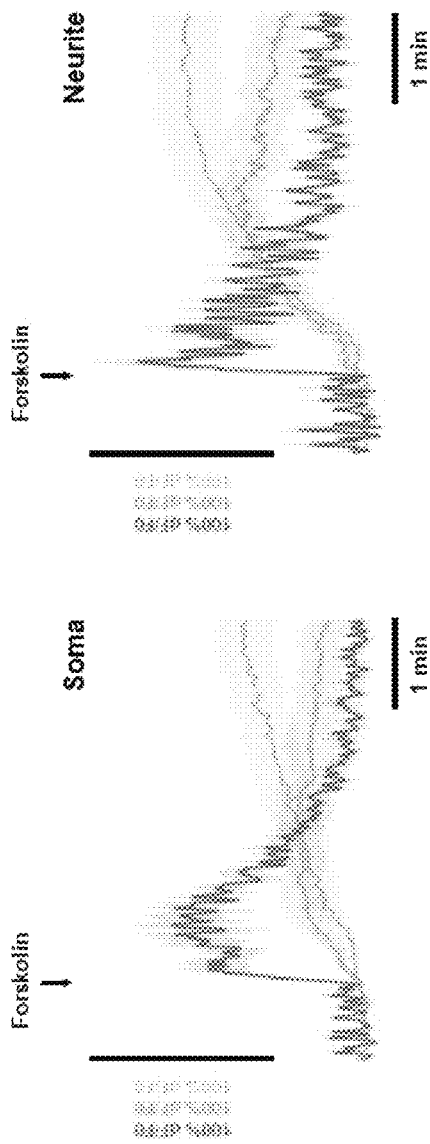
Figure 26J:
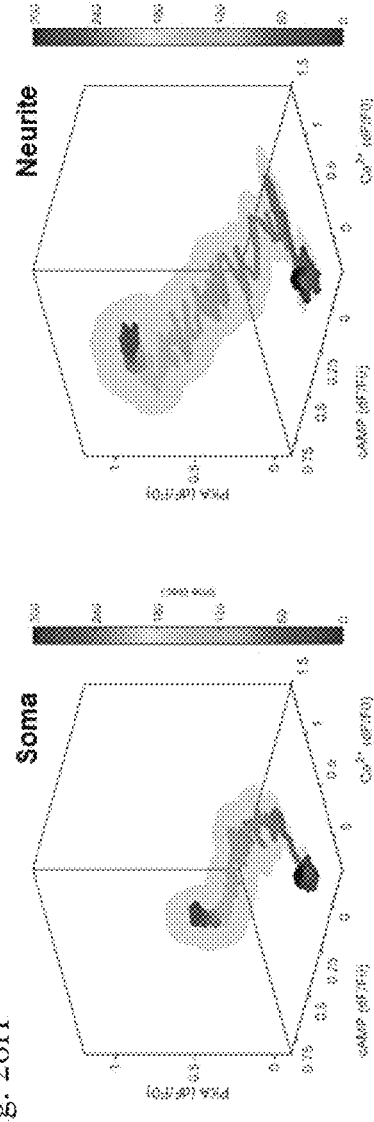

FIG. 26A-J presents photomicrographs and graphs describing the results of spatially multiplexed imaging of three GFP-based sensors in single neurons. FIG. 26A shows a maximum intensity projection (MIP) image in the miRFP channel of a representative live cultured mouse hippocampal neuron co-expressing S1-GCaMP6f, S2a-cAMPr, S3-ExRaiAKAR, and the cell morphological marker miRFP. Scale bar, 20 μm. FIG. 26B shows an MIP image in the GFP channel. Orange rectangles, boundaries of the regions to be shown in enlarged views in FIG. 26C-F. FIG. 26C, top left, shows the enlarged view of the soma region in FIG. 26B. FIG. 26C, top right, shows an MIP image of the same region after fixation and immunostaining against Xpress (magenta), HA (cyan), and V5 (yellow). Bottom, recorded fluorescent signals of $Ca^{2+}$ (magenta), cAMP (cyan), and PKA (yellow) activities in this region during live cell imaging under 5 μM forskolin stimulation. In each of FIG. 26D-F, the top left panels show an enlarged view of the corresponding neurite region in FIG. 26B, and the top right panels show an MIP image of the same region after fixation and immunostaining against Xpress (magenta), HA (cyan), and V5 (yellow). Each bottom panel in FIG. 26D-F shows a graph of the corresponding recorded fluorescent signals of $Ca^{2+}$ (magenta), cAMP (cyan), and PKA (yellow) activities in this region during live cell imaging under 5 μM forskolin stimulation. FIG. 26G shows graphs of the averaged fluorescent signals of $Ca^{2+}$ (magenta), cAMP (cyan), and PKA (yellow) activities at soma (left) and neurite (right) under 5 μM forskolin stimulation (n=10 neurons from 6 cultures). Colored lines, mean; colored, shaded boundaries, standard error of mean. FIG. 26H shows three-dimensional graphs of the averaged phase portraits of $Ca^{2+}$, cAMP, and PKA activities at soma (left) and neurite (right) during live cell imaging under 5 μM forskolin stimulation at t=60 sec (n=10 neurons from 6 cultures). Colored centerline, mean color-coded by time; gray, shaded boundaries, standard error of mean; black dot, the time point when forskolin was added. FIG. 26I shows a bar plot of the number of soma-localized or neurite-localized puncta per cell for S1-GCaMP6f, S2a-cAMPr, and S3-ExRaiAKAR identified by immunostaining in neurons co-expressing S1-GCaMP6f, S2a-cAMPr, S3-ExRaiAKAR, and miRFP (n=5 neurons from 4 cultures). FIG. 26J shows a bar plot of the percentage of the soma-localized or neurite-localized puncta of S1-GCaMP6f, S2a-cAMPr, or S3-ExRaiAKAR that did not contain the other types of sensors, per cell, as identified by immunostaining in neurons co-expressing S1-GCaMP6f, S2a-cAMPr, S3-ExRaiAKAR, and miRFP (n=5 neurons from 4 cultures).

Figure 27F:
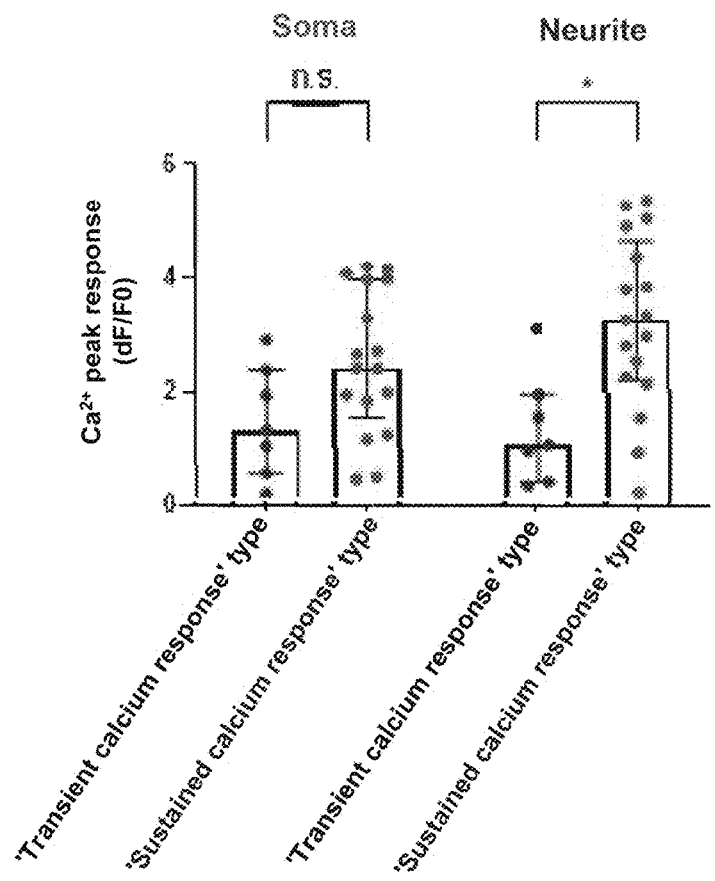
Figure 27G:
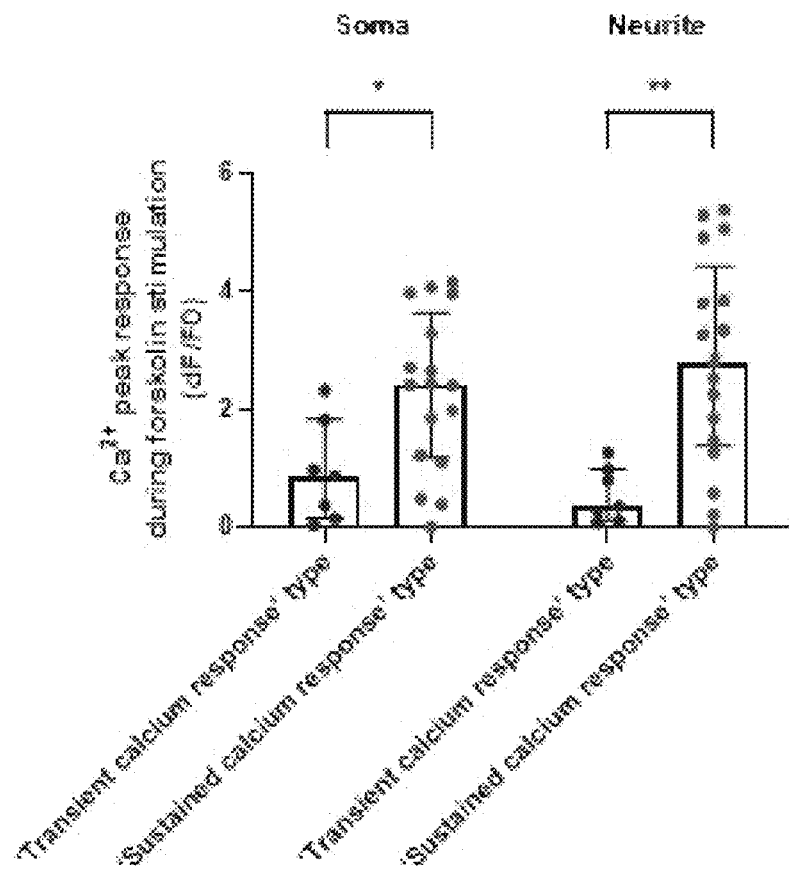
Figure 27H:
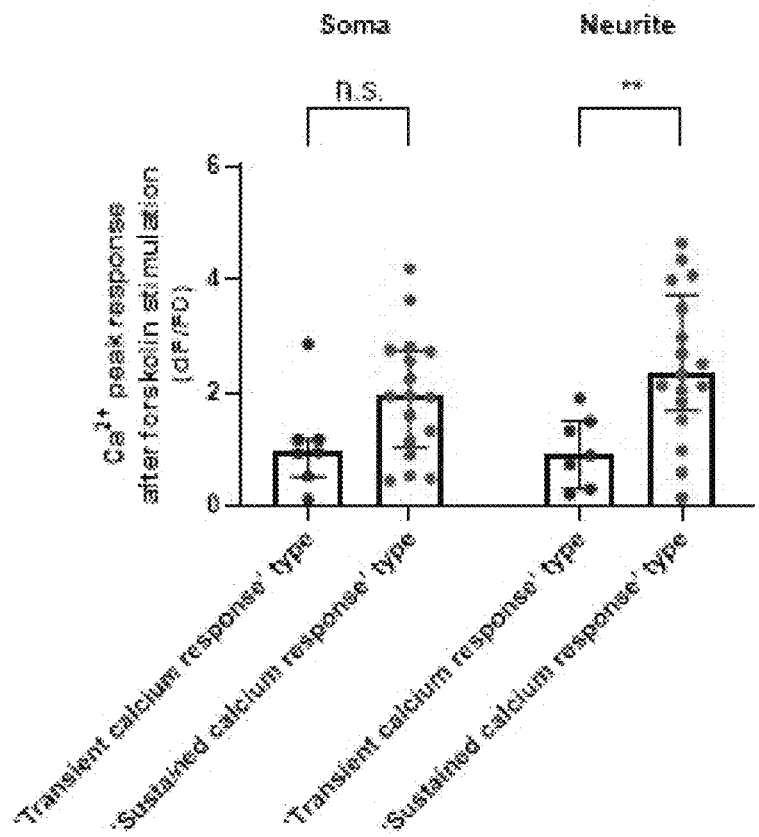
Figure 27I:
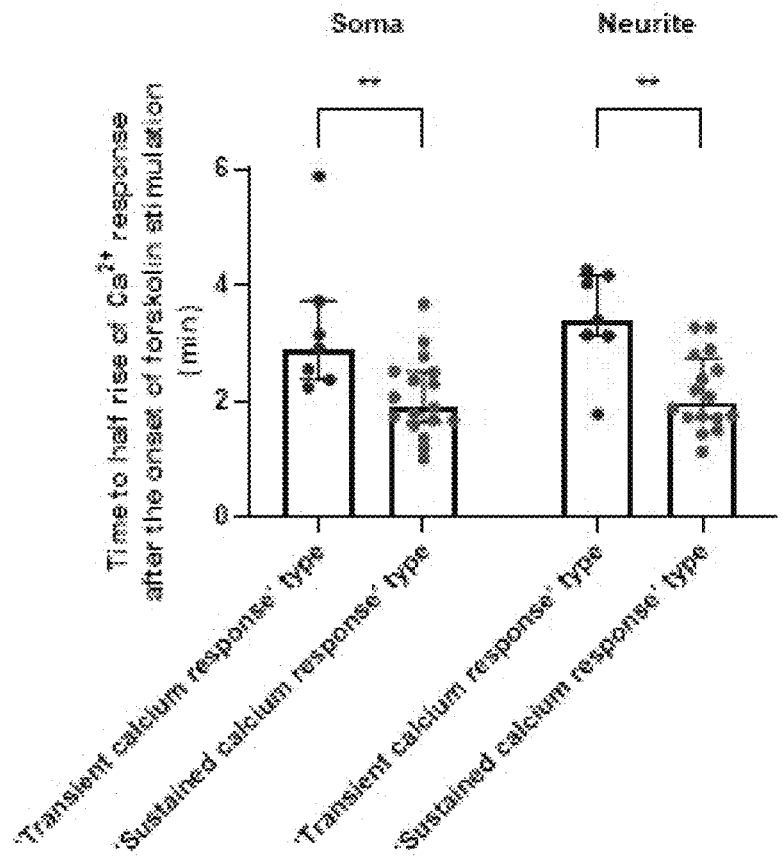
Figure 27J:
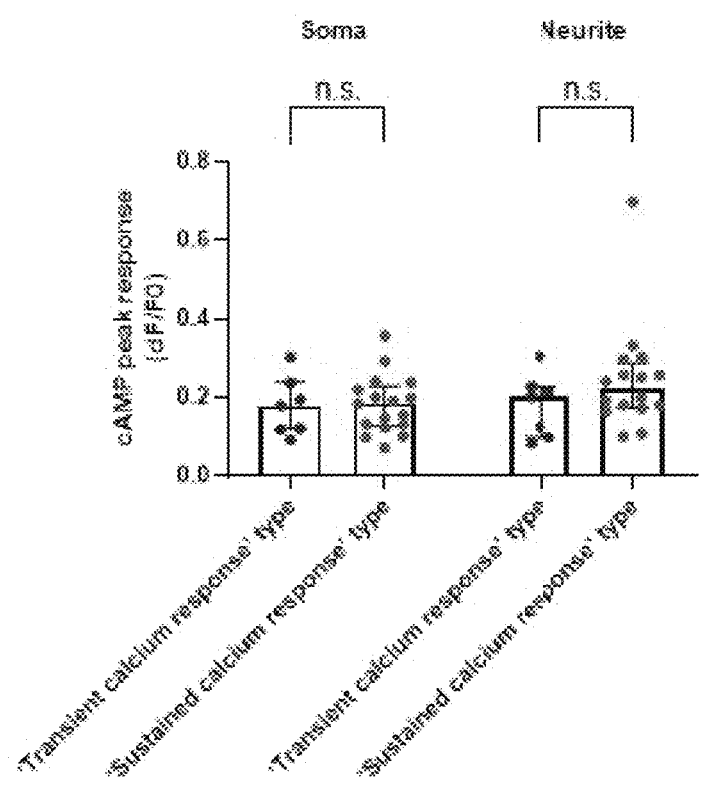
Figure 27K:
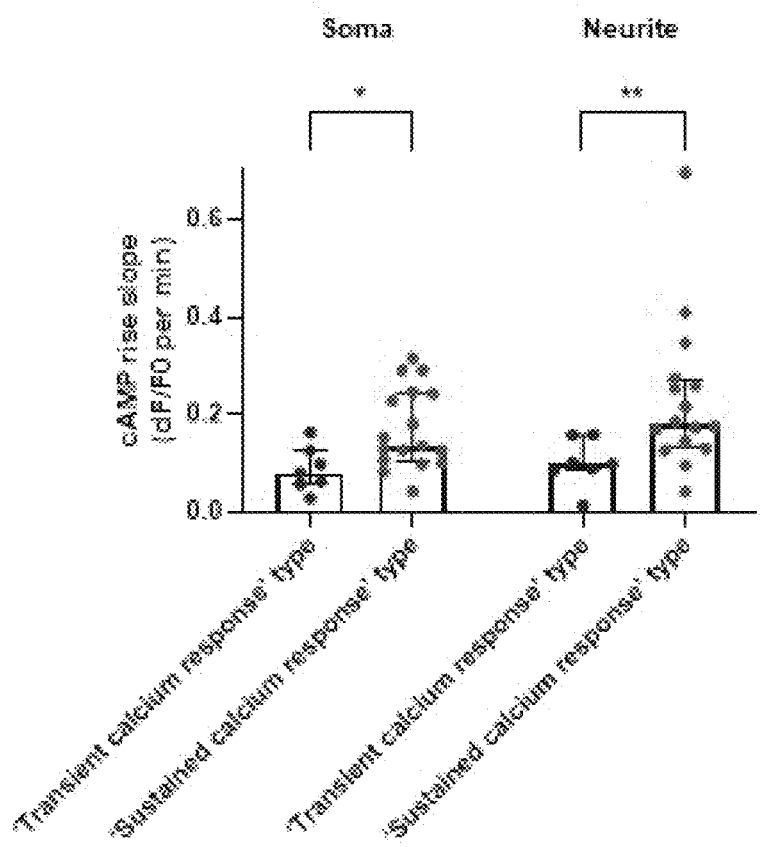
Figure 27L:
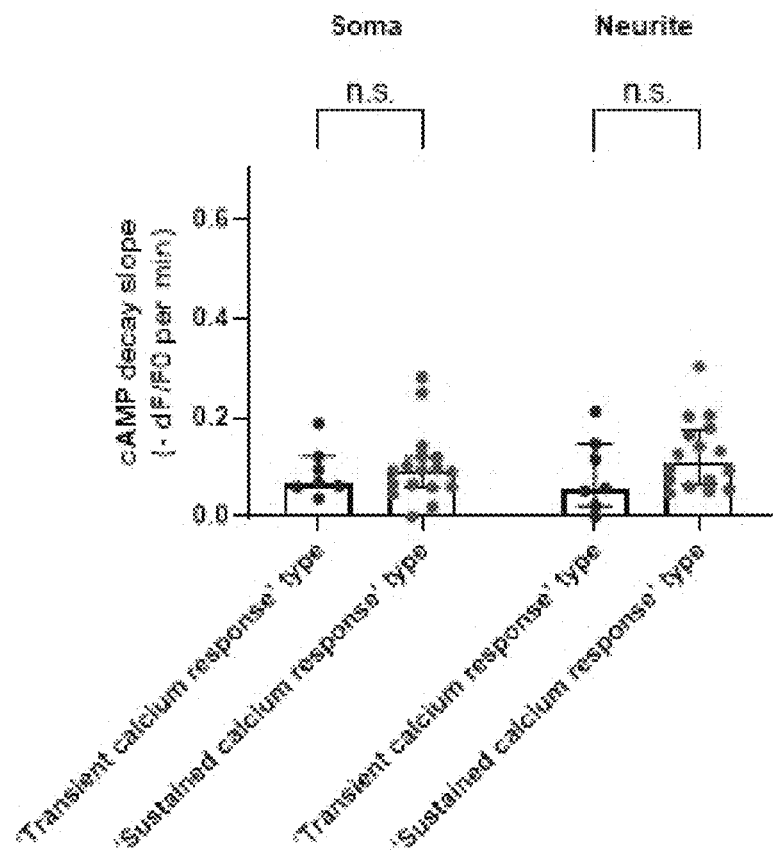
Figure 27M:
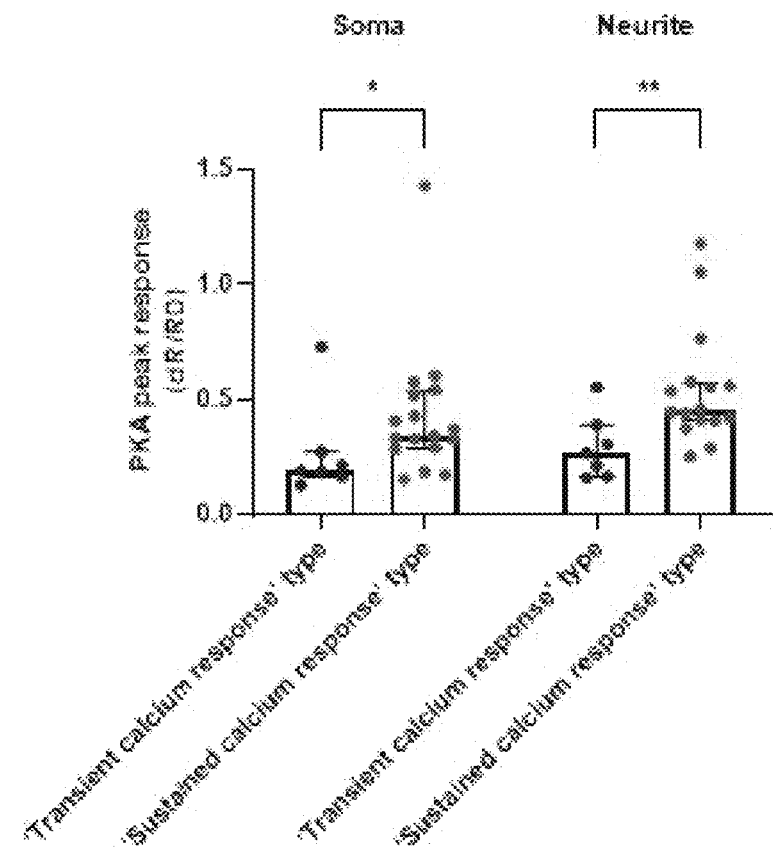
Figure 27N:
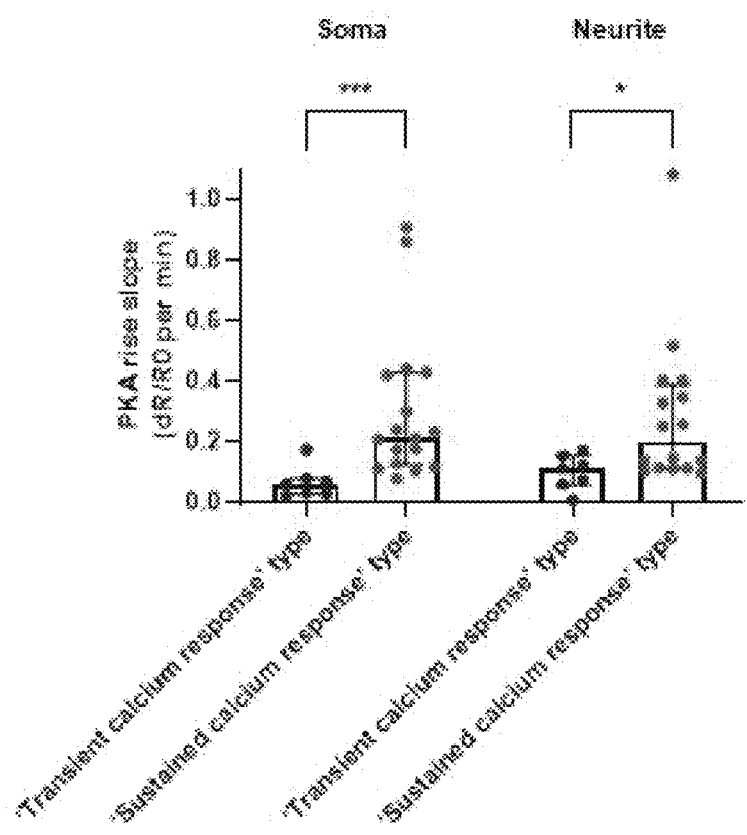
Figure 27O:
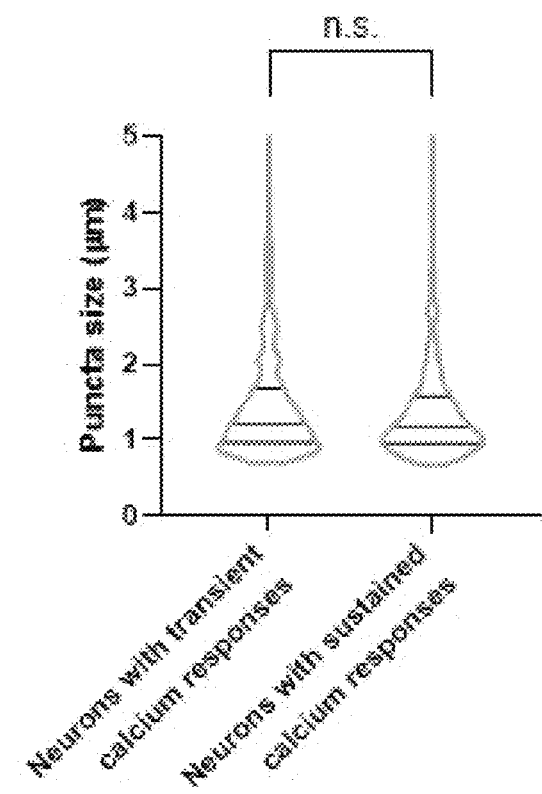

FIG. 27A-O provides graphs and traces from studies of waveform analysis of $Ca^{2+}$, cAMP, and PKA responses at soma and neurite locations in cultured mouse hippocampal neurons under forskolin stimulation. Related to FIG. 13. (FIG. 27A) Neurite $Ca^{2+}$, cAMP, and PKA activities from a representative neuron with a 'transient calcium response' at a neurite location (neurite locations were 20-60 μm away from soma) (left) and averaged across all neurons with 'transient calcium responses' (at neurite locations 20-60 μm away from soma) (right; n=7 neurons from 7 cultures; colored lines throughout this figure, mean; colored, shaded boundaries throughout this figure, standard error of mean). (FIG. 27B) Neurite $Ca^{2+}$, cAMP, and PKA activities from a representative neuron with a 'sustained calcium response' at a neurite location (left) and averaged across neurons with 'sustained calcium responses' (right; n=16 neurons from 12 cultures). (FIG. 27C) Averaged neurite $Ca^{2+}$ activity from neurons with 'transient calcium responses' at neurite locations (blue; n=7 neurons from 7 cultures) and from neurons with 'sustained calcium responses' at neurite locations (red; n=16 neurons from 12 cultures) under 50 μM forskolin stimulation for 3 minutes. Thin and light colored lines, neurite $Ca^{2+}$ activities from individual neurons. Results from statistical tests for peak responses over indicated time windows (horizontal lines), and times to half rise ($t_{1/2\ rise}$), are indicated. (FIG. 27D) Averaged neurite cAMP activity for the neurons of FIG. 27C. (FIG. 27E) Averaged neurite PKA activity for the neurons of FIG. 27C. Results from statistical tests for the rise slope, decay slope, and peak response were indicated on FIG. 27D and FIG. 27E by the arrow near the rise phase, the arrow near the decay phase, and the horizontal line near the peak response, respectively. Throughout this figure: n.s., not significant; *, P<0.05; , P<0.01; *, P<0.001; Wilcoxon rank sum tests; see Tables 49-51 for full statistics for FIG. 27. (FIG. 27F-O) Bar plots of the (FIG. 27F) $Ca^{2+}$ peak response over the entire recording, (FIG. 27G) $Ca^{2+}$ peak response during forskolin stimulation, (FIG. 27H) $Ca^{2+}$ peak response after the end of forskolin stimulation, (FIG. 27I) time to half rise of $Ca^{2+}$ response after the onset of forskolin stimulation, (FIG. 27J) cAMP peak response, (FIG. 27K) cAMP rise slope, (FIG. 27L) cAMP decay slope, (FIG. 27M) PKA peak response, and (FIG. 27N) PKA rise slope for neurons with 'transient calcium responses' and neurons with 'sustained calcium responses' at soma and neurite locations (20-60 μm away from soma) under 50 μM forskolin stimulation for 3 minutes. Bar plots of medians with interquartile ranges are used throughout this figure, with individual values plotted as dots. For 'transient calcium responses' type neurons, n=7 somata from 7 neurons from 6 cultures and n=7 neurites from 7 neurons from 7 cultures. For 'sustained calcium responses' type neurons, n=17 somata from 17 neurons from 12 cultures and n=16 neurites from 16 neurons from 12 cultures. (FIG. 27O) Violin plots of the punctum size of all puncta in the GFP channel in neurons with 'transient calcium responses' or neurons with 'sustained calcium responses' under 50 μM forskolin stimulation for 3 minutes (n=512 and 630 puncta in 5 and 5 neurons co-expressing S1-GCaMP6f, S2-cAMPr, S3-ExRaiAKAR, and miRFP from 5 and 5 cultures for neurons with 'transient calcium responses' and neurons with 'sustained calcium responses', respectively). Red line, median; black line, interquartile ranges.

Figure 28A:
Figure 28B:
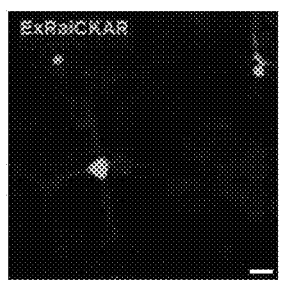
Figure 28C:
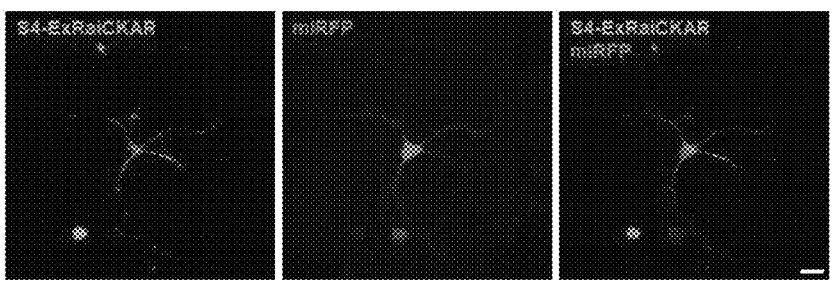
Figure 28D:
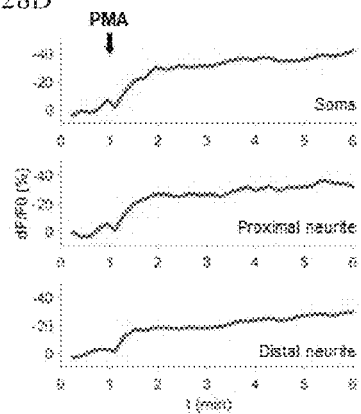
Figure 28E:
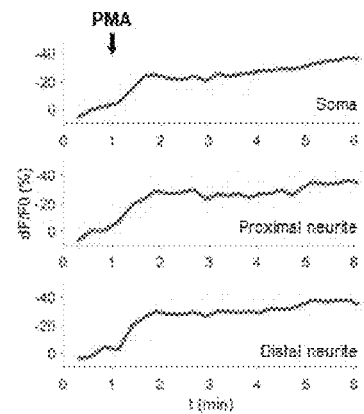
Figure 28E:
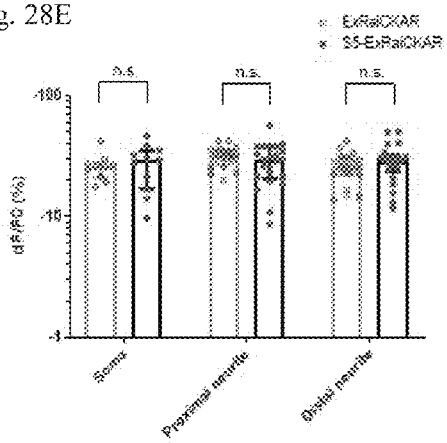
Figure 28F:
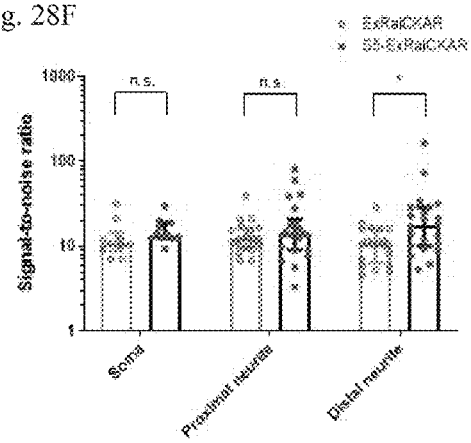
Figure 28G:
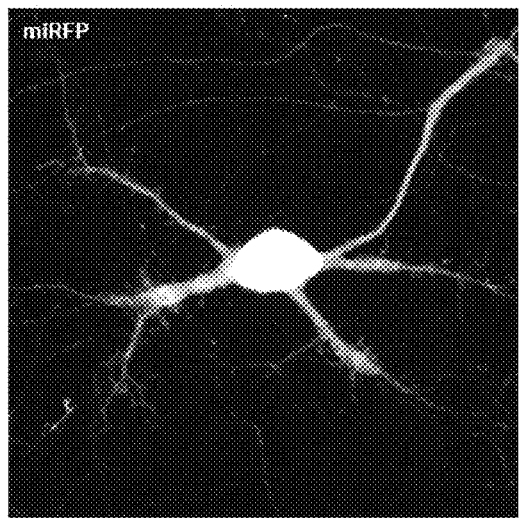
Figure 28H:
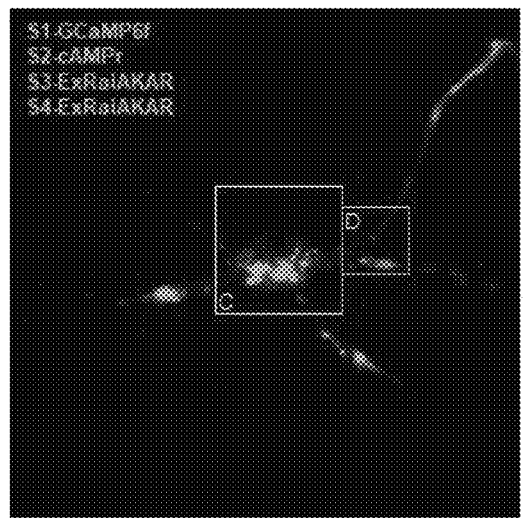
Figure 28I:
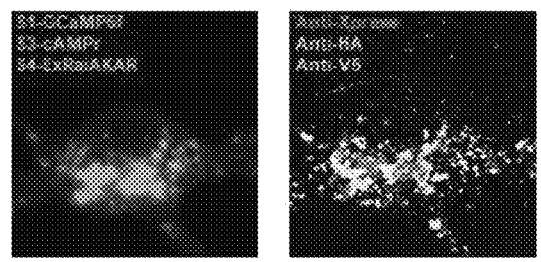
Figure 28I:
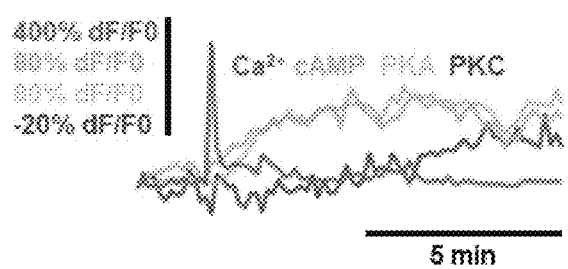
Figure 28J:
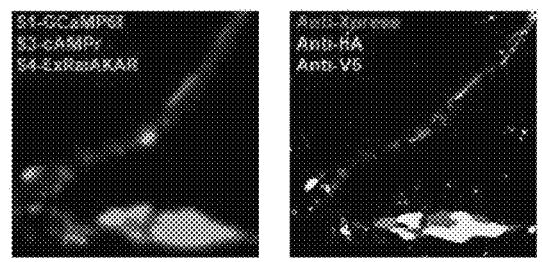
Figure 28J:
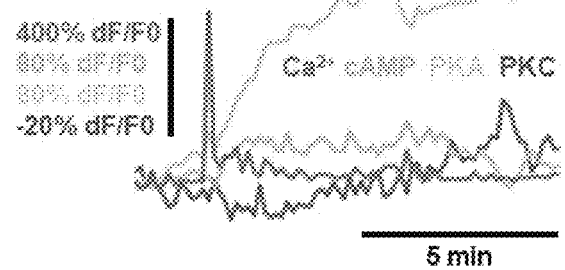
Figure 28K:
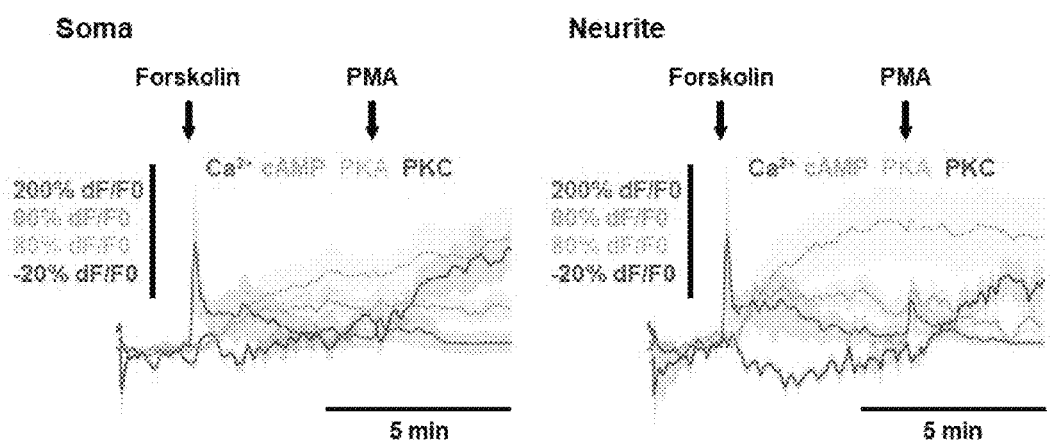
Figure 28L:
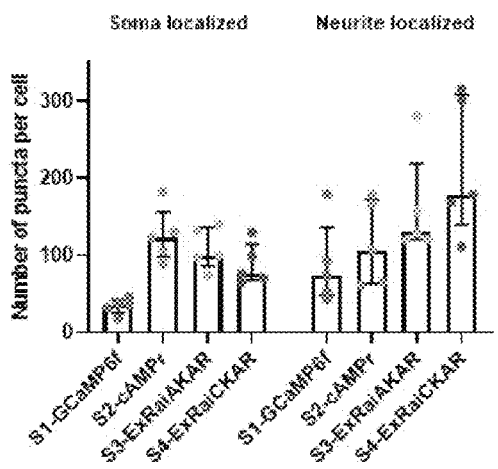
Figure 28M:
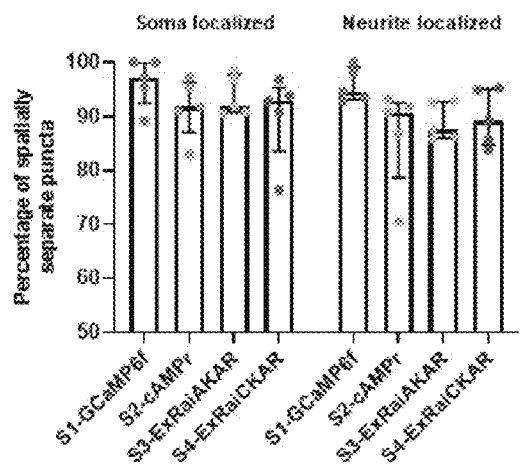

FIG. 28A-M presents a schematic, photomicrographs, and graphs of the results of spatially multiplexed imaging of four GFP-based sensors in single neurons. FIG. 28A shows a schematic diagram of the construct design of S4-ExRaiCKAR: I32-06B, self-assembling subunit B of I32-06 two-component icosahedron; OLLAS, E. coli OmpF linker and mouse langerin fusion sequence; I32-06A, self-assembling subunit A of I32-06 two-component icosahedron; AA, amino acid (Table 1, motif sequences; Table 2, all tested constructs). FIG. 28B shows a representative image of live cultured mouse hippocampal neurons expressing ExRaiCKAR. FIG. 28C shows representative images of live cultured mouse hippocampal neurons expressing S4-ExRaiCKAR and miRFP as a cell morphology marker. FIG. 28D shows graphs of representative fluorescent signals recorded from the soma, proximal neurites (5-25 μm away from soma throughout this figure), and distal neurites (50-250 μm away from soma throughout this figure) of cultured mouse hippocampal neurons expressing ExRaiCKAR or S4-ExRaiCKAR under 100 ng/ml phorbol 12-myristate 13-acetate (PMA) stimulation at t=1 min. dF/F0, fluorescence change in GFP channel. Each fluorescent signal for S4-ExRaiAKAR was measured from a single punctum. FIG. 28E shows a bar plot of the peak fluorescence change in GFP channel at the soma, proximal neurites, and distal neurites of cultured mouse hippocampal neurons expressing ExRaiCKAR or S4-ExRaiCKAR under 100 ng/ml PMA stimulation (n=10 somata, 20 proximal neurites, and 20 distal neurites from 10 neurons from 4 cultures for ExRaiCKAR; n=11 somata, 22 proximal neurites, and 22 distal neurites from 11 neurons from 4 cultures for S4-ExRaiCKAR). n.s., not significant; two-way analysis of variance followed by post-hoc Bonferroni corrected multiple comparisons test; Table 7, full statistics for FIG. 6. FIG. 28F shows a bar plot of the signal-to-noise ratio in the GFP channel at the soma, proximal neurites, and distal neurites (of cultured mouse hippocampal neurons expressing ExRaiCKAR or S4-ExRaiCKAR under 100 ng/ml PMA stimulation (n=10 somata, 20 proximal neurites, and 20 distal neurites from 10 neurons from 4 cultures for ExRaiCKAR; n=11 somata, 22 proximal neurites, and 22 distal neurites from 11 neurons from 4 cultures for S4-ExRaiCKAR). n.s., not significant; two-way analysis of variance followed by post-hoc Bonferroni corrected multiple comparisons test; Table 7 for full statistics for FIG. 64. FIG. 28G shows a maximum intensity projection (MIP) image in the miRFP channel of a representative live cultured mouse hippocampal neurons co-expressing S1-GCaMP6f, S2a-cAMPr, S3-ExRaiAKAR, S4-ExRaiCKAR, and the cell morphological marker miRFP. Scale bar, 20 μm. FIG. 28H shows an MIP image in the GFP channel of the same neuron shown in A. Orange rectangles, boundaries of the regions to be shown in enlarged views in FIG. 28C-D. In FIG. 28I, the top left panel shows an enlarged view of the soma region in FIG. 28H, and the top right panel, an MIP image of the same region after fixation and two rounds of immunostaining against HA (cyan) and OLLAS (red) in the first round and Xpress (magenta) and V5 (yellow) in the second round. The bottom panel shows a graph of recorded fluorescent signals of $Ca^{2+}$ (magenta), cAMP (cyan), PKA (yellow), and PKC (red) activities in this region during live cell imaging under 5 μM forskolin and then 100 ng/ml PMA stimulations. In FIG. 28J, the top left panel shows an enlarged view of the neurite region in H, and the top right panel shows an MIP image of the same region after fixation and two rounds of immunostaining against HA (cyan) and OLLAS (red) in the first round and Xpress (magenta) and V5 (yellow) in the second round. The bottom panel shows a graph of recorded fluorescent signals of $Ca^{2+}$ (magenta), cAMP (cyan), PKA (yellow), and PKC (red) activities in this region during live cell imaging under 5 μM forskolin and then 100 ng/ml PMA stimulations. FIG. 28K shows graphs of the averaged fluorescent signals of $Ca^{2+}$ (magenta), cAMP (cyan), PKA (yellow), and PKC (red) activities at soma (left) and neurite (right) under 5 μM forskolin and then 100 ng/ml PMA stimulations (n=4 neurons from 3 cultures). Colored lines, mean; colored, shaded boundaries, standard error of mean. FIG. 28L shows a bar plot of the number of soma-localized or neurite-localized puncta per cell for S1-GCaMP6f, S2a-cAMPr, S3-ExRaiAKAR, and S4-ExRaiCKAR identified by two rounds of immunostaining in neurons co-expressing S1-GCaMP6f, S2a-cAMPr, S3-ExRaiAKAR, S4-ExRaiCKAR, and miRFP (n=5 neurons from 4 cultures). FIG. 28M shows a bar plot of the percentage of the soma-localized or neurite-localized puncta of S1-GCaMP6f, S2a-cAMPr, S3-ExRaiAKAR, or S4-ExRaiCKAR that did not contain the other types of sensors, per cell, as identified by two rounds of immunostaining in neurons co-expressing S1-GCaMP6f, S2a-cAMPr, S3-ExRaiAKAR, S4-ExRaiCKAR, and miRFP (n=5 neurons from 4 cultures).

Figure 29B:
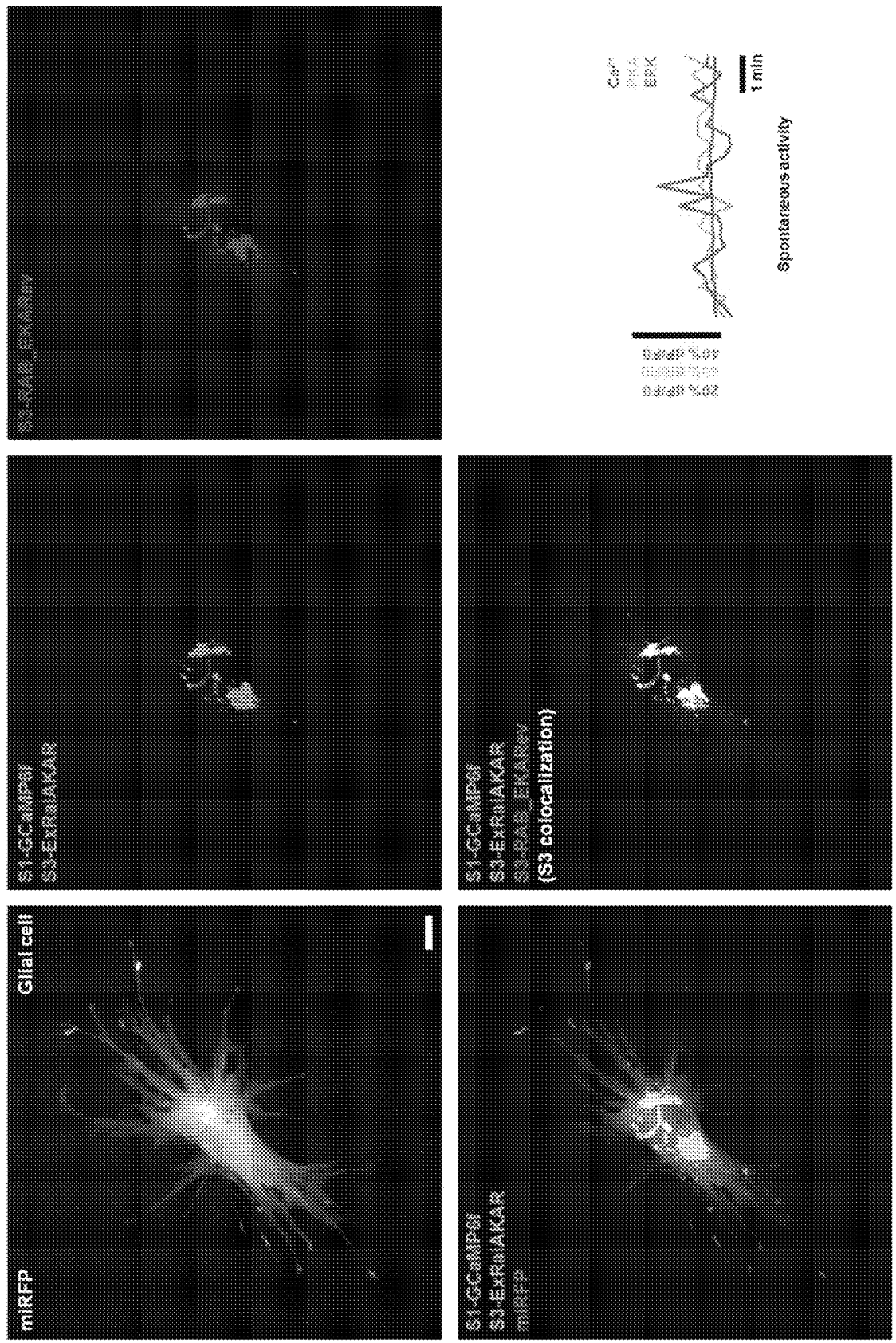

FIG. 29A-B provides photomicrographic images and graphs of results of studies indicating that for some combinations of SiRI reporters of more than one color, reporter types can be inferred during live cell imaging, without requiring post-hoc immunostaining. Related to FIG. 16. (FIG. 29A) Maximum intensity projection (MIP) confocal images of a live cultured mouse hippocampal neuron co-expressing S1-GCaMP6f (a GFP based reporter), S3-ExRaiAKAR (a GFP based reporter), S3-RAB_EKARev (an RFP based reporter), and the cell morphological marker miRFP, as well as the recorded fluorescent signals of spontaneous $Ca^{2+}$ (magenta), PKA (yellow), and ERK (green) activities at soma and at locations along neurites. Throughout this figure: in the composite images (those labeled 'S3 colocalization') from GFP and RFP channels, GFP and RFP channels were pseudo-colored in green and magenta, respectively, thus the puncta appearing in both channels would have white color in the composite images; puncta appearing in both GFP and RFP channels were identified as the puncta containing both S3-ExRaiAKAR (in the GFP channel) and S3-RAB_EKARev (in the RFP channel); puncta that appeared in the GFP channel only, were identified as puncta of S1-GCaMP6f. No punctum appeared in the RFP channel only. Scale bar, 20 μm. (FIG. 29B) Maximum intensity projection (MIP) confocal images of a live cultured mouse hippocampal glial cell co-expressing S1-GCaMP6f, S3-ExRaiAKAR, S3-RAB_EKARev, and the cell morphological marker miRFP, as well as recorded fluorescent signals of spontaneous $Ca^{2+}$ (magenta), PKA (yellow), and ERK (green) activities. Scale bar, 20 μm.

FIG. 30A-G presents photomicrographs and graphs of the results of immunohistochemical characterization of cellular and synaptic state markers in mouse brains expressing SiRIs. Related to FIG. 14. (FIG. 30A) Representative confocal images of brain slices from 5-7 week old mice expressing S1-GCaMP6f, S3-ExRaiAKAR, and mRuby3-6×FLAG in the right hemisphere following neonatal AAV injection. Neonatal (PO) Swiss Webster mice were injected with a mixture of three AAVs (pAAV-DJ-UBC-S1-GCaMP6f, pAAV-2/9-UBC-S3-ExRaiAKAR, and pAAV-2/9-hSyn-mRuby3-6×FLAG) in both the visual cortex and the hippocampus of the right hemisphere. When the mice reached the age of 5-7 weeks old, they were perfused with 4% PFA, sliced coronally at 100 μm in 1×PBS, and stained with antibodies against one of the cellular and synaptic markers below (see FIG. 30B-G) together with DAPI to label nuclei. Staining intensities of cellular and synaptic markers in the cortex (or CA1) were imaged volumetrically using a 40×objective on a spinning disk confocal microscope, with identical imaging conditions, measured in ImageJ as the averaged fluorescent intensities of the fluorescent secondary antibodies over imaged fields of view (185 μm×185 μm×50 μm for each fields of view), and compared between the injected hemisphere and the non-injected hemisphere. Scale bar, 1 mm. (FIG. 30B-G, top) Representative confocal images of cortex and CA1 in the injected hemisphere and non-injected hemisphere in the brain slices stained with antibodies against each of the cellular and synaptic markers indicated, and DAPI. Scale bars, 100 μm. (FIG. 30B-G, bottom) Bar plots of the staining intensities for each of the cellular and synaptic markers between the injected hemisphere and the non-injected hemisphere; for each marker, n=6 fields of view from 3 mice in the cortex (or in CA1) in the injected hemisphere (or non-injected hemisphere). Bar plots are medians with interquartile ranges, with individual values in arbitrary units (A.U.) plotted as circles and dots. (FIG. 30B) NeuN (neuronal nuclei marker). (FIG. 30C) Cleaved caspase-3 (apoptotic marker). (FIG. 30D) GFAP (astrocyte marker). (FIG. 30E) Iba1 (microglial marker). (FIG. 30F) Synaptophysin (a synaptic protein marker). (FIG. 30G) γH2AX (DNA damage marker). n.s., not significant; Wilcoxon rank sum test; see Tables 68-73 for full statistics for FIG. 30.

FIG. 31A-G presents photomicrographs and graphs of the results of waveform analysis of $Ca^{2+}$ and PKA responses at sites on apical dendrites and basal dendrites of CA1 pyramidal neurons, under forskolin stimulation, in acute mouse brain slices. Related to FIG. 4. (FIG. 31A) Maximum intensity projection (MIP) confocal images of the CA1 pyramidal neuron shown in FIGS. 14B and 14C in acute mouse brain slices (insets labeled 'Live') and after fixation and immunostaining (images labeled 'Fixed'). Scale bar, 20 μm. (FIG. 31B) Field excitatory postsynaptic potential (fEPSP) slopes (normalized to the baseline period before forskolin treatment) before, during, and after a 15-min-long 50 μM forskolin treatment starting at t=0 min (n=7 experiments on 7 slices from 5 mice co-expressing S1-GCaMP6f, S3-ExRaiAKAR, and mRuby3-6×FLAG, although imaging of these reporters was not performed). Black dots, mean; error bars, standard error of mean. ***, P<0.001; Wilcoxon rank sum test for fEPSP slopes before and 45 minutes after the onset of forskolin treatment. (FIG. 31C) $Ca^{2+}$ and PKA activities at locations on apical dendrites (30-100 μm away from soma) of CA1 pyramidal neurons from acute mouse brain slices averaged from neurons with delayed calcium responses (left; n=5 neurons from 5 slices from 3 mice), immediate calcium responses (middle; n=6 neurons from 2 slices from 2 mice), and spontaneous calcium responses (right; n=3 neurons from 2 slices from 2 mice), under 50 μM forskolin treatment for 15 minutes. Throughout this figure: colored lines, mean; colored, shaded boundaries, standard error of mean. (FIG. 31D) $Ca^{2+}$ and PKA activities at locations on the basal dendrites (10-40 μm away from soma) of CA1 pyramidal neurons from acute mouse brain slices, averaged across neurons with delayed calcium responses (left; n=5 neurons from 5 slices from 3 mice), immediate calcium responses (middle; n=6 neurons from 2 slices from 2 mice), and spontaneous calcium responses (right; n=3 neurons from 2 slices from 2 mice), under 50 μM forskolin treatment for 15 minutes. Throughout this figure: colored lines, mean; colored, shaded boundaries, standard error of mean. (FIG. 31E) PKA activities at locations on the apical dendrites of CA1 pyramidal neurons from acute mouse brain slices, averaged across neurons with delayed calcium responses (blue; n=5 neurons from 5 slices from 3 mice), immediate calcium responses (red; n=6 neurons from 2 slices from 2 mice), and spontaneous calcium responses (green; n=3 neurons from 2 slices from 2 mice), under 50 μM forskolin treatment for 15 minutes. (FIG. 31F) PKA activities at locations along the basal dendrites of CA1 pyramidal neurons from acute mouse brain slices averaged across neurons with delayed calcium responses (blue; n=5 neurons from 5 slices from 3 mice), immediate calcium responses (red; n=6 neurons from 2 slices from 2 mice), and spontaneous calcium responses (green; n=3 neurons from 2 slices from 2 mice), under 50 μM forskolin treatment for 15 minutes. For FIG. 31E and FIG. 31F, n.s., not significant; Kruskal-Wallis analysis of variance for rise slopes (arrow near the rise phase), peak responses (horizontal line near the peak response), and durations of PKA activation (arrow on the right hand side of the panel), followed by post-hoc test via Dunn's test. See Tables 76-78 for full statistics for FIG. 31. (FIG. 31G) Bar plot of Pearson correlation coefficients of the $Ca^{2+}$ or PKA responses recorded from soma-, apical dendrite-, and basal dendrite-localized puncta within single CA1 pyramidal neurons (n=13 neurons from 6 slices from 3 mice). Bar plots of medians with interquartile ranges are used, with individual values plotted as dots.

FIG. 32A-G presents photomicrographs and graphs of the results of spatially multiplexed imaging of $Ca^{2+}$ and PKA activities via two GFP-based sensors during long-term potentiation. FIG. 32A shows representative maximum intensity projection (MIP) images of the hippocampus in sagittal brain slices from mice co-expressing S1-GCaMP6f, S3-ExRaiAKAR, and the cell morphological marker mRuby3 by hippocampus targeted in utero electroporation. FIG. 32B shows representative MIP images of the CA1 pyramidal neurons in mice co-expressing S1-GCaMP6f (green), S3-ExRaiAKAR (green), and the cell morphological marker mRuby3 (magenta), before and after immunostaining against Xpress (cyan) and V5 (yellow). FIG. 32C shows a bar plot of the percentage of the soma-localized, apical neurite-localized, or basal neurite-localized puncta of S1-GCaMP6f or S3-ExRaiAKAR that did not contain the other type of sensor, per cell, as identified by immunostaining in brain slices from mice co-expressing S1-GCaMP6f, S3-ExRaiAKAR, and mRuby3 (n=5 CA1 pyramidal neurons from 4 slices from 3 mice). FIG. 32D shows a graph of representative field excitatory postsynaptic potentials (fEPSPs) recorded at the stratum radiatum of CA1 when electrically stimulated at the Schaffer collateral in sagittal brain slices from mice co-expressing S1-GCaMP6f, S3-ExRaiAKAR, and mRuby3. Gray trace, fEPSP before forskolin treatment; black trace, fEPSP 15 min after a 15-min-long 50 µM forskolin treatment. FIG. 32E shows a graph of the average fEPSP slope (normalized to the baseline period before forskolin treatment) before, during, and after a 15-min-long 50 µM forskolin treatment starting at t=0 min (n=7 experiments on 7 slices from 5 mice co-expressing S1-GCaMP6f, S3-ExRaiAKAR, and mRuby3). Black dots, mean; error bars, standard error of mean. FIG. 32F shows representative fluorescent signals of $Ca^{2+}$ (cyan) and PKA (yellow) activities at soma (middle), basal neurite (left), and apical neurite (right) of CA1 pyramidal neurons before, during, and after a 15-min-long 50 µM forskolin treatment. FIG. 32G shows graphs of the averaged fluorescent signals of $Ca^{2+}$ (cyan) and PKA (yellow) activities at soma (middle), basal neurite (left), and apical neurite (right) of CA1 pyramidal neurons before, during, and after a 15-min-long 50 µM forskolin treatment (n=11 neurons from 6 slices from 3 mice). Colored lines, mean; colored, shaded boundaries, standard error of mean.

REFERENCE TO AN ELECTRONIC SEQUENCE LISTING

The contents of the electronic sequence listing (MIT-32US(02)_ST25.txt; Size: 75,052 bytes; and Date of Creation: Sep. 14, 2020) is herein incorporated by reference in its entirety.

DETAILED DESCRIPTION

The invention in some aspects relates to novel methods of imaging that permit imaging of the physiology and activity within single cells with subcellular, nanoscale precision. The methods, in some aspects include clustering and stochastically distributing two or more compositions comprising one or more independently selected reporter protein elements inside a cell to be imaged. In certain embodiments, the composition is an RNA-protein-based clustering composition and in some embodiments, the composition is a protein self-assembly clustering composition. Certain embodiments of the invention may include one or more of each of an RNA-protein-based clustering composition and a protein self-assembly clustering composition.

Embodiments of methods and compositions of the invention can be used to prepare and use cluster sensors in signaling reporter islands (SiRIs). As used herein the term "SiRIs" means the engineered RNA and protein scaffolds that comprise clusters of sensors. The term "sensor" as used herein is a composition or molecule capable of producing a signal in response to a condition. Non-limiting examples of sensors are reporter protein elements such as those described elsewhere herein. Embodiments of SiRIs of the invention can be delivered into a cell and one or more of a condition, activity, change, in a physiological characteristic of the cell can be determined and assessed based on the signal produced by one or more sensors in the SiRIs. A general schematic of an embodiment of the invention is shown in FIG. 1A.

Figure 1B:
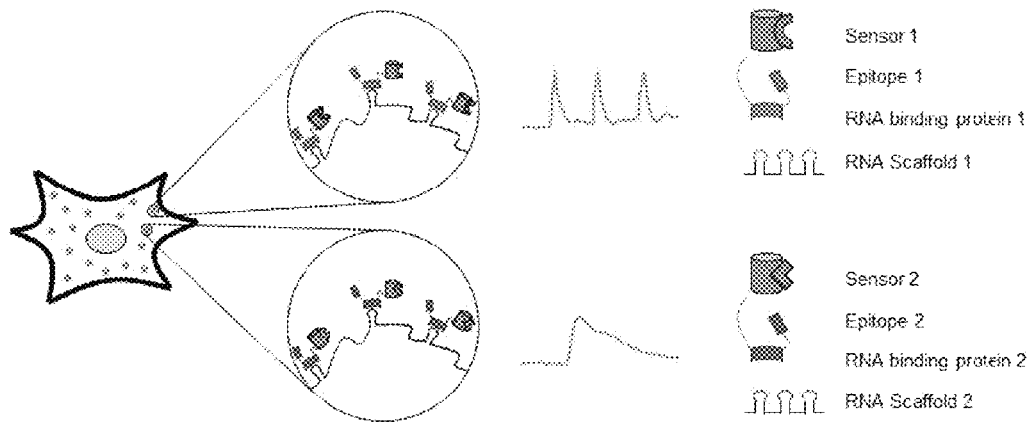
Figure 1C:
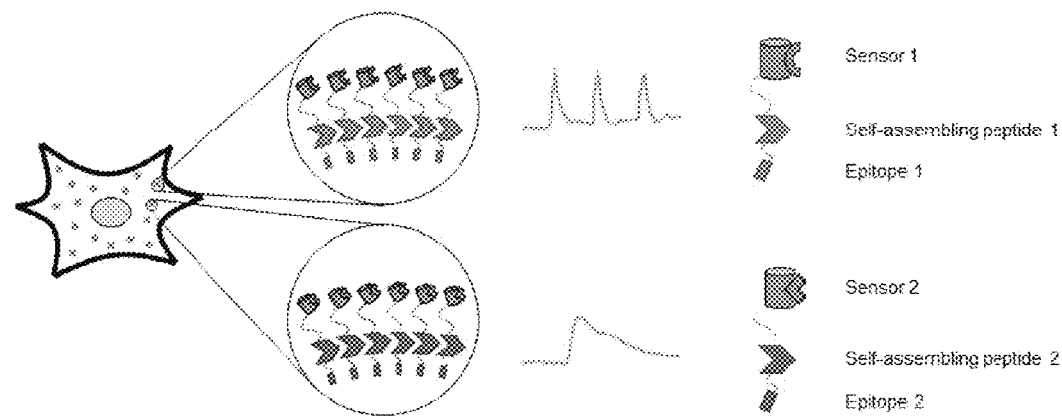
Figure 1D:
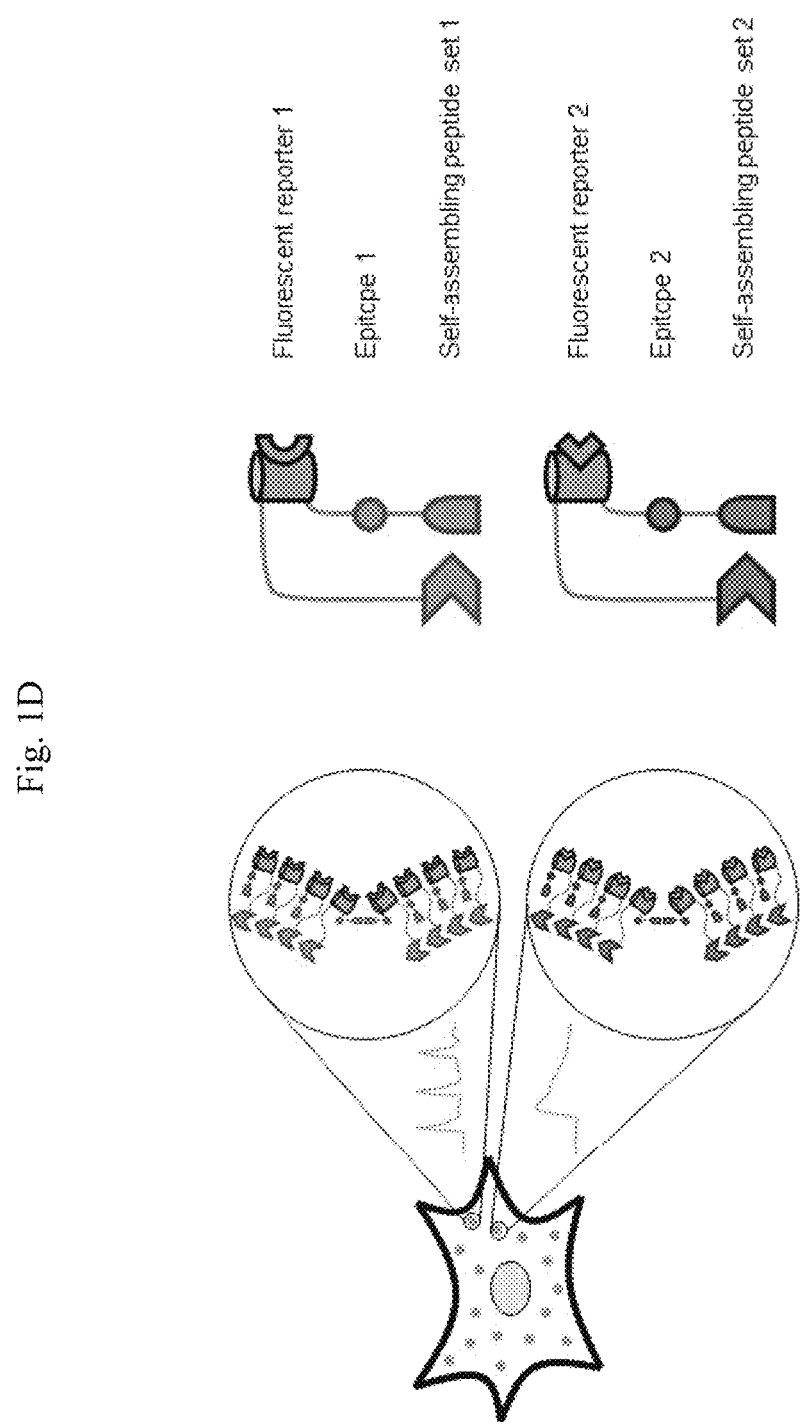

Different strategies can be used to prepare SiRIs of the invention. For example, one strategy includes scaffolding of different sensors onto distinct RNA strands (FIG. 1B) and another strategy includes clustering of different sensors mediated by distinct self-assembling proteins (FIG. 1C). Another strategy used in certain embodiments of the invention includes the linking of multiple self-assembling peptides (FIG. 1D). These linked fusion proteins form what are referred to herein as "puncta" or "clusters" in cells. In some embodiments of the invention, methods of the invention are used to prepare SiRIs in a single cell and the SiRIs in a single cell may be prepared using one or both of (i) scaffolding of different sensors onto distinct RNA strands and (ii) clustering of different sensors mediated by distinct self-assembling proteins. As a non-limiting example, compounds and methods of the invention are used to for clustering both fluorescence resonance energy transfer (FRET) sensors that are difficult to use in a spectrally multiplexed fashion because of the broad spectral range associated with each sensor, as well as non-FRET based reporters that contain a single fluorophore.

It has now been identified that it is possible to monitor different signals, non-limiting examples of which are $Ca^{2+}$ and cAMP signals, from spectrally overlapping or even spectrally identical fluorophores, in single cells and in single neurons in culture. The ability to use simultaneous measurement of these signals in individual cells has revealed very complex relationships between these signals, including variations in the timing, amplitude, and shape of the signals in relation to each other. These results demonstrate the value and importance of performing multiple measurements at the same time in individual cells, because prior methods that included measuring the signals in separate cells and then averaging the data across populations before comparing them to each other resulted in loss of these relationships. The ability to simultaneously detect and assess signals from two or more spectrally overlapping or even spectrally identical fluorophores in single cells, which supports the broad utility of compositions and methods of the invention in numerous scientific areas.

Unlike prior imaging methods, some of which permitted imaging of clusters of reporter polypeptides, which were capable of detecting and comparing simultaneous physiological processes only in different cells, methods and compositions of the invention described herein can be used to image clusters of different compositions in a single cell and thus can be used to acquire information about multiple simultaneous physiological processes occurring within a single cell. Non-limiting examples of physiological processes that can be assessed using embodiments of compositions and methods of the invention are one or more of: pH of the cell, voltage in the cell, and the presence of one or more of: calcium, magnesium, chloride, and potassium in the cell.

Compositions and methods of the invention can be used to localize, via engineered RNA and protein scaffolds that are bioorthogonal to mammalian cells, spectrally similar or even spectrally identical fluorescent reporters of different biological signals at different points in space, which are referred to herein as signaling reporter islands (SiRIs). Non-limiting examples of the use of compositions and methods of the invention include live imaging of the cell comprising SiRIs, post hoc reconstruction of sensor identity in fixed cells comprising SiRIs via epitope immunostaining, and RNA FISH, or other highly multiplexed fixed cell imaging methods. Using compositions and methods of the invention it is possible to record multiple fluorescent signals at different points in space within a cell, with minimal crosstalk, in a fashion where the identity of the signal can be clearly defined. In short, SiRIs allow the high multiplexing capacity of fixed cell imaging to be translated to help the live cell imaging case, using the spatial dimension as an asset.

SiRIs of the invention have been found to be stationary over timescales appropriate for live cell imaging. Methods of using two or more different scaffolds of the invention with different kinds of spacing can permit a balance between the number of signals that can be simultaneously observed, and the spatial sampling that is permitted. As set forth elsewhere herein, multiple different candidate scaffolds have been prepare and used, each showing clustering. Sequences included in embodiments of modular SiRIs of the invention are shown in Table 1. Table 2 provides details of components included in RNA-based and protein-based scaffolds that have been prepared. Sequences of SiRI components listed in Table 2 are available in Table 1 and also from Addgene (Watertown, MA; addgene.org); GenBank (NCBI, Bethesda, MD; ncbi.nlm.nih.gov/genbank); and FPbase (Lambert, T J (2019) Nature Methods. 16, 277-278; fpbase.org). In Tables 1 and 2 UBC is UBC promoter "human ubiquitin C promoter"; CAG is CAG promoter "CMV early enhancer/chicken β actin promoter"; PBS is "PP7 binding sequence", and PBS1 and PBS2 are functionally identical; MBS is "MS2 binding sequence"; KGC is "golgi export trafficking signal KGC"; SYN is "human synapsin I promoter"; and WPRE is "WHIP Posttranscriptional Response Element".

TABLE 1

Sequences and information relating to amino acid and nucleic acid sequences used in certain embodiments of the invention.

| SEQ ID NO | Motif name | Amino acid sequence (or nucleic acid sequence if specified) | Reference or description |
| --- | --- | --- | --- |
| 1 | Tandem dimer MS2 coat protein (tdMCP) | MASNFTQFVLVDNGGTGDVTVAPSNFA NGIAEWISSNSRSQAYKVTCSVRQSSAQ NRKYTIKVEVPKGAWRSYLNMELTIPIFA TNSDCELIVKAMQGLLKDGNPIPSAIAAN SGIYAMASNFTQFVLVDNGGTGDVTVAP SNFANGIAEWISSNSRSQAYKVTCSVRQS SAQNRKYTIKVEVPKGAWRSYLNMELTI PIFATNSDCELIVKAMQGLLKDGNPIPSAI AANSG | (Wu Chao and Singer, 2012) |
| 2 | Tandem dimer PP7 coat protein (tdPCP) | LASKTIVLSVGEATRTLTEIQSTADRQIFE EKVGPLVGRLRLTASLRQNGAKTAYRV NLKLDQADVVDSGLPKVRYTQVWSHDV TIVANSTEASRKSLYDLTKSLVATSQVED LVVNLVPLGRADPLASKTIVLSVGEATRT LTEIQSTADRQIFEEKVGPLVGRLRLTAS LRQNGAKTAYRVNLKLDQADVVDSGLP KVRYTQVWSHDVTIVANSTEASRKSLYD LTKSLVATSQVEDLVVNLVPLGR | (Wu Chao and Singer, 2012) |
| 3 | MS2 binding site (MBS) | (nucleic acid sequence) acatgaggatcacccatgt | (Wu, Chao and Singer, 2012) |
| 4 | PP7 binding site version 1 (PBS 1) | (nucleic acid sequence) ggagcagacgatatggcgtcgctcc | (Wu, Chao and Singer, 2012) |
| 5 | PP7 binding site version 2 (PBS 2) | (nucleic acid sequence) ccagcagagcatatgggctcgctgg | (Wu, Chao and Singer, 2012) |
| 6 | LambdaN22 protein (LNP) | MDAQTRRRERRAEKQAQWKAAN | (Franklin, 1985; Martin et al., 2013) |
| 7 | LambdaN22 binding site (BoxB) | (nucleic acid sequence) gggccctgaagaagggccc | (Martin et al., 2013) |
| 8 | Actb UTR | (nucleic acid sequence) gcggactgttactgagctgcgttttacacccttctttgacaaaac ctaacttgcgcagaaaaaaaaaaataagagacaacattggcat ggctttgttttttaaattttttttaaagtttttttttttttttttttttttttttta agtttttttgttttgttttggcgcttttgactcaggatttaaaaactgg aacggtgaaggcgacagcagttggttggagcaaacatccccc aaagttctacaaatgtggctgaggactttgtacattgtttttgttttttttt | 3' UTR of mouse β actin mRNA (nucleotide 1-441) (Wu et al., 2016) |

TABLE 1-continued

Sequences and information relating to amino acid and nucleic acid sequences used in certain embodiments of the invention.

| SEQ ID NO | Motif name | Amino acid sequence (or nucleic acid sequence if specified) | Reference or description |
|---|---|---|---|
| | | tttttttggttttgtattttttaatagtcattccaagtatccatgaaata agtggttacaggaagtccctcaccctcccaaaagccaccccca ctcctaagaggaggatggtcgcgtccatgccctgagtccaccc cggggaaggtgaca | |
| 9 | I3-01 | MKMEELFKKHKIVAVLRANSVEEAKKK ALAVFLGGVHLIEITFTVPDADTVIKELSF LKEMGAIIGAGTVTSVEQCRKAVESGAE FIVSPHLDEEISQFCKEKGVFYMPGVMTP TELVKAMKLGHTILKLFPGEVVGPQFVK AMKGPFPNVKFVPTGGVNLDNVCEWFK AGVLAVGVGSALVKGTPVEVAEKAKAF VEKIRGCTE | (Hsia et al., 2016) |
| 10 | O3-33 | MSQAIGILELTSIAAGMELGDAMLKSAN VDLLVSKTISPGKFLLMLGGDIGAIQQAI ETGTSQAGELLVDSLVLANIHPSVLPAIS GLNSVDKRQAVGIVETWSVAACISAADR AVKGSNVTLVRVHMAFGIGGKCYMVVA GDVSDVALAVTVASSSAGAYGLLVYAS LIPRPHEAMWRQMVEGLE | (King et al., 2012) |
| 11 | HexCoil-Ala | AEAESALEYAQQALEKAQLALQAARQA LKA | (Grigoryan et al., 2011) |
| 12 | 5H2L_2 | TQEDLLKKIMKLLKKQIKLLKKQIKMLK RLEKQ | (Huang et al., 2014) |
| 13 | Linker12 | GGSGGTGGSGGT | Flexible linker |
| 14 | Linker24 | GGSGGTGGSGGTGGSGGTGGSGGT | Flexible linker |
| 15 | Linker27 | GGSGGSGGTGGSGGSGGTGGSGGSGGT | Flexible linker |
| 16 | Linker29 | GGSGGSGGTGGSGGSGGTGGSGGSGGT GG | Flexible linker |
| 17 | Linker48 | GGSGGTGGSGGTGGSGGTGGSGGTGGS GGTGGSGGTGGSGGTGGSGGT | Flexible linker |
| 18 | Linker50 | GGSGGTGGSGGTGGSGGTGGSGGTGGS GGTGGSGGTGGSGGTGGSGGTGG | Flexible linker |
| 19 | T3-10 | MTEKEKMLAEKWYDANFDQTLINERLR AKVICFALNHTNPVATMMRKVLIDALFQ TTTDNVSISIPFDTDYGWNVKLGKNVYV NTNCYFMDGGQITIGDNVFIGPNCGFYT ATHPLNFHHRNEGFEKAGPIHIGSNTWFG GHVAVLPGVTIGEGSVIGAGSVVTKDIPP HSLAVGNPCKVVRKIDNDLPSETLNDETI K | (King et al., 2012) |
| 20 | 3VDX | MPFITVGQENSTSIDLYYEDHGTGVPVVL IHGFPLSGHSWERQSAALLDAGYRVITY DRRGFGQSSQPTTGYDYDTFAADLNTVL ETLDLQDAVLVGFSMGTGEVARYVSSY GTARIAAVAFLASLEPFLLKTDDNPDGA APQEFFDGIVAAVKADRYAFYTGFFNDF YNLDENLGTRISEEAVRNSWNTAASGGF FAAAAAPTTWYTDFRADIPRIDVPALILH GTGDRTLPIENTARVFHKALPSAEYVEVE GAPHGLLWTHAEEVNTALLAFLAKALE AQKQKLLTEVETYVLSIIPSGPLKAEIAQR LEDVFAGKNTDLEVLMEWLKTRPILSPL TKGILGFVFTLTVPSERGLQRRRFVQNAL NGNGDPNNMDKAVKLYRKLKREITFHG AKEISLSYSAGALASCMGLIYNRMGAVT TEVAFGLVCATCEQIADSQHRSHRQLE | (Lai, Cascio and Yeates, 2012; Lai et al., 2016) |
| 21 | 5L6HC3_1 | SEELRAVADLQRLNIELARKLLEAVARL QELNIDLVRKTSELTDEKTIREEIRKVKEE SKRIVEEAEEEIRRAKEESRYIADESRGS | (Boyken et al., 2016) |

TABLE 1-continued

Sequences and information relating to amino acid and nucleic acid sequences used in certain embodiments of the invention.

| SEQ ID NO | Motif name | Amino acid sequence (or nucleic acid sequence if specified) | Reference or description |
|---|---|---|---|
| 22 | 2L8HC4_15 | GSRVYESEKLAREADKLAQKSEDMARE ADKQARRAEERPDREEIARLAAIIARMV ALNSRIAMLMARMIMLNSQES | (Boyken et al., 2016) |
| 23 | ATC-HL3 | MQWQTKLPLIAILRGITPDEALAHVGAVI DAGFDAVEIPLNSPWEQSIPAIVDAYGD KALIGAGTVLKPEQVDALARMGCQLIVT PNIHSEVIRRAVGYGMTVCPGCATATEA FTALEAGAQALKIFPSSAFGPQYIKALKA VLPSDIAVFAVGGVTPENLAQWIDAGCA GAGLGSDLYRAGQSVERTAQQAAAFVK AYREAQKQKEQRQDQKSAYALGASLGR YMENSLKEQEKLGIKLDKDQLIAGVQDA FADKSKLSDQEIEQTLQAFEARVKSSAQ AKLE | (Lai et al., 2014) |
| 24 | T32-28 | MGEVPIGDPKELNGMEIAAVYLQPIEME PRGIDLAASLADIHLEADIHALKNNPNGF PEGFWMPYLTIAYALANADTGAIKTGTL MPMVADDGPHYGANIAMEKDKKGGFG VGTYALTFLISNPEKQGFGRHVDEETGV GKWFEPFVVTYFFKYTGTPKGGGSGGGS MSQAIGILELTSIAKGMELGDAMLKSAN VDLLVSKTISPGKFLLMLGGDIGAIQQAI ETGTSQAGEMLVDSLVLANIHPSVLPAIS GLNSVDKRQAVGIVETWSVAACISAADL AVKGSNVTLVRVHMAFGIGGKCYMVVA GDVLDVAAAVATASLAAGAKGLLVYAS IIPRPHEAMWRQMVEG | (King et al., 2014) |
| 25 | I32-06A | GMTDYIRDGSAIKALSFAIILAEADLRHIP QDLQRLAVRVIHA CGMVDVANDLAFSEGAGKAGRNALLAG APILCDARMVAEGITRSRLPADNRVIYTL SDPSVPELAKKIGNTRSAAALDLWLPHIE GSIVAIGNAPTALFRLFELLDAGAPKPALI IGMPVGFVGAAESKDELAANSRGVPYVI VRGRRGGSAMTAAAVNALASERE | (Bale et al., 2016) |
| 26 | I32-06B | MITVFGLKSKLAPRREKLAEVIYSSLHLG LDIPKGKHAIRFLCLEKEDFYYPFDRSDD YTVIEINLMAGRSEETKMLLIFLLFIALER KLGIRAHDVEITIKEQPAHCWGFRGRTG DSARDLDYDIYV | (Bale et al., 2016) |
| 27 | I52-03A | MGHTKGPTPQQHDGSALRIGIVHARWN KTIIMPLLIGTIAKLLECGVKASNIVVQSV PGSWELPIAVQRLYSASQLQTPSSGPSLS AGDLLGSSTTDLTALPTTTASSTGPFDALI AIGVLIKGETMHFEYIADSVSHGLMRVQ LDTGVPVIFGVLTVLTDDQAKARAGVIE GSHNHGEDWGLAAVEMGVRRRDWAAG KTE | (Bale et al., 2016) |
| 28 | I52-03B | MYEVDHADVYDLFYLGRGKDYAAEAS DIADLVRSRTPEASSLLDVACGTGTHLEH FTKEFGDTAGLELSEDMLTHARKRLPDA TLHQGDMRDFQLGRKFSAVVSMFSSVG YLKTVAELGAAVASFAEHLEPGGVVVV EPWWFPETFADGWVSADVVRRDGRTVA RVSHSVREGNATRMEVHFTVADPGKGV RHFSDVHLITLFHQREYEAAFMAAGLRV EYLEGGPSGRGLFVGVPALE | (Bale et al., 2016) |
| 29 | I53-34A | GMEGMDPLAVLAESRLLPLLTVRGGEDL AGLATVLELMGVGALEITLRTEKGLEAL KALRKSGLLLGAGTVRSPKEAEAALEAG AAFLVSPGLLEEVAALAQARGVPYLPGV LTPTEVERALALGLSALKFFPAEPFQGVR VLRAYAEVFPEVRFLPTGGIKEEHLPHYA ALPNLLAVGGSWLLQGDLAAVMKKVK AAKALLSPQAPG | (Bale et al., 2016) |

TABLE 1-continued

Sequences and information relating to amino acid and nucleic acid sequences used in certain embodiments of the invention.

| SEQ ID NO | Motif name | Amino acid sequence (or nucleic acid sequence if specified) | Reference or description |
|---|---|---|---|
| 30 | I53-34B | MTKKVGIVDTTFARVDMAEAAIRTLKAL SPNIKIIRKTVPGIKDLPVACKKLLEEEGC DIVMALGMPGKAEKDKVCAHEASLGLM LAQLMTNKHIIEVFVHEDEAKDDDELDIL ALVRAIEHAANVYYLLFKPEYLTRMAGK GLRQGREDAGPARE | (Bale et al., 2016) |
| 31 | 5L8HC4_6 | GSKDTEDSRKIWEDIRRLLEEARKNSEEI WKEITKNPDTSEIARLLSEQLLEIAEMLV RIAELLSRQTEQR | (Boyken et al., 2016) |
| 32 | 1D7A | GARVAIVMGSLSDWATMQFAALIFLILN VPHHVEVVSAHRTPDKLFSFAESAEENG YQVIIAGAGGAAHLPGMIAAKTLVPVLG VPVQSAALSGVDSLYSIVQMPRGIPVGTL AIGKAGAANAALLAAQILATHDKELHQR LNDWRKAQTDEVLENPLPRG | Engineered from a bacterial protein; (Garcia-Seisdedos et al., 2017) |
| 33 | 1FRW | MNLMTTITGVVLAGGKARRMGGVDKG LLELNGKPLWQHVADALMTQLSHVVVN ANRHQEIYQASGLKVIEDSLADYPGPLA GMLSVMQQEAGEWFLFCPCDTPYIPPDL AARLNHQRKDAPVVWVHDGERDHPTIA LVNRAIEPLLLEYLQAGERRVMVFMRLA GGHAVLFSLHLLAFVNVNTPEELARWQE KR | Engineered from a bacterial protein; (Garcia-Seisdedos et al., 2017) |
| 34 | 1L6W | MELYLDTSDVVAVKALSiRIFPLAGVTTN PSIIAAGKKPLDVVLPQLHEAMGGQGRL FAQVMATTAEGMVNDALKLRSIIADIVV KVPVTAEGLAAIYMLYAYGIPTLGTAVY GAAQGLLSALAGAEYVAPYVNRIDAQG GSGIQTVTDLHQLLKMHAPQAKVLAASF KTPRQALDCLLAGCESITLPLDVAQQMIS YPAVDAAVAKFEQDWQGAFGRTSI | Engineered from a bacterial protein; (Garcia-Seisdedos et al., 2017) |
| 35 | 1YAC | MTKPYVRLDKNDAAVLLVDHQAGLLSL VRDIEPDKFKNNVLALGDLAKYFNLPTIL TTSAETGPNGPLVPELKAQFPDAPYIARP GNINAWYNEYFVYAVYATGKKQLIIAGV VTEVCVAFPALSAIEEGFDVFVVTDASGT FNEITRHSAWDRMSQAGAQLMTWFGVA CELHRDWRNDIAGLATLFSNHIPDYRNL MTSYDTLTKQK | Engineered from a bacterial protein; (Garcia-Seisdedos et al., 2017) |
| 36 | 2IV1 | MIQSQINRNIRLDLADAILLSKAYYYLSF AEIADGTGLAEAFVTAALLGQQALPADA ARLVGAKLDLDEDSILLLQMIPLRGCIDD RIPTDPTMYQFYEMLQVYGTTLKALVHE KFGDGIISAINFKLDVKKVADPEGGERAV ITLDGKYLPTKPF | Engineered from a bacterial protein; (Garcia-Seisdedos et al., 2017) |
| 37 | 1M3U | MKPTTISLLQKYKQEKKRFATITAYDYSF AKLFADEGLNVMLVGDSLGMTVQGHDS TLPVTVADIAYHTAAVRRGAPNCLLLAD LPFMAYATPEQAFENAATVMRAGANMV KIEGGEWLVETVQMLTERAVPVCGHLG LTPQSVNIFGGYKVQGRGLLAGLQLLSD ALALEAAGAQLLVLECVPVELAKRITEA LAIPVIGIGAGNVTDGQILVMHDAFGITG GHIPKFAKNFLAETGDIRAAVRQYMAEV ESGVYPGEEHSFH | Engineered from a bacterial protein; (Garcia-Seisdedos et al., 2017) |
| 38 | 2CG4 | MENYLIDNLDRGILEALMGNARTAYAEL AKQFGVSPETIHVRVEKMKQAGIITGARI DVSPKQLGYDVGCFIGIILKSAKDYPSAL IDALQHVLINYIQTIYEIQSTETLIVLQNPI MRTIKP | Engineered from a bacterial protein; (Garcia-Seisdedos et al., 2017) |

TABLE 1-continued

Sequences and information relating to amino acid and nucleic acid sequences used in certain embodiments of the invention.

| SEQ ID NO | Motif name | Amino acid sequence (or nucleic acid sequence if specified) | Reference or description |
|---|---|---|---|
| 39 | 2AN9 | MAQGTLYIVSAPSGAGKSSLIQALLKTQP LYDTQVSVSHTTRQPRPGEVHGEHYFFV NHYYFYYMISRDAFLEHAEVFGNYYGTS REAIEQVLATGVDVFLDIDWQGAQQIRQ KMPHARSIFILPPSKIELDRRLRGRGQDSE EVIAKRMAQAVAEMSHYAEYDYLIVND DFDTALTDLKTIIRAERLRMSRQKQRHD ALISKLLAD | Engineered from a bacterial protein; (Garcia-Seisedos et al., 2017) |
| 40 | 2AN9-mutant1 | MAQGTLYIVSAPSGAGKSSLIQALLKTQP LYDTQVSVAHTTRQPRPGEVHGEHYFFV NHYYFYYMISRDAFLEHAEVFGNYYGTS REAIEQVLATGVDVFLDIDWQGAQQIRQ KMPHARSIFILPPSKIELDRRLRGRGQDSE EVIAKRMAQAVAEMSHYAEYDYLIVND DFDTALTDLKTIIRAERLRMSRQKQRHD ALISKLLAD | Mutated in this study from 2AN9 above to deactivate the enzymatic site in 2AN9. |
| 41 | 2AN9-mutant2 | MAQGTLYIVSAPSGAGKGSLIQALLKTQ PLYDTQVSVAHTTRQPGPGEVHGEHYFF VNHYYFYYMISRDAFLEHAEVFGNYYG TSREAIEQVLATGVDVFLDIDWQGAQQI RQKMPHARSIFILPPSKIELDRRLRGRGQ DSEEVIAKRMAQAVAEMSHYAEYDYLI VNDDFDTALTDLKTIIRAERLRMSRQKQ RHDALISKLLAD | Mutated in this study from 2AN9 above to deactivate the enzymatic site in 2AN9. |
| 42 | p3Z_11 Design | MEEVVLITVPSESVARIIAKALVASRLAA CVNIVPGLTSIYRWQGSVVEDQELLLLV KTTTHAFPKLKHTVKIIHPYTVPEIVALPI AEGNREYLDWLRENTGLEHEIHEIHE | (Gonen et al., 2015) |
| 43 | EE | LEIEAAFLEQENTALETEVAELEQEVQRL ENIVSQYETRYGPL | (Moll et al., 2001) |
| 44 | RR | LEIRAAFLRRRNTALRTRVAELRQRVQR LRNIVSQYETRYGPL | (Moll et al., 2001) |
| 45 | E5 | EVSALEKEVSALEKEVSALEKEVSALEK EVSALEK | (Tripet et al., 1996) |
| 46 | K5 | CGGKVSALKEKVSALKEKVSALKEKVS ALKEKVSALKE | (Tripet et al., 1996) |
| 47 | LZA | AQLEKELQALEKKLAQLEWENQALEKE LAQ | (Shekhawat et al., 2009) |
| 48 | LZB | AQLKKKLQANKKELAQLKWKLQALKK KLAQ | (Shekhawat et al., 2009) |
| 49 | ACID-p1 | AQLEKELQALEKENAQLEWELQALEKEL AQ | (Oakley and Kim, 1998) |
| 50 | BASE-p1 | AQLKKKLQALKKKNAQLKWKLQALKK KLAQ | (Oakley and Kim, 1998) |
| 51 | DoNAp1 | EIKALEQEIAALKQKIAWLKQ | (Boyle et al., 2012) |
| 52 | DoNAp2 | KIKALKQEIAALKQEIAYLEQ | (Boyle et al., 2012) |
| 53 | P3 | SPEDEIQQLEEEIAQLEQKNAALKEKNQA LKYG | (Gradigar et al., 2013) |
| 54 | P4 | SPEDKIAQLKQKIQALKQENQQLEEENA ALEYG | (Gradigar et al., 2013) |
| 55 | APH | MKQLEKELKQLEKELQAIEKQLAQLQW KAQARKKKLAQLKKKLQA | (Negron and Keating, 2014) |
| 56 | BCR | DIEQELERAKASIRRLEQEVNQERSRMA YLQTLLAK | (Gradigar et al., 2013) |

TABLE 1-continued

Sequences and information relating to amino acid and nucleic acid sequences used in certain embodiments of the invention.

| SEQ ID NO | Motif name | Amino acid sequence (or nucleic acid sequence if specified) | Reference or description |
|---|---|---|---|
| 57 | GCNsh | QLEDKVEELLSKNYHLENEVARLKKLVG | (Gradigar et al., 2013) |
| 58 | CC_Di | GEIAALKQEIAALKKENAALKWEIAALKQGYY | (Fletcher et al., 2012) |
| 59 | CC_Tri | GEIAAIKQEIAAIKKEIAAIKWEIAAIKQGYG | (Fletcher et al., 2012) |
| 60 | CC-Hept | GEIAQALKEIAKALKEIAWALKEIAQALKG | (Thomson et al., 2014) |
| 61 | CC-Hex2 | GEIAKSLKEIAKSLKEIAWSLKEIAKSLKG | (Thomson et al., 2014) |
| 62 | CC-Pent | GKIEQILQKIEKILQKIEWILQKIEQILQG | (Thomson et al., 2014) |
| 63 | CC-Tet | GELAAIKQELAAIKKELAAIKWELAAIKQGAG | (Zaccai et al., 2011) |
| 64 | HOTag6 | TLREIEELLRKIIEDSVRSVAELEDIEKWLKKI | (Zhang et al., 2018) |
|  | Linker2 | GS | Flexible linker |
|  | Linker2G | GG | Flexible linker |
|  | Linker3 | GSG | Flexible linker |
| 65 | Linker4 | GSGS | Flexible linker |
| 66 | Linker6 | GGSGGT | Flexible linker |
| 67 | Linker (GGGS)x2 | GGGSGGGS | Flexible linker |
| 68 | Linker (GGGS)x4 | GGGSGGGSGGGSGGGS | Flexible linker |
| 69 | Linker6AP | APAPAP | Rigid linker |
| 70 | Linker5EA | EAAAK | Rigid linker |
| 71 | Linker (EAAK)x2 | EAAKEAAK | Rigid linker |
| 72 | NLS | PKKKRKV | Nuclear localization sequence (NLS) from SV40 large T-antigen |
| 73 | CAAX | GAGAKEKMSKDGKKKKKKSKTKCVIM | CAAX plasma membrane targeting motif from ras proteins (Hancock et al., 1991) |
| 74 | Xpress | DLYDDDDK | Synthetic peptide Xpress epitope |
| 75 | HA | YPYDVPDYA | Influenza hemagglutin-in epitope (Wilson et al., 1984) |
| 76 | V5 | GKPIPNPLLGLDST | Simian virus 5-derived epitope (Southern et al., 1991) |

TABLE 1-continued

Sequences and information relating to amino acid and nucleic acid sequences used in certain embodiments of the invention.

| SEQ ID NO | Motif name | Amino acid sequence (or nucleic acid sequence if specified) | Reference or description |
|---|---|---|---|
| 77 | OLLAS | SGFANELGPRLMGK | |
| 78 | VSVg | YTDIEMNRLGK | |
| 79 | E_epitope | GAPVPYPDPLEPR | |
| 80 | FLAG | DYKDDDDK | Synthetic peptide FLAG epitope (Hopp et al., 1988) |
| 81 | mRuby3-6xFLAG | MDYKDDDDKGDYKDDDDKGDYKDDDDKGGGGGVSKGEELIKENMRMKVVMEGSVNGHQFKCTGEGEGRPYEGVQTMRIKVIEGGPLPFAFDILATSFMYGSRTFIKYPADIPDFFKQSFPEGFTWERVTRYEDGGVVTVTQDTSLEDGELVYNVKVRGVNFPSNGPVMQKKTKGWEPNTEMMYPADGGLRGYTDIALKVDGGGHLHCNFVTTYRSKKTVGNIKMPGVHAVDHRLERIEESDNETYVVQREVAVAKYSNLGGGMDELYKGGGGGDYKDDDDKGDYKDDDDKGDYKDDDDK | (Viswanathan et al., 2015) |

TABLE 2

Component details and results for constructs prepared and screened in HeLa cells and/or neurons - see Table 1 for sequences of certain components.

| Construct (non-coding regions are underlined; non-coding regions other than promoters, beta actin UTR, and MS2/PP7 binding sites are omitted; '+' denotes co-expression; '-'s in the motif names are changed to '_' since we use '-' to separate parts of constructs.) | Expressed and not causing cell death in the tested cell type(s)? | Degree of clustering ($D_C$) under optical microscope in the tested cell type(s)? ($D_C = 1$ means no resolvable puncta.) | Fluorescent reporter is functional in the tested cell type(s)? |
|---|---|---|---|
| <u>UBC</u>-NLS-HA-tdMCP-Linker12-Xpress-GCaMP6f (also known as MP-GCaMP6f) + <u>CAG</u>-miRFP-<u>ActbUTR</u>-<u>48xMBS</u> (also known as MR-SF) | Yes, in HeLa cells and neurons. | $D_C = 10$-$50$ in HeLa cells; $D_C = 1$ in neurons. | Yes, in HeLa cells and neurons. |
| <u>UBC</u>-NLS-V5-tdPCP-Linker24-ICUE3 (also known as PP-ICUE3) + <u>CAG</u>-miRFP-<u>ActbUTR</u>-<u>72xPBS</u> (also known as PR-SF) | Yes, in HeLa cells and neurons. | $D_C = 20$-$50$ in HeLa cells; $D_C = 1$ in neurons. | Yes, in HeLa cells and neurons. |
| <u>UBC</u>-NLS-HA-tdPCP-Linker12- GCaMP6f + <u>CAG</u>-miRFP-<u>ActbUTR</u>-<u>72xPBS</u> (also known as PR-SF) | Yes, in HeLa cells and neurons. | $D_C = 20$-$50$ in HeLa cells; $D_C \sim 1.2$ in the soma of neurons; $D_C = 1$ in the neurites of neurons. | Yes, in HeLa cells and neurons. |
| <u>UBC</u>-NLS-HA-tdMCP-Linker12- mRuby2 (also known as MP-mRuby2) + <u>CAG</u>-miRFP-<u>ActbUTR</u>-<u>48xMBS</u> (also known as MR-SF) | Yes, in neurons. | $D_C \sim 3$ in the soma of neurons; $D_C \sim 5$ in the neurites of neurons. | No fluorescent reporter in this construct. |
| <u>UBC</u>-NLS-HA-tdPCP-Linker12- GFP (also known as PP-GFP) + <u>CAG</u>-miRFP-<u>ActbUTR</u>-<u>72xPBS</u> (also known as PR-SF) | Yes, in neurons. | $D_C \sim 3$ in the soma of neurons; $D_C \sim 5$ in the neurites of neurons. | No fluorescent reporter in this construct. |
| <u>UBC</u>-HexCoil_Ala-Linker48-Xpress-GCaMP6f-Linker12-I3_01 | Yes, in HeLa cells and neurons. | $D_C \sim 10^3$ in the soma of neurons; $D_C \sim 10^4$ in | Yes, in HeLa cells and neurons. |

TABLE 2-continued

Component details and results for constructs prepared and screened in HeLa cells and/or neurons - see Table 1 for sequences of certain components.

| Construct (non-coding regions are underlined; non-coding regions other than promoters, beta actin UTR, and MS2/PP7 binding sites are omitted; '+' denotes co-expression; '-'s in the motif names are changed to '_' since we use '-' to separate parts of constructs.) | Expressed and not causing cell death in the tested cell type(s)? | Degree of clustering ($D_C$) under optical microscope in the tested cell type(s)? ($D_C = 1$ means no resolvable puncta.) | Fluorescent reporter is functional in the tested cell type(s)? |
|---|---|---|---|
| (also known as S1-GCaMP6f) | | the neurites of neurons. $D_C =$ 250-1000 in HeLa cells. | |
| <u>UBC</u>-1M3U-Linker48-cAMPr-gsg-HA-Linker27-2L8HC4_15 (also known as S2-cAMPr) | Yes, in HeLa cells and neurons. | $D_C \sim 10^2$ in the soma and neurites of neurons. | Yes, in HeLa cells and neurons. |
| <u>UBC</u>-3VDX-Linker50-ExRaiAKAR-Linker3-V5-Linker27-5L6HC3_1 (also known as S3-ExRaiAKAR) | Yes, in HeLa cells and neurons. | $D_C \sim 10^2$ in the soma and neurites of neurons. | Yes, in HeLa cells and neurons. |
| <u>UBC</u>-I32_06B-Linker29-ExRaiCKAR-Linker3-OLLAS-Linker24-I32_06A (also known as S4-ExRaiCKAR) | Yes, in neurons. | $D_C \sim 10^2$ in the soma and neurites of neurons. | Yes, in neurons. |
| <u>UBC</u>-1M3U-Linker48-RAB_EKARev-Linker3-VSVg-Linker27-2L8HC4_15 (also known as S2-RAB_EKARev) | Yes, in neurons. | $D_C \sim 10^2$ in the soma and neurites of neurons. | Yes, in neurons. |
| <u>UBC</u>-3VDX-Linker50-RAB_EKARev-Linker3-VSVg-Linker27-5L6HC3_1 (also known as S3-RAB_EKARev) | Yes, in neurons. | $D_C \sim 10^2$ in the soma and neurites of neurons. | Yes, in neurons. |
| <u>UBC</u>-O3_33-Linker48-HA-cAMPr-Linker27-5H2L_2 (also known as S2a-cAMPr) | Yes, in HeLa cells and neurons. | $D_C \sim 10^2$ in the soma and neurites of neurons. $D_C =$ 100-300 in HeLa cells. | Yes, in HeLa cells and neurons. |
| <u>UBC</u>-HexCoil_Ala-Linker12-Xpress-GCaMP6f-Linker12-I3_01 | Yes, in neurons. | $D_C \sim 10^3$ in the soma of neurons; $D_C \sim 10^4$ in the neurites of neurons. | Yes, in neurons. |
| <u>UBC</u>-HexCoil_Ala-Linker48-Xpress-GCaMP6f-Linker2G-KGC-Linker12-I3_01 | Yes, in neurons. | $D_C \sim 10^3$ in the soma of neurons; $D_C \sim 10^4$ in the neurites of neurons. | Yes, in neurons. |
| <u>UBC</u>-HexCoil_Ala-Linker12-Xpress-jRCaMP1a-Linker12-I3_01 | Yes, in neurons. | $D_C \sim 10^3$ in the soma of neurons; $D_C \sim 10^4$ in the neurites of neurons. | Yes, in neurons. |
| <u>UBC</u>-I52_03B-Linker29-ExRaiCKAR-gsg-OLLAS-Linker24-I52_03A | Yes, in neurons. | $D_C \sim 10^2$ in the soma and neurites of neurons. | Not tested. |
| <u>UBC</u>-1M3U-Linker50-ExRaiCKAR-gsg-OLLAS-Linker27-2L8HC4_15 | Yes, in neurons. | $D_C \sim 10^2$ in the soma and neurites of neurons. | Not tested. |
| <u>UBC</u>-I53_34B-Linker29-ExRaiCKAR-gsg-OLLAS-Linker24-I53_34A | Yes, in neurons. | No expression in neurons. | Not tested. |
| <u>UBC</u>-T3_10-Linker50-ExRaiCKAR-gsg-OLLAS-Linker27-5L8HC4_6 | Yes, in neurons. | $D_C = 1$ in neurons. | Not tested. |

TABLE 2-continued

Component details and results for constructs prepared and screened in HeLa cells and/or neurons - see Table 1 for sequences of certain components.

| Construct (non-coding regions are underlined; non-coding regions other than promoters, beta actin UTR, and MS2/PP7 binding sites are omitted; '+' denotes co-expression; '-'s in the motif names are changed to '_' since we use '-' to separate parts of constructs.) | Expressed and not causing cell death in the tested cell type(s)? | Degree of clustering ($D_C$) under optical microscope in the tested cell type(s)? ($D_C = 1$ means no resolvable puncta.) | Fluorescent reporter is functional in the tested cell type(s)? |
|---|---|---|---|
| Syn-I3_01-Linker12-Xpress-GCaMP6f | Yes, in neurons. | $D_C \sim 2$ in the soma of neurons; $D_C \sim 1.5$ in the neurites of neurons. | Yes, in neurons. |
| Syn-HexCoil_Ala-Linker48-Xpress-GCaMP6f-Linker12-I3_01 (S1-GCaMP6f in Syn promoter) | Yes, in neurons. | $D_C \sim 10^3$ in the soma of neurons; $D_C \sim 10^4$ in the neurites of neurons. | Yes, in neurons. |
| UBC-O3_33-Linker48-cAMPr-HA-Linker27-CC_Pent | Yes, in neurons. | $D_C \sim 40$ in the soma of neurons; $D_C \sim 10^2$ in the neurites of neurons. | Not tested. |
| UBC-O3_33-Linker48-cAMPr-HA-Linker27-CC_Hept | Yes, in neurons. | $D_C \sim 10^2$ in the soma of neurons; $D_C \sim 10^3$ in the neurites of neurons. | Not tested. |
| UBC-ATC_HL3-Linker48-cAMPr-HA-Linker27-CC_Hept | Yes, in neurons. | $D_C \sim 10^2$ in the soma of neurons; $D_C \sim 10^3$ in the neurites of neurons. | Not tested. |
| UBC-T3_10-Linker48-cAMPr-HA-Linker27-CC_Pent | Yes, in neurons. | $D_C \sim 5$ in the soma of neurons; $D_C \sim 9$ in the neurites of neurons. | Not tested. |
| UBC-3VDX-Linker48-cAMPr-HA-Linker27-CC_Pent | Yes, in neurons. | $D_C = 6\text{-}15$ in the soma of neurons; $D_C = 20\text{-}40$ in the neurites of neurons. | Not tested. |
| UBC-ATC_HL3-Linker48-cAMPr-HA-Linker27-CC_Pent | Yes, in neurons. | $D_C = 30\text{-}50$ in the soma of neurons; DC = 50-100 in the neurites of neurons. | Not tested. |
| UBC-T32_28-Linker48-cAMPr-HA-Linker27-CC_Pent | Yes, in neurons, but the expression was weak. | $D_C \sim 5$ in the soma of neurons; $D_C = 10\text{-}20$ in the neurites of neurons. | Not tested. |
| UBC-p3Z_11-Linker24-Xpress-GCaMP6f | Yes, in neurons. | $D_C = 1$ in neurons. | Yes, in neurons. |
| CAG-Xpress-GCaMP6f-Linker27-EE-Linker4-RR | Yes, in neurons. | $D_C = 1$ in neurons. | Yes, in neurons. |
| CAG-Xpress-GCaMP6f-Linker27-LZA-Linker4-LZB | Yes, in neurons. | $D_C = 1$ in neurons. | Yes, in neurons. |
| CAG-Xpress-GCaMP6f-Linker27-ACIDp1-Linker4-BASEp1 | Yes, in neurons. | $D_C = 1$ in neurons. | Yes, in neurons. |
| CAG-Xpress-GCaMP6f-Linker27-DoNAp1-Linker4-DoNAp2 | Yes, in neurons. | $D_C = 1$ in neurons. | Yes, in neurons. |
| CAG-Xpress-GCaMP6f-Linker27-P3-Linker4-P4 | Yes, in neurons. | $D_C = 1$ in neurons. | Yes, in neurons. |
| CAG-Xpress-GCaMP6f-Linker27-EE-Linker4-RR-Linker4-EE-Linker4-RR-Linker4-EE | Yes, in neurons. | $D_C = 1$ in neurons. | Yes, in neurons. |

TABLE 2-continued

Component details and results for constructs prepared and screened in HeLa cells and/or neurons - see Table 1 for sequences of certain components.

| Construct (non-coding regions are underlined; non-coding regions other than promoters, beta actin UTR, and MS2/PP7 binding sites are omitted; '+' denotes co-expression; '-'s in the motif names are changed to '_' since we use '-' to separate parts of constructs.) | Expressed and not causing cell death in the tested cell type(s)? | Degree of clustering ($D_C$) under optical microscope in the tested cell type(s)? ($D_C = 1$ means no resolvable puncta.) | Fluorescent reporter is functional in the tested cell type(s)? |
|---|---|---|---|
| <u>CAG</u>-Xpress-GCaMP6f-Linker27-ACIDp1-Linker4-BASEp1-Linker4-ACIDp1-Linker4-BASEp1-Linker4-ACIDp1 | Yes, in neurons. | $D_C = 1$ in neurons. | Yes, in neurons. |
| <u>CAG</u>-Xpress-GCaMP6f-Linker27-EE-Linker2-RR | Yes, in neurons. | $D_C = 1$ in neurons. | Yes, in neurons. |
| <u>CAG</u>-Xpress-GCaMP6f-Linker27-EE-Linker6-RR | Yes, in neurons. | $D_C = 1$ in neurons. | Yes, in neurons. |
| <u>CAG</u>-Xpress-GCaMP6f-Linker27-E5-Linker4-K5 | Yes, in neurons. | $D_C = 1$ in neurons. | Yes, in neurons. |
| <u>CAG</u>-Xpress-GCaMP6f-Linker27-E5-Linker4-K5-Linker4-E5-Linker4-K5-Linker4-E5 | Yes, in neurons. | $D_C = 1$ in neurons. | Yes, in neurons. |
| <u>CAG</u>-Xpress-GCaMP6f-Linker27-E5-Linker2-K5 | Yes, in neurons. | $D_C = 1$ in neurons. | Yes, in neurons. |
| <u>CAG</u>-Xpress-GCaMP6f-Linker27-CC_Di-Linker4-CC_Tri | Yes, in neurons. | $D_C = 1$ in neurons. | Yes, in neurons. |
| <u>UBC</u>-Xpress-GCaMP6f-Linker24-CC_Hex2-Linker6-HOTag6 | Yes, in neurons. | $D_C = 1$ in neurons. | Yes, in neurons. |
| <u>UBC</u>-Xpress-GCaMP6f-Linker24-HOTag6-Linker6-CC_Hex2 | Yes, in neurons. | $D_C = 1$ in neurons. | Yes, in neurons. |
| <u>UBC</u>-V5-Linker3-ICUE3-Linker24-CC_Hept-Linker6-CC_Tet | Yes, in neurons. | $D_C = 1$ in neurons. | Yes, in neurons. |
| <u>UBC</u>-V5-Linker3-ICUE3-Linker24-CC_Pent-Linker6-HexCoil_Ala-<u>WPRE</u> | Yes, in neurons. | $D_C = 1$ in neurons. | Yes, in neurons. |
| <u>UBC</u>-Xpress-GCaMP6f-Linker24-CC_Hept-Linker6AP-CC_Tet | Yes, in neurons. | $D_C = 1$ in neurons. | Yes, in neurons. |
| <u>UBC</u>-Xpress-GCaMP6f-Linker24-CC_Hept-Linker6AP-CC_Tet-Linker5EA-CC_Hex2 | Yes, in neurons. | $D_C = 1$ in neurons. | Yes, in neurons. |
| <u>UBC</u>-Xpress-GCaMP6f-Linker24-CC_Hept-Linker6-CC_Tet-Linker6-CC Hex2 | Yes, in neurons. | $D_C = 1$ in neurons. | Yes, in neurons. |
| <u>UBC</u>-Xpress-GCaMP6f-Linker24-HexCoil_Ala-Linker6-CC_Hept-Linker6-CC_Hex2-Linker6-CC_Tet | Yes, in neurons. | $D_C = 1$ in neurons. | Yes, in neurons. |
| <u>CAG</u>-2AN9 mutant1-Linker12-Xpress-GCaMP6f | Yes, in HeLa cells and neurons. | $D_C \sim 1.3$ in HeLa cells. $D_C = 1$ in neurons. | Yes, in HeLa cells and neurons. |
| <u>UBC</u>-Xpress-GCaMP6f-Linker27-1D7A | Yes, in HeLa cells and neurons. | $D_C = 1$ in HeLa cells. $D_C = 1$ in neurons. | Yes, in neurons. Not tested in HeLa. |
| <u>UBC</u>-1FRW-Linker12-Xpress-GCaMP6f | Yes, in HeLa cells and neurons. | $D_C = 1$ in HeLa cells. $D_C = 1$ in neurons. | Yes, in neurons. Not tested in HeLa. |
| <u>UBC</u>-1L6W-Linker12-Xpress-GCaMP6f | Yes, in HeLa cells and neurons. | $D_C = 1$ in HeLa cells. $D_C = 1$ in neurons. | Yes, in neurons. Not tested in HeLa. |
| <u>UBC</u>-1YAC-Linker12-Xpress-GCaMP6f | Yes, in HeLa cells and neurons. | $D_C = 1$ in HeLa cells. $D_C = 1$ in neurons. | Yes, in neurons. Not tested in HeLa. |
| <u>UBC</u>-2AN9-Linker12-Xpress-GCaMP6f | Yes, in HeLa cells and neurons. | $D_C \sim 1.6$ in HeLa cells. $D_C = 1$ in neurons. | Yes, in neurons. Not tested in HeLa. |
| <u>UBC</u>-2AN9_mutant1-Linker12-Xpress-GCaMP6f | Yes, in HeLa cells and neurons. | $D_C \sim 1.6$ in HeLa cells. $D_C = 1$ in neurons. | Yes, in neurons. Not tested in HeLa. |

TABLE 2-continued

Component details and results for constructs prepared and screened in HeLa cells and/or neurons - see Table 1 for sequences of certain components.

| Construct (non-coding regions are underlined; non-coding regions other than promoters, beta actin UTR, and MS2/PP7 binding sites are omitted; '+' denotes co-expression; '-'s in the motif names are changed to '_' since we use '-' to separate parts of constructs.) | Expressed and not causing cell death in the tested cell type(s)? | Degree of clustering ($D_C$) under optical microscope in the tested cell type(s)? ($D_C = 1$ means no resolvable puncta.) | Fluorescent reporter is functional in the tested cell type(s)? |
|---|---|---|---|
| UBC-2AN9_mutant2-Linker12-Xpress-GCaMP6f | Yes, in HeLa cells and neurons. | $D_C$ ~1.6 in HeLa cells. $D_C = 1$ in neurons. | Yes, in neurons. Not tested in HeLa. |
| UBC-2IV1-Linker12-Xpress-GCaMP6f | Yes, in HeLa cells and neurons. | $D_C$ ~1.5 in HeLa cells. $D_C = 1$ in neurons. | Yes, in neurons. Not tested in HeLa. |
| UBC-1M3U-Linker12-Xpress-GCaMP6f | Yes, in HeLa cells and neurons. | $D_C = 1$ in HeLa cells. $D_C = 1$ in neurons. | Yes, in neurons. Not tested in HeLa. |
| UBC-Xpress-GCaMP6f-Linker27-2CG4 | Yes, in HeLa cells and neurons. | $D_C = 1$ in HeLa cells. $D_C = 1$ in neurons. | Yes, in neurons. Not tested in HeLa. |
| UBC-NLS-Xpress-GCaMP6f-Linker27-1D7A | Yes, in HeLa cells and neurons. | $D_C = 1$ in HeLa cells. $D_C = 1$ in neurons. | Yes, in neurons. Not tested in HeLa. |
| UBC-NLS-1FRW-Linker12-Xpress-GCaMP6f | Yes, in HeLa cells and neurons. | $D_C = 1$ in HeLa cells. $D_C = 1$ in neurons. | Yes, in neurons. Not tested in HeLa. |
| UBC-NLS-1L6W-Linker12-Xpress-GCaMP6f | Yes, in HeLa cells and neurons. | $D_C = 1$ in HeLa cells. $D_C = 1$ in neurons. | Yes, in neurons. Not tested in HeLa. |
| UBC-NLS-1YAC-Linker12-Xpress-GCaMP6f | Yes, in HeLa cells and neurons. | $D_C$ ~12 in HeLa cells. $D_C = 1$ in neurons. | Yes, in neurons. Not tested in HeLa. |
| UBC-NLS-2AN9-Linker12-Xpress-GCaMP6f | Yes, in HeLa cells and neurons. | $D_C = 2$-$20$ in HeLa cells. $D_C = 1$ in neurons. | Yes, in neurons. Not tested in HeLa. |
| UBC-NLS-2AN9_mutant1-Linker12-Xpress-GCaMP6f | Yes, in HeLa cells and neurons. | $D_C = 2$-$20$ in HeLa cells. $D_C = 1$ in neurons. | Yes, in neurons. Not tested in HeLa. |
| UBC-NLS-2AN9_mutant2-Linker12-Xpress-GCaMP6f | Yes, in HeLa cells and neurons. | $D_C = 2$-$20$ in HeLa cells. $D_C = 1$ in neurons. | Yes, in neurons. Not tested in HeLa. |
| UBC-NLS-2IV1-Linker12-Xpress-GCaMP6f | Yes, in HeLa cells and neurons. | $D_C$ ~ 4.5 in HeLa cells. $D_C = 1$ in neurons. | Yes, in neurons. Not tested in HeLa. |
| UBC-NLS-1M3U-Linker12-Xpress-GCaMP6f | Yes, in HeLa cells and neurons. | $D_C = 5$-$100$ in HeLa cells. $D_C = 1$ in neurons. | Yes, in neurons. Not tested in HeLa. |
| UBC-NLS-Xpress-GCaMP6f-Linker27-2CG4 | Yes, in HeLa cells and neurons. | $D_C = 1$ in HeLa cells. $D_C = 1$ in neurons. | Yes, in neurons. Not tested in HeLa. |
| UBC-LNP-HA-NLS-Linker24-Xpress-GCaMP6f + CAG-miRFP-ActbUTR-75xBoxB (also known as LR-SF) | Yes, in HeLa cells. | $D_C$ ~7.5 in HeLa cells. | Yes, in HeLa cells. |
| UBC-LNP-FLAG-NLS Linker24-AKAR4 (also known as LP-AKAR4) + CAG-miRFP-ActbUTR-75xBoxB (also known as LR-SF) | Yes, in HeLa cells. | $D_C$ ~5 in HeLa cells. | Yes, in HeLa cells. |
| UBC-LNP-HA-NLS-Linker24-AKAR4 + CAG-miRFP-ActbUTR-75xBoxB (also known as LR-SF) | Yes, in HeLa cells. | $D_C$ ~5 in HeLa cells. | Yes, in HeLa cells. |
| UBC-NLS-HA-tdPCP-Linker12-Xpress-GCaMP6f-CAAX + UBC-miRFP-ActbUTR-72xPBS | Yes, in HeLa cells and neurons. | $D_C = 1$ in HeLa cells. $D_C = 1$ in neurons. | Yes, in neurons. Not tested in HeLa. |
| UBC-NLS-Xpress-GCaMP6f-Linker27-tdPCP-CAAX + UBC-miRFP-ActbUTR-72xPBS | Yes, in HeLa cells and neurons. | $D_C = 1$ in HeLa cells. $D_C = 1$ in neurons. | Yes, in neurons. Not tested in HeLa. |

TABLE 2-continued

Component details and results for constructs prepared and screened in HeLa cells and/or neurons - see Table 1 for sequences of certain components.

| Construct (non-coding regions are underlined; non-coding regions other than promoters, beta actin UTR, and MS2/PP7 binding sites are omitted; '+' denotes co-expression; '-'s in the motif names are changed to '_' since we use '-' to separate parts of constructs.) | Expressed and not causing cell death in the tested cell type(s)? | Degree of clustering ($D_C$) under optical microscope in the tested cell type(s)? ($D_C = 1$ means no resolvable puncta.) | Fluorescent reporter is functional in the tested cell type(s)? |
|---|---|---|---|
| UBC-Xpress-GCaMP6f-Linker27-tdPCP-CAAX + UBC-miRFP-ActbUTR-72xPBS UBC-3VDX-Linker50-ExRaiAktAR-Linker3-V5-Linker27-5L6HC3_1 (also known as S3-ExRaiAktAR) | Yes, in HeLa cells and neurons. Yes, in cultured mouse hippocampal neurons. | $D_C = 1$ in HeLa cells. $D_C = 1$ in neurons. $D_C \sim 10^2$ in the soma and neurites of neurons. | Yes, in neurons. Not tested in HeLa. Yes, in neurons. Not tested in HeLa. |

Certain embodiments of spatial multiplexing compositions and methods of the invention may be used to image fast cellular dynamics, such as those in neurons, under inexpensive single-camera microscopes with fluorescent sensors that can all be imaged in one shared optical channel (e.g. using all GFP-based sensors), because the imaging speed would then not be limited by the number of cameras available or any mechanical filter switching required to record from multiple channels. Use of spatial multiplexing compositions and methods of the invention can also free up optical channels for use for other purposes, such as cellular control. As a non-limiting example, the GFP channel may be used to observe cellular activity readout from multiple GFP-based sensors and then the red channel of the microscope used to operate red-light driven optogenetic tools (Chuong et al., 2014; Klapoetke et al., 2014).

SiRI Preparation and Use

An SiRI of the invention includes multiple components, each which may be independently selected. As used herein in reference to elements of SiRIs of the invention, the term "independently selected" means that each of a given type of element may differ from others of the same type of element in an SiRI and/or in multiple SiRIs in a cell. For example, though not intended to be limiting, an SiRI may include more than one reporter protein element and in instances when there are more than one, each may be selected so as to be different or the same as one or more other reporter protein elements in that SiRI. Similarly, in a cell that includes two or more SiRIs, each independently selected reporter protein element may be selected so as to be different than one or more other reporter protein elements in the cell, or may be selected so as to be the same as one or more other reporter protein elements in the cell. The independent election of elements in SiRIs of the invention, including reporter protein elements, RNA-binding protein elements, localization protein motif elements, protein linker elements, binding sequence elements may all be independently selected, thus permitting differences between SiRIs of the invention and permitting different SiRIs to be included in a single cell.

Different methods can be used to prepare SiRIs of the invention as is described herein using compositions capable of producing one or a plurality of SiRIs in a living cell. As used herein the term plurality means at least 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, or 1000. One such composition of the invention that can be used to prepare an SiRI using RNA-protein-binding-based clustering methods, is referred to herein as an RNA-protein binding (RPB) composition. Another composition of the invention that can be used to prepare an SiRI using protein self-assembly-based clustering of reporter molecules and to prepare an SiRI, is referred to herein as a protein self-assembly binding (PSA) composition. In certain embodiments of the invention, one or more different (PSA) compositions can be present in a live cell and produce one or more different SiRIs in that cell. In some embodiments of the invention, one or more different PSA compositions can be present in a live cell and produce one or more different SiRIs in that cell. In certain embodiments of the invention, one or more different RPB compositions and one or more different PSA compositions may be present in a live cell and produce one or more different SiRIs in that cell.

RPB and PSA Compositions

In certain embodiments of the invention an RPB composition comprises a fusion protein component and an RNA component. A fusion protein component of an RPB of the invention comprises independently selected elements such as (i) one or more independently selected reporter protein elements, (ii) one or more independently selected RNA binding protein elements; (iii) zero, one, or more independently selected epitope tag elements; (iv) zero, one, or more localization protein motif elements; and (v) zero, one, or more independently selected protein linker elements, wherein when present, each of the protein linker elements is positioned between two of the elements of (i), (ii), (iii), and (iv). An RNA component of an RPB composition of the invention comprises a plurality of independently selected RNA molecules, and each of the independently selected RNA molecules comprises a plurality of binding sequence elements that are recognized by the one or more RNA binding protein elements of (ii). It will be understood that in some embodiments, a composition of the invention comprises the sequences that encode the fusion protein of the RPB composition. For example, in some embodiments of the invention a composition of the invention includes a vector comprising sequences encoding an RPB fusion protein.

A PSA composition of the invention comprises a fusion protein component comprising independently selected elements, such as (a) one or more independently selected reporter protein element(s); (b) one or more independently selected self-assembly protein element(s); (c) zero, one, or more independently selected epitope tag element(s); (d) zero, one, or more protein localization motif element(s); and (e) zero, one, or more independently selected protein linker element(s), wherein when present, each of the protein linker elements is positioned between two of the elements of (a), (b), (c), and (d). It will be understood that in some embodiments, a composition of the invention comprises the sequences that encode the fusion protein of the PSA composition. For example, in some embodiments of the invention a composition of the invention includes a vector comprising sequences encoding a PSA fusion protein.

In both RPB and PSA compositions of the invention, the number of each type of element can differ or be the same in different prepared SiRIs. For example, an RPB and a PSA composition may each include one or more independently selected reporter protein elements, and so in some embodiments of the invention, each RPB and PSA has one, two, or other of the same number of independently selected reporter protein elements, and in certain embodiments of the invention each RPB and PSA has a different number of independently selected reporter protein elements. It will be understood that both situations may occur in a single cell, meaning that a cell may have the same number of independently selected reporter protein elements in two or more RPBs and/or PSAs, and may also have different independently selected reporter protein elements in each RPB and/or PSA in that cell. In some embodiments of RPB and PSA compositions of the invention, one or more of an independently selected element may be present. In some embodiments of the invention, the number of a particular element in an RPB and/or PSA composition is zero, meaning the element is not present in that component.

It will be understood that certain embodiments of the invention comprise nucleic acid sequences that encode protein elements as described herein. Compositions of the invention may be prepared using a nucleic acid sequence encoding one or more of: a reporter protein element, a localization protein element, an epitope tag element, a protein linker element, a binding sequence element, a self-assembly protein element, or a variant thereof.

Reporter Protein Elements

The invention in part, includes methods with which to perform simultaneous readout of a plurality of reporter proteins that can each be independently selected by the practitioner. As a result, a practitioner can select a plurality of different reporters to include in methods and compositions of the invention and when present in a cell, a signal from each of the plurality of reporter proteins can be detected singly or can be detected simultaneously with one or more other of the reporter proteins in the cell. As a non-limiting example, a practitioner can select three different reporter proteins, reporters A, B, and C, and include the reporters in different compositions in a cell, and read the signals of the reporter proteins one at a time, two at a time, or all three simultaneously.

RPBs and PSAs of the invention comprise a fusion protein comprising one or more independently selected reporter protein elements. Non-limiting examples of a reporter protein element that can be included in compositions and methods of the invention are: a voltage indicator polypeptide, a calcium indicator polypeptide, a potassium indicator polypeptide, a pH indicator polypeptide, and a magnesium indicator polypeptide. Additional non-limiting examples of reporter protein elements that can be included in certain embodiments of methods and compositions of the invention are: GCaMP6, GCaMP6f, GCaMP6m, GCaMP6s, jGCaMP7, jGCaMP7f, jGCaMP7m, jGCaMP7s, jGCaMP7b, jGCaMP7c, GCaMP-X, jRGECO1, jRCaMP1, NIRGECO, BCaMP, ICUE, ICUE3, cAMPr, Epac-based cAMP indicator, AKAR, AKAR4, ExRai-AKAR, ExRai-AKAR2, CKAR, ExRai-CKAR, EKARev, and RAB-EKARev. In some embodiments of the invention an independently selected reporter protein element is a GCaMP6f polypeptide, and in certain embodiments of the invention an independently selected reporter protein element is an ICUE3 polypeptide.

It will be understood that the methods and compositions of the invention may include one or more of numerous additional reporter proteins and that a practitioner will be able to select and include one or more independently selected reporter proteins such as those described herein and those otherwise available. Non-limiting examples of fluorescence reporter proteins that can be included in certain embodiments of methods and compositions of the invention are described in the 'Fluorescent Biosensor Database' (available at //biosensordb.ucsd.edu/), which lists numerous reporter proteins that can be used in compositions and methods of the invention.

Epitope Tag Elements

RPBs and PBAs of the invention comprise a fusion protein comprising zero, one, or more independently selected epitope tag elements, which may also be referred to herein as protein tags. In some embodiments of compositions and methods of the invention, a plurality of protein tags are included in a single fusion protein. The inclusion of a plurality of protein tags in one fusion protein results in tags capable for use as protein barcodes. Non-limiting examples of epitope tags that may be included in an embodiment of an RPB or a PBA composition of the invention are: an Xpress tag, an HA tag, and a V5 tag, an OLLAS tag, a VSVg tag, an S1 (Strep I) tag, an NWS (Strep II) tag, an E epitope (E tag), a FLAG tag, an E2 tag, an AU1 tag, an AU5 tag, an Myc tag, a Spot-tag, a NE tag, an AviTag™, a C-tag, a Calmodulin-tag, a polyglutamate tag, an Rho1D4-tag, an S-tag, an SBP-tag, a Softag™ 1, a Softag™ 3, a TC tag, and a Ty tag. As indicated elsewhere herein, in some embodiments of compositions of the invention the number of epitope tags in a fusion protein of an RPB or PBA of the invention is zero. Protein tags are polypeptide sequences that have been genetically added onto a recombinant protein. The preparation and use of epitope tags are routinely practiced in the art and numerous protein epitope tags and their encoding sequences are known and are suitable for use in compositions and methods of the invention.

Localization Protein Motif Elements

RPBs and PBAs of the invention comprise a fusion protein comprising zero, one, or more independently selected localization protein motif elements. In some embodiments of compositions and methods of the invention, a plurality of localization protein motifs elements are included in a single fusion protein. As indicated elsewhere herein, in some embodiments of compositions of the invention the number of localization protein motif elements included in a fusion protein of an RPB or PBA of the invention is zero. Localization protein motifs are proteins that are capable of delivering fusion proteins of RPBs and PBAs of the invention from their site of synthesis in a cell to their intended location in the cell and may be referred to as trafficking sequences/motifs and targeting sequences/motifs. Methods of preparing and using localization protein motif elements are routinely practiced in the art and numerous types of known localization protein motifs and their encoding sequences, are suitable for use in compositions and methods of the invention. In certain embodiments of methods and compositions of the invention a localization protein motif comprises one or more of a subcellular localization protein and a trafficking protein. Non-limiting types of localization protein motifs that may be used in certain embodiments of the invention are nucleus localization motif, plasma membrane localization motifs, and synapse localization motifs. Further information available in: Martin, K. C. & a. Ephrussi (2009) Cell 136, 719-730; Negi, S. et al. (2015) Database Vol. 2015: article ID bav003; Donnes, P. & A. Hoglund (2004) Geno. Prot. Bioinfo. Vol. 2 No. 4: 209-215, each of which is incorporated by reference herein.

Protein Linker Elements

RPBs and PBAs of the invention comprise a fusion protein comprising zero, one, or more independently selected protein linker elements, which may also be referred to herein as "linkers". Linkers are polypeptides that, when present, are positioned between other types of elements of an RPB and/or PBA of the invention. Non-limiting examples of positioning of linkers in a fusion protein of the invention are: a linker positioned between a reporter protein element and an epitope tag element, a linker between two epitope tag elements, two or more linkers between an RNA binding protein element and a reporter protein element, and two or more linkers between two RNA binding protein elements. Different types of linkers can be used in embodiments of the invention. For example, in some embodiments of compositions and methods of the invention a protein linker element comprises one or more glycine-rich linkers. Non-limiting examples of glycine-rich linkers comprise one or more of: a GSG linker, a (GGSGGT)x2 linker (SEQ ID NO: 13), a (GGSGGT)x4 linker (SEQ ID NO: 14), a (GGSGGSGGT)x3 linker (SEQ ID NO: 15), a (GGGS)x2 linker (SEQ ID NO: 67), and a (GGGS)x4 linker (SEQ ID NO: 68). Other glycine-rich linkers are known and routinely used in the art and a skilled artisan will recognize additional glycine-rich linkers suitable for use in compositions and methods of the invention. In some embodiments of the invention, a protein linker element comprises one or more non-glycine-rich linkers. Non-limiting examples of non-glycine-rich linkers that may be used in embodiments of compositions and methods of the invention are: (EAAAK)x2 (SEQ ID NO: 71), and APAPAP (SEQ ID NO: 69). Other non-glycine-rich linkers are known and routinely used in the art and a skilled artisan will recognize additional non-glycine-rich linkers suitable for use in compositions and methods of the invention.

A linker protein used in an embodiment of the invention may be a flexible linker or a rigid linker and may include at least 2, 3, 4, 5, 6, 7, 8, 9, 10, 11, 12, 13, 14, 15, 16, 17, 18, 19, 20, 25, 30, 25, or 40 amino acids. Additional linker proteins and their encoding polynucleotides are known and routinely used in the art and may be included in some embodiments of compositions and methods of the invention, see for example: Chichili, V. P. R, et al., Protein Science 2013 Vol 22:153-167; Chen, X. et al., Adv Drug Deliv Rev. 2013 Oct. 15; 65(10): 1357-1369; Arai et al. Protein Eng. 2001 August; 14(8):529-32; and Klein, J. S., et al. (2014) Protein Engineering, Design & Selection vol. 27 no. 10 pp. 325-330, each of which is incorporated herein by reference.

RNA Binding Protein Elements

RPBs of the invention comprise a fusion protein comprising one or more independently selected RNA binding protein elements. Each independently selected RNA binding protein element recognizes and selectively binds its partner binding sequence, which is present in the cell as an RNA component of the RPB. Non-limiting examples of RNA binding protein element that may be used in embodiments of the invention are non-programmable RNA binding elements and programmable RNA binding elements. Non-limiting examples of independently selected non-programmable RNA binding elements that can be included in compositions and methods of the invention are an MS2 coat protein, a PP7 coat protein, a Lambda N protein, a Q-beta coat protein, a BglG protein, a U1Ap protein, HTLV-1 Rex protein, a TAT protein, an REV protein, and an eiF4A protein. Non-limiting examples of independently selected programmable RNA binding elements that can be included in compositions and methods of the invention are one or more of a Pumilio homology domain (PumHD) and a Pumilio-based assembly (Pumby).

It will be understood that the methods and compositions of the invention may include one or more of other known RNA binding protein elements and that a practitioner will be able to select and include one or more independently selected non-programmable and/or programmable RNA binding protein elements such as those described herein and those otherwise available. Non-limiting examples of programmable RNA-binding proteins that can be included in certain embodiments of methods and compositions of the invention are described in Adamala, K. et al., (2016) PNAS; E2579-E2588, www.pnas.org/cgi/doi/10.1073/pnas.1519368113.

RNA Components of RPBs

An RPB of the invention comprises a plurality of independently selected RNA molecules comprising a plurality of independently selected binding sequence elements. Each independently selected binding sequence recognizes and selectively binds its partner RNA binding protein element, which is present in the cell in the fusion protein component of the RPB. In some embodiments of the invention the plurality of the independently selected binding sequence elements includes ten or more binding sequences. In certain embodiments of the invention the plurality of the independently selected binding sequence elements includes at least 2, 3, 4, 5, 6, 7, 8, 9, 10, 11, 12, 13, 14, 15, 16, 17, 18, 19, 20, 30, 40, or 50 binding sequences.

A composition of the invention may include one or a plurality of independently selected binding sequences. Non-limiting examples of binding sequence elements that may be included in an embodiment of the invention are: an MS2 binding sequence, a PP7 binding sequence, and a lambda N binding sequence (BoxB), a Q-beta binding sequence, a BglG binding sequence, an U1Ap aptamer sequence, an HTLV-1 Rex responsive element (RxRE), a TAR sequence, an RRE sequence, and an eiF4A aptamer sequence. Other binding sequences are known and routinely used in the art and a skilled artisan will recognize additional non-glycine-rich linkers suitable for use in certain compositions and methods of the invention. Further information is present in Chen, X., et al. Adv Drug Deliv Rev. 2013 Oct. 15; 65(10): 1357-1369 and Klein, J. S., et al. (2014) Protein Engineering, Design & Selection vol. 27 no. 10 pp. 325-330, each of which is incorporated herein by reference.

Binding Protein Elements: Binding Sequence Elements

Binding protein elements: binding sequence elements are also referred to herein as "binding pairs". A number of binding pairs are disclosed herein and known and routinely used in the art. Non-limiting examples of binding pairs that may be used in compositions and methods of the invention are: MS2 coat protein: MS2 binding sequence, PP7 coat protein: PP7 binding sequence, Lambda N protein: lambda N binding sequence (BoxB), Q-beta coat protein: Q-beta binding sequence, BglG protein: BglG binding sequence, U1Ap protein: U1Ap aptamer sequence, HTLV-1 Rex protein: HTLV-1 Rex responsive element (RxRE), TAT protein: TAR sequence, REV protein: RRE sequence, and eiF4A protein: eiF4A aptamer sequence. Other binding pairs and their encoding sequences are known and routinely used in the art and a skilled artisan will recognize additional binding pairs suitable for use in certain compositions and methods of the invention.

Additional details, such as a binding sequence and a binding partner name are provided after the following non-limiting examples of protein tags that may be included in compositions and methods of the invention are: AviTag™, which permits biotinylation by the enzyme BirA, thereby permitting the protein to be isolated by streptavidin (GLNDIFEAQKIEWHE, SEQ ID NO: 82); C-tag, Calmodulin-tag, which comprises a peptide binds calmodulin KRRWKKNFIAVSAANRFKKISSSGAL, SEQ ID NO: 83); a polyglutamate tag, which binds anion-exchange resins such as Mono-Q (EEEEEE, SEQ ID NO: 84); an E-tag, which is a peptide that binds an antibody comprising the sequence: GAPVPYPDPLEPR (SEQ ID NO: 79, which is also referred to herein as "E_epitope); a FLAG-tag, which binds antibody comprising the sequence: DYKDDDDK (SEQ ID NO: 80); an HA-tag, which binds a sequence set forth as YPYDVPDYA (SEQ ID NO: 75); a His-tag; a Myc-tag; an NE-tag, which comprises an 18-amino-acid synthetic peptide TKENPRSNQEESYDDNES (SEQ ID NO: 85) that binds a monoclonal IgG1 antibody; a Rho1D4-tag, which comprises nine amino acids of the intracellular C-terminus of bovine rhodopsin (TETSQVAPA, SEQ ID NO: 86); an S-tag, which is derived from Ribonuclease A (KETAAAKFERQHMDS, SEQ ID NO: 87); an SBP-tag, which binds streptavidin (MDEKTTGWRGGHVVEGLAGELEQLRARLEHHPQGQREP, SEQ ID NO: 88); Softag™ 1, for mammalian expression (SLAELLNAGLGGS, SEQ ID NO: 89); Softag™ 3, for prokaryotic expression (TQDPSRVG, SEQ ID NO: 90); Spot-tag, which binds a nanobody, set forth as: PDRVRAVSHWSS (SEQ ID NO: 91); Strep-tag, which binds to streptavidin or the modified streptavidin called streptactin (Strep-tag II: WSHPQFEK, SEQ ID NO: 92); TC tag, which binds FlAsH and ReAsH biarsenical compounds (CCPGCC, SEQ ID NO: 93); a Ty tag (EVHTNQDPLD, SEQ ID NO: 94); a V5 tag, which binds an antibody (GKPIPNPLLGLDST, SEQ ID NO: 76); a VSV-tag, which binds an antibody (YTDIEMNRLGK, SEQ ID NO: 78); and an Xpress tag (DLYDDDDK, SEQ ID NO: 74).

Self-Assembly Protein Elements

A PSA of the invention comprises one or more of an independently selected self-assembly protein element. Self-assembly proteins are capable of take a defined physical arrangement without outside guidance. Some embodiments of the invention comprise self-assembly proteins that are intramolecular self-assembly proteins. Certain embodiments of the invention comprise self-assembly proteins that are intermolecular self-assembly proteins.

Non-limiting examples of self-assembly proteins that can be used in embodiments of the invention are: a polyhedron-forming protein, a coiled-coil forming protein, a supramolecular self-assembly protein, and a protein oligomer. Non-limiting examples of a polyhedron-forming protein that may be used include: I3-01, O3-33, ATC-HL3, and 3VDX. Non-limiting examples of a coiled-coil forming protein include HexCoil-Ala, 5H2L_2, EE, and RR. Non-limiting examples of a supramolecular self-assembly protein that can be used are: 2AN9 and 1M3U. Non-limiting examples of a protein oligomer that can be used are: 5L6HC3-1 and 2L8HC4_15. Other self-assembly proteins are known and routinely used in the art and a skilled artisan will recognize additional self-assembly proteins suitable for use in certain compositions and methods of the invention.

Preparing and Using SiRIs

SiRIs of the invention can be prepared and used in methods of the invention in individual cells. Compositions that may be used in embodiments of the invention to prepare SiRIs in a cell comprise RPB and PSA compositions. The terms "PSA-based SiRI" and "RPB-based SiRI" mean an SiRI prepared from a PSA composition or an RPB composition, respectively. In some embodiments of the invention one, two, or more independently selected RPB compositions that are delivered into a cell produce one or more SiRIs in that cell. In some embodiments of the invention one, two, or more independently selected PSA compositions that are delivered into a cell produce one or more SiRIs in that cell. In certain embodiments of the invention one, two, or more independently selected RPB compositions and one, two, or more PSA compositions are delivered into a cell and in the cell, the RPB and PSA compositions produce SiRIs in that cell. In some embodiments, methods of the invention may include preparing two or more different clusters that are formed from two or more independently selected reporter protein elements and positioned in the cell, wherein each reporter protein element is capable of generating an identifiable signal.

In some embodiments of the invention, two or a plurality of RPB compositions can be delivered into a cell and form SiRIs that include components of the RPB compositions. The SiRIs may include different elements because of the independent selection of elements in the RPB compositions. In some embodiments of the invention, two or a plurality of PAS compositions can be delivered into a cell and form SiRIs that include components of the PSA compositions. The SiRIs may include different elements because of the independent selection of elements in the PSA compositions. In some embodiments of the invention, two or a plurality of RPB compositions and PSA compositions can be delivered into a cell and form SiRIs that include components of the RPB composition and SiRIs that include components of the PSA compositions. There may be differences between the SiRIs prepared using RPB compositions, differences between the SiRIs prepared using PSA compositions, and differences between SiRIs prepared using PSA compositions and SiRIs prepared using RPB compositions, and the differences can be predetermined because of the independent selection of elements in the RPB and PSA compositions.

SiRIs prepared and present in a cell can be used in methods of the invention to determine one or more physiological process or characteristic of the cell. Because of the options to include a plurality of independently selected elements in the SiRIs prepared using RPB and/or PSA compositions of the invention, it is possible to determine two or more simultaneous physiological processes or characteristics of the same cell. In some embodiments the invention one, two, or more RPB and/or PSA compositions of the invention can be placed into a cell and used in methods to determine one or more physiological processes in the cell.

In a non-limiting example, preparation of one or a plurality of SiRIs in a cell comprises the delivery into a cell of at least one RPB and/or PSA composition. Using either an RPB or PSA composition, fusion proteins are expressed in the cell. The expressed fusion proteins include a plurality of each of two or more independently selected reporter protein elements each capable of generating an identifiable signal. As used herein the term "identifiable signal" means that at least by using methods of the invention a signal generated by a reporter protein indicates the identity of the reporter protein generating the signal. The method also includes forming one or more clusters from the plurality of the two or more independently selected reporter protein elements in the cell, wherein each of the two or more independently selected reporter protein elements are in different clusters. The presence of the independently selected elements in the RPB and/or PSA compositions present in the cell result in the formation of clusters in the cell that include the reporter protein elements of that RPB or PSA, respectively.

As a non-limiting example, if one or more RPB compositions are present in a cell, the individually selected RNA binding protein elements bind with the independently selected RNA molecules of the RNA component that is also in the cell. As described elsewhere herein, each independently selected binding sequence recognizes and selectively binds its partner RNA binding protein element present in the fusion protein component of the RPB. The binding of the binding partners results in the formation of clusters that include the fusion protein component(s) and the RNA component (s) of one or a plurality of the RPB composition(s). In another non-limiting example, if a PSA composition is present in a cell, the independently selected self-assembly protein elements in the fusion protein component assemble to form clusters of the fusion protein components of the PSA composition.

Certain embodiments of methods of the invention include positioning the one or more formed clusters in the cell such that a distance between a cluster formed with one of the independently selected reporter protein elements and a cluster formed with another of the independently selected reporter protein elements is sufficient to (i) resolve the signal generated by the two independently selected reporter protein elements in the positioned clusters and (ii) simultaneously determine the signal generated by each of the independently selected reporter protein elements in the positioned clusters. In some embodiments of the invention a distance between a cluster formed that includes one of the independently selected reporter protein elements and a cluster formed that includes another of the independently selected reporter protein elements is about 1-2 microns, 1-3 microns, 1-4 microns, 1-5 microns, 1-6 microns, 1-7 microns, or 1-8 microns. In certain embodiments the distance between clusters that include two different independently selected reporter proteins is 2-8 microns.

Elements included in the RPB and PSA compositions can be independently selected to position the SiRIs that are prepared from the compositions. As a non-limiting example, in RPB and PSA compositions, a localization protein motif may be selected and included to assist with positioning the formed clusters in a cell. As another non-limiting example, the number and length of linkers included in a fusion protein of an RPB and/or PSA composition can assist in determining a physical conformation/size of a formed cluster, thereby assisting in positioning the cluster. Certain embodiments of methods of the invention include resolving signals generated by the independently selected reporter proteins in positioned clusters and detecting changes in the signals as measure of changes in physiological processes in the cell. Non-limiting examples of combinations of linkers, localization elements, and other elements that can be selected at least in part to determine size and position of SiRI clusters of the invention are described herein. Additional combinations of linkers, localization elements, and other elements of SiRIs of the invention are also suitable for use in methods of the invention and in view of the teaching provided herein can be prepared and utilized using routine methods.

Methods and components for preparing and using SiRIs of the invention include a number of independently selected elements, thereby permitting flexibility in SiRI design. For example, it will be understood that the individually selected binding pairing generated by a first RPB in a cell may be different from the independently selected binding pairing generated by a second RPB in the same cell, thereby resulting in the formation of different clusters, one including components of the first RPB and another including components of the second RPB. Similarly, it will be understood that the individually selected self-assembly protein elements in a first PSA composition in a cell may be different from the independently selected self-assembly protein elements in a second PSA composition in the same cell, thereby resulting in the formation of different clusters, one including components of the first PSA and another including components of the second PSA.

As described herein, different elements in one or more components in RPBs and PSAs in a cell result in one or more of: the same cluster formation, different cluster formation, the same reporter signal, different reporter signal, the same epitope tags, different epitope tags, etc. One of skill in the art will recognize the variations of elements in components of RPBs and PSAs of the invention and methods of their use for imaging in a cell, including simultaneous imaging of different physiological processes in a single cell.

Embodiments of methods of the invention may also include detecting the identifiable signals generated from the independently selected reporter protein elements in the positioned clusters; and the analysis of the detected signals as a determination of one or more physiological processes of the cell.

Signals

Certain methods of the invention include detecting a signal generated reporter protein elements that are present in one or more SiRIs in a cell. In some aspects of the invention a signal generated by a reporter protein is a fluorescent signal. An advantage of the invention described herein is the ability to detect signals from two or more different fluorescent reporter protein elements and to be able to distinguish between the two. Using methods and compositions of the invention it is possible to distinguish between the signals of two different fluorescent reporter protein elements even when the two reporters generate spectrally overlapping signals. In some embodiments of the invention a signal is a fluorescent signal. In certain embodiments of the invention a signal is a luminescent signal.

A reporter protein signal may be generated as a result of stimulation of the cell comprising the reporter protein. In some embodiments of the invention the stimulation of the cell is an external stimulation. Non-limiting examples of agents that can be used to externally stimulate a cell comprise: comprise one or more of tetradecanoylphorbol acetate (PMA), (S)-3,5-Dihydroxyphenylglycine (DHPG), N-Methyl-D-aspartic acid (NMDA), forskolin, a cancer drug, an antibody, a toxin, an agonist of a receptor, an antagonist of a receptor, an electrical field, a magnetic field, light, gas, a thermal change, a gravity change, a pH change, whole cell patch claim of the cell. Other agents that can be used to stimulate a cell comprising one or more SiRIs of the invention and a skilled artisan will be able to apply agents described herein as well as other agents to stimulate the cell. Factors that may be involved in applying stimulation to a cell that comprises one or more SiRIs include, but are not limited to one or more of: stimulation intensity, stimulation frequency, pattern of stimulation, and combinations of stimulating agents. These factors and their application are known and routinely practiced in the art and can be applied to embodiments of methods of the invention. As described herein, embodiments of methods of the invention include detecting and/or monitoring physiological response(s) to a stimulation of a cell comprising one or more SiRIs of the invention, and methods and compositions of the invention also permit simultaneous imaging of two or more different physiological processes in a single cell. In some embodiments of the invention one or more different agents can be used to stimulate a cell and can be administered simultaneously or sequentially. In some aspects of the invention the cell is not externally stimulated.

Analysis

Methods and compositions of the invention can be used to detect and analyze physiological processes in a cell that comprises one of more SiRIs of the invention. The flexibility of components in RPB and PSA compositions and in SiRIs of the invention permit detection and analysis of two or more different physiological processes in the same cell, and also permit detection and analysis of two or more simultaneous physiological processes in the same cell. To detect and assess a physiological process in a cell that includes one or more SiRIs of the invention a practitioner may externally stimulate the cell and determine the signals generated by the independently selected reporter protein elements in the positioned SiRIs. In certain embodiments of the invention a practitioner may determine signals generated by the independently selected reporter protein elements in the positioned SiRIs in the absence of stimulation. Non-limiting examples of physiological processes that can be assessed using compositions and methods of the invention include: a function of the cell, a response of the cell, ion flux in the cell, a therapeutic response of the cell; and an activation of the cell, etc.

An element in detection and analysis methods of the invention is detecting the signals generated by the independently selected reporter protein elements that are present in SiRIs in a cell. Detection methods may include, but are not limited to one or more of: video microscopy, computerized microscopic imaging, fluorescence microscopy, and confocal microscopy, light microscopy, light sheet microscopy, light field microscopy, and endoscopy. Methods used to detect physiological processes in a cell comprising one or more SiRIs of the invention included, but are not limited to: live cell imaging, immunostaining, RNA FISH, live cell recording, an immunostaining method, an in situ hybridization method, determining fluorescence intensity, subtracting background fluorescence, a cluster/puncta localization means, expansion microscopy, fluorescence microscopy, light microscopy, and fluorescence-lifetime imaging microscopy. It will be understood that in addition to detection methods described herein, additional art-known detection methods can also be used to detect a signal generated by a reporter protein, an epitope tag, or another element of an SiRI of the invention.

Methods for analysis of signals detected from one or more SiRIs in a cell may include data analysis, analysis programs, algorithms, etc. Information is provided herein regarding suitable methods of data analysis and a skilled artisan will recognize additional resources and programs suitable to evaluate data generated using compositions and methods of the invention.

Cells and Subjects

SiRIs of the invention can be used in single cells to detect and assess physiological processes, activities, changes, etc. in the cell. Compositions and methods of the invention may be used in prokaryotic and eukaryotic cells. Compositions and methods of the invention can also be used in artificial cells. Certain embodiments of the invention include preparing one or more SiRIs in a cell that is a mammalian cell; including but not limited to a human cell, a non-human primate cell, a cell of a dog, a cell of a cat, a cell of a rodent, etc. In some embodiments of the invention, compositions and methods of the invention may be used in non-mammalian cells; including but not limited to insect cells, avian cells, fish cells, invertebrate cells, single-cell organisms, plant cells, etc. Compositions and methods of the invention may be used in non-excitable cells and in excitable cells, the latter of which includes cells able to produce and respond to electrical stimulation/signals. Examples of excitable cell types include but are not limited, to neurons, muscle cells, cardiac cells, and secretory cells (such as pancreatic cells, adrenal medulla cells, pituitary cells, etc.). As used herein the term "plurality" when used in context of cells, means two or more cells.

Non-limiting examples of cells that may be used in methods of the invention include: neuronal cells, nervous system cells, cardiac cells, circulatory system cells, connective tissue cells, visual system cells, auditory system cells, secretory cells, endocrine cells, and muscle cells. In some embodiments, a cell used in conjunction with a method of the invention is a healthy normal cell, which is not known to have a disease, disorder, or abnormal condition. In some embodiments, a cell used in conjunction with a method of the invention is an abnormal cell, for example, a cell that is believed to have, or has been has been diagnosed as having, a disorder, disease, or condition, including, but not limited to a degenerative cell, a neurological disease-bearing cell, a cell model of a disease or condition, an injured cell, etc. In some embodiments of the invention, a cell is a control cell.

Compositions and methods of the invention may be used in cells from culture, cells in solution, cells obtained from subjects, isolated cells, recombinant cells, and/or cells in a subject (in vivo cells). Compositions and method of the invention may be used in cultured cells, cultured tissues (e.g., brain slice preparations, organ preparations, etc.), and in living subjects, etc. As used herein, a the term "subject" is used to refer to a human, non-human primate, cow, horse, pig, sheep, goat, dog, cat, bird, rodent, insect, or other vertebrate or invertebrate organism in which a method of the invention is applied. In certain embodiments of the invention, a subject is a mammal and in certain embodiments of the invention a subject is a human.

Controls and Candidate Compound Testing and Screening

One or more physiological processes in a single cell can be detected and analyzed using embodiments of methods of the invention. Methods of the invention can also be used to detect and analyze a change in a physiological process or a condition in a single cell. Certain embodiments of the invention permit determination of the presence or absence of one or more physiological processes, as well as changes or modulations of such processes in a cell. Some embodiments of methods of the invention can be used to identify an effect of candidate agent on a cell. For example, though not intended to be limiting, a cell comprising one or more SiRIs of the invention can be contacted with a candidate agent and one or more physiological processes of the cell analyzed. The results of the analysis can be compared with an analysis of a control cell that was not contacted with the candidate agent. In some embodiments of the invention one or more SiRIs can be prepared in a single cell and one or more of the same SiRIs can be prepared in other cells. These "identical" cells can then be used to assess an effect of candidate compounds on individual cells. A "test" cell may be a cell in which the activity in the cell may be tested or assayed. Results obtained using assays and tests of a test cell using a method of the invention may be compared results obtained from the assays and tests performed in other test cells or assays and/or may be compared to a control value.

As used herein a control value may be a predetermined value, which can take a variety of forms. It can be a single cut-off value, such as a median or mean. It can be established based upon comparative groups, such as cells or tissues that have been imaged under similar conditions using a method of the invention, but are not contacted with a candidate compound with which the test cell is contacted and imaged. Another example of comparative groups may include cells or tissues that have a disorder or condition and groups without the disorder or condition. Another comparative group may be cells from a group with a family history of a disease or condition and cells from a group without such a family history. A predetermined value can be arranged, for example, where a tested population is divided equally (or unequally) into groups based on results of testing. Those skilled in the art are able to select appropriate control groups and values for use in comparative methods of the invention.

As a non-limiting example of use of method of the invention to assess the presence or absence of a change in a cell as a means to identify a candidate compound, a physiological process in a cell may be determined using a method of the invention in culture or in a subject and the cell may then be contacted the candidate compound and re-determined using a method of the invention. Any change in the physiological process of the cell as determined using methods of the invention, may indicate an effect of the candidate compound on the cell. In some embodiments of the invention, methods of the invention may be used to determine and/or analyze a physiological process in one or more test cells before and after the one or more test cells is contacted with a candidate compound and the before and after results can be compared to determine whether or not contact with the candidate compound resulted in a change in the physiological process in the cell.

A cell, tissue, and/or subject that include a cell comprising one or more an SiRIs of the invention may be monitored for the presence or absence of a change that occurs in the cell. As a non-limiting example, in a cell, a change in a physiological process in the cell may include a change in depolarization of the cell, a change in a depolarization-mediated cell characteristic, response to stimuli, an action potential, pH change, release of a neurotransmitter, etc.

Certain Additional Methods

As described elsewhere herein, some embodiments of methods of the invention include preparing a cell that contains one type of RPB-based SiRIs, resulting in a cell in which all SiRIs are the same as each other. Certain embodiments of methods of the invention include preparing a cell that comprises two or more types of RPB-based SiRIs, resulting in a cell that includes two or more different SiRIs. Similarly, some embodiments of methods of the invention include preparing a cell that contains one type of PSA-based SiRIs, resulting in a cell in which all SiRIs are the same as each other. Certain embodiments of methods of the invention include preparing a cell that comprises two or more types of PSA-based SiRIs, resulting in a cell that includes two or more different SiRIs. In addition, some embodiments of methods of the invention include preparing a cell that contains one type of RPB-based SiRIs and one type of PSA-based SiRIs, resulting in a cell in which all SiRIs prepared from the RPB composition are the same as each other and the SiRIs prepared from the PSA composition are the same as each other. Certain embodiments of methods of the invention include preparing a cell that comprises two or more types of RPB-based SiRIs, resulting in a cell that includes two or more different SiRIs generated from RPB compositions and two or more different SiRIs generated from PSA compositions.

The resulting cell prepared using one of these combinations of RPB and/or PSA compositions can be used to identify the effect of a candidate agent on a physiological process in the cell. In such a method the cell would be prepared as described elsewhere herein and the RPB and/or PSA composition(s) would form and position clusters as described. Methods of the invention would then include contacting the cell with a candidate agent of interest, and detecting the presence or absence of an identifiable signal generated from the independently selected reporter protein elements present in the positioned clusters. The detected signals are then analyzed and compared to control results obtained in a cell not contacted with the candidate agent, and the comparison indicates whether or not the contact with candidate agent resulted in a change in a physiological process or processes in the contacted cell. Different candidate agents can be tested using methods of the invention. Non-limiting examples of candidate agents include: pharmaceutical agent, an electrical agent, a temperature change agent, an environmental agent, etc. A skilled artisan will recognize additional candidate agents that can be tested using compositions and methods of the invention.

Element Functional Variants

Proteins and RNA molecules used in methods and compounds of the invention may include functional variants of molecules disclosed herein and functional variants art-known molecules. For example, functional variants of reporter protein elements, localization protein elements, epitope tag elements, protein linker elements, binding sequence elements, self-assembly protein elements—and their encoding sequences, and functional variants of RNA component molecules can be used in methods of the invention. As used herein, the term "parent" when used in the context of a variant element of the invention means the element molecule of which the variant element molecule is the variant. Based on the teaching provided herein regarding elements that can be used in embodiments of the invention, functional variants of protein elements that have sufficient amino acid sequence similarity/identity to a parent protein element sequence and have at least a portion of the function of the parent protein element molecule can be prepared and used in embodiments of methods of the invention. Based on teaching provided herein regarding RNA molecule elements that can be used in embodiments of the invention, functional variants of the RNA molecule elements that have sufficient sequence similarity/identity to a parent RNA molecule element sequence and have at least a portion of the function of the parent RNA element molecule can be prepared and used in embodiments of methods of the invention.

As used herein, the term "identity" refers to the degree of relatedness or similarity between two or more polypeptide sequences [or polynucleotide (nucleic acid) sequences]. Sequence identity may be determined by the alignment and match between the sequences using standard methods. The percentage is obtained as the percentage of identical amino acids in two or more sequences taking account of gaps and other sequence features. The identity between polypeptide sequences can be determined by means of art-known procedures. Algorithms and programs are available and routinely used by those in the art to determine identity between polypeptide sequences and to determine identity between nucleic acid sequences. Non-limiting examples of programs and algorithms include BLASTP, BLASTN and FASTA (Altschul et al., NCB NLM NIH Bethesda Md. 20894; Altschul et al., 1990), Online BLAST programs from the National Library of Medicine are available, for example, at blast.ncbi.nlm.nih.gov/Blast.cgi.

The presence of functionality of a variant, for example the ability to be used in a method of the invention, can be determined using testing methods described herein. Functional variants of protein elements and RNA molecule elements disclosed herein can be used in compositions and methods of the invention. It will be understood that the level of sequence identity with a protein element or an RNA element of the invention, and the level of functionality with respect to methods of the invention can be characteristics used to identify protein element and RNA molecule element variants using teaching provided herein in conjunction with standard procedures for sequence alignment, comparisons, and knowledge of sequence modifications in the protein and nucleic acid arts.

A variant of a protein element (or its encoding sequence), or an RNA element includes one or more sequence modifications. As used herein the term "modified" or "modification" in reference to a protein sequence refers to a change such as one or more of an insertion, deletion, or substitution of 1, 2, 3, 4, 5, 6, 7, 8, 9, 10, or more amino acids in the sequence as compared to the unmodified parent sequence. As used herein the term "modified" or "modification" in reference to a nucleic acid sequence refers to a change such as one or more of an insertion, deletion, or substitution of 1, 2, 3, 4, 5, 6, 7, 8, 9, 10, 11, 12, 13, 14, 15, 16, 17, 18, 19, 20 nucleic acids in a sequence. As used herein the term "nucleic acid" is used interchangeably with the term "polynucleotide".

The sequence of a protein element or nucleic acid element can be modified with one or more substitutions, deletions, insertions, or other modifications and the resulting variant element can be tested using methods described herein for characteristics including, but not limited to: expression, cell localization, imaging, etc. Exemplary modifications include, but are not limited to conservative amino acid substitutions, which will produce molecules having functional characteristics similar to those of the parent molecule. Conservative amino acid substitutions are substitutions that do not result in a significant change in the activity or tertiary structure of a selected polypeptide or protein. Such substitutions typically involve replacing a selected amino acid residue with a different residue having similar physico-chemical properties. For example, substitution of Glu for Asp is considered a conservative substitution because both are similarly sized, negatively charged amino acids. Groupings of amino acids by physico-chemical properties are known to those of skill in the art. The following groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). RPB and PSA variant elements that include modifications such as, but not limited to one, two, three, four, or more conservative amino acid substitutions can be identified and tested for characteristics including, but not limited to: expression, cell localization, imaging characteristics, etc., using methods disclosed herein.

A protein element variant may include modifications that result in an amino acid sequence having at least 85%, 90%, 91%, 92%, 93%, 94%, 95%, 96%, 97%, 98%, or 99% identity to its parent sequence. Some embodiments of compositions and methods of the invention may include a functional variant of one or more of a reporter protein element, a localization protein element, an epitope tag element, a protein linker element, a binding sequence element, a self-assembly protein element and the variant may include modifications that result in an amino acid sequence having at least 80%, 85%, 90%, 91%, 92%, 93%, 94%, 95%, 96%, 97%, 98%, or 99% identity with the amino acid sequence of the parent molecule of the element. Some embodiments of the invention a composition and/or cell comprises one or more functional variants of a sequence encoding a protein element and/or one or more functional variants of an RNA molecule element.

It is understood in the art that the codon systems in different organisms can be slightly different, and that therefore where the expression of a given protein from a given organism is desired, the nucleic acid sequence can be modified for expression within that organism. Thus, in some embodiments, one or more of a reporter protein element, a localization protein element, an epitope tag element, a protein linker element, a binding sequence element, a self-assembly protein element or functional variant thereof, is encoded by a mammalian-codon-optimized nucleic acid sequence, which may in some embodiments be a human-codon optimized nucleic acid sequence.

Delivery of RPB and PSA Compositions

Delivery of a RPB and/or PSA compositions into a cell can be done using art-known delivery means. It is well known in the art how to prepare and utilize fusion proteins that comprise one or a plurality of protein sequences. In certain embodiments of the invention, a fusion protein comprising elements of an RPB and/or a PSA composition can be delivered into a cell. In some embodiments, delivery of an RPB and/or a PSA composition can be targeted to a particular cell or cell type utilizing routine means such as targeting sequences for delivery to, and expression in, a desired cell, tissue or region. Genetic targeting methods can be used to deliver an RPB and/or a PSA composition of the invention into a cell of a predetermined type, location within a subject, etc. Genetic targeting also relates to the control of the amount of expression of an RPB and/or a PSA composition that is expressed, and the timing of the expression. Routine genetic procedures can be used to control parameters of expression, such as but not limited to: the amount and/or timing of expression of a fusion protein of a RPB and/or a PSA composition in a cell.

Some embodiments of the invention include a reagent for delivering an RPB and/or a PSA composition into a cell, wherein the reagent comprises a vector comprising nucleic acid sequences encoding the protein elements of the RPB and/or a PSA composition fusion proteins. As used herein, the term "vector" refers to a nucleic acid molecule capable of transporting between different genetic environments another nucleic acid to which it has been operatively linked. The term "vector" also refers to a virus or organism that is capable of transporting the nucleic acid molecule. One type of vector is an episome, i.e., a nucleic acid molecule capable of extra-chromosomal replication. Some useful vectors are those capable of autonomous replication and/or expression of nucleic acids to which they are linked. Vectors capable of directing the expression of genes to which they are operatively linked are referred to herein as "expression vectors". Other useful vectors, include, but are not limited to viruses such as lentiviruses, retroviruses, adenoviruses, and phages. Vectors useful in some methods of the invention can genetically insert a sensor polypeptide and a soma-targeting polypeptide of the invention into dividing and non-dividing cells and can insert a sensor polypeptide and a soma-targeting polypeptide of the invention into a cell that is an in vivo, in vitro, or ex vivo cell.

Vectors useful in methods of the invention may include additional sequences including, but not limited to, one or more signal sequences and/or promoter sequences, or a combination thereof. In certain embodiments of the invention, a vector may be a lentivirus, adenovirus, adeno-associated virus, or other vector that comprises a gene encoding a sensor polypeptide and a gene encoding a soma-targeting polypeptide of the invention. An adeno-associated virus (AAV) such as AAV8, AAV1, AAV2, AAV4, AAV5, AAV9, are non-limiting examples of vectors that may be used to express a fusion protein of the invention in a cell and/or subject. Expression vectors and methods of their preparation and use are well known in the art. Non-limiting examples of suitable expression vectors and methods for their use are provided herein.

Promoters that may be used in methods and vectors of the invention include, but are not limited to, cell-specific promoters or general promoters. Non-limiting examples promoters that can be used in vectors of the invention are: ubiquitous promoters, such as, but not limited to: CMV, CAG, CBA, and EF1a promoters; and tissue-specific promoters, such as but not limited to: Synapsin, CamKIIa, GFAP, RPE, ALB, TBG, MBP, MCK, TNT, and aMHC promoters. Methods to select and use ubiquitous promoters and tissue-specific promoters are well known in the art. A non-limiting example of a tissue-specific promoter that can be used to express a fusion protein of the invention in a cell such as a neuron is a synapsin promoter, which can be used to express an RBP and/or a PSA fusion protein of the invention in embodiments of methods of the invention. Additional tissue-specific promoters and general promoters are well known in the art and, in addition to those provided herein, may be suitable for use in compositions and methods of the invention. Additional methods for generating fusion proteins and recombinant polypeptides are known in the art may include use of prokaryotic and eukaryotic expression systems including but not limited to bacterial and mammalian expression systems.

The present invention in some aspects includes one or more methods of preparing and using vectors encoding one or more RPB and/or PSA fusion proteins, including the delivery of the vectors encoding PRB and/or PSA fusion proteins into a cell, expression of the encoded fusion protein in the cell, delivery of additional components of one or more RPB compositions into the cell, detecting signals generated by one or more reporter protein elements in SiRIs generated from the RPB and/or PSA compositions delivered into the cell. The present invention enables simultaneous detection of two or more physiological processes in a single cell. The PRB and PSA compositions of the invention and their use, have broad-ranging applications for determining simultaneous physiological processes within cells, drug screening, therapeutic testing, and research applications, some of which are describe herein.

EXAMPLES

Example 1. Clustering Fluorescent Reporter Proteins on RNA Scaffolds

Materials and Methods
Experimental Model and Subject Details
NEB® Stable Competent *E. coli* (New England Biolabs, Ipswich, MA) were used for small-scale isolation of plasmids encoding repetitive RNA scaffolds and were grown in a shaking incubator (250 RPM) at 30° C. Small-scale isolations of all other plasmids were done with Z-Competent™ *E. coli* (Zymo Research, Ipswich, MA) grown in a shaking incubator (250 RPM) at 37° C.

All procedures involving animals at MIT were conducted in accordance with the US National Institutes of Health Guide for the Care and Use of Laboratory Animals and approved by the Massachusetts Institute of Technology Committee on Animal Care.

HeLa cells, passage 5-12 (ATCC) were maintained between 10% and 90% confluence at 37° C. with 5% CO2 in DMEM (Gibco, Waltham, MA) with the addition of 10% heat inactivated fetal bovine serum (HI-FBS) (Corning, Corning, NY), 1% penicillin/streptomycin (Gibco, Waltham, MA), and 1% sodium pyruvate (Gibco, Waltham, MA). Cells were authenticated by the manufacturer and tested for mycoplasma contamination to their standard levels of stringency and were used herein because they are common cell lines for testing new tools. Transfection and recordings for experiments that did not involve post hoc RNA FISH proceeded in glass 24-well plates treated with 75 µL diluted MATRIGEL™ (250 µL MATRIGEL™ (Corning, Corning, NY) diluted in 12 mL DMEM) per well at 37° C. for 30-60 minutes. Transfection and recordings for experiments involving post hoc RNA FISH proceeded in glass coverslips (Carolina Biological Supply, Burlington, NC) treated with the diluted MATRIGEL™ in glass 24-well plates.

Hippocampal neurons were prepared from postnatal day 0 or 1 Swiss Webster mice (Taconic Biosciences, Rensselaer, NY) (both male and female mice were used) as previously described (Klapoetke et al., 2014) with the following modifications: dissected hippocampal tissue was digested with 50 units of papain (Worthington Biochem, Lakewood, NJ) for 6-8 min, and the digestion was stopped with ovomucoid trypsin inhibitor (Worthington Biochem, Lakewood, NJ). Cells were plated at a density of 20,000-30,000 per glass coverslip coated with diluted MATRIGEL™ in a 24-well plate. Neurons were seeded in 100 µL plating medium containing MEM (no glutamine, no phenol, Life Technologies, Carlsbad, CA), glucose (33 mM, Millipore Sigma, Burlington, MA), holo-Transferrin bovine (0.01%, Millipore Sigma, Burlington, MA), HEPES (10 mM, Millipore Sigma, Burlington, MA), glutaGRO™ (2 mM, Corning, Corning, NY), insulin (0.13%, Millipore Sigma, Burlington, MA), B27 supplement (2%, Gibco, Waltham, MA), and HI-FBS. After cell adhesion, additional plating medium was added. AraC (0.002 mM, Millipore Sigma, Burlington, MA) was added when glial density was 50-70% of confluence. Neurons were grown at 37° C. and 5% $CO_2$ in a humidified atmosphere.

Molecular Cloning

The DNAs encoding the protein motifs (mammalian-codon optimized), the 24× MS2 binding sites (24×MBS), and the 24× PP7 binding sites (24×PBS) used in this study were synthesized by Epoch Life Science (Epoch Life Science, Sugar Land, TX) or GenScript (GenScript Biotech, Piscataway, NJ). The 48× MS2 binding sites (48×MBS) and 72× PP7 binding sites (72×PBS) were cloned from 24× MS2 and 24× PP7 arrays using the restriction cloning method described in (Golding and Cox, 2004). The sensor vectors for RNA scaffold-based clustering strategies were cloned into the pAAV-UBC backbone. The scaffold vectors for RNA scaffold-based clustering strategies were cloned into the pAAV-CAG backbone. The vectors for protein scaffold-based clustering strategies were cloned into the pAAV-UBC, pAAV-Syn, or pAAV-CAG backbones. For control experiments with unassembled sensors in HeLa cells, pAAV-CAG-GCaMP6f and pcDNA3-CMV-ICUE3 were used. For control experiments with unassembled sensors in neurons, pAAV-UBC-GCaMP6f and pAAV-UBC-cAMPr were used. (Table 1, motif sequences; Table 2, all tested constructs and their $D_C$s.)

Small-scale isolation of plasmid DNA was performed with Plasmid Mini-Prep kits (Qiagen, Germantown, MD), after transformation in either NEB® Stable Competent *E. coli* (New England Biolabs, Ipswich, MA) for plasmids encoding repetitive RNA scaffolds or in Z-Competent™ DH5a *E. coli* (Zymo Research, Irvine, CA) for plasmids that did not encode repetitive RNA scaffolds, per manufacturers' protocols.

Transfection

The DNA was transiently transfected into HeLa cells using a TransIT-X2® Dynamic Delivery System kit (Mirus Bio, Madison, WI). The 250-500 ng of total plasmid DNA per well was transfected into HeLa cells according to the manufacturer's protocol. Cell culture media in the wells was changed to fresh media 24 hours after transfection. The cells were then incubated for another 24 hours before live cell imaging.

Cultured neurons were transfected at 4-5 days in vitro (DIV) with a commercial calcium phosphate transfection kit (Invitrogen, Waltham, MA) as previously described (Piatkevich et al., 2018). Briefly, for transfection in each coverslip/well, 250 ng of each plasmid of interest, 500 ng pAAV-Syn-miRFP plasmid as a cell morphology marker, and pUC19 plasmid as a 'dummy' DNA plasmid to bring the total amount of DNA to 1500 ng (to avoid variation in DNA-calcium phosphate co-precipitate formation) were used. The cells were washed with acidic MEM buffer (containing 15 mM HEPES with final pH 6.7-6.8 adjusted with acetic acid (Millipore Sigma, Burlington, MA) after 45-60 minutes of calcium phosphate precipitate incubation to remove residual precipitates. The neurons were then incubated for another 4-5 days before live cell imaging at 8-9 DIV.

Fluorescence Microscopy of HeLa Cells and Primary Neurons

HeLa cells were imaged 48 hours after transfection. For 10-15 minutes at 37° C. right before imaging, 10 μL of NucBlue™ Live ReadyProbes Reagent™ (Invitrogen, Waltham, MA) was added to the media to stain the cell nucleus after which the media was replaced with FLUOROBRITE™ DMEM supplemented with 15 mM HEPES. Live cell imaging of HeLa cells was performed on an inverted epi-fluorescence wide-field Nikon® Eclipse Ti microscope (Nikon, Melville, NY) with a 40×1.15 NA water immersion objective (Nikon® MRD77410), a SPECTRA X LIGHT ENGINE™ (LumenCor, Beaverton, OR), and a Zyla® 5.5 camera (Andor Technology, South Windsor, CT) controlled by NIS-Elements® AR software. For imaging GFP intensity-based sensors (GCaMP6f and cAMPr), a 475/28 nm excitation filter (Semrock, Rochester, NY) and a 527/50 nm emission filter (Semrock, Rochester, NY) were used. For imaging the CFP/YFP FRET-based sensor (ICUE3 and AKAR4), a 438/24 nm donor excitation filter (Semrock, Rochester, NY), a 483/32 nm CFP emission filter (Semrock, Rochester, NY), and a 542/27 nm YFP emission filter (Semrock, Rochester, NY) were used. For imaging miRFP, a 631/28 nm excitation filter (Semrock, Rochester, NY) and a 664 long-pass emission filter (Semrock, Rochester, NY) were used. Under the 40×objective, cells were recorded for 5-15 minutes in the GFP, CFP and/or YFP channels at 10 seconds per frame (0.1 Hz), during which the reagents for extracellular stimulation, 10 mM final concentration of calcium chloride (Millipore Sigma, Burlington, MA) or 20 μM final concentration of forskolin (Millipore Sigma, Burlington, MA), was added into the FLUOROBRITE™ media. After recording, images were taken at 40× and 10× in the GFP, CFP, YFP, miRFP, and/or NucBlue™ channels, and then a tiled image in the NucBlue™ channel at 4× covering the entire glass coverslip was taken to facilitate registration with the images from downstream immunostaining or RNA FISH. HeLa cells were fixed for 10 minutes in TissuePrep™ buffered 10% formalin (Electron Microscopy Sciences, Hatfield, PA), followed by washing with 1× phosphate buffered saline (PBS) three times, 5 minutes each. If the cells were for downstream immunostaining, cells were stored in 1×PBS at 4° C. If the cells were for downstream RNA FISH, cells were stored in 70% ethanol at 4° C.

Live neuron imaging was performed on a spinning disk confocal microscope (a Yokogawa® CSU-W1 Confocal Scanner Unit (Yokogawa, Sugar Land, TX) on a Nikon® Eclipse Ti microscope (Nikon, Melville, NY) equipped with a 40×1.15 NA water immersion objective (Nikon® MRD77410) and a Zyla® PLUS 4.2 Megapixel camera (Andor Technology, South Windsor, CT) controlled by NIS-Elements® AR software. The filter set for GFP was used for imaging GFP intensity-based sensors. For primary neuron cultures, 4-5 days after transfection, cells were recorded for 1-3 minutes in the GFP channel at 50 ms per frame (20 Hz), during which 5 μM final concentration of forskolin was added into the media. After recording, z stacks were taken at 40× in GFP and miRFP channels, and then a tiled image in GFP channel at 4× covering the entire glass coverslip was taken for registration of live images with the images from downstream immunostaining. Neurons were then fixed for 10 minutes in TissuePrep™ buffered 10% formalin, followed by washing with 100 mM glycine (Millipore Sigma, Burlington, MA) in 1×PBS for 10 minutes, and then washing with 1×PBS three times, 5 minutes each. Cells were stored in 1×PBS at 4° C.

Immunostaining

All solutions described herein were made in 1×PBS unless otherwise specified, and incubations carried out at room temperature unless otherwise specified. Because it was observed that the miRFP fluorescence was not preserved after fixation, fluorescent antibodies that had spectral overlap with miRFP for immunostaining were used. Cells were permeabilized with 0.1% Triton™ X-100 for 15 minutes and then blocked with 5% normal donkey (ThermoFisher Scientific, Waltham, MA), horse (ThermoFisher Scientific, Waltham, MA), or bovine (Abcam, Cambridge, MA) serum for 15 minutes. Cells were incubated with primary antibodies in blocking buffer at 1:400 for 1 hour, and then washed in PBS three times for 5 minutes each. Cells were incubated with fluorescently-labeled secondary antibodies in blocking buffer at 1:400 for 2 hours for HeLa cells and 1 hour for cultured neurons, then washed in PBS three times. Nuclei were stained with DAPI at 1 μg/ml for 1-5 minutes followed by 1×PBS wash. Imaging was performed on the same spinning disk confocal microscope as in the live neuron imaging experiments. Antibodies used in certain of the experiments included: Xpress™ Monoclonal Antibody, Mouse, Invitrogen, Thermofisher Scientific, Waltham, MA; Anti-V5 Tag Antibody, Chicken, Abcam, Cambridge, MA; Anti-HA Tag Antibody, Rabbit, Abcam, Cambridge, MA; Goat anti-Mouse IgG1 Cross-Adsorbed Secondary Antibody, Alexa Fluor® 546, Invitrogen, Thermofisher Scientific, Waltham, MA; Goat anti-Mouse IgG (H+L) Highly Cross-Adsorbed Secondary Antibody, Alexa Fluor® 594, Invitrogen, Thermofisher Scientific, Waltham, MA; Goat anti-Chicken IgY (H+L) Secondary Antibody, Alexa Fluor® 647, Invitrogen, Thermofisher Scientific, Waltham, MA; Goat anti-Rabbit IgG (H+L) Secondary Antibody, Alexa Fluor® 647, Invitrogen, Thermofisher Scientific, Waltham, MA; and Donkey Anti-Rabbit IgG (H+L), Highly Cross-Adsorbed, CF®543, Biotium, Fremont, CA.

Multiplexed Immunostaining

Acryloyl-X (6-((acryloyl)amino)hexanoic acid, succinimidyl ester (AcX) (ThermoFisher Scientific, Waltham, MA) powder was dissolved in anhydrous DMSO (ThermoFisher Scientific, Waltham, MA) at a concentration of 10 mg/ml, and stored in a desiccated environment at −20° C. Cell cultures on a round coverslip were then incubated in 300-500 μl of AcX at a concentration of 0.1 mg/ml in 1×PBS with 0.5% Triton™-X for 30 minutes at 4° C. and then for 1.5 hours at 37° C. Then, cells were washed with 1×PBS three times for 5 minutes each.

A monomer solution composed of 2 M NaCl (Sigma-Aldrich, St. Louis, MO), 8.625% (w/v) sodium acrylate (Sigma-Aldrich, St. Louis, MO), 2.5% (w/v) acrylamide (Sigma-Aldrich, St. Louis, MO), and 0.10% (w/v) N,N'-methylenebisacrylamide (Sigma-Aldrich, St. Louis, MO) was then prepared in 1×PBS and aliquoted and stored it at −20° C. Next, a gelling solution composed of monomer solution and the chemicals 4-hydroxy-2,2,6,6-tetramethylpiperidin-1-oxyl (4HT) (Sigma-Aldrich, St. Louis, MO) was prepared as an inhibitor, and tetramethylethylenediamine (TEMED) (Sigma-Aldrich, St. Louis, MO) as an accelerator, and ammonium persulfate (APS) (Sigma-Aldrich, St. Louis, MO) was used as an initiator. 4HT, TEMED, and finally APS were then sequentially added to the monomer solution to prepare the gelling solution (final concentration, 0.01% (w/w) for 4HT, and 0.2% (w/w) for both APS and TEMED). Then, each coverslip containing a neuronal cell culture sample was placed on a glass slide with the cells facing up, and constructed a gel chamber by putting three No. 1.5 coverslips on top of each other unto the glass slide to function as spacers on either end of the neuronal coverslip to avoid compression. The sample was then covered with gelling solution and a coverslip placed over the sample and across the two spacers to ensure the sample was covered with gelling solution and no air bubbles were formed on the sample. Samples were first incubated at 4° C. for 30 minutes in a humidified atmosphere to prevent premature gelation and enable diffusion of solution into tissues, and subsequently incubated at 37° C. for 2.5 hours in a humidified atmosphere to complete gelation.

Afterward, the top coverslip was removed from the samples, and only the sample gel and original coverslip were removed and placed in a 50 ml large conical tube containing 5 ml of denaturation buffer, consisting of 20% (w/v) sodium dodecyl sulfate (SDS), 100 mM β-mercaptoethanol, 25 mM ethylenediaminetetraacetic acid (EDTA) and 0.5% Triton™-X in Tris 50 mM at pH 8. Samples were incubated in denaturation buffer for 30 minutes at 37° C. followed by 1 hour in an autoclave at 121° C. Samples were then cooled to RT for 30 minutes. At this stage, gels completely fell off the original coverslip during denaturation or immediately afterwards following gentle shaking and washing with 1×PBS 5 times for 3 min each at RT. The hydrogel embedded samples attained a final state of ~2.3× linear expansion given the use of an expandable hydrogel.

Next, samples underwent blocking by incubating for 30 minutes at 37° C. in MAXBlock™ Blocking medium (Active Motif, Carlsbad, CA), followed by three washes for 5 minutes each at RT in MAXWash™ Washing medium (Active Motif, Carlsbad, CA). Next, samples were immunostained by diluting primary antibodies in MAXStain™ Staining medium (Active Motif, Carlsbad, CA) and incubating for 1.5 hours at 37° C. or overnight at 4° C. This was followed by three washes for 5 minutes each at RT in MAXWash™ Washing medium. Then, samples were incubated with secondary antibodies for 1.5 hours at 37° C. or overnight at 4° C. Samples where then washed three times for 5 minutes each at RT in MAXWash™ Washing medium and stored in 1×PBS.

Antibodies used in certain of the experiments included: Xpress™ Monoclonal Antibody, Mouse, Invitrogen, Thermofisher Scientific, Waltham, MA; Anti-V5 Tag Antibody, Chicken, Abcam, Cambridge, MA; Anti-HA Tag Antibody, Rabbit, Abcam, Cambridge, MA; Goat anti-Mouse IgG1 Cross-Adsorbed Secondary Antibody, Alexa Fluor® 546, Invitrogen, Thermofisher Scientific, Waltham, MA; Goat anti-Mouse IgG (H+L) Highly Cross-Adsorbed Secondary Antibody, Alexa Fluor® 594, Invitrogen, Thermofisher Scientific, Waltham, MA; Goat anti-Chicken IgY (H+L) Secondary Antibody, Alexa Fluor® 647, Invitrogen, Thermofisher Scientific, Waltham, MA; Goat anti-Rabbit IgG (H+L) Secondary Antibody, Alexa Fluor® 647, Invitrogen, Thermofisher Scientific, Waltham, MA; and Donkey Anti-Rabbit IgG (H+L), Highly Cross-Adsorbed, CF®543, Biotium, Fremont, CA.

For spectral clearance to enable antibody stripping, samples were placed in a water tight container with denaturation buffer and incubated for 2 hours at 70° C. with shaking at 200 rpm. Then, excess denaturation buffer was removed, and samples were washed with 1×PBS at RT 5 times for 3 minutes. Samples then underwent immunostaining steps as noted in the previous paragraph for the subsequent rounds of staining.

RNA Fluorescent In Situ Hybridization (RNA FISH)

Quasar® 570 conjugated fluorescent oligonucleotides were purchased from LGC Biosearch Technologies (Biosearch Technologies, Petaluma, CA) as fluorescent RNA FISH probes including: MBS probe, gacatgggtgatcctcatgt (SEQ ID NO: 95); MBS/PBS Linker 1 probe, atctaatgaacccgggaata (SEQ ID NO: 96); MBS/PBS Linker 2 probe, ttctaggcaattaggtacct (SEQ ID NO: 97); PBS 1 probe, agcgacgccatatcgtctgc (SEQ ID NO: 98); and PBS 2 probe, agcgagcccatatgctctgc (SEQ ID NO: 99).

Cells were washed twice for 5 minutes each with wash buffer A (10% formamide in 2×SSC). Afterward, fluorescent RNA FISH probes were added into the hybridization buffer [10% formamide (Millipore Sigma, Burlington, MA) and 10% dextran sulfate (Millipore Sigma, Burlington, MA) in 2×SSC] to a total probe concentration of 50 nM. Cells were incubated in the FISH probe containing hybridization buffer for 16 hours at 37° C. in a humidity controlled incubator. The cells were then washed with wash buffer A twice at 37° C., each for 30 minutes, before nuclear staining with DAPI at 1 μg/ml for 1-5 minutes followed by a 1×PBS wash. The cells were then transferred to 24-well glass plates with 1×PBS for imaging. Imaging was performed on the same wide-field Nikon® Eclipse Ti microscope as the live HeLa imaging experiments.

Quantification and Statistical Analysis

Image Analysis

For each sample, the images and movies taken from live cell imaging and the images taken after immunostaining or RNA FISH were registered by the tiled images from the NucBlue™ channel (before fixation) and the DAPI channel (after immunostaining or RNA FISH), in each case taken under a 4× objective.

The analysis of the recorded movies from live cell imaging was performed in ImageJ (ImageJ, National Institutes of Health) and Excel (Microsoft, Redmond, WA). For the analysis of the movies from cells expressing fluorescent sensors assembled by RNA scaffolds or protein scaffolds, the time course of the fluorescence intensity from a punctum in the recorded optical channel was measured as the time course of the average fluorescence intensity within the apparent boundary of the punctum. Then the time course of the net fluorescence, F, from that punctum was obtained by subtracting the background fluorescence intensity measured from a region that had no cells in it from that movie. For the analysis of the movies from cells expressing non-assembled fluorescent sensors as control groups, the time course of the fluorescence intensity from a cell in the recorded optical channel was measured as the time course of the average fluorescence intensity within a random ROI in the cytosol of the cell with the area of that ROI similar to the size of individual puncta in the cells expressing assembled fluorescent sensors that these control groups were compared to, about 1 $\mu m^2$ in HeLa cells, 5-10 $\mu m^2$ in the somata of neurons, and 1 $\mu m^2$ in the neurites of neurons. This was for keeping the noise from the camera contained in the measured fluorescence time courses at a comparable level between cells expressing assembled fluorescent sensors and cells expressing non-assembled fluorescent sensors as control groups. Then the time course of the net fluorescence, F, from that cell was obtained by subtracting the background fluorescence intensity measured from a region that had no cells in it from that movie. For each neurite-localized ROI in neurons, the cumulative distance between the ROI and the soma was calculated by measuring along the neurite.

To calculate the dF/F0 for GCaMP6f or cAMPr expressing HeLa cells or neurons, the baseline fluorescence, F0, was first calculated as the average net fluorescence during the 2-minute period (for movies from live HeLa imaging) or 5-second period (for movies from live neuron imaging) right before adding the extracellular stimulation. dF/F0 was then calculated as $dF/F0=(F-F0)/F0$. To calculate the signal-to-noise ratio (SNR), the maximum dF/F0 was divided by the standard deviation of the net fluorescence during the 2-minute period (HeLa) or 5-second period (neuron) right before adding the extracellular stimulation.

To calculate the change of CFP/YFP ratio, d(C/Y)/(C/Y), for ICUE3 expressing HeLa cells, the CFP/YFP ratio, C/Y, was first calculated by dividing the net fluorescence from the CFP channel by the net fluorescence from the YFP channel. Then the baseline of the CFP/YFP ratio, $(C/Y)_0$, was calculated as the average of the CFP/YFP ratio during the 2-minute period right before adding the extracellular stimulation. d(C/Y)/(C/Y) was then calculated as $d(C/Y)/(C/Y)=[C/Y-(C/Y)0]/(C/Y)_0$. To calculate the signal-to-noise ratio (SNR), the maximum d(C/Y)/(C/Y) was divided by the standard deviation of the d(C/Y)/(C/Y) during the 2-minute period (HeLa) right before adding the extracellular stimulation.

For puncta size analysis and the distance to the nearest punctum analysis, StarDist™ was used to identify and segment the boundaries of puncta followed by geometrical analysis with a custom MATLAB® script. For the analysis of puncta spatial separation, a punctum with less than 5% overlap with the puncta of other sensors after immunostaining was counted as a spatially separate punctum. For the analysis of the motion of puncta in recorded and time-lapse movies (1 minute per frame; 1 hour total), puncta were automatically identified and tracked by the TrackMate™ plugin in ImageJ™, then mean squared displacement (MSD) and diffusion coefficient were calculated in MATLAB® (MathWorks, Natick, MA) with the script msdanalyzer [Tarantino, et al., 2014] based on the tracking results from TrackMate™.

Statistical Analysis

All statistical analysis was performed using the built-in statistical analysis tools in Prism™ (GraphPad, San Diego, CA), JMP™ (SAS), or MATLAB®. The statistical details of each statistical analysis can be found in the Brief Description of the Drawings section, the Experiments, Results, and Discussion section, and Tables 3-78.

Experiments, Results, and Discussion

RNA Scaffolds can Assemble Fluorescent Sensors into Subcellular Puncta in Mammalian Cells The MS2 system (Bertrand et al., 1998) and the PP7 system (Lim, Downey and Peabody, 2001), each of which comprises a specific viral RNA sequence and a viral coat protein that binds tightly to that sequence, were tested to determine whether either could be used to assemble fluorescent sensors fused to the protein component of each system onto the RNA component of the same system, in essence using the RNA components as scaffolds to assemble reporters fused to the protein components. Prior work (Bertrand et al., 1998; Wu, Chao and Singer, 2012) showed that fluorescent proteins fused to the RNA binding protein components from each of these systems could be used to fluorescently image the locations of mRNAs engineered to contain the RNA components. In studies described herein, fluorescent proteins previously described were replaced with a fluorescent reporter of calcium, the GFP-based sensor GCaMP6f (Chen et al., 2013), and a fluorescent CFP/YFP FRET reporter of cAMP, ICUE3 (DiPilato and Zhang, 2009) (FIG. 2A), with each fused to an immunoepitope tag (influenza hemagglutinin epitope (HA) (Wilson et al., 1984) and simian virus 5-derived epitope (V5) (Southern et al., 1991), respectively) so that later these spectrally overlapping signals could be post hoc identified by immunostaining as in FIG. 1A, right. Following earlier studies on using the MS2 and PP7 systems to image the location of mRNAs (Wu, Chao and Singer, 2012), a SV40 nuclear localization signal (NLS) was appended to the RNA binding protein component of each system to help scavenge any RNA-unbound protein to the nucleus to reduce background fluorescence not clustered into puncta. The RNA binding proteins were used in tandem dimer form (tdMCP, tandem dimer MS2 coat protein; tdPCP, tandem dimer PP7 coat protein), as before (Wu, Chao and Singer, 2012), to increase the binding efficiency to the RNA targets, with the fluorescent reporters appended to the C-termini of the RNA binding proteins with a flexible linker in between. This resulted in two sensor vectors, MP-GCaMP6f (short for MS2 protein component fused to GCaMP6f) and PP-ICUE3 (short for PP7 protein component fused to ICUE3) (FIG. 2A; Tables 1-2).

Figure 2A:
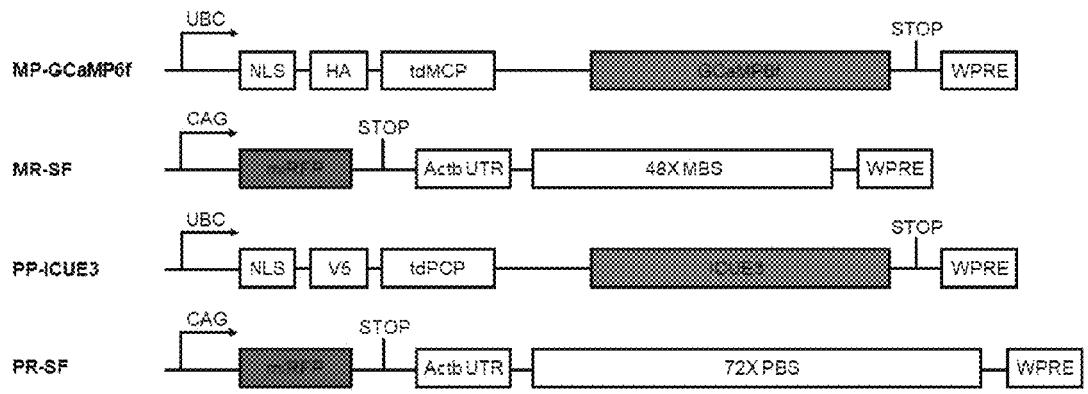
FIG. 2A-G presents schematic diagrams, photomicrographs, and plots showing the results of experiments assembling different fluorescent sensors onto distinct RNA scaffolds in mammalian cells.

For the scaffold vector, a tandem array encoding 48 MS2 binding sites ("48×MBS") and a tandem array encoding 72 PP7 binding sites ("72×PBS") were cloned from 24-component arrays of each kind previously developed (Wu, Chao and Singer, 2012) (FIG. 2A). The number of repeats were increased so that the resultant clusters would be as bright as possible, due to earlier work (Golding and Cox, 2004) showing that the number of fluorescent proteins binding to one target RNA would increase with the number of binding sites. RNA length was not successfully increased beyond the 48×MBS and 72×PBS repeats, perhaps because the probability of homologous recombination in bacteria shortening the final gene increases with the number of repeats, a known issue in cloning repetitive sequences (Wu et al., 2015). These repeated RNA components were inserted into the 3' untranslated region (UTR) of a mammalian expression vector as previously described (Wu, Chao and Singer, 2012) and appended to the gene encoding miRFP, a near-infrared fluorescent protein (Piatkevich et al., 2018), to serve as a marker of cell transfection and cell morphology. The 3' untranslated region of mouse beta actin mRNA (Actb UTR) was also added to help with cytoplasmic localization of the final RNA transcript (Buxbaum, Haimovich and Singer, 2015; Wu et al., 2016). These cloning efforts resulted in two scaffold vectors, MR-SF (short for MS2 RNA component scaffold) and PR-SF (short for PP7 RNA component scaffold) (FIG. 2A; Tables 1-2).

Figure 2B:
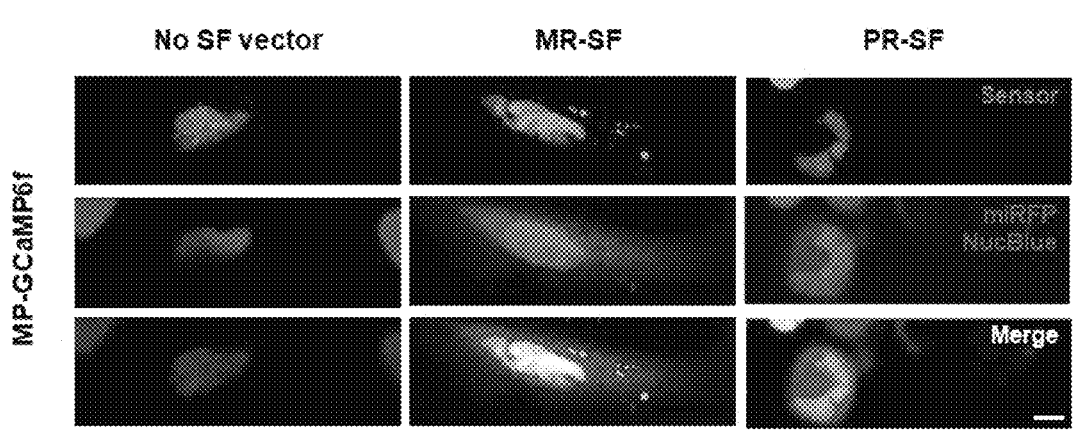
Figure 2C:
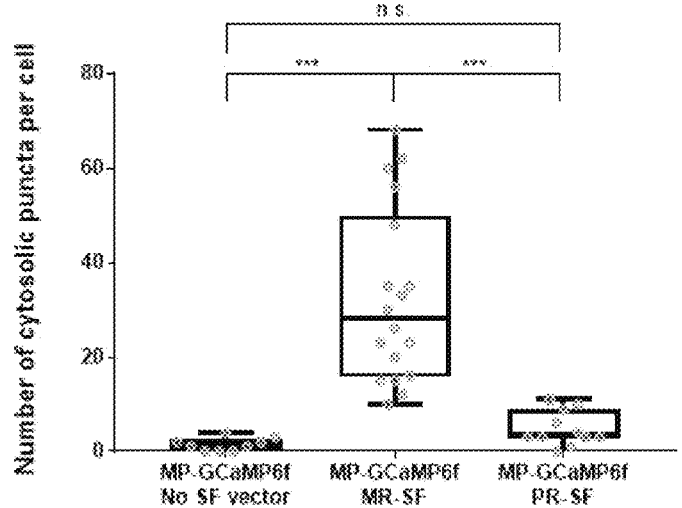
Figure 2D:
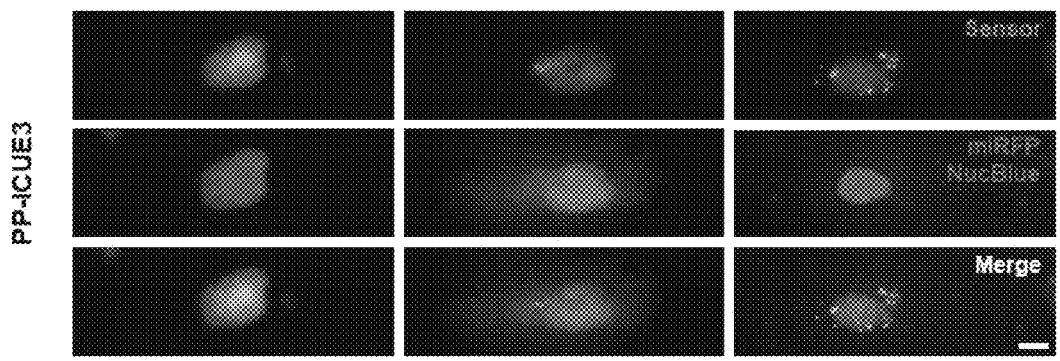
Figure 2E:
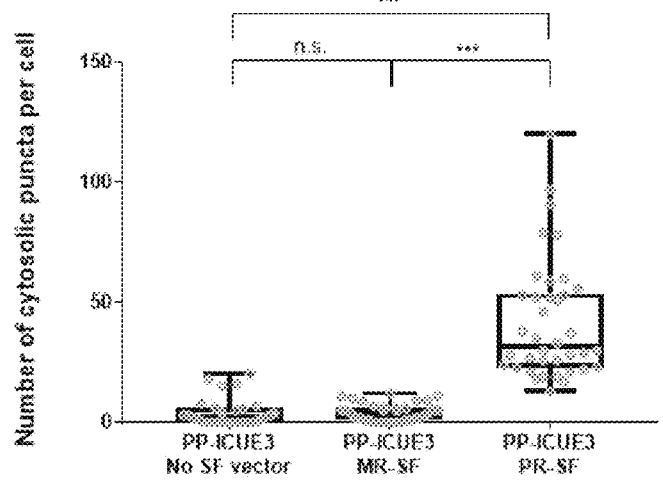

Transfecting the MS2-based sensor vector with its cognate scaffold vector into HeLa cells resulted in GCaMP6f puncta formation, but the MS2-based sensor vector was unable to form GCaMP6f puncta on the orthogonal PP7 scaffold vector, or when no scaffold vector was provided (FIG. 2B). This finding was reliable across cells, with many dozens of puncta visible when the correct pair was provided, but with few or zero puncta visible when the correct pair was not present (FIG. 2C). Similar results were observed when the PP7-based sensor vector, containing ICUE3, was provided (FIG. 2D-E). A quantitative metric was devised to compare how bright the puncta were versus the background, since background fluorescence could in principle contaminate the signals measured from a punctum. The fluorescence ratio between a punctum and the non-puncta-containing cytosol nearby was calculated and termed 'degree of clustering' ($D_C$). $D_C$ was about 20 on average for the MS2-clustered GCaMP6f reporter and 30 on average for the PP7-clustered ICUE3 reporter (Table 2). Table 3 provides statistical analysis for experiments results shown in FIG. 2C and Table 4 provides statistical analysis of experimental results shown in FIG. 2E.

TABLE 3

Statistical analysis for FIG. 2C

| Kruskal-Wallis test | |
|---|---|
| P value | <0.001 |
| Exact or approximate P value? | Approximate |
| P value summary | *** |
| Do the medians vary signif. (P < 0.05)? | Yes |
| Number of groups | 3 |
| Kruskal-Wallis statistic | 28.95 |

| Data summary | |
|---|---|
| Number of treatments (columns) | 3 |
| Number of values (total) | 38 |
| Number of families | 1 |
| Number of comparisons per family | 3 |
| Alpha | 0.05 |

| Dunn's multiple comparisons test | Mean rank diff. | Significant? | Summary | Adjusted P Value |
|---|---|---|---|---|
| MP-GCaMP6f No SF vector vs. MP-GCaMP6f MR-SF | -22.31 | Yes | *** | <001 |
| MP-GCaMP6f No SF vector vs. MP-GCaMP6fPR-SF | -6.298 | No | ns | .619 |
| MP-GCaMP6f MR-SF vs. MP-GCaMP6f PR-SF | 16.01 | Yes | *** | <001 |

| Test details | Mean rank 1 | Mean rank 2 | Mean rank diff. | n1 | n2 |
|---|---|---|---|---|---|
| MP-GCaMP6f No SF vector vs. MP-GCaMP6f MR-SF | 7.111 | 29.42 | -22.31 | 9 | 18 |
| MP-GCaMP6f No SF vector vs. MP-GCaMP6fPR-SF | 7.111 | 13.41 | -6.298 | 9 | 11 |
| MP-GCaMP6f MR-SF vs. MP-GCaMP6f PR-SF | 29.42 | 13.41 | 16.01 | 18 | 11 |

TABLE 4

Statistical analysis for FIG. 2E

| Kruskal-Wallis test | |
|---|---|
| P value | <0.001 |
| Exact or approximate P value? | Approximate |
| P value summary | *** |
| Do the medians vary signif. (P < 0.05)? | Yes |
| Number of groups | 3 |
| Kruskal-Wallis statistic | 69.95 |

| Data summary | |
|---|---|
| Number of treatments (columns) | 3 |
| Number of values (total) | 101 |
| Number of families | 1 |
| Number of comparisons per family | 3 |
| Alpha | 0.05 |

| Dunn's multiple comparisons test | Mean rank diff. | Significant? | Summary | Adjusted P Value |
|---|---|---|---|---|
| PP-ICUE3 No SF vector vs. PP-ICUE3 MR-SF | -3.711 | No | Ns | >0.999 |
| PP-ICUE3 No SF vector vs. PP-ICUE3 PR-SF | -52.16 | Yes | *** | <0.001 |
| PP-ICUE3 MR-SF vs. PP-ICUE3 PR-SF | -48.45 | Yes | *** | <0.001 |

| Test details | Mean rank 1 | Mean rank 2 | Mean rank diff. | n1 | n2 |
|---|---|---|---|---|---|
| PP-ICUE3 No SF vector vs. PP-ICUE3 MR-SF | 30.09 | 33.8 | -3.711 | 28 | 35 |
| PP-ICUE3 No SF vector vs. PP-ICUE3 PR-SF | 30.09 | 82.25 | -52.16 | 28 | 38 |
| PP-ICUE3 MR-SF vs. PP-ICUE3 PR-SF | 33.8 | 82.25 | -48.45 | 35 | 38 |

Figure 2F:
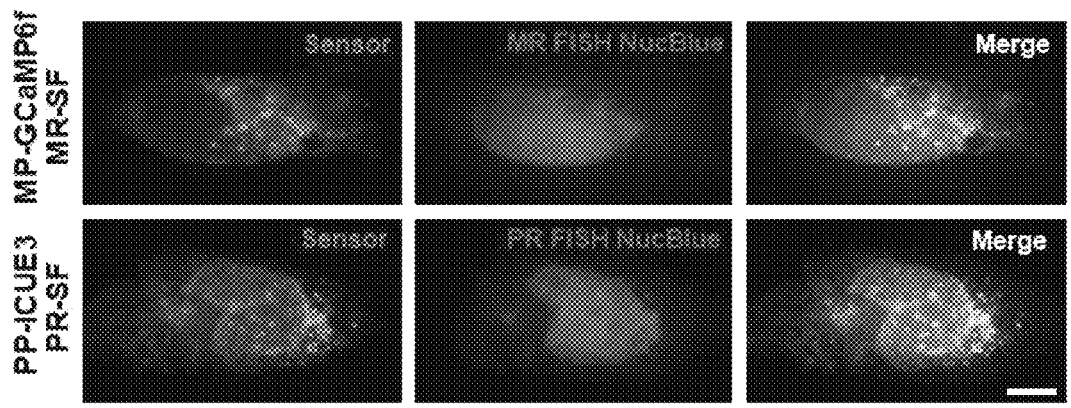
Figure 2G:
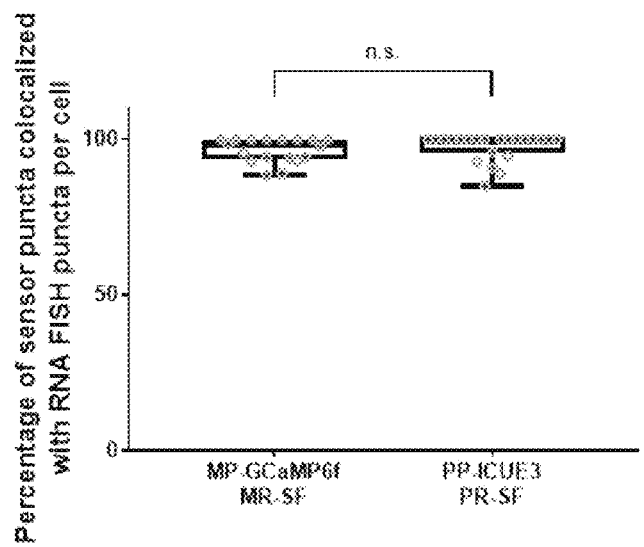
Figure 3A:
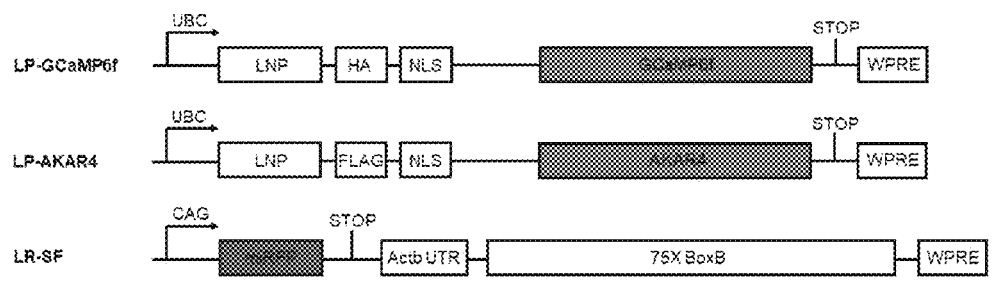
FIG. 3A-B presents schematic diagrams for fluorescent sensors and RNA scaffolds and photomicrographs of the results of assembling fluorescent sensors onto RNA scaffolds with the LambdaN22 RNA/RNA-binding-protein pair system in mammalian cells. Results related to FIG. 2.
Figure 3B:
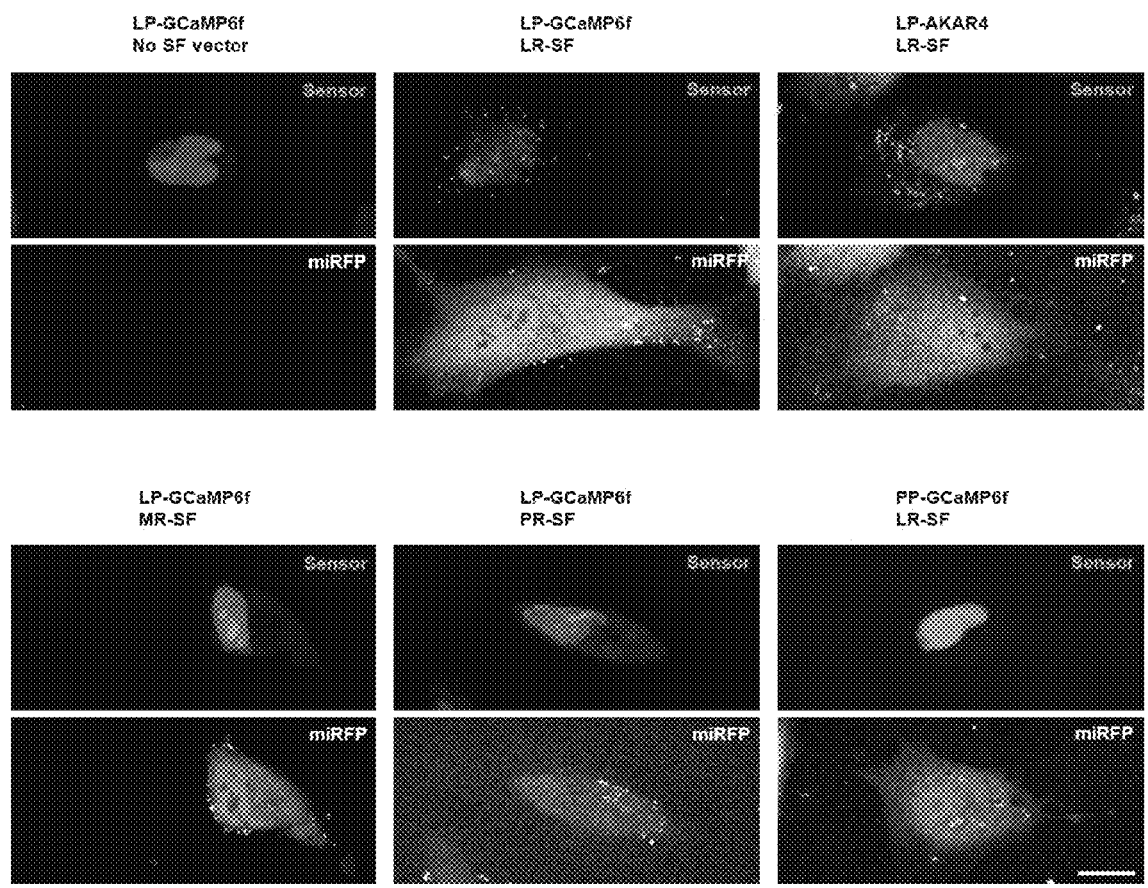

As an additional confirmation that the fluorescent puncta were indeed scaffolded by the RNAs, RNA FISH was performed against the MS2 and PP7 RNA sequences, on HeLa cells transfected as described above. Almost all the sensor puncta also bore appropriate RNA FISH puncta (FIG. 2F-G). To explore the generality of the finding that it was possible to use RNA scaffolds to assemble sensors into clusters, a third example was created as a proof-of-concept using the LambdaN22 RNA/RNA-binding-protein pair system (FIG. 3A; (Franklin, 1985; Martin et al., 2013)). This scaffold could also cluster GCaMP6f as well as a fluorescent CFP/YFP FRET reporter of protein kinase A, AKAR4, into functional puncta ($D_C$~5-7.5) in HeLa cells [FIG. 3B; (Depry, Allen and Zhang, 2011)]. Table 5 provides statistical analysis of experimental results shown in FIG. 2G.

TABLE 5

| Statistical analysis for FIG. 2G | |
| --- | --- |
| Column B | PP-ICUE3 PR-SF |
| vs. | vs. |
| Column A | MP-GCaMP6f MR-SF |
| Wilcoxon rank sum test | |
| P value | .153 |
| Exact or approximate P value? | Exact |
| P value summary | ns |
| Significantly different (P < 0.05)? | No |
| One- or two-tailed P value? | Two-tailed |
| Sum of ranks in column A, B | 322, 498 |
| Mann-Whitney U | 151 |
| Difference between medians | |
| Median of column A | 98.03, n = 18 |
| Median of column B | 100, n = 22 |

TABLE 5-continued

| Statistical analysis for FIG. 2G | |
| --- | --- |
| Difference: Actual | 1.966 |
| Difference: Hodges-Lehmann | 0 |

Puncta of Fluorescent Sensors Assembled by RNA Scaffolds are Functional in Mammalian Cells The puncta assembled by RNA scaffolding of fluorescent reporters were tested to determine whether they were functional. MS2-scaffolded GCaMP6f and PP7-scaffolded ICUE3 were expressed in HeLa cells and the resultant signals elicited by extracellular stimuli (10 mM $Ca^{2+}$ and 20 µM forskolin, respectively, as previously used (Williams et al., 2001; Miedlich, Gama and Breitwieser, 2002; Vay et al., 2007; Dipilato and Zhang, 2009)) were compared to those reported by the unscaffolded versions of the corresponding sensors. Both unscaffolded (FIG. 4A, 4D, left) and scaffolded (FIG. 4A, 4D, right) forms of each reporter exhibited quite heterogeneous responses to stimulation, including step-like, spike-like, and oscillatory waveforms, highlighting the complexity of such signals and raising the question of how a simple stimulus might result in such heterogeneous and complex outcomes. The peak changes in fluorescence, however, as well as the signal-to-noise ratios (with noise defined as the standard deviation of the baseline pre-stimulus throughout this paper), were indistinguishable between the conventional and scaffolded forms of the reporters (FIG. 4B-C, GCaMP6f, FIG. 4E-F, ICUE3). Thus the performance of the scaffolded forms of these reporters is comparable to those of the original, unscaffolded sensors. Table 6 provides Statistical analysis for experimental results shown in FIG. 4B, FIG. 4C, FIG. 4E, FIG. 4F, and FIG. 4H.

TABLE 6

Figure 4A:
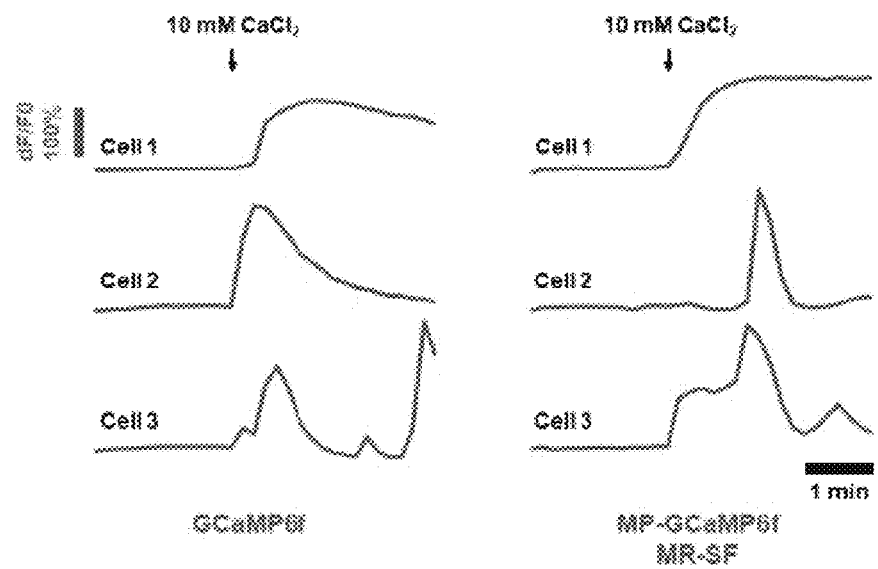
FIG. 4A-I presents graphs describing the functional characterization of fluorescent sensors assembled into puncta by RNA scaffolds in mammalian cells.
Figure 4B:
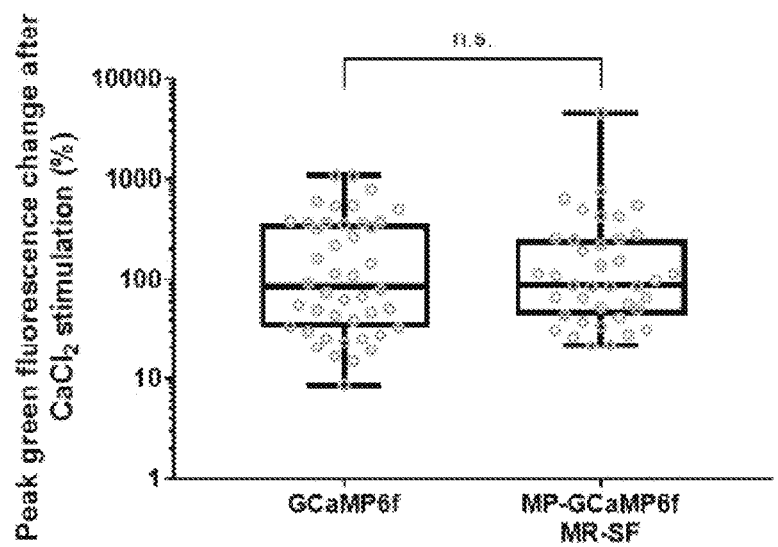
Figure 4C:
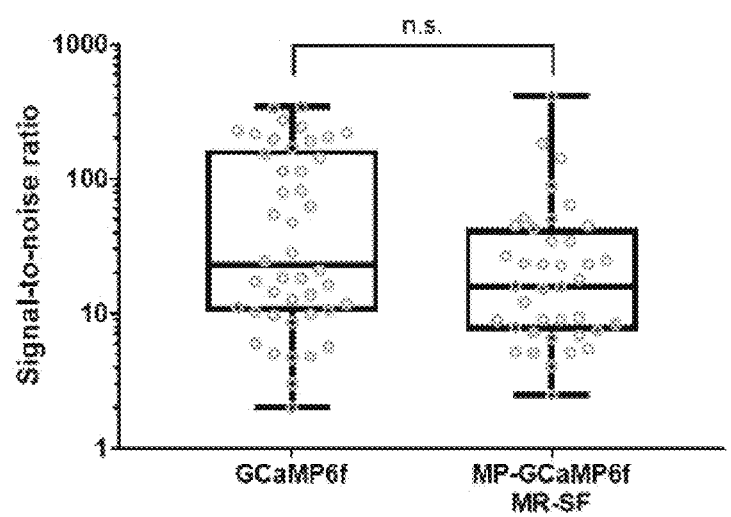
Figure 4D:
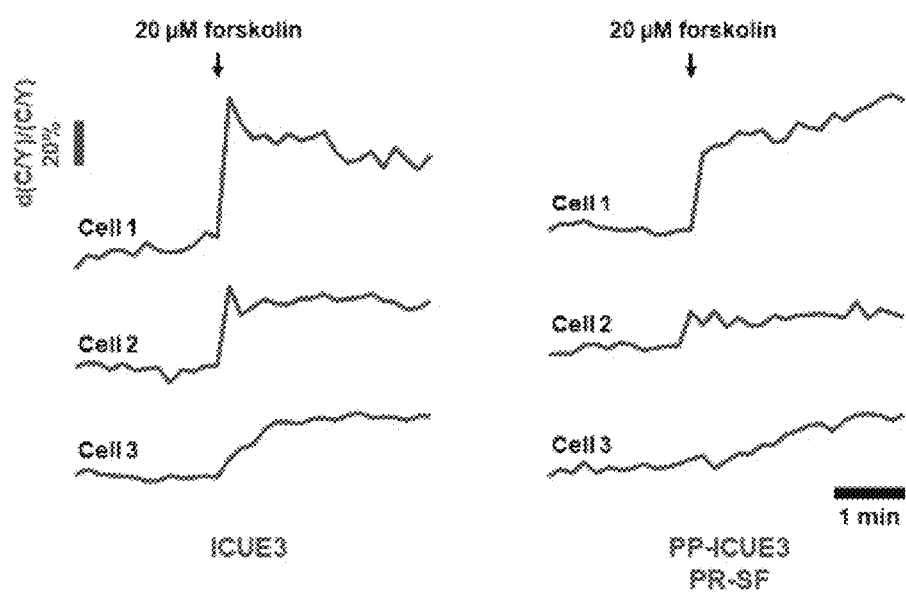
Figure 4E:
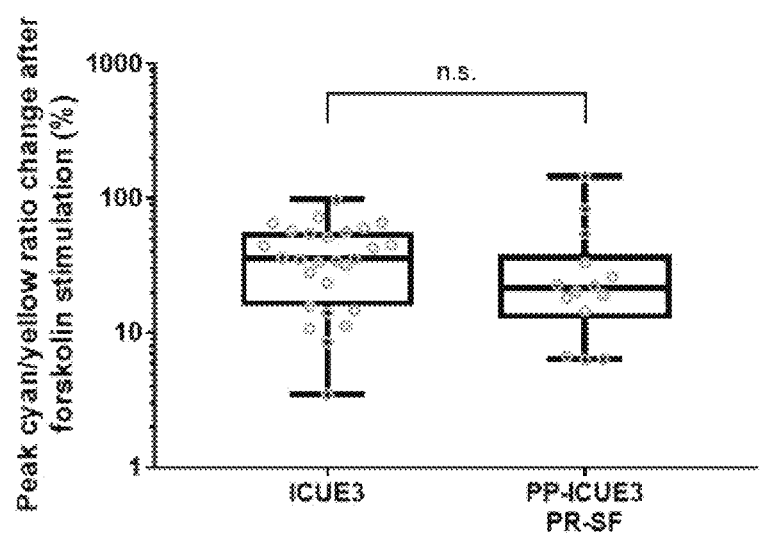
Figure 4F:
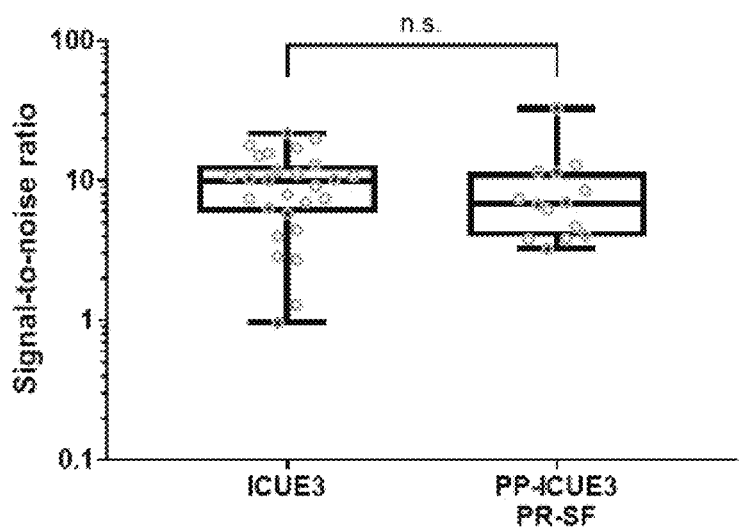
Figure 4G:
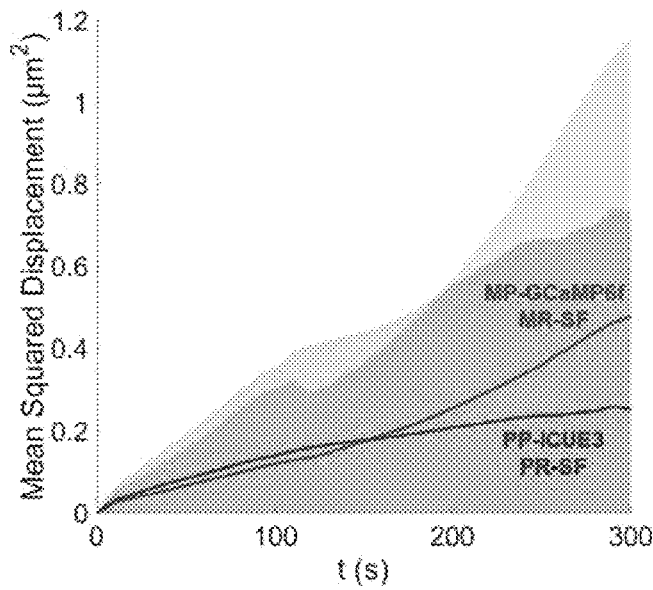
Figure 4H:
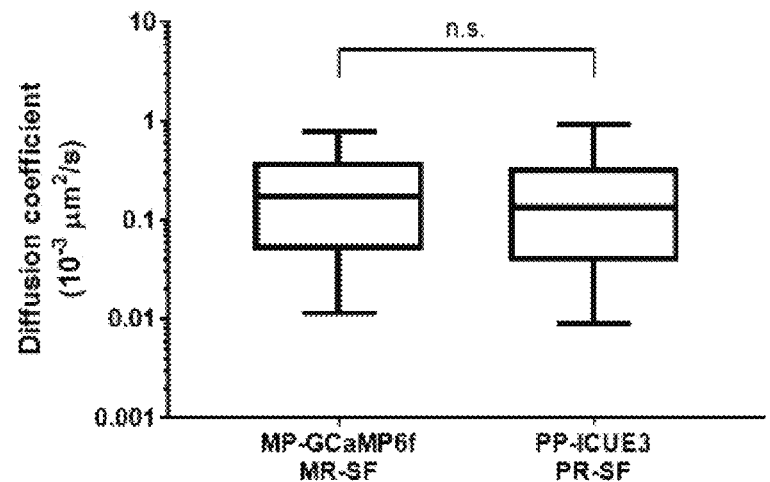

| Statistical analyses for FIG. 4B, FIG. 4C, FIG. 4E, FIG. 4F, and FIG. 4H. | | | | | |
| --- | --- | --- | --- | --- | --- |
| | FIG. 4B | FIG. 4C | FIG. 4E | FIG. 4F | FIG. 4H |
| Column B vs. Column A | MP-GCaMP6f MR-SF vs. GCaMP6f | MP-GCaMP6f MR-SF vs. GCaMP6f | PP-ICUE3 PR-SF vs. ICUE3 | PP-ICUE3 PR-SF vs. ICUE3 | PP-ICUE3 PR-SF vs. MP-GCaMP6f MR-SF |
| Wilcoxon rank sum test | | | | | |
| P value | 0.8222 | 0.057 | 0.128 | 0.347 | 0.053 |
| Exact or approximate P value? | Exact | Exact | Exact | Exact | Approximate |
| P value summary | ns | ns | ns | ns | ns |
| Significantly different (P < 0.05)? | No | No | No | No | No |
| One- or two-tailed P value? | Two-tailed | Two-tailed | Two-tailed | Two-tailed | Two-tailed |
| Sum of ranks in column A, B | 1823, 1663 | 2057, 1429 | 623, 238 | 602, 259 | 164012, 328517 |
| Mann-Whitney U | 833 | 649 | 133 | 154 | 98336 |
| Difference between medians | | | | | |
| Median of column A | 85.87, n = 44 | 23.04, n = 44 | 35.83, n = 27 | 10.05, n = 27 | 0.1742, n = 314 |
| Median of column B | 88.28, n = 39 | 15.95, n = 39 | 21.37, n = 14 | 6.89, n = 14 | 0.1334, n = 678 |
| Difference: Actual | 2.406 | −7.086 | −14.46 | −3.162 | −0.04087 |

TABLE 6-continued

Statistical analyses for FIG. 4B, FIG. 4C, FIG. 4E, FIG. 4F, and FIG. 4H.

|  | FIG. 4B | FIG. 4C | FIG. 4E | FIG. 4F | FIG. 4H |
|---|---|---|---|---|---|
| Difference: Hodges-Lehmann | 3.439 | −8.268 | −11.61 | −1.991 | −0.01886 |

Next, the scaffolded reporters were examined to determine whether they were stationary in the cell, or whether they moved over time. In order for the post hoc identification of the sensor via immunostaining (or other highly multiplexed fixed cell imaging methods, such as serial FISH) to usefully explain the live cell imaging (FIG. 1A, right), the sensors must remain in the same place throughout the live imaging session, and then be co-registered to the post hoc immunostaining dataset. Movement of puncta would result in inaccurate attribution of a given sensor identity to a given punctum. It could also corrupt the fluorescence signal changes observed for individual puncta, since motion of a punctum could be incorrectly interpreted as changes in punctum brightness. Puncta of both kinds were tracked in live HeLa cells using a previously published algorithm (Tinevez et al., 2017), and characterized the mean squared displacement (MSD) of sensor punctum locations (FIG. 4G) as well as the diffusion coefficients calculated from the MSD data (FIG. 4H). The deviations (FIG. 4G) were submicron over timescales of 5 minutes, resulting in diffusion coefficients of around 10-4 $\mu m^2/s$ (FIG. 4H), implying for all practical purposes acceptable stability of puncta over timecourses commonly used in physiological imaging of calcium and cAMP dynamics. Of course, for the measurement of other signals that transpire over longer periods of time, validation of puncta stability over longer timescales may be useful (although at some point, changes in cell shape, or even cell division, may make any kind of longitudinal imaging challenging).

Figure 4I:
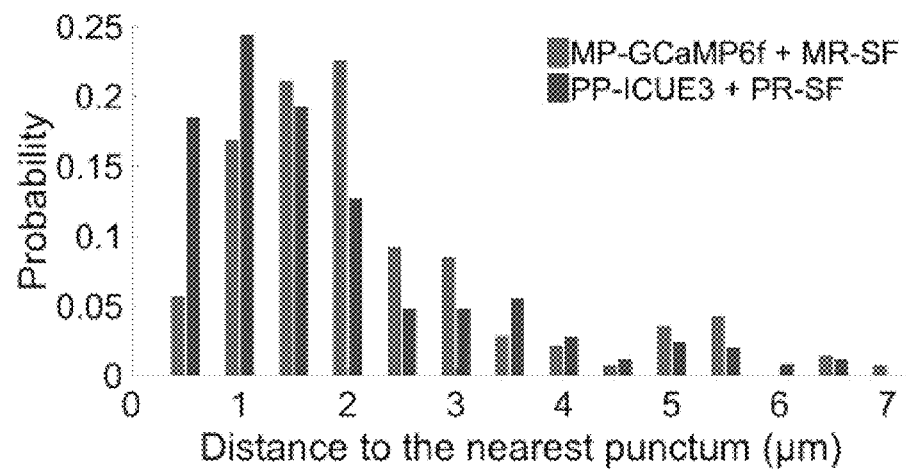

The density of puncta was also examined. Puncta should be separated by distances that are greater than the resolution limit of the microscope, or they will not be distinguishable. However, if they are too far apart, they may undersample any spatial heterogeneity of a biological signaling pathway within the cell that is desired to be measured. If obtaining a single measure from an entire cell is the goal, then this issue may not be a concern. But in cases where subcellular mapping of a biological signal is desired, having puncta spaced closer together than the characteristic length scales of the relevant biology will be helpful. For each punctum within a cell expressing either the MS2-scaffolded GCaMP6f or the PP7-scaffolded ICUE3, the distance to the nearest punctum was calculated (FIG. 4I). Most of the distances fell into the range of 1-2 microns, although a tail of the distribution indicated that some puncta had distances of several microns between nearest-neighbor puncta. Thus the RNA scaffolding of sensors may support cellular imaging, and subcellular imaging where length scales greater than a few microns are acceptable, but phenomena that occur over very short length scales may be missed. Of course, imaging physiological dynamics over very short length scales is in general challenging, and may require entirely new approaches different from classical fluorescent imaging on ordinary diffraction limited microscopes (Tadross, Tsien and Yue, 2013; Mo et al., 2017). Nevertheless, in many cases the ability of spatially multiplexed imaging to sample physiological signals with 1-2 micron resolution will be able to capture the relevant cell biology; see, for example, FIG. 5 where scaffolded versions of GCaMP6f and ICUE3 are able to pick up on signals at different subcellular locations within a cell in a fashion similar to unscaffolded forms of these indicators.

Figure 6A:
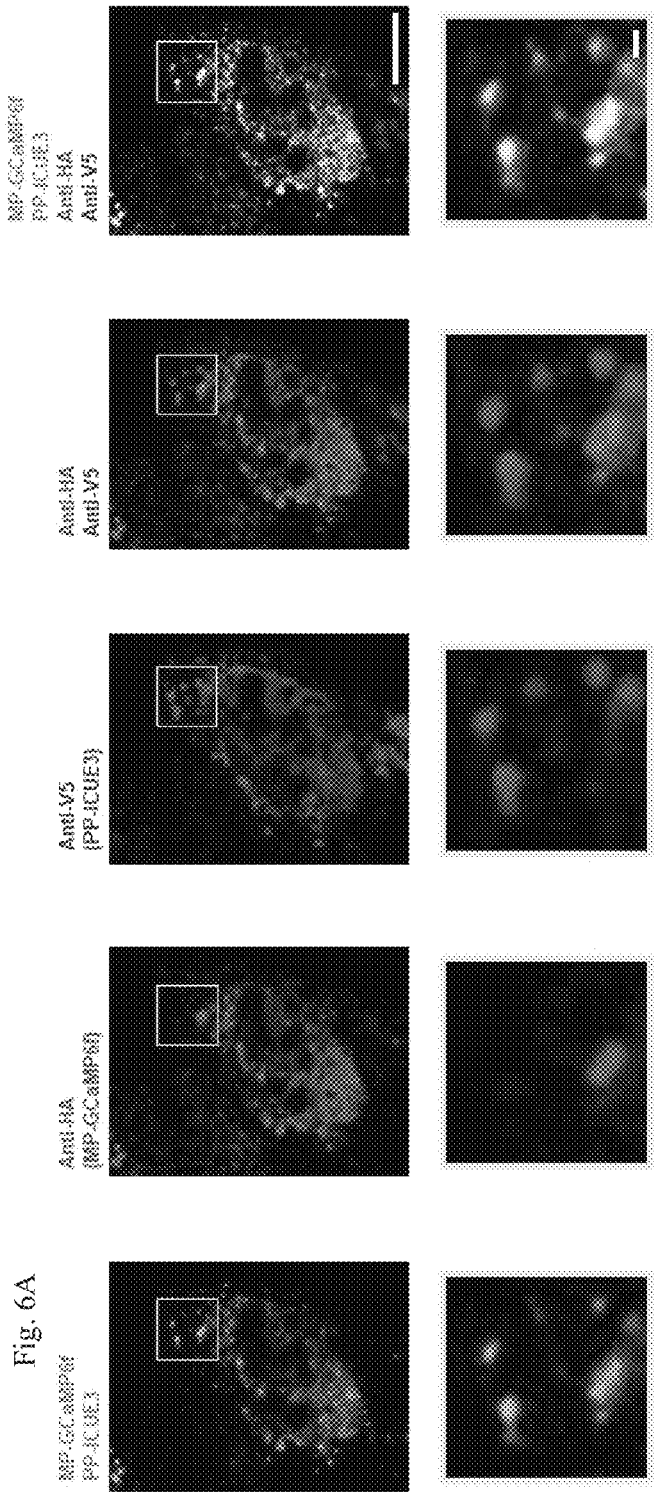
FIG. 6A-E presents photomicrographs and graphs reporting the results of spatially multiplexed simultaneous imaging of $Ca^{2+}$ and cAMP in mammalian cells using spectrum-overlapping fluorescent sensors clustered by RNA scaffolds.
Figure 6B:
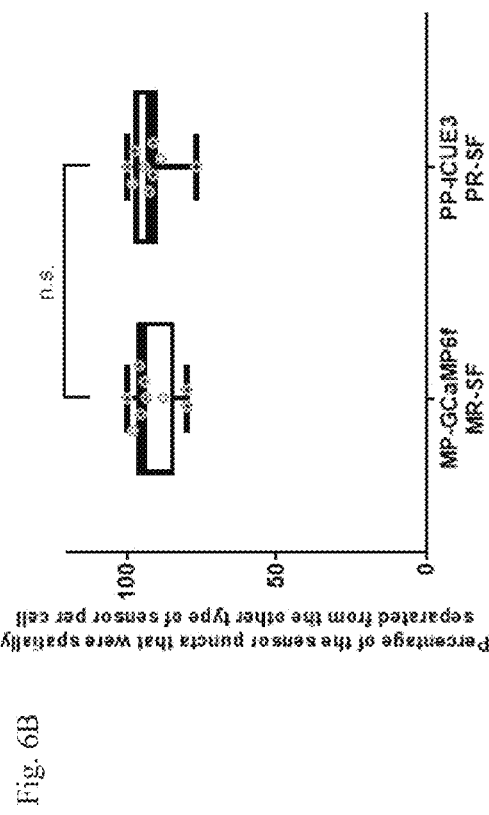
Figure 6C:
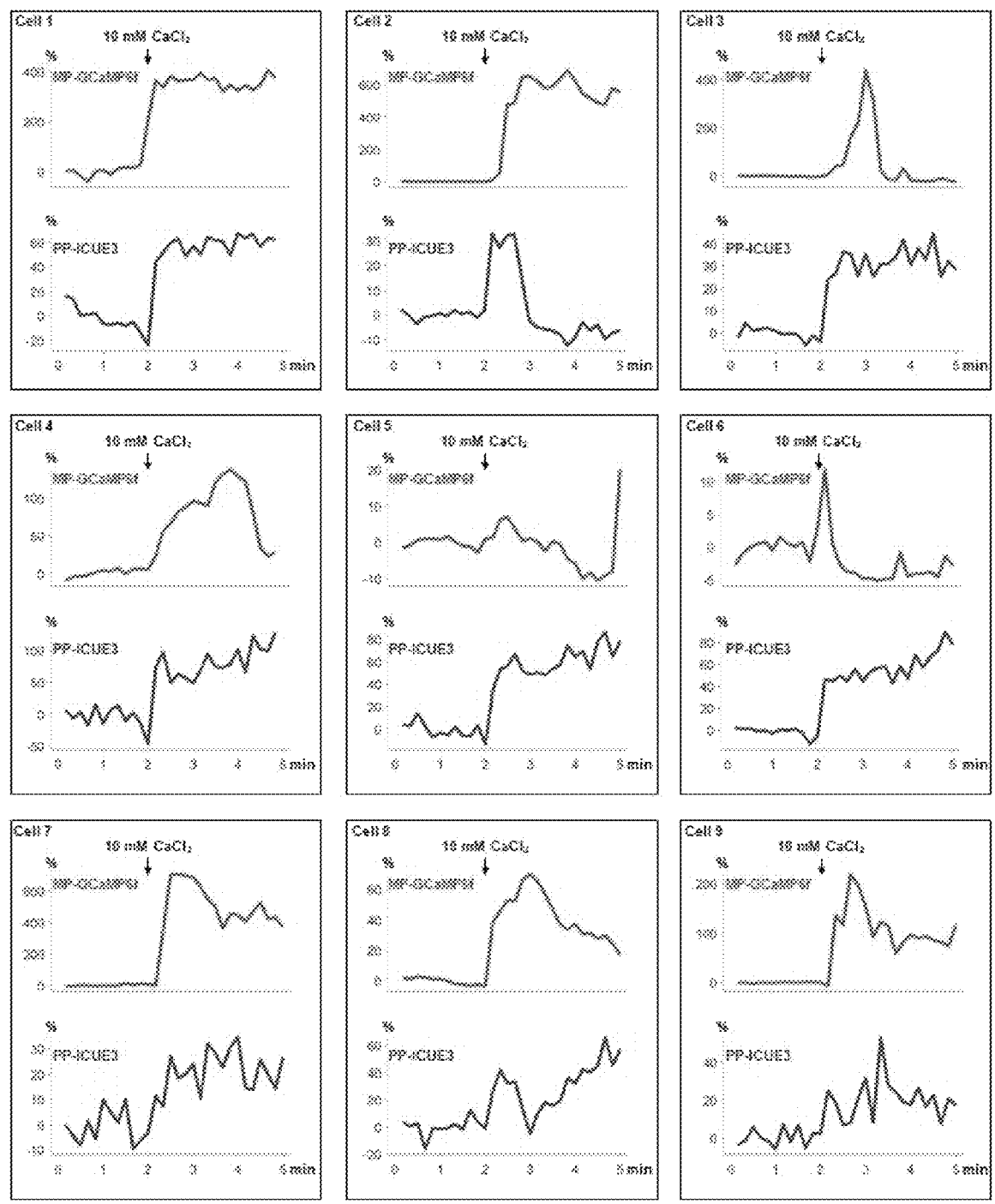
Figure 6D:
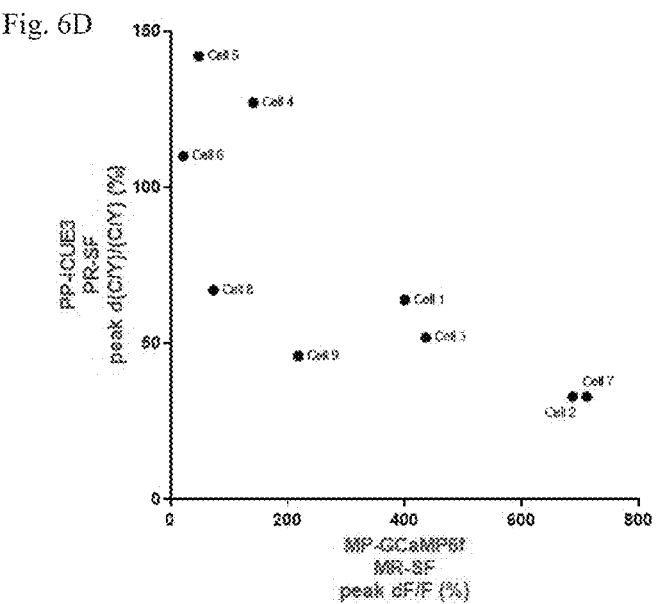
Figure 6E:
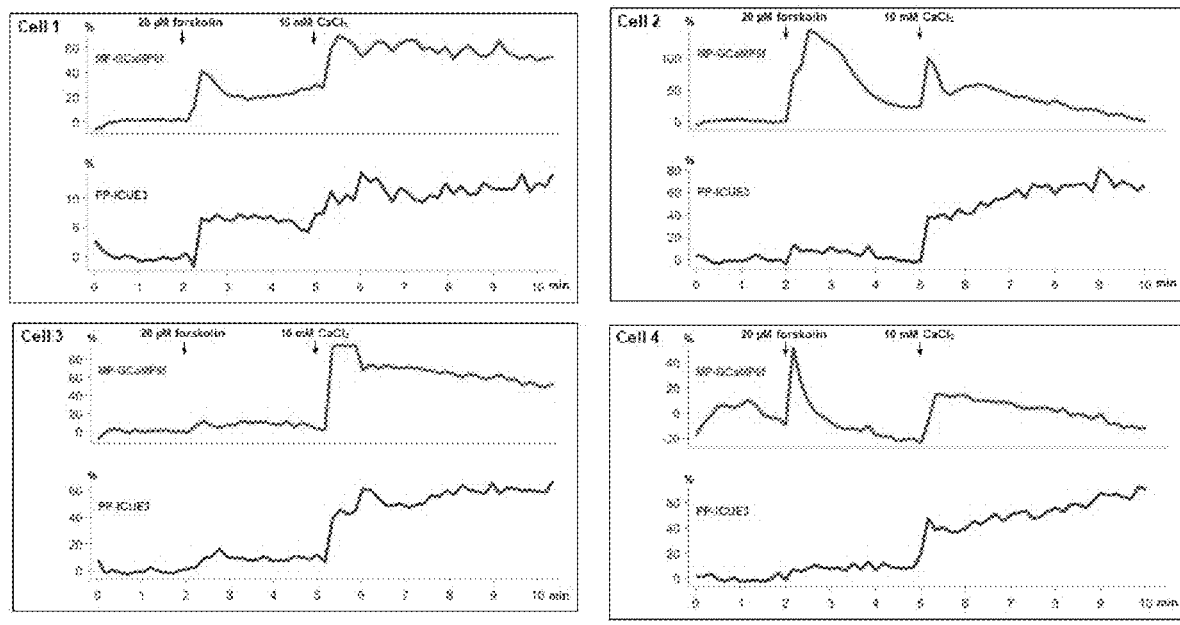

Multiplexed Physiological Imaging of $Ca^{2+}$ and cAMP in Single Cells Via Clustered Reporters of Overlapping Fluorescence Spectrum The MS2-scaffolded GCaMP6f system and the PP7-scaffolded ICUE3 system, were co-expressed in single cells and assessed, using post hoc antibody staining against the HA and V5 epitopes respectively, to determine whether the orthogonality of clustering that was observed when the clusters were formed separately (FIG. 2) persisted when the clusters were formed together in the same cell. The sensor puncta in the live state that exhibited post hoc anti-HA immunostaining (and thus were GCaMP6f positive) were quantified, as well as the puncta that exhibited post hoc anti-V5 immunostaining (and thus were ICUE3 positive), and were then examined to determine whether the GCaMP6f puncta bore ICUE3 and vice versa (FIG. 6A). Such co-localizations could result from puncta that, by chance, overlapped in space, or they could result from crosstalk between proteins and RNAs across the MS2 and PP7 systems (although previous usages of MS2 and PP7 together for RNA imaging have emphasized that crosstalk is low (Hocine et al., 2013)). Over 90% of the GCaMP6f puncta did not exhibit detectable ICUE3, and a similar finding held for the ICUE3 puncta (FIG. 6B). Thus the percentage contamination of signals was quite small; furthermore, eliminating puncta that contain both signals from further analysis could reduce the chance of such contamination affecting downstream conclusions to a very low level. Table 7 provides Statistical analysis for experimental results shown in FIG. 6B.

TABLE 7

Statistical analysis for FIG. 6B

| Column B vs. Column A | PP-ICUE3 PR-SF vs. MP-GCaMP6f MR-SF |
|---|---|
| Wilcoxon rank sum test | |
| P value | 0.949 |
| Exact or approximate P value? | Exact |
| P value summary | ns |
| Significantly different (P < 0.05)? | No |
| One- or two-tailed P value? | Two-tailed |
| Sum of ranks in column A, B | 86.5, 84.5 |
| Mann-Whitney U | 39.5 |
| Difference between medians | |
| Median of column A | 94.29, n = 9 |
| Median of column B | 92.68, n = 9 |
| Difference: Actual | −1.603 |
| Difference: Hodges-Lehmann | −0.08282 |

Having established the independence of these puncta, MS2 scaffolded GCaMP6f and PP7 scaffolded ICUE3 were then used to measure $Ca^{2+}$ and cAMP simultaneously in the same cells, under 10 mM $Ca^{2+}$ challenge. Interestingly, multiple kinds of responses emerged (FIG. 6C), with individual cells demonstrating great heterogeneity in their $Ca^{2+}$ responses (e.g., cells 1, 2, 7, 8, and 9 exhibited sustained responses, whereas cells 3 and 6 exhibited transient responses) as well as in their cAMP responses (e.g., cells 1, 3, 4, 5, 6, and 8 exhibited sustained responses, and cells 2 and 9 exhibited transient responses). In particular, the relationship between $Ca^{2+}$ and cAMP could differ from cell to cell: cells that had a sustained calcium response could have a transient cAMP response (cell 2), and cells that had a transient calcium response could have a sustained cAMP response (cell 3). Simply averaging the $Ca^{2+}$ signals from one population of cells, and the cAMP responses from a second population of cells, would miss out on such within-cell comparisons which might (with additional study) reveal interesting ways in which the coupling between one signal and another signal may be modulated by cell state. A plot of the peak $Ca^{2+}$ and cAMP amplitudes reveals the potential for complex relationships between these two variables, which emphasize the importance of measuring them simultaneously in single cells (FIG. 6D)-perhaps the way these two biological signals interact varies greatly from cell to cell because of different cell histories, epigenetic states, transcriptional states, or protein post-translational modification states.

Several cells were exposed to sequential stimuli, first to 20 µM forskolin and then to 10 mM $Ca^{2+}$. Cells again exhibited a variety of relationships between the $Ca^{2+}$ and cAMP responses (FIG. 6E), which would have been lost if the signals had been first averaged across separate populations of cells and then compared in the aggregate. Some cells had $Ca^{2+}$ and cAMP responses that exhibited similar time-courses and dependencies on the two stimuli (cells 1 and 3), whereas others exhibited $Ca^{2+}$ and cAMP responses that were differentially engaged by the two stimuli—specifically, cells 2 and 4 both had reliable $Ca^{2+}$ responses to both stimuli, but the cAMP responses were differentially engaged by the two stimuli. Thus, the ability to record multiple signals in a single cell may reveal correlations in how different signaling pathways respond to external stimuli, correlations that are lost if first averaged across cells before being compared.

Example 2. Protein Scaffold-Based Reporter Clustering

Figure 7A:
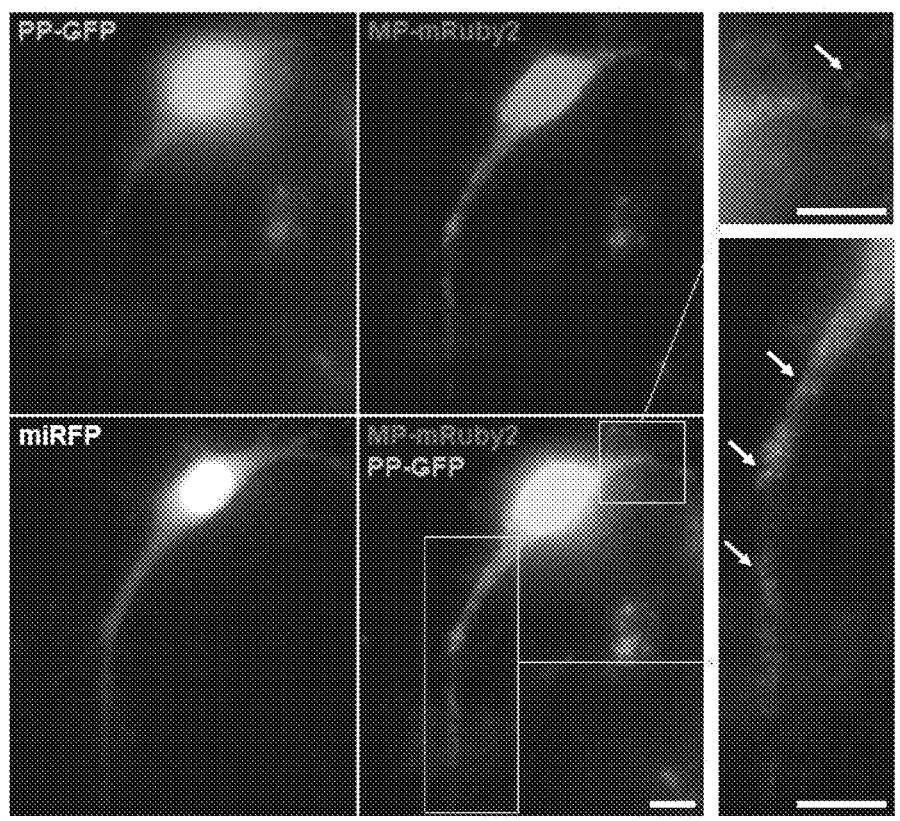
FIG. 7A-C presents photomicrographs of RNA scaffolds capable of assembling fluorescent proteins into spatially separated puncta in neurons but not capable of assembling fluorescent sensor GCaMP6f into resolvable puncta in neurons. Related to FIG. 6.
Figure 7B:
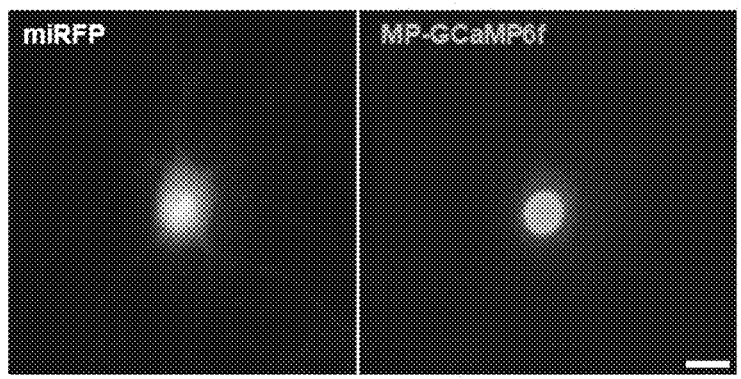
Figure 7C:
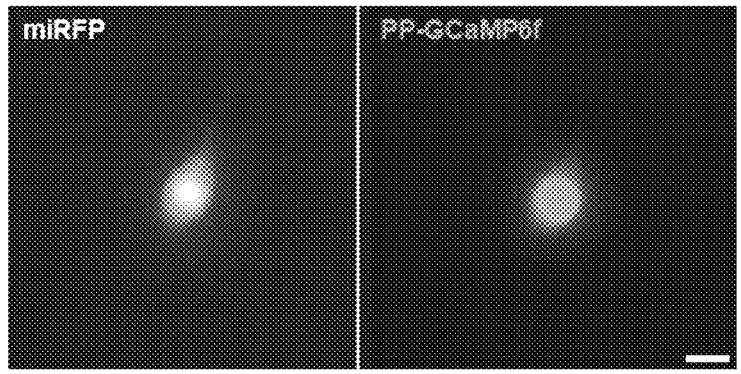

Neurons exhibit complex signaling cascades important for learning, memory, and development, and that are compromised in complex ways in disease states. Primary cultures of rodent hippocampal and cortical neurons have been critical for the study of calcium and cAMP signaling cascades (Sheng, Thompson and Greenberg, 1991; Bito, Deisseroth and Tsien, 1996; Hardingham, Arnold and Bading, 2001; Redmond, Kashani and Ghosh, 2002), and may be an ideal testbed for the deployment of spatially multiplexed indicators, as long as they are distributed closely enough to sample the relevant spatial scales of neurons (e.g., at different points on dendrites). Expression of the RNA scaffolded $Ca^{2+}$ and cAMP indicators that successfully worked in HeLa cells did not result in puncta in neurons (FIG. 7A-C). Instead, the fluorescent sensors and RNA scaffolds accumulated in the soma and in the proximal neurites, perhaps resulting in such a high density of expression that puncta were not detectable over background. One possibility is that the complex morphology of neurons is linked to more complex RNA trafficking machinery, as has been commented on by others (Davis, Banker and Steward, 1987; Lyford et al., 1995; Dictenberg et al., 2008; Holt and Schuman, 2013; Buxbaum, Wu and Singer, 2014), and further RNA engineering would be required. Accordingly, a reporter clustering method was developed based upon autonomous properties of expressed engineered proteins, ideally artificial ones that would be bioorthogonal to endogenous trafficking biases, to avoid confounds from endogenous machinery as much as possible.

Materials and Methods

Fluorescence Microscopy of Primary Neurons

Live neuron imaging was performed on a spinning disk confocal microscope (a Yokogawa® CSU-W1 Confocal Scanner Unit on a Nikon® Eclipse T1 microscope) equipped with a 40×1.15 NA water immersion objective (Nikon® MRD77410) and a Zyla® PLUS 4.2 Megapixel camera controlled by NIS-Elements® AR software. The filter set for GFP was used for imaging GFP intensity-based reporters (GCaMP6f and cAMPr), and the filter set for GFP and the 405 nm excitation filter was used for imaging 488 nm/405 nm excitation ratiometric reporters (ExRaiAKAR and ExRaiCKAR). The filter set for RFP was used for imaging RFP intensity-based reporters (RAB_EKARev). For electrophysiological characterizations of GCaMP6f and S1-GCaMP6f (FIGS. 8D-G, 9A-Q), neurons were recorded in the GFP emission channel at a single focal plane at 20 milliseconds per frame (50 Hz). In the characterization and spatially multiplexed imaging experiments in FIGS. 9R-V, 10D-10G, 10M-10O, neurons were recorded in the GFP emission channel at a single focal plane at 50 milliseconds per frame (20 Hz). In all other primary neuron imaging experiments, neurons were recorded by volumetric imaging (1.0-1.5 µm per Z step) in the GFP emission channel only (about 5 seconds per volume; each X-Y plane in the volume was captured twice, one under 405 nm excitation and the other under 488 nm excitation; 405 nm excitation is for ExRaiAKAR and ExRaiCKAR) or in the GFP and RFP emission channels (about 30 seconds per volume; each X-Y plane in the volume was captured three times, one under 405 nm excitation and GFP emission, another under 488 nm excitation and GFP emission, the last one under 561 nm excitation and RFP emission; 561 nm excitation is for RAB_EKARev).

In the experiments in FIGS. 8, 9, 10, and 11 where the drug stimulations (forskolin, PMA, DHPG, or $CaCl_2$) were indicated by black downwards arrows, drugs diluted in the corresponding media (FLUOROBRITE™ MEM for HeLa cells and MEM for cultured neurons) were added into the cell culture by pipetting gently dropwise. In the experiments in FIGS. 12, 13, 14, 15, 16, 27, and 31 where the drug stimulations (forskolin, PMA, or DHPG) were indicated by black horizontal bars, coverslips of cultured neurons were transferred to a perfusion chamber (Warner Instruments, Holliston, MA; RC-41LP plus DH-40iL) and continuously perfused with MEM for 10-15 minutes before imaging started. During the time periods indicated by the black horizontal bars, corresponding drugs diluted in MEM (50 µM for forskolin; 0.1 µg/ml for PMA; 100 µM for DHPG) were perfused into the perfusion chamber instead of the blank MEM.

After recording, z stacks were taken at 40× in the GFP and miRFP channels, and then a tiled image in the GFP channel at 10× covering a 4×4 grid and at 4× covering the entire glass coverslip was taken for registration of live images with the images from downstream immunostaining. Neurons were then fixed for 15 minutes in TissuePrep™ buffered 10% formalin, followed by washing with 100 mM glycine (Millipore Sigma, Burlington, MA) in 1×PBS for 15 minutes, and then washing with 1×PBS three times, 5 minutes each. Cells were stored in 1×PBS at 4° C.

Electrophysiology—Current and Voltage Clamp Recording of Cultured Neurons

Whole cell patch clamp recordings in were made using Axopatch™ 200B or Multiclamp™ 700B amplifiers, a Digidata™ 1440 digitizer, and a PC running pClamp™ (Molecular Devices, San Jose, CA). For in vitro current-clamp recordings, neurons were patched at 14-18 DIV (7-11 days after AAV transduction) to allow for sodium channel maturation. Neurons were bathed in room temperature Tyrode containing 125 mM NaCl, 2 mM KCl, 3 mM $CaCl_2$, 1 mM $MgCl_2$, 10 mM HEPES, 30 mM glucose and the synaptic blockers 0.01 mM NBQX and 0.01 mM GABAzine. The Tyrode pH was adjusted to 7.3 with NaOH and the osmolarity was adjusted to 300 mOsm with sucrose. For in vitro voltage-clamp recordings, neurons were patched at 19-21 DIV (17-20 days post-transfection) and were done under similar conditions as current-clamp recordings, except the Tyrode also contained 1 µM tetrodotoxin (TTX, Tocris Bioscience, Bristol, UK). For recordings, borosilicate glass pipettes (Warner Instruments, Holliston, MA) with an outer diameter of 1.2 mm and a wall thickness of 0.255 mm were pulled to a resistance of 5-10 MΩ with a P-97 Flaming/Brown micropipette puller (Sutter Instruments, Novato, CA) and filled with a solution containing 155 mM K-gluconate, 8 mM NaCl, 0.1 mM $CaCl_2$, 0.6 mM $MgCl_2$, 10 mM HEPES, 4 mM Mg-ATP, and 0.4 mM Na-GTP. The pipette solution pH was adjusted to 7.3 with KOH and the osmolarity was adjusted to 298 mOsm with sucrose.

For additional methods, see methods described in Example 1, and additional details provided herein.

Experiments, Results, and Discussion

Protein Scaffolds can Assemble Reporters into Functional Clusters in Neurons

De novo-designed short peptides of coiled-coil forming hetero-dimers (Tripet et al., 1996; Oakley and Kim, 1998; Moll et al., 2001; Shekhawat et al., 2009; Boyle et al., 2012; Gradisar et al., 2013) or homo-oligomers (Grigoryan et al., 2011; Zaccai et al., 2011; Fletcher et al., 2012; Huang et al., 2014; Negron and Keating, 2014; Thomson et al., 2014; Zhang et al., 2018) were tested to determine whether they could, when fused to GCaMP6f, help assemble GCaMP6f into puncta. Two to five of these motifs were fused to the N-terminus or C-terminus of GCaMP6f, with glycine and serine rich flexible linkers adapted from a previous study (Boyle et al., 2012; Indelicato et al., 2016) (Tables 1-2). None of these constructs produced puncta ($D_C$=1), perhaps because they formed small oligomers instead of larger protein assemblies, as had been observed in certain conditions (Boyle et al., 2012).

Next, de novo-designed self-assembling peptides were tested that were not coiled-coil forming proteins, but that had been shown in solution to form large protein assemblies beyond oligomers (such as polyhedrons). These peptides included the I3-01 peptide that forms a 60-subunit 25 nm sized 1.33 MDa protein dodecahedron (Hsia et al., 2016); other supramolecular assembly forming peptides were also tested (Gonen et al., 2015; Garcia-Seisdedos et al., 2017) (Tables 1-2). The I3-01 peptide was able to form identifiable puncta of GCaMP6f in neurons that were modestly brighter than the non-puncta cytosol ($D_C$=2); none of the other designs produced any puncta in neurons ($D_C$=1). Thus, I3-01 served as a prototype for a general strategy for creating such puncta, to which improvements could be made, including improved brightness, and as a baseline for identifying other peptides with similar properties.

Dual-Self-Assembling Peptides

It was hypothesized that self-assembling peptides could generate meaningful puncta if they were scalably assembled beyond the sizes achievable with a single self-assembling peptide: for example, if a fluorescent reporter was fused to two self-assembling peptides, it could form more scalable assemblies because each kind of reporter could enable new bridges to form (FIG. 1D). Experiments were therefore performed in which GCaMP6f was fused to a pair of self-assembling peptides—one a coiled-coil forming protein, and one a polyhedron-forming protein—to determine whether the combination of two peptides could enable the formation of more bright macroscopic clusters. One possible outcome was that such a dual peptide strategy could, for example, enable small puncta to be formed via the polyhedron-assembling motifs (which, as noted, had some degree of clustering, albeit very dim), which in turn could link up into larger puncta via the coiled-coil forming motifs.

A first goal of studies carried out was to increase the brightness of the puncta. To increase the number of GCaMP6f molecules per punctum, a short coiled-coil-forming homo-tetramer HexCoil-Ala [(Grigoryan et al., 2011); 30 amino acids long, abbreviated Coil1 in this study; four Coil1 peptides will assemble into a 12.8 kDa coiled-coil assembly] was added to the I3-01-fused GCaMP6f with the goal of allowing the I3-01-assembled puncta further assemble into even larger structures. The resulting dual self-assembling motif was named S1, and the reporter construct (including the immunoepitope Xpress™ for later antibody staining identification) was named S1-GCaMP6f (FIG. 17A; Tables 1-2).

Figure 8S:
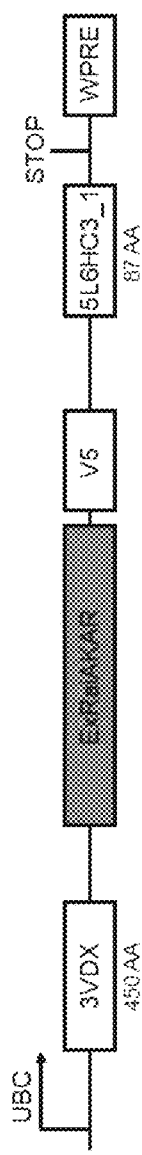
Figure 8S:
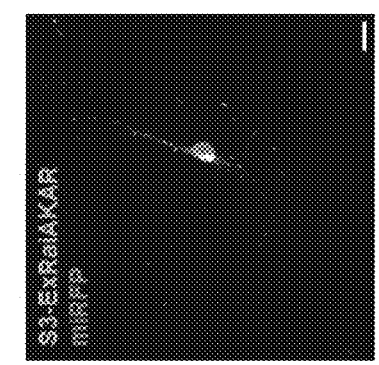
Figure 8S:
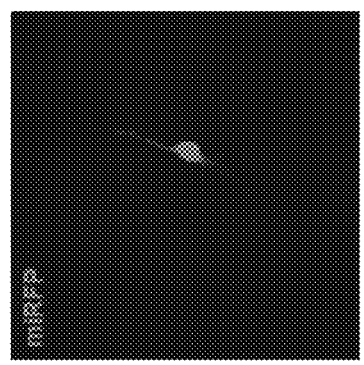
Figure 9A:
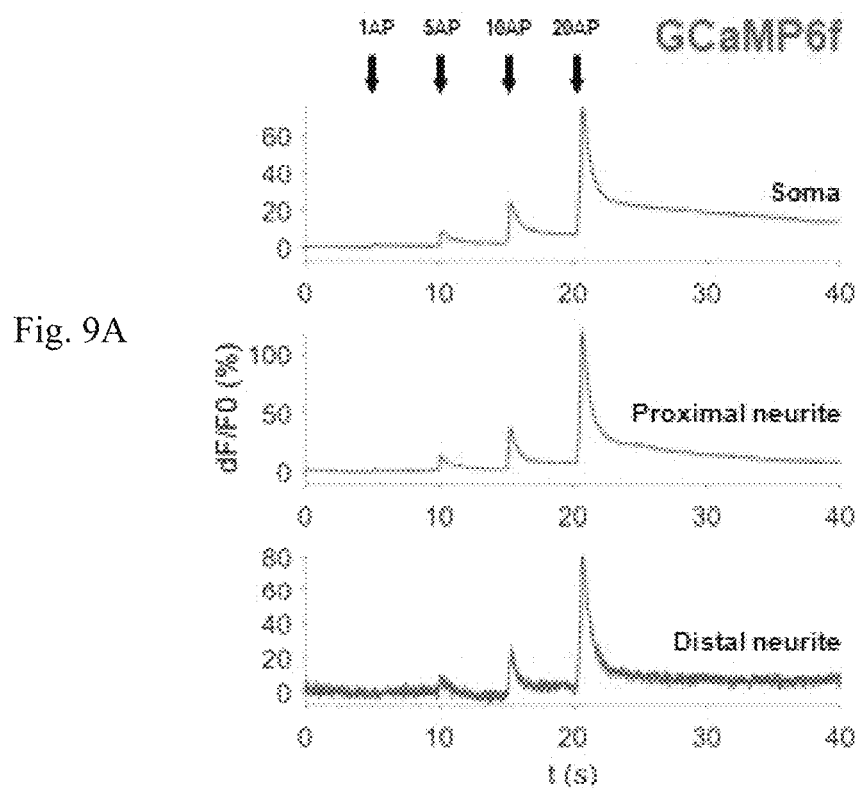
FIG. 9A-Z provides photomicrographic images, traces, and graphs illustrating further characterization of S1-GCaMP6f. Related to FIG. 8.
Figure 9B:
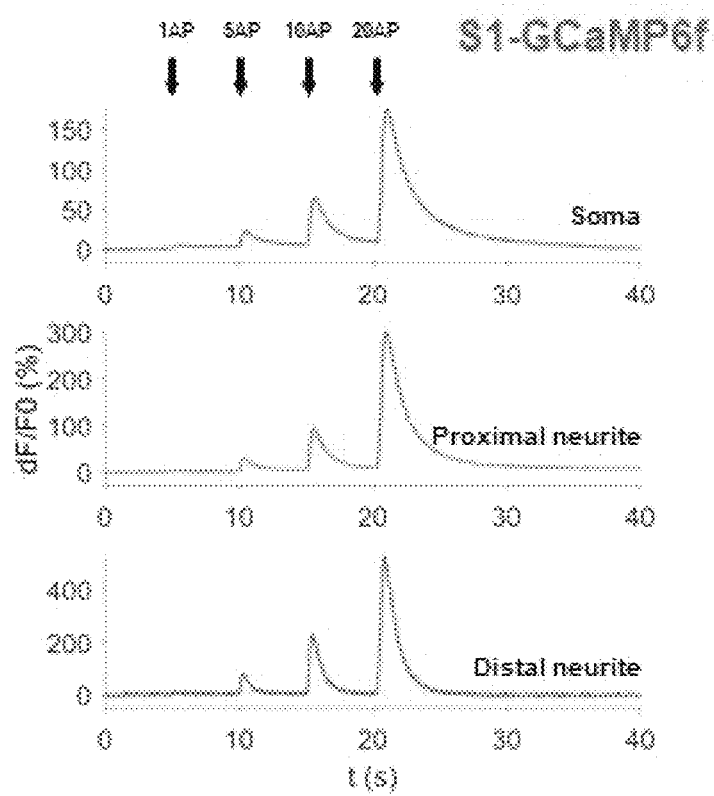

S1-GCaMP6f had an extremely high $D_C$ of $>10^3$ in the soma and $>10^4$ in the neurites (compare FIG. 17B with FIG. 17C; quantitation in FIG. 21A-B, Tables 28-29), indicating promise as a protein scaffold based SiRI construct for spatially multiplexed imaging. As seen in FIGS. 17D-I and FIGS. 8D-H (Tables 9-13) $Ca^{2+}$ transients reported by S1-GCaMP6f compared at the soma, the proximal neurites (5-25 µm away from soma; distances to soma were measured along the neurites throughout this study), and the distal neurites (50-250 µm away from soma) appeared similar to those of conventional GCaMP6f in response to either a single action potential (1 AP) at t=5 seconds (s) triggered by current injection via whole-cell patch clamp at the soma (FIG. 17D-F), when elicited by 5 µM forskolin stimulation at t=10 s (FIG. 17G-I), or in response to multiple APs (FIG. 9A-B). $Ca^{2+}$ transients reported by S1-GCaMP6f also showed similar transient amplitudes (dF/F0, measured as peak fluorescence change in the GFP channel) for both single AP (FIG. 17E, FIG. 17H, Tables 8 and 9), multiple APs (FIG. 9C, Table 14), as well as similar signal-to-noise ratios in the GFP channel (FIG. 17F, FIG. 17I, Tables 8 and 10) in neurons as those of conventional GCaMP6f. The rise time and decay time of reported $Ca^{2+}$ transients at the soma elicited by single APs were similar between GCaMP6f and S1-GCaMP6f as well (FIG. 8G, Table 13). The amplitude, rise time, and decay time of S1-GCaMP6f-reported somatic $Ca^{2+}$ transients elicited by single APs had no correlation with the number of puncta, the brightness of puncta, or the size of puncta (FIG. 9E-P, Tables 15-19), with one reported $Ca^{2+}$ peak per single AP (FIG. 9Q, Table 20). When elicited by extracellular forskolin stimulation, which drives cAMP production and induces extracellular $Ca^{2+}$ influx and/or intracellular $Ca^{2+}$ release in multiple types of cultured neurons (Zanassi et al., 2001; Gorbunova and Spitzer, 2002; Otsuguro et al., 2005), $Ca^{2+}$ signals reported by S1-GCaMP6f appeared similar to those reported by GCaMP6f in amplitude, signal-to-noise ratio, and number of peaks observed (FIG. 9R-V, Tables 21-23). Thus, S1 clustering of GCaMP6f into puncta did not alter GCaMP6f functionality. S1-GCaMP6f puncta were ~0.5-2 μm in diameter (FIG. 8H, left; consistent across gene dosages, FIG. 9W, Table 24), with the median distance to the nearest punctum of ~5 μm (FIG. 2H, middle; consistent across gene dosages, FIG. 9X, Table 25), and remained almost completely spatially stationary over one hour periods, with mean squared displacement of 1.8 μm² per hour, or an estimated diffusion coefficient of 0.006 μm² per minute (FIG. 8H, right) in live neurons. S1-GCaMP6f puncta brightness (FIG. 9Y, Table 26), but not puncta count (FIG. 9Z, Table 27), increased with gene dosage. S1-GCaMP6f expression did not alter the basal or active electrophysiological properties of neurons (FIG. 18) and S1-GCaMP6f puncta did not co-localize with subcellular organelles in neurons, including mitochondria, endosomes, lysosomes, Golgi apparatus, and endoplasmic reticulum (FIG. 19). Tables 8-10 show measurements and statistical analyses for FIGS. 17E-F and H-I; Tables 11-13 show statistical analyses for FIGS. 8E-G; Tables 14-27 show statistical analyses for FIGS. 9C-D, M-O, P-U, and W-Z; and Tables 28-29 show statistical analyses for FIGS. 21A-B.

TABLE 8

Neuronal measurements used in FIG. 17E-F and FIG. 17H-I

Peak fluorescence change, GFP channel (dF/F0)

| Single action potential (1 AP) | Somata | Proximal neurites | Distal neurites | Total neurons | Cultures | Corresponding FIG. |
|---|---|---|---|---|---|---|
| GCaMP6f | 11 | 22 | 22 | 11 | 3 | FIG. 17E |
| S1-GCaMP6f | 11 | 22 | 22 | 11 | 3 | FIG. 17E |
| 5 μM forskolin | | | | | | |
| GCaMP6f | 6 | 12 | 12 | 6 | 4 | FIG. 17H |
| S1-GCaMP6f | 9 | 18 | 18 | 9 | 6 | FIG. 17H |

Signal-to-noise-ratio

| 1 AP | Somata | Proximal neurites | Distal neurites | Total neurons | Cultures | Corresponding FIG. |
|---|---|---|---|---|---|---|
| GCaMP6f | 11 | 22 | 22 | 11 | 3 | FIG. 17F |
| S1-GCaMP6f | 11 | 22 | 22 | 11 | 3 | FIG. 17F |
| Forskolin | | | | | | |
| GCaMP6f | 6 | 12 | 12 | 6 | 4 | FIG. 17I |
| S1-GCaMP6f | 9 | 18 | 18 | 9 | 6 | FIG. 17I |

TABLE 9

Statistical analysis for FIG. 17H

| Two-way ANOVA | Ordinary | | | | |
|---|---|---|---|---|---|
| Alpha | 0.05 | | | | |
| Source of Variation | % of total variation | P value | P value summary | Significant? | |
| Interaction | 4.434 | 0.273 | ns | No | |
| Locations | 1.773 | 0.59 | ns | No | |
| Molecules | 1.847 | 0.297 | ns | No | |

| ANOVA table | SS (Type III) | DF | MS | F (DFn, DFd) | P value |
|---|---|---|---|---|---|
| Interaction | 354628 | 2 | 177314 | F (2, 54) = 1.33 | P = 0.273 |
| Locations | 141828 | 2 | 70914 | F (2, 54) = 0.5321 | P = 0.590 |
| Molecules | 147722 | 1 | 147722 | F (1, 54) = 1.108 | P = 0.297 |
| Residual | 7197259 | 54 | 133283 | | |
| Number of families | 1 | | | | |

TABLE 9-continued

Statistical analysis for FIG. 17H

| | | | | | |
|---|---|---|---|---|---|
| Number of comparisons per family | 3 | | | | |
| Alpha | 0.05 | | | | |

| Sidak's multiple comparisons test | Mean Diff. | 95.00 % CI of diff. | Significant? | Summary | Adjusted P Value |
|---|---|---|---|---|---|
| GCaMP6f-S1-GCaMP6f | | | | | |
| Soma | 83.54 | −435.8 to 602.9 | No | ns | 0.971 |
| Proximal neurite | −81.96 | −449.2 to 285.3 | No | ns | 0.928 |
| Distal neurite | −315.4 | −682.6 to 51.85 | No | ns | 0.112 |

| Test details | Mean 1 | Mean 2 | Mean Diff. | SE of diff. | N1 | N2 | t | DF |
|---|---|---|---|---|---|---|---|---|
| GCaMP6f-S1-GCaMP6f | | | | | | | | |
| Soma | 544.1 | 460.6 | 83.54 | 210.8 | 6 | 6 | 0.3963 | 54 |
| Proximal neurite | 508.1 | 590.1 | −81.96 | 149 | 12 | 12 | 0.5499 | 54 |
| Distal neurite | 468.7 | 784.1 | −315.4 | 149 | 12 | 12 | 2.116 | 54 |

TABLE 10

Statistical analysis for FIG. 17I

Two-way ANOVA Ordinary
Alpha 0.05

| Source of Variation | % of total variation | P value | P value summary | Significant? |
|---|---|---|---|---|
| Interaction | 5.618 | .139 | ns | No |
| Row Factor | 19.88 | .002 | ** | Yes |
| Column Factor | 1.384 | .320 | ns | No |

| ANOVA table | SS (Type III) | DF | MS | F (DFn, DFd) | P value |
|---|---|---|---|---|---|
| Interaction | 143900 | 2 | 71950 | F (2, 54) = 2.045 | P = 0.139 |
| Row Factor | 509284 | 2 | 254642 | F (2, 54) = 7.237 | P = 0.002 |
| Column Factor | 35443 | 1 | 35443 | F (1, 54) = 1.007 | P = 0.320 |
| Residual | 1900038 | 54 | 35186 | | |

TABLE 10-continued

Statistical analysis for FIG. 17I

Number of families 1
Number of comparisons per family 3
Alpha 0.05

| Sidak's multiple comparisons test | Mean Diff. | 95.00% CI of diff. | Significant? | Summary | Adjusted P Value |
|---|---|---|---|---|---|
| GCaMP6f-S1-GCaMP6f | | | | | |
| Soma | 192 | −74.87 to 458.8 | No | ns | 0.226 |
| Proximal neurite | 36.34 | −152.4 to 225 | No | ns | 0.952 |
| Distal neurite | −74.61 | −263.3 to 114.1 | No | ns | 0.705 |

| Test details | Mean 1 | Mean 2 | Mean Diff. | SE of diff. | N1 | N2 | t | DF |
|---|---|---|---|---|---|---|---|---|
| GCaMP6f-S1-GCaMP6f | | | | | | | | |
| Soma | 454 | 262 | 192 | 108.3 | 6 | 6 | 1.773 | 54 |
| Proximal neurite | 158.2 | 121.8 | 36.34 | 76.58 | 12 | 12 | 0.4746 | 54 |
| Distal neurite | 80.64 | 155.3 | −74.61 | 76.58 | 12 | 12 | 0.9743 | 54 |

TABLE 11

Statistical analysis for FIG. 8E
Peak fluorescence changes in the GFP channel at the soma, proximal neurites, and distal neurites of cultured mouse hippocampal neurons expressing GCaMP6f or S1-GCaMP6f in response to single action potental (n = 11 values from soma, 22 values from proximal neurites, and 22 values from distal neurites from 11 total trials from 6 neurons from 3 cultures for each of GCaMP6f and S1-GCaMP6f; for each trial, the calcium responses from the soma and two proximal neurites and two distal neurites were analyzed).
Two way analysis of variance followed by post-hoc Bonferroni corrected multiple comparisons test.

Two-way ANOVA Ordinary
Alpha 0.05

| Source of Variation | % of total variation | P value | P value summary | Significant? |
|---|---|---|---|---|
| Interaction | 0.1647 | .912 | ns | No |
| Subcellular location | 1.958 | .337 | ns | No |
| Molecule | 4.426 | .028 | * | Yes |

| ANOVA table | SS (Type III) | DF | MS | F (DFn, DFd) | P value |
|---|---|---|---|---|---|
| Interaction | 8.895 | 2 | 4.447 | F (2, 104) = 0.09254 | P = .912 |
| Subcellular location | 105.8 | 2 | 52.88 | F (2, 104) = 1.100 | P = .337 |
| Molecule | 239.0 | 1 | 239.0 | F (1, 104) = 4.974 | P = .028 |
| Residual | 4998 | 104 | 48.06 | | |

| Difference between column means | | |
|---|---|---|
| Predicted (LS) mean of GCaMP6f | 4.676 | |

TABLE 11-continued

Statistical analysis for FIG. 8E
Peak fluorescence changes in the GFP channel at the soma, proximal neurites, and distal
neurites of cultured mouse hippocampal neurons expressing GCaMP6f or S1-GCaMP6f
in response to single action potental (n = 11 values from soma, 22 values from proximal
neurites, and 22 values from distal neurites from 11 total trials from 6 neurons from 3
cultures for each of GCaMP6f and S1-GCaMP6f; for each trial, the calcium responses
from the soma and two proximal neurites and two distal neurites were analyzed).
Two way analysis of variance followed by post-hoc Bonferroni corrected multiple
comparisons test.

|  |  |  |
| --- | --- | --- |
| Predicted (LS) mean of S1-GCaMP6f | 7.784 |  |
| Difference between predicted means | −3.108 |  |
| SE of difference | 1.394 |  |
| 95% CI of difference | −5.871 to −0.3444 |  |

Number of families 1
Number of comparisons per family 3
Alpha 0.05

| Bonferroni's multiple comparisons test | Predicted (LS) mean diff. | 95% CI of diff. | Significant? | Summary | Adjusted P Value |
| --- | --- | --- | --- | --- | --- |
| GCaMP6f-S1-GCaMP6f |  |  |  |  |  |
| Soma | −2.465 | −9.658 to 4.728 | No | ns | >.999 |
| Proximal neurite | −2.962 | −8.048 to 2.125 | No | ns | .479 |
| Distal neurite | −3.897 | −8.983 to 1.190 | No | ns | .195 |

| Test details | Predicted (LS) mean 1 | Predicted (LS) mean 2 | Predicted (LS) mean diff. | SE of diff. | N1 | N2 | t | DF |
| --- | --- | --- | --- | --- | --- | --- | --- | --- |
| GCaMP6f-S1-GCaMP6f |  |  |  |  |  |  |  |  |
| Soma | 4.109 | 6.574 | −2.465 | 2.956 | 11 | 11 | 0.8340 | 104.0 |
| Proximal neurite | 6.113 | 9.075 | −2.962 | 2.090 | 22 | 22 | 1.417 | 104.0 |
| Distal neurite | 3.805 | 7.702 | −3.897 | 2.090 | 22 | 22 | 1.864 | 104.0 |

TABLE 12

Statistical analysis for FIG. 8F
Signal-to-noise ratio in the GFP channel at the soma, proximal neurites, and distal neurites of
cultured mouse hippocampal neurons expressing GCaMP6f or S1-GCaMP6f in response to
single action potential (n = 11 values from soma, 22 values from proximal neurites, and 22
values from distal neurites from 11 total trials from 6 neutrons from 3 cultures for each of
GCaMP6f and S1-GCaMP6f; for each trial, the calcium responses from the soma and two
proximal neurites and two distal neurites were analyzed). Two-way analysis of variance
followed by post-hoc Bonferroni corrected multiple comparisons test.

Two-way ANOVA Ordinary
Alpha 0.05

| Source of Variation | % of total variation | P value | P value summary | Significant? |
| --- | --- | --- | --- | --- |
| Interaction | 0.2732 | .788 | ns | No |
| Subcellular location | 38.22 | <.001 | *** | Yes |
| Molecule | 1.508 | .107 | ns | No |

TABLE 12-continued

Statistical analysis for FIG. 8F
Signal-to-noise ratio in the GFP channel at the soma, proximal neurites, and distal neurites of cultured mouse hippocampal neurons expressing GCaMP6f or S1-GCaMP6f in response to single action potential (n = 11 values from soma, 22 values from proximal neurites, and 22 values from distal neurites from 11 total trials from 6 neutrons from 3 cultures for each of GCaMP6f and S1-GCaMP6f; for each trial, the calcium responses from the soma and two proximal neurites and two distal neurites were analyzed). Two-way analysis of variance followed by post-hoc Bonferroni corrected multiple comparisons test.

| ANOVA table | SS (Type III) | DF | MS | F (DFn, DFd) | P value |
|---|---|---|---|---|---|
| Interaction | 3.710 | 2 | 1.855 | F (2, 104) = 0.2392 | P = .788 |
| Subcellular location | 519.0 | 2 | 259.5 | F (2, 104) = 33.47 | P < .001 |
| Molecule | 20.47 | 1 | 20.47 | F (1, 104) = 2.641 | P = .107 |
| Residual | 806.4 | 104 | 7.754 | | |

| | Difference between column means |
|---|---|
| Predicted (LS) mean of GCaMP6f | 3.821 |
| Predicted (LS) mean of S1-GCaMP6f | 4.731 |
| Difference between predicted means | −0.9095 |
| SE of difference | 0.5597 |
| 95% CI of difference | −2.019 to 0.2004 |

Number of families 1
Number of comparisons per family 3
Alpha 0.05

| Bonferroni's multiple comparisons test | Predicted (LS) mean diff. | 95% CI of diff. | Significant? | Summary | Adjusted P Value |
|---|---|---|---|---|---|
| GCaMP6f-S1-GCaMP6f | | | | | |
| Soma | −0.3286 | −3.218 to 2.561 | No | ns | >.999 |
| Proximal neurite | −1.071 | −3.114 to 0.9722 | No | ns | .615 |
| Distal neurite | −1.329 | −3.372 to 0.7136 | No | ns | .349 |

| Test details | Predicted (LS) mean 1 | Predicted (LS) mean 2 | Predicted (LS) mean diff. | SE of diff. | N1 | N2 | t | DF |
|---|---|---|---|---|---|---|---|---|
| GCaMP6f-S1-GCaMP6f | | | | | | | | |
| Soma | 7.527 | 7.55 | −0.3286 | 1.187 | 11 | 11 | 0.2767 | 104.0 |
| Proximal neurite | 2.839 | 3.909 | −1.071 | 0.8396 | 22 | 22 | 1.275 | 104.0 |
| Distal neurite | 1.098 | 2.427 | −1.329 | 0.8396 | 22 | 22 | 1.583 | 104.0 |

TABLE 13

Statistical analysis for FIG. 8G
Wilcoxon rank sum test of the half rise
time and the half decay time of reported
calcium transients at soma when elicited
by single action potential (n = 11 total
trials from 6 neurons from 3 cultures
for each of GCaMP6f and S1-GCaMP6f).

Half rise time

| | |
|---|---|
| P value | 0.3540 |
| ranksum | 140.5 |
| zval | 0.9269 |

TABLE 13-continued

Statistical analysis for FIG. 8G
Wilcoxon rank sum test of the half rise
time and the half decay time of reported
calcium transients at soma when elicited
by single action potential (n = 11 total
trials from 6 neurons from 3 cultures
for each of GCaMP6f and S1-GCaMP6f).

Half decay time

| | |
|---|---|
| P value | 0.4301 |
| ranksum | 139 |
| zval | 0.7891 |

TABLE 14

Statistical analysis for FIG. 9C
Peak fluorescence changes in the GFP channel at the soma, proximal neurites, and distal
neurites of cultured mouse hippocampal neurons expressing GCaMP6f or S1-GCaMP6f
in response to a single (n = 11 values from soma, 22 values from proximal neurites, and
22 values from distal neurites from 11 total trials from 6 neurons from 3 cultures for each
of GCaMP6f and S1-GCaMP6f; for each trial, the calcium responses from the soma and
two proximal neurites and two distal neurites were analyzed) or multiple (5AP, 10AP, or
20AP; n = 5 values from soma, 10 values from proximal neurites, and 10 values from
distal neurites from 5 total trials from 5 neurons from 3 cultures for GCaMP6f;
n = 6 values from soma, 12 values from proximal neurites, and 12 values from distal
neurites from 6 total trials from 6 neurons from 3 cultures for S1-GCaMP6f; for each trial,
the calcium responses from the soma and two proximal neurites and two distal neurites
were analyzed) action potentials. Two-way analysis of variance followed by post-hoc
Bonferroni corrected multiple comparisons test.

At the soma:
Two-way ANOVA Ordinary
Alpha 0.05

| Source of Variation | % of total variation | P value | P value summary | Significant? |
|---|---|---|---|---|
| Interaction | 0.4787 | .929 | ns | No |
| AP number | 47.90 | <.001 | *** | Yes |
| Molecule | 0.9601 | .347 | ns | No |

| ANOVA table | SS (Type III) | DF | MS | F (DFn, DFd) | P value |
|---|---|---|---|---|---|
| Interaction | 4908 | 3 | 1636 | F (3, 47) = 0.1500 | P = .929 |
| AP number | 491117 | 3 | 163706 | F (3, 47) = 15.01 | P < .001 |
| Molecule | 9844 | 1 | 9844 | F (1, 47) = 0.9025 | P = .347 |
| Residual | 512648 | 47 | 10907 | | |

| | Difference between column means | |
|---|---|---|
| Predicted (LS) mean of GCaMP6f | 87.79 | |
| Predicted (LS) mean of S1-GCaMP6f | 115.9 | |
| Difference between predicted means | −28.08 | |
| SE of difference | 29.56 | |
| 95% CI of difference | −87.55 to 31.39 | |

TABLE 14-continued

Statistical analysis for FIG. 9C
Peak fluorescence changes in the GFP channel at the soma, proximal neurites, and distal
neurites of cultured mouse hippocampal neurons expressing GCaMP6f or S1-GCaMP6f
in response to a single (n = 11 values from soma, 22 values from proximal neurites, and
22 values from distal neurites from 11 total trials from 6 neurons from 3 cultures for each
of GCaMP6f and S1-GCaMP6f; for each trial, the calcium responses from the soma and
two proximal neurites and two distal neurites were analyzed) or multiple (5AP, 10AP, or
20AP; n = 5 values from soma, 10 values from proximal neurites, and 10 values from
distal neurites from 5 total trials from 5 neurons from 3 cultures for GCaMP6f;
n = 6 values from soma, 12 values from proximal neurites, and 12 values from distal
neurites from 6 total trials from 6 neurons from 3 cultures for S1-GCaMP6f; for each trial,
the calcium responses from the soma and two proximal neurites and two distal neurites
were analyzed) action potentials. Two-way analysis of variance followed by post-hoc
Bonferroni corrected multiple comparisons test.

Number of families 1
Number of comparisons per family 4
Alpha 0.05

| Bonferroni's multiple comparisons test | Predicted (LS) mean diff. | 95.00% CI of diff. | Significant? | Summary | Adjusted P Value |
|---|---|---|---|---|---|
| GCaMP6f-S1-GCaMP6f | | | | | |
| 1 AP | −2.465 | −118.1 to 113.2 | No | ns | >.999 |
| 5 APs | −23.33 | −187.6 to 140.9 | No | ns | >.999 |
| 10 APs | −51.26 | −215.5 to 113.0 | No | ns | >.999 |
| 20 APs | −35.28 | −199.5 to 129.0 | No | ns | >.999 |

| Test details | Predicted (LS) mean 1 | Predicted (LS) mean 2 | Predicted (LS) mean diff. | SE of diff. | N1 | N2 | t | DF |
|---|---|---|---|---|---|---|---|---|
| GCaMP6f-S1-GCaMP6f | | | | | | | | |
| 1 AP | 4.109 | 6.574 | −2.465 | 44.53 | 11 | 11 | 0.05536 | 47.00 |
| 5 APs | 26.73 | 50.06 | −23.33 | 63.24 | 5 | 6 | 0.3688 | 47.00 |
| 10 APs | 80.85 | 132.1 | −51.26 | 63.24 | 5 | 6 | 0.8105 | 47.00 |
| 20 APs | 239.5 | 274.8 | −35.28 | 63.24 | 5 | 6 | 0.5579 | 47.00 |

At the proximal neurites:
Two-way ANOVA Ordinary
Alpha 0.05

| Source of Variation | % of total variation | P value | P value summary | Significant? |
|---|---|---|---|---|
| Interaction | 0.4886 | .829 | ns | No |
| AP number | 43.64 | <.001 | *** | Yes |
| Molecule | 0.05651 | .750 | ns | No |

| ANOVA table | SS (Type III) | DF | MS | F (DFn, DFd) | P value |
|---|---|---|---|---|---|
| Interaction | 30931 | 3 | 10310 | F (3, 102) = 0.2952 | P = .829 |
| AP number | 2763045 | 3 | 921015 | F (3, 102) = 26.37 | P < .001 |
| Molecule | 3578 | 1 | 3578 | F (1, 102) = 0.1024 | P = .750 |
| Residual | 3562545 | 102 | 34927 | | |

| | Difference between column means |
|---|---|
| Predicted (LS) mean of GCaMP6f | 184.1 |
| Predicted (LS) mean of S1-GCaMP6f | 172.2 |

TABLE 14-continued

Statistical analysis for FIG. 9C
Peak fluorescence changes in the GFP channel at the soma, proximal neurites, and distal
neurites of cultured mouse hippocampal neurons expressing GCaMP6f or S1-GCaMP6f
in response to a single (n = 11 values from soma, 22 values from proximal neurites, and
22 values from distal neurites from 11 total trials from 6 neurons from 3 cultures for each
of GCaMP6f and S1-GCaMP6f; for each trial, the calcium responses from the soma and
two proximal neurites and two distal neurites were analyzed) or multiple (5AP, 10AP, or
20AP; n = 5 values from soma, 10 values from proximal neurites, and 10 values from
distal neurites from 5 total trials from 5 neurons from 3 cultures for GCaMP6f;
n = 6 values from soma, 12 values from proximal neurites, and 12 values from distal
neurites from 6 total trials from 6 neurons from 3 cultures for S1-GCaMP6f; for each trial,
the calcium responses from the soma and two proximal neurites and two distal neurites
were analyzed) action potentials. Two-way analysis of variance followed by post-hoc
Bonferroni corrected multiple comparisons test.

| | | |
|---|---|---|
| | Difference between predicted means | 11.97 |
| | SE of difference | 37.40 |
| | 95% CI of difference | −62.22 to 86.16 |

Number of families 1
Number of comparisons per family 4
Alpha 0.05

| Bonferroni's multiple comparisons test | Predicted (LS) mean diff. | 95.00% CI of diff. | Significant? | Summary | Adjusted P Value |
|---|---|---|---|---|---|
| GCaMP6f-S1-GCaMP6f | | | | | |
| 1 AP | −2.962 | −146.2 to 140.3 | No | ns | >.999 |
| 5 APs | −16.26 | −219.7 to 187.2 | No | ns | >.999 |
| 10 APs | −8.503 | −212.0 to 195.0 | No | ns | >.999 |
| 20 APs | 75.61 | −127.9 to 279.1 | No | ns | >.999 |

| Test details | Predicted (LS) mean 1 | Predicted (LS) mean 2 | Predicted (LS) mean diff. | SE of diff. | N1 | N2 | t | DF |
|---|---|---|---|---|---|---|---|---|
| GCaMP6f-S1-GCaMP6f | | | | | | | | |
| 1 AP | 6.113 | 9.075 | −2.962 | 56.35 | 22 | 22 | 0.05256 | 102.0 |
| 5 APs | 64.54 | 80.81 | −16.26 | 80.02 | 10 | 12 | 0.2033 | 102.0 |
| 10 APs | 200.6 | 209.2 | −8.503 | 80.02 | 10 | 12 | 0.1063 | 102.0 |
| 20 APs | 465.2 | 389.6 | 75.61 | 80.02 | 10 | 12 | 0.9449 | 102.0 |

At the distal neurites:
Two-way ANOVA Ordinary
Alpha 0.05

| Source of Variation | % of total variation | P value | P value summary | Significant? |
|---|---|---|---|---|
| Interaction | 0.4329 | .847 | ns | No |
| AP number | 44.72 | <.001 | *** | Yes |
| Molecule | 0.3078 | .449 | ns | No |

| ANOVA table | SS (Type III) | DF | MS | F (DFn, DFd) | P value |
|---|---|---|---|---|---|
| Interaction | 20545 | 3 | 6848 | F (3, 102) = 0.2704 | P = .847 |
| AP number | 2122396 | 3 | 707465 | F (3, 102) = 27.94 | P < .001 |
| Molecule | 14609 | 1 | 14609 | F (1, 102) = 0.5769 | P = .449 |
| Residual | 2582979 | 102 | 25323 | | |

TABLE 14-continued

Statistical analysis for FIG. 9C
Peak fluorescence changes in the GFP channel at the soma, proximal neurites, and distal
neurites of cultured mouse hippocampal neurons expressing GCaMP6f or S1-GCaMP6f
in response to a single (n = 11 values from soma, 22 values from proximal neurites, and
22 values from distal neurites from 11 total trials from 6 neurons from 3 cultures for each
of GCaMP6f and S1-GCaMP6f; for each trial, the calcium responses from the soma and
two proximal neurites and two distal neurites were analyzed) or multiple (5AP, 10AP, or
20AP; n = 5 values from soma, 10 values from proximal neurites, and 10 values from
distal neurites from 5 total trials from 5 neurons from 3 cultures for GCaMP6f;
n = 6 values from soma, 12 values from proximal neurites, and 12 values from distal
neurites from 6 total trials from 6 neurons from 3 cultures for S1-GCaMP6f; for each trial,
the calcium responses from the soma and two proximal neurites and two distal neurites
were analyzed) action potentials. Two-way analysis of variance followed by post-hoc
Bonferroni corrected multiple comparisons test.

|  | Difference between column means |
|---|---|
| Predicted (LS) mean of GCaMP6f | 133.4 |
| Predicted (LS) mean of S1-GCaMP6f | 157.6 |
| Difference between predicted means | −24.19 |
| SE of difference | 31.85 |
| 95% CI of difference | −87.36 to 38.98 |

Number of families 1
Number of comparisons per family 4
Alpha 0.05

| Bonferroni's multiple comparisons test | Predicted (LS) mean diff. | 95.00% CI of diff. | Significant? | Summary | Adjusted P Value |
|---|---|---|---|---|---|
| GCaMP6f-S1-GCaMP6f | | | | | |
| 1 AP | −3.982 | −126.0 to 118.0 | No | ns | >.999 |
| 5 APs | −34.16 | −207.4 to 139.1 | No | ns | >.999 |
| 10 APs | −67.22 | −240.5 to 106.0 | No | ns | >.999 |
| 20 APs | 8.607 | −164.6 to 181.9 | No | ns | >.999 |

| Test details | Predicted (LS) mean 1 | Predicted (LS) mean 2 | Predicted (LS) mean diff. | SE of diff. | N1 | N2 | t | DF |
|---|---|---|---|---|---|---|---|---|
| GCaMP6f-S1-GCaMP6f | | | | | | | | |
| 1 AP | 3.720 | 7.702 | −3.982 | 47.98 | 22 | 22 | 0.08299 | 102.0 |
| 5 APs | 30.28 | 64.44 | −34.16 | 68.14 | 10 | 12 | 0.5014 | 102.0 |
| 10 APs | 121.4 | 188.6 | −67.22 | 68.14 | 10 | 12 | 0.9866 | 102.0 |
| 20 APs | 378.2 | 369.6 | 8.607 | 68.14 | 10 | 12 | 0.1263 | 102.0 |

TABLE 15

Statistical analysis for FIG. 9D
Signal-to-noise in the GFP channel at the soma, proximal neurites, and distal neurites of cultured mouse hippocampal neurons expressing GCaMP6f or S1-GCaMP6f in response to a single (n = 11 values from soma, 22 values from proximal neurites, and 22 values from distal neurites from 11 total trials from 6 neurons from 3 cultures for each of GCaMP6f and S1-GCaMP6f; for each trial, the calcium responses from the soma and two proximal neurites and two distal neurites were analyzed) or multiple (5AP, 10AP, or 20AP; n = 5 values from soma, 10 values from proximal neurites, and 10 values from distal neurites from 5 total trials from 5 neurons from 3 cultures for GCaMP6f; n = 6 values from soma, 12 values from proximal neurites, and 12 values from distal neurites from 6 total trials from 6 neurons from 3 cultures for S1-GCaMP6f; for each trial, the calcium responses from the soma and two proximal neurites and two distal neurites were analyzed) action potentials. Two-way analysis of variance followed by post-hoc Bonferroni corrected multiple comparisons test.

At the soma:
Two-way ANOVA Ordinary
Alpha 0.05

| Source of Variation | % of total variation | P value | P value summary | Significant? |
|---|---|---|---|---|
| Interaction | 1.708 | .593 | ns | No |
| AP number | 57.28 | <.001 | *** | Yes |
| Molecule | 0.8561 | .332 | ns | No |

| ANOVA table | SS (Type III) | DF | MS | F (DFn, DFd) | P value |
|---|---|---|---|---|---|
| Interaction | 17403 | 3 | 5801 | F (3, 47) = 0.6401 | P = .593 |
| AP number | 583612 | 3 | 194537 | F (3, 47) = 21.46 | P < .001 |
| Molecule | 8723 | 1 | 8723 | F (1, 47) = 0.9625 | P = .332 |
| Residual | 425968 | 47 | 9063 | | |

| | Difference between column means | |
|---|---|---|
| | Predicted (LS) mean of GCaMP6f | 121.2 |
| | Predicted (LS) mean of S1-GCaMP6f | 94.78 |
| | Difference between predicted means | 26.44 |
| | SE of difference | 26.95 |
| | 95% CI of difference | −27.77 to 80.64 |

Number of families 1
Number of comparisons per family 4
Alpha 0.05

| Bonferroni's multiple comparisons test | Predicted (LS) mean diff. | 95.00% CI of diff. | Significant? | Summary | Adjusted P Value |
|---|---|---|---|---|---|
| GCaMP6f-S1-GCaMP6f | | | | | |
| 1 AP | −0.3286 | −105.8 to 105.1 | No | ns | >.999 |
| 5 APs | 1.815 | −147.9 to 151.6 | No | ns | >.999 |
| 10 APs | 12.39 | −137.3 to 162.1 | No | ns | >.999 |
| 20 APs | 91.86 | −57.87 to 241.6 | No | ns | .471 |

TABLE 15-continued

Statistical analysis for FIG. 9D
Signal-to-noise in the GFP channel at the soma, proximal neurites, and distal neurites of cultured mouse hippocampal neurons expressing GCaMP6f or S1-GCaMP6f in response to a single (n = 11 values from soma, 22 values from proximal neurites, and 22 values from distal neurites from 11 total trials from 6 neurons from 3 cultures for each of GCaMP6f and S1-GCaMP6f; for each trial, the calcium responses from the soma and two proximal neurites and two distal neurites were analyzed) or multiple (5AP, 10AP, or 20AP; n = 5 values from soma, 10 values from proximal neurites, and 10 values from distal neurites from 5 total trials from 5 neurons from 3 cultures for GCaMP6f; n = 6 values from soma, 12 values from proximal neurites, and 12 values from distal neurites from 6 total trials from 6 neurons from 3 cultures for S1-GCaMP6f; for each trial, the calcium responses from the soma and two proximal neurites and two distal neurites were analyzed) action potentials. Two-way analysis of variance followed by post-hoc Bonferroni corrected multiple comparisons test.

| Test details | Predicted (LS) mean 1 | Predicted (LS) mean 2 | Predicted (LS) mean diff. | SE of diff. | N1 | N2 | t | DF |
|---|---|---|---|---|---|---|---|---|
| GCaMP6f-S1-GCaMP6f | | | | | | | | |
| 1 AP | 7.527 | 7.855 | −0.3286 | 40.59 | 11 | 11 | 0.008094 | 47.00 |
| 5 APs | 37.80 | 35.98 | 1.815 | 57.65 | 5 | 6 | 0.03149 | 47.00 |
| 10 APs | 111.8 | 99.40 | 12.39 | 57.65 | 5 | 6 | 0.2150 | 47.00 |
| 20 APs | 327.8 | 235.9 | 91.86 | 63.24 | 5 | 6 | 0.5579 | 47.00 |

At the proximal neurites:
Two-way ANOVA Ordinary
Alpha 0.05

| Source of Variation | % of total variation | P value | P value summary | Significant? |
|---|---|---|---|---|
| Interaction | 0.4543 | .676 | ns | No |
| AP number | 67.38 | <.001 | *** | Yes |
| Molecule | 0.8342 | .096 | ns | No |

| ANOVA table | SS (Type III) | DF | MS | F (DFn, DFd) | P value |
|---|---|---|---|---|---|
| Interaction | 3167 | 3 | 1056 | F (3, 102) = 0.5109 | P = .676 |
| AP number | 469804 | 3 | 156601 | F (3, 102) = 75.78 | P < .001 |
| Molecule | 5817 | 1 | 5817 | F (1, 102) = 2.815 | P = .096 |
| Residual | 210774 | 102 | 2066 | | |

| Difference between column means | |
|---|---|
| Predicted (LS) mean of GCaMP6f | 61.33 |
| Predicted (LS) mean of S1-GCaMP6f | 76.60 |
| Difference between predicted means | −15.26 |
| SE of difference | 9.098 |
| 95% CI of difference | −33.31 to 2.782 |

TABLE 15-continued

Statistical analysis for FIG. 9D
Signal-to-noise in the GFP channel at the soma, proximal neurites, and distal neurites of cultured mouse hippocampal neurons expressing GCaMP6f or S1-GCaMP6f in response to a single (n = 11 values from soma, 22 values from proximal neurites, and 22 values from distal neurites from 11 total trials from 6 neurons from 3 cultures for each of GCaMP6f and S1-GCaMP6f; for each trial, the calcium responses from the soma and two proximal neurites and two distal neurites were analyzed) or multiple (5AP, 10AP, or 20AP; n = 5 values from soma, 10 values from proximal neurites, and 10 values from distal neurites from 5 total trials from 5 neurons from 3 cultures for GCaMP6f; n = 6 values from soma, 12 values from proximal neurites, and 12 values from distal neurites from 6 total trials from 6 neurons from 3 cultures for S1-GCaMP6f; for each trial, the calcium responses from the soma and two proximal neurites and two distal neurites were analyzed) action potentials. Two-way analysis of variance followed by post-hoc Bonferroni corrected multiple comparisons test.

Number of families 1
Number of comparisons per family 4
Alpha 0.05

| Bonferroni's multiple comparisons test | Predicted (LS) mean diff. | 95.00% CI of diff. | Significant? | Summary | Adjusted P Value |
|---|---|---|---|---|---|
| GCaMP6f-S1-GCaMP6f | | | | | |
| 1 AP | −1.071 | −35.92 to 33.78 | No | ns | >.999 |
| 5 APs | −10.08 | −59.57 to 39.41 | No | ns | >.999 |
| 10 APs | −24.15 | −73.64 to 195.0 | No | ns | .870 |
| 20 APs | −25.76 | −75.25 to 23.74 | No | ns | .755 |

| Test details | Predicted (LS) mean 1 | Predicted (LS) mean 2 | Predicted (LS) mean diff. | SE of diff. | N1 | N2 | t | DF |
|---|---|---|---|---|---|---|---|---|
| GCaMP6f-S1-GCaMP6f | | | | | | | | |
| 1 AP | 2.839 | 3.909 | −1.071 | 13.71 | 22 | 22 | 0.07812 | 102.0 |
| 5 APs | 18.57 | 28.65 | −10.08 | 19.46 | 10 | 12 | 0.5179 | 102.0 |
| 10 APs | 59.77 | 83.92 | −24.15 | 19.46 | 10 | 12 | 1.241 | 102.0 |
| 20 APs | 164.1 | 189.9 | −25.76 | 19.46 | 10 | 12 | 1.323 | 102.0 |

At the distal neurites:
Two-way ANOVA Ordinary
Alpha 0.05

| Source of Variation | % of total variation | P value | P value summary | Significant? |
|---|---|---|---|---|
| Interaction | 1.741 | .290 | ns | No |
| AP number | 47.02 | <.001 | *** | Yes |
| Molecule | 3.579 | .006 | ** | Yes |

| ANOVA table | SS (Type III) | DF | MS | F (DFn, DFd) | P value |
|---|---|---|---|---|---|
| Interaction | 2580 | 3 | 860.0 | F (3, 102) = 1.265 | P = .290 |
| AP number | 69669 | 3 | 23223 | F (3, 102) = 34.16 | P < .001 |
| Molecule | 5303 | 1 | 5303 | F (1, 102) = 7.800 | P = .006 |
| Residual | 69350 | 102 | 679.9 | | |

| Difference between column means | |
|---|---|
| Predicted (LS) mean of GCaMP6f | 20.06 |
| Predicted (LS) mean of S1-GCaMP6f | 34.63 |

TABLE 15-continued

Statistical analysis for FIG. 9D
Signal-to-noise in the GFP channel at the soma, proximal neurites, and distal neurites of cultured mouse hippocampal neurons expressing GCaMP6f or S1-GCaMP6f in response to a single (n = 11 values from soma, 22 values from proximal neurites, and 22 values from distal neurites from 11 total trials from 6 neurons from 3 cultures for each of GCaMP6f and S1-GCaMP6f; for each trial, the calcium responses from the soma and two proximal neurites and two distal neurites were analyzed) or multiple (5AP, 10AP, or 20AP; n = 5 values from soma, 10 values from proximal neurites, and 10 values from distal neurites from 5 total trials from 5 neurons from 3 cultures for GCaMP6f; n = 6 values from soma, 12 values from proximal neurites, and 12 values from distal neurites from 6 total trials from 6 neurons from 3 cultures for S1-GCaMP6f; for each trial, the calcium responses from the soma and two proximal neurites and two distal neurites were analyzed) action potentials. Two-way analysis of variance followed by post-hoc Bonferroni corrected multiple comparisons test.

| | | |
|---|---|---|
| Difference between predicted means | −14.57 | |
| SE of difference | 5.219 | |
| 95% CI of difference | −24.93 to 4.223 | |

Number of families 1
Number of comparisons per family 4
Alpha 0.05

| Bonferroni's multiple comparisons test | Predicted (LS) mean diff. | 95.00% CI of diff. | Significant? | Summary | Adjusted P Value |
|---|---|---|---|---|---|
| GCaMP6f-S1-GCaMP6f | | | | | |
| 1 AP | −1.525 | −21.52 to 18.47 | No | ns | >.999 |
| 5 APs | −10.45 | −38.83 to 17.94 | No | ns | >.999 |
| 10 APs | −23.28 | −51.67 to 5.111 | No | ns | .158 |
| 20 APs | −23.05 | −51.44 to 5.339 | No | ns | .166 |

| Test details | Predicted (LS) mean 1 | Predicted (LS) mean 2 | Predicted (LS) mean diff. | SE of diff. | N1 | N2 | t | DF |
|---|---|---|---|---|---|---|---|---|
| GCaMP6f-S1-GCaMP6f | | | | | | | | |
| 1 AP | 0.9025 | 2.427 | −1.525 | 7.862 | 22 | 22 | 0.1939 | 102.0 |
| 5 APs | 4.582 | 15.03 | −10.45 | 11.16 | 10 | 12 | 0.9356 | 102.0 |
| 10 APs | 17.86 | 41.14 | −23.28 | 11.16 | 10 | 12 | 2.085 | 102.0 |
| 20 APs | 56.89 | 79.94 | −23.05 | 11.16 | 10 | 12 | 2.065 | 102.0 |

TABLE 16

Statistical analysis for FIG. 9M
Half rise time versus somatic punctum size for the recorded somatic calcium transients in response to a single action potential in S1-GCaMP6f expressing neurons (n = 6 neurons from 3 cultures). Kruskal-Wallis analysis of variance followed by post-hoc test via Dunn's test with '<1 μm' as control group.

| Kruskal-Wallis test | |
|---|---|
| P value | 0.9835 |
| Exact or approximate P value? | Approximate |
| P value summary | ns |
| Do the medians vary signif. (P < 0.05)? | No |
| Number of groups | 3 |
| Kruskal-Wallis statistic | 0.03328 |

TABLE 16-continued

Statistical analysis for FIG. 9M Half rise time versus somatic punctum size for the recorded somatic calcium transients in response to a single action potential in S1-GCaMP6f expressing neurons (n = 6 neurons from 3 cultures). Kruskal-Wallis analysis of variance followed by post-hoc test via Dunn's test with '<1 µm' as control group.

| Dunn's multiple comparisons test | Mean rank diff. | Significant? | Summary | Adjusted P Value |
|---|---|---|---|---|
| <1 µm vs. 1-2 µm | 0.3681 | No | ns | >0.9999 |
| <1 µm vs. >2 µm | −0.2778 | No | ns | >0.9999 |

TABLE 17

Statistical analysis for FIG. 9N Half decay time versus somatic punctum size for the recorded somatic calcium transient: in response to a single action potential in S1-GCaMP6f expressing neurons (n = 6 neurons from 3 cultures). Kruskal-Wallis analysis of variance followed by post-hoc test via Dunn's test with '<1 µm' as control group.

| Kruskal-Wallis test | |
|---|---|
| P value | 0.5999 |
| Exact or approximate P value? | Approximate |
| P value summary | ns |
| Do the medians vary signif. (P < 0.05)? | No |
| Number of groups | 3 |
| Kruskal-Wallis statistic | 1.022 |

| Dunn's multiple comparisons test | Mean rank diff. | Significant? | Summary | Adjusted P Value |
|---|---|---|---|---|
| <1 µm vs. 1-2 µm | 2.771 | No | ns | 0.8003 |
| <1 µm vs. >2 µm | −0.5000 | No | ns | >0.9999 |

TABLE 18

Statistical analysis for FIG. 9O Peak fluorescence changes versus somatic punctum size for the recorded somatic calcium transients in response to a single action potential in S1-GCaMP6f expressing neurons (n = 6 neurons from 3 cultures). Kruskal-Wallis analysis of variance followed by post-hoc test via Dunn's test with '<1 µm' as control group.

| Kruskal-Wallis test | |
|---|---|
| P value | 0.5082 |
| Exact or approximate P value? | Approximate |
| P value summary | ns |
| Do the medians vary signif. (P < 0.05)? | No |
| Number of groups | 3 |
| Kruskal-Wallis statistic | 1.354 |

TABLE 18-continued

Statistical analysis for FIG. 9O Peak fluorescence changes versus somatic punctum size for the recorded somatic calcium transients in response to a single action potential in S1-GCaMP6f expressing neurons (n = 6 neurons from 3 cultures). Kruskal-Wallis analysis of variance followed by post-hoc test via Dunn's test with '<1 µm' as control group.

| Dunn's multiple comparisons test | Mean rank diff. | Significant? | Summary | Adjusted P Value |
|---|---|---|---|---|
| <1 µm vs. 1-2 µm | 2.389 | No | ns | 0.9371 |
| <1 µm vs. >2 µm | 4.056 | No | ns | 0.5131 |

TABLE 19

Statistical analysis for FIG. 9P Punctum brightness versus somatic punctum size for the recorded somatic calcium transients in response to a single action potential in S1-GCaMP6f expressing neurons (n = 6 neurons from 3 cultures). Kruskal-Wallis analysis of variance followed by post-hoc test via Dunn's test with '<1 µm' as control group.

| Kruskal-Wallis test | |
|---|---|
| P value | 0.2427 |
| Exact or approximate P value? | Approximate |
| P value summary | ns |
| Do the medians vary signif. (P < 0.05)? | No |
| Number of groups | 3 |
| Kruskal-Wallis statistic | 2.832 |

| Dunn's multiple comparisons test | Mean rank diff. | Significant? | Summary | Adjusted P Value |
|---|---|---|---|---|
| <1 µm vs. 1-2 µm | −4.139 | No | ns | 0.4183 |
| <1 µm vs. >2 µm | −5.556 | No | ns | 0.2403 |

TABLE 20

Statistical analysis for FIG. 9Q Wilcoxon rank sum test for the number of somatic calcium peaks in response to a single action potential for GCaMP6f and S1-GCaMP6f expressing neurons (n = 11 total trials from 6 neurons from 3 cultures for each of GCaMP6f and S1-GCaMP6f).

| | |
|---|---|
| P value | 1 |
| ranksum | 60.50 |

TABLE 21

Figure 9S:
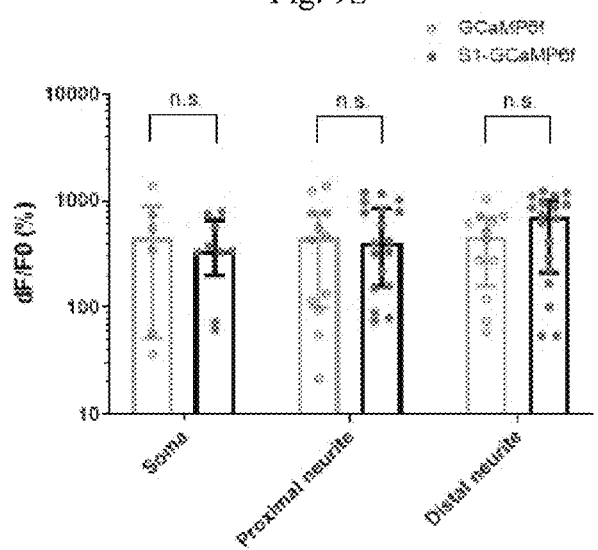

Statistical analysis for FIG. 9S
Peak fluorescence changes in the GFP channel at the soma, proximal neurites, and distal neurites of cultured mouse hippocampal neurons expressing GCaMP6f or S1-GCaMP6f under 5 μM forskolin stimulation (n = 6 somata, 12 proximal neurites, and 12 distal neurites from 6 neurons from 4 cultures for GCaMP6f; n = 9 somata, 18 proximal neurites, and 18 distal neurites from 9 neurons from 9 cultures for S1-GCaMP6f). Two-way analysis of variance followed by post-hoc Bonferroni corrected multiple comparisons test.

Two-way ANOVA Ordinary
Alpha 0.05

| Source of Variation | % of total variation | P value | P value summary | Significant? |
|---|---|---|---|---|
| Interaction | 2.126 | .469 | ns | No |
| Subcellular location | 0.6935 | .780 | ns | No |
| Molecule | 0.1744 | .724 | ns | No |

| ANOVA table | SS (Type III) | DF | MS | F (DFn, DFd) | P value |
|---|---|---|---|---|---|
| Interaction | 238598 | 2 | 119299 | $F_{(2, 69)} = 0.7649$ | $P = .469$ |
| Subcellular location | 77840 | 2 | 38920 | $F_{(2, 69)} = 0.2495$ | $P = .780$ |
| Molecule | 19569 | 1 | 19569 | $F_{(1, 69)} = 0.1255$ | $P = .724$ |
| Residual | 10761802 | 69 | 155968 | | |

| Difference between column means | |
|---|---|
| Predicted (LS) mean of GCaMP6f | 495.0 |
| Predicted (LS) mean of S1-GCaMP6f | 529.7 |
| Difference between predicted means | −34.76 |
| SE of difference | 98.12 |
| 95% CI of difference | −230.5 to 161.0 |

Number of families 1
Number of comparisons per family 3
Alpha 0.05

| Bonferroni's multiple comparisons test | Predicted (LS) mean diff. | 95.00% CI of diff. | Significant? | Summary | Adjusted P Value |
|---|---|---|---|---|---|
| GCaMP6f-S1-GCaMP6f | | | | | |
| Soma | 117.3 | −393.4 to 628.0 | No | ns | >.999 |
| Proximal neurite | −32.28 | −393.4 to 328.9 | No | ns | >.999 |
| Distal neurite | −189.3 | −550.4 to 171.8 | No | ns | .608 |

| Test details | Predicted (LS) mean 1 | Predicted (LS) mean 2 | Predicted (LS) mean diff. | SE of diff. | N1 | N2 | t | DF |
|---|---|---|---|---|---|---|---|---|
| GCaMP6f-S1-GCaMP6f | | | | | | | | |
| Soma | 522.3 | 405.0 | 117.3 | 208.1 | 6 | 9 | 0.5636 | 69.00 |
| Proximal neurite | 503.6 | 535.9 | −32.28 | 147.2 | 12 | 18 | 0.2193 | 69.00 |
| Distal neurite | 458.9 | 648.2 | −189.3 | 147.2 | 12 | 18 | 1.286 | 69.00 |

TABLE 22R

Figure 9T:
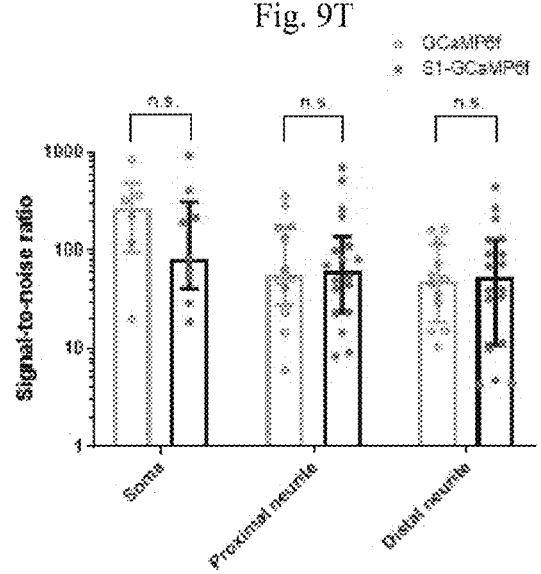
(FIG. 9T) Bar plot of the signal-to-noise ratio in the GFP channel at the soma, proximal neurites, and distal neurites for the neurons of FIG. 9S.

Statistical analysis for FIG. 9T
Signal-to-noise ratio in the GFP channel at the soma, proximal neurites, and distal neurites of cultured
mouse hippocampal neurons expressing GCaMP6f or S1-GCaMP6f under 5 μM forskolin stimulation
(n = 6 somata, 12 proximal neurites, and 12 distal neurites from 6 neurons from 4 cultures for
GCaMP6f; n = 9 somata, 18 proximal neurites, and 18 distal neurites neurons from 9 neurons
from 9 cultures for S1-GCaMP6f). Two-way analysis of variance followed by post-hoc Bonferroni
corrected multiple comparisons test.

Two-way ANOVA Ordinary
Alpha 0.05

| Source of Variation | % of total variation | P value | P value summary | Significant? |
|---|---|---|---|---|
| Interaction | 1.643 | .518 | ns | No |
| Subcellular location | 14.28 | .005 | ** | Yes |
| Molecule | 0.1566 | .723 | ns | No |

| ANOVA table | SS (Type III) | DF | MS | F (DFn, DFd) | P value |
|---|---|---|---|---|---|
| Interaction | 40270 | 2 | 20135 | F (2, 69) = 0.6636 | P = .518 |
| Subcellular location | 350060 | 2 | 175030 | F (2, 69) = 5.769 | P = .005 |
| Molecule | 3839 | 1 | 3839 | F (1, 69) = 0.1265 | P = .723 |
| Residual | 2093606 | 69 | 30342 | | |

Difference between column means

| | |
|---|---|
| Predicted (LS) mean of GCaMP6f | 165.3 |
| Predicted (LS) mean of S1-GCaMP6f | 149.9 |
| Difference between predicted means | 15.39 |
| SE of difference | 43.28 |
| 95% CI of difference | −70.94 to 101.7 |

Number of families 1
Number of comparisons per family 3
Alpha 0.05

| Sidak's multiple comparisons test | Predicted (LS) mean diff. | 95.00% CI of diff. | Significant? | Summary | Adjusted P Value |
|---|---|---|---|---|---|
| GCaMP6f-S1-GCaMP6f | | | | | |
| Soma | 93.94 | −130.7 to 628.0 | No | ns | .671 |
| Proximal neurite | −19.35 | −178.2 to 139.5 | No | ns | .987 |
| Distal neurite | −28.40 | −187.3 to 130.5 | No | ns | .962 |

| Test details | Predicted (LS) mean 1 | Predicted (LS) mean 2 | Predicted (LS) mean diff. | SE of diff. | N1 | N2 | t | DF |
|---|---|---|---|---|---|---|---|---|
| GCaMP6f-S1-GCaMP6f | | | | | | | | |
| Soma | 316.0 | 222.1 | 93.94 | 91.81 | 6 | 9 | 1.023 | 69.00 |
| Proximal neurite | 114.4 | 133.8 | −19.35 | 64.92 | 12 | 18 | 0.2981 | 69.00 |
| Distal neurite | 65.53 | 93.94 | −28.40 | 64.92 | 12 | 18 | 0.4376 | 69.00 |

TABLE 23

Figure 9U:
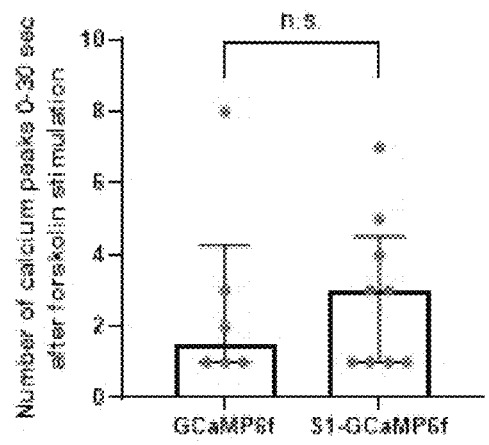
(FIG. 9U) Bar plot of the number of somatic calcium peaks 0-30 seconds after forskolin stimulation for the neurons of FIG. 9S.
Figure 9V:
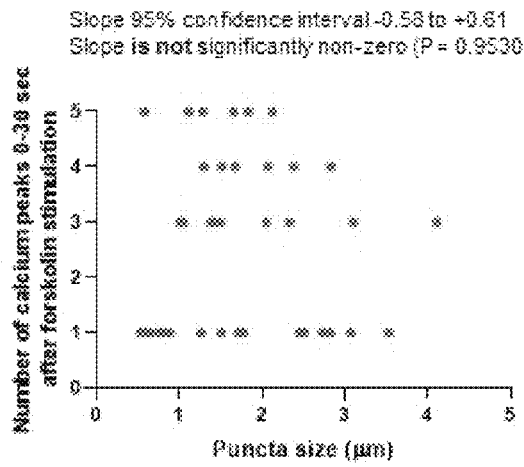
(FIG. 9V) Scatter plot of the number of S1-GCaMP6f reported somatic calcium spikes 0-30 seconds after forskolin stimulation versus somatic punctum size in S1-GCaMP6f expressing neurons (n=5 neurons from 5 cultures).

Statistical analysis for FIG. 9U
Wilcoxon rank sum test of the number
of somatic calcium spikes 0-30
seconds after forskolin stimulation
(n = 6 neurons from 4 cultures
for GCaMP6f; n = 9 neurons
from 9 cultures for S1-GCaMP6f).

| | |
|---|---|
| P value | 0.7832 |
| ranksum | 45 |

TABLE 24

Figure 9W:
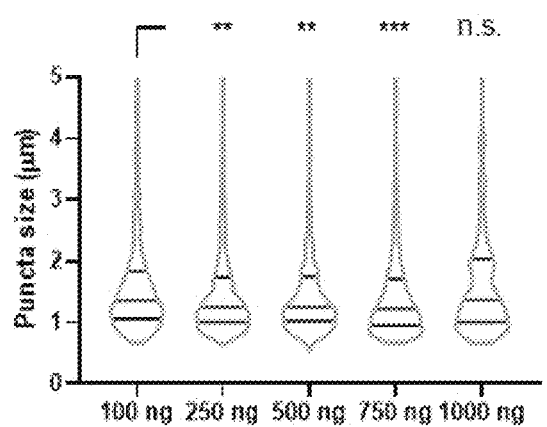

Statistical analysis for Figure 9W
Kruskal-Wallis analysis of variance of the puncta size followed by post-hoc test via
Dunn's test with '100 ng' as control group (n = 792, 1314, 1230, 881, and 283 puncta in 9, 11,
11, 10, and 4 neurons from 1, 1, 1, 1, and 1 culture for 100 ng, 250 ng, 500 ng, 750 ng, and 1000 ng, respectively).

| Kruskal-Wallis test | |
|---|---|
| P value | <0.0001 |
| Exact or approximate P value? | Approximate |
| P value summary | **** |
| Do the medians vary signif. (P < 0.05)? | Yes |
| Number of groups | 5 |
| Kruskal-Wallis statistic | 31.10 |
| Data summary | |
| Number of treatments (columns) | 5 |
| Number of values (total) | 4500 |
| Number of families | 1 |
| Number of comparisons per family | 4 |
| Alpha | 0.05 |

| Dunn's multiple comparisons test | Mean rank diff. | Significant? | Summary | Adjusted P Value | A-? | |
|---|---|---|---|---|---|---|
| 100 ng vs. 250 ng | 191.2 | Yes | ** | 0.0043 | B | 250 ng |
| 100 ng vs. 500 ng | 194.9 | Yes | ** | 0.0040 | C | 500 ng |
| 100 ng vs. 750 ng | 317.0 | Yes | *** | <0.0001 | D | 750 ng |
| 100 ng vs. 1000 ng | -10.46 | No | ns | >0.9999 | E | 1000 ng |

| Test details | Mean rank 1 | Mean rank 2 | Mean rank diff. | n1 | n2 | Z |
|---|---|---|---|---|---|---|
| 100 ng vs. 250 ng | 2421 | 2230 | 191.2 | 792 | 1314 | 3.272 |
| 100 ng vs. 500 ng | 2421 | 2226 | 194.9 | 792 | 1230 | 3.293 |
| 100 ng vs. 750 ng | 2421 | 2104 | 317.0 | 792 | 881 | 4.983 |
| 100 ng vs. 1000 ng | 2421 | 2431 | -10.46 | 792 | 283 | 0.1162 |

TABLE 25

Figure 9X:
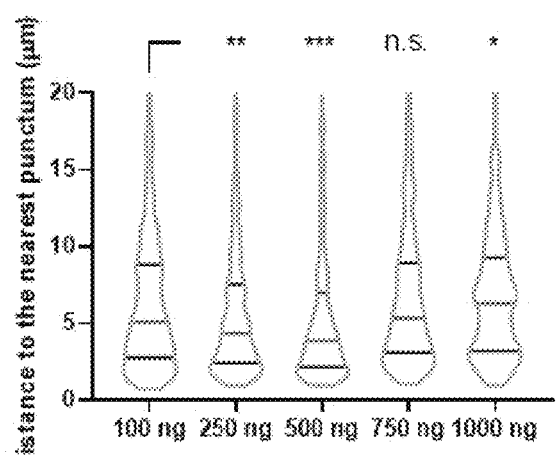

Statistical analysis for Figure 9X
Kruskal-Wallis analysis of variance of the distance to the nearest punctum followed by
post-hoc test via Dunn's test with '100 ng' as control group (n = 792, 1314, 1230, 881, and 283
puncta in 9, 11, 11, 10, and 4 neurons from 1, 1, 1, 1, and 1 culture for 100 ng, 250 ng, 500 ng,
750 ng, and 1000 ng, respectively).

| Kruskal-Wallis test | |
|---|---|
| P value | <0.0001 |
| Exact or approximate P value? | Approximate |
| P value summary | **** |
| Do the medians vary signif. (P < 0.05)? | Yes |
| Number of groups | 5 |
| Kruskal-Wallis statistic | 94.72 |
| Data summary | |
| Number of treatments (columns) | 5 |
| Number of values (total) | 4164 |
| Number of families | 1 |
| Number of comparisons per family | 4 |
| Alpha | 0.05 |

TABLE 25-continued

Statistical analysis for Figure 9X
Kruskal-Wallis analysis of variance of the distance to the nearest punctum followed by
post-hoc test via Dunn's test with '100 ng' as control group (n = 792, 1314, 1230, 881, and 283
puncta in 9, 11, 11, 10, and 4 neurons from 1, 1, 1, 1, and 1 culture for 100 ng, 250 ng, 500 ng,
750 ng, and 1000 ng, respectively).

| Dunn's multiple comparisons test | Mean rank diff. | Significant? | Summary | Adjusted P Value | A-? | |
|---|---|---|---|---|---|---|
| 100 ng vs. 250 ng | 193.2 | Yes | ** | 0.0024 | B | 250 ng |
| 100 ng vs. 500 ng | 324.7 | Yes | *** | <0.0001 | C | 500 ng |
| 100 ng vs. 750 ng | −107.6 | No | ns | 0.3137 | D | 750 ng |
| 100 ng vs. 1000 ng | −218.4 | Yes | * | 0.0441 | E | 1000 ng |

| Test details | Mean rank 1 | Mean rank 2 | Mean rank diff. | n1 | n2 | Z |
|---|---|---|---|---|---|---|
| 100 ng vs. 250 ng | 2191 | 1998 | 193.2 | 727 | 1224 | 3.433 |
| 100 ng vs. 500 ng | 2191 | 1867 | 324.7 | 727 | 1120 | 5.672 |
| 100 ng vs. 750 ng | 2191 | 2299 | −107.6 | 727 | 825 | 1.760 |
| 100 ng vs. 1000 ng | 2191 | 2410 | −218.4 | 727 | 268 | 2.542 |

TABLE 26

Figure 9Y:
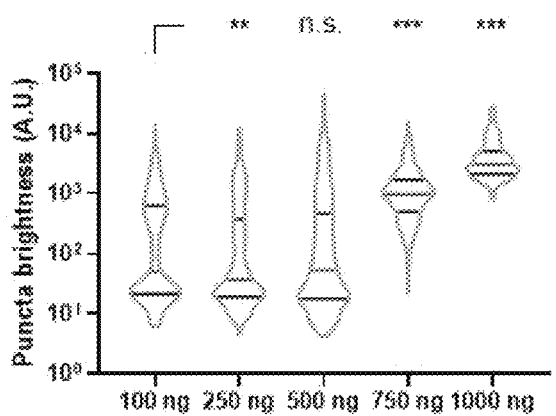

Statistical analysis for Figure 9Y
Kruskal-Wallis analysis of variance of the puncta brightness followed by post-hoc test via
Dunn's test with '100 ng' as control group (n = 792, 1314, 1230, 881, and 283 puncta in 9, 11,
11, 10, and 4 neurons from 1, 1, 1, 1, and 1 culture for 100 ng, 250 ng, 500 ng, 750 ng, and 1000
ng, respectively).

| Kruskal-Wallis test | |
|---|---|
| P value | <0.0001 |
| Exact or approximate P value? | Approximate |
| P value summary | **** |
| Do the medians vary signif. (P < 0.05)? | Yes |
| Number of groups | 5 |
| Kruskal-Wallis statistic | 1370 |
| Data summary | |
| Number of treatments (columns) | 5 |
| Number of values (total) | 4500 |
| Number of families | 1 |
| Number of comparisons per family | 4 |
| Alpha | 0.05 |

| Dunn's multiple comparisons test | Mean rank diff | Significant? | Summary | Adjusted P Value | A-? | |
|---|---|---|---|---|---|---|
| 100 ng vs. 250 ng | 182.3 | Yes | ** | 0.0072 | B | 250 ng |
| 100 ng vs. 500 ng | 97.19 | No | ns | 0.4023 | C | 500 ng |
| 100 ng vs. 750 ng | −1261 | Yes | *** | <0.0001 | D | 750 ng |
| 100 ng vs. 1000 ng | −2112 | Yes | *** | <0.0001 | E | 1000 ng |

| Test details | Mean rank 1 | Mean rank 2 | Mean rank diff. | n1 | n2 | Z |
|---|---|---|---|---|---|---|
| 100 ng vs. 250 ng | 1951 | 1768 | 182.3 | 792 | 1314 | 3.120 |
| 100 ng vs. 500 ng | 1951 | 1854 | 97.19 | 792 | 1230 | 1.642 |
| 100 ng vs. 750 ng | 1951 | 3211 | −1261 | 792 | 881 | 19.82 |
| 100 ng vs. 1000 ng | 1951 | 4062 | −2112 | 792 | 283 | 23.47 |

TABLE 27

Figure 9Z:
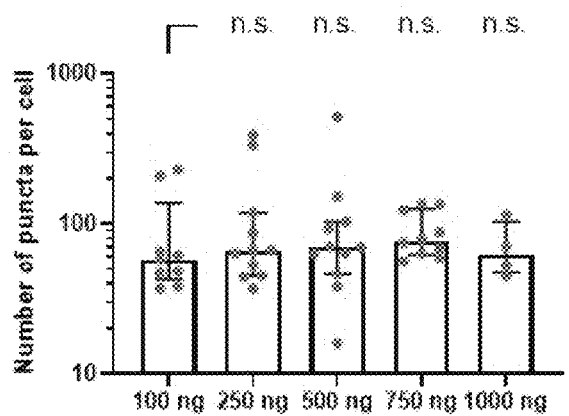

Statistical analysis for Figure 9Z
Kruskal-Wallis analysis of variance of the number of puncta per cell followed by post-
hoc test via Dunn's test with '100 ng' as control group (n = 9, 11, 11, 10, and 4 neurons from 1,
1, 1, 1, and 1 culture for 100 ng, 250 ng, 500 ng, 750 ng, and 1000 ng, respectively).

| Kruskal-Wallis test | |
|---|---|
| P value | 0.6170 |
| Exact or approximate P value? | Approximate |

TABLE 27-continued

Statistical analysis for Figure 9Z
Kruskal-Wallis analysis of variance of the number of puncta per cell followed by post-
hoc test via Dunn's test with '100 ng' as control group (n = 9, 11, 11, 10, and 4 neurons from 1,
1, 1, 1, and 1 culture for 100 ng, 250 ng, 500 ng, 750 ng, and 1000 ng, respectively).

| | |
|---|---|
| P value summary | ns |
| Do the medians vary signif. (P < 0.05)? | No |
| Number of groups | 5 |
| Kruskal-Wallis statistic | 2.656 |
| Data summary | |
| Number of treatments (columns) | 5 |
| Number of values (total) | 45 |
| Number of families | 1 |
| Number of comparisons per family | 4 |
| Alpha | 0.05 |

| Dunn's multiple comparisons test | Mean rank diff. | Significant? | Summary | Adjusted P Value | A-? | |
|---|---|---|---|---|---|---|
| 100 ng vs. 250 ng | −4.394 | No | ns | >0.9999 | B | 250 ng |
| 100 ng vs. 500 ng | −5.212 | No | ns | >0.9999 | C | 500 ng |
| 100 ng vs. 750 ng | −9.517 | No | ns | 0.4588 | D | 750 ng |
| 100 ng vs. 1000 ng | −2.292 | No | ns | >0.9999 | E | 1000 ng |

| Test details | Mean rank 1 | Mean rank 2 | Mean rank diff. | n1 | n2 | Z |
|---|---|---|---|---|---|---|
| 100 ng vs. 250 ng | 18.33 | 22.73 | −4.394 | 9 | 11 | 0.7445 |
| 100 ng vs. 500 ng | 18.33 | 23.55 | −5.212 | 9 | 11 | 0.8832 |
| 100 ng vs. 750 ng | 18.33 | 27.85 | −9.517 | 9 | 10 | 1.577 |
| 100 ng vs. 1000 ng | 18.33 | 20.63 | −2.292 | 9 | 4 | 0.2904 |

TABLE 28

Figure 21A:
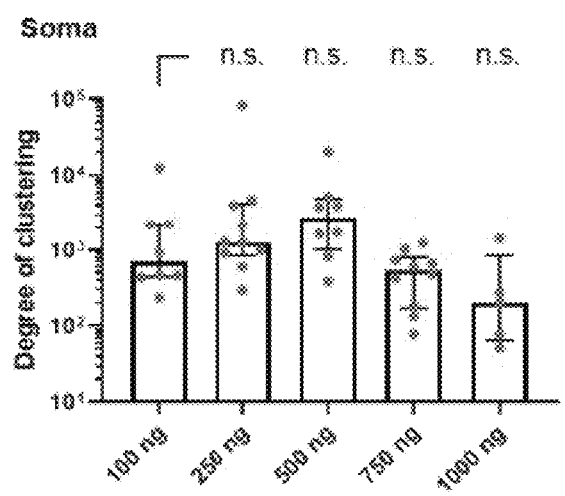

Statistical analysis for Figure 21A
Kruskal-Wallis analysis of variance of the degree of clustering followed by post-hoc test
via Dunn's test with the degree of clustering at '100 ng' transfection as control group.

| | |
|---|---|
| Kruskal-Wallis test | |
| P value | 0.0055 |
| Exact or approximate P value? | Approximate |
| P value summary | ** |
| Do the medians vary signif. (P < 0.05)? | Yes |
| Number of groups | 5 |
| Kruskal-Wallis statistic | 14.64 |
| Data summary | |
| Number of treatments (columns) | 5 |
| Number of values (total) | 41 |
| Number of families | 1 |
| Number of comparisons per family | 4 |
| Alpha | 0.05 |

| Dunn's multiple comparisons test | Mean rank diff. | Significant? | Summary | Adjusted P Value | A-? | |
|---|---|---|---|---|---|---|
| 100 ng vs. 250 ng | −5.200 | No | ns | >0.9999 | B | 250 ng |
| 100 ng vs. 500 ng | −8.000 | No | ns | 0.7266 | C | 500 ng |
| 100 ng vs. 750 ng | 7.400 | No | ns | 0.7712 | D | 750 ng |
| 100 ng vs. 1000 ng | 12.50 | No | ns | 0.2688 | E | 1000 ng |

| Test details | Mean rank 1 | Mean rank 2 | Mean rank diff. | n1 | n2 | Z |
|---|---|---|---|---|---|---|
| 100 ng vs. 250 ng | 21.50 | 26.70 | −5.200 | 8 | 10 | 0.9151 |
| 100 ng vs. 500 ng | 21.50 | 29.50 | −8.000 | 8 | 8 | 1.336 |
| 100 ng vs. 750 ng | 21.50 | 14.10 | 7.400 | 8 | 10 | 1.302 |
| 100 ng vs. 1000 ng | 21.50 | 9.000 | 12.50 | 8 | 5 | 1.830 |

TABLE 29

Figure 21B:
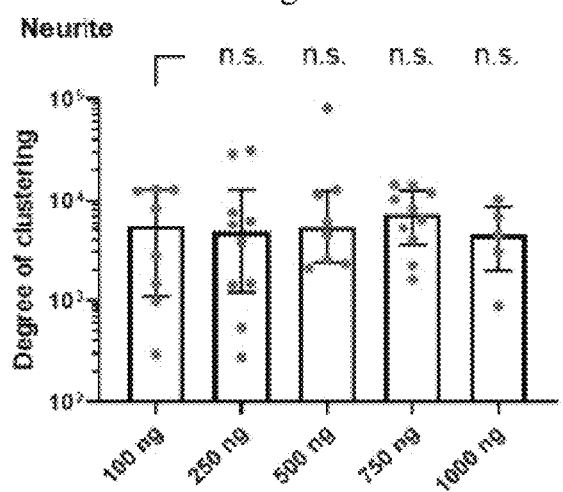

Statistical analysis for Figure 21B
Kruskal-Wallis analysis of variance of the degree of clustering followed by post-hoc test
via Dunn's test with the degree of clustering at '100 ng' transfection as control group.

| Kruskal-Wallis test | |
|---|---|
| P value | 0.7494 |
| Exact or approximate P value? | Approximate |
| P value summary | ns |
| Do the medians vary signif. (P < 0.05)? | No |
| Number of groups | 5 |
| Kruskal-Wallis statistic | 1.926 |
| Data summary | |
| Number of treatments (columns) | 5 |
| Number of values (total) | 41 |
| Number of families | 1 |
| Number of comparisons per family | 4 |
| Alpha | 0.05 |

| Dunn's multiple comparisons test | Mean rank diff. | Significant? | Summary | Adjusted P Value | A-? | |
|---|---|---|---|---|---|---|
| 100 ng vs. 250 ng | 1.575 | No | ns | >0.9999 | B | 250 ng |
| 100 ng vs. 500 ng | −2.875 | No | ns | >0.9999 | C | 500 ng |
| 100 ng vs. 750 ng | −4.725 | No | ns | >0.9999 | D | 750 ng |
| 100 ng vs. 1000 ng | 1.675 | No | ns | >0.9999 | E | 1000 ng |

| Test details | Mean rank 1 | Mean rank 2 | Mean rank diff. | n1 | n2 | Z |
|---|---|---|---|---|---|---|
| 100 ng vs. 250 ng | 19.88 | 18.30 | 1.575 | 8 | 10 | 0.2772 |
| 100 ng vs. 500 ng | 19.88 | 22.75 | −2.875 | 8 | 8 | 0.4800 |
| 100 ng vs. 750 ng | 19.88 | 24.60 | −4.725 | 8 | 10 | 0.8315 |
| 100 ng vs. 1000 ng | 19.88 | 18.20 | 1.675 | 8 | 5 | 0.2453 |

Development of Modular, Multiplexable Clustering Reagents

The same strategy was further tested to determine whether it could be generalized to make many such clustering reagents. If the design were modular, and an existing fluorescent indicator could be adapted into a multiplexable form, compatible with simultaneous use with other similarly adapted reagents, any desired set of existing fluorescent reporters could in principle be enabled to become a multiplexable set for simultaneous imaging of multiple parts of a signal transduction network, without the laborious trial-and-error optimization common in protein engineering. Due to broad interest in the interplay between $Ca^{2+}$, cAMP, and PKA dynamics, where feedforward and feedback connections between these signals has been shown to result in complex temporal dynamics of importance for driving cellular functions and states (Cooper, Mons and Karpen, 1995; Borodinsky and Spitzer, 2006; Mehta and Zhang, 2011; Sassone-Corsi, 2012), a high-performance cAMP reporter, cAMPr (Hackley, Mazzoni and Blau, 2018), and a high-performance protein kinase A (PKA) activity reporter, ExRaiAKAR (Mehta et al., 2018) were chosen for these experiments. The GFP-based, non-FRET-based cAMP sensor cAMPr (Hackley, Mazzoni and Blau, 2018) was chosen because a non-FRET-based sensor might require simpler optics than a FRET-based sensor, and might therefore facilitate the higher-speed simultaneous imaging of $Ca^{2+}$ and cAMP in neurons by eliminating the need for filter switching for the single-camera microscopes commonly used in biology. Additionally, because cAMPr and GCaMP6f have identical fluorophores and therefore identical fluorescence spectra, one of skill in the art would expect that they would be indistinguishable to traditional fluorescence imaging strategies based upon spectral information. Both cAMPr and ExRaiAKAR are GFP-based (and thus cannot be used simultaneously with a conventional microscope).

cAMPr-Based Designs cAMPr fusions to a variety of de novo-designed coiled-coil-forming peptides and polyhedron-forming peptides designed by analogy to the Coil1/I3-01 combination were screened. A short coiled-coil-forming homo-oligomer previously tested in GCaMP6f fusions was paired with each of the following self-assembling polyhedron-forming peptides: O3-33 (forms a 24-subunit 14 nm sized 480 kDa protein octahedron; King et al., 2012), T3-10 (forms a 12-subunit 11 nm sized 263 kDa protein tetrahedron; King et al., 2012), 3VDX (forms a 12-subunit 16 nm 593 kDa sized protein tetrahedron; Lai, Cascio and Yeates, 2012; Lai et al., 2016), ATC-HL3 (forms a 12-subunit 10 nm sized 365 kDa protein tetrahedron or a 24-subunit 20 nm sized 729 kDa protein octahedron; Lai et al., 2014), and T32-28 (forms a 24-subunit 15 nm sized 440 kDa protein tetrahedron; King et al., 2014), as well as with a group of fiber/foci-forming dihedral homomers (Garcia-Seisdedos et al., 2017) (Tables 1-2). In support of the generality of this approach, all five of these designs formed cAMPr puncta in cultured mouse hippocampal neurons ($D_C$>1), although the expression level of the design with T32-28 was significantly lower than the other ones (FIG. 20; Table 2).

The construct with the largest $D_C$ ($D_C$~$10^2$; see FIG. 21C-D for $D_C$ at soma and neurites, Tables HHH-III) for cAMPr consisted of 2L8HC4_15, a homo-tetramer (Boyken et al., 2016), 1M3U, a self-assembling subunit of the 1M3U fiber assembly (Garcia-Seisdedos et al., 2017), and HA, an epitope tag, which was called S2-cAMPr (FIG. 17J; FIG. 8I). S2-cAMPr produced bright puncta in the soma and neurites of cultured mouse hippocampal neurons (FIG. 17K-L; FIG. 8J-K). S2-cAMPr transients appeared similar to those of conventional cAMPr (FIG. 17M), and reported cAMP amplitudes as accurately as conventional cAMPr (FIG. 17N; FIG. 8L-M, Table 30), with similar signal-to-noise ratio (FIG. 17O; FIG. 8N, Table 31) and rise time (FIG. 8O, Table 32) as conventional cAMPr, when stimulated with forskolin in the culture media and compared at the soma, the proximal neurites (5-25 μm away from soma), and the distal neurites (50-250 μm away from soma). (Decay time was not measured because the stimulated cAMP remained elevated throughout these cAMPr and S2-cAMPr imaging sessions, perhaps because forskolin was not removed.) S2-cAMPr puncta were comparable in diameter (FIG. 8P, left), punctum-punctum distance (FIG. 8P, middle), and spatial stationarity (FIG. 8P, right) to those of S1-GCaMP6f. Finally, as with S1-GCaMP6f, S2-cAMPr did not alter the electrophysiological properties of neurons (FIG. 18) nor colocalize with subcellular organelles within neurons (FIG. 19). Tables 30-32 show statistical analyses for FIGS. 8M-O; Tables 33-34 show statistical analyses for FIGS. 21C-D.

TABLE 30

Statistical analysis for Figure 8M
Peak fluorescence changes in GFP channel at the soma, proximal neurites, and distal neurites of cultured mouse hippocampal neurons expressing cAMPr or 52-cAMPr under 5 μM forskolin stimulation (n = 11 somata, 22 proximal neurites, and 22 distal neurites from 11 neurons from 5 cultures for cAMPr; n = 13 somata, 26 proximal neurites, and 26 distal neurites from 13 neurons from 6 cultures for S2-cAMPr). Two-way analysis of variance followed by post-hoc Bonferroni corrected multiple comparisons test.

| Two-way ANOVA | Ordinary | | | | |
|---|---|---|---|---|---|
| Alpha | 0.05 | | | | |
| Source of Variation | % of total variation | P value | P value summary | Significant? | |
| Interaction | 0.4967 | .718 | ns | No | |
| Subcellular location | 14.54 | <.001 | *** | Yes | |
| Molecule | 0.004988 | .935 | ns | No | |
| ANOVA table | SS (Type III) | DF | MS | F (DFn, DFd) | P value |
| Interaction | 5456 | 2 | 2728 | F (2, 114) = 0.3321 | P = .718 |
| Subcellular location | 159678 | 2 | 79839 | F (2, 114) = 9.721 | P < .001 |
| Molecule | 54.79 | 1 | 54.79 | F (1, 114) = 0.006672 | P = .935 |
| Residual | 936263 | 114 | 8213 | | |
| Difference between column means | | | | | |
| Predicted (LS) mean of cAMPr | 76.96 | | | | |
| Predicted (LS) mean of S2-cAMPr | 78.39 | | | | |
| Difference between predicted means | −1.430 | | | | |
| SE of difference | 17.50 | | | | |
| 95% CI of difference | −36.10 to 33.24 | | | | |
| Number of families | 1 | | | | |
| Number of comparisons per family | 3 | | | | |
| Alpha | 0.05 | | | | |

| Bonferroni's multiple comparisons test | Predicted (LS) mean diff. | 95.00% CI of diff. | Significant? | Summary | Adjusted P Value |
|---|---|---|---|---|---|
| cAMPr-S2-cAMPr | | | | | |
| Soma | −8.429 | −98.64 to 81.78 | No | ns | >.999 |
| Proximal neurite | −12.31 | −76.10 to 51.48 | No | ns | >.999 |
| Distal neurite | 16.45 | −47.34 to 80.24 | No | ns | >.999 |

TABLE 30-continued

Statistical analysis for Figure 8M
Peak fluorescence changes in GFP channel at the soma, proximal neurites, and distal
neurites of cultured mouse hippocampal neurons expressing cAMPr or S2-cAMPr under 5 μM
forskolin stimulation (n = 11 somata, 22 proximal neurites, and 22 distal neurites from 11
neurons from 5 cultures for cAMPr; n = 13 somata, 26 proximal neurites, and 26 distal neurites
from 13 neurons from 6 cultures for S2-cAMPr). Two-way analysis of variance followed by
post-hoc Bonferroni corrected multiple comparisons test.

| Test details | Predicted (LS) mean 1 | Predicted (LS) mean 2 | Predicted (LS) mean diff. | SE of diff. | N1 | N2 | t | DF |
|---|---|---|---|---|---|---|---|---|
| cAMPr-S2-cAMPr | | | | | | | | |
| Soma | 24.78 | 33.21 | −8.429 | 37.13 | 11 | 13 | 0.2270 | 114.0 |
| Proximal neurite | 71.20 | 83.51 | −12.31 | 26.25 | 22 | 26 | 0.4690 | 114.0 |
| Distal neurite | 134.9 | 118.5 | 16.45 | 26.25 | 22 | 26 | 0.6267 | 114.0 |

TABLE 31

Statistical analysis for Figure 8N
Signal-to-noise ratio in the GFP channel at the soma, proximal neurites, and distal
neurites (of cultured mouse hippocampal neurons expressing cAMPr or S2-cAMPr under 5 μM
forskolin stimulation (n = 11 somata, 22 proximal neurites, and 22 distal neurites from 11
neurons from 5 cultures for cAMPr; n = 13 somata, 26 proximal neurites, and 26 distal neurites
from 13 neurons from 6 cultures for S2-cAMPr). Two-way analysis of variance followed by
post-hoc Bonferroni corrected multiple comparisons test.

| Two-way ANOVA | Ordinary |
|---|---|
| Alpha | 0.05 |

| Source of Variation | % of total variation | P value | P value summary | Significant? |
|---|---|---|---|---|
| Interaction | 0.06049 | .960 | ns | No |
| Subcellular location | 2.115 | .245 | ns | No |
| Molecule | 12.23 | <.001 | *** | Yes |

| ANOVA table | SS (Type III) | DF | MS | F (DFn, DFd) | P value |
|---|---|---|---|---|---|
| Interaction | 61.93 | 2 | 30.97 | F (2, 114) = 0.04075 | P = .960 |
| Subcellular location | 2166 | 2 | 1083 | F (2, 114) = 1.425 | P = .245 |
| Molecule | 12523 | 1 | 12523 | F (1, 114) = 16.48 | P < .001 |
| Residual | 86623 | 114 | 759.8 | | |
| Difference between column means | | | | | |
| Predicted (LS) mean of cAMPr | 43.33 | | | | |
| Predicted (LS) mean of S2-cAMPr | 21.72 | | | | |
| Difference between predicted means | 21.61 | | | | |
| SE of difference | 5.323 | | | | |
| 95% CI of difference | 11.07 to 32.16 | | | | |
| Number of families | 1 | | | | |
| Number of comparisons per family | 3 | | | | |
| Alpha | 0.05 | | | | |

| Bonferroni's multiple comparisons test | Predicted (LS) mean diff. | 95.00% CI of diff. | Significant? | Summary | Adjusted P Value |
|---|---|---|---|---|---|
| cAMPr-S2-cAMPr | | | | | |
| Soma | 22.97 | −4.468 to 50.41 | No | ns | .133 |
| Proximal neurite | 22.26 | 2.858 to 41.66 | Yes | * | .019 |
| Distal neurite | 19.60 | 0.1998 to 39.00 | Yes | * | .047 |

| Test details | Predicted (LS) mean 1 | Predicted (LS) mean 2 | Predicted (LS) mean diff. | SE of diff. | N1 | N2 | t | DF |
|---|---|---|---|---|---|---|---|---|

TABLE 31-continued

Statistical analysis for Figure 8N
Signal-to-noise ratio in the GFP channel at the soma, proximal neurites, and distal
neurites (of cultured mouse hippocampal neurons expressing cAMPr or S2-cAMPr under 5 µM
forskolin stimulation (n = 11 somata, 22 proximal neurites, and 22 distal neurites from 11
neurons from 5 cultures for cAMPr; n = 13 somata, 26 proximal neurites, and 26 distal neurites
from 13 neurons from 6 cultures for S2-cAMPr). Two-way analysis of variance followed by
post-hoc Bonferroni corrected multiple comparisons test.

| cAMPr-S2-cAMPr | | | | | | | | |
|---|---|---|---|---|---|---|---|---|
| Soma | 50.81 | 27.84 | 22.97 | 11.29 | 11 | 13 | 2.034 | 114.0 |
| Proximal neurite | 41.64 | 19.38 | 22.26 | 7.985 | 22 | 26 | 2.788 | 114.0 |
| Distal neurite | 37.54 | 17.94 | 19.60 | 7.985 | 22 | 26 | 2.455 | 114.0 |

TABLE 32

Statistical analysis for FIG. 8O
Wilcoxon rank sum test of the half
rise time of reported cAMP signals
at the soma after 5 µM forskolin
stimulation (n = 11 neurons from
5 cultures for cAMPr; n = 13
neurons from 6 cultures for S2-cAMPr).

| | |
|---|---|
| P value | 0.4093 |
| ranksum | 335.5 |
| zval | 0.8252 |

TABLE 33

Figure 21C:
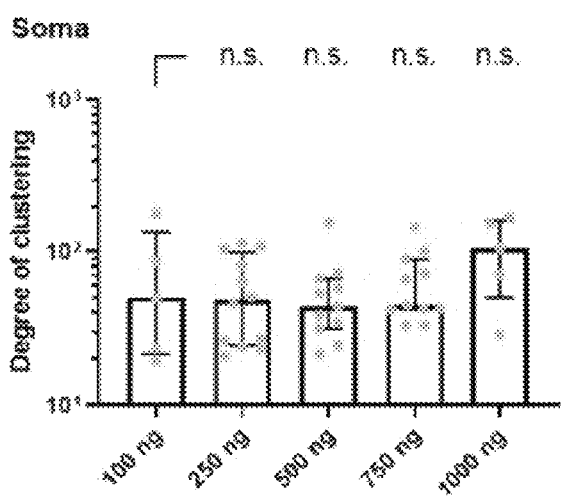

Statistical analysis for Figure 21C
Kruskal-Wallis analysis of variance of the degree of clustering followed by post-hoc test
via Dunn's test with the degree of clustering at '100 ng' transfection as control group.

| Kruskal-Wallis test | |
|---|---|
| P value | 0.4470 |
| Exact or approximate P value? | Approximate |
| P value summary | ns |
| Do the medians vary signif. (P < 0.05)? | No |
| Number of groups | 5 |
| Kruskal-Wallis statistic | 3.708 |
| Data summary | |
| Number of treatments (columns) | 5 |
| Number of values (total) | 44 |
| Number of families | 1 |
| Number of comparisons per family | 4 |
| Alpha | 0.05 |

| Dunn's multiple comparisons test | Mean rank diff. | Significant? | Summary | Adjusted P Value | A-? | |
|---|---|---|---|---|---|---|
| 100 ng vs. 250 ng | 0.6667 | No | ns | >0.9999 | B | 250 ng |
| 100 ng vs. 500 ng | 1.091 | No | ns | >0.9999 | C | 500 ng |
| 100 ng vs. 750 ng | −2.818 | No | ns | >0.9999 | D | 750 ng |
| 100 ng vs. 1000 ng | −11.00 | No | ns | 0.7029 | E | 1000 ng |

| Test details | Mean rank 1 | Mean rank 2 | Mean rank diff. | n1 | n2 | Z |
|---|---|---|---|---|---|---|
| 100 ng vs. 250 ng | 21.00 | 20.33 | 0.6667 | 5 | 12 | 0.09750 |
| 100 ng vs. 500 ng | 21.00 | 19.91 | 1.091 | 5 | 11 | 0.1575 |
| 100 ng vs. 750 ng | 21.00 | 23.82 | −2.818 | 5 | 11 | 0.4068 |
| 100 ng vs. 1000 ng | 21.00 | 32.00 | −11.00 | 5 | 5 | 1.354 |

TABLE 34

Figure 21D:
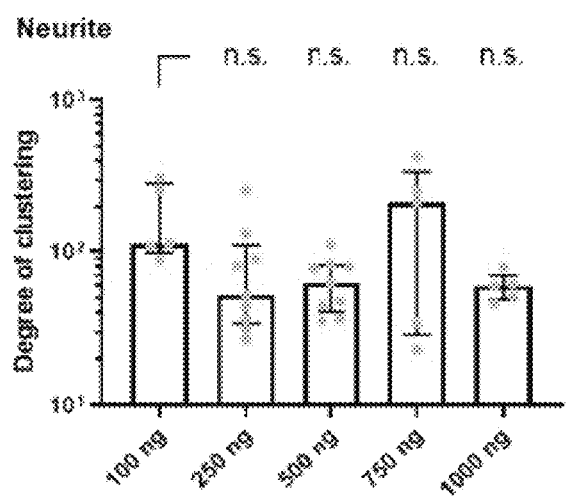

Statistical analysis for Figure 21D
Kruskal-Wallis analysis of variance of the degree of clustering followed by post-hoc test
via Dunn's test with the degree of clustering at '100 ng' transfection as control group.

| Kruskal-Wallis test | |
|---|---|
| P value | 0.1223 |
| Exact or approximate P value? | Approximate |
| P value summary | ns |
| Do the medians vary signif. (P < 0.05)? | No |
| Number of groups | 5 |
| Kruskal-Wallis statistic | 7.269 |
| Data summary | |
| Number of treatments (columns) | 5 |
| Number of values (total) | 33 |
| Number of families | 1 |
| Number of comparisons per family | 4 |
| Alpha | 0.05 |

| Dunn's multiple comparisons test | Mean rank diff | Significant? | Summary | Adjusted P Value | A-? | |
|---|---|---|---|---|---|---|
| 100 ng vs. 250 ng | 12.22 | No | ns | 0.0938 | B | 250 ng |
| 100 ng vs. 500 ng | 12.67 | No | ns | 0.0754 | C | 500 ng |
| 100 ng vs. 750 ng | 8.000 | No | ns | 0.7633 | D | 750 ng |
| 100 ng vs. 1000 ng | 13.20 | No | ns | 0.1236 | E | 1000 ng |

| Test details | Mean rank 1 | Mean rank 2 | Mean rank diff. | n1 | n2 | Z |
|---|---|---|---|---|---|---|
| 100 ng vs. 250 ng | 27.00 | 14.78 | 12.22 | 5 | 9 | 2.266 |
| 100 ng vs. 500 ng | 27.00 | 14.33 | 12.67 | 5 | 9 | 2.349 |
| 100 ng vs. 750 ng | 27.00 | 19.00 | 8.000 | 5 | 5 | 1.308 |
| 100 ng vs. 1000 ng | 27.00 | 13.80 | 13.20 | 5 | 5 | 2.158 |

To further explore the generality of this design strategy, a second successful punctum-forming cAMPr reporter, S2a-cAMPr, was thoroughly characterized using a different set of scaffolding peptides and showed excellent performance (FIG. 17J; Tables 1-2). S2a-cAMPr produced bright puncta in both the soma and neurites in cultured mouse hippocampal neurons, with $D_C>10^2$ in the soma and $D_C>10^3$ in the neurites, showing S2a-cAMPr as a promising construct for spatial multiplexing (compare FIG. 17K with FIG. 17L). S2a-cAMPr transients appeared similar to those of conventional cAMPr (FIG. 17M), with similar transient amplitudes (FIG. 17N) and signal-to-noise (FIG. 17O) in neurons, when elicited by forskolin and compared at the soma, the proximal neurites (5-25 μm away from soma), and the distal neurites (50-250 μm away from soma). (FIG. 10, Tables 38-40). Tables 11-13 show measurements and statistical analyses of FIGS. 17 J-K; Tables 38-40 show statistical analyses of FIGS. 10E-G.

TABLE 35

Neuronal measurements used in Fig. 17N-O
Peak fluorescence change, GFP channel (dF/F0)

| 5 μM forskolin | Somata | Proximal neurites | Distal neurites | Total neurons | Cultures | Corresponding Fig. |
|---|---|---|---|---|---|---|
| cAMPr | 11 | 22 | 22 | 11 | 5 | 17N |
| S2-cAMPr | 13 | 26 | 26 | 13 | 6 | 17N |
| Signal-to-noise-ratio | | | | | | |
| 5 μM forskolin | | | | | | |
| cAMPr | 11 | 22 | 22 | 11 | 5 | 17O |
| S2-cAMPr | 13 | 26 | 26 | 13 | 6 | 17O |

TABLE 36

Statistical analysis of Fig. 17J

| Two-way ANOVA Alpha | Ordinary 0.05 | | | | |
|---|---|---|---|---|---|
| Source of Variation | % of total variation | P value | P value summary | Significant? | |
| Interaction | 0.1388 | 0.956 | ns | No | |
| Row Factor | 7.643 | 0.094 | ns | No | |
| Column Factor | 0.6707 | 0.513 | ns | No | |
| ANOVA table | SS (Type III) | DF | MS | F (DFn, DFd) | P value |
| Interaction | 691.2 | 2 | 345.6 | F (2, 59) = 0.0448 | P = 0.956 |
| Row Factor | 38071 | 2 | 19035 | F (2, 59) = 2.468 | P = 0.094 |
| Column Factor | 3341 | 1 | 3341 | F (1, 59) = 0.4331 | P = 0.513 |
| Residual | 455141 | 59 | 7714 | | |
| Number of families | 1 | | | | |
| Number of comparisons per family | 3 | | | | |
| Alpha | 0.05 | | | | |

| Sidak's multiple comparisons test | Mean Diff. | 95.00% CI of diff. | Significant? | Summary | Adjusted P Value |
|---|---|---|---|---|---|
| cAMPr-S2-cAMPr | | | | | |
| Soma | 20.62 | −99.46 to 140.7 | No | ns | 0.966 |
| Proximal neurite | 18.75 | −66.16 to 103.7 | No | ns | 0.931 |
| Distal neurite | 6.098 | −78.81 to 91.01 | No | ns | 0.997 |

| Test details | Mean 1 | Mean 2 | Mean Diff. | SE of diff. | N1 | N2 | t | DF |
|---|---|---|---|---|---|---|---|---|
| cAMPr-S2-cAMPr | | | | | | | | |
| Soma | 59.52 | 38.9 | 20.62 | 48.86 | 6 | 7 | 0.4221 | 59 |
| Proximal neurite | 84.39 | 65.63 | 18.75 | 34.55 | 12 | 14 | 0.5428 | 59 |
| Distal neurite | 115.1 | 109 | 6.098 | 34.55 | 12 | 14 | 0.1765 | 59 |

TABLE 37

Statistical analysis of FIG. 17K.

Two-way ANOVA Ordinary Alpha 0.05

| Source of Variation | % of total variation | P value | P value summary | Significant? | |
|---|---|---|---|---|---|
| Interaction | 6.28 | 0.098 | ns | No | |
| Row Factor | 17.95 | 0.002 | ** | Yes | |
| Column Factor | 2.121 | 0.206 | ns | No | |
| ANOVA table | SS (Type III) | DF | MS | F (DFn, DFd) | P value |
| Interaction | 7397 | 2 | 3698 | F (2, 59) = 2.42 | P = 0.098 |
| Row Factor | 21140 | 2 | 10570 | F (2,59) = 6.916 | P = 0.002 |
| Column Factor | 2498 | 1 | 2498 | F (1, 59) = 1.634 | P = 0.206 |
| Residual | 90171 | 59 | 1528 | | |

TABLE 37-continued

Statistical analysis of FIG. 17K.

Number of families 1
Number of comparisons per family 3
Alpha 0.05

| Sidak's multiple comparisons test | Mean Diff. | 95.00% CI of diff. | Significant? | Summary | Adjusted P Value |
|---|---|---|---|---|---|
| cAMPr-S2-cAMPr | | | | | |
| Soma | 48.51 | −4.937 to 102 | No | ns | 0.086 |
| Proximal neurite | −7.483 | −45.28 to 30.31 | No | ns | 0.949 |
| Distal neurite | −1.705 | −39.5 to 36.09 | No | ns | >0.999 |

| Test details | Mean 1 | Mean 2 | Mean Diff. | SE of diff. | N1 | N2 | t | DF |
|---|---|---|---|---|---|---|---|---|
| cAMPr-S2-cAMPr | | | | | | | | |
| Soma | 97.62 | 49.11 | 48.51 | 21.75 | 6 | 7 | 2.23 | 59 |
| Proximal neurite | 35.54 | 43.02 | −7.483 | 15.38 | 12 | 14 | 0.4866 | 59 |
| Distal neurite | 23 | 24.7 | −1.705 | 15.38 | 12 | 14 | 0.1109 | 59 |

TABLE 38

Figure 10H:
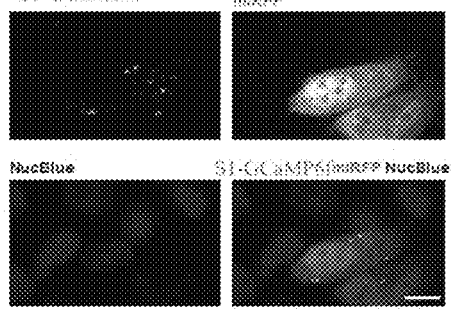
(FIG. 10H) A representative confocal image of live HeLa cells expressing S1-GCaMP6f, as well as the morphological marker miRFP, and stained with a live cell nuclear stain, NucBlue™. Scale bars, 10 µm throughout this figure.
Figure 10I:
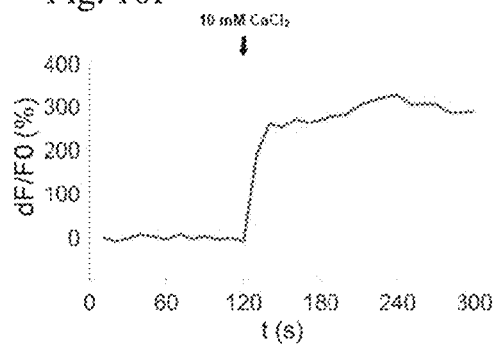
(FIG. 10I) Representative fluorescent signal recorded during live cell imaging from the HeLa cell in FIG. 10H under 10 mM $CaCl_2$ stimulation at t=120 s. Throughout this figure: dF/F0, fluorescence changes in the GFP channel.
Figure 10J:
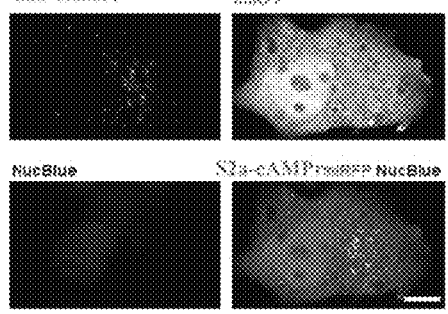
(FIG. 10J) A representative confocal image of a live HeLa cell expressing S2a-cAMPr, as well as the morphological marker miRFP, and stained with NucBlue™.
Figure 10K:
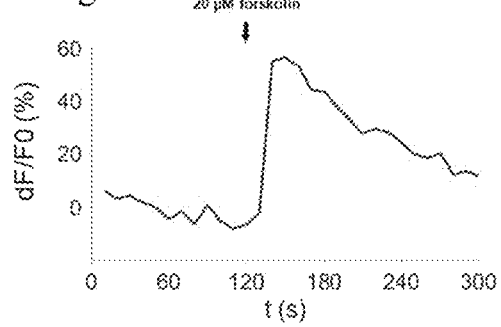
(FIG. 10K) Representative fluorescent signal recorded during live cell imaging from the HeLa cell in FIG. 10J under 20 µM forskolin stimulation at t=120 s.
Figure 10L:
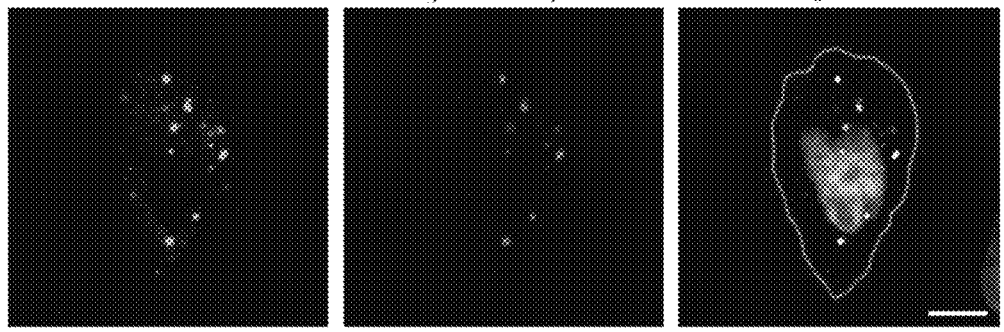
(FIG. 10L) Representative images of HeLa cells co-expressing S1-GCaMP6f and S2a-cAMPr. All images in FIG. 10L were taken after fixation, immunostaining against the Xpress epitope and HA epitope, and DAPI staining against the cell nucleus.
Figure 10M:
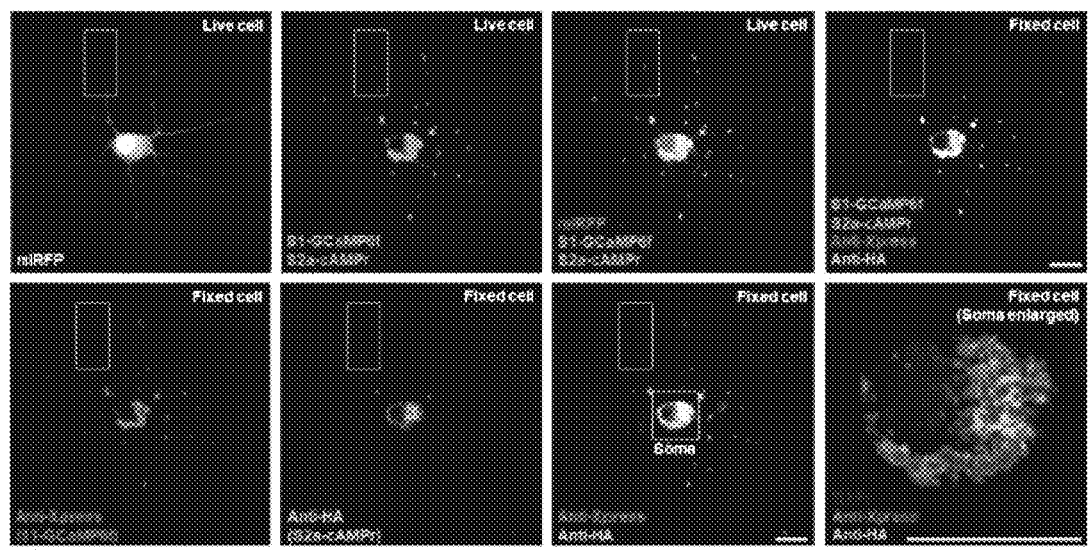
(FIG. 10M) Representative confocal images of live cultured mouse hippocampal neurons co-expressing S1-GCaMP6f, S2a-cAMPr, and the morphological marker miRFP (first three panels in the top row) and after fixation, immunostaining (with anti-Xpress to mark GCaMP6f and anti-HA to mark cAMPr), and DAPI staining to mark the cell nucleus (the remaining five panels). Yellow rectangle, boundary of the region shown in enlarged view in N. White square, boundary of the soma region shown in the enlarged view in the right most panel in the bottom row. All scale bars, 20 µm.
Figure 10N:
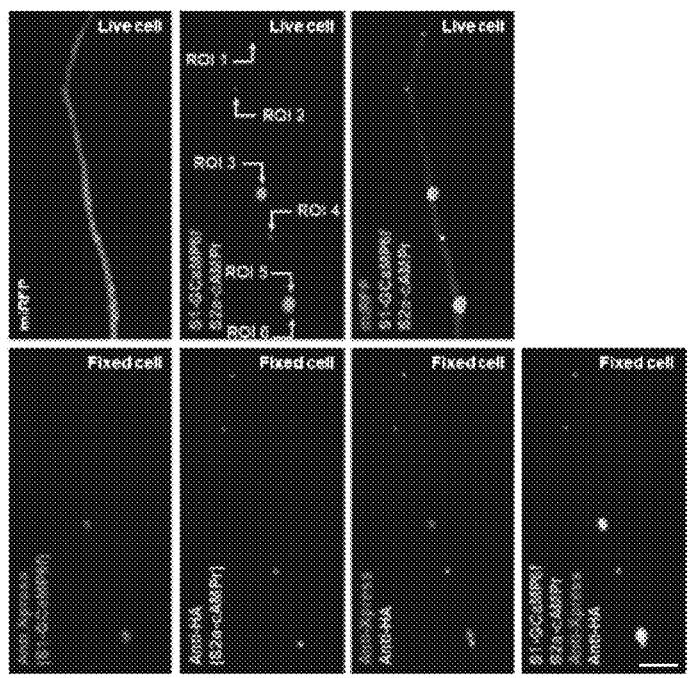
(FIG. 10N) Enlarged views of the neurite region in the yellow rectangle in FIG. 10M. Arrows indicate the regions-of-interest (ROIs) of individual puncta whose fluorescent signal time courses are plotted in FIG. 10O. Scale bar, 5 µm.
Figure 10O:
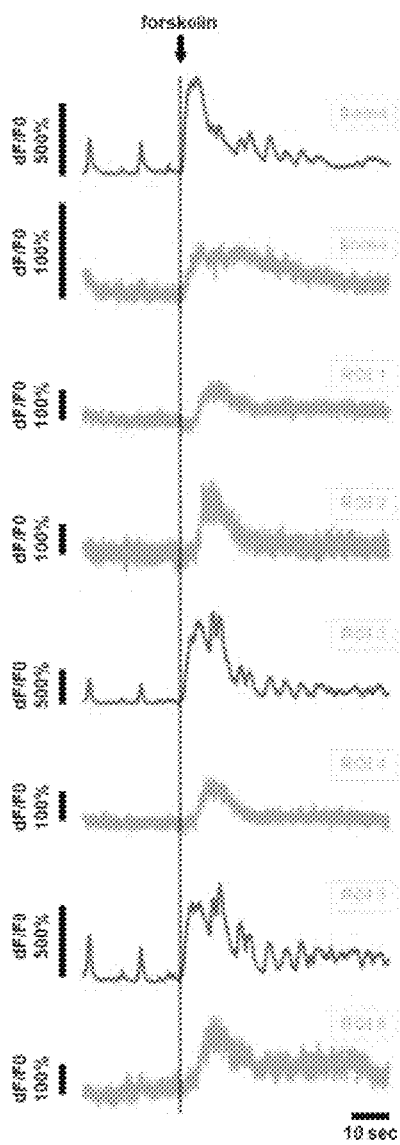
(FIG. 10O) Recorded fluorescent signals at the soma and the ROIs along the neurite marked in FIG. 10N during live cell imaging with 5 µM forskolin stimulation.
Figure 10P:
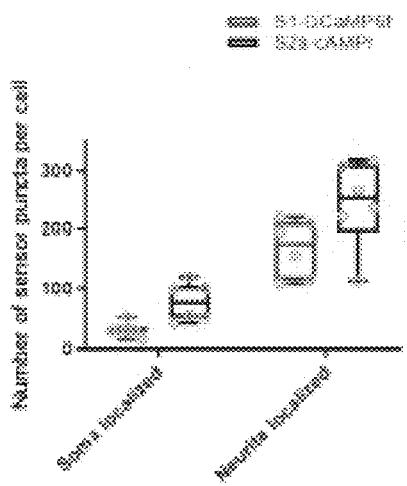
(FIG. 10P) Box plot of the number of soma-localized or neurite-localized S1-GCaMP6f or S2a-cAMPr puncta per cell identified by immunostaining in neurons co-expressing S1-GCaMP6f, S2a-cAMPr, and miRFP (n=6 neurons from 6 cultures). Box plots throughout this figure: middle horizontal line, median; top and bottom horizontal lines, 25% and 75% percentiles; top and bottom whiskers, minimum and maximum values; hollow circles, individual values.
Figure 10Q:
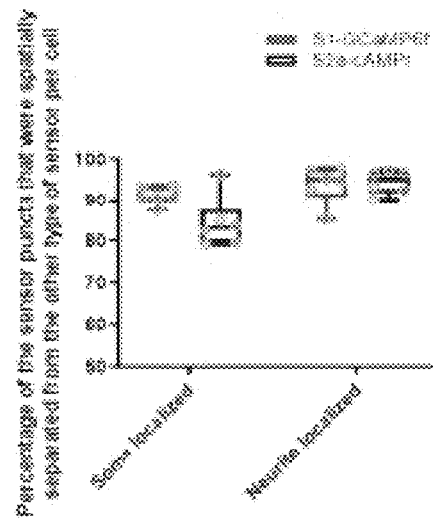

Statistical analysis for FIG. 10E
Peak fluorescence changes in GFP channel at the soma, proximal neurites (5-25 away from soma), and distal neurites (50-250 away from soma) of cultured mouse hippocampal neurons expressing cAMPr or S2a-cAMPr after 5 μM forskolin stimulation (n = 8 somata, 16 proximal neurites, and 16 distal neurites from 8 neurons from 5 cultures for cAMPr; n = 13 somata, 26 proximal neurites, and 26 distal neurites from 13 neurons from 9 cultures for S2a-cAMPr). Two-way analysis of variance followed by post-hoc Sidak's multiple comparisons test.

Two-way ANOVA Ordinary
Alpha 0.05

| Source of Variation | % of total variation | P value | P value summary | Significant? | | |
|---|---|---|---|---|---|---|
| Interaction | 0.1095 | .940 | ns | No | | |
| Subcellular location | 10.05 | .005 | ** | Yes | | |
| Molecule | 1.866 | .149 | ns | No | | |
| ANOVA table | SS (Type III) | DF | MS | F (DFn, DFd) | P value | |
| Interaction | 685.5 | 2 | 342.7 | F (2, 99) = 0.06195 | P = .940 | |
| Subcellular location | 62914 | 2 | 31457 | F (2, 99) = 5.686 | P = .005 | |
| Molecule | 11681 | 1 | 11681 | F (1, 99) = 2.111 | P = .149 | |
| Residual | 547707 | 99 | 5532 | | | |

| Difference between column means | | |
|---|---|---|
| Predicted (LS) mean of cAMPr | 91.80 | |
| Predicted (LS) mean of S2a-cAMPr | 68.90 | |
| Difference between predicted means | 22.89 | |

TABLE 38-continued

Statistical analysis for FIG. 10E
Peak fluorescence changes in GFP channel at the soma, proximal neurites (5-25 away from soma), and distal neurites (50-250 away from soma) of cultured mouse hippocampal neurons expressing cAMPr or S2a-cAMPr after 5 µM forskolin stimulation (n = 8 somata, 16 proximal neurites, and 16 distal neurites from 8 neurons from 5 cultures for cAMPr; n = 13 somata, 26 proximal neurites, and 26 distal neurites from 13 neurons from 9 cultures for S2a-cAMPr). Two-way analysis of variance followed by post-hoc Sidak's multiple comparisons test.

| | |
|---|---|
| SE of difference | 15.76 |
| 95% CI of difference | −8.369 to 54.16 |

Number of families 1
Number of comparisons per family 3
Alpha 0.05

| Sidak's multiple comparisons test | Predicted (LS) mean diff. | 95.00% CI of diff. | Significant? | Summary | Adjusted P Value |
|---|---|---|---|---|---|
| cAMPr-S2a-cAMPr | | | | | |
| Soma | 21.07 | −60.11 to 102.3 | No | ns | .896 |
| Proximal neurite | 18.05 | −39.35 to 75.45 | No | ns | .831 |
| Distal neurite | 29.56 | −27.84 to 86.96 | No | ns | .514 |

| Test details | Predicted (LS) mean 1 | Predicted (LS) mean 2 | Predicted (LS) mean diff. | SE of diff. | N1 | N2 | t | DF |
|---|---|---|---|---|---|---|---|---|
| cAMPr-S2a-cAMPr | | | | | | | | |
| Soma | 57.49 | 36.42 | 21.07 | 33.42 | 8 | 13 | 0.6305 | 99.00 |
| Proximal neurite | 88.98 | 70.93 | 18.05 | 23.63 | 16 | 26 | 0.7638 | 99.00 |
| Distal neurite | 128.9 | 99.36 | 29.56 | 23.63 | 16 | 26 | 1.251 | 99.00 |

TABLE 39

Statistical analysis for FIG. 10F
Signal-to-noise ratio in the GFP channel at the soma, proximal neurites (5-25 µm away from soma), and distal neurites (50-250 µm away from soma) of cultured mouse hippocampal neurons expressing cAMPr or S2a-cAMPr under 5 µM forskolin stimulation (n = 8 somata, 16 proximal neurites, and 16 distal neurites from 8 neurons from 5 cultures for cAMPr; n = 13 somata, 26 proximal neurites, and 26 distal neurites from 13 neurons from 9 cultures for S2a-cAMPr). Two-way analysis of variance followed by post-hoc Sidak's multiple comparisons test.

Two-way ANOVA Ordinary
Alpha 0.05

| Source of Variation | % of total variation | P value | P value summary | Significant? | | |
|---|---|---|---|---|---|---|
| Interaction | 3.822 | .109 | ns | No | | |
| Subcellular location | 10.56 | .003 | ** | Yes | | |
| Molecule | 6.620 | .006 | ** | Yes | | |
| ANOVA table | SS (Type III) | DF | MS | F (DFn, DFd) | P value | |
| Interaction | 5549 | 2 | 2775 | F (2, 99) = 2.264 | P = .109 | |
| Subcellular location | 15328 | 2 | 7664 | F (2, 99) = 6.252 | P = .003 | |
| Molecule | 9610 | 1 | 9610 | F (1, 99) = 7.840 | P = .006 | |
| Residual | 121350 | 99 | 1226 | | | |

TABLE 39-continued

Statistical analysis for FIG. 10F
Signal-to-noise ratio in the GFP channel at the soma, proximal neurites (5-25 μm away
from soma), and distal neurites (50-250 μm away from soma) of cultured mouse hippocampal
neurons expressing cAMPr or S2a-cAMPr under 5 μM forskolin stimulation (n = 8 somata, 16
proximal neurites, and 16 distal neurites from 8 neurons from 5 cultures for cAMPr; n = 13
somata, 26 proximal neurites, and 26 distal neurites from 13 neurons from 9 cultures for S2a-
cAMPr). Two-way analysis of variance followed by post-hoc Sidak's multiple comparisons test.

| Difference between column means | |
| --- | --- |
| Predicted (LS) mean of cAMPr | 48.58 |
| Predicted (LS) mean of S2a-cAMPr | 27.81 |
| Difference between predicted means | 20.77 |
| SE of difference | 7.416 |
| 95% CI of difference | 6.050 to 35.48 |

Number of families 1
Number of comparisons per family 3
Alpha 0.05

| Sidak's multiple comparisons test | Predicted (LS) mean diff. | 95.00% CI of diff. | Significant? | Summary | Adjusted P Value |
| --- | --- | --- | --- | --- | --- |
| cAMPr-S2a-cAMPr | | | | | |
| Soma | 45.13 | 6.915 to 83.34 | Yes | * | .015 |
| Proximal neurite | 12.20 | −14.82 to 39.22 | No | ns | .620 |
| Distal neurite | 4.970 | −22.05 to 31.99 | No | ns | .959 |

| Test details | Predicted (LS) mean 1 | Predicted (LS) mean 2 | Predicted (LS) mean diff. | SE of diff. | N1 | N2 | t | DF |
| --- | --- | --- | --- | --- | --- | --- | --- | --- |
| cAMPr-S2a-cAMPr | | | | | | | | |
| Soma | 79.73 | 34.61 | 45.13 | 15.73 | 8 | 13 | 2.868 | 99.00 |
| Proximal neurite | 40.41 | 28.21 | 12.20 | 11.12 | 16 | 26 | 1.097 | 99.00 |
| Distal neurite | 25.59 | 20.62 | 4.970 | 11.12 | 16 | 26 | 0.4467 | 99.00 |

TABLE 40

Statistical analysis for FIG. 10G
Wilcoxon rank sum test of the half rise
time of reported cAMP signals at the
soma after 5 μM forskolin stimulation
(n = 8 neurons from 5 cultures for
cAMPr; n = 13 neurons from 9
cultures for S2a-cAMPr).

| P value | 0.3649 |
| --- | --- |
| ranksum | 0.9061 |
| zval | 101 |

Movements of the puncta of S1-GCaMP6f (FIG. 22A) and S2-cAMPr (FIG. 22B) were not detectable during imaging sessions here performed. The nearest-neighbor distances between S1-GCaMP6f (or S2-cAMPr) puncta were in the few micron range at the soma (FIG. 17P; n=54 puncta from 5 neurons from 5 cultures for S1-GCaMP6f, n=86 puncta from 5 neurons from 5 cultures for S2-cAMPr), and were within a wider range of distances (but still primarily in the range 2-8 microns) in the dendrites (FIG. 17Q; n=270 puncta from 5 neurons from 5 cultures for S1-GCaMP6f, n=313 puncta from 5 neurons from 5 cultures for S2-cAMPr).

Experimental results showed that the dual peptide-scaffolded SiRIs indeed were modularly assemblable: almost all the polyhedron/coil hybrid scaffolds that were tested provided $D_C>100$, and a given scaffold could be used successfully with different sensors, showing the generality of the strategy (although of course, testing in cells is required for validation, as with any protein engineering project) (Table 2).

ExRaiAKAR-Based Designs

Figure 8R:
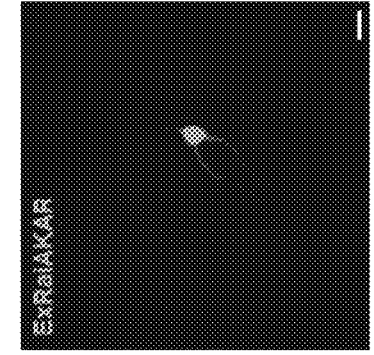
Figure 21E:
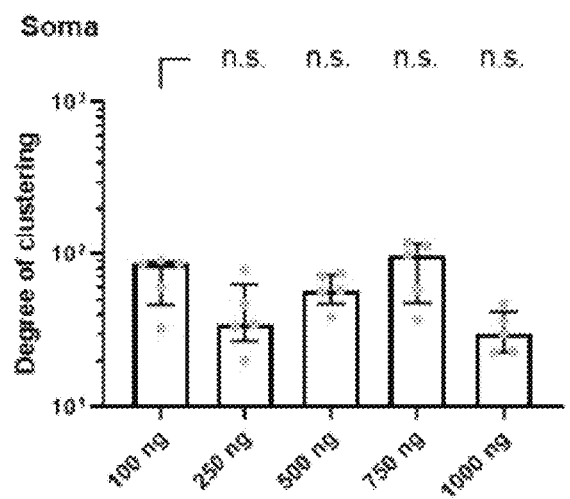
Figure 21F:
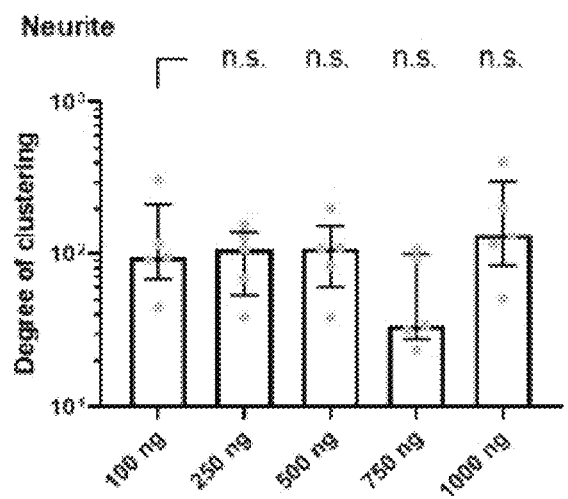

Additional constructs were made using ExRaiAKAR and were similarly tested to further demonstrate this strategy (FIG. 17R, Tables 1-2). S3-ExRaiAKAR, the construct with the largest $D_C$ ($D_C \sim 10^2$; FIG. 17R; FIG. 21E-F for $D_C$ at soma and neurites, Tables 44-45) for ExRaiAKAR consisted of 5L6HC3_1, a homo-trimer (Boyken et al., 2016), 3VDX, a self-assembling subunit of a tetrahedron (Lai et al., 2016), and V5, an epitope tag (FIG. 8Q; Tables 1-2). Unlike ExRaiAKAR, S3-ExRaiAKAR formed puncta in live cultured mouse hippocampal neurons (compare FIG. 17S and FIG. 17T; FIG. 8R-S). As in previous experiments, fluorescent signals were recorded from the soma, proximal neurites, and distal neurites of cultured mouse hippocampal neurons expressing ExRaiAKAR (FIG. 17U; left panel) or S3-ExRaiAKAR (FIG. 175U; right panel) under 5 µM forskolin stimulation at t=1 minute (min). Each fluorescent signal for S3-ExRaiAKAR was measured from a single punctum. Similar to the results observed with S1-GCaMP6f and S2a-cAMPr, S3-ExRaiAKAR transients appeared similar to those of conventional ExRaiAKAR under 5 µM forskolin stimulation at t=1 minute (min) and compared at the soma, the proximal neurites (5-25 µm away from soma), and the distal neurites (50-250 µm away from soma) (FIG. 17U), with similar transient amplitudes (FIG. 17V; n=9 somata, 18 proximal neurites, and 18 distal neurites from 9 neurons from 3 cultures for ExRaiAKAR; n=22 somata, 44 proximal neurites, and 44 distal neurites from 22 neurons from 6 cultures for S3-ExRaiAKAR) and signal-to-noise ratios (FIG. 17W; n=9 somata, 18 proximal neurites, and 18 distal neurites from 9 neurons from 3 cultures for ExRaiAKAR; n=22 somata, 44 proximal neurites, and 44 distal neurites from 22 neurons from 6 cultures for S3-ExRaiAKAR). S3-ExRaiAKAR reported PKA activity as accurately (FIG. 8T-U, Table 41) and with as good signal-to-noise ratio (FIG. 8V, Table 42) and rise time (FIG. 8W, Table 43) as conventional ExRaiAKAR, when stimulated with forskolin in the culture media. (Decay time was not measured because the stimulated PKA remained activated throughout these imaging sessions.) As with S1- and S2-clustered puncta, S3-ExRaiAKAR puncta were small (FIG. 8X, left), closely packed (FIG. 8X, middle), and stationary (FIG. 8X, right), and did not alter the electrophysiological properties of neurons (FIG. 18) nor colocalize with subcellular organelles (FIG. 19). Tables 41-43 show statistical analyses for FIGS. 8U-W; Tables 44-45 show statistical analyses for FIGS. 21E-F.

TABLE 41

Statistical analysis for FIG. 8U
Peak fluorescence changes in GFP channel at the soma, proximal neurites, and distal neurites of cultured mouse hippocampal neurons expressing ExRaiAKAR or S3-ExRaiAKAR under 5 µM forskolin stimulation (n = 5 somata, 10 proximal neurites, and 10 distal neurites from 5 neurons from 4 cultures for ExRaiAKAR; n = 5 somata, 10 proximal neurites, and 10 distal neurites from 5 neurons from 5 cultures for S3-ExRaiAKAR). Two-way analysis of variance followed by post-hoc Bonferroni corrected multiple comparisons test.

| | Two-way ANOVA Ordinary Alpha 0.05 | | | | |
|---|---|---|---|---|---|
| Source of Variation | % of total variation | P value | P value summary | Significant? | |
| Interaction | 12.20 | .055 | ns | No | |
| Subcellular location | 1.197 | .739 | ns | No | |
| Molecule | 0.6771 | .560 | ns | No | |
| ANOVA table | SS (Type III) | DF | MS | F (DFn, DFd) | P value |
| Interaction | 759.3 | 2 | 379.7 | F (2, 44) = 3.105 | P = .055 |
| Subcellular location | 74.51 | 2 | 37.26 | F (2, 44) = 0.3047 | P = .739 |
| Molecule | 42.15 | 1 | 42.15 | F (1, 44) = 0.3447 | P = .560 |
| Residual | 5381 | 44 | 122.3 | | |
| Difference between column means | | | | | |
| Predicted (LS) mean of ExRaiAKAR | 48.05 | | | | |
| Predicted (LS) mean of S3-ExRaiAKAR | 46.12 | | | | |
| Difference between predicted means | 1.936 | | | | |
| SE of difference | 3.297 | | | | |
| 95% CI of difference | −4.709 to 8.580 | | | | |

| | Number of families 1 Number of comparisons per family 3 Alpha 0.05 | | | | |
|---|---|---|---|---|---|
| Bonferroni's multiple comparisons test | Predicted (LS) mean diff. | 95.00% CI of diff. | Significant? | Summary | Adjusted P Value |

TABLE 41-continued

Statistical analysis for FIG. 8U
Peak fluorescence changes in GFP channel at the soma, proximal neurites, and distal neurites of cultured mouse hippocampal neurons expressing ExRaiAKAR or S3-ExRaiAKAR under 5 μM forskolin stimulation (n = 5 somata, 10 proximal neurites, and 10 distal neurites from 5 neurons from 4 cultures for ExRaiAKAR; n = 5 somata, 10 proximal neurites, and 10 distal neurites from 5 neurons from 5 cultures for S3-ExRaiAKAR). Two-way analysis of variance followed by post-hoc Bonferroni corrected multiple comparisons test.

| ExRaiAKAR-S3-ExRaiAKAR | | | | | |
|---|---|---|---|---|---|
| Soma | 6.890 | −10.52 to 24.30 | No | ns | .990 |
| Proximal neurite | 7.513 | −4.796 to 19.82 | No | ns | .408 |
| Distal neurite | −8.597 | −20.91 to 3.712 | No | ns | .267 |

| Test details | Predicted (LS) mean 1 | Predicted (LS) mean 2 | Predicted (LS) mean diff. | SE of diff. | N1 | N2 | t | DF |
|---|---|---|---|---|---|---|---|---|
| ExRaiAKAR-S3-ExRaiAKA | | | | | | | | |
| Soma | 49.52 | 42.63 | 6.890 | 6.994 | 5 | 5 | 0.9852 | 44.00 |
| Proximal neurite | 52.53 | 45.02 | 7.513 | 4.946 | 10 | 10 | 1.519 | 44.00 |
| Distal neurite | 42.10 | 50.70 | −8.597 | 4.946 | 10 | 10 | 1.738 | 44.00 |

TABLE 42

Statistical analysis for FIG. 8V
Signal-to-noise ratio in the GFP channel at the soma, proximal neurites, and distal neurites (of cultured mouse hippocampal neurons expressing ExRaiAKAR or S3-ExRaiAKAR under 5 μM forskolin stimulation (n = 5 somata, 10 proximal neurites, and 10 distal neurites 10 from 5 neurons from 4 cultures for ExRaiAKAR; n = 5 somata, 10 proximal neurites, and 10 distal neurites from 5 neurons from 5 cultures for S3-ExRaiAKAR). Two-way analysis of variance followed by post-hoc Bonferroni corrected multiple comparisons test.

Two-way ANOVA Ordinary
Alpha 0.05

| Source of Variation | % of total variation | P value | P value summary | Significant? | |
|---|---|---|---|---|---|
| Interaction | 6.918 | .139 | ns | No | |
| Subcellular location | 18.91 | .007 | ** | Yes | |
| Molecule | 0.8782 | .473 | ns | No | |
| ANOVA table | SS (Type III) | DF | MS | F (DFn, DFd) | P value |
| Interaction | 785.5 | 2 | 392.8 | F (2, 44) = 2.062 | P = .139 |
| Subcellular location | 2147 | 2 | 1074 | F (2, 44) = 5.636 | P = .007 |
| Molecule | 99.72 | 1 | 99.72 | F (1, 44) = 0.5234 | P = .473 |
| Residual | 8383 | 44 | 190.5 | | |

| Difference between column means | | 
|---|---|
| Predicted (LS) mean of ExRaiAKAR | 25.16 |
| Predicted (LS) mean of S3-ExRaiAKAR | 22.18 |
| Difference between predicted means | 2.977 |
| SE of difference | 4.115 |
| 95% CI of difference | −5.316 to 11.27 |

TABLE 42-continued

Statistical analysis for FIG. 8V
Signal-to-noise ratio in the GFP channel at the soma, proximal neurites, and distal neurites (of cultured mouse hippocampal neurons expressing ExRaiAKAR or S3-ExRaiAKAR under 5 µM forskolin stimulation (n = 5 somata, 10 proximal neurites, and 10 distal neurites 10 from 5 neurons from 4 cultures for ExRaiAKAR; n = 5 somata, 10 proximal neurites, and distal neurites from 5 neurons from 5 cultures for S3-ExRaiAKAR). Two-way analysis of variance followed by post-hoc Bonferroni corrected multiple comparisons test.

Number of families 1
Number of comparisonsper family 3
Alpha 0.05

| Bonferroni's multiple comparisons test | Predicted (LS) mean diff. | 95.00% CI of diff. | Significant? | Summary | Adjusted P Value |
|---|---|---|---|---|---|
| ExRaiAKAR-S3-ExRaiAKAR | | | | | |
| Soma | 8.965 | −12.76 to 30.69 | No | ns | .930 |
| Proximal neurite | 7.884 | −7.480 to 23.25 | No | ns | .625 |
| Distal neurite | −7.917 | −23.28 to 7.447 | No | ns | .619 |

| Test details | Predicted (LS) mean 1 | Predicted (LS) mean 2 | Predicted (LS) mean diff. | SE of diff. | N1 | N2 | t | DF |
|---|---|---|---|---|---|---|---|---|
| ExRaiAKAR-S3-ExRaiAKAR | | | | | | | | |
| Soma | 36.40 | 27.44 | 8.965 | 8.730 | 5 | 5 | 1.027 | 44.00 |
| Proximal neurite | 28.28 | 20.40 | 7.884 | 6.173 | 10 | 10 | 1.277 | 44.00 |
| Distal neurite | 10.78 | 18.70 | −7.917 | 6.173 | 10 | 10 | 1.283 | 44.00 |

TABLE 43

Statistical analysis for FIG. 8W
Wilcoxon rank sum test of the half rise time of reported PKA signals at the soma after 5 µM forskolin stimulation (n = 5 neurons from 4 cultures for ExRaiAKAR; n = 5 neurons from 5 cultures for S3-ExRaiAKAR).

| P value | 0.8413 |
|---|---|
| ranksum | 29 |

TABLE 44

Statistical analysis for FIG. 21E
Kruskal-Wallis analysis of variance of the degree of clustering followed by post-hoc test via Dunn's test with the degree of clustering at '100 ng' transfection as control group.

| Kruskal-Wallis test | |
|---|---|
| P value | 0.0217 |
| Exact or approximate P value? | Approximate |
| P value summary | * |
| Do the medians vary signif. (P <0.05)? | Yes |
| Number of groups | 5 |
| Kruskal-Wallis statistic | 11.48 |
| Data summary | |
| Number of treatments (columns) | 5 |
| Number of values (total) | 25 |

TABLE 44-continued

Statistical analysis for FIG. 21E
Kruskal-Wallis analysis of variance of the degree of clustering followed by post-hoc test
via Dunn's test with the degree of clustering at '100 ng' transfection as control group.

Number of families 1
Number of comparisons per family 4
Alpha 0.05

| Dunn's multiple comparisons test | Mean rank diff. | Significant? | Summary | Adjusted P Value | A-? | |
|---|---|---|---|---|---|---|
| 100 ng vs. 250 ng | 8.000 | No | ns | 0.3427 | B | 250 ng |
| 100 ng vs. 500 ng | 2.400 | No | ns | >0.9999 | C | 500 ng |
| 100 ng vs. 750 ng | −2.400 | No | ns | >0.9999 | D | 750 ng |
| 100 ng vs. 1000 ng | 11.00 | No | ns | 0.0725 | E | 1000 ng |

| Test details | Mean rank 1 | Mean rank 2 | Mean rank diff. | n1 | n2 | Z |
|---|---|---|---|---|---|---|
| 100 ng vs. 250 ng | 16.80 | 8.800 | 8.000 | 5 | 5 | 1.719 |
| 100 ng vs. 500 ng | 16.80 | 14.40 | 2.400 | 5 | 5 | 0.5156 |
| 100 ng vs. 750 ng | 16.80 | 19.20 | −2.400 | 5 | 5 | 0.5156 |
| 100 ng vs. 1000 ng | 16.80 | 5.800 | 11.00 | 5 | 5 | 2.363 |

TABLE 45

Statistical analysis for FIG. 21F
Kruskal-Wallis analysis of variance of the degree of clustering followed by post-hoc test
via Dunn's test with the degree of clustering at '100 ng' transfection as control group.

| Kruskal-Wallis test | |
|---|---|
| P value | 0.1207 |
| Exact or approximate P value? | Approximate |
| P value summary | ns |
| Do the medians vary signif. (P <0.05)? | No |
| Number of groups | 5 |
| Kruskal-Wallis statistic | 7.303 |
| Data summary | |
| Number of treatments (columns) | 5 |
| Number of values (total) | 25 |

Number of families 1
Number of comparisons per family 4
Alpha 0.05

| Dunn's multiple comparisons test | Mean rank diff. | Significant? | Summary | Adjusted P Value | A-? | |
|---|---|---|---|---|---|---|
| 100 ng vs. 250 ng | 0.4000 | No | ns | >0.9999 | B | 250 ng |
| 100 ng vs. 500 ng | 0.4000 | No | ns | >0.9999 | C | 500 ng |
| 100 ng vs. 750 ng | 7.800 | No | ns | 0.3752 | D | 750 ng |
| 100 ng vs. 1000 ng | −4.600 | No | ns | >0.9999 | E | 1000 ng |

| Test details | Mean rank 1 | Mean rank 2 | Mean rank diff. | n1 | n2 | Z |
|---|---|---|---|---|---|---|
| 100 ng vs. 250 ng | 13.80 | 13.40 | 0.4000 | 5 | 5 | 0.08593 |
| 100 ng vs. 500 ng | 13.80 | 13.40 | 0.4000 | 5 | 5 | 0.08593 |
| 100 ng vs. 750 ng | 13.80 | 6.000 | 7.800 | 5 | 5 | 1.676 |
| 100 ng vs. 1000 ng | 13.80 | 18.40 | −4.600 | 5 | 5 | 0.9882 |

To further test the strategy and investigate Akt (Protein Kinase B (PKB)) activity, an S3-ExRaiAktAR reporter was prepared by replacing the ExRaiAKAR sequence in the S3-ExRaiAKAR polypeptide with ExRaiAktAR, a fluorescent sensor for Akt/PKB (Mehta et al., 2018). S3-ExRaiAktAR was expressed in cultured mouse hippocampal neurons, and as with S3-ExRaiAKAR, green puncta were observed at the soma and neurites in neurons via fluorescent imaging. Following stimulation of neurons expressing S3-ExRaiAktAR with N-Methyl-d-aspartic acid (NMVDA) which is known to increase Akt activity, the S3-ExRaiAktAR green puncta reported increased Akt activity (data not shown).

Thus, the results of these experiments showed that the combination of polyhedron-assembling motifs and coiled-coil forming motifs enables multiple kinds of fluorescent reporter to self-assemble into clusters, effectively, robustly, and safely.

Example 3. Simultaneous Spatially Multiplexed Imaging

These experiments were performed to investigate whether the SiRI toolbox for $Ca^{2+}$, cAMP, and PKA could be used simultaneously to map out relationships between signals within this complex network, in response to a biologically meaningful stimulus. Simultaneous measurements of $Ca^{2+}$, cAMP, and PKA within a single cell is important because of the many ways that these signals may interact with one another, with both feedforward pathways and feedback loops potentially connecting them, in their coupling of cellular input to cellular output. For example, the time dynamics of one signal may influence the amplitude of another signal within this network, important because such relationships determine whether this signal transduction network may effectively drive a cellular output function or state in response to a given cellular input stimulus (Abrams, Karl and Kandel, 1991; Cooper, Mons and Karpen, 1995; Borodinsky and Spitzer, 2006; Mehta and Zhang, 2011; Sassone-Corsi, 2012).

Materials and Methods

See methods described in Examples 1-2 and described in Experiments, Results, and Discussion section.

Experiments, Results, and Discussion

Spatially Multiplexed Imaging of GFP-Based Sensors in Neurons

First, S1-GCaMP6f, S2a-cAMPr, and the cell morphology marker miRFP were co-expressed in cultured mouse hippocampal neurons. Live cell imaging was performed at 20 frames per second in the GFP channel with extracellular stimulation by 5 μM forskolin, and two-color immunostaining was performed against the Xpress™ epitope (which was added as part of the S1-GCaMP6f protein; FIG. 17A) and against the HA epitope (which was added as part of the S2a-cAMPr protein, FIG. 17J). The S1-GCaMP6f and S2a-cAMPr puncta were identified post-hoc via the post-hoc immunostaining (FIG. 23A, entire neuron; FIG. 23B, highlighted dendrite), observing simultaneous $Ca^{2+}$ and cAMP response from sites along a dendrite that were ~5 microns away (FIG. 23C). The number of puncta ranged in the dozens in somata, and in the few hundreds in the neurites (FIG. 23D). To evaluate whether there was crosstalk between the two self-assembling systems, the number of S1-GCaMP6f puncta (as identified by Xpress™ staining) that did not contain S2a-cAMPr (as identified by HA staining) was quantified, and vice versa. It was found that ~90% of the puncta of one kind were free from contamination from the other kind (FIG. 23E), indicating a low level of crosstalk; one could always exclude the puncta with both stains from analysis if more stringency is desired. This high orthogonality of clustering, as well as the function of clustered sensors, held when these two constructs were tried in HeLa cells as well (see FIG. 24A-E).

As with HeLa cells, $Ca^{2+}$, and cAMP responses in neurons exhibited different relationships that were apparent when simultaneously measured, but which would be lost if measured in separate populations of neurons and then compared in the aggregate. For example, when measured at the soma (FIG. 25), neurons exhibited $Ca^{2+}$ responses that could be oscillatory (cells 1, 3, 4, 6) or smooth (cells 2, 5), whereas cAMP responses were relatively smooth and non-oscillatory (cells 1-6). This finding raises the question of whether $Ca^{2+}$-cAMP coupling might vary from neuron to neuron as a function of cell state. These relationships varied in the soma vs. the dendrite: for example, some neurons had similar $Ca^{2+}$-cAMP relationships in the dendrites as in the soma (cells 1, 3, 4), but others varied in the oscillatory quality of the $Ca^{2+}$ responses at different points in the cell (cells 2, 5, 6). These results hint at how the interactions between different signaling cascades might be modulated by cell state, although full characterization of whether and how these interactions are modulated would require scientific probing via many different techniques (pharmacological blockade, gene silencing, etc.) and thus are beyond the scope of this technology-oriented study.

Spatially Multiplexed Imaging of Three GFP-Based Sensors in Single Neurons

Figure 13A:
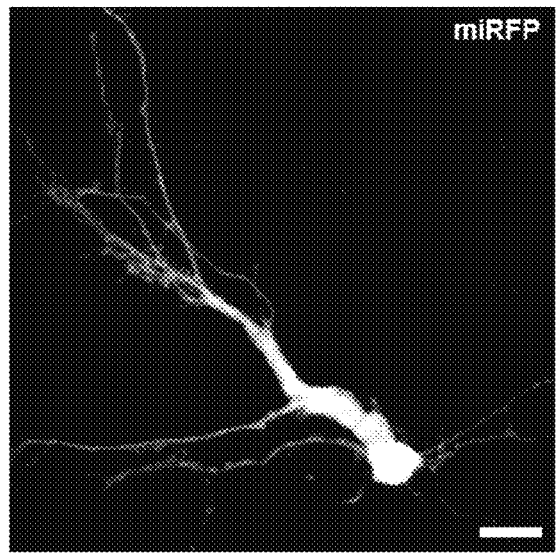
Figure 13A:
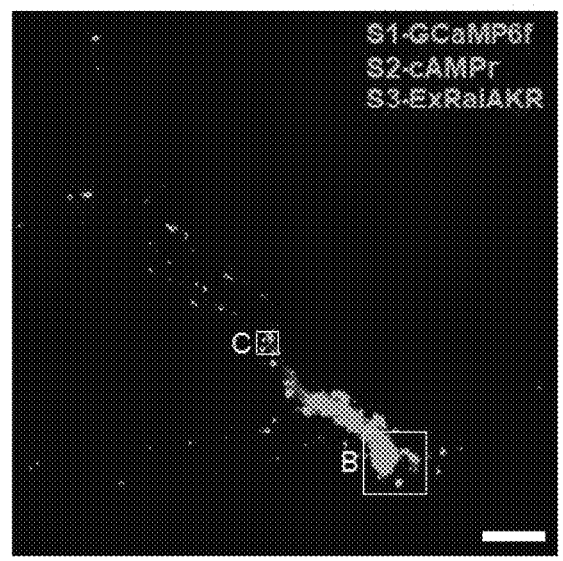
Figure 13A:
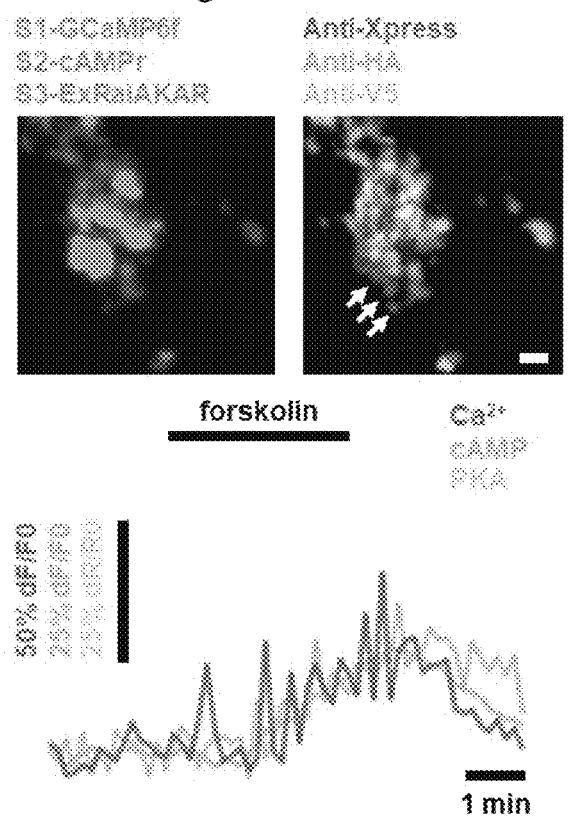
Figure 13A:
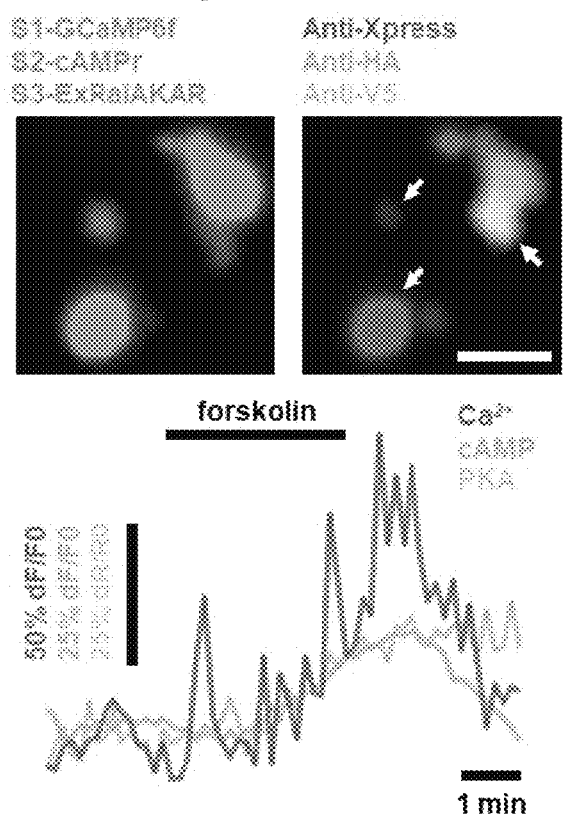
Figure 13F:
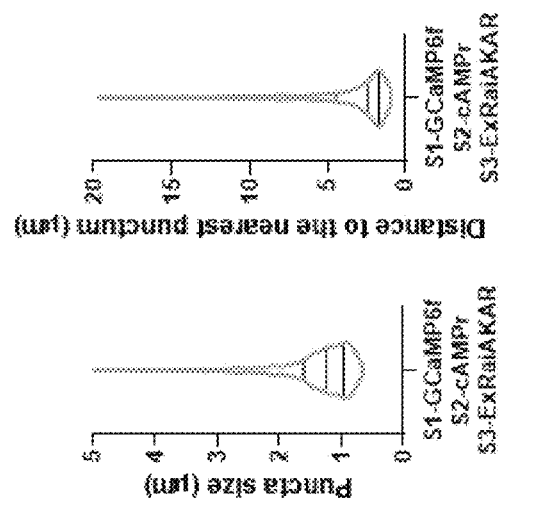
Figure 13E:
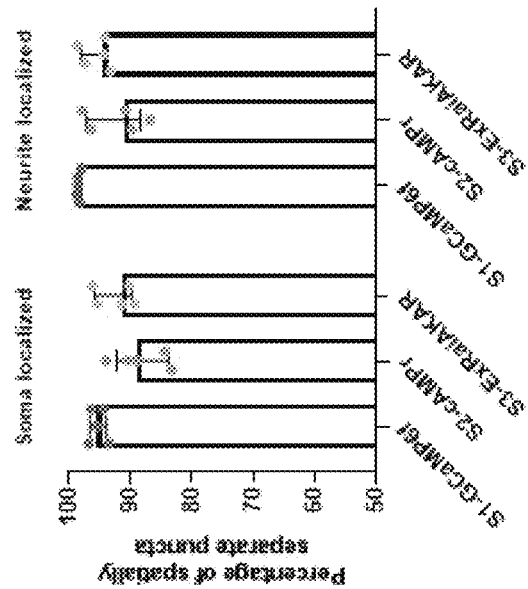

Spatially multiplexed imaging was further tested by co-expressing three (S1-GCaMP6f, S2a-cAMPr, and S3-ExRaiAKAR; FIGS. 26A-J; FIGS. 13A-C) and the cell morphology marker miRFP in cultured mouse hippocampal neurons. Volumetric live imaging of neurons was performed in the GFP channel to record simultaneous $Ca^{2+}$, cAMP and PKA responses to forskolin stimulation, which as a pharmacological driver of cAMP production has been used as one of many model stimuli for inducing synaptic plasticity (such as long-term potentiation, LTP (Chavez-Noriega and Stevens, 1992; Barco, Alarcon and Kandel, 2002; Otmakhov et al., 2004; Wozny et al., 2008; Li et al., 2018)), neural survival (Hanson et al., 1998), neural growth (Chijiwa et al., 1990), and many other important functions and disease-related processes in neurons. Furthermore, as described elsewhere herein, cAMP production can directly drive PKA activation, and through cAMP-dependent ion channels and effects downstream of PKA, modulate $Ca^{2+}$ influx and intracellular store release as well (which in turn can modulate cAMP production via $Ca^{2+}$-modulated adenylyl cyclases), making it a meaningful node of this signal transduction network to selectively control. Forskolin has been used on multiple kinds of cultured neurons and been shown to engage not only cAMP production, but also cAMP-dependent modulation of $Ca^{2+}$ concentration and PKA activity (Zanassi et al., 2001; Gorbunova and Spitzer, 2002; Otsuguro et al., 2005). Forskolin-induced changes in cAMP have also been shown to increase the frequency of $Ca^{2+}$ oscillations in some, but not all, neurons thus treated (Gorbunova and Spitzer, 2002), motivating further the simultaneous imaging of multiple signals within individual cells, so that any heterogeneity across cells of cAMP-$Ca^{2+}$ coupling may be observed and analyzed in terms of how such variation in cellular state might modulate cellular output.

Simultaneous imaging of three fluorescent reporters of $Ca^{2+}$, cAMP, and PKA that are based on different fluorescent proteins (Mehta et al., 2018) would require either filter switching and the reuse of the camera for serial imaging of the three channels, which may slow down the frame rate of imaging, or multiple light paths and cameras, increasing instrument complexity and expense. In addition, the use of multiple fluorophores would typically involve the risk of bleedthrough of light from one sensor into a separate spectral channel, requiring extensive characterization of how sets of sensors overlap before they are used in a given experiment, and computational correction to unmix the signals could add additional complexity or error due to potential sample-to-sample variation of the bleedthrough. These experiments therefore investigated whether the use of SiRIs with fluorophores all of the same color, made possible a recording rate of 5 seconds per volume, using just one filter set, and whether SiRIs avoided bleedthrough concerns due to their spatially multiplexed nature.

Figure 11A:
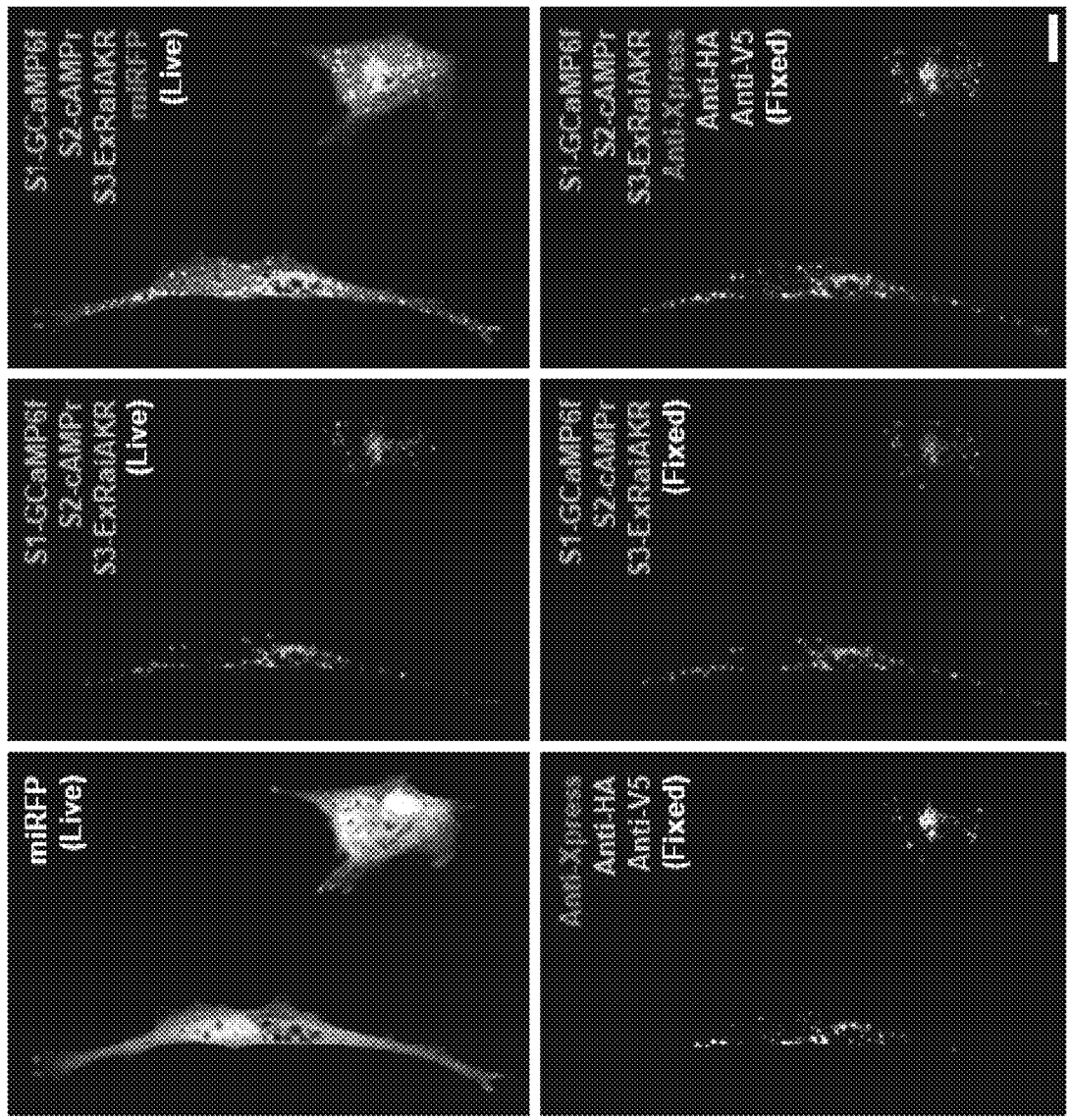
FIG. 11A-C provides photomicrographic images, traces, and graphs illustrating results from studies of spatially multiplexed imaging of three GFP-based reporters for calcium, cAMP, and PKA activities in a human cell line. Related to FIG. 3.
Figures 11B, 11C:
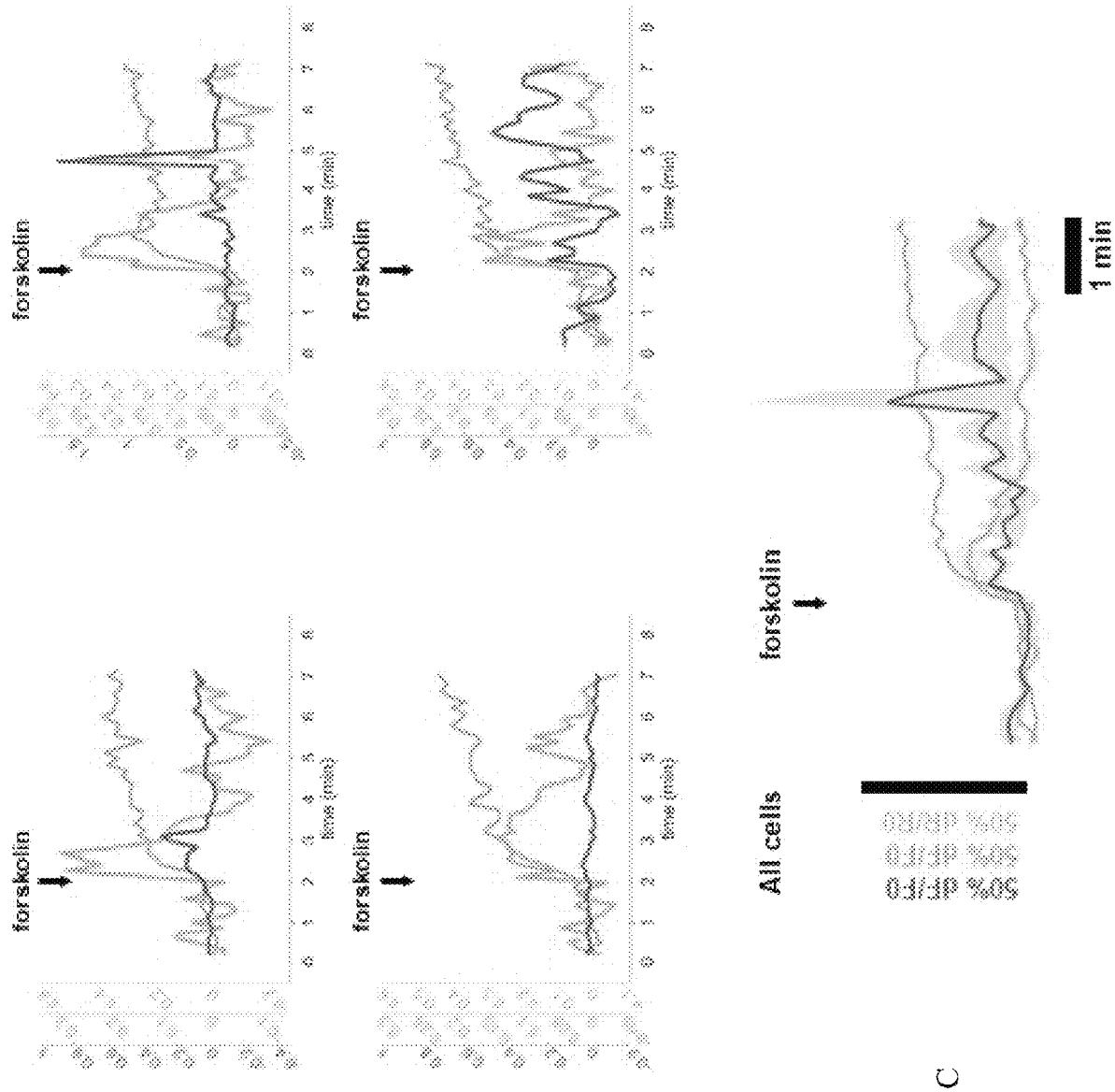

After performing live imaging, the neurons were fixed and three-color immunostaining was performed against the epitopes associated with each scaffold (FIG. 8A, 8H, 8O, Table 32), so that the reporter identity associated with each puncta could be derived (FIG. 13B-C, top; FIG. 12A-F, additional fields of view of the neuron), and time courses of each signal associated with each punctum (FIG. 13B-C, bottom; FIG. 12A-F, additional fields of view of the neuron). Each reporter was found in tens of distinct locations within cell bodies, and hundreds of distinct locations along neurites of neurons (FIG. 13D). The vast majority (~90%) of the puncta were unique to one reporter, and not colocalized with puncta of other kinds, indicating orthogonality of the clustering reagents, and spatial separation between the reporters (FIG. 13E; puncta with multi-reporter overlap were not analyzed in the dynamics studies that follow). Puncta were comparable in size (FIG. 13F, left) and punctum-punctum distance (FIG. 13F, right) when expressed together, as when expressed alone (FIG. 8, Tables 11-13, 30-32, and 41-43). For forskolin provided in this globally administered fashion, it was observed that $Ca^{2+}$ responses were highly correlated across different sites within the soma, across different points within single neurites (sampled along neurite locations 20-60 μm away from the soma), and across neurites within a given neuron, although comparing $Ca^{2+}$ at a point in the soma vs. a point in a neurite showed a somewhat lower correlation (FIG. 12G, Table 46); cAMP (FIG. 12H, Table 47) and PKA activity (FIG. 12I, Table 48) were also highly correlated across different points within a neuron. These three SiRIs were used simultaneously in HeLa cells as well (FIG. 11). Tables 46-48 show statistical analyses of FIGS. 12G-I.

TABLE 46

Figure 12C:
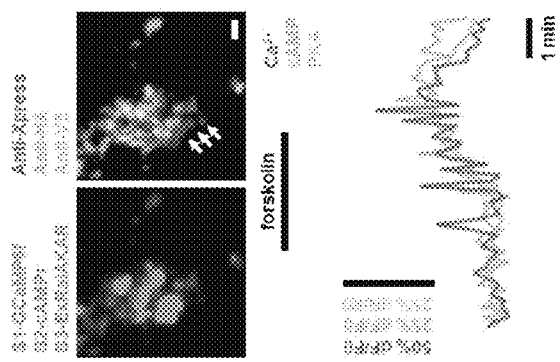
FIG. 12A-I presents schematics, photomicrographs, and graphs reporting results of spatially multiplexed imaging of three GFP-based reporters for calcium, cAMP, and PKA activities at different subcellular locations in single neuron. Related to FIG. 13.
Figure 12E:
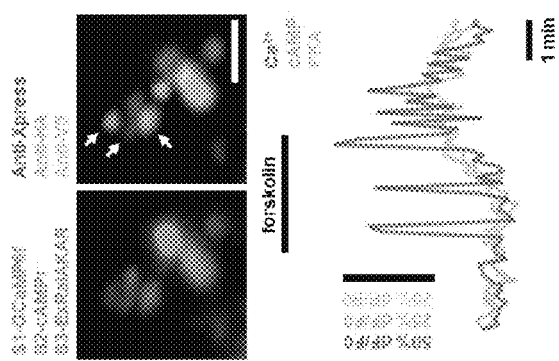
Figure 12B:
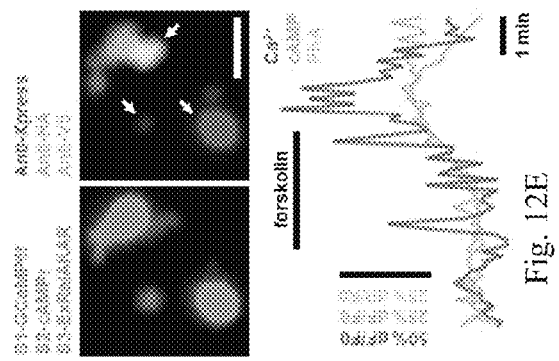
Figure 12D:
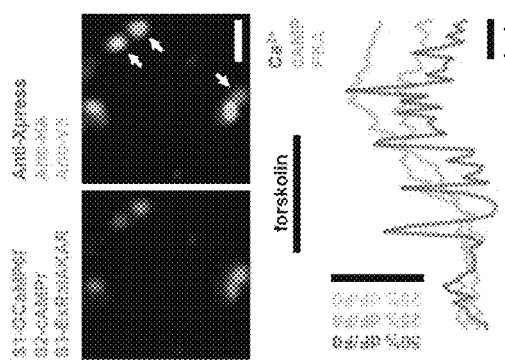
Figure 12A:
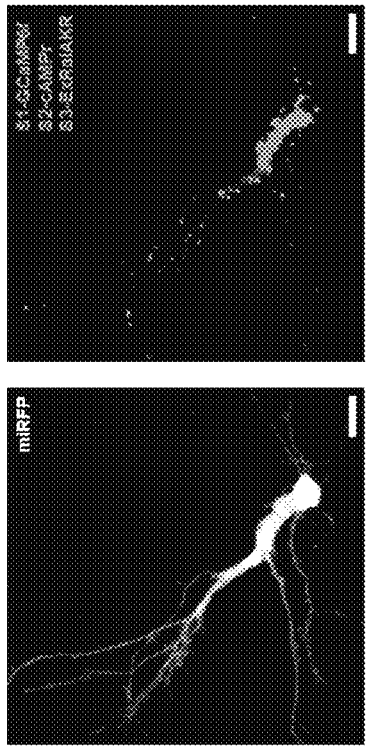
Figure 12F:
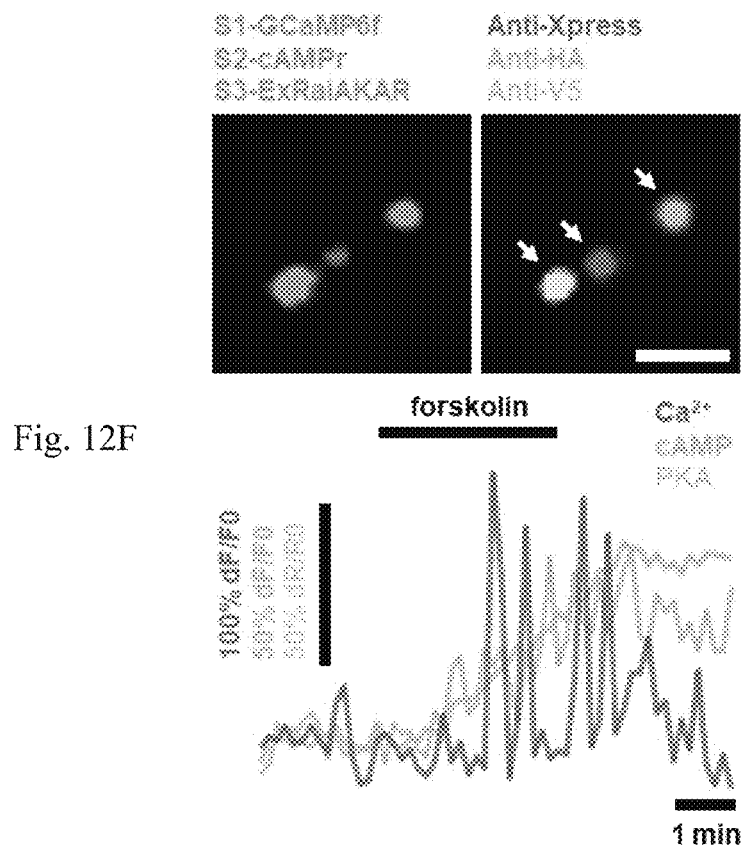
Figure 12G:
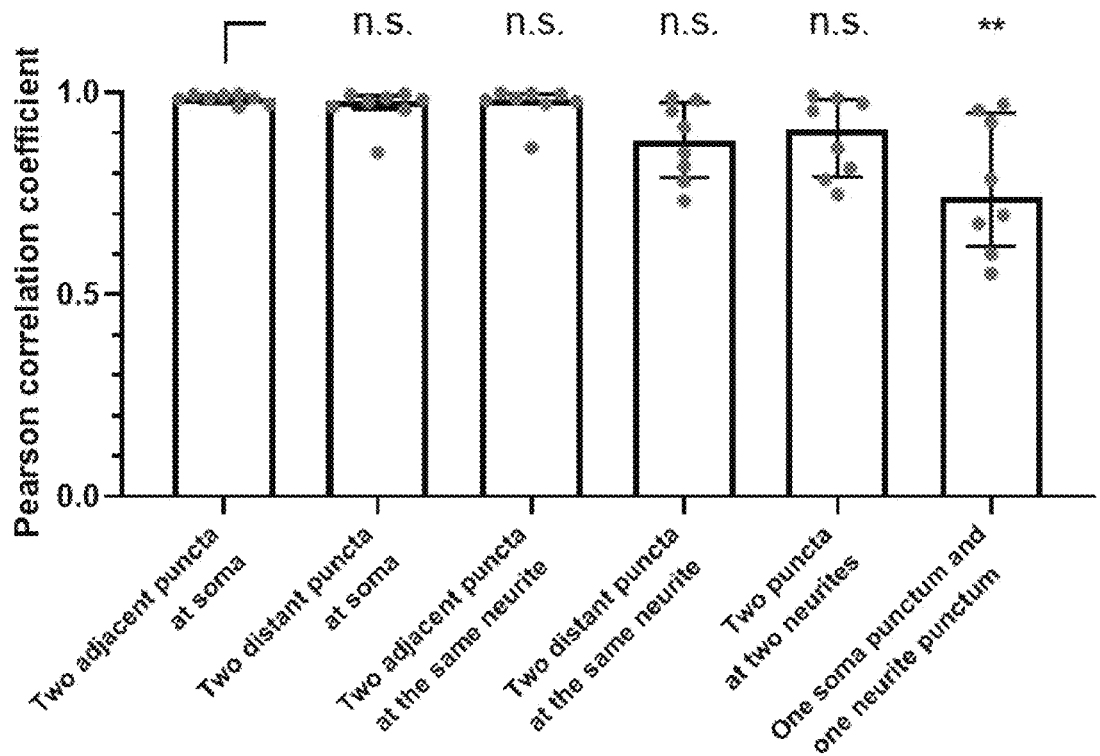
Figure 13D:
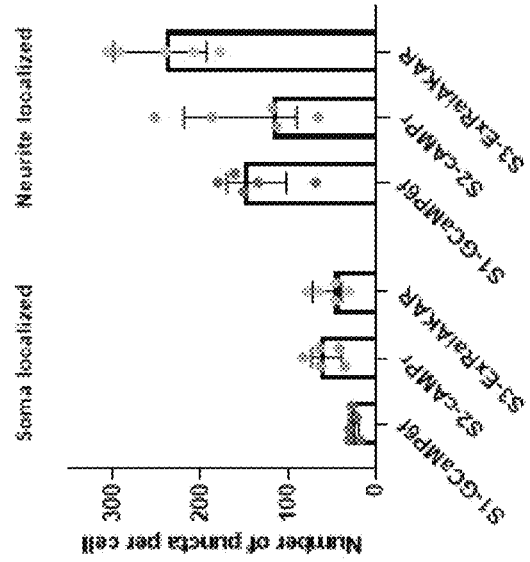

Statistical analysis for FIG. 12G
Kruskal-Wallis analysis of variance for Pearson correlation coefficients of the $Ca^{2+}$ responses recorded from soma and neurite localized puncta within single cultured mouse hippocampal neurons co-expressing S1-GCaMP6f, S2-cAMPr, S3-ExRaiAKAR, and miRFP, followed by post-hoc Dunn's multiple comparisons test with 'two adjacent puncta at soma' as control group (n = 8 neurons from 8 cultures).

| Kruskal-Wallis test | |
| --- | --- |
| P value | 0.0008 |
| Exact or approximate P value? | Approximate |
| P value summary | *** |
| Do the medians vary signif. (P <0.05)? | Yes |
| Number of groups | 6 |
| Kruskal-Wallis statistic | 21.08 |

| Dunn's multiple comparisons test | Mean rank diff. | Significant? | Summary | Adjusted P Value |
| --- | --- | --- | --- | --- |
| Two adjacent puncta at soma vs. Two distant puncta at soma | 4.750 | No | ns | >0.9999 |
| Two adjacent puncta at soma vs. Two adjacent puncta at the same neurite | 1.000 | No | ns | >0.9999 |
| Two adjacent puncta at soma vs. Two distant puncta at the same neurite | 17.75 | No | ns | 0.0561 |
| Two adjacent puncta at soma vs. Two puncta at two neurites | 15.38 | No | ns | 0.1403 |
| Two adjacent puncta at soma vs. One soma punctum and one neurite punctum | 24.88 | Yes | ** | 0.0019 |

| Test details | Mean rank 1 | Mean rank 2 | Mean rank diff. | n1 | n2 | Z |
| --- | --- | --- | --- | --- | --- | --- |
| Two adjacent puncta at soma vs. Two distant puncta at soma | 35.13 | 30.38 | 4.750 | 8 | 8 | 0.6786 |
| Two adjacent puncta at soma vs. Two adjacent puncta at the same neurite | 35.13 | 34.13 | 1.000 | 8 | 8 | 0.1429 |
| Two adjacent puncta at soma vs. Two distant puncta at the same neurite | 35.13 | 17.38 | 17.75 | 8 | 8 | 2.536 |
| Two adjacent puncta at soma vs. Two puncta at two neurites | 35.13 | 19.75 | 15.38 | 8 | 8 | 2.196 |

TABLE 46-continued

Statistical analysis for FIG. 12G
Kruskal-Wallis analysis of variance for Pearson correlation coefficients of the $Ca^{2+}$
responses recorded from soma and neurite localized puncta within single cultured mouse
hippocampal neurons co-expressing S1-GCaMP6f, S2-cAMPr, S3-ExRaiAKAR, and miRFP,
followed by post-hoc Dunn's multiple comparisons test with 'two adjacent puncta at soma' as
control group (n = 8 neurons from 8 cultures).

| | | | | | | |
|---|---|---|---|---|---|---|
| Two adjacent puncta at soma vs. One soma punctum and one neurite punctum | 35.13 | 10.25 | 24.88 | 8 | 8 | 3.554 |

TABLE 47

Figure 12H:
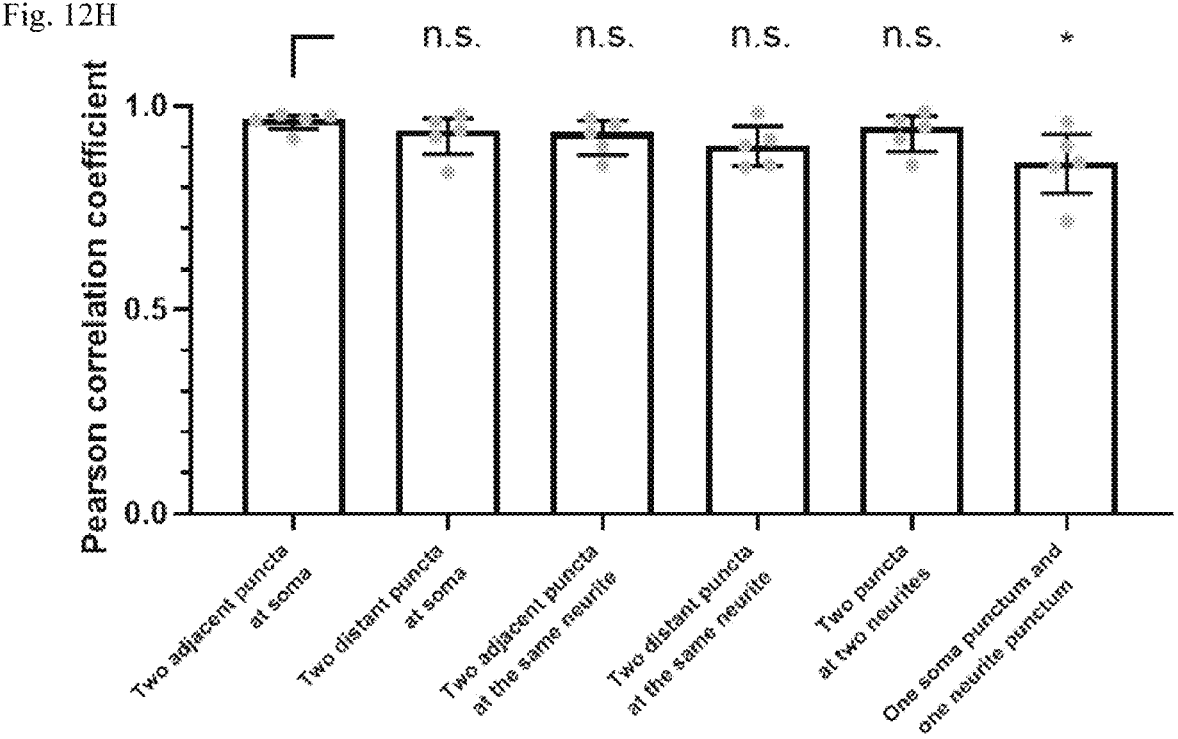

Statistical analysis for FIG. 12H
Kruskal-Wallis analysis of variance for Pearson correlation coefficients of the cAMP
responses recorded from soma and neurite localized puncta within single cultured mouse
hippocampal neurons co-expressing S1-GCaMP6f, S2-cAMPr, S3-ExRaiAKAR, and miRFP,
followed by post-hoc Dunn's multiple comparisons test with 'two adjacent puncta at soma' as
control group (n = 5 neurons from 5 cultures).

| Kruskal-Wallis test | |
|---|---|
| P value | 0.1526 |
| Exact or approximate P value? | Approximate |
| P value summary | ns |
| Do the medians vary signif. (P <0.05)? | No |
| Number of groups | 6 |
| Kruskal-Wallis statistic | 8.066 |

| Dunn's multiple comparisons test | Mean rank diff. | Significant? | Summary | Adjusted P Value |
|---|---|---|---|---|
| Two adjacent puncta at soma vs. Two distant puncta at soma | 6.600 | No | ns | >0.9999 |
| Two adjacent puncta at soma vs. Two adjacent puncta at the same neurite | 7.600 | No | ns | 0.8613 |
| Two adjacent puncta at soma vs. Two distant puncta at the same neurite | 11.00 | No | ns | 0.2410 |
| Two adjacent puncta at soma vs. Two puncta at two neurites | 5.200 | No | ns | >0.9999 |
| Two adjacent puncta at soma vs. One soma punctum and one neurite punctum | 14.60 | Yes | * | 0.0437 |

| Test details | Mean rank 1 | Mean rank 2 | Mean rank diff. | n1 | n2 | Z |
|---|---|---|---|---|---|---|
| Two adjacent puncta at soma vs. Two distant puncta at soma | 23.00 | 16.40 | 6.600 | 5 | 5 | 1.185 |
| Two adjacent puncta at soma vs. Two adjacent puncta at the same neurite | 23.00 | 15.40 | 7.600 | 5 | 5 | 1.365 |
| Two adjacent puncta at soma vs. Two distant puncta at the same neurite | 23.00 | 12.00 | 11.00 | 5 | 5 | 1.976 |
| Two adjacent puncta at soma vs. Two puncta at two neurites | 23.00 | 17.80 | 5.200 | 5 | 5 | 0.9339 |

TABLE 47-continued

Statistical analysis for FIG. 12H
Kruskal-Wallis analysis of variance for Pearson correlation coefficients of the cAMP
responses recorded from soma and neurite localized puncta within single cultured mouse
hippocampal neurons co-expressing S1-GCaMP6f, S2-cAMPr, S3-ExRaiAKAR, and miRFP,
followed by post-hoc Dunn's multiple comparisons test with 'two adjacent puncta at soma' as
control group (n = 5 neurons from 5 cultures).

| | | | | | | |
|---|---|---|---|---|---|---|
| Two adjacent puncta at soma vs. One soma punctum and one neurite punctum | 23.00 | 8.400 | 14.60 | 5 | 5 | 2.622 |

TABLE 48

Figure 12I:
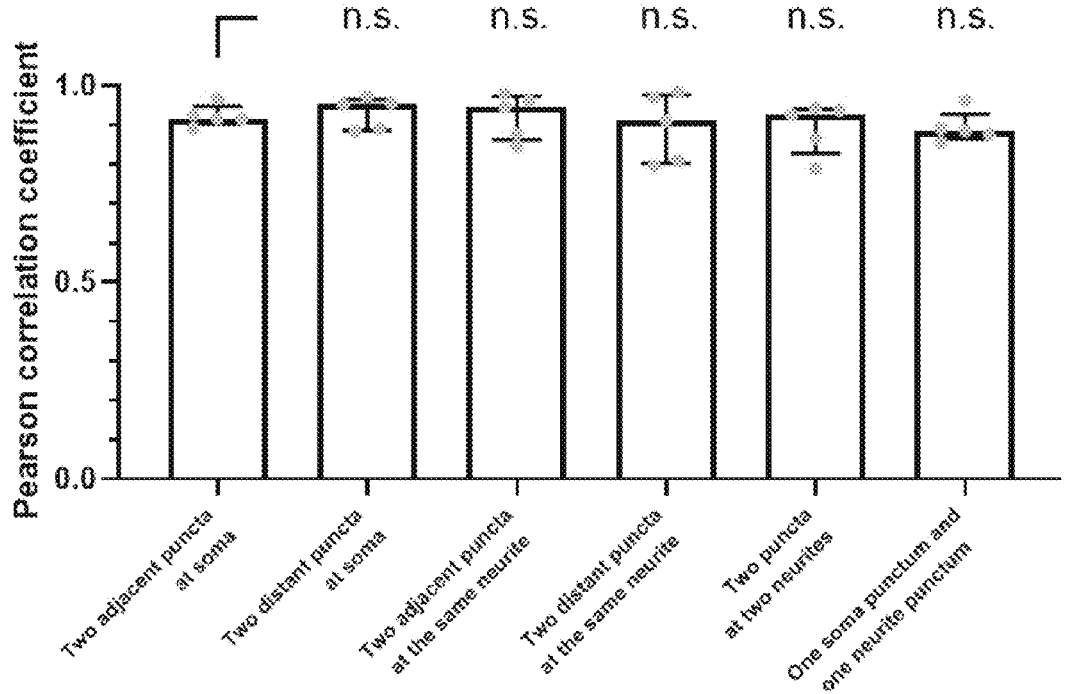

Statistical analysis for FIG. 12I
Kruskal-Wallis analysis of variance for Pearson correlation coefficients of the PKA
responses recorded from soma and neurite localized puncta within single cultured mouse
hippocampal neurons co-expressing S1-GCaMP6f, S2-cAMPr, S3-ExRaiAKAR, and miRFP,
followed by post-hoc Dunn's multiple comparisons test with 'two adjacent puncta at soma' as
control group (n = 5 neurons from 5 cultures).

| Kruskal-Wallis test | |
|---|---|
| P value | 0.7511 |
| Exact or approximate P value? | Approximate |
| P value summary | ns |
| Do the medians vary signif. (P <0.05)? | No |
| Number of groups | 6 |
| Kruskal-Wallis statistic | 2.667 |

| Dunn's multiple comparisons test | Mean rank diff. | Significant? | Summary | Adjusted P Value |
|---|---|---|---|---|
| Two adjacent puncta at soma vs. Two distant puncta at soma | −1.000 | No | ns | >0.9999 |
| Two adjacent puncta at soma vs. Two adjacent puncta at the same neurite | 0.2000 | No | ns | >0.9999 |
| Two adjacent puncta at soma vs. Two distant puncta at the same neurite | 2.400 | No | ns | >0.9999 |
| Two adjacent puncta at soma vs. Two puncta at two neurites | 5.000 | No | ns | >0.9999 |
| Two adjacent puncta at soma vs. One soma punctum and one neurite punctum | 6.000 | No | ns | >0.9999 |

| Test details | Mean rank 1 | Mean rank 2 | Mean rank diff. | n1 | n2 | Z |
|---|---|---|---|---|---|---|
| Two adjacent puncta at soma vs. Two distant puncta at soma | 17.60 | 18.60 | −1.000 | 5 | 5 | 0.1796 |
| Two adjacent puncta at soma vs. Two adjacent puncta at the same neurite | 17.60 | 17.40 | 0.2000 | 5 | 5 | 0.03592 |
| Two adjacent puncta at soma vs. Two distant puncta at the same neurite | 17.60 | 15.20 | 2.400 | 5 | 5 | 0.4311 |
| Two adjacent puncta at soma vs. Two puncta at two neurites | 17.60 | 12.60 | 5.000 | 5 | 5 | 0.8980 |

TABLE 48-continued

Statistical analysis for FIG. 121
Kruskal-Wallis analysis of variance for Pearson correlation coefficients of the PKA
responses recorded from soma and neurite localized puncta within single cultured mouse
hippocampal neurons co-expressing S1-GCaMP6f, S2-cAMPr, S3-ExRaiAKAR, and miRFP,
followed by post-hoc Dunn's multiple comparisons test with 'two adjacent puncta at soma' as
control group (n = 5 neurons from 5 cultures).

| | | | | | | |
|---|---|---|---|---|---|---|
| Two adjacent puncta at soma vs. One soma punctum and one neurite punctum | 17.60 | 11.60 | 6.000 | 5 | 5 | 1.078 |

$Ca^{2+}$, cAMP, and PKA activity was imaged in 24 neurons during and after 3 min of forskolin stimulation (FIG. 27, raw data; Tables 49-52). When averaged across all neurons, it was observed that increases in $Ca^{2+}$ and cAMP levels decayed after removal of forskolin, and PKA activity persisted after removal of forskolin, at both somatic (FIG. 13G, left) and neurite locations (FIG. 13G, right; sampled at neurite locations 20-60 m away from the soma; responses were highly correlated across neurite locations within a neuron). Thus, SiRIs were used to perform simultaneous imaging of multiple signals within single living cells, revealing their response to a stimulus.

Figure 13J:
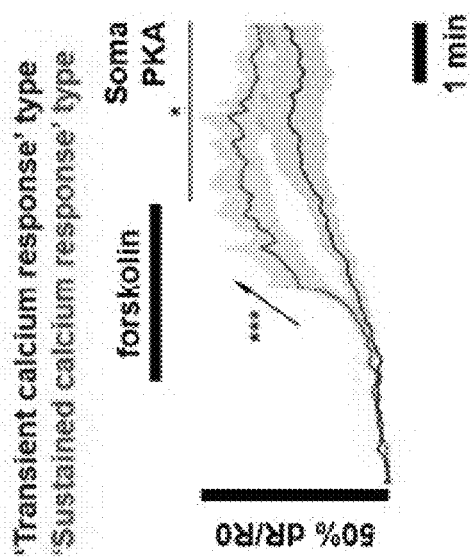

As referred to elsewhere herein, forskolin-driven cAMP has been shown to increase the frequency of spontaneous $Ca^{2+}$ oscillations, in some, but not all, neurons thus treated (Gorbunova and Spitzer, 2002). It was observed that some cultured hippocampal neurons exhibited transient, often oscillatory, somatic $Ca^{2+}$ responses, with each increase in $Ca^{2+}$ concentration lasting 1 minute or less (FIG. 13H), whereas others exhibited sustained $Ca^{2+}$ responses at the soma, with at least one $Ca^{2+}$ elevation event lasting for ~2-6 minutes (FIG. 13I). Analyzing whether the transient versus sustained $Ca^{2+}$ responses differed in other ways revealed that neurons with sustained $Ca^{2+}$ responses had significantly higher peak $Ca^{2+}$ increases during forskolin stimulation than neurons with transient $Ca^{2+}$ responses (FIG. 13J, Table 49). However, the peak $Ca^{2+}$ amplitudes measured after forskolin removal, and the peak $Ca^{2+}$ amplitudes when considered over the entire time course of the experiment, were similar across the two groups (FIG. 13J, Table 49). It was therefore hypothesized that neurons with transient $Ca^{2+}$ responses were also delayed in their $Ca^{2+}$ responses, relative to the neurons with sustained $Ca^{2+}$ responses. When the time after forskolin administration when $Ca^{2+}$ reached the half-rise point to its peak was analyzed, and considered over the entire time course of the experiment, transient $Ca^{2+}$ response neurons had latencies ~1.2 minutes longer (~58% longer) than sustained $Ca^{2+}$ response neurons (FIG. 13J, Table 49). These variations may have resulted from the presence of different kinds, or amounts, of signal transduction machinery that connect cAMP signals to $Ca^{2+}$ signals.

Figure 13K:
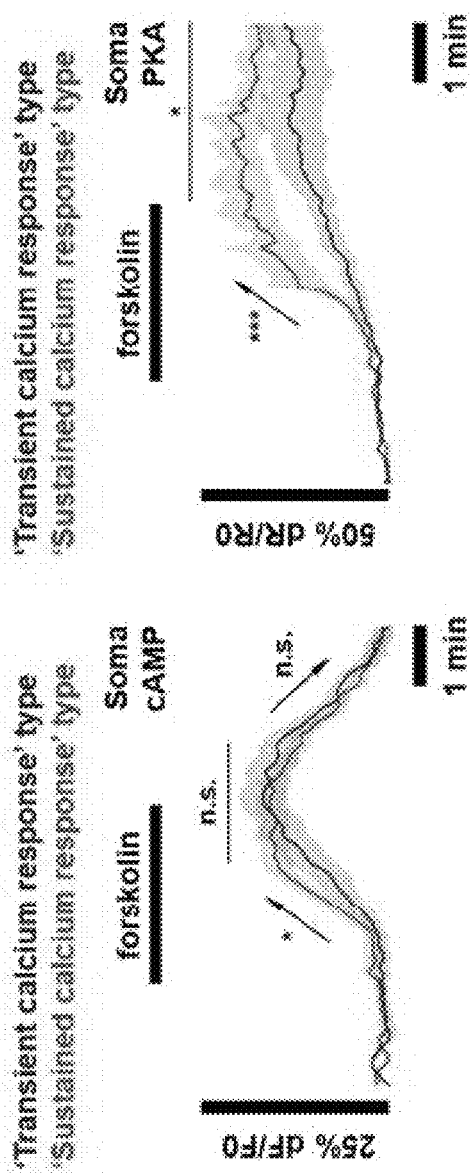
Figure 13L:
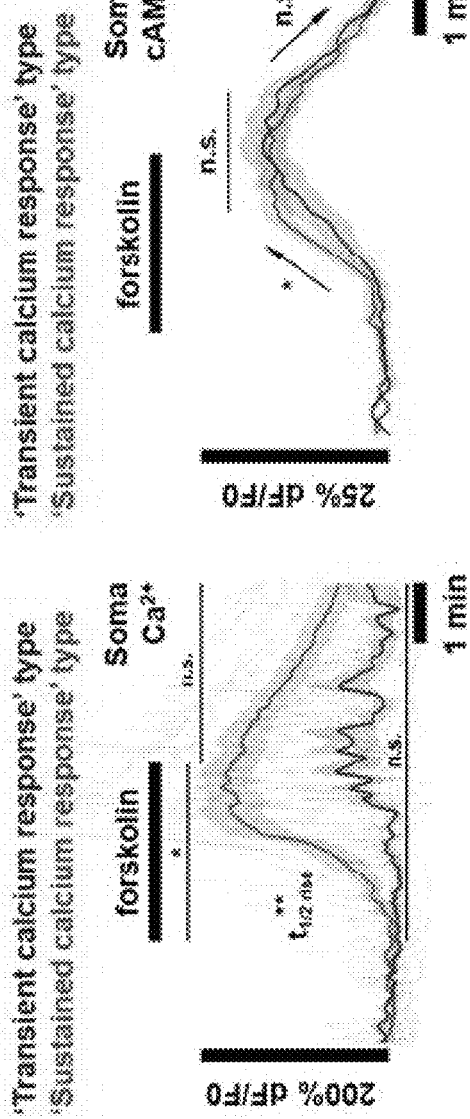

Because $Ca^{2+}$ and cAMP signals could influence each other bidirectionally, experiments were then performed to investigate whether such variations in $Ca^{2+}$ dynamics were associated with any variations in cAMP dynamics. Neurons that exhibited sustained, shorter-latency $Ca^{2+}$ responses at the soma had faster rises in cAMP at the soma than did those with transient, longer-latency $Ca^{2+}$ responses (FIG. 13K, Table 50). This could have resulted because the sustained, shorter-latency $Ca^{2+}$ responses fed back upon the forskolin-driven cAMP responses to accelerate them, or because the faster initial cAMP response to forskolin fed forward to result in faster $Ca^{2+}$ responses. Next, these variations in cAMP and $Ca^{2+}$ dynamics were analyzed to determine whether they were associated with variations in PKA signaling, which as a sustained activity that persists beyond the duration of forskolin stimulation (FIG. 13G), might represent a potential output state of this signaling network, in the context of this experiment. PKA signals at the soma not only rose faster in neurons with sustained, short-latency $Ca^{2+}$ responses and fast cAMP increases, than in neurons with transient, longer-latency $Ca^{2+}$ responses and slower cAMP increases, but also achieved higher activity levels at the end of the experiment (FIG. 13L, Table 51). Similar relationships were apparent when $Ca^{2+}$, cAMP, and PKA activities were analyzed at sites along neurites (FIG. 27, Tables 49-52).

Thus, the simultaneous nature of SiRI-based imaging of multiple components of a signal transduction network allowed the derivation of relationships between the different components, and, ultimately, the analysis of how dynamics within the network related to network output. Importantly, such relationships could not be derived by inspecting FIG. 13G—that is, the relationship between the temporal structure of $Ca^{2+}$ dynamics, the rate of cAMP signaling, and the rate and magnitude of PKA signaling could not be derived by observing these signals in separate cells, and then comparing them after averaging. Future studies could use SiRIs to help determine whether there are different factors present in cells with sustained versus transient $Ca^{2+}$ responses—e.g. whether the former have more $Ca^{2+}$ conducting channels, or more proteins that couple cAMP to $Ca^{2+}$, or whether there are additional connections within the feedback loops that couple different messengers to each other. Tables 49-52 show statistical analyses for FIGS. 13J-L, and FIGS. 27C-O.

TABLE 49

Statistical analysis for FIG. 13J, FIG. 27C, and FIGS. 27F-27I
Throughout this table (unless specified otherwise): statistical tests were performed between the 'transient calcium responses' type and the 'sustained calcium responses' type; for 'transient calcium responses' type, n = 7 somata from 7 neurons from 6 cultures and n = 7 neurites from 7 neurons from 7 cultures; for 'sustained calcium responses' type, n = 17 somata from 17 neurons from 12 cultures and n = 16 neurites from 16 neurons from 12 cultures.

| Wilcoxon rank sum test for somatic $Ca^{2+}$ overall peak response (from the onset of forskolin stimulation to the end of recording) | |
|---|---|
| P value | 0.0754 |
| zval | −1.7783 |
| ranksum | 59 |

TABLE 49-continued

Statistical analysis for FIG. 13J, FIG. 27C, and FIGS. 27F-27I
Throughout this table (unless specified otherwise): statistical tests were performed between the 'transient calcium responses' type and the 'sustained calcium responses' type; for 'transient calcium responses' type, n = 7 somata from 7 neurons from 6 cultures and n = 7 neurites from 7 neurons from 7 cultures; for 'sustained calcium responses' type, n = 17 somata from 17 neurons from 12 cultures and n = 16 neurites from 16 neurons from 12 cultures.

Wilcoxon rank sum test for somatic $Ca^{2+}$ peak response during forskolin stimulation

| | |
|---|---|
| P value | 0.0158 |
| zval | −2.4134 |
| ranksum | 49 |

Wilcoxon rank sum test for somatic $Ca^{2+}$ peak response after forskolin stimulation (from the end of forskolin stimulation to the end of recording)

| | |
|---|---|
| P value | 0.1274 |
| zval | −1.5243 |
| ranksum | 63 |

Wilcoxon rank sum test for the time to half rise of somatic $Ca^{2+}$ response (the duration from the onset of forskolin stimulation to the time when $Ca^{2+}$ response first reaches half of the overall peak response)

| | |
|---|---|
| P value | 0.0092 |
| zval | 2.6039 |
| ranksum | 129 |

Wilcoxon rank sum test for neurite $Ca^{2+}$ overall peak response (from the onset of forskolin stimulation to the end of recording)

| | |
|---|---|
| P value | 0.0111 |
| zval | −2.5404 |
| ranksum | 47 |

Wilcoxon rank sum test for neurite $Ca^{2+}$ peak response during forskolin stimulation

| | |
|---|---|
| P value | 0.0052 |
| zval | −2.7945 |
| ranksum | 43 |

Wilcoxon rank sum test for neurite $Ca^{2+}$ peak response after forskolin stimulation (from the end of forskolin stimulation to the end of recording)

| | |
|---|---|
| P value | 0.0076 |
| zval | −2.6675 |
| ranksum | 45 |

TABLE 49-continued

Statistical analysis for FIG. 13J, FIG. 27C, and FIGS. 27F-27I
Throughout this table (unless specified otherwise): statistical tests were performed between the 'transient calcium responses' type and the 'sustained calcium responses' type; for 'transient calcium responses' type, n = 7 somata from 7 neurons from 6 cultures and n = 7 neurites from 7 neurons from 7 cultures; for 'sustained calcium responses' type, n = 17 somata from 17 neurons from 12 cultures and n = 16 neurites from 16 neurons from 12 cultures.

Wilcoxon rank sum test for the time to half rise of neurite $Ca^{2+}$ response (the duration from the onset of forskolin stimulation to the time when $Ca^{2+}$ response first reaches half of the overall peak response)

| | |
|---|---|
| P value | 0.0045 |
| zval | 2.8404 |
| ranksum | 127 |

TABLE 50

Statistical analysis for FIG. 3K, FIG. S10D, and FIGS. S10J-S10L

Wilcoxon rank sum test for somatic cAMP peak response

| | |
|---|---|
| P value | 0.7995 |
| ranksum | 83 |
| zval | −0.2540 |

Wilcoxon rank sum test for neurite cAMP peak response

| | |
|---|---|
| P value | 0.8673 |
| ranksum | 81 |
| zval | −0.1670 |

Wilcoxon rank sum test for somatic cAMP rise slope

| | |
|---|---|
| P value | 0.0158 |
| ranksum | 49 |
| zval | −2.4134 |

Wilcoxon rank sum test for neurite cAMP rise slope

| | |
|---|---|
| P value | 0.0083 |
| ranksum | 44 |
| zval | −2.6392 |

Wilcoxon rank sum test for somatic cAMP decay slope

| | |
|---|---|
| P value | 0.8489 |
| ranksum | 91 |
| zval | 0.1905 |

Wilcoxon rank sum test for neurite cAMP decay slope

| | |
|---|---|
| P value | 0.2703 |
| ranksum | 101 |
| zval | 1.1025 |

TABLE 51

Statistical analysis for FIG. 13L, FIG. 27E, and FIGS. 27M-27N

Wilcoxon rank sum test for somatic PKA peak response

| | |
|---|---|
| P value | 0.0490 |
| ranksum | 56 |
| zval | −1.9688 |

TABLE 51-continued

Statistical analysis for FIG. 13L, FIG. 27E, and FIGS. 27M-27N

Wilcoxon rank sum test for
neurite PKA peak response

| | |
|---|---|
| P value | 0.0083 |
| ranksum | 44 |
| zval | −2.6392 |

Wilcoxon rank sum test for
somatic PKA rise slope

| | |
|---|---|
| P value | 7.6248e−04 |
| ranksum | 34 |
| zval | −3.3661 |

Wilcoxon rank sum test for
neurite PKA rise slope

| | |
|---|---|
| P value | 0.0353 |
| ranksum | 52 |
| zval | −2.1047 |

TABLE 52

Statistical analysis for FIG. 27O
Wilcoxon rank sum test for the punctum sizes
of puncta in the GFP channel, between those in
neurons with 'transient calcium responses' and
those in neurons with 'sustained calcium responses'
under 50 μM forskolin stimulation for 3 minutes
(n = 512 and 630 puncta in 5 and 5 neurons
co-expressing S1-GCaMP6f, S2-cAMPr, S3-ExRaiAKAR,
and miRFP from 5 and 5 cultures for neurons with
'transient calcium responses' and neurons with
'sustained calcium responses', respectively).

| | |
|---|---|
| P value | 0.1890 |
| ranksum | 2.9989e+05 |
| zval | 1.3137 |

Figure 21G:
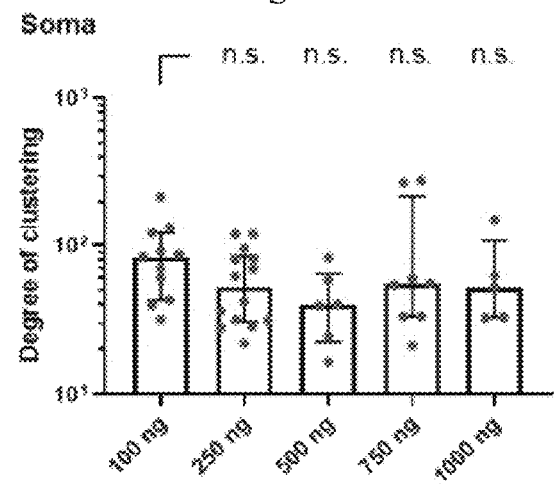
Figure 21H:
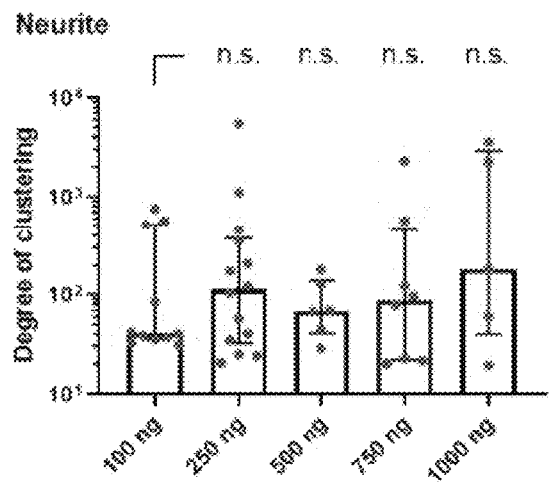

Spatially Multiplexed Imaging of More than 3 Fluorescent Reporters in Neurons, and Combined Spatial and Spectral Multiplexing Spatially multiplexed imaging was further tested by co-expressing multiple (S1-GCaMP6f, S2a-cAMPr, S3-ExRaiAKAR, and S4-ExRaiCKAR; FIG. 28A-M) GFP-based sensors in single live cultured mouse hippocampal neurons. The modularity of SiRI design, generation, and utilization, was further explored by attempting to generate, and use, 4 and even 5 SiRIs at once. Examples of 4 or 5 fluorescent reporters of dynamic signaling being used at once were not known to the investigators, perhaps because not enough dynamic fluorescent reporters of different colors had been generated to date. First, a clustered variant of ExRaiCKAR, a GFP-based protein kinase C (PKC) activity reporter (Mehta et al., 2018) was engineered by using pairs of two-component polyhedron-forming peptides rather than re-applying the previous design that combined one single-component polyhedron-forming peptide and one homo-oli-gomer-forming short peptide. Designs using pairs of two-component polyhedron-forming peptides would be advantageous because their abundance (over a hundred pairs were computationally designed and characterized in (Bale et al., 2016) alone) could potentially open up a new family of designs for SiRI constructs-still within the domain of dual peptide-scaffolding, but of a different kind. Pairs of two-component icosahedron-forming peptides (I32-06A+I32-06B, I52_03A+I52_03B, and I53_34A+I53_34B, randomly selected from (Bale et al., 2016); Table 1) were fused to ExRaiCKAR, with one component to the N-terminus and the other to the C-terminus, together with an epitope tag OLLAS (Table 2). Both I32-06A+I32-06B fused to ExRaiCKAR (named S4-ExRaiCKAR; FIG. 15A, construct design; compare expression in 15B-C; FIG. 21G-H, $D_C$ at soma and neurites, Tables LLL-MAM) and I52_03A+I52_03B fused to ExRaiCKAR produced bright puncta ($D_C \sim 10^2$) in the soma and neurites of cultured mouse hippocampal neurons. S4-ExRaiCKAR had a slightly larger $D_C$ and was thus chosen for further characterization. In contrast, I53_34A+I53_34B fused to ExRaiCKAR did not yield any expression. S4-ExRaiCKAR exhibited responses similar to those of conventional ExRaiCKAR (FIG. 15D), with comparable amplitude (FIG. 15E, Table 53), signal-to-noise ratio (FIG. 15F, Table 54), and rise time (FIG. 15G, Table 55), when elicited by phorbol 12-myristate 13-acetate (PMA), a PKC activator. S4-ExRaiCKAR puncta were similar in size (FIG. 15H, left) and punctum-punctum distance (FIG. 15H, middle) as other SiRIs, with good stationarity in neurons over periods of 1 hour (FIG. 15H, right). S4-ExRaiCKAR did not alter the electrophysiological properties of neurons (FIG. 18, Tables 56-62) nor colocalize with markers of subcellular organelles (FIG. 19). Tables 53-55 show statistical analyses for FIGS. 15E-G; Tables 56-62 show statistical analyses for FIGS. 18A-G; and Tables 63-64 show statistical analyses for FIGS. 21G-H.

TABLE 53

Statistical analysis for FIG. 15E
Peak fluorescence changes in GFP channel at the soma, proximal neurites, and distal
neurites of cultured mouse hippocampal neurons expressing ExRaiCKAR or S4-ExRaiCKAR
under 100 ng/ml PMA stimulation (n = 10 somata, 20 proximal neurites, and 20 distal neurites
from 10 neurons from 4 cultures for ExRaiCKAR; n = 11 somata, 22 proximal neurites, and 22
distal neurites from 11 neurons from 4 cultures for S4-ExRaiCKAR). Two-way analysis of
variance followed by post-hoc Bonferroni corrected multiple comparisons test.

| | Two-way ANOVA Ordinary Alpha 0.05 | | | | |
|---|---|---|---|---|---|
| Source of Variation | % of total variation | P value | P value summary | Significant? | |
| Interaction | 14.39 | <.001 | *** | Yes | |
| Subcellular location | 2.360 | .226 | ns | No | |
| Molecule | 0.2092 | .606 | ns | No | |
| ANOVA table | SS (Type III) | DF | MS | F (DFn, DFd) | P value |
| Interaction | 1417 | 2 | 708.6 | F (2, 104) = 9.182 | P = .001 |

TABLE 53-continued

Statistical analysis for FIG. 15E
Peak fluorescence changes in GFP channel at the soma, proximal neurites, and distal neurites of cultured mouse hippocampal neurons expressing ExRaiCKAR or S4-ExRaiCKAR under 100 ng/ml PMA stimulation (n = 10 somata, 20 proximal neurites, and 20 distal neurites from 10 neurons from 4 cultures for ExRaiCKAR; n = 11 somata, 22 proximal neurites, and 22 distal neurites from 11 neurons from 4 cultures for S4-ExRaiCKAR). Two-way analysis of variance followed by post-hoc Bonferroni corrected multiple comparisons test.

| | | | | | |
|---|---|---|---|---|---|
| Subcellular location | 232.5 | 2 | 116.3 | $F_{(2, 104)} = 1.506$ | $P = .226$ |
| Molecule | 20.61 | 1 | 20.61 | $F_{(1, 104)} = 0.2670$ | $P = .606$ |
| Residual | 8025 | 104 | 77.17 | | |

Difference between column means

| | |
|---|---|
| Predicted (LS) mean of ExRaiCKAR | 26.36 |
| Predicted (LS) mean of S4-ExRaiCKAR | 27.28 |
| Difference between predicted means | −0.9163 |
| SE of difference | 1.773 |
| 95% CI of difference | −4.432 to 2.600 |

Number of families 1
Number of comparisons per family 3
Alpha 0.05

| Bonferroni's multiple comparisons test | Predicted (LS) mean diff. | 95.00% CI of diff. | Significant? | Summary | Adjusted P Value |
|---|---|---|---|---|---|
| ExRaiCKAR-S4-ExRaiCKAR | | | | | |
| Soma | 8.481 | −0.6718 to 17.63 | No | ns | .079 |
| Proximal neurite | −0.5930 | −7.065 to 5.879 | No | ns | >.999 |
| Distal neurite | −10.64 | −17.11 to −4.165 | Yes | *** | <.001 |

| Test details | Predicted (LS) mean 1 | Predicted (LS) mean 2 | Predicted (LS) mean diff. | SE of diff. | N1 | N2 | t | DF |
|---|---|---|---|---|---|---|---|---|
| ExRaiCKAR-S4-ExRaiCKAR | | | | | | | | |
| Soma | 33.30 | 24.82 | 8.481 | 3.761 | 10 | 12 | 2.255 | 104.0 |
| Proximal neurite | 24.77 | 25.36 | −0.5930 | 2.660 | 20 | 24 | 0.2230 | 104.0 |
| Distal neurite | 21.01 | 31.65 | −10.64 | 2.660 | 20 | 24 | 3.999 | 104.0 |

TABLE 54

Statistical analysis for FIG. 15F
Signal-to-noise ratio in the GFP channel at the soma, proximal neurites, and distal neurites (of cultured mouse hippocampal neurons expressing ExRaiCKAR or S4-ExRaiCKAR under 100 ng/ml PMA stimulation (n = 10 somata, 20 proximal neurites, and 20 distal neurites from 10 neurons from 4 cultures for ExRaiCKAR; n = 11 somata, 22 proximal neurites, and 22 distal neurites from 11 neurons from 4 cultures for S4-ExRaiCKAR). Two-way analysis of variance followed by post-hoc Bonferroni corrected multiple comparisons test.

Two-way ANOVA Ordinary
Alpha 0.05

| Source of Variation | % of total variation | P value | P value summary | Significant? | | |
|---|---|---|---|---|---|---|
| Interaction | 1.398 | .399 | ns | No | | |
| Subcellular location | 16.00 | <.001 | *** | Yes | | |
| Molecule | 4.137 | .021 | * | Yes | | |
| ANOVA table | SS (Type III) | DF | MS | $F_{(DFn, DFd)}$ | | P value |

TABLE 54-continued

Statistical analysis for FIG. 15F
Signal-to-noise ratio in the GFP channel at the soma, proximal neurites, and distal neurites (of cultured mouse hippocampal neurons expressing ExRaiCKAR or S4-ExRaiCKAR under 100 ng/ml PMA stimulation (n = 10 somata, 20 proximal neurites, and 20 distal neurites from 10 neurons from 4 cultures for ExRaiCKAR; n = 11 somata, 22 proximal neurites, and 22 distal neurites from 11 neurons from 4 cultures for S4-ExRaiCKAR). Two-way analysis of variance followed by post-hoc Bonferroni corrected multiple comparisons test.

| | | | | | |
|---|---|---|---|---|---|
| Interaction | 88.21 | 2 | 44.10 | $F_{(2, 104)} = 0.9258$ | $P = .399$ |
| Subcellular location | 1009 | 2 | 504.7 | $F_{(2, 104)} = 10.60$ | $P = .001$ |
| Molecule | 261.1 | 1 | 261.1 | $F_{(1, 104)} = 5.481$ | $P = .021$ |
| Residual | 4954 | 104 | 47.64 | | |

| Difference between column means | |
|---|---|
| Predicted (LS) mean of ExRaiCKAR | 10.21 |
| Predicted (LS) mean of S4-ExRaiCKAR | 13.47 |
| Difference between predicted means | −3.261 |
| SE of difference | 1.393 |
| 95% CI of difference | −6.024 to −0.4988 |

Number of families 1
Number of comparisons per family 3
Alpha 0.05

| Bonferroni's multiple comparisons test | Predicted (LS) mean diff. | 95.00% CI of diff. | Significant? | Summary | Adjusted P Value |
|---|---|---|---|---|---|
| ExRaiCKAR-S4-ExRaiCKAR | | | | | |
| Soma | −5.246 | −12.44 to 1.945 | No | ns | .236 |
| Proximal neurite | −0.7623 | −5.847 to 4.323 | No | ns | >.999 |
| Distal neurite | −3.776 | −8.861 to 1.309 | No | ns | .221 |

| Test details | Predicted (LS) mean 1 | Predicted (LS) mean 2 | Predicted (LS) mean diff. | SE of diff. | N1 | N2 | t | DF |
|---|---|---|---|---|---|---|---|---|
| ExRaiCKAR-S4-ExRaiCKAR | | | | | | | | |
| Soma | 14.15 | 19.39 | −5.246 | 2.955 | 10 | 12 | 1.775 | 104.0 |
| Proximal neurite | 9.792 | 10.55 | −0.7623 | 2.090 | 20 | 24 | 0.3648 | 104.0 |
| Distal neurite | 6.692 | 10.47 | −3.776 | 2.090 | 20 | 24 | 1.807 | 104.0 |

TABLE 55

Statistical analysis for FIG. 15G
Wilcoxon rank sum test of the half rise time of reported PKC signals at the soma after 100 ng/ml PMA stimulation (n = 10 somata, 20 proximal neurites, and 20 distal neurites from 10 neurons from 4 cultures for ExRaiCKAR; n = 11 somata, 22 proximal neurites, and 22 distal neurites from 11 neurons from 4 cultures for S4-ExRaiCKAR).

| | |
|---|---|
| P value | 0.6923 |
| ranksum | 108.5 |
| zval | −0.3957 |

TABLE 56

Figure 18A:
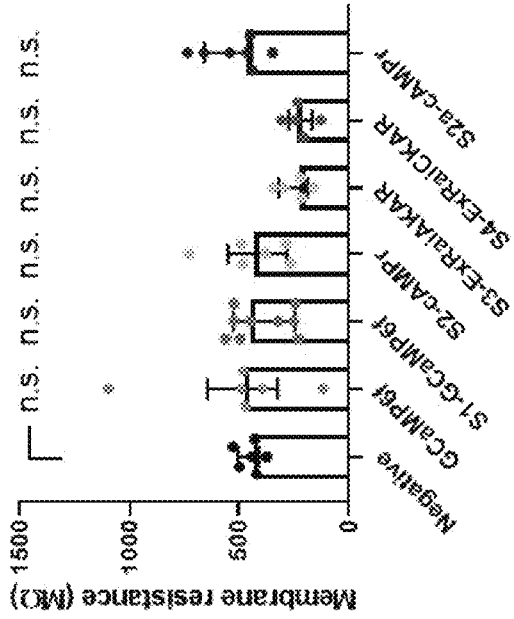

Statistical analysis for FIG. 18A (Resting potential)
Kruskal-Wallis analysis of variance followed by post-hoc test via Dunn's test with non-expressing neurons, labeled as 'Negative', as control group. n = 6 neurons from 4 cultures for Negative; n = 6 neurons from 2 cultures for GCaMP6f; n = 9 neurons from 5 cultures for S1-GCaMP6f; n = 6 neurons from 4 cultures for S2-cAMPr; n = 5 neurons from 3 cultures for S3-ExRaiAKAR; n = 5 neurons from 3 cultures for S4-ExRaiCKAR; n = 7 neurons from 3 cultures for S2a-cAMPr.

Kruskal-Wallis test

| | |
|---|---|
| P value | 0.8238 |
| Exact or approximate P value? | Approximate |
| P value summary | ns |
| Do the medians vary signif. (P <0.05)? | No |
| Number of groups | 7 |
| Kruskal-Wallis statistic | 2.879 |
| Data summary | |
| Number of treatments (columns) | 7 |
| Number of values (total) | 44 |

Number of families 1
Number of comparisons per family 6
Alpha 0.05

| Dunn's multiple comparisons test | Mean rank diff. | Significant? | Summary | Adjusted P Value | A-? | |
|---|---|---|---|---|---|---|
| Negative vs. GCaMP6f | 4.167 | No | ns | >0.9999 | B | GCaMP6f |
| Negative vs. S1-GCaMP6f | −3.500 | No | ns | >0.9999 | C | S1-GCaMP6f |
| Negative vs. S2-cAMPr | 3.917 | No | ns | >0.9999 | D | S2-cAMPr |
| Negative vs. S3-ExRaiAKAR | −1.667 | No | ns | >0.9999 | E | S3-ExRaiAKAR |
| Negative vs. S4-ExRaiCKAR | 6.033 | No | ns | >0.9999 | F | S4-ExRaiCKAR |
| Negative vs. S2a-cAMPr | −0.3095 | No | ns | >0.9999 | G | S2a-cAMPr |

| Test details | Mean rank 1 | Mean rank 2 | Mean rank diff. | n1 | n2 | Z |
|---|---|---|---|---|---|---|
| Negative vs. GCaMP6f | 23.33 | 19.17 | 4.167 | 6 | 6 | 0.5634 |
| Negative vs. S1-GCaMP6f | 23.33 | 26.83 | −3.500 | 6 | 9 | 0.5184 |
| Negative vs. S2-cAMPr | 23.33 | 19.42 | 3.917 | 6 | 6 | 0.5296 |
| Negative vs. S3-ExRaiAKAR | 23.33 | 25.00 | −1.667 | 6 | 5 | 0.2149 |
| Negative vs. S4-ExRaiCKAR | 23.33 | 17.30 | 6.033 | 6 | 5 | 0.7778 |
| Negative vs. S2a-cAMPr | 23.33 | 23.64 | −0.3095 | 6 | 7 | 0.04343 |

TABLE 57

Figure 18B:
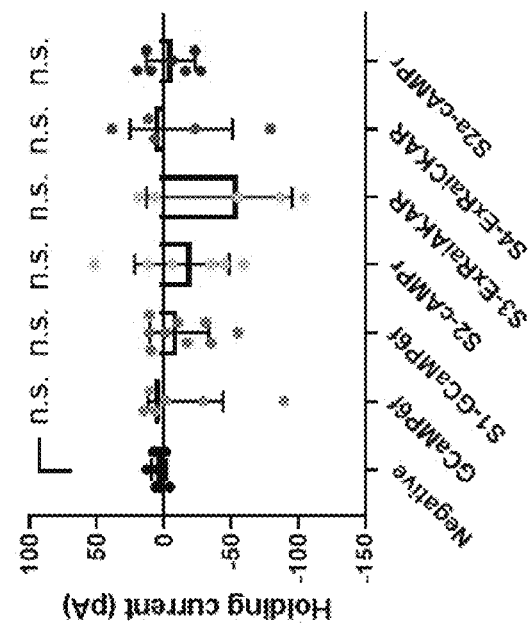

Statistical analysis for FIG. 18B (Membrane resistance)
Kruskal-Wallis analysis of variance followed by post-hoc test via Dunn's test with non-expressing neurons, labeled as 'Negative', as control group. n = 6 neurons from 4 cultures for Negative; n = 6 neurons from 2 cultures for GCaMP6f; n = 9 neurons from 5 cultures for S1-GCaMP6f; n = 6 neurons from 4 cultures for S2-cAMPr; n = 5 neurons from 3 cultures for S3-ExRaiAKAR; n = 5 neurons from 3 cultures for S4-ExRaiCKAR; n = 7 neurons from 3 cultures for S2a-cAMPr.

Kruskal-Wallis test

| | |
|---|---|
| P value | 0.0082 |
| Exact or approximate P value? | Approximate |
| P value summary | ** |
| Do the medians vary signif. (P <0.05)? | Yes |
| Number of groups | 7 |
| Kruskal-Wallis statistic | 17.31 |
| Data summary | |
| Number of treatments (columns) | 7 |
| Number of values (total) | 44 |

TABLE 57-continued

Statistical analysis for FIG. 18B (Membrane resistance)
Kruskal-Wallis analysis of variance followed by post-hoc test via Dunn's test with non-expressing neurons, labeled as 'Negative', as control group. n = 6 neurons from 4 cultures for Negative; n = 6 neurons from 2 cultures for GCaMP6f; n = 9 neurons from 5 cultures for S1-GCaMP6f; n = 6 neurons from 4 cultures for S2-cAMPr; n = 5 neurons from 3 cultures for S3-ExRaiAKAR; n = 5 neurons from 3 cultures for S4-ExRaiCKAR; n = 7 neurons from 3 cultures for S2a-cAMPr.

Number of families 1
Number of comparisons per family 6
Alpha 0.05

| Dunn's multiple comparisons test | Mean rank diff. | Significant? | Summary | Adjusted P Value | A-? | |
|---|---|---|---|---|---|---|
| Negative vs. GCaMP6f | 0.6667 | No | ns | >0.9999 | B | GCaMP6f |
| Negative vs. S1-GCaMP6f | 2.722 | No | ns | >0.9999 | C | S1-GCaMP6f |
| Negative vs. S2-cAMPr | 1.667 | No | ns | >0.9999 | D | S2-cAMPr |
| Negative vs. S3-ExRaiAKAR | 17.83 | No | ns | 0.1312 | E | S3-ExRaiAKAR |
| Negative vs. S4-ExRaiCKAR | 19.23 | No | ns | 0.0805 | F | S4-ExRaiCKAR |
| Negative vs. S2a-cAMPr | −4.738 | No | ns | >0.9999 | G | S2a-cAMPr |

| Test details | Mean rank 1 | Mean rank 2 | Mean rank diff. | n1 | n2 | Z |
|---|---|---|---|---|---|---|
| Negative vs. GCaMP6f | 26.83 | 26.17 | 0.6667 | 6 | 6 | 0.08989 |
| Negative vs. S1-GCaMP6f | 26.83 | 24.11 | 2.722 | 6 | 9 | 0.4021 |
| Negative vs. S2-cAMPr | 26.83 | 25.17 | 1.667 | 6 | 6 | 0.2247 |
| Negative vs. S3-ExRaiAKAR | 26.83 | 9.000 | 17.83 | 6 | 5 | 2.293 |
| Negative vs. S4-ExRaiCKAR | 26.83 | 7.600 | 19.23 | 6 | 5 | 2.473 |
| Negative vs. S2a-cAMPr | 26.83 | 31.57 | −4.738 | 6 | 7 | 0.6630 |

TABLE 58

Figure 18C:
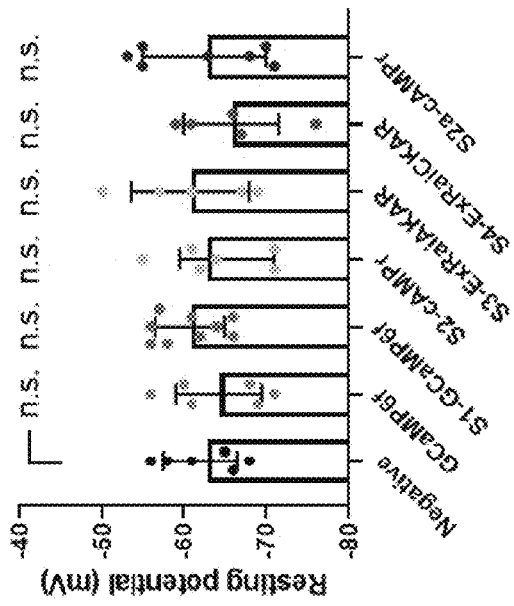

Statistical analysis for FIG. 18C (Membrane capacitance)
Kruskal-Wallis analysis of variance followed by post-hoc test via Dunn's test with non-expressing neurons, labeled as 'Negative', as control group. n = 6 neurons from 4 cultures for Negative; n = 6 neurons from 2 cultures for GCaMP6f; n = 9 neurons from 5 cultures for S1-GCaMP6f; n = 6 neurons from 4 cultures for S2-cAMPr; n = 5 neurons from 3 cultures for S3-ExRaiAKAR; n = 5 neurons from 3 cultures for S4-ExRaiCKAR; n = 7 neurons from 3 cultures for S2a-cAMPr.

Kruskal-Wallis test

| | |
|---|---|
| P value | 0.6134 |
| Exact or approximate P value? | Approximate |
| P value summary | ns |
| Do the medians vary signif. (P <0.05)? | No |
| Number of groups | 7 |
| Kruskal-Wallis statistic | 4.470 |
| Data summary | |
| Number of treatments (columns) | 7 |
| Number of values (total) | 44 |

Number of families 1
Number of comparisons per family 6
Alpha 0.05

| Dunn's multiple comparisons test | Mean rank diff. | Significant? | Summary | Adjusted P Value | A-? | |
|---|---|---|---|---|---|---|
| Negative vs. GCaMP6f | −7.833 | No | ns | >0.9999 | B | GCaMP6f |
| Negative vs. S1-GCaMP6f | −1.750 | No | ns | >0.9999 | C | S1-GCaMP6f |
| Negative vs. S2-cAMPr | −6.917 | No | ns | >0.9999 | D | S2-cAMPr |
| Negative vs. S3-ExRaiAKAR | −6.650 | No | ns | >0.9999 | E | S3-ExRaiAKAR |
| Negative vs. S4-ExRaiCKAR | −11.15 | No | ns | 0.9084 | F | S4-ExRaiCKAR |
| Negative vs. S2a-cAMPr | 0.8929 | No | ns | >0.9999 | G | S2a-cAMPr |

| Test details | Mean rank 1 | Mean rank 2 | Mean rank diff. | n1 | n2 | Z |
|---|---|---|---|---|---|---|
| Negative vs. GCaMP6f | 18.25 | 26.08 | −7.833 | 6 | 6 | 1.057 |
| Negative vs. S1-GCaMP6f | 18.25 | 20.00 | −1.750 | 6 | 9 | 0.2587 |
| Negative vs. S2-cAMPr | 18.25 | 25.17 | −6.917 | 6 | 6 | 0.9334 |
| Negative vs. S3-ExRaiAKAR | 18.25 | 24.90 | −6.650 | 6 | 5 | 0.8556 |

TABLE 58-continued

Statistical analysis for FIG. 18C (Membrane capacitance)
Kruskal-Wallis analysis of variance followed by post-hoc test via Dunn's test with non-expressing neurons, labeled as 'Negative', as control group. n = 6 neurons from 4 cultures for Negative; n = 6 neurons from 2 cultures for GCaMP6f; n = 9 neurons from 5 cultures for S1-GCaMP6f; n = 6 neurons from 4 cultures for S2-cAMPr; n = 5 neurons from 3 cultures for S3-ExRaiAKAR; n = 5 neurons from 3 cultures for S4-ExRaiCKAR; n = 7 neurons from 3 cultures for S2a-cAMPr.

| | | | | | | |
|---|---|---|---|---|---|---|
| Negative vs. S4-ExRaiCKAR | 18.25 | 29.40 | −11.15 | 6 | 5 | 1.435 |
| Negative vs. S2a-cAMPr | 18.25 | 17.36 | 0.8929 | 6 | 7 | 0.1250 |

TABLE 59

Figure 18D:
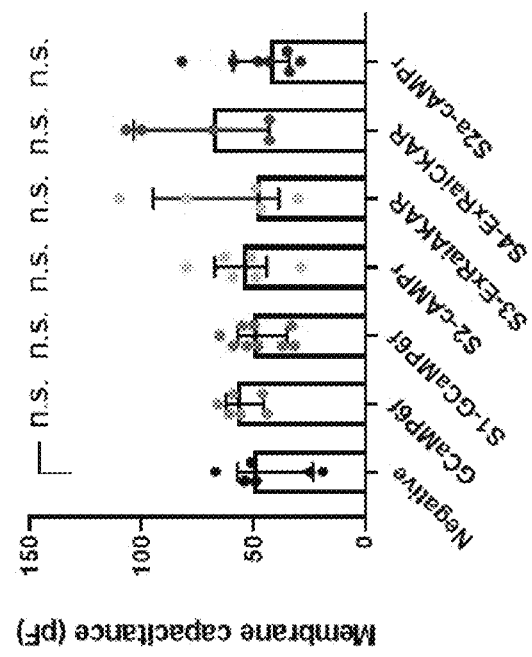

Statistical analysis for FIG. 18D (Holding current while held at −65 mV)
Kruskal-Wallis analysis of variance followed by post-hoc test via Dunn's test with non-expressing neurons, labeled as 'Negative', as control group. n = 6 neurons from 4 cultures for Negative; n = 6 neurons from 2 cultures for GCaMP6f; n = 9 neurons from 5 cultures for S1-GCaMP6f; n = 6 neurons from 4 cultures for S2-cAMPr; n = 5 neurons from 3 cultures for S3-ExRaiAKAR; n = 5 neurons from 3 cultures for S4-ExRaiCKAR; n = 7 neurons from 3 cultures for S2a-cAMPr.

| Kruskal-Wallis test | |
|---|---|
| P value | 0.7989 |
| Exact or approximate P value? | Approximate |
| P value summary | ns |
| Do the medians vary signif. (P <0.05)? | No |
| Number of groups | 7 |
| Kruskal-Wallis statistic | 3.079 |
| Data summary | |
| Number of treatments (columns) | 7 |
| Number of values (total) | 44 |

Number of families 1
Number of comparisons per family 6
Alpha 0.05

| Dunn's multiple comparisons test | Mean rank diff. | Significant? | Summary | Adjusted P Value | A-? | |
|---|---|---|---|---|---|---|
| Negative vs. GCaMP6f | 4.083 | No | ns | >0.9999 | B | GCaMP6f |
| Negative vs. S1-GCaMP6f | 6.861 | No | ns | >0.9999 | C | S1-GCaMP6f |
| Negative vs. S2-cAMPr | 6.833 | No | ns | >0.9999 | D | S2-cAMPr |
| Negative vs. S3-ExRaiAKAR | 11.35 | No | ns | 0.8654 | E | S3-ExRaiAKAR |
| Negative vs. S4-ExRaiCKAR | 2.050 | No | ns | >0.9999 | F | S4-ExRaiCKAR |
| Negative vs. S2a-cAMPr | 2.107 | No | ns | >0.9999 | G | S2a-cAMPr |

| Test details | Mean rank 1 | Mean rank 2 | Mean rank diff. | n1 | n2 | Z |
|---|---|---|---|---|---|---|
| Negative vs. GCaMP6f | 27.25 | 23.17 | 4.083 | 6 | 6 | 0.5510 |
| Negative vs. S1-GCaMP6f | 27.25 | 20.39 | 6.861 | 6 | 9 | 1.014 |
| Negative vs. S2-cAMPr | 27.25 | 20.42 | 6.833 | 6 | 6 | 0.9220 |
| Negative vs. S3-ExRaiAKAR | 27.25 | 15.90 | 11.35 | 6 | 5 | 1.460 |
| Negative vs. S4-ExRaiCKAR | 27.25 | 25.20 | 2.050 | 6 | 5 | 0.2637 |
| Negative vs. S2a-cAMPr | 27.25 | 25.14 | 2.107 | 6 | 7 | 0.2951 |

TABLE 60

Figure 18E:
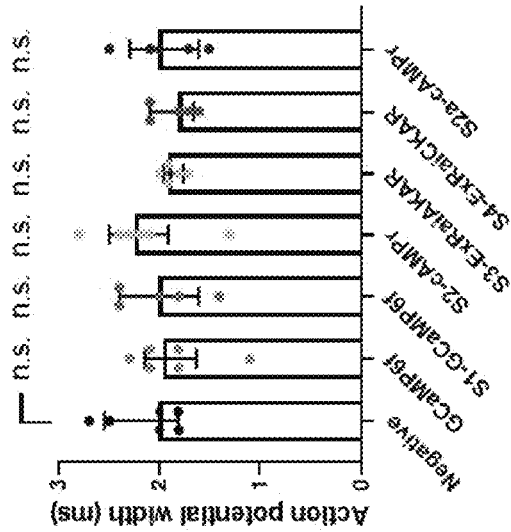

Statistical analysis for FIG. 18E (Action potential amplitude)
Kruskal-Wallis analysis of variance followed by post-hoc test via Dunn's test with non-expressing neurons, labeled as 'Negative', as control group. n = 6 neurons from 2 cultures for Negative; n = 6 neurons from 2 cultures for GCaMP6f; n = 5 neurons from 3 cultures for S1-GCaMP6f; n = 6 neurons from 4 cultures for S2-cAMPr; n = 5 neurons from 3 cultures for S3-ExRaiAKAR; n = 5 neurons from 3 cultures for S4-ExRaiCKAR; n = 5 neurons from 3 cultures for S2a-cAMPr.

| Kruskal-Wallis test | |
|---|---|
| P value | 0.0343 |
| Exact or approximate P value? | Approximate |

TABLE 60-continued

Statistical analysis for FIG. 18E (Action potential amplitude)
Kruskal-Wallis analysis of variance followed by post-hoc test via Dunn's test with non-expressing neurons, labeled as 'Negative', as control group. n = 6 neurons from 2 cultures for Negative; n = 6 neurons from 2 cultures for GCaMP6f; n = 5 neurons from 3 cultures for S1-GCaMP6f; n = 6 neurons from 4 cultures for S2-cAMPr; n = 5 neurons from 3 cultures for S3-ExRaiAKAR; n = 5 neurons from 3 cultures for S4-ExRaiCKAR; n = 5 neurons from 3 cultures for S2a-cAMPr.

| | |
|---|---|
| P value summary | * |
| Do the medians vary signif. (P <0.05)? | Yes |
| Number of groups | 7 |
| Kruskal-Wallis statistic | 13.61 |
| Data summary | |
| Number of treatments (columns) | 7 |
| Number of values (total) | 38 |

Number of families 1
Number of comparisons per family 6
Alpha 0.05

| Dunn's multiple comparisons test | Mean rank diff. | Significant? | Summary | Adjusted P Value | A-? | |
|---|---|---|---|---|---|---|
| Negative vs. GCaMP6f | 1.500 | No | ns | >0.9999 | B | GCaMP6f |
| Negative vs. S1-GCaMP6f | 9.367 | No | ns | 0.9835 | C | S1-GCaMP6f |
| Negative vs. S2-cAMPr | 14.00 | No | ns | 0.1746 | D | S2-cAMPr |
| Negative vs. S3-ExRaiAKAR | 0.9667 | No | ns | >0.9999 | E | S3-ExRaiAKAR |
| Negative vs. S4-ExRaiCKAR | −6.933 | No | ns | >0.9999 | F | S4-ExRaiCKAR |
| Negative vs. S2a-cAMPr | 9.667 | No | ns | 0.9050 | G | S2a-cAMPr |

| Test details | Mean rank 1 | Mean rank 2 | Mean rank diff. | n1 | n2 | Z |
|---|---|---|---|---|---|---|
| Negative vs. GCaMP6f | 23.67 | 22.17 | 1.500 | 6 | 6 | 0.2338 |
| Negative vs. S1-GCaMP6f | 23.67 | 14.30 | 9.367 | 6 | 5 | 1.392 |
| Negative vs. S2-cAMPr | 23.67 | 9.667 | 14.00 | 6 | 6 | 2.182 |
| Negative vs. S3-ExRaiAKAR | 23.67 | 22.70 | 0.9667 | 6 | 5 | 0.1437 |
| Negative vs. S4-ExRaiCKAR | 23.67 | 30.60 | −6.933 | 6 | 5 | 1.030 |
| Negative vs. S2a-cAMPr | 23.67 | 14.00 | 9.667 | 6 | 5 | 1.437 |

TABLE 61

Figure 18F:
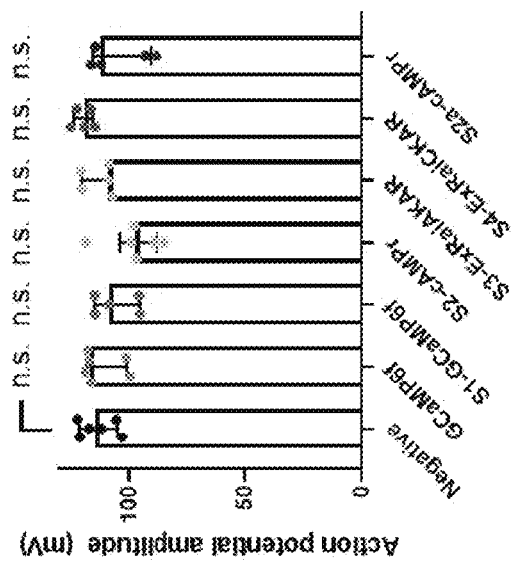

Statistical analysis for FIG. 18F (Action potential width)
Kruskal-Wallis analysis of variance followed by post-hoc test via Dunn's test with non-expressing neurons, labeled as 'Negative', as control group. n = 6 neurons from 2 cultures for Negative; n = 6 neurons from 2 cultures for GCaMP6f; n = 5 neurons from 3 cultures for S1-GCaMP6f; n = 6 neurons from 4 cultures for S2-cAMPr; n = 5 neurons from 3 cultures for S3-ExRaiAKAR; n = 5 neurons from 3 cultures for S4-ExRaiCKAR; n = 5 neurons from 3 cultures for S2a-cAMPr.

| Kruskal-Wallis test | |
|---|---|
| P value | 0.5518 |
| Exact or approximate P value? | Approximate |
| P value summary | ns |
| Do the medians vary signif. (P <0.05)? | No |
| Number of groups | 7 |
| Kruskal-Wallis statistic | 4.938 |
| Data summary | |
| Number of treatments (columns) | 7 |
| Number of values (total) | 38 |

Number of families 1
Number of comparisons per family 6
Alpha 0.05

| Dunn's multiple comparisons test | Mean rank diff. | Significant? | Summary | Adjusted P Value | A-? | |
|---|---|---|---|---|---|---|
| Negative vs. GCaMP6f | 5.000 | No | ns | >0.9999 | B | GCaMP6f |
| Negative vs. S1-GCaMP6f | 2.550 | No | ns | >0.9999 | C | S1-GCaMP6f |
| Negative vs. S2-cAMPr | −3.583 | No | ns | >0.9999 | D | S2-cAMPr |
| Negative vs. S3-ExRaiAKAR | 8.350 | No | ns | >0.9999 | E | S3-ExRaiAKAR |

TABLE 61-continued

Statistical analysis for FIG. 18F (Action potential width)
Kruskal-Wallis analysis of variance followed by post-hoc test via Dunn's test with non-expressing neurons, labeled as 'Negative', as control group. n = 6 neurons from 2 cultures for Negative; n = 6 neurons from 2 cultures for GCaMP6f; n = 5 neurons from 3 cultures for S1-GCaMP6f; n = 6 neurons from 4 cultures for S2-cAMPr; n = 5 neurons from 3 cultures for S3-ExRaiAKAR; n = 5 neurons from 3 cultures for S4-ExRaiCKAR; n = 5 neurons from 3 cultures for S2a-cAMPr.

| | | | | | | |
|---|---|---|---|---|---|---|
| Negative vs. S4-ExRaiCKAR | 7.750 | No | ns | >0.9999 | F | S4-ExRaiCKAR |
| Negative vs. S2a-cAMPr | 4.350 | No | ns | >0.9999 | G | S2a-cAMPr |

| Test details | Mean rank 1 | Mean rank 2 | Mean rank diff. | n1 | n2 | Z |
|---|---|---|---|---|---|---|
| Negative vs. GCaMP6f | 22.75 | 17.75 | 5.000 | 6 | 6 | 0.7845 |
| Negative vs. S1-GCaMP6f | 22.75 | 20.20 | 2.550 | 6 | 5 | 0.3815 |
| Negative vs. S2-cAMPr | 22.75 | 26.33 | −3.583 | 6 | 6 | 0.5623 |
| Negative vs. S3-ExRaiAKAR | 22.75 | 14.40 | 8.350 | 6 | 5 | 1.249 |
| Negative vs. S4-ExRaiCKAR | 22.75 | 15.00 | 7.750 | 6 | 5 | 1.159 |
| Negative vs. S2a-cAMPr | 22.75 | 18.40 | 4.350 | 6 | 5 | 0.6508 |

TABLE 62

Figure 18G:
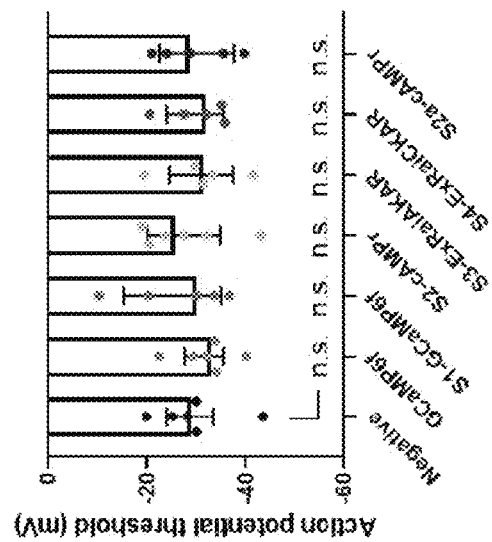
Figure 19A:
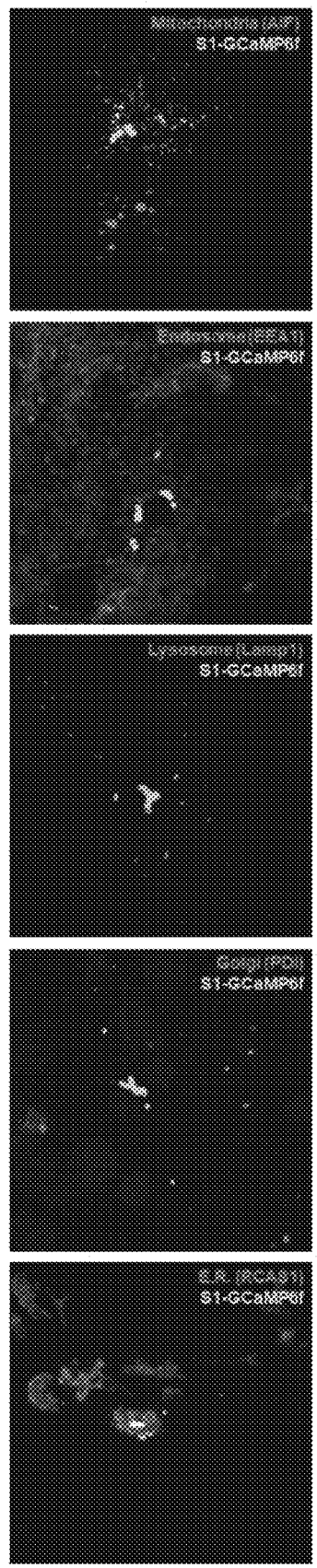
Figure 19B:
Figure 19C:
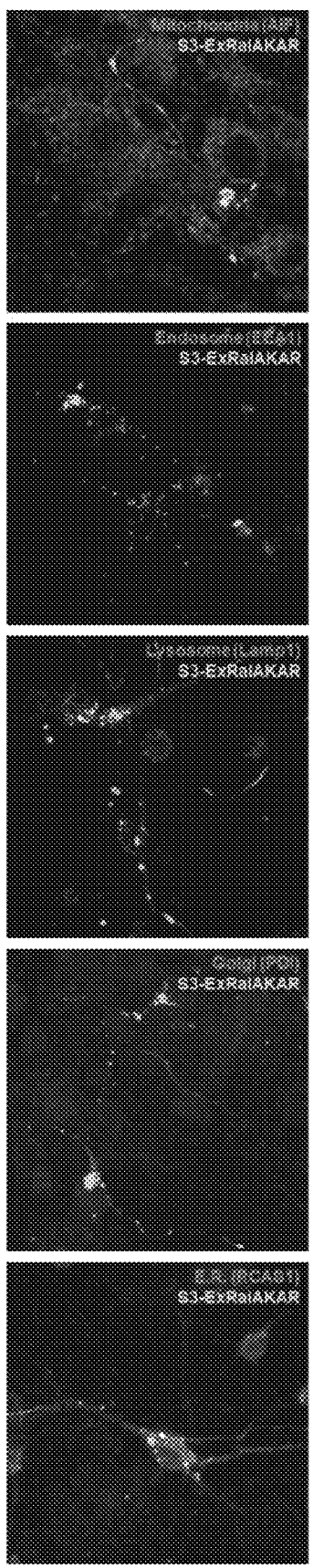
Figure 19D:
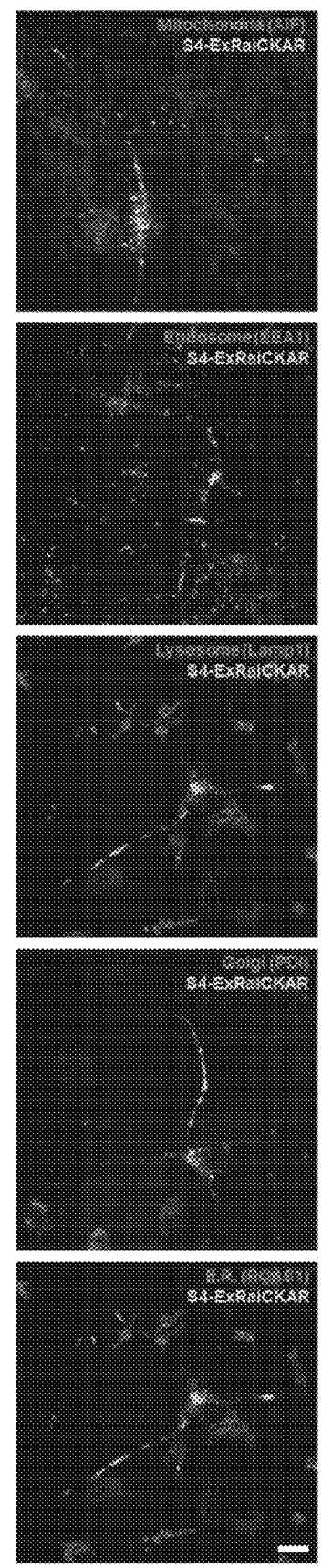

Statistical analysis for FIG. 18G (Action potential threshold)
Kruskal-Wallis analysis of variance followed by post-hoc test via Dunn's test with non-expressing neurons, labeled as 'Negative', as control group. n = 6 neurons from 2 cultures for Negative; n = 6 neurons from 2 cultures for GCaMP6f; n = 5 neurons from 3 cultures for S1-GCaMP6f; n = 6 neurons from 4 cultures for S2-cAMPr; n = 5 neurons from 3 cultures for S3-ExRaiAKAR; n = 5 neurons from 3 cultures for S4-ExRaiCKAR; n = 5 neurons from 3 cultures for S2a-cAMPr.

Kruskal-Wallis test

| | |
|---|---|
| P value | 0.9034 |
| Exact or approximate P value? | Approximate |
| P value summary | ns |
| Do the medians vary signif. (P <0.05)? | No |
| Number of groups | 7 |
| Kruskal-Wallis statistic | 2.170 |
| Data summary | |
| Number of treatments (columns) | 7 |
| Number of values (total) | 38 |

Number of families 1
Number of comparisons per family 6
Alpha 0.05

| Dunn's multiple comparisons test | Mean rank diff. | Significant? | Summary | Adjusted P Value | A-? | |
|---|---|---|---|---|---|---|
| Negative vs. GCaMP6f | 5.833 | No | ns | >0.9999 | B | GCaMP6f |
| Negative vs. S1-GCaMP6f | −0.6000 | No | ns | >0.9999 | C | S1-GCaMP6f |
| Negative vs. S2-cAMPr | −2.500 | No | ns | >0.9999 | D | S2-cAMPr |
| Negative vs. S3-ExRaiAKAR | 3.000 | No | ns | >0.9999 | E | S3-ExRaiAKAR |
| Negative vs. S4-ExRaiCKAR | 3.000 | No | ns | >0.9999 | F | S4-ExRaiCKAR |
| Negative vs. S2a-cAMPr | 2.000 | No | ns | >0.9999 | G | S2a-cAMPr |

| Test details | Mean rank 1 | Mean rank 2 | Mean rank diff. | n1 | n2 | Z |
|---|---|---|---|---|---|---|
| Negative vs. GCaMP6f | 21.00 | 15.17 | 5.833 | 6 | 6 | 0.9092 |
| Negative vs. S1-GCaMP6f | 21.00 | 21.60 | −0.6000 | 6 | 5 | 0.08916 |
| Negative vs. S2-cAMPr | 21.00 | 23.50 | −2.500 | 6 | 6 | 0.3896 |
| Negative vs. S3-ExRaiAKAR | 21.00 | 18.00 | 3.000 | 6 | 5 | 0.4458 |
| Negative vs. S4-ExRaiCKAR | 21.00 | 18.00 | 3.000 | 6 | 5 | 0.4458 |
| Negative vs. S2a-cAMPr | 21.00 | 19.00 | 2.000 | 6 | 5 | 0.2972 |

TABLE 63

Statistical analysis for FIG. 21G
Kruskal-Wallis analysis of variance of the degree of clustering followed by post-hoc test
via Dunn's test with the degree of clustering at '100 ng' transfection as control group.

| Kruskal-Wallis test | |
|---|---|
| P value | 0.2777 |
| Exact or approximate P value? | Approximate |
| P value summary | ns |
| Do the medians vary signif. (P <0.05)? | No |
| Number of groups | 5 |
| Kruskal-Wallis statistic | 5.095 |
| Data summary | |
| Number of treatments (columns) | 5 |
| Number of values (total) | 44 |

Number of families 1
Number of comparisons per family 4
Alpha 0.05

| Dunn's multiple comparisons test | Mean rank diff. | Significant? | Summary | Adjusted P Value | A-? | |
|---|---|---|---|---|---|---|
| 100 ng vs. 250 ng | 8.519 | No | ns | 0.3990 | B | 250 ng |
| 100 ng vs. 500 ng | 13.76 | No | ns | 0.1393 | C | 500 ng |
| 100 ng vs. 750 ng | 6.466 | No | ns | >0.9999 | D | 750 ng |
| 100 ng vs. 1000 ng | 7.291 | No | ns | >0.9999 | E | 1000 ng |

| Test details | Mean rank 1 | Mean rank 2 | Mean rank diff. | n1 | n2 | Z |
|---|---|---|---|---|---|---|
| 100 ng vs. 250 ng | 29.09 | 20.57 | 8.519 | 11 | 14 | 1.646 |
| 100 ng vs. 500 ng | 29.09 | 15.33 | 13.76 | 11 | 6 | 2.110 |
| 100 ng vs. 750 ng | 29.09 | 22.63 | 6.466 | 11 | 8 | 1.083 |
| 100 ng vs. 1000 ng | 29.09 | 21.80 | 7.291 | 11 | 5 | 1.052 |

TABLE 64

Statistical analysis for FIG. 21H
Kruskal-Wallis analysis of variance of the degree of clustering followed by post-hoc test
via Dunn's test with the degree of clustering at '100 ng' transfection as control group.

| Kruskal-Wallis test | |
|---|---|
| P value | 0.8805 |
| Exact or approximate P value? | Approximate |
| P value summary | ns |
| Do the medians vary signif. (P <0.05)? | No |
| Number of groups | 5 |
| Kruskal-Wallis statistic | 1.185 |
| Data summary | |
| Number of treatments (columns) | 5 |
| Number of values (total) | 44 |

Number of families 1
Number of comparisons per family 4
Alpha 0.05

| Dunn's multiple comparisons test | Mean rank diff. | Significant? | Summary | Adjusted P Value | A-? | |
|---|---|---|---|---|---|---|
| 100 ng vs. 250 ng | −3.006 | No | ns | >0.9999 | B | 250 ng |
| 100 ng vs. 500 ng | −1.030 | No | ns | >0.9999 | C | 500 ng |
| 100 ng vs. 750 ng | −0.1136 | No | ns | >0.9999 | D | 750 ng |
| 100 ng vs. 1000 ng | −6.564 | No | ns | >0.9999 | E | 1000 ng |

| Test details | Mean rank 1 | Mean rank 2 | Mean rank diff. | n1 | n2 | Z |
|---|---|---|---|---|---|---|
| 100 ng vs. 250 ng | 20.64 | 23.64 | −3.006 | 11 | 14 | 0.5809 |
| 100 ng vs. 500 ng | 20.64 | 21.67 | −1.030 | 11 | 6 | 0.1580 |
| 100 ng vs. 750 ng | 20.64 | 20.75 | −0.1136 | 11 | 8 | 0.01904 |
| 100 ng vs. 1000 ng | 20.64 | 27.20 | −6.564 | 11 | 5 | 0.9474 |

Figure 15K:
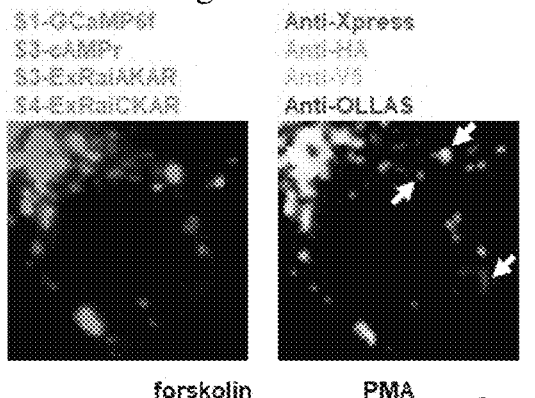
Figure 15K:
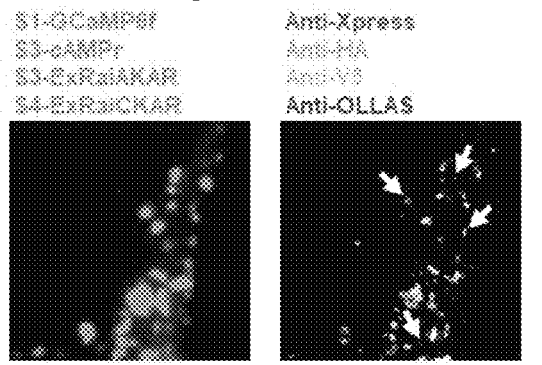
Figure 15K:
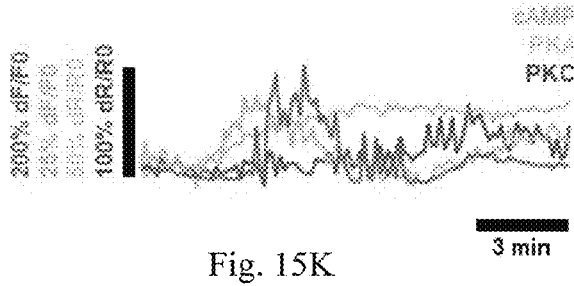
Figure 15L:
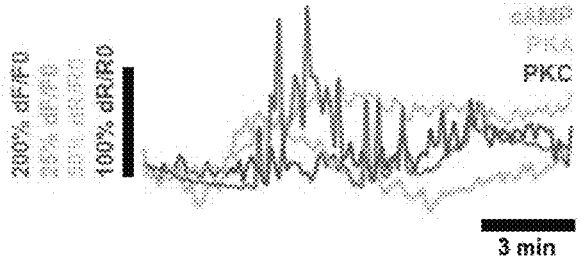

When S1-GCaMP6f, S2-cAMPr, S3-ExRaiAKAR, and S4-ExRaiCKAR were co-expressed in neurons, all 4 kinds of puncta were observed (FIG. 15I-J) of, as determined by post-fixation immunostaining (FIG. 15K-L, top). To facilitate performing the immunostaining in a multiplexed way, samples were first subjected to tissue expansion protocols (Chen, Tillberg and Boyden, 2015; Tillberg et al., 2016; Asano et al., 2018), in which target molecules in cells or tissues are covalently anchored into an expandable hydrogel network; then, samples undergo mechanical homogenization by denaturing treatments (Bodenmiller, 2016; Ku et al., 2016; Lin et al., 2018). Then, conventional immunostaining was performed with commercially available primary and secondary antibodies with repeated rounds of immunostaining and antibody stripping for clearance (by applying the same denaturing solution at lower temperatures), allowing visualization of more targets than spectrally available.

To show functionality of all 4 sensors, neurons were challenged with two drugs, 50 µM forskolin (which as described elsewhere herein modulates cAMP, $Ca^{2+}$, and PKA) for 3 minutes, followed after a break of 3 minutes by 100 ng/mL phorbol 12-myristate 13-acetate (PMA), a drug known to drive PKC activation, for 3 minutes, and observed responses of S1-GCaMP6f, S2-cAMPr, S3-ExRaiAKAR, and S4-ExRaiCKAR to these interventions (FIG. 15K-L, bottom, representative traces; FIG. 15M-N, population data). As expected, forskolin induced cAMP, $Ca^{2+}$, and PKA activities similar to previous results and PMA-induced increases of PKC activity. Simultaneous expression of four reporters resulted in many puncta at the soma and along neurites (FIG. 15O), with good lack of colocalization of multiple reporters within individual puncta (FIG. 15P; puncta containing multiple reporters were not analyzed for their dynamics). Puncta were comparable in size (FIG. 15Q, left) and punctum-punctum distance (FIG. 15Q, right) when expressed together, as when expressed alone.

Spatial and Spectral Multiplexing

Figures 16E, 16F, 16G:
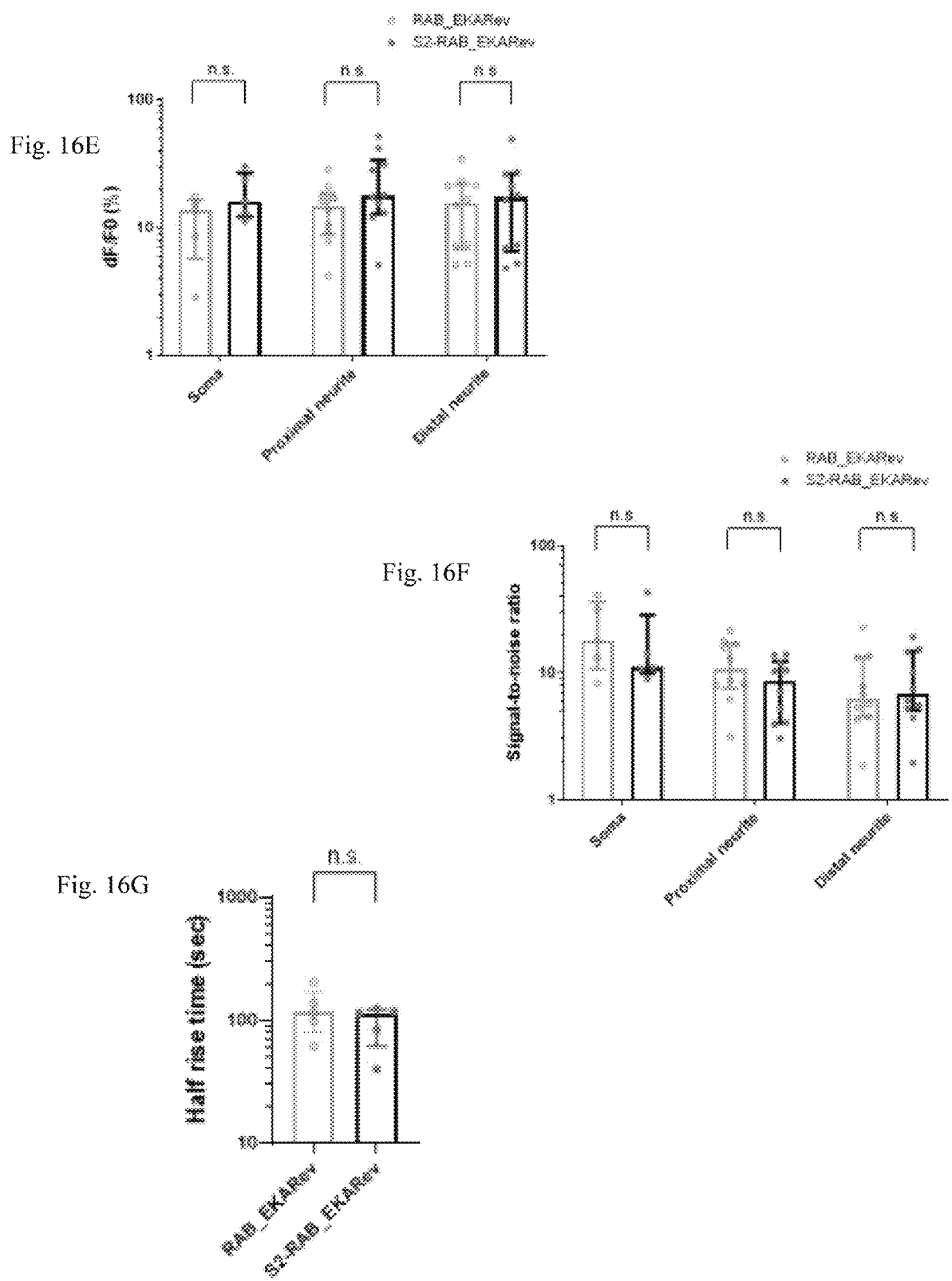
Figure 16H:
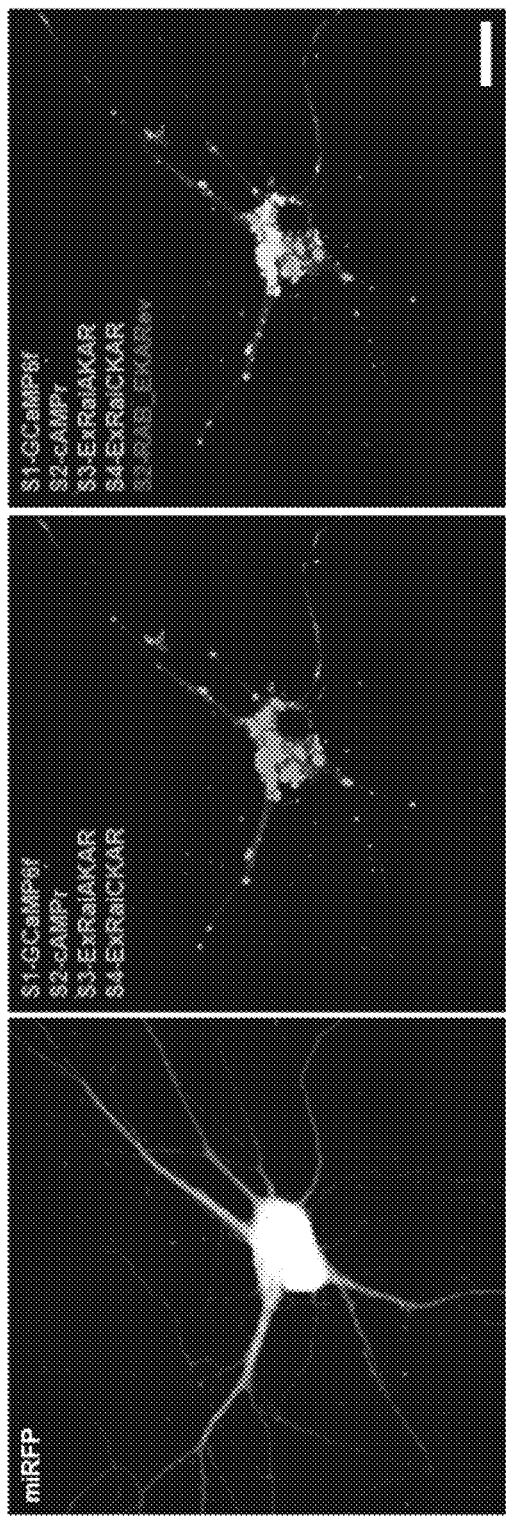
Figure 16I:
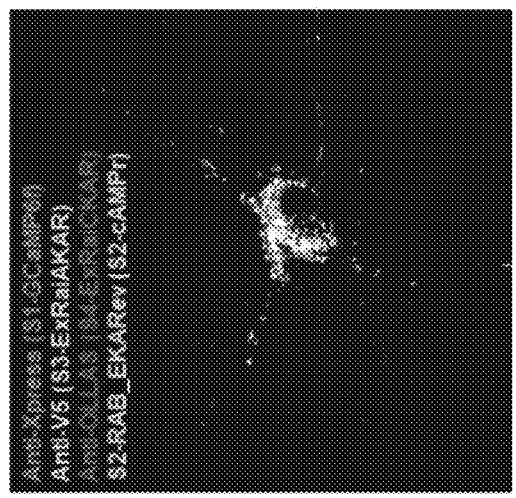
Figure 16J:
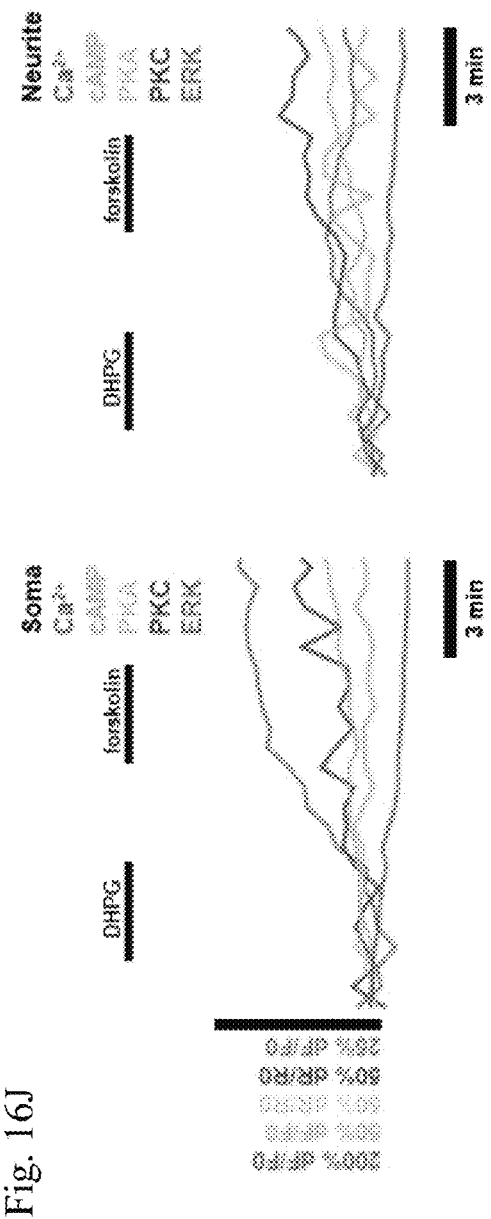
Figure 16K:
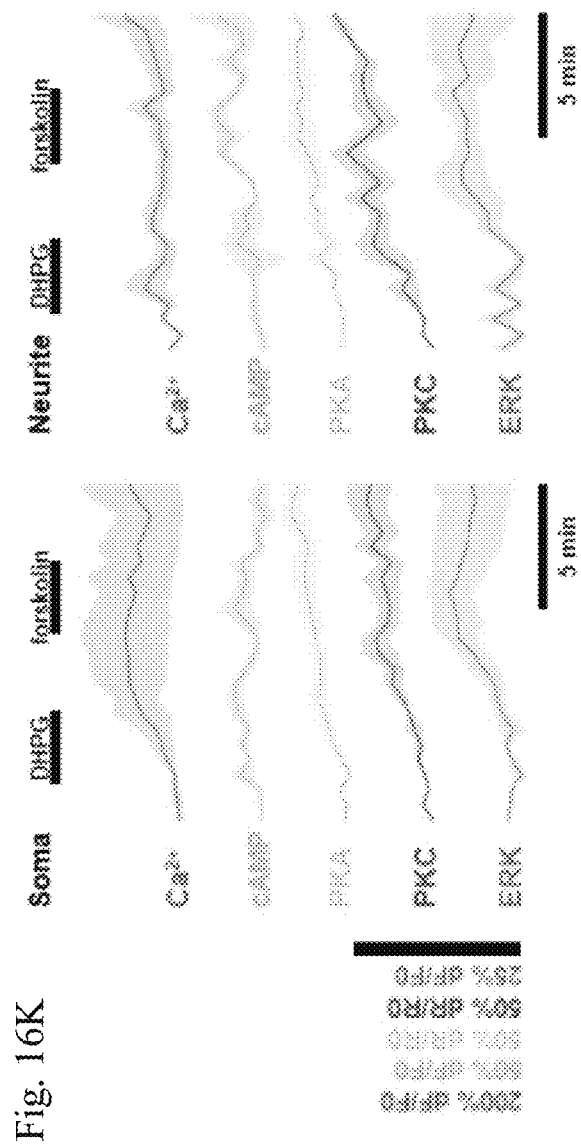

Spatial multiplexing does not replace spectral multiplexing, but instead is complementary. To investigate the compatibility of spatial and spectral multiplexing techniques for even greater multiplexing capabilities, spatial and spectral multiplexing were combined by sharing one protein scaffold among multiple reporters that emitted different colors. The S2 scaffold, used in Example 1 for cAMPr, was adapted for a red fluorescent protein (RFP)-based reporter for extracellular signal-regulated kinase (ERK), RAB-EKARev (Ding et al., 2015; Mehta et al., 2018), resulting in S2-RAB_EKARev (FIG. 16A). S2-RAB_EKARev produced bright puncta (FIGS. 16B-C), and exhibited similar transients to those of conventional RAB-EKARev (FIG. 16D), with comparable amplitude (FIG. 16E, Table 65), signal-to-noise ratio (FIG. 16F, Table 66), and rise time (FIG. 16G, Table 67), when elicited by (S)-3,5-Dihydroxyphenylglycine (DHPG), an agonist of group I metabotropic glutamate receptors (mGluR1 and mGluR5) shown to drive ERK activity in cultured rat neurons (Mao et al., 2005). When S1-GCaMP6f, S2-cAMPr, S3-ExRaiAKAR, S4-ExRaiCKAR, and S2-RAB_EKARev were co-expressed in mouse hippocampal neurons, they formed puncta (FIG. 16H) that could be identified by post-fixation immunostaining (FIG. 16I). S2-cAMPr and S2-RAB_EKARev co-occupied the same puncta, but could be distinguished by their different spectra. When imaged in the GFP and RFP channels after stimulation with 100 µM DHPG for 3 minutes, followed by a 3-minute break, then 50 µM forskolin for 3 minutes, in order to see responses from all 5 indicators, signals reported by all 5 indicators could be identified (FIG. 16J; FIG. 16K population data). DHPG produced increases in cAMP, PKA, PKC, and ERK levels, as expected from previous studies (Mironov et al., 2009; Ménard and Quirion, 2012; Wang and Zhuo, 2012; Careaga et al., 2014; Partridge et al., 2014). In some neurons, DHPG produced $Ca^{2+}$ increased, but in one neuron it did not. Forskolin, delivered after DHPG washout, appeared not to have much effect, perhaps because DHPG had already saturated the signaling network before forskolin administration. Tables 65-67 show statistical analyses for FIGS. 16E-G.

TABLE 65

Statistical analysis for FIG. 16E
Peak fluorescence changes in RFP channel at the soma, proximal neurites, and distal neurites of cultured mouse hippocampal neurons expressing RAB_EKARev or S2-RAB_EKARev under 100 µM DHPG stimulation (n = 5 somata, 10 proximal neurites, and 10 distal neurites from 5 neurons from 5 cultures for RAB_EKARev; n = 5 somata, 10 proximal neurites, and 10 distal neurites from 5 neurons from 5 cultures for S2-RAB_EKARev). Two-way analysis of variance followed by post-hoc Bonferroni corrected multiple comparisons test.

| Two-way ANOVA Ordinary Alpha 0.05 | | | | | |
|---|---|---|---|---|---|
| Source of Variation | % of total variation | P value | P value summary | Significant? | |
| Interaction | 1.693 | .660 | ns | No | |
| Subcellular location | 1.725 | .655 | ns | No | |
| Molecule | 7.315 | .064 | ns | No | |
| ANOVA table | SS (Type III) | DF | MS | $F$ (DFn, DFd) | P value |
| Interaction | 101.8 | 2 | 50.90 | $F (2, 44) = 0.4187$ | P = .660 |
| Subcellular location | 103.7 | 2 | 51.87 | $F (2, 44) = 0.4267$ | P = .655 |
| Molecule | 439.9 | 1 | 439.9 | $F (1, 44) = 3.619$ | P = .064 |
| Residual | 5349 | 44 | 121.6 | | |

TABLE 65-continued

Statistical analysis for FIG. 16E
Peak fluorescence changes in RFP channel at the soma, proximal neurites, and distal neurites of cultured mouse hippocampal neurons expressing RAB_EKARev or S2-RAB_EKARev under 100 µM DHPG stimulation (n = 5 somata, 10 proximal neurites, and 10 distal neurites from 5 neurons from 5 cultures for RAB_EKARev; n = 5 somata, 10 proximal neurites, and 10 distal neurites from 5 neurons from 5 cultures for S2-RAB_EKARev). Two-way analysis of variance followed by post-hoc Bonferroni corrected multiple comparisons test.

| Difference between column means | |
|---|---|
| Predicted (LS) mean of RAB_EKARev | 14.00 |
| Predicted (LS) mean of S2-RAB_EKARev | 20.25 |
| Difference between predicted means | −6.253 |
| SE of difference | 3.287 |
| 95% CI of difference | −12.88 to 0.3718 |

Number of families 1
Number of comparisons per family 3
Alpha 0.05

| Bonferroni's multiple comparisons test | Predicted (LS) mean diff. | 95.00% CI of diff. | Significant? | Summary | Adjusted P Value |
|---|---|---|---|---|---|
| RAB_EKARev-S2-RAB_EKARev | | | | | |
| Soma | −7.209 | −24.57 to 10.15 | No | ns | .921 |
| Proximal neurite | −8.901 | −21.17 to 3.372 | No | ns | .234 |
| Distal neurite | −2.650 | −14.92 to 9.623 | No | ns | >.999 |

| Test details | Predicted (LS) mean 1 | Predicted (LS) mean 2 | Predicted (LS) mean diff. | SE of diff. | N1 | N2 | t | DF |
|---|---|---|---|---|---|---|---|---|
| RAB_EKARev-S2-RAB_EKARev | | | | | | | | |
| Soma | 11.68 | 18.88 | −7.209 | 6.973 | 5 | 5 | 1.034 | 44.00 |
| Proximal neurite | 14.63 | 23.53 | −8.901 | 4.931 | 10 | 10 | 1.805 | 44.00 |
| Distal neurite | 15.69 | 18.34 | −2.650 | 4.931 | 10 | 10 | 0.5374 | 44.00 |

TABLE 66

Statistical analysis for FIG. 6F
Signal-to-noise ratio in the RFP channel at the soma, proximal neurites, and distal neurites (of cultured mouse hippocampal neurons expressing RAB_EKARev or S2-RAB_EKARev under 100 µM DHPG stimulation (n = 5 somata, 10 proximal neurites, and 10 distal neurites from 5 neurons from 5 cultures for RAB EKARev; n = 5 somata, 10 proximal neurites, and 10 distal neurites from 5 neurons from 5 cultures for S2-RAB_EKARev). Two-way analysis of variance followed by post-hoc Bonferroni corrected multiple comparisons test.

Two-way ANOVA Ordinary
Alpha 0.05

| Source of Variation | % of total variation | P value | P value summary | Significant? | | |
|---|---|---|---|---|---|---|
| Interaction | 1.603 | .618 | ns | No | | |
| Subcellular location | 24.38 | .002 | ** | Yes | | |
| Molecule | 2.116 | .263 | ns | No | | |
| ANOVA table | SS (Type III) | DF | MS | F (DFn, DFd) | | P value |
| Interaction | 58.76 | 2 | 29.38 | F (2, 44) = 0.4872 | | P = .618 |
| Subcellular location | 893.7 | 2 | 446.9 | F (2, 44) = 7.409 | | P = .002 |

TABLE 66-continued

Statistical analysis for FIG. 6F
Signal-to-noise ratio in the RFP channel at the soma, proximal neurites, and distal
neurites (of cultured mouse hippocampal neurons expressing RAB_EKARev or S2-
RAB_EKARev under 100 μM DHPG stimulation (n = 5 somata, 10 proximal neurites, and 10
distal neurites from 5 neurons from 5 cultures for RAB EKARev; n = 5 somata, 10 proximal
neurites, and 10 distal neurites from 5 neurons from 5 cultures for S2-RAB_EKARev). Two-
way analysis of variance followed by post-hoc Bonferroni corrected multiple comparisons test.

| | | | | | |
|---|---|---|---|---|---|
| Molecule | 77.59 | 1 | 77.59 | $F(1, 44) = 1.287$ | $P = .263$ |
| Residual | 2654 | 44 | 60.31 | | |

| | |
|---|---|
| Difference between column means | |
| Predicted (LS) mean of RAB_EKARev | 14.26 |
| Predicted (LS) mean of S2-RAB_EKARev | 11.64 |
| Difference between predicted means | 2.626 |
| SE of difference | 2.315 |
| 95% CI of difference | −2.040 to 7.292 |

Number of families 1
Number of comparisons per family 3
Alpha 0.05

| Bonferroni's multiple comparisons test | Predicted (LS) mean diff. | 95.00% CI of diff. | Significant? | Summary | Adjusted P Value |
|---|---|---|---|---|---|
| RAB_EKARev-S2-RAB_EKARev | | | | | |
| Soma | 4.765 | −7.460 to 16.99 | No | ns | >.999 |
| Proximal neurite | 3.511 | −5.134 to 12.15 | No | ns | .953 |
| Distal neurite | −0.3970 | −9.041 to 8.247 | No | ns | >.999 |

| Test details | Predicted (LS) mean 1 | Predicted (LS) mean 2 | Predicted (LS) mean diff. | SE of diff. | N1 | N2 | t | DF |
|---|---|---|---|---|---|---|---|---|
| RAB_EKARev-S2-RAB_EKARev | | | | | | | | |
| Soma | 22.31 | 17.55 | 4.765 | 4.912 | 5 | 5 | 0.9702 | 44.00 |
| Proximal neurite | 11.87 | 8.357 | 3.511 | 3.473 | 10 | 10 | 1.011 | 44.00 |
| Distal neurite | 8.613 | 9.010 | −0.3970 | 3.473 | 10 | 10 | 0.1143 | 44.00 |

TABLE 67

Statistical analysis for FIG. 16G
Wilcoxon rank sum test of the half rise
time of reported ERK signals at the soma after
100 μM DHPG stimulation (n = 5 somata,
10 proximal neurites, and 10 distal neurites
from 5 neurons from 5 cultures for RAB_EKARev;
n = 5 somata, 10 proximal neurites, and 10
distal neurites from 5 neurons from 5 cultures
for S2-RAB_EKARev).

| | |
|---|---|
| P value | 0.5476 |
| ranksum | 31 |

This combination of spatial and spectral multiplexing could enable the readout of SiRI reporter identity without requiring immunostaining: for example, in cells co-expressing S1-GCaMP6f, S3-ExRaiAKAR, and S3-RAB_EKARev (generated by replacing ExRaiAKAR in S3-ExRaiAKAR with RAB_EKARev), S3-ExRaiAKAR and S3-RAB_EKARev co-clustered into puncta because they shared the same protein scaffold (FIG. 29), and could be identified as the only puncta sharing both green and red fluorescence, with the remaining purely green puncta therefore identified as the S1-GCaMP6f puncta.

Example 4. Spatially Multiplexed Imaging of Two GFP-Based Sensors During Long-Term Potentiation Spatially multiplexed imaging of $Ca^{2+}$ and PKA activities via two GFP-based sensors was performed during long-term potentiation to examine whether the methods described in the preceding Examples could also be used over longer time periods, and whether signals within the $Ca^{2+}$/cAMP/PKA signal transduction network could be measured in an intact biological preparation.

Materials and Methods

In Utero Electroporation

Embryonic day (E) 15.5 timed-pregnant female Swiss Webster (Taconic Biosciences, Rensselaer, NY) mice were deeply anaesthetized with 2% isoflurane. Uterine horns were exposed and periodically rinsed with warm sterile PBS. Plasmid DNA was injected into the lateral ventricle of one cerebral hemisphere of an embryo. Final plasmid DNA concentration was 4.5 μg/l in water (DNA mass ratio of pAAV-CAG-S1-GCaMP6f, pAAV-CAG-S3-ExRaiAKAR, and pAAV-CAG-mRuby3-6×FLAG at 1:2:2). Fast Green FCF dye (Millipore Sigma, Burlington, MA) was added to the DNA mixture to visualize the mixture during DNA injection. Five voltage pulses (50 V, 50 ms duration, 1 Hz) were delivered two times using 5-mm round plate electrodes (Harvard Apparatus, Holliston, MA), with the cathode placed on top of the skull to target the hippocampus. Electroporated embryos were placed back into the dam, and allowed to mature for delivery.

Electrophysiology and Imaging of Acute Brain Slice 3 to 4 week-old mice expressing SiRIs and miRFP (from in utero electroporation) were anesthetized with isoflurane and decapitated; the brains were taken out and placed in ice-cold choline-based cutting solution containing the following: 110 mM choline chloride, 7 mM $MgCl_2$, 2.5 mM KCl, 0.5 mM $CaCl_2$, 1.25 mM $NaHPO_4$, 25 mM $NaHCO_3$, 25 mM D-glucose, 11.6 mM ascorbic acid, and 3.1 mM pyruvic acid to a final pH of 7.75. The sagittal brain slices containing the hippocampus (300 μm) were cut in cold choline-based cutting solution with a Compresstome® VF-300 (Precisionary Instruments, Natick, MA), and transferred to a holding chamber containing ACSF: 124 mM NaCl, 2 mM $MgSO_4$, 2.5 mM KCl, 2 mM $CaCl_2$, 1.2 mM $NaHPO_4$, 24 mM $NaHCO_3$, 5 mM HEPES, and 12.5 mM D-glucose to a final pH of 7.35, and recovered for 20 minutes at 30-32° C. Slices were subsequently maintained at room temperature until use. The cutting solution, ACSF, and ACSF with 50 μM forskolin added (or 'forskolin-ACSF') were constantly bubbled with 95% $O_2$, 5% $CO_2$. Slices were screened for positive green expression with a hand-held LED and filter.

Individual slices were transferred to a submersion perfusion chamber and continuously perfused with room temperature (23-26° C.) ACSF, constantly bubbled with 95% $O_2$, 5% $CO_2$, at a 4-5 ml/minute rate. Recording pipettes (4-6MΩ resistance) were pulled from borosilicate glass (Warner Instruments, Holliston, MA) and filled with ACSF. fEPSP recordings were made with a microelectrode amplifier (Multiclamp™ 700B, Molecular Devices, San Jose, CA). Signals were low-pass-filtered at 3 kHz and sampled at 20 kHz with a Digidata™ 1550B plus Humsilencer™ (Molecular Devices, San Jose, CA), and data were stored on a computer for subsequent offline analysis. In fEPSP recordings, recording pipettes were placed in the stratum radiatum of CA1. All evoked responses were elicited by delivering constant current pulses (duration 0.2 millisecond, 0.05 Hz) through a bipolar tungsten stimulating electrode placed into the mid stratum radiatum to activate Schaffer collateral/commissural fibers. In LTP experiments, stimulation intensity was adjusted to about 50% of the threshold for maximum fEPSPs and maintained at that level throughout all the recordings. Chemical LTP was induced by perfusing forskolin-ACSF, instead of ACSF, to the slice for 15 minutes, after which the perfusion was switched back to ACSF. fEPSP was recorded every 3 minutes, from 12 minutes before the onset of forskolin-ACSF perfusion to 57 minutes after the onset of forskolin-ACSF perfusion, in 24 fEPSP recordings. fEPSP slopes were measured by calculating the slopes between 10-60% of the fEPSP rising phase.

Acute brain slice neuron imaging was performed on a spinning disk confocal microscope (a Yokogawa® CSU-W1 Confocal Scanner Unit on a Nikon® Eclipse Ti microscope) equipped with a 40×1.15 NA water immersion objective (Nikon® MRD77410) and a Zyla® PLUS 4.2 Megapixel camera controlled by NIS-Elements® AR software. Individual slices were transferred to a submersion perfusion chamber and continuously perfused with room temperature (23-26° C.) ACSF, constantly bubbled with 95% $O_2$, 5% $CO_2$, at a 4-5 ml/minute rate.

A volume containing the soma, apical dendrites, and basal dendrites of CA1 pyramidal neurons in the slice were imaged under the GFP (for SiRIs) and RFP (for the morphological marker mRuby3-FLAG) channels, and then volumetric time-lapse imaging (1.5-2.0 μm per Z step) was performed in the GFP emission channel (30 seconds per volume; each X-Y plane in the volume was captured twice, once under 405 nm excitation and the other under 488 nm excitation). Chemical stimulation was by perfusing forskolin-ACSF, instead of ACSF, to the slice for 15 minutes, after which the perfusion was switched back to ACSF. Time-lapse imaging started 5 minutes before the onset of forskolin-ACSF perfusion and ended 60 minutes after the onset of forskolin-ACSF perfusion, in total 65 minutes.

For the CA1 pyramidal neurons recorded from acute mouse brain slice, apical dendrites and basal dendrites were identified by cell morphology. For ExRaiAKAR or ExRaiCKAR, the time courses of the fluorescence intensity in the GFP emission channel under 488 nm and 405 nm excitations were measured as F_488 and F_405, respectively.

Significant photobleaching was observed in the fluorescence time courses measured from cAMPr and RAB_EKARev in recordings longer than 5 minutes in cultured neurons, as well as those measured from GCaMP6f and ExRaiAKAR in the 65-minute-long recordings in slice. Photobleaching correction was performed on these fluorescence time courses as described herein. Fluorescence time courses during the pre-stimulation baseline periods measured from cAMPr or RAB_EKARev were fitted to exponential decay functions, and the exponential decay components were then removed from the full-length time courses. Fluorescence time courses during the pre-stimulation baseline periods measured from GCaMP6f in the 65-minute-long recordings in slice were fitted to a bi-exponential decay function, and the bi-exponential decay components were then removed from the full-length time courses. The fluorescence time courses during the pre-stimulation baseline periods measured from ExRaiAKAR in the 65-minute-long recordings in slice under 488 nm excitation, i.e. F_488_baseline, were fitted to a bi-exponential decay function, and the bi-exponential decay components were then removed from the full-length time courses. The fluorescence time courses during the pre-stimulation baseline periods measured from ExRaiAKAR in slice under 405 nm excitation, i.e. F_405_baseline, were fitted to a bi-exponential decay function with the time constants fixed to those obtained from the curve fitting of the corresponding F_488_baseline time courses (so that the resultant time constants from the bi-exponential fitting were identical between each F_488_baseline/F_405_baseline pair), and the resulted bi-exponential decay components were then removed from the full-length time courses.

To calculate the dF/F0 for GCaMP6f, cAMPr, or RAB_EKARev expressing HeLa cells or neurons, the baseline fluorescence, F0, was first calculated as the average net fluorescence during the pre-stimulation baseline period. dF/F0 was then calculated as dF/F0=(F−F0)/F0. To calculate the signal-to-noise ratio (SNR) the maximum dF/F0 was divided by the standard deviation of the net fluorescence during the pre-stimulation baseline period.

To calculate the dR/R0 for ExRaiAKAR or ExRaiCKAR expressing HeLa cells or neurons, the baseline fluorescence, F0_488 and F0_405, was first calculated as the average net fluorescence during the pre-stimulation baseline period in the GFP emission channel under 488 nm and 405 nm excitations, respectively. dR/R0 was then calculated as dR/R0=(F_488/F_405)/(F0_488/F0_405) -1. To calculate the signal-to-noise ratio (SNR) the maximum dF/F0 was divided by the standard deviation of the net fluorescence during the pre-stimulation baseline period.

The slice was then fixed in TissuePrep™ buffered 10% formalin for 15 minutes at room temperature (RT) followed by incubation in 100 mM glycine in 1×PBS for 15-30 minutes at RT and three washes in 1×PBS. The slice was then stained against the epitope tags and morphological markers.

Additional materials and methods were as described in Examples 1-3 and in Experiments, Results, and Discussion section.

Experiments, Results, and Discussion

Figure 14A:
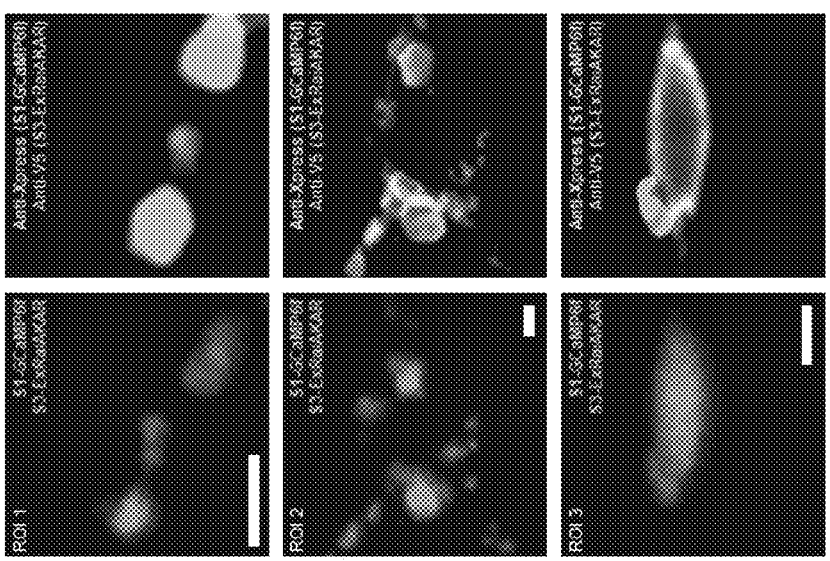
Figure 14B:
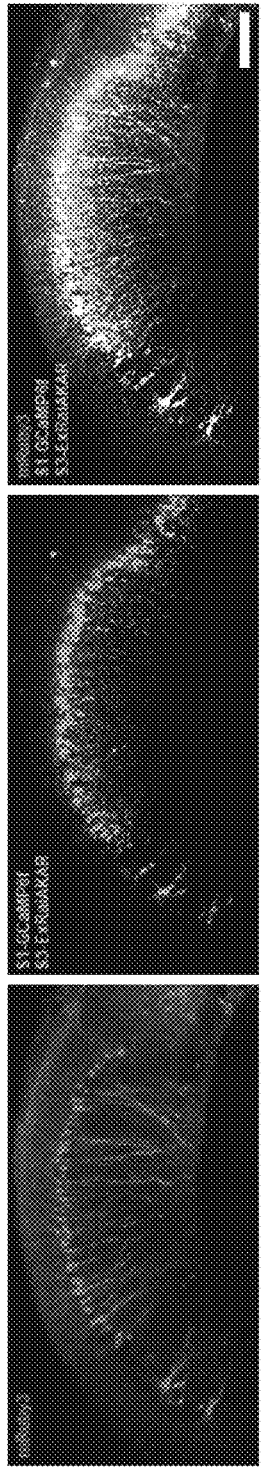
Figure 14C:
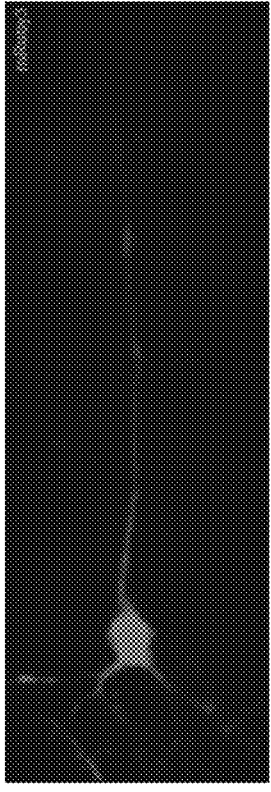

S1-GCaMP6f, S3-ExRaiAKAR, and the cell morphological marker mRuby3 were expressed in pyramidal neurons in mouse hippocampal area CA1 by targeted in utero electroporation, to examine the relationship between these signals over timescales of ~1 hour. S1-GCaMP6f (green) and S3-ExRaiAKAR (green) SiRIs formed puncta (FIG. 32A; FIG. 14A-B) which were distributed in somata as well as in neurites of hippocampal CA1 pyramidal neurons (FIG. 14B). SiRI expression in the hippocampus and cortex of mice for 5-7 weeks did not alter markers of cellular and synaptic health, including the neuronal nucleus marker NeuN, the apoptotic marker cleaved caspase-3, the astrocyte marker GFAP, the microglial marker Iba1, the synaptic marker Synaptophysin, and the DNA damage marker γH2AX (FIG. 30, Tables 68-73). The reporter within each punctum was identified with post-fixation immunostaining (FIG. 14C, close-up views; FIG. 31A, full-neuron views); plentiful puncta were observed (FIG. 14D) and >90% of the S1-GCaMP6f or S3-ExRaiAKAR puncta did not colocalize with reporters of the other kind (FIG. 14E; puncta containing multiple reporters were not analyzed in the following dynamics studies). SiRI puncta in brain slices were comparable in size to those in neuron culture (FIG. 14F, left), as were punctum-punctum distances (FIG. 14F, right). Tables 68-73 show statistical analyses for FIGS. 30B-G.

TABLE 68

Figure 30B:
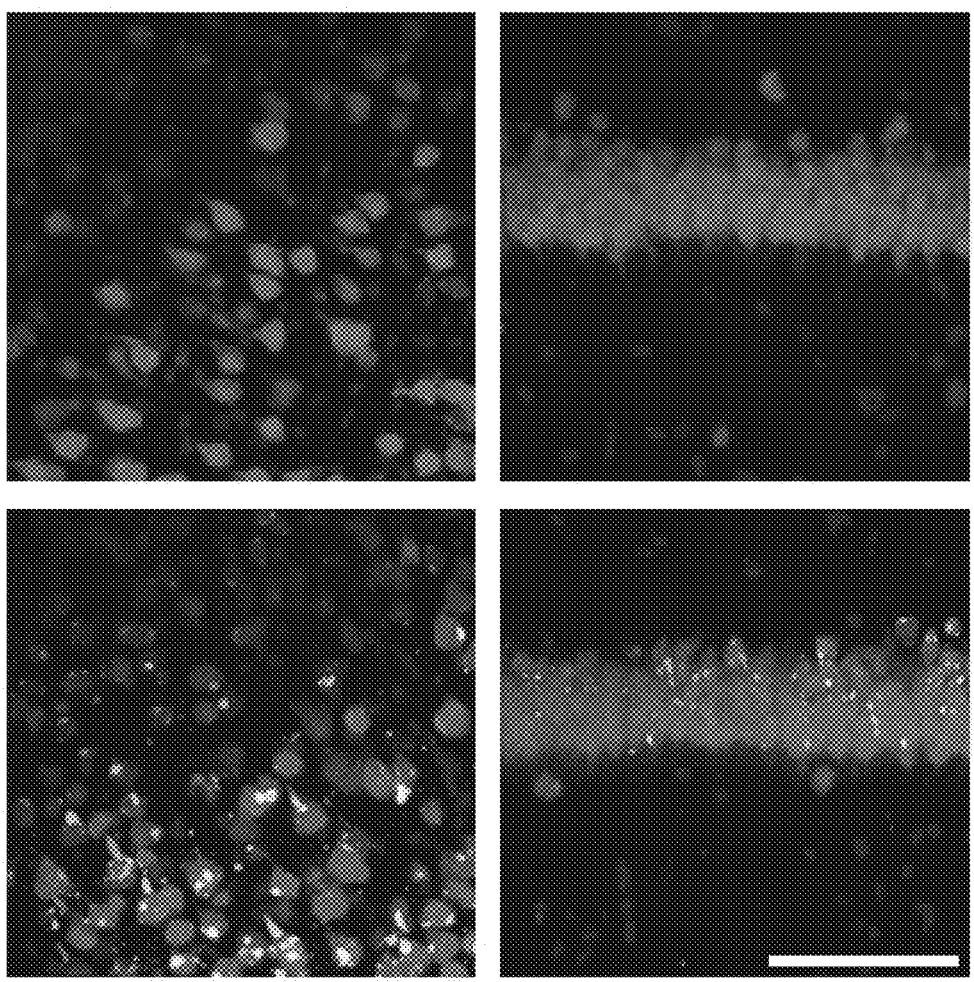
Figure 30B:
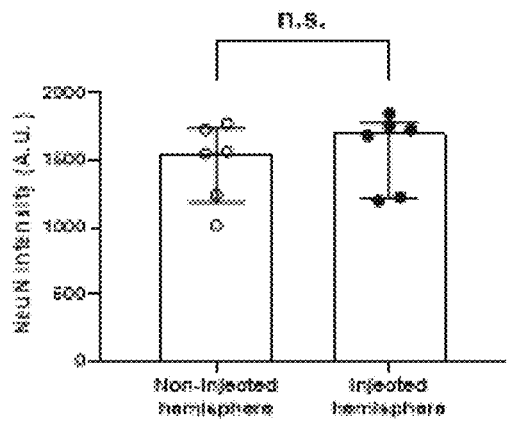
Figure 30B:
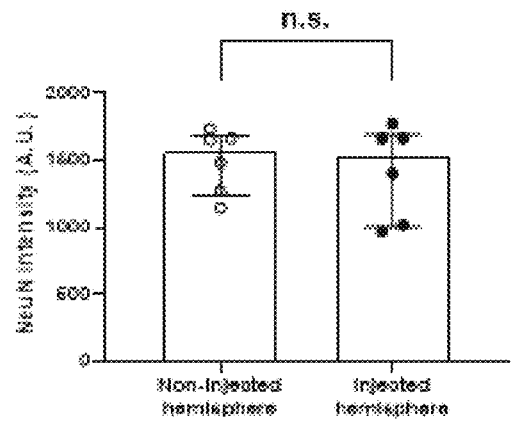
Figure 31A:
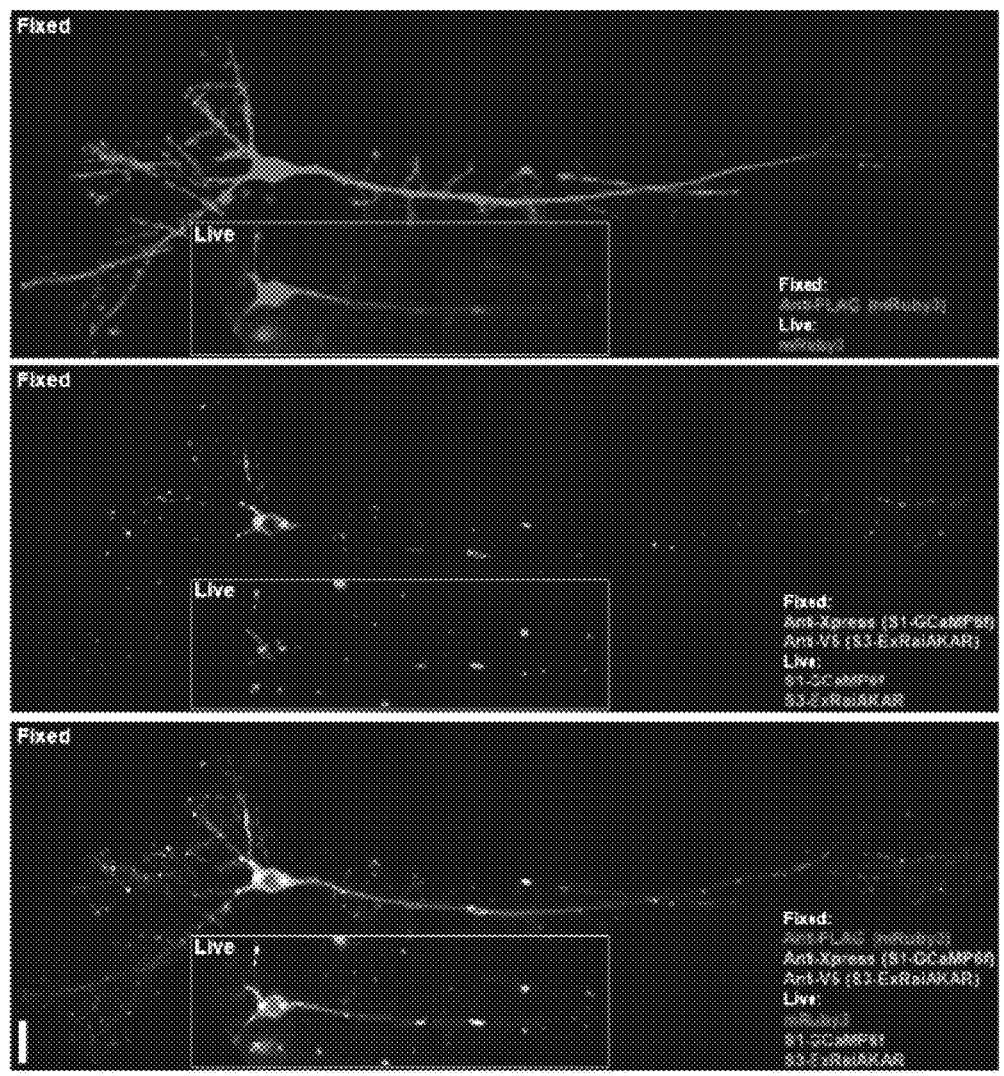

Statistical analysis for FIG. 30B

The staining intensities of NeuN
(neuronal nuclei marker) at the cortex. Wilcoxon rank sum
test; n = 6 fields of view from 3 mice in the
injected hemisphere; n = 6 fields of view from
3 mice in the non-injected hemisphere.

| P value | 0.6991 |
|---|---|
| ranksum | 36 |

The staining intensities of NeuN
(neuronal nuclei marker) at CA1. Wilcoxon rank sum
test; n = 6 fields of view from 3 mice in the
injected hemisphere; n = 6 fields of view from
3 mice in the non-injected hemisphere.

| P value | 0.8182 |
|---|---|
| ranksum | 41 |

TABLE 69

Figure 30C:
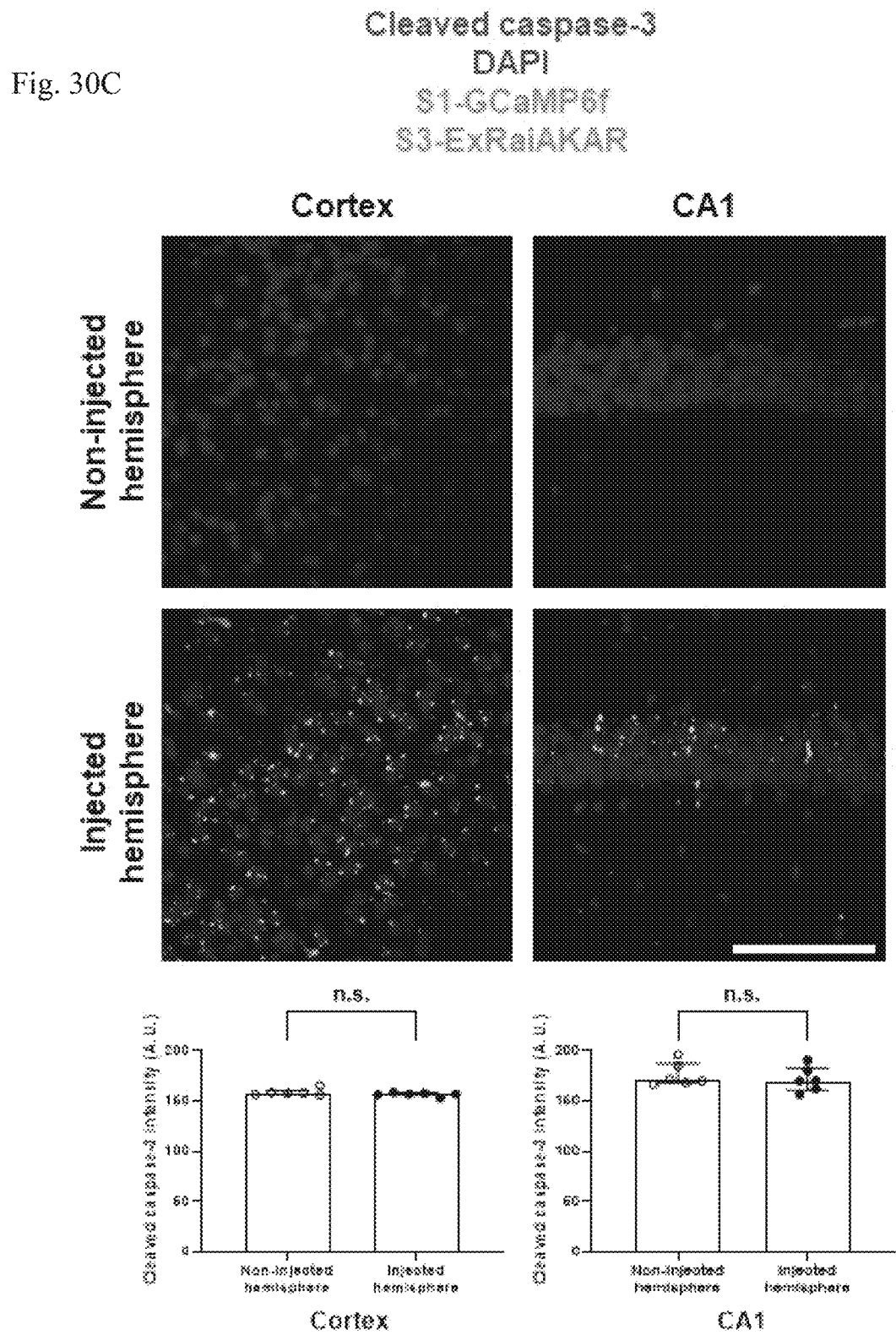

Statistical analysis for FIG. 30C

The staining intensities of cleaved caspase-3
(apoptotic marker) at the cortex. Wilcoxonrank sum
test; n = 6 fields of view from 3 mice in the
injected hemisphere; n = 6 fields of view from
3 mice in the non-injected hemisphere.

| P value | 0.4848 |
|---|---|
| ranksum | 44 |

The staining intensities of cleaved caspase-3
(apoptotic marker) at CA1. Wilcoxon rank sum
test; n = 6 fields of view from 3 mice in the
injected hemisphere; n = 6 fields of view from
3 mice in the non-injected hemisphere.

| P value | 0.5887 |
|---|---|
| ranksum | 43 |

TABLE 70

Figure 30D:
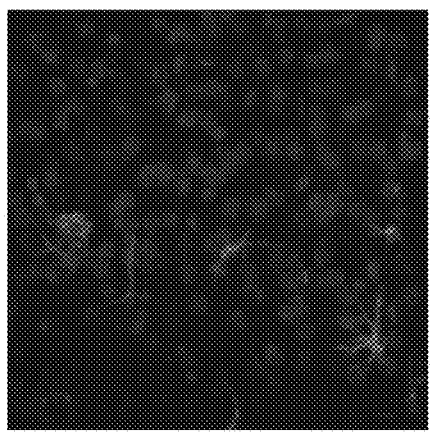
Figure 30D:
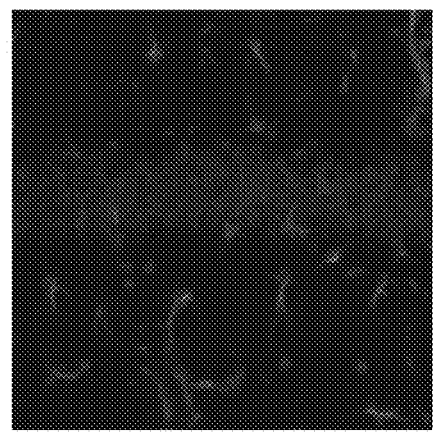
Figure 30D:
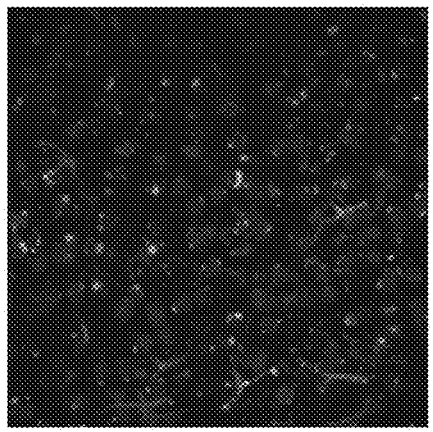
Figure 30D:
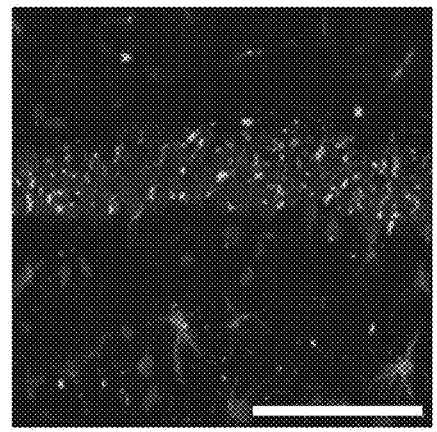
Figure 30D:
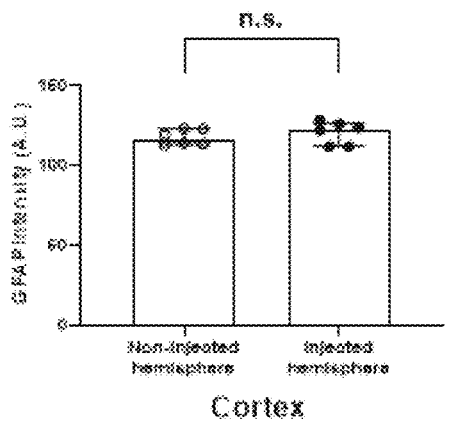
Figure 30D:
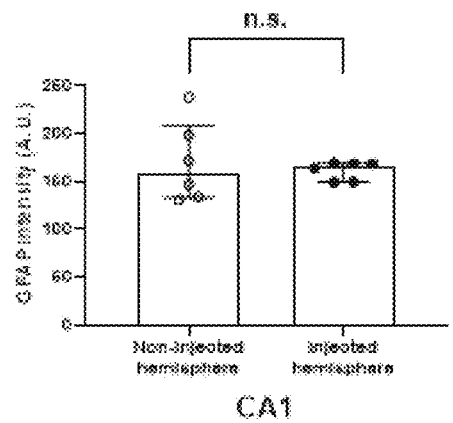

Statistical analysis for FIG. 30D

The staining intensities of GFAP
(astrocyte marker) at the cortex. Wilcoxon rank sum
test; n = 6 fields of view from 3 mice in the
injected hemisphere; n = 6 fields of view from
3 mice in the non-injected hemisphere.

| P value | 0.5887 |
|---|---|
| ranksum | 35 |

The staining intensities of GFAP
(astrocyte marker) at CA1. Wilcoxon rank sum
test; n = 6 fields of view from 3 mice in the
injected hemisphere; n = 6 fields of view from
3 mice in the non-injected hemisphere.

| P value | 1 |
|---|---|
| ranksum | 39 |

TABLE 71

Figure 30E:
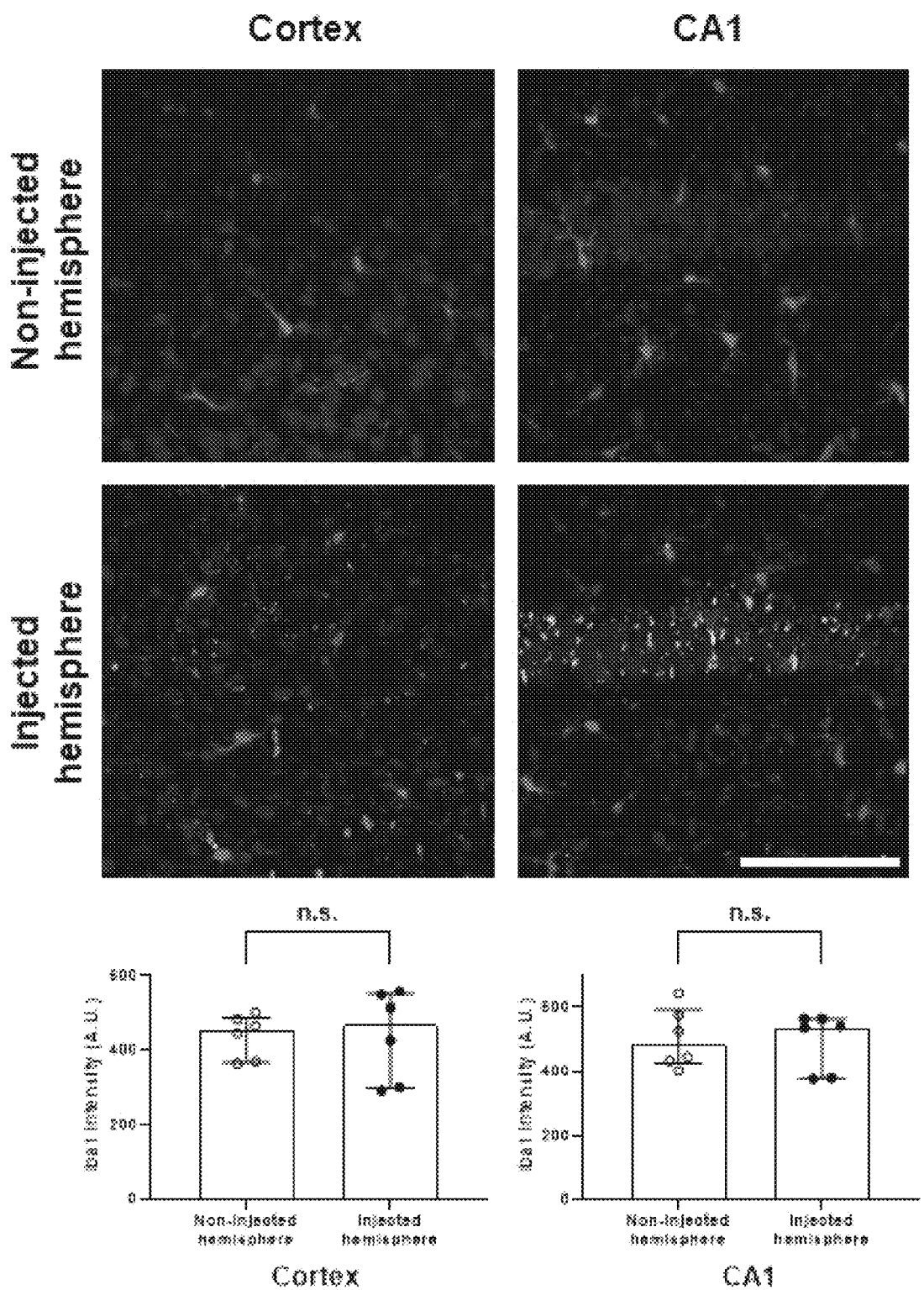

Statistical analysis for FIG. 30E

The staining intensities of Iba1
(microglial marker) at the cortex. Wilcoxon rank sum
test; n = 6 fields of view from 3 mice in the
injected hemisphere; n = 6 fields of view from
3 mice in the non-injected hemisphere.

| P value | 0.8182 |
|---|---|
| ranksum | 37 |

The staining intensities of Iba1
(microglial marker) at CA1. Wilcoxon rank sum
test; n = 6 fields of view from 3 mice in the
injected hemisphere; n = 6 fields of view from
3 mice in the non-injected hemisphere.

| P value | 0.8182 |
|---|---|
| ranksum | 41 |

TABLE 72

Figure 30F:
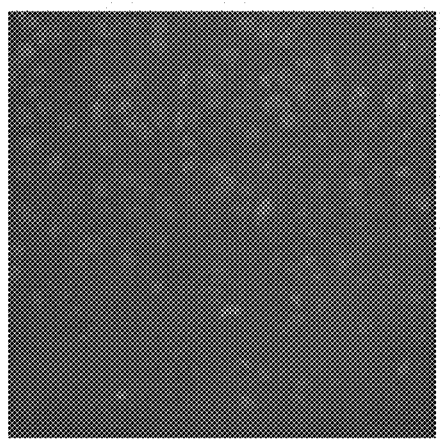
Figure 30F:
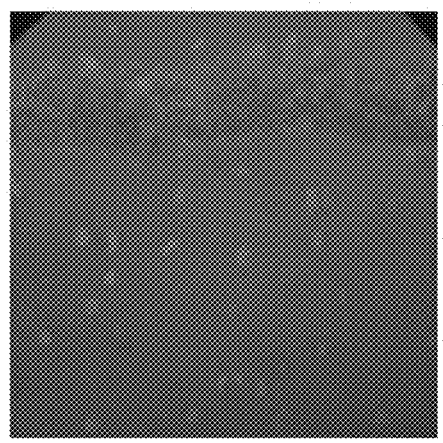
Figure 30F:
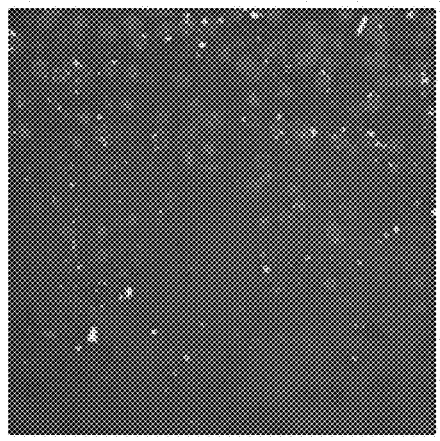
Figure 30F:
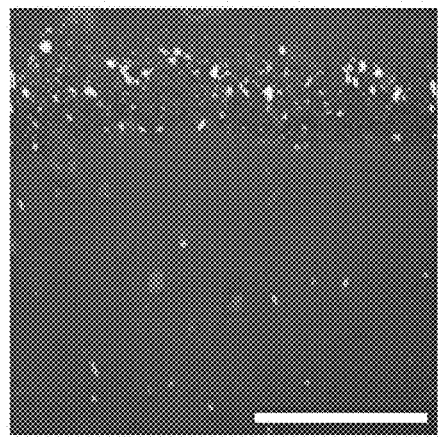
Figure 30F:
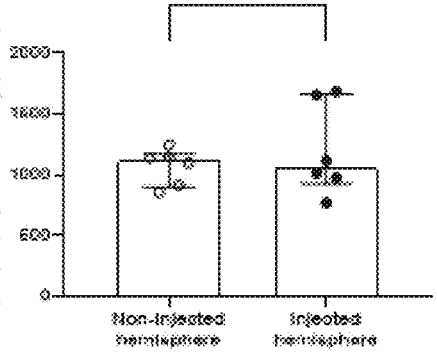
Figure 30F:
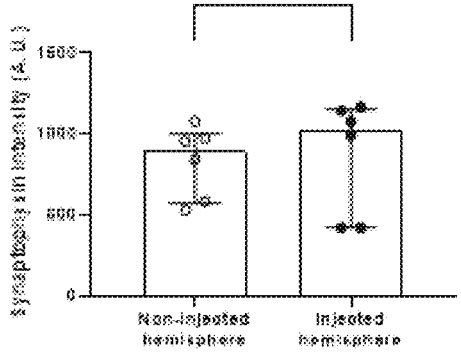

Statistical analysis for FIG. 30F

The staining intensities of synaptophysin (synaptic marker) at the cortex. Wilcoxon rank sum test; n = 6 fields of view from 3 mice in the injected hemisphere; n = 6 fields of view from 3 mice in the non-injected hemisphere.

| | |
|---|---|
| P value | 0.9372 |
| ranksum | 38 |

The staining intensities of synaptophysin (synaptic marker) at CA1. Wilcoxon rank sum test; n = 6 fields of view from 3 mice in the injected hemisphere; n = 6 fields of view from 3 mice in the non-injected hemisphere.

| | |
|---|---|
| P value | 0.4848 |
| ranksum | 34 |

TABLE 73

Figure 30G:
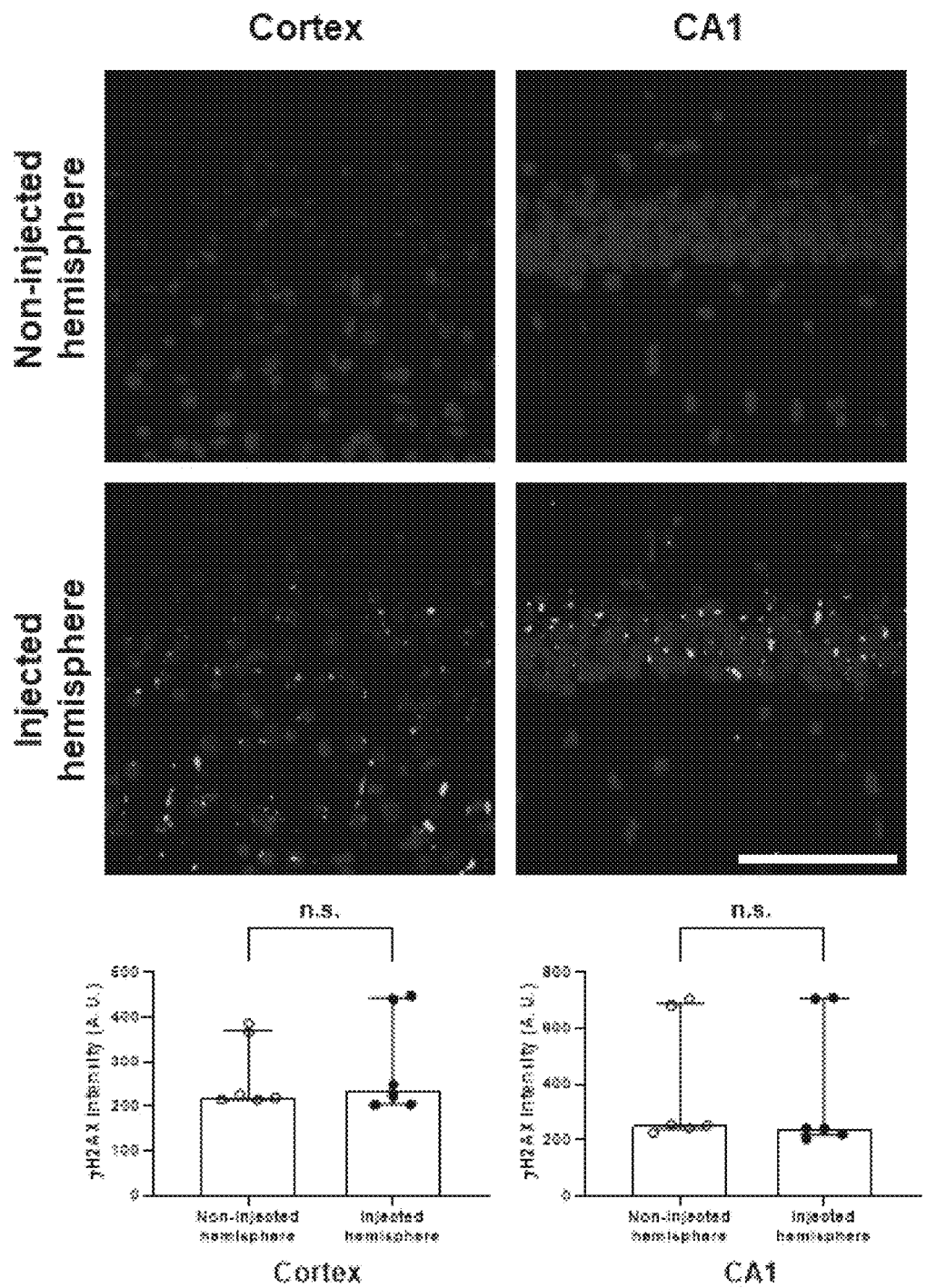

Statistical analysis for FIG. 30G

The staining intensities of γH2AX (DNA damage marker) at the cortex. Wilcoxon rank sum test; n = 6 fields of view from 3 mice in the injected hemisphere; n = 6 fields of view from 3 mice in the non-injected hemisphere.

| | |
|---|---|
| P value | 0.9372 |
| ranksum | 38 |

The staining intensities of γH2AX (DNA damage marker) at CA1. Wilcoxon rank sum test; n = 6 fields of view from 3 mice in the injected hemisphere; n = 6 fields of view from 3 mice in the non-injected hemisphere.

| | |
|---|---|
| P value | 0.5887 |
| ranksum | 43 |

Figure 14G:
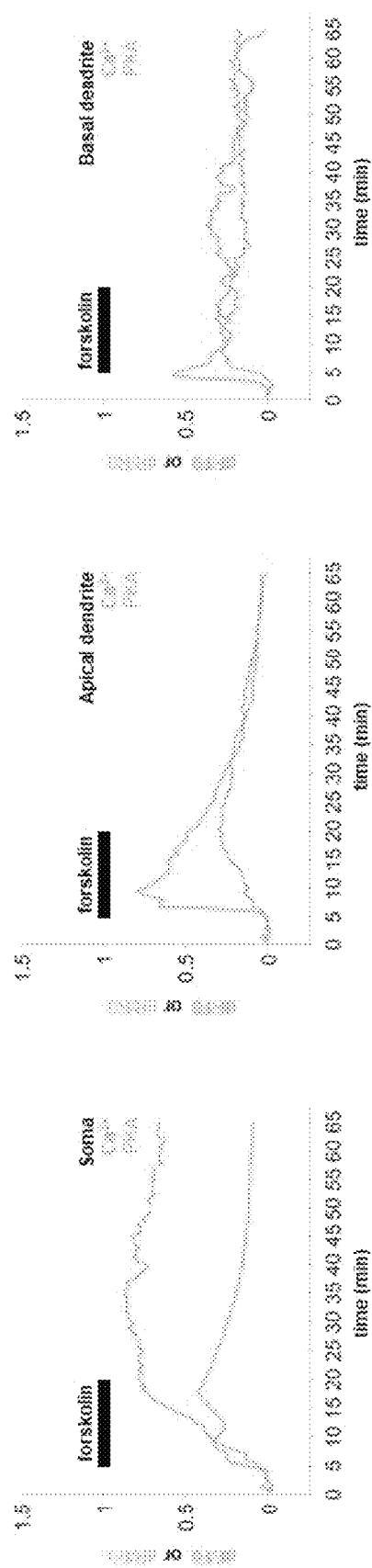
Figure 14H:
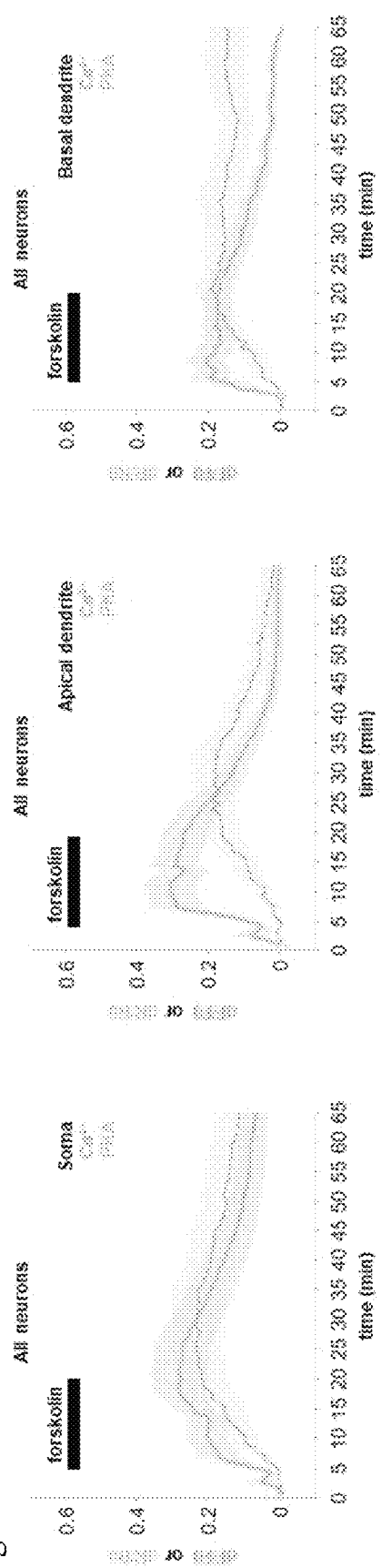
Figure 31B:
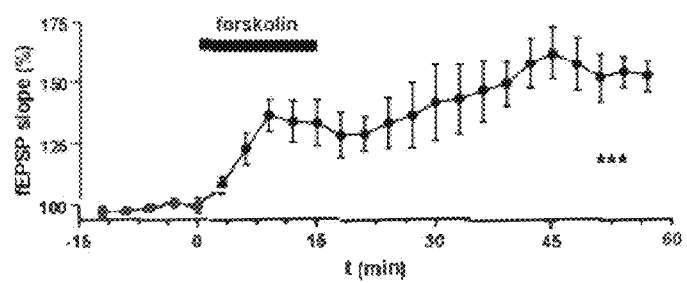

Volumetric imaging of SiRIs was performed in in 14 hippocampal CA1 pyramidal neurons in acute brain slices before, during, and after a 15 minute administration of 50 µM forskolin (FIG. 31B). The acute brain slices were kept in a perfusion chamber with continuous flow of carbonated aCSF solution, and were continuously and volumetrically imaged at the GFP channel in the CA1 region for 1 hour under 40× objective on a spinning disk confocal microscope. In the middle of the imaging, carbonated aCSF solution containing 50 µM forskolin was perfused in the perfusion chamber for 15 minutes to induce long-term potentiation (LTP) in the hippocampus, after which the solution was switched back to carbonated aCSF solution without forskolin. Reporter types were identified by post hoc immunostaining. $Ca^{2+}$ and PKA activities at the soma, apical neurites, and basal neurites of CA1 pyramidal neurons were recorded before, during, and after forskolin application (FIG. 32F, FIG. 14G, representative responses from a single neuron; FIG. 32G, averaged response from 12 neurons from 6 slices from 3 mice; FIG. 14H, average response from all recorded neurons; responses at basal dendrites were sampled at locations 10-40 µm away from the soma; responses at apical dendrites were sampled at locations 30-100 µm away from the soma). Forskolin-induced LTP were confirmed by separate electrophysiology experiments in the mice expressing S1-GCaMP6f, S3-ExRaiAKAR, and mRuby3 (FIG. 32D-E).

Figure 14K:
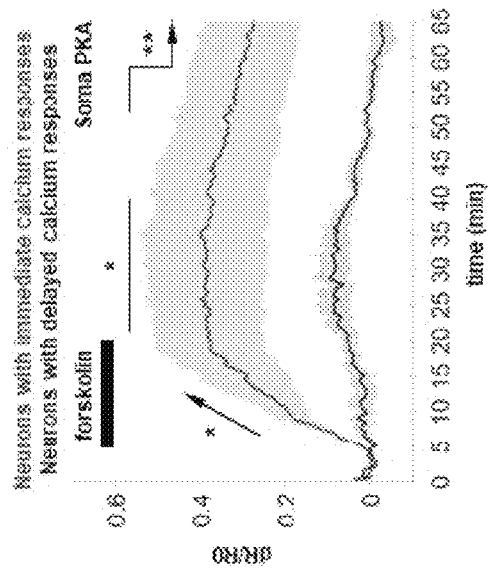

At a population level, neurons exhibited a $Ca^{2+}$ increase during the forskolin administration period, which decayed after forskolin removal, accompanied by a ramp up in PKA activity that was more sustained similar to the cultured neuron experiments of FIG. 13. In contrast to the cultured neuron studies, however, prominent $Ca^{2+}$ oscillations were not observed within individual cells. However, some neurons had immediate $Ca^{2+}$ increases (i.e., within 1 minute of the onset of forskolin stimulation, FIG. 14J), whereas others had delayed $Ca^{2+}$ responses (i.e., starting 3-15 minutes after the onset of forskolin stimulation, FIG. 14I; one neuron did not have a $Ca^{2+}$ response above baseline at all (>5% dF/F0) and one neuron had spontaneous $Ca^{2+}$ activity before forskolin stimulation, and those two neurons were not analyzed further) at the cell body, reminiscent of the short-latency versus long-latency responses observed in cultured neurons as described in Examples 2-3. The delayed $Ca^{2+}$ response neurons had latencies 12 minutes longer (880% longer) than did immediate $Ca^{2+}$ response neurons (FIG. 14K, Table 74). Analogous to the cultured-neuron case, neurons with immediate $Ca^{2+}$ responses had significantly higher peak $Ca^{2+}$ increases within the first half of the forskolin stimulation period than did neurons with delayed $Ca^{2+}$ responses (FIG. 14K, Table 74), whereas the peak $Ca^{2+}$ increased within a similar time period after the end of forskolin stimulation and the peak $Ca^{2+}$ increased over the entire experimental time-course were similar between the two groups (FIG. 14K, Table 74). These variations may have resulted from the presence of different kinds, or amounts, of signal transduction machinery that connect cAMP signals to $Ca^{2+}$ signals.

Figure 14L:
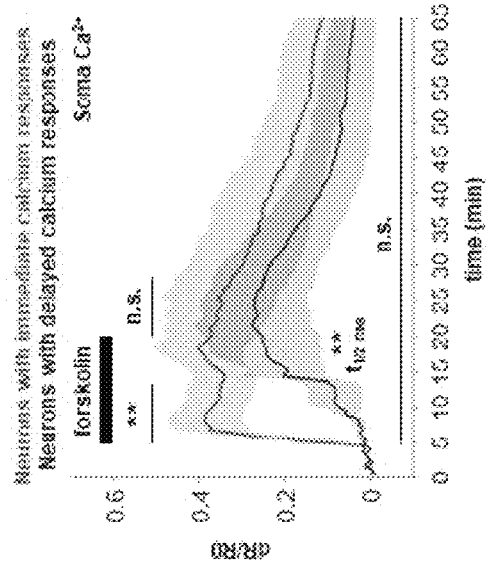

Next, experiments were performed to determine whether neurons with immediate versus delayed $Ca^{2+}$ signals had different PKA outputs from this signaling network. Neurons with immediate $Ca^{2+}$ increases had PKA responses that were faster, and that achieved higher ultimate magnitudes, than those of neurons with delayed $Ca^{2+}$ responses (FIG. 14L, Table 75). Furthermore, neurons that had immediate $Ca^{2+}$ increases had enduring PKA activation, lasting for the entire hour of monitoring, whereas neurons with delayed $Ca^{2+}$ increases had their PKA activity drop to baseline within 30 minutes (FIG. 14L, Table 75). These results in brain slices parallel the results in cultured neurons in Examples 2-3: in both cases, neurons with shorter latency $Ca^{2+}$ responses exhibited faster, and larger, PKA signals than did neurons with longer latency $Ca^{2+}$ responses. It is the simultaneous imaging of $Ca^{2+}$ and PKA that enables such relationships between $Ca^{2+}$ and PKA to be derived; such relationships are not apparent if these signals are inspected only after they are averaged across cell populations and then compared (FIG. 14H). These different $Ca^{2+}$-PKA relationships may highlight different cellular states that differently couple cAMP to $Ca^{2+}$, or that differently couple these signals to PKA output.

Figure 31G:
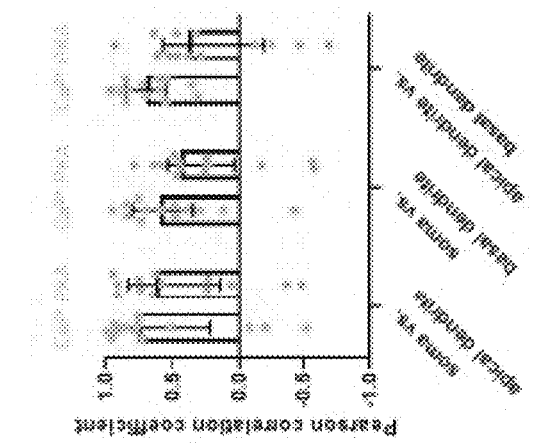

Responses in apical and basal dendrites (identified based on morphology) were then analyzed under forskolin stimulation. As at the soma, some dendrites exhibited immediate $Ca^{2+}$ responses, while others exhibited delayed responses. Some also exhibited spontaneous $Ca^{2+}$ activities before forskolin stimulation. However, analysis of PKA rise slope, ultimate amplitude, and duration of signaling showed no clear relationship to the timing of the $Ca^{2+}$ signals (FIG. 31C-F, Tables 76-78), either at sites along the apical dendrites (FIG. 31C, 31E) or basal dendrites (FIG. 31D, 31F), in contrast to the cultured neuron experiments described elsewhere herein, where dendritic conclusions paralleled somatic conclusions. Analysis of the correlations between $Ca^{2+}$ signals across different dendritic sites, or between PKA signals across different dendritic sites, showed much lower site-to-site correlations than in the cultured neuron experiments described elsewhere herein (FIG. 31G). Thus, in brain slices, $Ca^{2+}$-PKA relationships in hippocampal neurons might follow different rules in dendritic compartments than at the cell body, perhaps due to variability in the presence or distribution of factors that modulate this coupling at different locations within neurons. Tables 74-75 show statistical analyses for FIGS. 14K-L; Tables 76-78 show statistical analyses for FIGS. 31B, E, and F.

TABLE 74

Statistical analysis for FIG. 14K
$Ca^{2+}$ activities at the somata
of CA1 pyramidal neurons with delayed somatic
calcium responses (n = 6 neurons from 5
slices from 3 mice) and those with immediate somatic
calcium response (n = 6 neurons from 2
slices from 2 mice) under 50 µM forskolin
treatment for 15 minutes (over 5 min < t < 20 min).

Wilcoxon rank sum test for somatic $Ca^{2+}$
overall peak response (over t > 5 min;
i.e. from the onset of forskolin
stimulation to the end of recording)

| | |
|---|---|
| P value | 0.2403 |
| ranksum | 31 |

Wilcoxon rank sum test for somatic $Ca^{2+}$
peak response within 8 minutes
after the onset of forskolin
treatment (over 5 min < t < 13 min)

| | |
|---|---|
| P value | 0.0087 |
| ranksum | 23 |

Wilcoxon rank sum test for somatic $Ca^{2+}$
peak response within 8 minutes
after the end of forskolin treatment
(over 20 min < t < 28 min)

| | |
|---|---|
| P value | 0.5887 |
| ranksum | 35 |

Wilcoxon rank sum test for the time
to half rise of somatic $Ca^{2+}$
response (the duration from the onset
of forskolin stimulation to the time
when $Ca^{2+}$ response first reaches half
of the overall peak response)

| | |
|---|---|
| P value | 0.0022 |
| ranksum | 57 |

TABLE 75

Statistical analysis for FIG. 14L
PKA activities at the somata of CA1 pyramidal
neurons with delayed somatic calcium
responses (n = 6 neurons from 5 slices
from 3 mice) and those with immediate somatic
calcium response (n = 6 neurons from 2 slices
from 2 mice) under 50 µM forskolin treatment
for 15 minutes.

Wilcoxon rank sum test for
somatic PKA rise slope

| | |
|---|---|
| P value | 0.0260 |
| ranksum | 25 |

Wilcoxon rank sum test for
somatic PKA peak response

| | |
|---|---|
| P value | 0.0152 |
| ranksum | 24 |

Wilcoxon rank sum test for
duration of somatic PKA activation

| | |
|---|---|
| P value | 0.0043 |
| ranksum | 22 |

TABLE 76

Statistical analysis for FIG. 31B
Wilcoxon rank sum test for fEPSP slopes
before and 45 minutes after the onset of
forskolin treatment (n = 7 experiments
on 7 slices from 5 mice co-expressing
S1-GCaMP6f, S3-ExRaiAKAR, and
mRuby3-6xFLAG).

| | |
|---|---|
| P value | 2.1704e−12 |
| ranksum | 630 |
| zval | −7.0231 |

TABLE 77

Figure 31F:
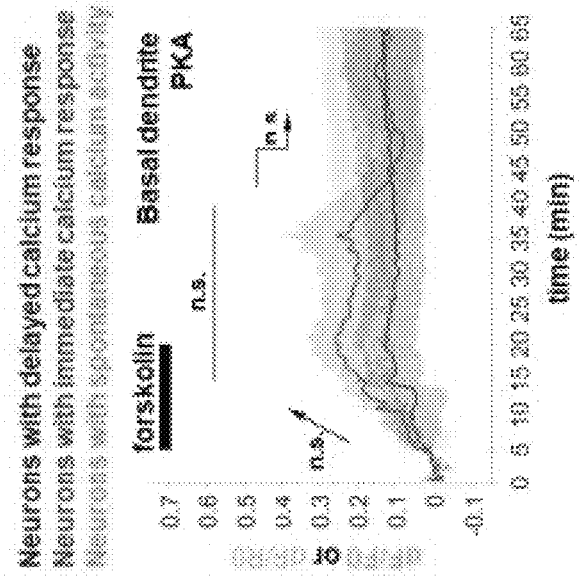
Figure 31E:
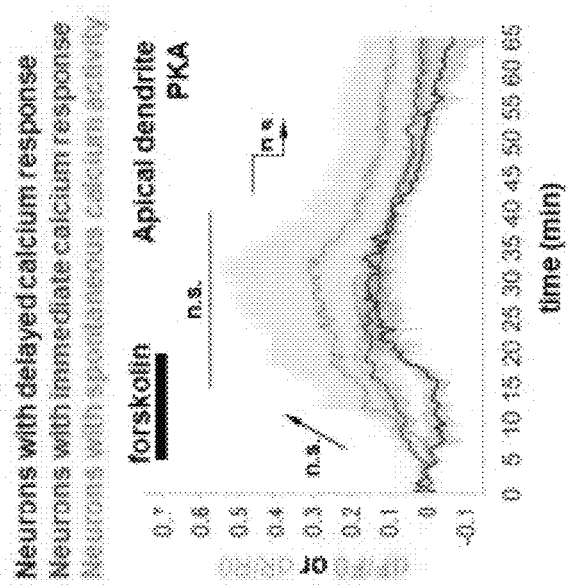

Statistical analysis for FIG. 31E
PKA activities at the apical dendrites
among the CA1 pyramidal neurons with delayed
calcium responses (n = 5 neurons from 5
slices from 3 mice), immediate calcium
responses (n = 6 neurons from 2 slices
from 2 mice), and spontaneous calcium
responses (n = 3 neurons from 2 slices
from 2 mice), under 50 µM forskolin
treatment for 15 minutes.

Kruskal-Wallis analysis of variance for
PKA rise slope at the apical dendrites

Kruskal-Wallis test

| | |
|---|---|
| P value | 0.5720 |
| Exact or approximate P value? | Exact |
| P value summary | ns |
| Do the medians vary signif. (P < 0.05)? | No |
| Number of groups | 3 |
| Kruskal-Wallis statistic | 1.223 |

TABLE 77-continued

Statistical analysis for FIG. 31E
PKA activities at the apical dendrites
among the CA1 pyramidal neurons with delayed
calcium responses (n = 5 neurons from 5
slices from 3 mice), immediate calcium
responses (n = 6 neurons from 2 slices
from 2 mice), and spontaneous calcium
responses (n = 3 neurons from 2 slices
from 2 mice), under 50 μM forskolin
treatment for 15 minutes.

| Dunn's multiple comparisons test | Mean rank diff. | Significant? | Summary | Adjusted P Value |
|---|---|---|---|---|
| Delayed calcium response vs. Immediate calcium response | −2.048 | No | ns | >0.9999 |
| Delayed calcium response vs. Early calcium response | 0.6667 | No | ns | >0.9999 |
| Immediate calcium response vs. Early calcium response | 2.714 | No | ns | 0.9017 |

Kruskal-Wallis analysis of variance for
PKA peak response at the apical dendrites Kruskal-Wallis test

| | |
|---|---|
| P value | 0.8364 |
| Exact or approximate P value? | Exact |
| P value summary | ns |
| Do the medians vary signif. (P < 0.05)? | No |
| Number of groups | 3 |
| Kruskal-Wallis statistic | 0.3986 |

| Dunn's multiple comparisons test | Mean rank diff. | Significant? | Summary | Adjusted P Value |
|---|---|---|---|---|
| Delayed calcium response vs. Immediate calcium response | −0.8095 | No | ns | >0.9999 |
| Delayed calcium response vs. Early calcium response | 0.8333 | No | ns | >0.9999 |
| Immediate calcium response vs. Early calcium response | 1.643 | No | ns | >0.9999 |

Kruskal-Wallis analysis of variance for duration of
PKA activation at the apical dendrites Kruskal-Wallis test

| | |
|---|---|
| P value | 0.5806 |
| Exact or approximate P value? | Exact |
| P value summary | ns |
| Do the medians vary signif. (P < 0.05)? | No |
| Number of groups | 3 |
| Kruskal-Wallis statistic | 1.139 |

| Dunn's multiple comparisons test | Mean rank diff. | Significant? | Summary | Adjusted P Value |
|---|---|---|---|---|
| Delayed calcium response vs. Immediate calcium response | −1.976 | No | ns | >0.9999 |
| Delayed calcium response vs. Early calcium response | 0.5417 | No | ns | >0.9999 |
| Immediate calcium response vs. Early calcium response | 2.518 | No | ns | 0.9681 |

TABLE 78

Statistical analysis for FIG. 31F
PKA activities at the basal dendrites
among the CA1 pyramidal neurons with delayed
calcium responses (n = 5 neurons from 5
slices from 3 mice), immediate calcium
responses (n = 6 neurons from 2 slices
from 2 mice), and spontaneous calcium responses
(n = 3 neurons from 2 slices from 2 mice),
under 50 μM forskolin treatment for 15 minutes.

Kruskal-Wallis analysis of variance for
PKA rise slope at the basal dendrites

Kruskal-Wallis test

| | |
|---|---|
| P value | 0.6107 |
| Exact or approximate P value? | Exact |
| P value summary | ns |
| Do the medians vary signif. (P < 0.05)? | No |
| Number of groups | 3 |
| Kruskal-Wallis statistic | 1.067 |

| Dunn's multiple comparisons test | Mean rank diff. | Significant? | Summary | Adjusted P Value |
|---|---|---|---|---|
| Delayed calcium response vs. Immediate calcium response | −2.333 | No | ns | >0.9999 |
| Delayed calcium response vs. Early calcium response | 0.000 | No | ns | >0.9999 |
| Immediate calcium response vs. Early calcium response | 2.333 | No | ns | >0.9999 |

Kruskal-Wallis analysis of variance for
PKA peak response at the basal dendrites Kruskal-Wallis test

| | |
|---|---|
| P value | 0.6816 |
| Exact or approximate P value? | Exact |
| P value summary | ns |
| Do the medians vary signif. (P < 0.05)? | No |
| Number of groups | 3 |
| Kruskal-Wallis statistic | 0.8571 |

| Dunn's multiple comparisons test | Mean rank diff. | Significant? | Summary | Adjusted P Value |
|---|---|---|---|---|
| Delayed calcium response vs. Immediate calcium response | −2.500 | No | ns | >0.9999 |
| Delayed calcium response vs. Early calcium response | −1.500 | No | ns | >0.9999 |
| Immediate calcium response vs. Early calcium response | 1.000 | No | ns | >0.9999 |

Kruskal-Wallis analysis of variance for duration of
PKA activation at the basal dendrites Kruskal-Wallis test

| | |
|---|---|
| P value | 0.8288 |
| Exact or approximate P value? | Exact |
| P value summary | ns |
| Do the medians vary signif. (P < 0.05)? | No |
| Number of groups | 3 |
| Kruskal-Wallis statistic | 0.4231 |

| Dunn's multiple comparisons test | Mean rank diff. | Significant? | Summary | Adjusted P Value |
|---|---|---|---|---|
| Delayed calcium response vs. Immediate calcium response | −1.400 | No | ns | >0.9999 |
| Delayed calcium response vs. Early calcium response | −1.500 | No | ns | >0.9999 |
| Immediate calcium response vs. Early calcium response | −0.1000 | No | ns | >0.9999 |

Overview/Discussion Results Examples 1-4

Results of experiments and studies that have been performed, some of which are described herein, demonstrated that it is possible to localize, via engineered RNA and protein scaffolds that are bio-orthogonal to mammalian cells, spectrally similar or even spectrally identical fluorescent reporters of different biological signals at different points in space, safely clustered into bright, stationary puncta (with brightness 100-1000× brighter than the surrounding background) within living cells. This protein architecture, termed a signaling reporter island (SiRI), is very modular—that is, given a desired set of signals to be imaged at once within a single living cell, a set of existing fluorescent indicators may be reliably adapted by fusing each to a different pair of self-assembling peptides, so that each will cluster, stochastically, at a different set of points in space. These puncta end up several microns from each other, so that many different signals may be dynamically imaged within a living cell at the same time, even if they all possess the same fluorescent spectrum. After live imaging of the cell, post hoc reconstruction of sensor identity in fixed cells may proceed via epitope immunostaining, RNA FISH, or other highly multiplexed fixed cell imaging methods. In this way, multiple fluorescent signals may be recorded at different points in space, with minimal crosstalk, in a fashion where the identity of the signal may be clearly defined. SiRIs allow the high multiplexing capacity of fixed cell imaging to be translated to help the live cell imaging case, using the spatial dimension as an asset. Results indicated methods and compositions if the invention could be used for spatially multiplexed imaging to sample physiological signals with 1-2 micron resolution and that such imaging was able to capture the relevant cell biology; see, for example, FIG. 5 where scaffolded versions of GCaMP6f and ICUE3 were able to pick up on signals at different subcellular locations within a cell in a fashion similar to unscaffolded forms of these indicators.

SiRIs are easy to design, with a highly modular architecture—most of the SiRIs designed and tested herein worked well upon initial validation testing, with minimal trial-and-error refinement required. In this way, SiRIs may offer a highly complementary strategy to traditional fluorescent reporter engineering: rather than having to engineer a set of fluorescent reporters with different fluorophores in order to use them simultaneously within the same cell, a nonmodular strategy that often requires significant post-design optimization and sometimes even directed evolution of each reporter (Piatkevich et al., 2018), one could simply create reporters all with a single fluorophore, or utilize existing fluorescent reporters without regard to the fluorophores utilized, and then to modularly attach them to different SiRI peptide pairs, without the need for significant post-design iterative work.

Unlike live cell imaging, where distinguishing different fluorescent reporters on a conventional microscope almost exclusively relies on having different excitation and/or emission spectra for the fluorescent reporters, fixed cell imaging may be highly multiplexed. For example, fluorescent probes that bind to different targets may be washed in and out over many cycles, with some procedures (e.g., serial antibody staining against immunoepitopes (Micheva and Smith, 2007; Murray et al., 2015), serial FISH against RNA sequences (Moffitt et al., 2016; Shah et al., 2017)) enable dozens to even hundreds of distinct biomolecules to be identified. In addition, combinations of immunoepitopes as protein barcodes (Wroblewska et al., 2018) may be used in methods of the invention to tag individual kinds of fluorescent reporters, expanding the number of fluorescent reporters that may be identified in a single round of antibody staining. Here, the high degree of multiplexing of fixed cell imaging technologies has been used and demonstrated to boost the multiplexing capability of live cell imaging technologies.

Important components of the success of this strategy are the findings that the scaffolded reporters of the invention are stationary over timescales appropriate for live cell imaging (else the identity of a given punctum could not be reconstructed), and that the puncta be located distant enough to be resolved by a microscope but close enough to spatially sample the relevant biology. It was observed that the puncta engineered in these studies were spaced typically a few microns from each other, and thus appropriate for cellular imaging and also for subcellular imaging where length scales of a few microns do not matter. In the future, creating a wide diversity of such scaffolds with different kinds of spacing may be used to allow tradeoffs between the number of signals that may be simultaneously observed, and the spatial sampling that is permitted. For a cell with 10,000 resolvable spots, for example, one might have 100 kinds of sensors distributed at each of 100 points, or 10 sensors distributed at each of 1000 points. Reported herein are >10 candidate scaffolds that showed at least some degree of clustering (both RNA-based and protein-based), which enable many different kinds of signals to be observed simultaneously in a single cell. Programmable RNA scaffolds such as the Pumby system (Adamala, Martin-Alarcon and Boyden, 2016), new kinds of engineered protein polyhedra, and the simultaneous use of RNA scaffolds and protein polyhedral systems together in cells that may permit the utility of both, rapidly allow the expansion of this system. Certain embodiments of methods of the invention also include de novo/computationally designed, bio-orthogonal protein motifs (King et al., 2012; Hsia et al., 2016; Huang, Boyken and Baker, 2016; Lai et al., 2016; Garcia-Seisdedos et al., 2017) and RNA motifs (Delebecque et al., 2011). Methods of the invention may also be used in vivo in multiple model organisms of interest in biology, such as *C. elegans*, zebrafish, *Drosophila*, and mice, to monitor simultaneous pathways in the cells of an intact organism.

Coupling between $Ca^{2+}$, cAMP, and PKA signals, three signals of immense importance for a large number of normal biological functions, and that go awry in many pathological contexts, was examined herein in cultured hippocampal neurons and in acute mouse hippocampal brain slices. Understanding how these signals relate to each other is complex, because of the many feedforward and feedback connections between these signals. Using neurons of both cultured hippocampus and acute hippocampal slice, experiments described herein investigated how the timing of $Ca^{2+}$ and cAMP signals relate to the amplitude of PKA signals. In summary, neurons that had shorter-latency cAMP and $Ca^{2+}$ responses to forskolin, exhibited stronger PKA activation than neurons with longer-latency cAMP and $Ca^{2+}$ responses, showing how an output signal like PKA may be governed by the properties of the second messengers upstream. In cultured neurons, the neurons with longer-latency $Ca^{2+}$ responses also exhibited transient, even oscillatory, responses, indicated that the interactions within this signal transduction network might generate extremely complex, nonlinear, dynamics with computational consequences for how cells filter, integrate, and combine information towards the generation of precise cellular outputs. Importantly, such relationships between the different components of this signal transduction network could not be derived by observing these signals in separate cells, and then comparing them after averaging.

Spatial multiplexing may be particularly useful for imaging fast cellular dynamics, such as those in neurons, under inexpensive single-camera microscopes with fluorescent sensors that may all be imaged in one shared optical channel (e.g. using all GFP-based sensors), because using methods of the invention, the imaging speed is not limited by the number of cameras available or any mechanical filter switching required to record from multiple channels. By reducing the reliance on spectral multiplexing, methods of the invention may also avoid concerns related to bleed-through caused by using multiple, spectrally similar fluorescent reporters within the same cell. Spatial multiplexing methods of the invention are also capable of freeing up optical channels for use for other purposes, such as cellular control. For example, the GFP channel may be used to observe cellular activity readout from multiple GFP-based sensors, and then the red channel of the microscope may be utilized to operate red-light driven optogenetic tools (Chuong et al., 2014; Klapoetke et al., 2014).

REFERENCES

Abrams, T. W., Karl, K. A. and Kandel, E. R. (1991) "Biochemical studies of stimulus convergence during classical conditioning in Aplysia: Dual regulation of adenylate cyclase by Ca2+/calmodulin and transmitter," *Journal of Neuroscience*. Society for *Neuroscience*, 11(9), pp. 2655-2665. doi: 10.1523/jneurosci.11-09-02655.1991.

Adamala, K. P., Martin-Alarcon, D. A. and Boyden, E. S. (2016) "Programmable RNA-binding protein composed of repeats of a single modular unit," *Proceedings of the National Academy of Sciences of the United States of America*. National Academy of Sciences, 113(19), pp. E2579-88. doi: 10.1073/pnas.1519368113.

Asano, S. M. et al. (2018) "Expansion Microscopy: Protocols for Imaging Proteins and RNA in Cells and Tissues," *Current Protocols in Cell Biology*. John Wiley and Sons Inc., 80(1). doi: 10.1002/cpcb.56.

Averaimo, S. and Nicol, X. (2014) "Intermingled cAMP, cGMP and calcium spatiotemporal dynamics in developing neuronal circuits," *Frontiers in Cellular Neuroscience*. Frontiers, 8, p. 376. doi: 10.3389/fncel.2014.00376.

Bale, J. B. et al. (2016) "Accurate design of megadalton-scale two-component icosahedral protein complexes," *Science*. American Association for the Advancement of Science, 353(6297), pp. 389-394. doi: 10.1126/science.aaf8818.

Barco, A., Alarcon, J. M. and Kandel, E. R. (2002) "Expression of constitutively active CREB protein facilitates the late phase of long-term potentiation by enhancing synaptic capture," *Cell*. Cell Press, 108(5), pp. 689-703. doi: 10.1016/S0092-8674(02)00657-8.

Belousov, V. V et al. (2006) "Genetically encoded fluorescent indicator for intracellular hydrogen peroxide," *Nature Methods*, 3(4), pp. 281-286. doi: 10.1038/nmeth866.

Berg, J., Hung, Y. P. and Yellen, G. (2009) "A genetically encoded fluorescent reporter of ATP:ADP ratio," *Nature Methods*. Nature Publishing Group, 6(2), pp. 161-166. doi: 10.1038/nmeth.1288.

Bito, H., Deisseroth, K. and Tsien, R. W. (1996) "CREB Phosphorylation and Dephosphorylation: A Ca2+- and Stimulus Duration-Dependent Switch for Hippocampal Gene Expression," *Cell*. Cell Press, 87(7), pp. 1203-1214. doi: 10.1016/S0092-8674(00)81816-4.

Bodenmiller, B. (2016) "Multiplexed Epitope-Based Tissue Imaging for Discovery and Healthcare Applications," *Cell Systems*. Cell Press, pp. 225-238. doi: 10.1016/j.cels.2016.03.008.

Borodinsky, L. N. and Spitzer, N. C. (2006) "Second messenger pas de deux: the coordinated dance between calcium and cAMP.," *Science's STKE: signal transduction knowledge environment*. American Association for the Advancement of Science, pp. pe22-pe22. doi: 10.1126/stke.3362006pe22.

Boyken, S. E. et al. (2016) "De novo design of protein homo-oligomers with modular hydrogen-bond network-mediated specificity," *Science*. American Association for the Advancement of Science, 352(6286), pp. 680-687. doi: 10.1126/science.aad8865.

Boyle, A. L. et al. (2012) "Squaring the Circle in Peptide Assembly: From Fibers to Discrete Nanostructures by de Novo Design," *Journal of the American Chemical Society*, 134(37), pp. 15457-15467. doi: 10.1021/ja3053943.

Buxbaum, A. R., Haimovich, G. and Singer, R. H. (2015) "In the right place at the right time: visualizing and understanding mRNA localization," *Nature Reviews Molecular Cell Biology*. Nature Publishing Group, 16(2), pp. 95-109. doi: 10.1038/nrm3918.

Buxbaum, A. R., Wu, B. and Singer, R. H. (2014) "Single β-actin mRNA detection in neurons reveals a mechanism for regulating its translatability.," *Science* (New York, N.Y.). American Association for the Advancement of Science, 343(6169), pp. 419-22. doi: 10.1126/science.1242939.

Careaga, M. et al. (2014) "Group I metabotropic glutamate receptor mediated dynamic immune dysfunction in children with fragile X syndrome," *Journal of Neuroinflammation*, 11(1), p. 110. doi: 10.1186/1742-2094-11-110.

Chalifoux, J. R. and Carter, A. G. (2010) "GABAB Receptors Modulate NMDA Receptor Calcium Signals in Dendritic Spines," *Neuron*. Cell Press, 66(1), pp. 101-113. doi: 10.1016/j.neuron.2010.03.012.

Chavez-Noriega, L. E. and Stevens, C. F. (1992) "Modulation of synaptic efficacy in field CA1 of the rat hippocampus by forskolin.," *Brain research*, 574(1-2), pp. 85-92. doi: 10.1016/0006-8993(92)90803-h.

Chen, F., Tillberg, P. W. and Boyden, E. S. (2015) "Expansion microscopy," *Science*. American Association for the Advancement of Science, 347(6221), pp. 543-548. doi: 10.1126/science.1260088.

Chen, T.-W. et al. (2013) "Ultrasensitive fluorescent proteins for imaging neuronal activity," *Nature*. Nature Publishing Group, 499(7458), pp. 295-300. doi: 10.1038/nature12354.

Chen, Z. et al. (2019) "Programmable design of orthogonal protein heterodimers," *Nature*. Nature Publishing Group, pp. 106-111. doi: 10.1038/s41586-018-0802-y.

Chijiwa, T. et al. (1990) "Inhibition of forskolin-induced neurite outgrowth and protein phosphorylation by a newly synthesized selective inhibitor of cyclic AMP-dependent protein kinase, N-[2-(p-bromocinnamylamino)ethyl]-5-isoquinolinesulfonamide (H-89), of PC12D pheochromocytoma cells," *Journal of Biological Chemistry*, 265(9), pp. 5267-5272.

Cho-Chung, Y. S. (1990) "Role of cyclic AMP receptor proteins in growth, differentiation, and suppression of malignancy: new approaches to therapy," *Cancer research*. American Association for Cancer Research, 50(22), pp. 7093-100. Available at: http://www.ncbi.nlm.nih.gov/pubmed/2224844 (Accessed: Oct. 17, 2018).

Chuong, A. S. et al. (2014) "Noninvasive optical inhibition with a red-shifted microbial rhodopsin," *Nature Neuroscience*. Nature Publishing Group, 17(8), pp. 1123-1129. doi: 10.1038/nn.3752.

Cooper, D. M. F., Mons, N. and Karpen, J. W. (1995) "Adenylyl cyclases and the interaction between calcium and cAMP signalling," *Nature*. Nature Publishing Group, 374(6521), pp. 421-424. doi: 10.1038/374421a0.

Davis, L., Banker, G. A. and Steward, O. (1987) "Selective dendritic transport of RNA in hippocampal neurons in culture," *Nature*. Nature Publishing Group, 330(6147), pp. 477-479. doi: 10.1038/330477a0.

Delebecque, C. J. et al. (2011) "Organization of Intracellular Reactions with Rationally Designed RNA Assemblies," *Science*, 333(6041), pp. 470-474. doi: 10.1126/science.1206938.

Depry, C., Allen, M. D. and Zhang, J. (2011) "Visualization of PKA activity in plasma membrane microdomains.," *Molecular bioSystems*, 7(1), pp. 52-8. doi: 10.1039/c0mb00079e.

Dictenberg, J. B. et al. (2008) "A Direct Role for FMRP in Activity-Dependent Dendritic mRNA Transport Links Filopodial-Spine Morphogenesis to Fragile X Syndrome," *Developmental Cell*. Cell Press, 14(6), pp. 926-939. doi: 10.1016/J.DEVCEL.2008.04.003.

Ding, Y. et al. (2015) "Ratiometric biosensors based on dimerization-dependent fluorescent protein exchange," *Nature Methods*. Nature Publishing Group, 12(3), pp. 195-198. doi: 10.1038/nmeth.3261.

DiPilato, L. M. and Zhang, J. (2009) "The role of membrane microdomains in shaping beta2-adrenergic receptor-mediated cAMP dynamics.," *Molecular bioSystems*, 5(8), pp. 832-7. doi: 10.1039/b823243a.

Dyachok, O. et al. (2006) "Oscillations of cyclic AMP in hormone-stimulated insulin-secreting β-cells," *Nature*. Nature Publishing Group, 439(7074), pp. 349-352. doi: 10.1038/nature04410.

Ferguson, G. D. and Storm, D. R. (2004) "Why calcium-stimulated adenylyl cyclases?," *Physiology*. American Physiological Society, pp. 271-276. doi: 10.1152/physiol.00010.2004.

Fletcher, J. M. et al. (2012) "A Basis Set of de Novo Coiled-Coil Peptide Oligomers for Rational Protein Design and Synthetic Biology," *ACS Synthetic Biology*, 1(6), pp. 240-250. doi: 10.1021/sb300028q.

Fourcaudot, E. et al. (2009) "L-type voltage-dependent Ca2+ channels mediate expression of presynaptic LTP in amygdala," *Nature Neuroscience*, 12(9), pp. 1093-1095. doi: 10.1038/nn.2378.

Franklin, N. C. (1985) "Conservation of genome form but not sequence in the transcription antitermination determinants of bacteriophages lambda, phi 21 and P22," *Journal of molecular biology*, 181(1), pp. 75-84. Available at: http://www.ncbi.nlm.nih.gov/pubmed/3157001 (Accessed: Oct. 14, 2018).

Frey, U., Huang, Y. Y. and Kandel, E. R. (1993) "Effects of cAMP simulate a late stage of LTP in hippocampal CA1 neurons," *Science* (New York, N.Y.), 260(5114), pp. 1661-4. Available at: http://www.ncbi.nlm.nih.gov/pubmed/8389057 (Accessed: Oct. 17, 2018).

Garcia-Seisdedos, H. et al. (2017) "Proteins evolve on the edge of supramolecular self-assembly," *Nature*. Nature Publishing Group, 548(7666), p. 244. doi: 10.1038/nature23320.

Giese, K. P. and Mizuno, K. (2013) "The roles of protein kinases in learning and memory," *Learning and Memory*, pp. 540-552. doi: 10.1101/lm.028449.112.

Golding, I. and Cox, E. C. (2004) "RNA dynamics in live Escherichia coli cells," *Proceedings of the National Academy of Sciences*, 101(31), pp. 11310-11315. doi: 10.1073/pnas.0404443101.

Gonen, S. et al. (2015) "Design of ordered two-dimensional arrays mediated by noncovalent protein-protein interfaces," *Science* (New York, N.Y.). American Association for the Advancement of Science, 348(6241), pp. 1365-8. doi: 10.1126/science.aaa9897.

Gorbunova, Y. V. and Spitzer, N. C. (2002) "Dynamic interactions of cyclic AMP transients and spontaneous Ca2+ spikes," *Nature*. Nature Publishing Group, 418(6893), pp. 93-96. doi: 10.1038/nature00835.

Govindarajan, A. et al. (2011) "The Dendritic Branch Is the Preferred Integrative Unit for Protein Synthesis-Dependent LTP," *Neuron*, 69(1), pp. 132-146. doi: 10.1016/j.neuron.2010.12.008.

Gradisar, H. et al. (2013) "Design of a single-chain polypeptide tetrahedron assembled from coiled-coil segments," *Nature Chemical Biology*. Nature Publishing Group, 9(6), pp. 362-366. doi: 10.1038/nchembio.1248.

Grigoryan, G. et al. (2011) "Computational design of virus-like protein assemblies on carbon nanotube surfaces," *Science* (New York, N.Y.). NIH Public Access, 332(6033), pp. 1071-6. doi: 10.1126/science.1198841.

Grigoryan, G. and Segal, M. (2013) "Prenatal stress alters noradrenergic modulation of LTP in hippocampal slices," *Journal of Neurophysiology*. American Physiological Society, 110(2), pp. 279-285. doi: 10.1152/jn.00834.2012.

Hackley, C. R., Mazzoni, E. O. and Blau, J. (2018) "cAMPr: A single-wavelength fluorescent sensor for cyclic AMP.," *Science signaling*. American Association for the Advancement of Science, 11(520), p. eaah3738. doi: 10.1126/scisignal.aah3738.

Hancock, J. F. et al. (1991) "A CAAX or a CAAL motif and a second signal are sufficient for plasma membrane targeting of ras proteins," *The EMBO journal*. European Molecular Biology Organization, 10(13), pp. 4033-9. Available at: http://www.ncbi.nlm.nih.gov/pubmed/1756714 (Accessed: Oct. 15, 2018).

Hanson, M. G. et al. (1998) "Cyclic AMP elevation is sufficient to promote the survival of spinal motor neurons in vitro," *Journal of Neuroscience*, 18(18), pp. 7361-7371. doi: 10.1523/JNEUROSCI.18-18-07361.1998.

Hardingham, G. E., Arnold, F. J. L. and Bading, H. (2001) "Nuclear calcium signaling controls CREB-mediated gene expression triggered by synaptic activity," *Nature Neuroscience*. Nature Publishing Group, 4(3), pp. 261-267. doi: 10.1038/85109.

Hocine, S. et al. (2013) "Single-molecule analysis of gene expression using two-color RNA labeling in live yeast," *Nature Methods*, 10(2), pp. 119-121. doi: 10.1038/nmeth.2305.

Holt, C. E. and Schuman, E. M. (2013) "The Central Dogma Decentralized: New Perspectives on RNA Function and Local Translation in Neurons," *Neuron*. Cell Press, 80(3), pp. 648-657. doi: 10.1016/J.NEURON.2013.10.036.

Hopp, T. P. et al. (1988) "A Short Polypeptide Marker Sequence Useful for Recombinant Protein Identification and Purification," *Bio/Technology*. Nature Publishing Group, 6(10), pp. 1204-1210. doi: 10.1038/nbt1088-1204.

Howe, A. K. (2011) "Cross-talk between calcium and protein kinase A in the regulation of cell migration," *Current Opinion in Cell Biology*, pp. 554-561. doi: 10.1016/j.ceb.2011.05.006.

Hsia, Y. et al. (2016) "Design of a hyperstable 60-subunit protein icosahedron," *Nature*. Nature Publishing Group, 535(7610), pp. 136-139. doi: 10.1038/nature18010.

Huang, P.-S. et al. (2014) "High thermodynamic stability of parametrically designed helical bundles.," *Science* (New York, N.Y.). Europe PMC Funders, 346(6208), pp. 481-485. doi: 10.1126/science.1257481.

Huang, P.-S., Boyken, S. E. and Baker, D. (2016) "The coming of age of de novo protein design," *Nature*. Nature Publishing Group, 537(7620), pp. 320-327. doi: 10.1038/nature19946.

Huang, Y.-Y. and Kandel, E. R. (1994) *Recruitment of Long-lasting and Protein Kinase A-dependent Long-term Potentiation in the CA I Region of Hippocampus Requires Repeated Tetanization*.

Indelicato, G. et al. (2016) "Principles Governing the Self-Assembly of Coiled-Coil Protein Nanoparticles," *Biophysical Journal*, 110(3), pp. 646-660. doi: 10.1016/j.bpj.2015.10.057.

Kandel, E. R., Dudai, Y. and Mayford, M. R. (2014) "The molecular and systems biology of memory," *Cell*. Cell Press, pp. 163-186. doi: 10.1016/j.cell.2014.03.001.

King, N. P. et al. (2012) "Computational design of self-assembling protein nanomaterials with atomic level accuracy.," *Science* (New York, N.Y.). Howard Hughes Medical Institute, 336(6085), pp. 1171-4. doi: 10.1126/science.1219364.

King, N. P. et al. (2014) "Accurate design of co-assembling multi-component protein nanomaterials.," *Nature*. NIH Public Access, 510(7503), pp. 103-8. doi: 10.1038/nature13404.

Klapoetke, N. C. et al. (2014) "Independent optical excitation of distinct neural populations.," *Nature methods*. NIH Public Access, 11(3), pp. 338-46. doi: 10.1038/nmeth.2836.

Ku, T. et al. (2016) "Multiplexed and scalable super-resolution imaging of three-dimensional protein localization in size-adjustable tissues," *Nature Biotechnology*. Nature Publishing Group, 34(9), pp. 973-981. doi: 10.1038/nbt.3641.

Lai, Y.-T. et al. (2014) "Structure of a designed protein cage that self-assembles into a highly porous cube.," *Nature chemistry*. NIH Public Access, 6(12), pp. 1065-71. doi: 10.1038/nchem.2107.

Lai, Y.-T. et al. (2016) "Designing and defining dynamic protein cage nanoassemblies in solution," *Science Advances*. American Association for the Advancement of Science, 2(12), pp. e1501855-e1501855. doi: 10.1126/sciadv.1501855.

Lai, Y.-T., Cascio, D. and Yeates, T. O. (2012) "Structure of a 16-nm cage designed by using protein oligomers.," *Science* (New York, N.Y.), 336(6085), p. 1129. doi: 10.1126/science.1219351.

Lee, H. K. et al. (1998) "NMDA induces long-term synaptic depression and dephosphorylation of the GluR1 subunit of AMPA receptors in hippocampus," *Neuron*. Cell Press, 21(5), pp. 1151-1162. doi: 10.1016/S0896-6273(00)80632-7.

Li, S. et al. (2013) "Environmental novelty activates β2-adrenergic signaling to prevent the impairment of hippocampal LTP by Aβ oligomers," *Neuron*. Cell Press, 77(5), pp. 929-941. doi: 10.1016/j.neuron.2012.12.040.

Li, W. et al. (2018) "Reduced Cyclic Adenosine Monophosphate Level in Hippocampal CA1 Participates in Propofol Induced Amnesia in Rats," *Frontiers in Neuroscience*, 12. doi: 10.3389/fnins.2018.00337.

Lim, F., Downey, T. P. and Peabody, D. S. (2001) "Translational repression and specific RNA binding by the coat protein of the *Pseudomonas* phage PP7.," *The Journal of biological chemistry*. American Society for Biochemistry and Molecular Biology, 276(25), pp. 22507-13. doi: 10.1074/jbc.M102411200.

Lin, J. R. et al. (2018) "Highly multiplexed immunofluorescence imaging of human tissues and tumors using t-CyCIF and conventional optical microscopes," *eLife*. eLife Sciences Publications Ltd, 7. doi: 10.7554/eLife.31657.

Lyford, G. L. et al. (1995) "Arc, a growth factor and activity-regulated gene, encodes a novel cytoskeleton-associated protein that is enriched in neuronal dendrites," *Neuron*. Cell Press, 14(2), pp. 433-445. doi: 10.1016/0896-6273(95)90299-6.

Makino, H. and Malinow, R. (2009) "AMPA Receptor Incorporation into Synapses during LTP: The Role of Lateral Movement and Exocytosis," *Neuron*, 64(3), pp. 381-390. doi: 10.1016/j.neuron.2009.08.035.

Mao, L. et al. (2005) "Role of protein phosphatase 2A in mGluR5-regulated MEK/ERK phosphorylation in neurons," *Journal of Biological Chemistry*, 280(13), pp. 12602-12610. doi: 10.1074/jbc.M411709200.

Martin, R. M. et al. (2013) "Live-Cell Visualization of Pre-mRNA Splicing with Single-Molecule Sensitivity," *Cell Reports*, 4(6), pp. 1144-1155. doi: 10.1016/j.celrep.2013.08.013.

Mehta, S. et al. (2018) "Single-fluorophore biosensors for sensitive and multiplexed detection of signalling activities," *Nature Cell Biology*. Nature Publishing Group, 20(10), pp. 1215-1225. doi: 10.1038/s41556-018-0200-6.

Mehta, S. and Zhang, J. (2011) "Reporting from the Field: Genetically Encoded Fluorescent Reporters Uncover Signaling Dynamics in Living Biological Systems," *Annual Review of Biochemistry*. Annual Reviews, 80(1), pp. 375-401. doi: 10.1146/annurev-biochem-060409-093259.

Ménard, C. and Quirion, R. (2012) "Group 1 metabotropic glutamate receptor function and its regulation of learning and memory in the aging brain," *Frontiers in Pharmacology*, 3 October. doi: 10.3389/fphar.2012.00182.

Micheva, K. D. and Smith, S. J. (2007) "Array Tomography: A New Tool for Imaging the Molecular Architecture and Ultrastructure of Neural Circuits," *Neuron*. Cell Press, 55(1), pp. 25-36. doi: 10.1016/J.NEURON.2007.06.014.

Miedlich, S., Gama, L. and Breitwieser, G. E. (2002) "Calcium Sensing Receptor Activation by a Calcimimetic Suggests a Link between Cooperativity and Intracellular Calcium Oscillations," *Journal of Biological Chemistry*, 277(51), pp. 49691-49699. doi: 10.1074/jbc.M205578200.

Mironov, S. L. et al. (2009) "Imaging cytoplasmic cAMP in mouse brainstem neurons," *BMC Neuroscience*, 10. doi: 10.1186/1471-2202-10-29.

Mo, G. C. H. et al. (2017) "Genetically encoded biosensors for visualizing live-cell biochemical activity at super-resolution," *Nature Methods*. Nature Publishing Group, 14(4), pp. 427-434. doi: 10.1038/nmeth.4221.

Moffitt, J. R. et al. (2016) "High-performance multiplexed fluorescence in situ hybridization in culture and tissue with matrix imprinting and clearing," *Proceedings of the National Academy of Sciences of the United States of*

America. National Academy of Sciences, 113(50), pp. 14456-14461. doi: 10.1073/pnas.1617699113.

Moll, J. R. et al. (2001) "Designed heterodimerizing leucine zippers with a ranger of pIs and stabilities up to 10-15 M," *Protein Science*. Wiley-Blackwell, 10(3), pp. 649-655. doi: 10.1110/ps.39401.

Murphy, J. G. et al. (2014) "AKAP-anchored PKA maintains neuronal L-type calcium channel activity and NFAT transcriptional signaling," *Cell Reports*. Elsevier, 7(5), pp. 1577-1588. doi: 10.1016/j.celrep.2014.04.027.

Murray, E. et al. (2015) "Simple, Scalable Proteomic Imaging for High-Dimensional Profiling of Intact Systems," *Cell*. Cell Press, 163(6), pp. 1500-1514. doi: 10.1016/J.CELL.2015.11.025.

Negron, C. and Keating, A. E. (2014) "A Set of Computationally Designed Orthogonal Antiparallel Homodimers that Expands the Synthetic Coiled-Coil Toolkit," *Journal of the American Chemical Society*. American Chemical Society, 136(47), pp. 16544-16556. doi: 10.1021/ja507847t.

Ni, Q. et al. (2011) "Signaling diversity of PKA achieved via a Ca2+-cAMP-PKA oscillatory circuit," *Nature Chemical Biology*. Nature Publishing Group, 7(1), pp. 34-40. doi: 10.1038/nchembio.478.

Oakley, M. G. and Kim, P. S. (1998) "A Buried Polar Interaction Can Direct the Relative Orientation of Helices in a Coiled Coil," *Biochemistry*, 37(36), pp. 12603-12610. doi: 10.1021/bi981269m.

Ohadi, D. et al. (2019) "Computational Modeling Reveals Frequency Modulation of Calcium-cAMP/PKA Pathway in Dendritic Spines," *Biophysical Journal*. Biophysical Society, 117(10), pp. 1963-1980. doi: 10.1016/j.bpj.2019.10.003.

Ohta, Y. et al. (2018) "Red fluorescent cAMP indicator with increased affinity and expanded dynamic range," *Scientific Reports*. Nature Publishing Group, 8(1). doi: 10.1038/s41598-018-20251-1.

Oliveira, A. F. and Yasuda, R. (2013) "An Improved Ras Sensor for Highly Sensitive and Quantitative FRET-FLIM Imaging," *PLoS ONE*. Edited by D. Holowka. Public Library of Science, 8(1), p. e52874. doi: 10.1371/journal.pone.0052874.

Otmakhov, N. et al. (2004) "Forskolin-Induced LTP in the CA1 Hippocampal Region Is NMDA Receptor Dependent," *Journal of Neurophysiology*, 91(5), pp. 1955-1962. doi: 10.1152/jn.00941.2003.

Otsuguro, K. et al. (2005) "Characterization of forskolin-induced Ca2+ signals in rat olfactory receptor neurons.," *Journal of pharmacological sciences*, 97(4), pp. 510-8. doi: 10.1254/jphs.fp0040883.

Partridge, J. G. et al. (2014) "Contrasting actions of group I metabotropic glutamate receptors in distinct mouse striatal neurones," *Journal of Physiology*. Blackwell Publishing Ltd, 592(13), pp. 2721-2733. doi: 10.1113/jphysiol.2014.272773.

Piatkevich, K. D. et al. (2018) "A robotic multidimensional directed evolution approach applied to fluorescent voltage reporters article," *Nature Chemical Biology*. Nature Publishing Group, 14(4), pp. 352-360. doi: 10.1038/s41589-018-0004-9.

Qian, H. et al. (2017) "Phosphorylation of Ser1928 mediates the enhanced activity of the L-type Ca2+ channel Cav1.2 by the β2-adrenergic receptor in neurons," *Science Signaling*. American Association for the Advancement of Science, 10(463). doi: 10.1126/scisignal.aaf9659.

Redmond, L., Kashani, A. H. and Ghosh, A. (2002) "Calcium Regulation of Dendritic Growth via CaM Kinase IV and CREB-Mediated Transcription," *Neuron*. Cell Press, 34(6), pp. 999-1010. doi: 10.1016/S0896-6273(02)00737-7.

Roberson, E. D. and David Sweatt, J. (1996) *Transient Activation of Cyclic AMP-dependent Protein Kinase during Hippocampal Long-term Potentiation*\* Downloaded from, *The Journal of Biological Chemistry*. Available at: http://www-jbc.stanford.edu/jbc/(Accessed: Dec. 3, 2019).

Sassone-Corsi, P. (2012) "The Cyclic AMP pathway," *Cold Spring Harbor Perspectives in Biology*. Cold Spring Harbor Laboratory Press, 4(12). doi: 10.1101/cshperspect.a011148.

Schmidt, U. et al. (2018) "Cell detection with star-convex polygons," in *Lecture Notes in Computer Science (including subseries Lecture Notes in Artificial Intelligence and Lecture Notes in Bioinformatics)*. Springer Verlag, pp. 265-273. doi: 10.1007/978-3-030-00934-2_30.

Shah, S. et al. (2017) "seqFISH Accurately Detects Transcripts in Single Cells and Reveals Robust Spatial Organization in the Hippocampus," *Neuron*. Elsevier, 94(4), p. 752-758.e1. doi: 10.1016/j.neuron.2017.05.008.

Shekhawat, S. S. et al. (2009) "An Autoinhibited Coiled-Coil Design Strategy for Split-Protein Protease Sensors," *Journal of the American Chemical Society*. American Chemical Society, 131(42), pp. 15284-15290. doi: 10.1021/ja9050857.

Shelly, M. et al. (2010) "Local and long-range reciprocal regulation of cAMP and cGMP in axon/dendrite formation," *Science*, 327(5965), pp. 547-552. doi: 10.1126/science.1179735.

Sheng, M., Thompson, M. A. and Greenberg, M. E. (1991) "CREB: a Ca(2+)-regulated transcription factor phosphorylated by calmodulin-dependent kinases," *Science* (New York, N.Y.). American Association for the Advancement of Science, 252(5011), pp. 1427-30. doi: 10.1126/SCIENCE.1646483.

Shimozono, S. et al. (2013) "Visualization of an endogenous retinoic acid gradient across embryonic development," *Nature*. Nature Publishing Group, 496(7445), pp. 363-366. doi: 10.1038/nature2037.

Siso-Nadal, F. et al. (2009) "Cross-talk between signaling pathways can generate robust oscillations in calcium and cAMP," *PLoS ONE*, 4(10). doi: 10.1371/journal.pone.0007189.

Skeberdis, V. A. et al. (2006) "Protein kinase A regulates calcium permeability of NMDA receptors," *Nature Neuroscience*. Nature Publishing Group, 9(4), pp. 501-510. doi: 10.1038/nn1664.

Song, Y. et al. (2013) "High-resolution comparative modeling with RosettaCM," *Structure*, 21(10), pp. 1735-1742. doi: 10.1016/j.str.2013.08.005.

Southern, J. A. et al. (1991) "Identification of an epitope on the P and V proteins of simian virus 5 that distinguishes between two isolates with different biological characteristics," *Journal of General Virology*, 72(7), pp. 1551-1557. doi: 10.1099/0022-1317-72-7-1551.

Tadross, M. R., Tsien, R. W. and Yue, D. T. (2013) "Ca2+ channel nanodomains boost local Ca2+ amplitude," *Proceedings of the National Academy of Sciences of the United States of America*. National Academy of Sciences, 110(39), pp. 15794-9. doi: 10.1073/pnas.1313898110.

Tarantino, N. et al. (2014) "Tnf and il-1 exhibit distinct ubiquitin requirements for inducing NEMO-IKK supramolecular structures," *Journal of Cell Biology*, 204(2), pp. 231-245. doi: 10.1083/jcb.201307172.

Tenner, B. et al. (2020) "Spatially compartmentalized phase regulation of a Ca2+-cAMP-PKA oscillatory circuit," bioRxiv. Cold Spring Harbor Laboratory, p. 2020.01.10.902312. doi: 10.1101/2020.01.10.902312.

Thomas, M. J. et al. (1996) "Activity-dependent β-adrenergic modulation of low frequency stimulation induced LTP in the hippocampal CA1 region," Neuron. Cell Press, 17(3), pp. 475-482. doi: 10.1016/S0896-6273(00)80179-8.

Thomson, A. R. et al. (2014) "Computational design of water-soluble α-helical barrels," Science, 346(6208), pp. 485-488. doi: 10.1126/science.1257452.

Tillberg, P. W. et al. (2016) "Protein-retention expansion microscopy of cells and tissues labeled using standard fluorescent proteins and antibodies," Nature Biotechnology. Nature Publishing Group, 34(9), pp. 987-992. doi: 10.1038/nbt.3625.

Tinevez, J.-Y. et al. (2017) "TrackMate: An open and extensible platform for single-particle tracking," Methods. Academic Press, 115, pp. 80-90. doi: 10.1016/J.YMETH.2016.09.016.

Tripet, B. et al. (1996) "Engineering a de novo-designed coiled-coil heterodimerization domain for the rapid detection, purification and characterization of recombinantly expressed peptides and proteins," "Protein Engineering, Design and Selection." Oxford University Press, 9(11), pp. 1029-1042. doi: 10.1093/protein/9.11.1029.

Trudeau, L. E., Emery, D. G. and Haydon, P. G. (1996) "Direct modulation of the secretory machinery underlies PKA-dependent synaptic facilitation in hippocampal neurons," Neuron, 17(4), pp. 789-97. Available at: http://www.ncbi.nlm.nih.gov/pubmed/8893035 (Accessed: Oct. 17, 2018).

Vay, L. et al. (2007) "Modulation of Ca(2+) release and Ca(2+) oscillations in HeLa cells and fibroblasts by mitochondrial Ca(2+) uniporter stimulation.," The Journal of physiology. Wiley-Blackwell, 580(Pt 1), pp. 39-49. doi: 10.1113/jphysiol.2006.126391.

Vinkenborg, J. L. et al. (2009) "Genetically encoded FRET sensors to monitor intracellular Zn2+ homeostasis," Nature Methods. Nature Publishing Group, 6(10), pp. 737-740. doi: 10.1038/nmeth.1368.

Violin, J. D. et al. (2003) "A genetically encoded fluorescent reporter reveals oscillatory phosphorylation by protein kinase C.," The Journal of cell biology, 161(5), pp. 899-909. doi: 10.1083/jcb.200302125.

Viswanathan, S. et al. (2015) "High-performance probes for light and electron microscopy," Nature Methods. Nature Publishing Group, 12(6), pp. 568-576. doi: 10.1038/nmeth.3365.

Waltereit, R. and Weller, M. (2003) "Signaling from cAMP/PKA to MAPK and synaptic plasticity," Molecular Neurobiology. Humana Press, 27(1), pp. 99-106. doi: 10.1385/MN:27:1:99.

Wang, G. et al. (2006) "Identification of genes targeted by the androgen and PKA signaling pathways in prostate cancer cells," Oncogene, 25(55), pp. 7311-7323. doi: 10.1038/sj.onc.1209715.

Wang, H. and Zhuo, M. (2012) "Group I metabotropic glutamate receptor-mediated gene transcription and implications for synaptic plasticity and diseases," Frontiers in Pharmacology, 3 November. doi: 10.3389/fphar.2012.00189.

Weigert, M. et al. (2019) "Star-convex Polyhedra for 3D Object Detection and Segmentation in Microscopy." Available at: http://arxiv.org/abs/1908.03636 (Accessed: Dec. 16, 2019).

Williams, M. R. et al. (2001) "Role of the endoplasmic reticulum in shaping calcium dynamics in human lens cells," Investigative ophthalmology & visual science, 42(5), pp. 1009-17. Available at: http://www.ncbi.nlm.nih.gov/pubmed/11274079 (Accessed: Oct. 14, 2018).

Wilson, I. A. et al. (1984) "The structure of an antigenic determinant in a protein.," Cell, 37(3), pp. 767-78. Available at: http://www.ncbi.nlm.nih.gov/pubmed/6204768 (Accessed: Oct. 22, 2018).

Wong, S T et al. (1999) "Calcium-stimulated adenylyl cyclase activity is critical for hippocampus-dependent long-term memory and late phase LTP.," Neuron, 23(4), pp. 787-98. doi: 10.1016/s0896-6273(01)80036-2.

Wong, Scott T. et al. (1999) "Calcium-stimulated adenylyl cyclase activity is critical for hippocampus-dependent long-term memory and late phase LTP," Neuron. Cell Press, 23(4), pp. 787-798. doi: 10.1016/50896-6273(01)80036-2.

Wozny, C. et al. (2008) "Brief Communications Differential cAMP Signaling at Hippocampal Output Synapses." doi: 10.1523/JNEUROSCI.4973-08.2008.

Wroblewska, A. et al. (2018) "Protein Barcodes Enable High-Dimensional Single-Cell CRISPR Screens," Cell. Elsevier, 175(4), p. 1141-1155.e16. doi: 10.1016/j.cell.2018.09.022.

Wu, B. et al. (2015) "Synonymous modification results in high-fidelity gene expression of repetitive protein and nucleotide sequences.," Genes & development. Cold Spring Harbor Laboratory Press, 29(8), pp. 876-86. doi: 10.1101/gad.259358.115.

Wu, B. et al. (2016) "Translation dynamics of single mRNAs in live cells and neurons.," Science (New York, N.Y.). American Association for the Advancement of Science, 352(6292), pp. 1430-5. doi: 10.1126/science.aaf1084.

Wu, B., Chao, J. A. and Singer, R. H. (2012) "Fluorescence Fluctuation Spectroscopy Enables Quantitative Imaging of Single mRNAs in Living Cells," Biophysical Journal, 102(12), pp. 2936-2944. doi: 10.1016/j.bpj.2012.05.017.

Van Der Zee, E. A. and Douma, B. R. K. (1997) "Historical review of research on protein kinase C in learning and memory," Progress in Neuro-Psychopharmacology and Biological Psychiatry. Elsevier Inc., 21(3), pp. 379-406. doi: 10.1016/S0278-5846(97)00010-9.

Zaccai, N. R. et al. (2011) "A de novo peptide hexamer with a mutable channel," Nature Chemical Biology, 7(12), pp. 935-941. doi: 10.1038/nchembio.692.

Zanassi, P. et al. (2001) "cAMP-dependent protein kinase induces cAMP-response element-binding protein phosphorylation via an intracellular calcium release/ERK-dependent pathway in striatal neurons.," The Journal of biological chemistry. American Society for Biochemistry and Molecular Biology, 276(15), pp. 11487-95. doi: 10.1074/jbc.M007631200.

Zhang, Q. et al. (2018) "Visualizing Dynamics of Cell Signaling In Vivo with a Phase Separation-Based Kinase Reporter.," Molecular cell. NIH Public Access, 69(2), pp. 334-346.e4. doi: 10.1016/j.molcel.2017.12.008.

EQUIVALENTS

Although several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated by reference in their entirety herein.

What is claimed is:

1. A composition comprising a fusion protein, wherein the fusion protein comprises:
   (a) one or more independently selected reporter protein elements,
   (b) two or more independently selected self-assembly protein elements,
   (c) zero, one, or more independently selected epitope tag elements,
   (d) zero, one, or more localization protein motif elements, and
   (e) zero, one, or more independently selected protein linker elements, wherein when present, each one of the protein linker elements is positioned between two of the elements of (a), (b), (c), and (d), and wherein the fusion protein comprises: S1-GCaMP6f, S2-cAMPr, S2a-cAMPr, S3-EXRaiAKAR, S4-EXRaiCKAR, S3-ExRaiAktAR, or S2-RAB EKARev.

2. The composition of claim 1, wherein the two or more independently selected self-assembly protein elements comprise two or more of a polyhedron-forming protein, a coiled-coil-forming protein, a supramolecular self-assembly protein, and a protein oligomer.

3. The composition of claim 1, wherein the localization protein motif element comprises one or more of a nucleus localization motif, a plasma membrane localization motif, and a synapse localization motif.

4. The composition of claim 1, wherein the independently selected reporter protein element is a voltage indicator polypeptide, a calcium indicator polypeptide, a potassium indicator polypeptide, a pH indicator polypeptide, or a magnesium indicator polypeptide.

5. The composition of claim 1, wherein the independently selected reporter protein element is GCaMP6, GcaMP6f, GcaMP6m, GcaMP6s, jGCaMP7, jGCaMP7f, jGCaMP7m, jGCaMP7s, jGCaMP7b, jGCaMP7c, GcaMP-X, XcaMP, XcaMP-R, jRGECO1, jRCaMP1, NIRGECO, BcaMP, ICUE, ICUE3, cAMPr, Epac-based cAMP indicator, AKAR, AKAR4, ExRaiAKAR, ExRaiAKAR2, CKAR, ExRa-iCKAR, EKARev, ExRaiAktAR or RAB-EKARev.

6. The composition of claim 1, wherein the fusion protein is detectable by one or more microscopy methods.

7. The composition of claim 6, wherein the one or more of the microscopy methods comprise immunostaining and optionally one or more of the independently selected reporter protein elements are immunologically detectable.

8. The composition of claim 6, wherein the one or more of the microscopy methods comprise fluorescence detection, and optionally one or more of the independently selected reporter protein elements comprises at least one fluorescent label.

9. A cell comprising the composition of claim 1.

10. A method of simultaneously assessing physiological processes in a cell, comprising:
   (a) expressing two or more different compositions of claim 1 in the cell,
   (b) determining one or more activities of the independently selected reporter elements in the cell; wherein the determined activities provide an assessment of physiological processes in the cell.

11. The method of claim 10, wherein each of the independently selected reporter protein elements, when activated, produces a detectable signal distinguishable from that produced by any other of the independently selected reporter protein elements.

12. The method of claim 10, further comprising determining a location of one or more of the fusion proteins in the cell.

13. The method of claim 12, wherein the location of the fusion protein in the cell is detectable by one or more microscopy methods.

14. The method of claim 10, wherein two or more simultaneous physical processes are assessed in the cell.

15. The method of claim 10, further comprising stimulating one or more of the independently selected reporter elements in the cell before determining the one or more activities of the independently selected reporter elements in the cell.

16. The method of claim 10, wherein the two or more fusion proteins each form puncta in the cell.

17. The method of claim 16, wherein detecting a location of the independently selected reporter protein element of a fusion protein expressed in the cell identifies the location of the puncta formed by the fusion protein comprising the independently selected reporter molecule.

18. A method of identifying an effect of a candidate agent on a physiological process in a cell, the method comprising:
   (a) preparing a cell comprising one or more compositions of claim 1, wherein the prepared cell comprises preformed clusters of the one or more fusion proteins;
   (b) contacting the prepared cell with a candidate agent;
   (c) detecting one or more signals generated from the independently selected reporter protein elements in the preformed clusters of the one or more fusion proteins;
   (d) analyzing the detected one or more signals to determine a physiological process of the contacted cell; and
   (e) comparing the determined physiological process of the contacted cell with the determined physiological process of a control prepared cell that is not contacted with the candidate agent, wherein a difference identifies an effect of the candidate agent on a physiological process in the contacted cell.

\* \* \* \* \*

SEQUENCE LISTING

```
<160> NUMBER OF SEQ ID NOS: 99

<210> SEQ ID NO 1
<211> LENGTH: 233
<212> TYPE: PRT
<213> ORGANISM: Artificial sequence
<220> FEATURE:
<223> OTHER INFORMATION: Synthetic polypetide

<400> SEQUENCE: 1

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Ile Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Asn Arg Lys Tyr Thr Ile Lys Val Glu
    50                  55                  60

Val Pro Lys Gly Ala Trp Arg Ser Tyr Leu Asn Met Glu Leu Thr Ile
65                  70                  75                  80

Pro Ile Phe Ala Thr Asn Ser Asp Cys Glu Leu Ile Val Lys Ala Met
                85                  90                  95

Gln Gly Leu Leu Lys Asp Gly Asn Pro Ile Pro Ser Ala Ile Ala Ala
            100                 105                 110

Asn Ser Gly Ile Tyr Ala Met Ala Ser Asn Phe Thr Gln Phe Val Leu
        115                 120                 125

Val Asp Asn Gly Gly Thr Gly Asp Val Thr Val Ala Pro Ser Asn Phe
    130                 135                 140

Ala Asn Gly Ile Ala Glu Trp Ile Ser Ser Asn Ser Arg Ser Gln Ala
145                 150                 155                 160

Tyr Lys Val Thr Cys Ser Val Arg Gln Ser Ser Ala Gln Asn Arg Lys
                165                 170                 175

Tyr Thr Ile Lys Val Glu Val Pro Lys Gly Ala Trp Arg Ser Tyr Leu
            180                 185                 190

Asn Met Glu Leu Thr Ile Pro Ile Phe Ala Thr Asn Ser Asp Cys Glu
        195                 200                 205

Leu Ile Val Lys Ala Met Gln Gly Leu Leu Lys Asp Gly Asn Pro Ile
```

```
            210                 215                 220
Pro Ser Ala Ile Ala Ala Asn Ser Gly
225                 230

<210> SEQ ID NO 2
<211> LENGTH: 249
<212> TYPE: PRT
<213> ORGANISM: Artificial sequence
<220> FEATURE:
<223> OTHER INFORMATION: Synthetic Polypeptide

<400> SEQUENCE: 2

Leu Ala Ser Lys Thr Ile Val Leu Ser Val Gly Glu Ala Thr Arg Thr
1               5                   10                  15

Leu Thr Glu Ile Gln Ser Thr Ala Asp Arg Gln Ile Phe Glu Glu Lys
            20                  25                  30

Val Gly Pro Leu Val Gly Arg Leu Arg Leu Thr Ala Ser Leu Arg Gln
        35                  40                  45

Asn Gly Ala Lys Thr Ala Tyr Arg Val Asn Leu Lys Leu Asp Gln Ala
    50                  55                  60

Asp Val Val Asp Ser Gly Leu Pro Lys Val Arg Tyr Thr Gln Val Trp
65                  70                  75                  80

Ser His Asp Val Thr Ile Val Ala Asn Ser Thr Glu Ala Ser Arg Lys
                85                  90                  95

Ser Leu Tyr Asp Leu Thr Lys Ser Leu Val Ala Thr Ser Gln Val Glu
            100                 105                 110

Asp Leu Val Val Asn Leu Val Pro Leu Gly Arg Ala Asp Pro Leu Ala
        115                 120                 125

Ser Lys Thr Ile Val Leu Ser Val Gly Glu Ala Thr Arg Thr Leu Thr
    130                 135                 140

Glu Ile Gln Ser Thr Ala Asp Arg Gln Ile Phe Glu Glu Lys Val Gly
145                 150                 155                 160

Pro Leu Val Gly Arg Leu Arg Leu Thr Ala Ser Leu Arg Gln Asn Gly
                165                 170                 175

Ala Lys Thr Ala Tyr Arg Val Asn Leu Lys Leu Asp Gln Ala Asp Val
            180                 185                 190

Val Asp Ser Gly Leu Pro Lys Val Arg Tyr Thr Gln Val Trp Ser His
        195                 200                 205

Asp Val Thr Ile Val Ala Asn Ser Thr Glu Ala Ser Arg Lys Ser Leu
    210                 215                 220

Tyr Asp Leu Thr Lys Ser Leu Val Ala Thr Ser Gln Val Glu Asp Leu
225                 230                 235                 240

Val Val Asn Leu Val Pro Leu Gly Arg
                245

<210> SEQ ID NO 3
<211> LENGTH: 19
<212> TYPE: DNA
<213> ORGANISM: Artificial sequence
<220> FEATURE:
<223> OTHER INFORMATION: Synthetic Polypeptide

<400> SEQUENCE: 3
acatgaggat cacccatgt                                              19

<210> SEQ ID NO 4
<211> LENGTH: 25
<212> TYPE: DNA
```

-continued

```
<213> ORGANISM: Artificial sequence
<220> FEATURE:
<223> OTHER INFORMATION: Synthetic oligonucleotide

<400> SEQUENCE: 4
ggagcagacg atatggcgtc gctcc                                            25

<210> SEQ ID NO 5
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 5
ccagcagagc atatgggctc gctgg                                            25

<210> SEQ ID NO 6
<211> LENGTH: 22
<212> TYPE: PRT
<213> ORGANISM: Artificial sequence
<220> FEATURE:
<223> OTHER INFORMATION: Synthetic polypeptide

<400> SEQUENCE: 6

Met Asp Ala Gln Thr Arg Arg Arg Glu Arg Arg Ala Glu Lys Gln Ala
1               5                   10                  15

Gln Trp Lys Ala Ala Asn
            20

<210> SEQ ID NO 7
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 7
gggccctgaa gaagggccc                                                   19

<210> SEQ ID NO 8
<211> LENGTH: 441
<212> TYPE: DNA
<213> ORGANISM: Mus musculus

<400> SEQUENCE: 8
gcggactgtt actgagctgc gttttacacc ctttctttga caaaacctaa cttgcgcaga      60
aaaaaaaaaa ataagagaca acattggcat ggctttgttt ttttaaattt tttttaaagt     120
tttttttttt tttttttttt ttttttttaa gttttttttgt tttgttttgg cgcttttgac    180
tcaggattta aaaactggaa cggtgaaggc gacagcagtt ggttggagca aacatccccc     240
aaagttctac aaatgtggct gaggactttg tacattgttt tgttttttttt tttttttggt    300 tttgtctttt tttaatagtc attccaagta tccatgaaat aagtggttac aggaagtccc     360
tcaccctccc aaaagccacc cccactccta agaggaggat ggtcgcgtcc atgccctgag     420
tccaccccgg ggaaggtgac a                                               441

<210> SEQ ID NO 9
<211> LENGTH: 205
<212> TYPE: PRT
<213> ORGANISM: Artificial sequence
<220> FEATURE:
<223> OTHER INFORMATION: Synthetic polypeptide
```

<400> SEQUENCE: 9

| Met | Lys | Met | Glu | Glu | Leu | Phe | Lys | Lys | His | Lys | Ile | Val | Ala | Val | Leu |
| 1   |     |     |     | 5   |     |     |     |     | 10  |     |     |     |     | 15  |     |

| Arg | Ala | Asn | Ser | Val | Glu | Glu | Ala | Lys | Lys | Lys | Ala | Leu | Ala | Val | Phe |
|     |     |     | 20  |     |     |     |     | 25  |     |     |     |     | 30  |     |     |

| Leu | Gly | Gly | Val | His | Leu | Ile | Glu | Ile | Thr | Phe | Thr | Val | Pro | Asp | Ala |
|     |     |     | 35  |     |     |     |     | 40  |     |     |     |     | 45  |     |     |

| Asp | Thr | Val | Ile | Lys | Glu | Leu | Ser | Phe | Leu | Lys | Glu | Met | Gly | Ala | Ile |
|     | 50  |     |     |     |     |     | 55  |     |     |     |     | 60  |     |     |     |

| Ile | Gly | Ala | Gly | Thr | Val | Thr | Ser | Val | Glu | Gln | Cys | Arg | Lys | Ala | Val |
| 65  |     |     |     |     | 70  |     |     |     |     | 75  |     |     |     |     | 80  |

| Glu | Ser | Gly | Ala | Glu | Phe | Ile | Val | Ser | Pro | His | Leu | Asp | Glu | Glu | Ile |
|     |     |     |     | 85  |     |     |     |     | 90  |     |     |     |     | 95  |     |

| Ser | Gln | Phe | Cys | Lys | Glu | Lys | Gly | Val | Phe | Tyr | Met | Pro | Gly | Val | Met |
|     |     |     | 100 |     |     |     |     | 105 |     |     |     |     | 110 |     |     |

| Thr | Pro | Thr | Glu | Leu | Val | Lys | Ala | Met | Lys | Leu | Gly | His | Thr | Ile | Leu |
|     |     |     | 115 |     |     |     |     | 120 |     |     |     |     | 125 |     |     |

| Lys | Leu | Phe | Pro | Gly | Glu | Val | Val | Gly | Pro | Gln | Phe | Val | Lys | Ala | Met |
|     | 130 |     |     |     |     |     | 135 |     |     |     |     | 140 |     |     |     |

| Lys | Gly | Pro | Phe | Pro | Asn | Val | Lys | Phe | Val | Pro | Thr | Gly | Gly | Val | Asn |
| 145 |     |     |     |     | 150 |     |     |     |     | 155 |     |     |     |     | 160 |

| Leu | Asp | Asn | Val | Cys | Glu | Trp | Phe | Lys | Ala | Gly | Val | Leu | Ala | Val | Gly |
|     |     |     |     | 165 |     |     |     |     | 170 |     |     |     |     | 175 |     |

| Val | Gly | Ser | Ala | Leu | Val | Lys | Gly | Thr | Pro | Val | Glu | Val | Ala | Glu | Lys |
|     |     |     | 180 |     |     |     |     | 185 |     |     |     |     | 190 |     |     |

| Ala | Lys | Ala | Phe | Val | Glu | Lys | Ile | Arg | Gly | Cys | Thr | Glu |
|     |     | 195 |     |     |     |     | 200 |     |     |     |     | 205 |

<210> SEQ ID NO 10
<211> LENGTH: 186
<212> TYPE: PRT
<213> ORGANISM: Artificial sequence
<220> FEATURE:
<223> OTHER INFORMATION: Synthetic polypeptide

<400> SEQUENCE: 10

| Met | Ser | Gln | Ala | Ile | Gly | Ile | Leu | Glu | Leu | Thr | Ser | Ile | Ala | Ala | Gly |
| 1   |     |     |     | 5   |     |     |     |     | 10  |     |     |     |     | 15  |     |

| Met | Glu | Leu | Gly | Asp | Ala | Met | Leu | Lys | Ser | Ala | Asn | Val | Asp | Leu | Leu |
|     |     |     | 20  |     |     |     |     | 25  |     |     |     |     | 30  |     |     |

| Val | Ser | Lys | Thr | Ile | Ser | Pro | Gly | Lys | Phe | Leu | Leu | Met | Leu | Gly | Gly |
|     |     |     | 35  |     |     |     |     | 40  |     |     |     |     | 45  |     |     |

| Asp | Ile | Gly | Ala | Ile | Gln | Gln | Ala | Ile | Glu | Thr | Gly | Thr | Ser | Gln | Ala |
|     | 50  |     |     |     |     |     | 55  |     |     |     |     | 60  |     |     |     |

| Gly | Glu | Leu | Leu | Val | Asp | Ser | Leu | Val | Leu | Ala | Asn | Ile | His | Pro | Ser |
| 65  |     |     |     |     | 70  |     |     |     |     | 75  |     |     |     |     | 80  |

| Val | Leu | Pro | Ala | Ile | Ser | Gly | Leu | Asn | Ser | Val | Asp | Lys | Arg | Gln | Ala |
|     |     |     |     | 85  |     |     |     |     | 90  |     |     |     |     | 95  |     |

| Val | Gly | Ile | Val | Glu | Thr | Trp | Ser | Val | Ala | Ala | Cys | Ile | Ser | Ala | Ala |
|     |     |     | 100 |     |     |     |     | 105 |     |     |     |     | 110 |     |     |

| Asp | Arg | Ala | Val | Lys | Gly | Ser | Asn | Val | Thr | Leu | Val | Arg | Val | His | Met |
|     |     |     | 115 |     |     |     |     | 120 |     |     |     |     | 125 |     |     |

| Ala | Phe | Gly | Ile | Gly | Gly | Lys | Cys | Tyr | Met | Val | Val | Ala | Gly | Asp | Val |
|     | 130 |     |     |     |     |     | 135 |     |     |     |     | 140 |     |     |     |

Ser Asp Val Ala Leu Ala Val Thr Val Ala Ser Ser Ala Gly Ala
145                 150                 155                 160

Tyr Gly Leu Leu Val Tyr Ala Ser Leu Ile Pro Arg Pro His Glu Ala
                165                 170                 175

Met Trp Arg Gln Met Val Glu Gly Leu Glu
            180                 185

<210> SEQ ID NO 11
<211> LENGTH: 30
<212> TYPE: PRT
<213> ORGANISM: Artificial sequence
<220> FEATURE:
<223> OTHER INFORMATION: Synthetic polypeptide

<400> SEQUENCE: 11

Ala Glu Ala Glu Ser Ala Leu Glu Tyr Ala Gln Gln Ala Leu Glu Lys
1               5                   10                  15

Ala Gln Leu Ala Leu Gln Ala Ala Arg Gln Ala Leu Lys Ala
            20                  25                  30

<210> SEQ ID NO 12
<211> LENGTH: 33
<212> TYPE: PRT
<213> ORGANISM: Artificial sequence
<220> FEATURE:
<223> OTHER INFORMATION: Synthetic polypeptide

<400> SEQUENCE: 12

Thr Gln Glu Asp Leu Leu Lys Lys Ile Met Lys Leu Leu Lys Lys Gln
1               5                   10                  15

Ile Lys Leu Leu Lys Lys Gln Ile Lys Met Leu Lys Arg Leu Glu Lys
            20                  25                  30

Gln

<210> SEQ ID NO 13
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 13

Gly Gly Ser Gly Gly Thr Gly Gly Ser Gly Gly Thr
1               5                   10

<210> SEQ ID NO 14
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 14

Gly Gly Ser Gly Gly Thr Gly Gly Ser Gly Gly Thr Gly Gly Ser Gly
1               5                   10                  15

Gly Thr Gly Gly Ser Gly Gly Thr
            20

<210> SEQ ID NO 15
<211> LENGTH: 27
<212> TYPE: PRT
<213> ORGANISM: Artificial sequence
<220> FEATURE:
<223> OTHER INFORMATION: Synthetic polypeptide

<400> SEQUENCE: 15

Gly Gly Ser Gly Gly Ser Gly Gly Thr Gly Gly Ser Gly Gly Ser Gly
1               5                   10                  15

Gly Thr Gly Gly Ser Gly Gly Ser Gly Gly Thr
            20                  25

<210> SEQ ID NO 16
<211> LENGTH: 29
<212> TYPE: PRT
<213> ORGANISM: Artificial sequence
<220> FEATURE:
<223> OTHER INFORMATION: Synthetic polypeptide

<400> SEQUENCE: 16

Gly Gly Ser Gly Gly Ser Gly Gly Thr Gly Gly Ser Gly Gly Ser Gly
1               5                   10                  15

Gly Thr Gly Gly Ser Gly Gly Ser Gly Gly Thr Gly Gly
            20                  25

<210> SEQ ID NO 17
<211> LENGTH: 48
<212> TYPE: PRT
<213> ORGANISM: Artificial sequence
<220> FEATURE:
<223> OTHER INFORMATION: Synthetic polypeptide

<400> SEQUENCE: 17

Gly Gly Ser Gly Gly Thr Gly Gly Ser Gly Gly Thr Gly Gly Ser Gly
1               5                   10                  15

Gly Thr Gly Gly Ser Gly Gly Thr Gly Gly Ser Gly Gly Thr Gly Gly
            20                  25                  30

Ser Gly Gly Thr Gly Gly Ser Gly Gly Thr Gly Gly Ser Gly Gly Thr
        35                  40                  45

<210> SEQ ID NO 18
<211> LENGTH: 50
<212> TYPE: PRT
<213> ORGANISM: Artificial sequence
<220> FEATURE:
<223> OTHER INFORMATION: Synthetic polypeptide

<400> SEQUENCE: 18

Gly Gly Ser Gly Gly Thr Gly Gly Ser Gly Gly Thr Gly Gly Ser Gly
1               5                   10                  15

Gly Thr Gly Gly Ser Gly Gly Thr Gly Gly Ser Gly Gly Thr Gly Gly
            20                  25                  30

Ser Gly Gly Thr Gly Gly Ser Gly Gly Thr Gly Gly Ser Gly Gly Thr
        35                  40                  45

Gly Gly
    50

<210> SEQ ID NO 19
<211> LENGTH: 199
<212> TYPE: PRT
<213> ORGANISM: Artificial sequence
<220> FEATURE:
<223> OTHER INFORMATION: Synthetic polypeptide

<400> SEQUENCE: 19

Met Thr Glu Lys Glu Lys Met Leu Ala Glu Lys Trp Tyr Asp Ala Asn
1               5                   10                  15

Phe Asp Gln Thr Leu Ile Asn Glu Arg Leu Arg Ala Lys Val Ile Cys
                20                  25                  30

Phe Ala Leu Asn His Thr Asn Pro Val Ala Thr Met Met Arg Lys Val
            35                  40                  45

Leu Ile Asp Ala Leu Phe Gln Thr Thr Thr Asp Asn Val Ser Ile Ser
        50                  55                  60

Ile Pro Phe Asp Thr Asp Tyr Gly Trp Asn Val Lys Leu Gly Lys Asn
65                  70                  75                  80

Val Tyr Val Asn Thr Asn Cys Tyr Phe Met Asp Gly Gly Gln Ile Thr
                85                  90                  95

Ile Gly Asp Asn Val Phe Ile Gly Pro Asn Cys Gly Phe Tyr Thr Ala
            100                 105                 110

Thr His Pro Leu Asn Phe His His Arg Asn Glu Gly Phe Glu Lys Ala
        115                 120                 125

Gly Pro Ile His Ile Gly Ser Asn Thr Trp Phe Gly Gly His Val Ala
    130                 135                 140

Val Leu Pro Gly Val Thr Ile Gly Glu Gly Ser Val Ile Gly Ala Gly
145                 150                 155                 160

Ser Val Val Thr Lys Asp Ile Pro Pro His Ser Leu Ala Val Gly Asn
                165                 170                 175

Pro Cys Lys Val Val Arg Lys Ile Asp Asn Asp Leu Pro Ser Glu Thr
            180                 185                 190

Leu Asn Asp Glu Thr Ile Lys
        195

<210> SEQ ID NO 20
<211> LENGTH: 450
<212> TYPE: PRT
<213> ORGANISM: Artificial sequence
<220> FEATURE:
<223> OTHER INFORMATION: Synthetic polypeptide

<400> SEQUENCE: 20

Met Pro Phe Ile Thr Val Gly Gln Glu Asn Ser Thr Ser Ile Asp Leu
1               5                   10                  15

Tyr Tyr Glu Asp His Gly Thr Gly Val Pro Val Val Leu Ile His Gly
                20                  25                  30

Phe Pro Leu Ser Gly His Ser Trp Glu Arg Gln Ser Ala Ala Leu Leu
            35                  40                  45

Asp Ala Gly Tyr Arg Val Ile Thr Tyr Asp Arg Arg Gly Phe Gly Gln
        50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Asp Asp Asn Pro Asp Gly Ala Ala Pro Gln Glu
    130                 135                 140

Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Asp Glu Asn Leu Gly
                165                 170                 175

```
Thr Arg Ile Ser Glu Ala Val Arg Asn Ser Trp Asn Thr Ala Ala
            180                 185                 190

Ser Gly Gly Phe Phe Ala Ala Ala Ala Pro Thr Thr Trp Tyr Thr
            195                 200                 205

Asp Phe Arg Ala Asp Ile Pro Arg Ile Asp Val Pro Ala Leu Ile Leu
    210                 215                 220

His Gly Thr Gly Asp Arg Thr Leu Pro Ile Glu Asn Thr Ala Arg Val
225                 230                 235                 240

Phe His Lys Ala Leu Pro Ser Ala Glu Tyr Val Glu Val Glu Gly Ala
            245                 250                 255

Pro His Gly Leu Leu Trp Thr His Ala Glu Glu Val Asn Thr Ala Leu
            260                 265                 270

Leu Ala Phe Leu Ala Lys Ala Leu Glu Ala Gln Lys Gln Lys Leu Leu
            275                 280                 285

Thr Glu Val Glu Thr Tyr Val Leu Ser Ile Ile Pro Ser Gly Pro Leu
            290                 295                 300

Lys Ala Glu Ile Ala Gln Arg Leu Glu Asp Val Phe Ala Gly Lys Asn
305                 310                 315                 320

Thr Asp Leu Glu Val Leu Met Glu Trp Leu Lys Thr Arg Pro Ile Leu
            325                 330                 335

Ser Pro Leu Thr Lys Gly Ile Leu Gly Phe Val Phe Thr Leu Thr Val
            340                 345                 350

Pro Ser Glu Arg Gly Leu Gln Arg Arg Phe Val Gln Asn Ala Leu
            355                 360                 365

Asn Gly Asn Gly Asp Pro Asn Asn Met Asp Lys Ala Val Lys Leu Tyr
            370                 375                 380

Arg Lys Leu Lys Arg Glu Ile Thr Phe His Gly Ala Lys Glu Ile Ser
385                 390                 395                 400

Leu Ser Tyr Ser Ala Gly Ala Leu Ala Ser Cys Met Gly Leu Ile Tyr
            405                 410                 415

Asn Arg Met Gly Ala Val Thr Thr Glu Val Ala Phe Gly Leu Val Cys
            420                 425                 430

Ala Thr Cys Glu Gln Ile Ala Asp Ser Gln His Arg Ser His Arg Gln
            435                 440                 445

Leu Glu
    450

<210> SEQ ID NO 21
<211> LENGTH: 87
<212> TYPE: PRT
<213> ORGANISM: Artificial sequence
<220> FEATURE:
<223> OTHER INFORMATION: Synthetic polypeptide

<400> SEQUENCE: 21

Ser Glu Glu Leu Arg Ala Val Ala Asp Leu Gln Arg Leu Asn Ile Glu
1               5                   10                  15

Leu Ala Arg Lys Leu Leu Glu Ala Val Ala Arg Leu Gln Glu Leu Asn
            20                  25                  30

Ile Asp Leu Val Arg Lys Thr Ser Glu Leu Thr Asp Glu Lys Thr Ile
            35                  40                  45

Arg Glu Glu Ile Arg Lys Val Lys Glu Glu Ser Lys Arg Ile Val Glu
            50                  55                  60

Glu Ala Glu Glu Glu Ile Arg Arg Ala Lys Glu Glu Ser Arg Tyr Ile
65                  70                  75                  80
```

Ala Asp Glu Ser Arg Gly Ser
            85

<210> SEQ ID NO 22
<211> LENGTH: 76
<212> TYPE: PRT
<213> ORGANISM: Artificial sequence
<220> FEATURE:
<223> OTHER INFORMATION: Synthetic polypeptide

<400> SEQUENCE: 22

Gly Ser Arg Val Tyr Glu Ser Glu Lys Leu Ala Arg Glu Ala Asp Lys
1               5                   10                  15

Leu Ala Gln Lys Ser Glu Asp Met Ala Arg Glu Ala Asp Lys Gln Ala
            20                  25                  30

Arg Arg Ala Glu Glu Arg Pro Asp Arg Glu Glu Ile Ala Arg Leu Ala
        35                  40                  45

Ala Ile Ile Ala Arg Met Val Ala Leu Asn Ser Arg Ile Ala Met Leu
    50                  55                  60

Met Ala Arg Met Ile Met Leu Asn Ser Gln Glu Ser
65                  70                  75

<210> SEQ ID NO 23
<211> LENGTH: 285
<212> TYPE: PRT
<213> ORGANISM: Artificial sequence
<220> FEATURE:
<223> OTHER INFORMATION: Synthetic polypeptide

<400> SEQUENCE: 23

Met Gln Trp Gln Thr Lys Leu Pro Leu Ile Ala Ile Leu Arg Gly Ile
1               5                   10                  15

Thr Pro Asp Glu Ala Leu Ala His Val Gly Ala Val Ile Asp Ala Gly
            20                  25                  30

Phe Asp Ala Val Glu Ile Pro Leu Asn Ser Pro Gln Trp Glu Gln Ser
        35                  40                  45

Ile Pro Ala Ile Val Asp Ala Tyr Gly Asp Lys Ala Leu Ile Gly Ala
    50                  55                  60

Gly Thr Val Leu Lys Pro Glu Gln Val Asp Ala Leu Ala Arg Met Gly
65                  70                  75                  80

Cys Gln Leu Ile Val Thr Pro Asn Ile His Ser Glu Val Ile Arg Arg
                85                  90                  95

Ala Val Gly Tyr Gly Met Thr Val Cys Pro Gly Cys Ala Thr Ala Thr
            100                 105                 110

Glu Ala Phe Thr Ala Leu Glu Ala Gly Ala Gln Ala Leu Lys Ile Phe
        115                 120                 125

Pro Ser Ser Ala Phe Gly Pro Gln Tyr Ile Lys Ala Leu Lys Ala Val
    130                 135                 140

Leu Pro Ser Asp Ile Ala Val Phe Ala Val Gly Gly Val Thr Pro Glu
145                 150                 155                 160

Asn Leu Ala Gln Trp Ile Asp Ala Gly Cys Ala Gly Ala Gly Leu Gly
                165                 170                 175

Ser Asp Leu Tyr Arg Ala Gly Gln Ser Val Glu Arg Thr Ala Gln Gln
            180                 185                 190

Ala Ala Ala Phe Val Lys Ala Tyr Arg Glu Ala Gln Lys Gln Lys Glu
        195                 200                 205

Gln Arg Gln Asp Gln Lys Ser Ala Tyr Ala Leu Gly Ala Ser Leu Gly
    210                 215                 220

```
Arg Tyr Met Glu Asn Ser Leu Lys Glu Gln Glu Lys Leu Gly Ile Lys
225                 230                 235                 240

Leu Asp Lys Asp Gln Leu Ile Ala Gly Val Gln Asp Ala Phe Ala Asp
                245                 250                 255

Lys Ser Lys Leu Ser Asp Gln Glu Ile Glu Gln Thr Leu Gln Ala Phe
            260                 265                 270

Glu Ala Arg Val Lys Ser Ser Ala Gln Ala Lys Leu Glu
        275                 280                 285

<210> SEQ ID NO 24
<211> LENGTH: 351
<212> TYPE: PRT
<213> ORGANISM: Artificial sequence
<220> FEATURE:
<223> OTHER INFORMATION: Synthetic polypeptide

<400> SEQUENCE: 24

Met Gly Glu Val Pro Ile Gly Asp Pro Lys Glu Leu Asn Gly Met Glu
1               5                   10                  15

Ile Ala Ala Val Tyr Leu Gln Pro Ile Glu Met Glu Pro Arg Gly Ile
            20                  25                  30

Asp Leu Ala Ala Ser Leu Ala Asp Ile His Leu Glu Ala Asp Ile His
        35                  40                  45

Ala Leu Lys Asn Pro Asn Gly Phe Pro Glu Gly Phe Trp Met Pro
    50                  55                  60

Tyr Leu Thr Ile Ala Tyr Ala Leu Ala Asn Ala Asp Thr Gly Ala Ile
65              70                  75                  80

Lys Thr Gly Thr Leu Met Pro Met Val Ala Asp Asp Gly Pro His Tyr
            85                  90                  95

Gly Ala Asn Ile Ala Met Glu Lys Asp Lys Lys Gly Phe Gly Val
            100                 105                 110

Gly Thr Tyr Ala Leu Thr Phe Leu Ile Ser Asn Pro Glu Lys Gln Gly
        115                 120                 125

Phe Gly Arg His Val Asp Glu Glu Thr Gly Val Gly Lys Trp Phe Glu
130                 135                 140

Pro Phe Val Val Thr Tyr Phe Phe Lys Tyr Thr Gly Thr Pro Lys Gly
145                 150                 155                 160

Gly Gly Ser Gly Gly Ser Met Ser Gln Ala Ile Gly Ile Leu Glu
            165                 170                 175

Leu Thr Ser Ile Ala Lys Gly Met Glu Leu Gly Asp Ala Met Leu Lys
        180                 185                 190

Ser Ala Asn Val Asp Leu Leu Val Ser Lys Thr Ile Ser Pro Gly Lys
        195                 200                 205

Phe Leu Leu Met Leu Gly Gly Asp Ile Gly Ala Ile Gln Gln Ala Ile
210                 215                 220

Glu Thr Gly Thr Ser Gln Ala Gly Glu Met Leu Val Asp Ser Leu Val
225                 230                 235                 240

Leu Ala Asn Ile His Pro Ser Val Leu Pro Ala Ile Ser Gly Leu Asn
                245                 250                 255

Ser Val Asp Lys Arg Gln Ala Val Gly Ile Val Glu Thr Trp Ser Val
            260                 265                 270

Ala Ala Cys Ile Ser Ala Ala Asp Leu Ala Val Lys Gly Ser Asn Val
        275                 280                 285

Thr Leu Val Arg Val His Met Ala Phe Gly Ile Gly Gly Lys Cys Tyr
        290                 295                 300
```

```
Met Val Val Ala Gly Asp Val Leu Asp Val Ala Ala Val Ala Thr
305                 310                 315                 320

Ala Ser Leu Ala Ala Gly Ala Lys Gly Leu Val Tyr Ala Ser Ile
            325                 330                 335

Ile Pro Arg Pro His Glu Ala Met Trp Arg Gln Met Val Glu Gly
            340                 345                 350

<210> SEQ ID NO 25
<211> LENGTH: 209
<212> TYPE: PRT
<213> ORGANISM: Artificial sequence
<220> FEATURE:
<223> OTHER INFORMATION: Synthetic polypeptide

<400> SEQUENCE: 25

Gly Met Thr Asp Tyr Ile Arg Asp Gly Ser Ala Ile Lys Ala Leu Ser
1               5                   10                  15

Phe Ala Ile Ile Leu Ala Glu Ala Asp Leu Arg His Ile Pro Gln Asp
                20                  25                  30

Leu Gln Arg Leu Ala Val Arg Val Ile His Ala Cys Gly Met Val Asp
            35                  40                  45

Val Ala Asn Asp Leu Ala Phe Ser Glu Gly Ala Gly Lys Ala Gly Arg
        50                  55                  60

Asn Ala Leu Leu Ala Gly Ala Pro Ile Leu Cys Asp Ala Arg Met Val
65                  70                  75                  80

Ala Glu Gly Ile Thr Arg Ser Arg Leu Pro Ala Asp Asn Arg Val Ile
                85                  90                  95

Tyr Thr Leu Ser Asp Pro Ser Val Pro Glu Leu Ala Lys Lys Ile Gly
            100                 105                 110

Asn Thr Arg Ser Ala Ala Ala Leu Asp Leu Trp Leu Pro His Ile Glu
        115                 120                 125

Gly Ser Ile Val Ala Ile Gly Asn Ala Pro Thr Ala Leu Phe Arg Leu
130                 135                 140

Phe Glu Leu Leu Asp Ala Gly Ala Pro Lys Pro Ala Leu Ile Ile Gly
145                 150                 155                 160

Met Pro Val Gly Phe Val Gly Ala Ala Glu Ser Lys Asp Glu Leu Ala
                165                 170                 175

Ala Asn Ser Arg Gly Val Pro Tyr Val Ile Val Arg Gly Arg Arg Gly
            180                 185                 190

Gly Ser Ala Met Thr Ala Ala Val Asn Ala Leu Ala Ser Glu Arg
        195                 200                 205

Glu

<210> SEQ ID NO 26
<211> LENGTH: 128
<212> TYPE: PRT
<213> ORGANISM: Artificial sequence
<220> FEATURE:
<223> OTHER INFORMATION: Synthetic polypeptide

<400> SEQUENCE: 26

Met Ile Thr Val Phe Gly Leu Lys Ser Lys Leu Ala Pro Arg Arg Glu
1               5                   10                  15

Lys Leu Ala Glu Val Ile Tyr Ser Ser Leu His Leu Gly Leu Asp Ile
                20                  25                  30

Pro Lys Gly Lys His Ala Ile Arg Phe Leu Cys Leu Glu Lys Glu Asp
            35                  40                  45
```

```
Phe Tyr Tyr Pro Phe Asp Arg Ser Asp Asp Tyr Thr Val Ile Glu Ile
    50                  55                  60

Asn Leu Met Ala Gly Arg Ser Glu Glu Thr Lys Met Leu Leu Ile Phe
 65              70                  75                  80

Leu Leu Phe Ile Ala Leu Glu Arg Lys Leu Gly Ile Arg Ala His Asp
                85                  90                  95

Val Glu Ile Thr Ile Lys Glu Gln Pro Ala His Cys Trp Gly Phe Arg
            100                 105                 110

Gly Arg Thr Gly Asp Ser Ala Arg Asp Leu Asp Tyr Asp Ile Tyr Val
                115                 120                 125
```

<210> SEQ ID NO 27
<211> LENGTH: 201
<212> TYPE: PRT
<213> ORGANISM: Artificial sequence
<220> FEATURE:
<223> OTHER INFORMATION: Synthetic polypeptide

<400> SEQUENCE: 27

```
Met Gly His Thr Lys Gly Pro Thr Pro Gln Gln His Asp Gly Ser Ala
 1               5                  10                  15

Leu Arg Ile Gly Ile Val His Ala Arg Trp Asn Lys Thr Ile Ile Met
                20                  25                  30

Pro Leu Leu Ile Gly Thr Ile Ala Lys Leu Leu Glu Cys Gly Val Lys
            35                  40                  45

Ala Ser Asn Ile Val Val Gln Ser Val Pro Gly Ser Trp Glu Leu Pro
 50                  55                  60

Ile Ala Val Gln Arg Leu Tyr Ser Ala Ser Gln Leu Gln Thr Pro Ser
 65              70                  75                  80

Ser Gly Pro Ser Leu Ser Ala Gly Asp Leu Leu Gly Ser Ser Thr Thr
                85                  90                  95

Asp Leu Thr Ala Leu Pro Thr Thr Thr Ala Ser Ser Thr Gly Pro Phe
                100                 105                 110

Asp Ala Leu Ile Ala Ile Gly Val Leu Ile Lys Gly Glu Thr Met His
                115                 120                 125

Phe Glu Tyr Ile Ala Asp Ser Val Ser His Gly Leu Met Arg Val Gln
                130                 135                 140

Leu Asp Thr Gly Val Pro Val Ile Phe Gly Val Leu Thr Val Leu Thr
145                 150                 155                 160

Asp Asp Gln Ala Lys Ala Arg Ala Gly Val Ile Glu Gly Ser His Asn
                165                 170                 175

His Gly Glu Asp Trp Gly Leu Ala Ala Val Glu Met Gly Val Arg Arg
                180                 185                 190

Arg Asp Trp Ala Ala Gly Lys Thr Glu
                195                 200
```

<210> SEQ ID NO 28
<211> LENGTH: 239
<212> TYPE: PRT
<213> ORGANISM: Artificial sequence
<220> FEATURE:
<223> OTHER INFORMATION: Synthetic polypeptide

<400> SEQUENCE: 28

```
Met Tyr Glu Val Asp His Ala Asp Val Tyr Asp Leu Phe Tyr Leu Gly
 1               5                  10                  15

Arg Gly Lys Asp Tyr Ala Ala Glu Ala Ser Asp Ile Ala Asp Leu Val
```

```
              20                  25                  30
Arg Ser Arg Thr Pro Glu Ala Ser Ser Leu Leu Asp Val Ala Cys Gly
        35                  40                  45
Thr Gly Thr His Leu Glu His Phe Thr Lys Glu Phe Gly Asp Thr Ala
    50                  55                  60
Gly Leu Glu Leu Ser Glu Asp Met Leu Thr His Ala Arg Lys Arg Leu
65                  70                  75                  80
Pro Asp Ala Thr Leu His Gln Gly Asp Met Arg Asp Phe Gln Leu Gly
                85                  90                  95
Arg Lys Phe Ser Ala Val Val Ser Met Phe Ser Ser Val Gly Tyr Leu
            100                 105                 110
Lys Thr Val Ala Glu Leu Gly Ala Ala Val Ala Ser Phe Ala Glu His
        115                 120                 125
Leu Glu Pro Gly Gly Val Val Val Glu Pro Trp Trp Phe Pro Glu
    130                 135                 140
Thr Phe Ala Asp Gly Trp Val Ser Ala Asp Val Val Arg Arg Asp Gly
145                 150                 155                 160
Arg Thr Val Ala Arg Val Ser His Ser Val Arg Glu Gly Asn Ala Thr
                165                 170                 175
Arg Met Glu Val His Phe Thr Val Ala Asp Pro Gly Lys Gly Val Arg
            180                 185                 190
His Phe Ser Asp Val His Leu Ile Thr Leu Phe His Gln Arg Glu Tyr
        195                 200                 205
Glu Ala Ala Phe Met Ala Ala Gly Leu Arg Val Glu Tyr Leu Glu Gly
    210                 215                 220
Gly Pro Ser Gly Arg Gly Leu Phe Val Gly Val Pro Ala Leu Glu
225                 230                 235

<210> SEQ ID NO 29
<211> LENGTH: 208
<212> TYPE: PRT
<213> ORGANISM: Artificial sequence
<220> FEATURE:
<223> OTHER INFORMATION: Synthetic polypeptide

<400> SEQUENCE: 29

Gly Met Glu Gly Met Asp Pro Leu Ala Val Leu Ala Glu Ser Arg Leu
1               5                   10                  15
Leu Pro Leu Leu Thr Val Arg Gly Gly Glu Asp Leu Ala Gly Leu Ala
            20                  25                  30
Thr Val Leu Glu Leu Met Gly Val Gly Ala Leu Glu Ile Thr Leu Arg
        35                  40                  45
Thr Glu Lys Gly Leu Glu Ala Leu Lys Ala Leu Arg Lys Ser Gly Leu
    50                  55                  60
Leu Leu Gly Ala Gly Thr Val Arg Ser Pro Lys Glu Ala Glu Ala Ala
65                  70                  75                  80
Leu Glu Ala Gly Ala Ala Phe Leu Val Ser Pro Gly Leu Leu Glu Glu
                85                  90                  95
Val Ala Ala Leu Ala Gln Ala Arg Gly Val Pro Tyr Leu Pro Gly Val
            100                 105                 110
Leu Thr Pro Thr Glu Val Glu Arg Ala Leu Ala Leu Gly Leu Ser Ala
        115                 120                 125
Leu Lys Phe Phe Pro Ala Glu Pro Phe Gln Gly Val Arg Val Leu Arg
    130                 135                 140
Ala Tyr Ala Glu Val Phe Pro Glu Val Arg Phe Leu Pro Thr Gly Gly
```

```
              145                 150                 155                 160
Ile Lys Glu Glu His Leu Pro His Tyr Ala Ala Leu Pro Asn Leu Leu
                    165                 170                 175

Ala Val Gly Gly Ser Trp Leu Leu Gln Gly Asp Leu Ala Ala Val Met
            180                 185                 190

Lys Lys Val Lys Ala Ala Lys Ala Leu Leu Ser Pro Gln Ala Pro Gly
            195                 200                 205

<210> SEQ ID NO 30
<211> LENGTH: 156
<212> TYPE: PRT
<213> ORGANISM: Artificial sequence
<220> FEATURE:
<223> OTHER INFORMATION: Synthetic polypeptide

<400> SEQUENCE: 30

Met Thr Lys Lys Val Gly Ile Val Asp Thr Thr Phe Ala Arg Val Asp
1               5                   10                  15

Met Ala Glu Ala Ala Ile Arg Thr Leu Lys Ala Leu Ser Pro Asn Ile
            20                  25                  30

Lys Ile Ile Arg Lys Thr Val Pro Gly Ile Lys Asp Leu Pro Val Ala
        35                  40                  45

Cys Lys Lys Leu Leu Glu Glu Gly Cys Asp Ile Val Met Ala Leu
    50                  55                  60

Gly Met Pro Gly Lys Ala Glu Lys Asp Lys Val Cys Ala His Glu Ala
65                  70                  75                  80

Ser Leu Gly Leu Met Leu Ala Gln Leu Met Thr Asn Lys His Ile Ile
                85                  90                  95

Glu Val Phe Val His Glu Asp Glu Ala Lys Asp Asp Glu Leu Asp
            100                 105                 110

Ile Leu Ala Leu Val Arg Ala Ile Glu His Ala Ala Asn Val Tyr Tyr
        115                 120                 125

Leu Leu Phe Lys Pro Glu Tyr Leu Thr Arg Met Ala Gly Lys Gly Leu
    130                 135                 140

Arg Gln Gly Arg Glu Asp Ala Gly Pro Ala Arg Glu
145                 150                 155

<210> SEQ ID NO 31
<211> LENGTH: 71
<212> TYPE: PRT
<213> ORGANISM: Artificial sequence
<220> FEATURE:
<223> OTHER INFORMATION: Synthetic polypeptide

<400> SEQUENCE: 31

Gly Ser Lys Asp Thr Glu Asp Ser Arg Lys Ile Trp Glu Asp Ile Arg
1               5                   10                  15

Arg Leu Leu Glu Glu Ala Arg Lys Asn Ser Glu Glu Ile Trp Lys Glu
            20                  25                  30

Ile Thr Lys Asn Pro Asp Thr Ser Glu Ile Ala Arg Leu Leu Ser Glu
        35                  40                  45

Gln Leu Leu Glu Ile Ala Glu Met Leu Val Arg Ile Ala Glu Leu Leu
    50                  55                  60

Ser Arg Gln Thr Glu Gln Arg
65                  70

<210> SEQ ID NO 32
<211> LENGTH: 161
```

```
<212> TYPE: PRT
<213> ORGANISM: Artificial sequence
<220> FEATURE:
<223> OTHER INFORMATION: Synthetic polypeptide

<400> SEQUENCE: 32

Gly Ala Arg Val Ala Ile Val Met Gly Ser Leu Ser Asp Trp Ala Thr
1               5                   10                  15

Met Gln Phe Ala Ala Leu Ile Phe Leu Ile Leu Asn Val Pro His His
            20                  25                  30

Val Glu Val Val Ser Ala His Arg Thr Pro Asp Lys Leu Phe Ser Phe
        35                  40                  45

Ala Glu Ser Ala Glu Glu Asn Gly Tyr Gln Val Ile Ile Ala Gly Ala
    50                  55                  60

Gly Gly Ala Ala His Leu Pro Gly Met Ile Ala Ala Lys Thr Leu Val
65                  70                  75                  80

Pro Val Leu Gly Val Pro Val Gln Ser Ala Ala Leu Ser Gly Val Asp
                85                  90                  95

Ser Leu Tyr Ser Ile Val Gln Met Pro Arg Gly Ile Pro Val Gly Thr
            100                 105                 110

Leu Ala Ile Gly Lys Ala Gly Ala Ala Asn Ala Ala Leu Leu Ala Ala
        115                 120                 125

Gln Ile Leu Ala Thr His Asp Lys Glu Leu His Gln Arg Leu Asn Asp
    130                 135                 140

Trp Arg Lys Ala Gln Thr Asp Glu Val Leu Glu Asn Pro Leu Pro Arg
145                 150                 155                 160

Gly

<210> SEQ ID NO 33
<211> LENGTH: 194
<212> TYPE: PRT
<213> ORGANISM: Artificial sequence
<220> FEATURE:
<223> OTHER INFORMATION: Synthetic polypeptide

<400> SEQUENCE: 33

Met Asn Leu Met Thr Thr Ile Thr Gly Val Val Leu Ala Gly Gly Lys
1               5                   10                  15

Ala Arg Arg Met Gly Gly Val Asp Lys Gly Leu Leu Glu Leu Asn Gly
            20                  25                  30

Lys Pro Leu Trp Gln His Val Ala Asp Ala Leu Met Thr Gln Leu Ser
            35                  40                  45

His Val Val Asn Ala Asn Arg His Gln Glu Ile Tyr Gln Ala Ser
        50                  55                  60

Gly Leu Lys Val Ile Glu Asp Ser Leu Ala Asp Tyr Pro Gly Pro Leu
65                  70                  75                  80

Ala Gly Met Leu Ser Val Met Gln Gln Glu Ala Gly Glu Trp Phe Leu
                85                  90                  95

Phe Cys Pro Cys Asp Thr Pro Tyr Ile Pro Pro Asp Leu Ala Ala Arg
            100                 105                 110

Leu Asn His Gln Arg Lys Asp Ala Pro Val Val Trp Val His Asp Gly
        115                 120                 125

Glu Arg Asp His Pro Thr Ile Ala Leu Val Asn Arg Ala Ile Glu Pro
    130                 135                 140

Leu Leu Leu Glu Tyr Leu Gln Ala Gly Glu Arg Arg Val Met Val Phe
145                 150                 155                 160
```

```
Met Arg Leu Ala Gly Gly His Ala Val Leu Phe Ser Leu His Leu Leu
                165                 170                 175

Ala Phe Val Asn Val Asn Thr Pro Glu Glu Leu Ala Arg Trp Gln Glu
            180                 185                 190

Lys Arg

<210> SEQ ID NO 34
<211> LENGTH: 221
<212> TYPE: PRT
<213> ORGANISM: Artificial sequence
<220> FEATURE:
<223> OTHER INFORMATION: Synthetic polypeptide

<400> SEQUENCE: 34

Met Glu Leu Tyr Leu Asp Thr Ser Asp Val Ala Val Lys Ala Leu
1               5                   10                  15

Ser Ile Arg Ile Phe Pro Leu Ala Gly Val Thr Thr Asn Pro Ser Ile
                20                  25                  30

Ile Ala Ala Gly Lys Lys Pro Leu Asp Val Val Leu Pro Gln Leu His
            35                  40                  45

Glu Ala Met Gly Gly Gln Gly Arg Leu Phe Ala Gln Val Met Ala Thr
        50                  55                  60

Thr Ala Glu Gly Met Val Asn Asp Ala Leu Lys Leu Arg Ser Ile Ile
65                  70                  75                  80

Ala Asp Ile Val Val Lys Val Pro Val Thr Ala Glu Gly Leu Ala Ala
                85                  90                  95

Ile Tyr Met Leu Tyr Ala Tyr Gly Ile Pro Thr Leu Gly Thr Ala Val
            100                 105                 110

Tyr Gly Ala Ala Gln Gly Leu Leu Ser Ala Leu Ala Gly Ala Glu Tyr
        115                 120                 125

Val Ala Pro Tyr Val Asn Arg Ile Asp Ala Gln Gly Gly Ser Gly Ile
130                 135                 140

Gln Thr Val Thr Asp Leu His Gln Leu Leu Lys Met His Ala Pro Gln
145                 150                 155                 160

Ala Lys Val Leu Ala Ala Ser Phe Lys Thr Pro Arg Gln Ala Leu Asp
                165                 170                 175

Cys Leu Leu Ala Gly Cys Glu Ser Ile Thr Leu Pro Leu Asp Val Ala
            180                 185                 190

Gln Gln Met Ile Ser Tyr Pro Ala Val Asp Ala Ala Val Ala Lys Phe
        195                 200                 205

Glu Gln Asp Trp Gln Gly Ala Phe Gly Arg Thr Ser Ile
210                 215                 220

<210> SEQ ID NO 35
<211> LENGTH: 208
<212> TYPE: PRT
<213> ORGANISM: Artificial sequence
<220> FEATURE:
<223> OTHER INFORMATION: Synthetic polypeptide

<400> SEQUENCE: 35

Met Thr Lys Pro Tyr Val Arg Leu Asp Lys Asn Asp Ala Ala Val Leu
1               5                   10                  15

Leu Val Asp His Gln Ala Gly Leu Leu Ser Leu Val Arg Asp Ile Glu
                20                  25                  30

Pro Asp Lys Phe Lys Asn Asn Val Leu Ala Leu Gly Asp Leu Ala Lys
            35                  40                  45
```

```
Tyr Phe Asn Leu Pro Thr Ile Leu Thr Thr Ser Ala Glu Thr Gly Pro
 50                  55                  60

Asn Gly Pro Leu Val Pro Glu Leu Lys Ala Gln Phe Pro Asp Ala Pro
 65                  70                  75                  80

Tyr Ile Ala Arg Pro Gly Asn Ile Asn Ala Trp Tyr Asn Glu Tyr Phe
                 85                  90                  95

Val Tyr Ala Val Tyr Ala Thr Gly Lys Lys Gln Leu Ile Ile Ala Gly
                100                 105                 110

Val Val Thr Glu Val Cys Val Ala Phe Pro Ala Leu Ser Ala Ile Glu
            115                 120                 125

Glu Gly Phe Asp Val Phe Val Thr Asp Ala Ser Gly Thr Phe Asn
            130                 135                 140

Glu Ile Thr Arg His Ser Ala Trp Asp Arg Met Ser Gln Ala Gly Ala
145                 150                 155                 160

Gln Leu Met Thr Trp Phe Gly Val Ala Cys Glu Leu His Arg Asp Trp
                165                 170                 175

Arg Asn Asp Ile Ala Gly Leu Ala Thr Leu Phe Ser Asn His Ile Pro
                180                 185                 190

Asp Tyr Arg Asn Leu Met Thr Ser Tyr Asp Thr Leu Thr Lys Gln Lys
                195                 200                 205

<210> SEQ ID NO 36
<211> LENGTH: 156
<212> TYPE: PRT
<213> ORGANISM: Artificial sequence
<220> FEATURE:
<223> OTHER INFORMATION: Synthetic polypeptide

<400> SEQUENCE: 36

Met Ile Gln Ser Gln Ile Asn Arg Asn Ile Arg Leu Asp Leu Ala Asp
1               5                   10                  15

Ala Ile Leu Leu Ser Lys Ala Tyr Tyr Tyr Leu Ser Phe Ala Glu Ile
                20                  25                  30

Ala Asp Gly Thr Gly Leu Ala Glu Ala Phe Val Thr Ala Ala Leu Leu
            35                  40                  45

Gly Gln Gln Ala Leu Pro Ala Asp Ala Ala Arg Leu Val Gly Ala Lys
        50                  55                  60

Leu Asp Leu Asp Glu Asp Ser Ile Leu Leu Gln Met Ile Pro Leu
65                  70                  75                  80

Arg Gly Cys Ile Asp Asp Arg Ile Pro Thr Asp Pro Thr Met Tyr Gln
                85                  90                  95

Phe Tyr Glu Met Leu Gln Val Tyr Gly Thr Thr Leu Lys Ala Leu Val
                100                 105                 110

His Glu Lys Phe Gly Asp Gly Ile Ile Ser Ala Ile Asn Phe Lys Leu
            115                 120                 125

Asp Val Lys Lys Val Ala Asp Pro Glu Gly Gly Glu Arg Ala Val Ile
        130                 135                 140

Thr Leu Asp Gly Lys Tyr Leu Pro Thr Lys Pro Phe
145                 150                 155

<210> SEQ ID NO 37
<211> LENGTH: 264
<212> TYPE: PRT
<213> ORGANISM: Artificial sequence
<220> FEATURE:
<223> OTHER INFORMATION: Synthetic polypeptide

<400> SEQUENCE: 37
```

Met Lys Pro Thr Thr Ile Ser Leu Leu Gln Lys Tyr Lys Gln Glu Lys
1               5                   10                  15

Lys Arg Phe Ala Thr Ile Thr Ala Tyr Asp Tyr Ser Phe Ala Lys Leu
            20                  25                  30

Phe Ala Asp Glu Gly Leu Asn Val Met Leu Val Gly Asp Ser Leu Gly
        35                  40                  45

Met Thr Val Gln Gly His Asp Ser Thr Leu Pro Val Thr Val Ala Asp
    50                  55                  60

Ile Ala Tyr His Thr Ala Ala Val Arg Arg Gly Ala Pro Asn Cys Leu
65                  70                  75                  80

Leu Leu Ala Asp Leu Pro Phe Met Ala Tyr Ala Thr Pro Glu Gln Ala
                85                  90                  95

Phe Glu Asn Ala Ala Thr Val Met Arg Ala Gly Ala Asn Met Val Lys
            100                 105                 110

Ile Glu Gly Gly Glu Trp Leu Val Glu Thr Val Gln Met Leu Thr Glu
        115                 120                 125

Arg Ala Val Pro Val Cys Gly His Leu Gly Leu Thr Pro Gln Ser Val
    130                 135                 140

Asn Ile Phe Gly Gly Tyr Lys Val Gln Gly Arg Gly Leu Leu Ala Gly
145                 150                 155                 160

Leu Gln Leu Leu Ser Asp Ala Leu Ala Leu Glu Ala Ala Gly Ala Gln
                165                 170                 175

Leu Leu Val Leu Glu Cys Val Pro Val Glu Leu Ala Lys Arg Ile Thr
            180                 185                 190

Glu Ala Leu Ala Ile Pro Val Ile Gly Ile Gly Ala Gly Asn Val Thr
        195                 200                 205

Asp Gly Gln Ile Leu Val Met His Asp Ala Phe Gly Ile Thr Gly Gly
    210                 215                 220

His Ile Pro Lys Phe Ala Lys Asn Phe Leu Ala Glu Thr Gly Asp Ile
225                 230                 235                 240

Arg Ala Ala Val Arg Gln Tyr Met Ala Glu Val Ser Gly Val Tyr
                245                 250                 255

Pro Gly Glu Glu His Ser Phe His
            260

<210> SEQ ID NO 38
<211> LENGTH: 152
<212> TYPE: PRT
<213> ORGANISM: Artificial sequence
<220> FEATURE:
<223> OTHER INFORMATION: Synthetic polypeptide

<400> SEQUENCE: 38

Met Glu Asn Tyr Leu Ile Asp Asn Leu Asp Arg Gly Ile Leu Glu Ala
1               5                   10                  15

Leu Met Gly Asn Ala Arg Thr Ala Tyr Ala Glu Leu Ala Lys Gln Phe
            20                  25                  30

Gly Val Ser Pro Glu Thr Ile His Val Arg Val Glu Lys Met Lys Gln
        35                  40                  45

Ala Gly Ile Ile Thr Gly Ala Arg Ile Asp Val Ser Pro Lys Gln Leu
    50                  55                  60

Gly Tyr Asp Val Gly Cys Phe Ile Gly Ile Ile Leu Lys Ser Ala Lys
65                  70                  75                  80

Asp Tyr Pro Ser Ala Leu Ala Lys Leu Glu Ser Leu Asp Glu Val Thr
                85                  90                  95

Glu Ala Tyr Tyr Thr Thr Gly His Tyr Ser Ile Phe Ile Lys Val Met
                100                 105                 110

Cys Arg Ser Ile Asp Ala Leu Gln His Val Leu Ile Asn Tyr Ile Gln
            115                 120                 125

Thr Ile Tyr Glu Ile Gln Ser Thr Glu Thr Leu Ile Val Leu Gln Asn
        130                 135                 140

Pro Ile Met Arg Thr Ile Lys Pro
145                 150

<210> SEQ ID NO 39
<211> LENGTH: 207
<212> TYPE: PRT
<213> ORGANISM: Artificial sequence
<220> FEATURE:
<223> OTHER INFORMATION: Synthetic polypeptide

<400> SEQUENCE: 39

Met Ala Gln Gly Thr Leu Tyr Ile Val Ser Ala Pro Ser Gly Ala Gly
1               5                   10                  15

Lys Ser Ser Leu Ile Gln Ala Leu Leu Lys Thr Gln Pro Leu Tyr Asp
            20                  25                  30

Thr Gln Val Ser Val Ser His Thr Arg Gln Pro Arg Pro Gly Glu
        35                  40                  45

Val His Gly Glu His Tyr Phe Phe Val Asn His Tyr Tyr Phe Tyr Tyr
    50                  55                  60

Met Ile Ser Arg Asp Ala Phe Leu Glu His Ala Glu Val Phe Gly Asn
65                  70                  75                  80

Tyr Tyr Gly Thr Ser Arg Glu Ala Ile Glu Gln Val Leu Ala Thr Gly
                85                  90                  95

Val Asp Val Phe Leu Asp Ile Asp Trp Gln Gly Ala Gln Gln Ile Arg
            100                 105                 110

Gln Lys Met Pro His Ala Arg Ser Ile Phe Ile Leu Pro Pro Ser Lys
        115                 120                 125

Ile Glu Leu Asp Arg Arg Leu Arg Gly Arg Gly Gln Asp Ser Glu Glu
    130                 135                 140

Val Ile Ala Lys Arg Met Ala Gln Ala Val Ala Glu Met Ser His Tyr
145                 150                 155                 160

Ala Glu Tyr Asp Tyr Leu Ile Val Asn Asp Asp Phe Asp Thr Ala Leu
                165                 170                 175

Thr Asp Leu Lys Thr Ile Ile Arg Ala Glu Arg Leu Arg Met Ser Arg
            180                 185                 190

Gln Lys Gln Arg His Asp Ala Leu Ile Ser Lys Leu Leu Ala Asp
        195                 200                 205

<210> SEQ ID NO 40
<211> LENGTH: 207
<212> TYPE: PRT
<213> ORGANISM: Artificial sequence
<220> FEATURE:
<223> OTHER INFORMATION: Synthetic polypeptide

<400> SEQUENCE: 40

Met Ala Gln Gly Thr Leu Tyr Ile Val Ser Ala Pro Ser Gly Ala Gly
1               5                   10                  15

Lys Ser Ser Leu Ile Gln Ala Leu Leu Lys Thr Gln Pro Leu Tyr Asp
            20                  25                  30

Thr Gln Val Ser Val Ala His Thr Thr Arg Gln Pro Arg Pro Gly Glu

```
                35                  40                  45
Val His Gly Glu His Tyr Phe Phe Val Asn His Tyr Tyr Phe Tyr Tyr
 50                  55                  60

Met Ile Ser Arg Asp Ala Phe Leu Glu His Ala Glu Val Phe Gly Asn
 65                  70                  75                  80

Tyr Tyr Gly Thr Ser Arg Glu Ala Ile Glu Gln Val Leu Ala Thr Gly
                 85                  90                  95

Val Asp Val Phe Leu Asp Ile Asp Trp Gln Gly Ala Gln Gln Ile Arg
                100                 105                 110

Gln Lys Met Pro His Ala Arg Ser Ile Phe Ile Leu Pro Pro Ser Lys
                115                 120                 125

Ile Glu Leu Asp Arg Arg Leu Arg Gly Arg Gly Gln Asp Ser Glu Glu
                130                 135                 140

Val Ile Ala Lys Arg Met Ala Gln Ala Val Ala Glu Met Ser His Tyr
145                 150                 155                 160

Ala Glu Tyr Asp Tyr Leu Ile Val Asn Asp Asp Phe Asp Thr Ala Leu
                165                 170                 175

Thr Asp Leu Lys Thr Ile Ile Arg Ala Glu Arg Leu Arg Met Ser Arg
                180                 185                 190

Gln Lys Gln Arg His Asp Ala Leu Ile Ser Lys Leu Leu Ala Asp
                195                 200                 205
```

<210> SEQ ID NO 41
<211> LENGTH: 207
<212> TYPE: PRT
<213> ORGANISM: Artificial sequence
<220> FEATURE:
<223> OTHER INFORMATION: Synthetic polypeptide

<400> SEQUENCE: 41

```
Met Ala Gln Gly Thr Leu Tyr Ile Val Ser Ala Pro Ser Gly Ala Gly
  1               5                  10                  15

Lys Gly Ser Leu Ile Gln Ala Leu Leu Lys Thr Gln Pro Leu Tyr Asp
                 20                  25                  30

Thr Gln Val Ser Val Ala His Thr Thr Arg Gln Pro Gly Pro Gly Glu
                 35                  40                  45

Val His Gly Glu His Tyr Phe Phe Val Asn His Tyr Tyr Phe Tyr Tyr
 50                  55                  60

Met Ile Ser Arg Asp Ala Phe Leu Glu His Ala Glu Val Phe Gly Asn
 65                  70                  75                  80

Tyr Tyr Gly Thr Ser Arg Glu Ala Ile Glu Gln Val Leu Ala Thr Gly
                 85                  90                  95

Val Asp Val Phe Leu Asp Ile Asp Trp Gln Gly Ala Gln Gln Ile Arg
                100                 105                 110

Gln Lys Met Pro His Ala Arg Ser Ile Phe Ile Leu Pro Pro Ser Lys
                115                 120                 125

Ile Glu Leu Asp Arg Arg Leu Arg Gly Arg Gly Gln Asp Ser Glu Glu
                130                 135                 140

Val Ile Ala Lys Arg Met Ala Gln Ala Val Ala Glu Met Ser His Tyr
145                 150                 155                 160

Ala Glu Tyr Asp Tyr Leu Ile Val Asn Asp Asp Phe Asp Thr Ala Leu
                165                 170                 175

Thr Asp Leu Lys Thr Ile Ile Arg Ala Glu Arg Leu Arg Met Ser Arg
                180                 185                 190

Gln Lys Gln Arg His Asp Ala Leu Ile Ser Lys Leu Leu Ala Asp
```

```
                195                 200                 205

<210> SEQ ID NO 42
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 42

Met Glu Glu Val Val Leu Ile Thr Val Pro Ser Glu Ser Val Ala Arg
1               5                   10                  15

Ile Ile Ala Lys Ala Leu Val Ala Ser Arg Leu Ala Ala Cys Val Asn
            20                  25                  30

Ile Val Pro Gly Leu Thr Ser Ile Tyr Arg Trp Gln Gly Ser Val Val
        35                  40                  45

Glu Asp Gln Glu Leu Leu Leu Val Lys Thr Thr Thr His Ala Phe
    50                  55                  60

Pro Lys Leu Lys His Thr Val Lys Ile Ile His Pro Tyr Thr Val Pro
65                  70                  75                  80

Glu Ile Val Ala Leu Pro Ile Ala Glu Gly Asn Arg Glu Tyr Leu Asp
                85                  90                  95

Trp Leu Arg Glu Asn Thr Gly Leu Glu His His His His His His
            100                 105                 110

<210> SEQ ID NO 43
<211> LENGTH: 43
<212> TYPE: PRT
<213> ORGANISM: Artificial sequence
<220> FEATURE:
<223> OTHER INFORMATION: Synthetic polypeptide

<400> SEQUENCE: 43

Leu Glu Ile Glu Ala Ala Phe Leu Glu Gln Glu Asn Thr Ala Leu Glu
1               5                   10                  15

Thr Glu Val Ala Glu Leu Glu Gln Glu Val Gln Arg Leu Glu Asn Ile
            20                  25                  30

Val Ser Gln Tyr Glu Thr Arg Tyr Gly Pro Leu
        35                  40

<210> SEQ ID NO 44
<211> LENGTH: 43
<212> TYPE: PRT
<213> ORGANISM: Artificial sequence
<220> FEATURE:
<223> OTHER INFORMATION: Synthetic polypeptide

<400> SEQUENCE: 44

Leu Glu Ile Arg Ala Ala Phe Leu Arg Arg Arg Asn Thr Ala Leu Arg
1               5                   10                  15

Thr Arg Val Ala Glu Leu Arg Gln Arg Val Gln Arg Leu Arg Asn Ile
            20                  25                  30

Val Ser Gln Tyr Glu Thr Arg Tyr Gly Pro Leu
        35                  40

<210> SEQ ID NO 45
<211> LENGTH: 35
<212> TYPE: PRT
<213> ORGANISM: Artificial sequence
<220> FEATURE:
<223> OTHER INFORMATION: Synthetic polypeptide
```

-continued

```
<400> SEQUENCE: 45

Glu Val Ser Ala Leu Glu Lys Glu Val Ser Ala Leu Glu Lys Glu Val
1               5                   10                  15

Ser Ala Leu Glu Lys Glu Val Ser Ala Leu Glu Lys Glu Val Ser Ala
            20                  25                  30

Leu Glu Lys
        35

<210> SEQ ID NO 46
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 46

Cys Gly Gly Lys Val Ser Ala Leu Lys Glu Lys Val Ser Ala Leu Lys
1               5                   10                  15

Glu Lys Val Ser Ala Leu Lys Glu Lys Val Ser Ala Leu Lys Glu Lys
            20                  25                  30

Val Ser Ala Leu Lys Glu
        35

<210> SEQ ID NO 47
<211> LENGTH: 30
<212> TYPE: PRT
<213> ORGANISM: Artificial sequence
<220> FEATURE:
<223> OTHER INFORMATION: Synthetic polypeptide

<400> SEQUENCE: 47

Ala Gln Leu Glu Lys Glu Leu Gln Ala Leu Glu Lys Lys Leu Ala Gln
1               5                   10                  15

Leu Glu Trp Glu Asn Gln Ala Leu Glu Lys Glu Leu Ala Gln
            20                  25                  30

<210> SEQ ID NO 48
<211> LENGTH: 30
<212> TYPE: PRT
<213> ORGANISM: Artificial sequence
<220> FEATURE:
<223> OTHER INFORMATION: Synthetic polypeptide

<400> SEQUENCE: 48

Ala Gln Leu Lys Lys Lys Leu Gln Ala Asn Lys Lys Glu Leu Ala Gln
1               5                   10                  15

Leu Lys Trp Lys Leu Gln Ala Leu Lys Lys Lys Leu Ala Gln
            20                  25                  30

<210> SEQ ID NO 49
<211> LENGTH: 30
<212> TYPE: PRT
<213> ORGANISM: Artificial sequence
<220> FEATURE:
<223> OTHER INFORMATION: Synthetic polypeptide

<400> SEQUENCE: 49

Ala Gln Leu Glu Lys Glu Leu Gln Ala Leu Glu Lys Glu Asn Ala Gln
1               5                   10                  15

Leu Glu Trp Glu Leu Gln Ala Leu Glu Lys Glu Leu Ala Gln
            20                  25                  30
```

```
<210> SEQ ID NO 50
<211> LENGTH: 30
<212> TYPE: PRT
<213> ORGANISM: Artificial sequence
<220> FEATURE:
<223> OTHER INFORMATION: Synthetic polypeptide

<400> SEQUENCE: 50

Ala Gln Leu Lys Lys Lys Leu Gln Ala Leu Lys Lys Lys Asn Ala Gln
1               5                   10                  15

Leu Lys Trp Lys Leu Gln Ala Leu Lys Lys Leu Ala Gln
            20                  25                  30

<210> SEQ ID NO 51
<211> LENGTH: 21
<212> TYPE: PRT
<213> ORGANISM: Artificial sequence
<220> FEATURE:
<223> OTHER INFORMATION: Synthetic polypeptide

<400> SEQUENCE: 51

Glu Ile Lys Ala Leu Glu Gln Glu Ile Ala Ala Leu Lys Gln Lys Ile
1               5                   10                  15

Ala Trp Leu Lys Gln
            20

<210> SEQ ID NO 52
<211> LENGTH: 21
<212> TYPE: PRT
<213> ORGANISM: Artificial sequence
<220> FEATURE:
<223> OTHER INFORMATION: Synthetic polypeptide

<400> SEQUENCE: 52

Lys Ile Lys Ala Leu Lys Gln Glu Ile Ala Ala Leu Lys Gln Glu Ile
1               5                   10                  15

Ala Tyr Leu Glu Gln
            20

<210> SEQ ID NO 53
<211> LENGTH: 33
<212> TYPE: PRT
<213> ORGANISM: Artificial sequence
<220> FEATURE:
<223> OTHER INFORMATION: Synthetic polypeptide

<400> SEQUENCE: 53

Ser Pro Glu Asp Glu Ile Gln Gln Leu Glu Glu Glu Ile Ala Gln Leu
1               5                   10                  15

Glu Gln Lys Asn Ala Ala Leu Lys Glu Lys Asn Gln Ala Leu Lys Tyr
            20                  25                  30

Gly

<210> SEQ ID NO 54
<211> LENGTH: 33
<212> TYPE: PRT
<213> ORGANISM: Artificial sequence
<220> FEATURE:
<223> OTHER INFORMATION: Synthetic polypeptide

<400> SEQUENCE: 54

Ser Pro Glu Asp Lys Ile Ala Gln Leu Lys Gln Lys Ile Gln Ala Leu
1               5                   10                  15

Lys Gln Glu Asn Gln Gln Leu Glu Glu Glu Asn Ala Ala Leu Glu Tyr
```

Gly

<210> SEQ ID NO 55
<211> LENGTH: 45
<212> TYPE: PRT
<213> ORGANISM: Artificial sequence
<220> FEATURE:
<223> OTHER INFORMATION: Synthetic polypeptide

<400> SEQUENCE: 55

Met Lys Gln Leu Glu Lys Glu Leu Lys Gln Leu Glu Lys Glu Leu Gln
1               5                   10                  15

Ala Ile Glu Lys Gln Leu Ala Gln Leu Gln Trp Lys Ala Gln Ala Arg
            20                  25                  30

Lys Lys Lys Leu Ala Gln Leu Lys Lys Leu Gln Ala
        35                  40                  45

<210> SEQ ID NO 56
<211> LENGTH: 36
<212> TYPE: PRT
<213> ORGANISM: Artificial sequence
<220> FEATURE:
<223> OTHER INFORMATION: Synthetic polypeptide

<400> SEQUENCE: 56

Asp Ile Glu Gln Glu Leu Glu Arg Ala Lys Ala Ser Ile Arg Arg Leu
1               5                   10                  15

Glu Gln Glu Val Asn Gln Glu Arg Ser Arg Met Ala Tyr Leu Gln Thr
            20                  25                  30

Leu Leu Ala Lys
        35

<210> SEQ ID NO 57
<211> LENGTH: 28
<212> TYPE: PRT
<213> ORGANISM: Artificial sequence
<220> FEATURE:
<223> OTHER INFORMATION: Synthetic polypeptide

<400> SEQUENCE: 57

Gln Leu Glu Asp Lys Val Glu Glu Leu Leu Ser Lys Asn Tyr His Leu
1               5                   10                  15

Glu Asn Glu Val Ala Arg Leu Lys Lys Leu Val Gly
            20                  25

<210> SEQ ID NO 58
<211> LENGTH: 32
<212> TYPE: PRT
<213> ORGANISM: Artificial sequence
<220> FEATURE:
<223> OTHER INFORMATION: Synthetic polypeptide

<400> SEQUENCE: 58

Gly Glu Ile Ala Ala Leu Lys Gln Glu Ile Ala Ala Leu Lys Lys Glu
1               5                   10                  15

Asn Ala Ala Leu Lys Trp Glu Ile Ala Ala Leu Lys Gln Gly Tyr Tyr
            20                  25                  30

<210> SEQ ID NO 59
<211> LENGTH: 32
<212> TYPE: PRT
<213> ORGANISM: Artificial sequence
<220> FEATURE:
<223> OTHER INFORMATION: Synthetic polypeptide

<400> SEQUENCE: 59

Gly Glu Ile Ala Ala Ile Lys Gln Glu Ile Ala Ala Ile Lys Lys Glu
1               5                   10                  15

Ile Ala Ala Ile Lys Trp Glu Ile Ala Ala Ile Lys Gln Gly Tyr Gly
            20                  25                  30

<210> SEQ ID NO 60
<211> LENGTH: 30
<212> TYPE: PRT
<213> ORGANISM: Artificial sequence
<220> FEATURE:
<223> OTHER INFORMATION: Synthetic polypeptide

<400> SEQUENCE: 60

Gly Glu Ile Ala Gln Ala Leu Lys Glu Ile Ala Lys Ala Leu Lys Glu
1               5                   10                  15

Ile Ala Trp Ala Leu Lys Glu Ile Ala Gln Ala Leu Lys Gly
            20                  25                  30

<210> SEQ ID NO 61
<211> LENGTH: 30
<212> TYPE: PRT
<213> ORGANISM: Artificial sequence
<220> FEATURE:
<223> OTHER INFORMATION: Synthetic polypeptide

<400> SEQUENCE: 61

Gly Glu Ile Ala Lys Ser Leu Lys Glu Ile Ala Lys Ser Leu Lys Glu
1               5                   10                  15

Ile Ala Trp Ser Leu Lys Glu Ile Ala Lys Ser Leu Lys Gly
            20                  25                  30

<210> SEQ ID NO 62
<211> LENGTH: 30
<212> TYPE: PRT
<213> ORGANISM: Artificial sequence
<220> FEATURE:
<223> OTHER INFORMATION: Synthetic polypeptide

<400> SEQUENCE: 62

Gly Lys Ile Glu Gln Ile Leu Gln Lys Ile Glu Lys Ile Leu Gln Lys
1               5                   10                  15

Ile Glu Trp Ile Leu Gln Lys Ile Glu Gln Ile Leu Gln Gly
            20                  25                  30

<210> SEQ ID NO 63
<211> LENGTH: 32
<212> TYPE: PRT
<213> ORGANISM: Artificial sequence
<220> FEATURE:
<223> OTHER INFORMATION: Synthetic polypeptide

<400> SEQUENCE: 63

Gly Glu Leu Ala Ala Ile Lys Gln Glu Leu Ala Ala Ile Lys Lys Glu
1               5                   10                  15

Leu Ala Ala Ile Lys Trp Glu Leu Ala Ala Ile Lys Gln Gly Ala Gly
            20                  25                  30

<210> SEQ ID NO 64
<211> LENGTH: 33
<212> TYPE: PRT

```
<213> ORGANISM: Artificial sequence
<220> FEATURE:
<223> OTHER INFORMATION: Synthetic polypeptide

<400> SEQUENCE: 64

Thr Leu Arg Glu Ile Glu Glu Leu Leu Arg Lys Ile Ile Glu Asp Ser
1               5                   10                  15

Val Arg Ser Val Ala Glu Leu Glu Asp Ile Glu Lys Trp Leu Lys Lys
            20                  25                  30

Ile

<210> SEQ ID NO 65
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 65

Gly Ser Gly Ser
1

<210> SEQ ID NO 66
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 66

Gly Gly Ser Gly Gly Thr
1               5

<210> SEQ ID NO 67
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 67

Gly Gly Gly Ser Gly Gly Gly Ser
1               5

<210> SEQ ID NO 68
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 68

Gly Gly Gly Ser Gly Gly Gly Ser Gly Gly Ser Gly Gly Gly Ser
1               5                   10                  15

<210> SEQ ID NO 69
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 69

Ala Pro Ala Pro Ala Pro
1               5
```

```
<210> SEQ ID NO 70
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 70

Glu Ala Ala Ala Lys
1               5

<210> SEQ ID NO 71
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 71

Glu Ala Ala Lys Glu Ala Ala Lys
1               5

<210> SEQ ID NO 72
<211> LENGTH: 7
<212> TYPE: PRT
<213> ORGANISM: Simian virus 40

<400> SEQUENCE: 72

Pro Lys Lys Lys Arg Lys Val
1               5

<210> SEQ ID NO 73
<211> LENGTH: 26
<212> TYPE: PRT
<213> ORGANISM: Artificial sequence
<220> FEATURE:
<223> OTHER INFORMATION: Synthetic polypeptide

<400> SEQUENCE: 73

Gly Ala Gly Ala Lys Glu Lys Met Ser Lys Asp Gly Lys Lys Lys Lys
1               5                   10                  15

Lys Lys Ser Lys Thr Lys Cys Val Ile Met
            20                  25

<210> SEQ ID NO 74
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 74

Asp Leu Tyr Asp Asp Asp Asp Lys
1               5

<210> SEQ ID NO 75
<211> LENGTH: 9
<212> TYPE: PRT
<213> ORGANISM: Influenza virus

<400> SEQUENCE: 75

Tyr Pro Tyr Asp Val Pro Asp Tyr Ala
1               5

<210> SEQ ID NO 76
```

-continued

<211> LENGTH: 14
<212> TYPE: PRT
<213> ORGANISM: Artificial sequence
<220> FEATURE:
<223> OTHER INFORMATION: Synthetic polypeptide

<400> SEQUENCE: 76

Gly Lys Pro Ile Pro Asn Pro Leu Leu Gly Leu Asp Ser Thr
1               5                   10

<210> SEQ ID NO 77
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 77

Ser Gly Phe Ala Asn Glu Leu Gly Pro Arg Leu Met Gly Lys
1               5                   10

<210> SEQ ID NO 78
<211> LENGTH: 11
<212> TYPE: PRT
<213> ORGANISM: Vesicular stomatitis virus

<400> SEQUENCE: 78

Tyr Thr Asp Ile Glu Met Asn Arg Leu Gly Lys
1               5                   10

<210> SEQ ID NO 79
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 79

Gly Ala Pro Val Pro Tyr Pro Asp Pro Leu Glu Pro Arg
1               5                   10

<210> SEQ ID NO 80
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 80

Asp Tyr Lys Asp Asp Asp Asp Lys
1               5

<210> SEQ ID NO 81
<211> LENGTH: 299
<212> TYPE: PRT
<213> ORGANISM: Artificial sequence
<220> FEATURE:
<223> OTHER INFORMATION: Synthetic polypeptide

<400> SEQUENCE: 81

Met Asp Tyr Lys Asp Asp Asp Asp Lys Gly Asp Tyr Lys Asp Asp Asp
1               5                   10                  15

Asp Lys Gly Asp Tyr Lys Asp Asp Asp Asp Lys Gly Gly Gly Gly Gly
            20                  25                  30

Val Ser Lys Gly Glu Glu Leu Ile Lys Glu Asn Met Arg Met Lys Val
        35                  40                  45

Val Met Glu Gly Ser Val Asn Gly His Gln Phe Lys Cys Thr Gly Glu
        50                  55                  60

Gly Glu Gly Arg Pro Tyr Glu Gly Val Gln Thr Met Arg Ile Lys Val
 65                  70                  75                  80

Ile Glu Gly Gly Pro Leu Pro Phe Ala Phe Asp Ile Leu Ala Thr Ser
                 85                  90                  95

Phe Met Tyr Gly Ser Arg Thr Phe Ile Lys Tyr Pro Ala Asp Ile Pro
            100                 105                 110

Asp Phe Phe Lys Gln Ser Phe Pro Glu Gly Phe Thr Trp Glu Arg Val
        115                 120                 125

Thr Arg Tyr Glu Asp Gly Gly Val Val Thr Val Thr Gln Asp Thr Ser
    130                 135                 140

Leu Glu Asp Gly Glu Leu Val Tyr Asn Val Lys Val Arg Gly Val Asn
145                 150                 155                 160

Phe Pro Ser Asn Gly Pro Val Met Gln Lys Lys Thr Lys Gly Trp Glu
                165                 170                 175

Pro Asn Thr Glu Met Met Tyr Pro Ala Asp Gly Gly Leu Arg Gly Tyr
            180                 185                 190

Thr Asp Ile Ala Leu Lys Val Asp Gly Gly His Leu His Cys Asn
        195                 200                 205

Phe Val Thr Thr Tyr Arg Ser Lys Lys Thr Val Gly Asn Ile Lys Met
    210                 215                 220

Pro Gly Val His Ala Val Asp His Arg Leu Glu Arg Ile Glu Glu Ser
225                 230                 235                 240

Asp Asn Glu Thr Tyr Val Val Gln Arg Glu Val Ala Val Ala Lys Tyr
                245                 250                 255

Ser Asn Leu Gly Gly Gly Met Asp Glu Leu Tyr Lys Gly Gly Gly Gly
            260                 265                 270

Gly Asp Tyr Lys Asp Asp Asp Lys Gly Asp Tyr Lys Asp Asp Asp
        275                 280                 285

Asp Lys Gly Asp Tyr Lys Asp Asp Asp Lys
    290                 295

<210> SEQ ID NO 82
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 82

Gly Leu Asn Asp Ile Phe Glu Ala Gln Lys Ile Glu Trp His Glu
1               5                   10                  15

<210> SEQ ID NO 83
<211> LENGTH: 26
<212> TYPE: PRT
<213> ORGANISM: Artificial sequence
<220> FEATURE:
<223> OTHER INFORMATION: Synthetic polypeptide

<400> SEQUENCE: 83

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

```
<210> SEQ ID NO 84
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 84

Glu Glu Glu Glu Glu Glu
1               5

<210> SEQ ID NO 85
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 85

Thr Lys Glu Asn Pro Arg Ser Asn Gln Glu Glu Ser Tyr Asp Asp Asn
1               5                   10                  15

Glu Ser

<210> SEQ ID NO 86
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 86

Thr Glu Thr Ser Gln Val Ala Pro Ala
1               5

<210> SEQ ID NO 87
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 87

Lys Glu Thr Ala Ala Ala Lys Phe Glu Arg Gln His Met Asp Ser
1               5                   10                  15

<210> SEQ ID NO 88
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 88

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 89
<211> LENGTH: 13
<212> TYPE: PRT
<213> ORGANISM: Artificial sequence
<220> FEATURE:
<223> OTHER INFORMATION: Synthetic polypeptide
```

<400> SEQUENCE: 89

Ser Leu Ala Glu Leu Leu Asn Ala Gly Leu Gly Gly Ser
1               5                   10

<210> SEQ ID NO 90
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 90

Thr Gln Asp Pro Ser Arg Val Gly
1               5

<210> SEQ ID NO 91
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 91

Pro Asp Arg Val Arg Ala Val Ser His Trp Ser Ser
1               5                   10

<210> SEQ ID NO 92
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 92

Trp Ser His Pro Gln Phe Glu Lys
1               5

<210> SEQ ID NO 93
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 93

Cys Cys Pro Gly Cys Cys
1               5

<210> SEQ ID NO 94
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 94

Glu Val His Thr Asn Gln Asp Pro Leu Asp
1               5                   10

<210> SEQ ID NO 95
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 95
gacatgggtg atcctcatgt                                               20

<210> SEQ ID NO 96
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 96
atctaatgaa cccgggaata                                               20

<210> SEQ ID NO 97
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 97
ttctaggcaa ttaggtacct                                               20

<210> SEQ ID NO 98
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 98
agcgacgcca tatcgtctgc                                               20

<210> SEQ ID NO 99
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 99
agcgagccca tatgctctgc                                               20
```